United States Patent
Umetani et al.

(10) Patent No.: US 11,051,513 B2
(45) Date of Patent: *Jul. 6, 2021

(54) PYRIDONE COMPOUNDS AND AGRICULTURAL AND HORTICULTURAL FUNGICIDES CONTAINING THE SAME AS ACTIVE INGREDIENTS

(71) Applicant: MITSUI CHEMICALS AGRO, INC., Tokyo (JP)

(72) Inventors: Hideki Umetani, Ritto (JP); Takeshi Fukumoto, Chiba (JP); Ryohei Naito, Kusatsu (JP); Hideaki Ikishima, Chiba (JP); Toshiyuki Kouno, Chiba (JP); Akihiro Nishida, Chiba (JP); Masanori Yanagi, Mobara (JP); Kazuki Kitajima, Mobara (JP); Satoshi Yutani, Ratchaburi (TH); Tomomi Shirakawa, Ritto (JP); Toshiaki Ohara, Moriyama (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/479,347

(22) PCT Filed: Jan. 26, 2018

(86) PCT No.: PCT/JP2018/002370
§ 371 (c)(1),
(2) Date: Jul. 19, 2019

(87) PCT Pub. No.: WO2018/139560
PCT Pub. Date: Aug. 2, 2018

(65) Prior Publication Data
US 2019/0380340 A1    Dec. 19, 2019

(30) Foreign Application Priority Data
Jan. 26, 2017 (JP) .............................. JP2017-012467

(51) Int. Cl.
*A01N 43/40* (2006.01)
*C07D 213/62* (2006.01)
*C07D 221/00* (2006.01)

(52) U.S. Cl.
CPC ........... *A01N 43/40* (2013.01); *C07D 213/62* (2013.01); *C07D 221/00* (2013.01)

(58) Field of Classification Search
CPC ........................................................ A01N 43/40
USPC ......................................................... 546/257
See application file for complete search history.

(56) References Cited

U.S. PATENT DOCUMENTS

| | | |
|---|---|---|
| 6,200,982 B1 | 3/2001 | Collins et al. |
| 2001/0018438 A1 | 8/2001 | Collins et al. |
| 2010/0256202 A1 | 10/2010 | Barre et al. |
| 2017/0267656 A1 | 9/2017 | Short et al. |
| 2018/0279614 A1 | 10/2018 | Umetani et al. |

FOREIGN PATENT DOCUMENTS

| | | |
|---|---|---|
| EP | 0308020 A2 | 3/1989 |
| JP | 01-128969 A | 5/1989 |
| JP | 02-121970 A | 5/1990 |
| JP | 2002503244 A | 1/2002 |
| JP | 2011500543 A | 1/2011 |
| WO | 9855480 A1 | 12/1998 |
| WO | 2016044662 A1 | 3/2016 |
| WO | 2017061525 A1 | 4/2017 |

OTHER PUBLICATIONS

International Search Report (PCT/ISA/210) dated Apr. 10, 2018, by the Japan Patent Office as the International Searching Authority for International Application No. PCT/JP2018/002370.
Krishnaraj, K. U. et al.,"Synthesis of 2-hydroxy-5,6-diarylnicotinonitriles and 2-chloro-5,6-diarylnicotinonitriles from β-chloroenones", Tetrahedron, 70 (37), pp. 6450-6456, 2014.
Written Opinion (PCT/ISA/237) dated Apr. 10, 2018, by the Japan Patent Office as the International Searching Authority for International Application No. PCT/JP2018/002370.

*Primary Examiner* — Taofiq A Solola
(74) *Attorney, Agent, or Firm* — Buchanan Ingersoll & Rooney PC

(57) ABSTRACT

An object of the invention is to provide compounds of formula (1) or salts thereof which are effective as agricultural and horticultural fungicides. In the formula, R1 represents, for example, a hydroxy group or a cyano group, R2, R3 and R4 are independent of one another and each represent, for example, a hydrogen atom or a halogen atom, R5 represents, for example, a hydrogen atom or a halogen atom, X represents an oxygen atom or a sulfur atom, Y represents, for example, a phenyl group or a pyridyl group, and the bond including the broken line represents a double bond or a single bond.

8 Claims, No Drawings

PYRIDONE COMPOUNDS AND AGRICULTURAL AND HORTICULTURAL FUNGICIDES CONTAINING THE SAME AS ACTIVE INGREDIENTS

TECHNICAL FIELD

The present invention relates to pyridone compounds and to agricultural chemicals containing the compounds as active ingredients.

BACKGROUND ART

The protection of agricultural and horticultural crops from diseases is important to ensure stable agricultural production, and various fungicides are used for this purpose. However, fungi become resistant to fungicides over years, and thus novel fungicides that are effective not only to drug-sensitive fungi but also to drug-resistant fungi are demanded.

Regarding 1,3,5,6-substituted-2-pyridone compounds, for example, 1,3,5,6-substituted-2-pyridone compounds having an aryl group or a heteroaryl group at the 3-position are disclosed as GABA alpha 2/3 ligands (see, for example, WO 98/55480). Further, 1,3,5,6-substituted-2-pyridone compounds having a carboxyl group at the 3-position are disclosed as drugs for treating bacterial infections (see, for example, European Patent No. 0308020).

CITATION LIST

Patent Literature

Patent Literature 1: WO 98/55480
Patent Literature 2: European Patent No. 0308020

SUMMARY OF INVENTION

Technical Problem

The compounds described in WO 98/55480 and European Patent No. 0308020 are for medicinal use and do not pertain to the field of art to which the agricultural and horticultural fungicides of the present invention belong.

An object of the present invention is to provide novel compounds that are effective as agricultural and horticultural fungicides.

Solution to Problem

To achieve the above object, the present inventors carried out extensive studies on 1,3,5,6-substituted-2-pyridone compounds and 1,5,6-substituted-2-pyridone compounds. As a result, the present inventors have found that novel compounds synthesized by introducing an ortho-substituted aryl or heteroaryl group to the 5-position of the 2-pyridone skeleton have superior activity in preventing and treating plant diseases. The present invention has been completed based on the finding.

Specifically, the present invention pertains to the following.

[1]

A compound represented by the formula (1), or a salt thereof:

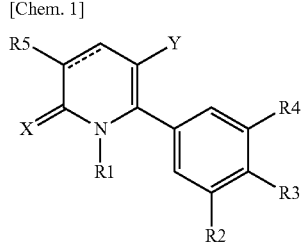

[Chem. 1]

wherein R1 represents:
a hydroxy group,
a cyano group,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C3-C8 cycloalkoxy group optionally substituted with substituent(s) A,
a C2-C6 alkenyloxy group optionally substituted with substituent(s) A,
a C2-C6 haloalkenyloxy group,
a C3-C6 alkynyloxy group optionally substituted with substituent(s) A,
a C3-C6 haloalkynyloxy group, or
RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group);

R2, R3 and R4 are independent of one another and each represent:
a hydrogen atom,
a halogen atom,
a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C, a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
an aryloxy group optionally substituted with 0 to 5 substituents D,
a heteroaryloxy group optionally substituted with 0 to 2 substituents D,
an aralkyloxy group optionally substituted with 0 to 5 substituents D,
Rx1C(=O)— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)),
Rx1C(=O)O— (wherein Rx1 is the same as defined hereinabove),
a 3 to 6-membered ring group containing 1 to 2 oxygen atoms, Rc-L- (wherein Rc represents a C1-C6 alkyl group or a C1-C6 haloalkyl group, and L represents S, SO or $SO_2$),
RaRbN— (wherein Ra and Rb are the same as defined hereinabove), or
Rx2C(=O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), and Rx3 represents a hydrogen atom, a C1-C6 alkyl group optionally substituted with substituent(s) B, a C1-C6 haloalkyl group or a C3-C8 cycloalkyl group);
R5 represents:
a hydrogen atom,
a halogen atom,
a cyano group,
a nitro group,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C3-C8 cycloalkoxy group optionally substituted with substituent(s) A,
a C2-C6 alkenyloxy group optionally substituted with substituent(s) A,
a C2-C6 haloalkenyloxy group,
a C3-C6 alkynyloxy group optionally substituted with substituent(s) A,
a C3-C6 haloalkynyloxy group,
Rc-L- (wherein Rc and L are the same as defined hereinabove),
RaRbN— (wherein Ra and Rb are the same as defined hereinabove), or R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);
X represents an oxygen atom or a sulfur atom;
Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group,
the phenyl group is substituted with R6 at an ortho position and is further optionally substituted with 0 to 4 substituents R7 independent of one another,
the pyridyl group, the pyrazinyl group, the pyrimidinyl group, the pyridazinyl group, the triazinyl group or the tetrazinyl group is substituted with R6 at an ortho position and is further optionally substituted with 0 to 3 substituents R7 independent of one another,
the thienyl group, the thiazolyl group, the isothiazolyl group or the thiadiazolyl group is substituted with R6 at an ortho position and is further optionally substituted with 0 to 2 substituents R7 independent of one another;
R6 represents:
a halogen atom,
a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
an aryloxy group optionally substituted with 0 to 5 substituents D,
a heteroaryloxy group optionally substituted with 0 to 2 substituents D,
an aralkyloxy group optionally substituted with 0 to 5 substituents D,
Rx1C(=O)— (wherein Rx1 is the same as defined hereinabove),
Rx1C(=O)O— (wherein Rx1 is the same as defined hereinabove),
a 3 to 6-membered ring group containing 1 to 2 oxygen atoms,
Rc-L- (wherein Rc and L are the same as defined hereinabove),
RaRbN— (wherein Ra and Rb are the same as defined hereinabove), or
Rx2C(=O)N(Rx3)- (wherein Rx2 and Rx3 are the same as defined hereinabove);
R7 is defined the same as R6 described hereinabove;

the bond including the broken line represents a double bond or a single bond;

the substituent(s) A is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove);

the substituent(s) B is at least one selected from the group consisting of cyano group, C1-C6 alkoxy groups, C1-C6 haloalkoxy groups and C3-C8 cycloalkoxy groups;

the substituent(s) C is at least one selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— (wherein Ra and Rb are the same as defined hereinabove), Rc-L- (wherein Rc and L are the same as defined hereinabove), RdC(=O)— (wherein Rd is defined the same as Rx1 described hereinabove) and 3 to 6-membered ring groups containing 1 to 2 oxygen atoms; and the substituent(s) D is at least one selected from the group consisting of halogen atoms, hydroxy group, cyano group, nitro group, C1-C6 alkyl groups optionally substituted with substituent(s) B, C1-C6 haloalkyl groups, C3-C8 cycloalkyl groups, C1-C6 alkoxy groups, C1-C6 haloalkoxy groups and C3-C8 cycloalkoxy groups.

[2]
The compound or a salt thereof described in [1], wherein R1 represents:
a C1-C6 alkyl group optionally substituted with substituent(s) A,
a C1-C6 haloalkyl group,
a C2-C6 alkenyl group optionally substituted with substituent(s) A, or
a C2-C6 haloalkenyl group;
R2, R3 and R4 are independent of one another and each represent:
a hydrogen atom,
a halogen atom,
a hydroxy group,
a cyano group,
a C1-C6 alkyl group optionally substituted with substituent(s) C,
a C1-C6 haloalkyl group,
a C2-C6 alkenyl group optionally substituted with substituent(s) C,
a C2-C6 alkynyl group optionally substituted with substituent(s) C,
a C1-C6 alkoxy group optionally substituted with substituent(s) C,
a C1-C6 haloalkoxy group,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
an aralkyloxy group optionally substituted with 0 to 5 substituents D, or
Rx1C(=O)O— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group));

R5 represents:
a hydrogen atom,
a halogen atom,
a C1-C6 alkyl group optionally substituted with substituent(s) A,
a C1-C6 haloalkyl group,
a C2-C6 alkenyl group optionally substituted with substituent(s) A,
a C2-C6 alkynyl group optionally substituted with substituent(s) A,
a C1-C6 alkoxy group optionally substituted with substituent(s) A,
a C2-C6 alkenyloxy group optionally substituted with substituent(s) A,
a C3-C6 alkynyloxy group optionally substituted with substituent(s) A, or
R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);

Y represents a phenyl group or a pyridyl group,
the phenyl group is substituted with R6 at an ortho position and is further optionally substituted with 0 to 4 substituents R7 independent of one another,
the pyridyl group is substituted with R6 at an ortho position and is further optionally substituted with 0 to 3 substituents R7 independent of one another;

R6 represents:
a halogen atom,
a hydroxy group,
a cyano group,
a C1-C6 alkyl group optionally substituted with substituent(s) C,
a C1-C6 alkoxy group optionally substituted with substituent(s) C,
a C2-C6 alkenyloxy group optionally substituted with substituent(s) C, or
a C3-C6 alkynyloxy group optionally substituted with substituent(s) C; and R7 represents:
a halogen atom,
a hydroxy group,
a cyano group,
a C1-C6 alkyl group optionally substituted with substituent(s) C,
a C1-C6 haloalkyl group,
a C2-C6 alkenyl group optionally substituted with substituent(s) C,
a C2-C6 alkynyl group optionally substituted with substituent(s) C,
a C1-C6 alkoxy group optionally substituted with substituent(s) C,
a C1-C6 haloalkoxy group,
a C2-C6 alkenyloxy group optionally substituted with substituent(s) C,
a C3-C6 alkynyloxy group optionally substituted with substituent(s) C,
a heteroaryloxy group optionally substituted with 0 to 2 substituents D,
an aralkyloxy group optionally substituted with 0 to 5 substituents D, Rx1C(=O)— (wherein Rx1 is the same as defined hereinabove), or Rx1C(=O)O— (wherein Rx1 is the same as defined hereinabove).

[3]

The compound or a salt thereof described in [2], wherein

R1 represents:
a C1-C6 alkyl group optionally substituted with substituent(s) A,
a C1-C6 haloalkyl group, or
a C2-C6 haloalkenyl group;

R2, R3 and R4 are independent of one another and each represent:
a hydrogen atom,
a halogen atom,
a hydroxy group,
a cyano group,
a C1-C6 alkyl group optionally substituted with substituent(s) C,
a C1-C6 haloalkyl group,
a C2-C6 alkynyl group optionally substituted with substituent(s) C,
a C1-C6 alkoxy group optionally substituted with substituent(s) C,
a C1-C6 haloalkoxy group,
a C2-C6 alkenyloxy group optionally substituted with substituent(s) C,
a C3-C6 alkynyloxy group optionally substituted with substituent(s) C,
an aralkyloxy group optionally substituted with 0 to 5 substituents D, or
Rx1C(=O)O— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group));

R5 represents:
a hydrogen atom,
a halogen atom,
a C1-C6 alkyl group optionally substituted with substituent(s) A,
a C1-C6 haloalkyl group,
a C2-C6 alkynyl group optionally substituted with substituent(s) A,
a C1-C6 alkoxy group optionally substituted with substituent(s) A, or
R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);

R6 represents:
a halogen atom,
a cyano group,
a C1-C6 alkyl group optionally substituted with substituent(s) C, or
a C1-C6 alkoxy group optionally substituted with substituent(s) C; and R7 represents:
a halogen atom,
a hydroxy group,
a C1-C6 alkyl group optionally substituted with substituent(s) C,
a C1-C6 haloalkyl group,
a C1-C6 alkoxy group optionally substituted with substituent(s) C,
a C1-C6 haloalkoxy group,
a C3-C6 alkynyloxy group optionally substituted with substituent(s) C,
a heteroaryloxy group optionally substituted with 0 to 2 substituents D,
an aralkyloxy group optionally substituted with 0 to 5 substituents D,
Rx1C(=O)— (wherein Rx1 is the same as defined hereinabove), or
Rx1C(=O)O— (wherein Rx1 is the same as defined hereinabove).

[4]

A compound or a salt thereof represented by the formula (2):

[Chem. 2]

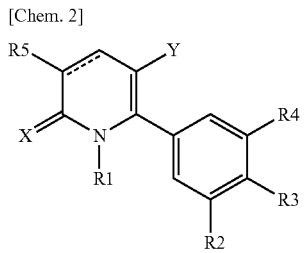

wherein R2, R3 and R4 are independent of one another and each represent:
a hydrogen atom,
a halogen atom,
a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
an aryloxy group optionally substituted with 0 to 5 substituents D,
heteroaryloxy group optionally substituted with 0 to 2 substituents D, an aralkyloxy group optionally substituted with 0 to 5 substituents D, Rx1C(=O)— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group)), Rx1C(=O)O— (wherein Rx1 is the same as defined hereinabove), a 3 to 6-membered ring group containing 1 to 2 oxygen atoms, Rc-L- (wherein Rc represents a C1-C6 alkyl group or a C1-C6 haloalkyl group, and L represents S, SO or $SO_2$), RaRbN— (wherein Ra and Rb are the same as defined hereinabove), or Rx2C(=O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), and Rx3 represents a hydrogen atom, a C1-C6 alkyl group optionally substituted with substituent(s) B, a C1-C6 haloalkyl group or a C3-C8 cycloalkyl group);

R5 represents:
a hydrogen atom,
a halogen atom,
a cyano group,
a nitro group,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C2-C6 alkenyloxy group optionally substituted with substituent(s) A,
a C2-C6 haloalkenyloxy group,
a C3-C6 alkynyloxy group optionally substituted with substituent(s) A,
a C3-C6 haloalkynyloxy group,
Rc-L- (wherein Rc and L are the same as defined hereinabove),
RaRbN— (wherein Ra and Rb are the same as defined hereinabove), or
R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);

X represents an oxygen atom or a sulfur atom;

Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, the phenyl group is substituted with R6 at an ortho position and is further optionally substituted with 0 to 4 substituents R7 independent of one another, the pyridyl group, the pyrazinyl group, the pyrimidinyl group, the pyridazinyl group, the triazinyl group or the tetrazinyl group is substituted with R6 at an ortho position and is further optionally substituted with 0 to 3 substituents R7 independent of one another, the thienyl group, the thiazolyl group, the isothiazolyl group or the thiadiazolyl group is substituted with R6 at an ortho position and is further optionally substituted with 0 to 2 substituents R7 independent of one another;

R6 represents:
a halogen atom,
a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
an aryloxy group optionally substituted with 0 to 5 substituents D,
a heteroaryloxy group optionally substituted with 0 to 2 substituents D,
an aralkyloxy group optionally substituted with 0 to 5 substituents D,
Rx1C(=O)— (wherein Rx1 is the same as defined hereinabove),
Rx1C(=O)O— (wherein Rx1 is the same as defined hereinabove),
a 3 to 6-membered ring group containing 1 to 2 oxygen atoms,
Rc-L- (wherein Rc and L are the same as defined hereinabove),
RaRbN— (wherein Ra and Rb are the same as defined hereinabove), or
Rx2C(=O)N(Rx3)- (wherein Rx2 and Rx3 are the same as defined hereinabove);

R7 is defined the same as R6 described hereinabove; the substituent(s) A is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove);

the substituent(s) B is at least one selected from the group consisting of cyano group, C1-C6 alkoxy groups, C1-C6 haloalkoxy groups and C3-C8 cycloalkoxy groups;

the substituent(s) C is at least one selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— (wherein Ra and Rb are the same as defined hereinabove), Rc-L- (wherein Rc and L are the same as defined hereinabove), RdC(=O)— (wherein Rd is defined the same as Rx1 described hereinabove) and 3 to 6-membered ring groups containing 1 to 2 oxygen atoms; and the substituent(s) D is at least one selected from the group consisting of halogen atoms, hydroxy group, cyano group, nitro group, C1-C6 alkyl groups optionally substituted with substituent(s) B, C1-C6 haloalkyl groups, C3-C8 cycloalkyl groups, C1-C6 alkoxy groups, C1-C6 haloalkoxy groups and C3-C8 cycloalkoxy groups.

[5]

The compound or a salt thereof described in any one of [1] to [3], wherein R1 represents a C1-C6 alkyl group optionally substituted with substituent(s) A, or a C1-C6 haloalkyl group.

[6]

The compound or a salt thereof described in any one of [1] to [3], wherein R1 is a methyl group, an ethyl group, a propyl group, a 2,2-difluoroethyl group, a 2,2,2-trifluoroethyl group or a 2,2-difluorovinyl group.

[7]

The compound or a salt thereof described in any one of [1] to [3], wherein R1 is a methyl group, an ethyl group, a 2,2-difluoroethyl group or a 2,2,2-trifluoroethyl group.

[8]

The compound or a salt thereof described in any one of [1] to [3] and [5] to [7], wherein R2, R3 and R4 are independent of one another and each represent a hydrogen atom, a halogen atom, a hydroxy group, a cyano group, a C1-C6 alkyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C2-C6 alkenyloxy group optionally substituted with substituent(s) C, a C3-C6 alkynyloxy group optionally substituted with substituent(s) C, or Rx1C(=O)O— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group)).

[9]

The compound or a salt thereof described in any one of [1] to [3] and [5] to [7], wherein R2, R3 and R4 are independent of one another and each represent a hydrogen atom, a fluorine atom, a chlorine atom, a bromine atom, a hydroxy group, a cyano group, a methyl group, a trifluoromethyl group, an ethynyl group, a methoxy group, a methoxymethoxy group, a cyanomethoxy group, an ethoxy group, a methoxyethoxy group, a propyloxy group, a methoxypropyloxy group, an isopropyloxy group, a butoxy group, a 2,2-difluoroethoxy group, a 2,2,2-trifluoroethoxy group, an allyloxy group, a propargyloxy group, a benzyloxy group or an acetyloxy group.

[10]

The compound or a salt thereof described in any one of [1] to [3] and [5] to [7], wherein R2, R3 and R4 are independent of one another and each represent a hydrogen atom, a fluorine atom, a chlorine atom, a bromine atom, a hydroxy group, a cyano group, a methyl group, an ethynyl group, a methoxy group, a methoxymethoxy group, a cyanomethoxy group, an ethoxy group, a methoxyethoxy group, a methoxypropyloxy group, a 2,2-difluoroethoxy group, a 2,2,2-trifluoroethoxy group, an allyloxy group, a propargyloxy group or an acetyloxy group.

[11]

The compound or a salt thereof described in any one of [1] to [3] and [5] to [10], wherein R5 represents a hydrogen atom, a halogen atom, a C1-C6 alkyl group optionally substituted with substituent(s) A, or a C1-C6 alkoxy group optionally substituted with substituent(s) A.

[12]

The compound or a salt thereof described in any one of [1] to [3] and [5] to [10], wherein R5 represents a hydrogen atom, a fluorine atom, a chlorine atom, a bromine atom, an iodine atom, a methyl group, a trifluoromethyl group, an ethynyl group, a methoxy group or an acetyl group.

[13]

The compound or a salt thereof described in any one of [1] to [3] and [5] to [10], wherein R5 represents a hydrogen atom, a chlorine atom, a bromine atom, an iodine atom, a methyl group, an ethynyl group or a methoxy group.

[14]

The compound or a salt thereof described in any one of [1] to [3] and [5] to [13], wherein R6 represents a halogen atom or a C1-C6 alkyl group optionally substituted with substituent(s) C.

[15]

The compound or a salt thereof described in any one of [1] to [3] and [5] to [13], wherein R6 represents a fluorine atom, a chlorine atom, a bromine atom, an iodine atom, a cyano group, a methyl group or a methoxy group.

[16]

The compound or a salt thereof described in any one of [1] to [3] and [5] to [13], wherein R6 represents a fluorine atom, a chlorine atom, a bromine atom, an iodine atom or a methyl group.

[17]

The compound or a salt thereof described in any one of [1] to [3] and [5] to [16], wherein R7 represents a halogen atom, a hydroxy group, a C1-C6 alkyl group optionally substituted with substituent(s) C, a C1-C6 alkoxy group optionally substituted with substituent(s) C, a C1-C6 haloalkoxy group, a C3-C6 alkynyloxy group optionally substituted with substituent(s) C, or Rx1C(=O)O— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group)).

[18]

The compound or a salt thereof described in any one of [1] to [3] and [5] to [16], wherein R7 represents a fluorine atom, a chlorine atom, a bromine atom, a hydroxy group, a methyl group, a trifluoromethyl group, a methoxy group, a cyanomethoxy group, a methoxymethoxy group, a (methylthio)methoxy group, a (methylsulfonyl)methoxy group, a (1,3-dioxolan-2-yl)methoxy group, an ethoxy group, a methoxyethoxy group, a (1,3-dioxan-2-yl)ethoxy group, a propyloxy group, an iso-propyloxy group, a 2,2-difluoroethoxy group, a 2,2,2-trifluoroethoxy group, a propargyloxy group, a (3-chloro-5-(trifluoromethyl)pyridin-2-yl)oxy group, a benzyloxy group, an acetyl group, an acetyloxy group, a methoxycarbonyloxy group or an ethoxycarbonyloxy group.

[19]

The compound or a salt thereof described in any one of [1] to [3] and [5] to [16], wherein R7 represents a fluorine atom, a chlorine atom, a bromine atom, a hydroxy group, a methyl group, a methoxy group, a cyanomethoxy group, a methoxymethoxy group, a (methylthio)methoxy group, a (methylsulfonyl)methoxy group, an ethoxy group, a methoxyethoxy group, a 2,2-difluoroethoxy group, a 2,2,2-trifluoroethoxy group, a propargyloxy group, an acetyloxy group, a methoxycarbonyloxy group or an ethoxycarbonyloxy group.

[20]

The compound or a salt thereof described in any one of [1] to [3] and [5] to [19], wherein Y represents a phenyl group.

[21]

The compound or a salt thereof described in any one of [1] to [3] and [5] to [19], wherein Y represents a pyridyl group.

[22]

The compound or a salt thereof described in any one of [1] to [3] and [5] to [21], wherein X represents an oxygen atom.

[23]

The compound or a salt thereof described in any one of [1] to [3] and [5] to [21], wherein X represents a sulfur atom.

[24]

The compound or a salt thereof described in any one of [1] to [3] and [5] to [23], wherein the bond including the broken line is a double bond.

[25]

The compound or a salt thereof described in any one of [1] to [3] and [5] to [23], wherein the bond including the broken line is a single bond.

[26]

An agricultural and horticultural pest control agent including the compound or a salt thereof described in any one of [1] to [3] and [5] to [25] as an active ingredient.

[27]

An agricultural and horticultural fungicide including the compound or a salt thereof described in any one of [1] to [3] and [5] to [25], as an active ingredient.

[28]

A method for preventing and/or treating a plant disease, including applying the agricultural and horticultural pest control agent described in [26] to a plant, a plant seed or a soil for plant cultivation.

[29]

A method for preventing and/or treating a plant disease, including applying the agricultural and horticultural fungicide described in [27] to a plant, a plant seed or a soil for plant cultivation.

[30]

Use of the compound described in any one of [1] to [3] and [5] to [25] as an agricultural and horticultural pest control agent.

[31]

Use of the compound described in any one of [1] to [3] and [5] to [25] as an agricultural and horticultural fungicide.

Advantageous Effects of Invention

The novel compounds provided according to the present invention are effective as agricultural and horticultural fungicides.

DESCRIPTION OF EMBODIMENTS

Hereinbelow, embodiments of the present invention will be described in detail.

The terms used in the claims and the description have definitions generally used in the technical field unless otherwise mentioned.

The abbreviations in the specification are described below.

DMF: N,N-dimethylformamide, THF: tetrahydrofuran, Me: methyl group, Et: ethyl group, Pr: propyl group, Bu: butyl group, Ac: acetyl group, Ph: phenyl group, Py: pyridyl group, i: iso, sec: secondary, t: tertiary, =: double bond, and ≡: triple bond. In the columns in the tables, Pr and Bu without prefix are normal.

Hereinbelow, the definitions of the terms used in the specification will be described.

The expression Cx-Cy means that the number of carbon atoms that are possessed ranges from x to y. Here, x and y are integers and are understood to disclose all individual integers between x and y inclusive. For example, C1-C6 means that the number of carbon atoms that are possessed is 1, 2, 3, 4, 5 or 6; C1-C5 means that the number of carbon atoms that are possessed is 1, 2, 3, 4 or 5; C1-C3 means that the number of carbon atoms that are possessed is 1, 2 or 3; C2-C6 means that the number of carbon atoms that are possessed is 2, 3, 4, 5 or 6; C3-C8 means that the number of carbon atoms that are possessed is 3, 4, 5, 6, 7 or 8; and C3-C6 means that the number of carbon atoms that are possessed is 3, 4, 5 or 6.

The phrase "optionally substituted" means that the group, compound or the like may be substituted or unsubstituted. When this phrase is used without explicit indication of the number of substituents, the number of substituents is one.

The C1-C6 alkyl group may be linear or branched. Specific examples thereof include methyl group, ethyl group, propyl group, isopropyl group, butyl group, isobutyl group, sec-butyl group, t-butyl group, pentyl group, isopentyl group, 1-methylbutyl group, 2-methylbutyl group, neopentyl group, 1-ethylpropyl group, 1,2-dimethylpropyl group, hexyl group, 1-methylpentyl group, 2-methylpentyl group, 3-methylpentyl group, 4-methylpentyl group, 1,1-dimethylbutyl group, 2,2-dimethylbutyl group, 3,3-dimethylbutyl group, 1,2-dimethylbutyl group, 1,3-dimethylbutyl group, 2,3-dimethylbutyl group, 2-ethylbutyl group, 1-isopropylpropyl group, 1,1,2-trimethylpropyl group, 1,2,2-trimethylpropyl group, and the like.

Specific examples of the halogen atoms include fluorine atom, chlorine atom, bromine atom, iodine atom, and the like.

The C1-C6 haloalkyl group is a group resulting from the substitution of the above C1-C6 alkyl group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C1-C6 haloalkyl groups include monofluoromethyl group, difluoromethyl group, trifluoromethyl group, monochloromethyl group, monobromomethyl group, monoiodomethyl group, chlorodifluoromethyl group, bromodifluoromethyl group, 1-fluoroethyl group, 2-fluoroethyl group, 1,1-difluoroethyl group, 2,2-difluoroethyl group, 2,2,2-trifluoroethyl group, 1,1,2,2-tetrafluoroethyl group, pentafluoroethyl group, 2,2,2-trichloroethyl group, 3,3-difluoropropyl group, 3,3,3-trifluoropropyl group, heptafluoropropyl group, heptafluoroisopropyl group, 2,2,2-trifluoro-1-(trifluoromethyl)ethyl group, nonafluorobutyl group, nonafluoro-sec-butyl group, 3,3,4,4,5,5,5-heptafluoropentyl group, undecafluoropentyl group, tridecafluorohexyl group, and the like.

Specific examples of the C3-C8 cycloalkyl groups include cyclopropyl group, cyclobutyl group, cyclopentyl group, cyclohexyl group, cycloheptyl group, cyclooctyl group, and the like.

The C2-C6 alkenyl group is an unsaturated hydrocarbon group which has one, or two or more double bonds and is linear or branched. When the group has geometric isomeric forms, the group may be E-isomer, Z-isomer or a mixture containing E-isomer and Z-isomer in any proportions without limitation as long as the number of carbon atoms indicated is satisfied. Specific examples of the C2-C6 alkenyl groups include vinyl group, 1-propenyl group, allyl group, 1-butenyl group, 2-butenyl group, 3-butenyl group, 1-pentenyl group, 2-pentenyl group, 3-pentenyl group, 4-pentenyl group, 3-methyl-2-butenyl group, 1-hexenyl group, 2-hexenyl group, 3-hexenyl group, 4-hexenyl group, 5-hexenyl group, 4-methyl-3-pentenyl group, 3-methyl-2-pentenyl group, and the like.

The C2-C6 haloalkenyl group is a group resulting from the substitution of the above C2-C6 alkenyl group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C2-C6 haloalkenyl groups include 2-fluorovinyl group, 2,2-difluorovinyl group, 2,2-dichlorovinyl group, 3-fluoroallyl group, 3,3-difluoroallyl group, 3,3-dichloroallyl group, 4,4-difluoro-3-butenyl group, 5,5-difluoro-4-pentenyl group, 6,6-difluoro-5-hexenyl group, and the like.

The C2-C6 alkynyl group is an unsaturated hydrocarbon group which has one, or two or more triple bonds and is linear or branched. Specific examples of the C2-C6 alkynyl groups include ethynyl group, 1-propynyl group, propargyl group, 1-butynyl group, 2-butynyl group, 3-butynyl group, 1-pentynyl group, 2-pentynyl group, 3-pentynyl group, 4-pentynyl group, 1,1-dimethyl-2-propynyl group, 1-hexynyl group, 2-hexynyl group, 3-hexynyl group, 4-hexynyl group, 5-hexynyl group, and the like.

The C2-C6 haloalkynyl group is a group resulting from the substitution of the above C2-C6 alkynyl group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C2-C6 haloalkynyl groups include 2-fluoroethynyl group, 2-chloroethynyl group, 2-bromoethynyl group, 2-iodoethynyl group, 3,3-difluoro-1-propynyl group, 3-chloro-3,3-difluoro-1-propynyl group, 3-bromo-3,3-difluoro-1-propynyl group, 3,3,3-trifluoro-1-propynyl group, 4,4-difluoro-1-butynyl group, 4,4-difluoro-2-butynyl group, 4-chloro-4,4-difluoro-1-butynyl group, 4-chloro-4,4-difluoro-2-butynyl group, 4-bromo-4,4-difluoro-1-butynyl group, 4-bromo-4,4-difluoro-2-butynyl group, 4,4,4-trifluoro-1-butynyl group, 4,4,4-trifluoro-2-butynyl group, 5,5-difluoro-3-pentynyl group, 5-chloro-5,5-difluoro-3-pentynyl group, 5-bromo-5,5-difluoro-3-pentynyl group, 5,5,5-trifluoro-3-pentynyl group, 6,6-difluoro-4-hexynyl group, 6-chloro-6,6-difluoro-4-hexynyl group, 6-bromo-6,6-difluoro-4-hexynyl group, 6,6,6-trifluoro-4-hexynyl group, and the like.

The C1-C6 alkoxy group is a combination of the C1-C6 alkyl group described hereinabove and an oxygen atom as a bonding site. Specific examples of the C1-C6 alkoxy groups include methoxy group, ethoxy group, propyloxy group, isopropyloxy group, butoxy group, isobutoxy group, sec-butoxy group, t-butoxy group, pentyloxy group, isopentyloxy group, 1-methylbutoxy group, 2-methylbutoxy group, neopentyloxy group, 1-ethylpropyloxy group, 1,2-dimethylpropyloxy group, hexyloxy group, 1-methylpentyloxy group, 2-methylpentyloxy group, 3-methylpentyloxy group, 4-methylpentyloxy group, 1,1-dimethylbutoxy group, 2,2-dimethylbutoxy group, 3,3-dimethylbutoxy group, 1,2-dimethylbutoxy group, 1,3-dimethylbutoxy group, 2,3-dimethylbutoxy group, 2-ethylbutoxy group, 1-isopropylpropyloxy group, 1,1,2-trimethylpropyloxy group, 1,2,2-trimethylpropyloxy group, and the like.

The C1-C6 haloalkoxy group is a group resulting from the substitution of the above C1-C6 alkoxy group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C1-C6 haloalkoxy groups include difluoromethoxy group, trifluoromethoxy group, chlorodifluoromethoxy group, bromodifluoromethoxy group, 2-fluoroethoxy group, 2,2-difluoroethoxy group, 2,2,2-trifluoroethoxy group, 1,1,2,2-tetrafluoroethoxy group, pentafluoroethoxy group, 2,2,2-trichloroethoxy group, 3,3-difluoropropyloxy group, 3,3,3-trifluoropropyloxy group, heptafluoropropyloxy group, heptafluoroisopropyloxy group, 2,2,2-trifluoro-1-(trifluoromethyl)-ethoxy group, nonafluorobutoxy group, nonafluoro-sec-butoxy group, 3,3,4,4,5,5,5-heptafluoropentyloxy group, undecafluoropentyloxy group, tridecafluorohexyloxy group, and the like.

The C3-C8 cycloalkoxy group is a combination of the C3-C8 cycloalkyl group described hereinabove and an oxygen atom as a bonding site. Specific examples of the C3-C8 cycloalkoxy groups include cyclopropyloxy group, cyclobutoxy group, cyclopentyloxy group, cyclohexyloxy group, cycloheptyloxy group, cyclooctyloxy group, and the like.

The C2-C6 alkenyloxy group is a combination of the C2-C6 alkenyl group described hereinabove and an oxygen atom as a bonding site. When the group has geometric isomeric forms, the group may be E-isomer, Z-isomer or a mixture containing E-isomer and Z-isomer in any proportions without limitation as long as the number of carbon atoms indicated is satisfied. Specific examples of the C2-C6 alkenyloxy groups include vinyloxy group, 1-propenyloxy group, allyloxy group, 1-butenyloxy group, 2-butenyloxy group, 3-butenyloxy group, 1-pentenyloxy group, 2-pentenyloxy group, 3-pentenyloxy group, 4-pentenyloxy group, 3-methyl-2-butenyloxy group, 1-hexenyloxy group, 2-hexenyloxy group, 3-hexenyloxy group, 4-hexenyloxy group, 5-hexenyloxy group, 3-methyl-2-pentenyloxy group, 4-methyl-3-pentenyloxy group, and the like.

The C2-C6 haloalkenyloxy group is a group resulting from the substitution of the above C2-C6 alkenyloxy group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C2-C6 haloalkenyloxy groups include 2-fluorovinyloxy group, 2,2-difluorovinyloxy group, 2,2-dichlorovinyloxy group, 3-fluoroallyloxy group, 3,3-difluoroallyloxy group, 3,3-dichloroallyloxy group, 4,4-difluoro-3-butenyloxy group, 5,5-difluoro-4-pentenyloxy group, 6,6-difluoro-5-hexenyloxy group, and the like.

The C3-C6 alkynyloxy group is a combination of any C3-C6 alkynyl group belonging to the C2-C6 alkynyl groups described hereinabove, and an oxygen atom as a bonding site. Specific examples of the C3-C6 alkynyloxy groups include propargyloxy group, 2-butynyloxy group, 3-butynyloxy group, 2-pentynyloxy group, 3-pentynyloxy group, 4-pentynyloxy group, 1,1-dimethyl-2-propynyloxy group, 2-hexynyloxy group, 3-hexynyloxy group, 4-hexynyloxy group, 5-hexynyloxy group, and the like.

The C3-C6 haloalkynyloxy group is a group resulting from the substitution of the above C3-C6 alkynyloxy group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C3-C6 haloalkynyloxy groups include 1,1-difluoro-2-propynyloxy group, 4,4-difluoro-2-butynyloxy group, 4-chloro-4,4-difluoro-2-butynyloxy group, 4-bromo-4,4-difluoro-2-butynyloxy group, 4,4,4-trifluoro-2-butynyloxy group, 5,5-difluoro-3-pentynyloxy group, 5-chloro-5,5-difluoro-3-pentynyloxy group, 5-bromo-5,5-difluoro-3-pentynyloxy group, 5,5,5-trifluoro-3-pentynyloxy group, 6,6-difluoro-4-hexynyloxy group, 6-chloro-6,6-difluoro-4-hexynyloxy group, 6-bromo-6,6-difluoro-4-hexynyloxy group, 6,6,6-trifluoro-4-hexynyloxy group, and the like.

The aryloxy group is a combination of an aryl group such as a phenyl group or a naphthyl group, and an oxygen atom as a bonding site. Specific examples of the aryloxy groups include phenoxy group, naphthyloxy group, and the like.

The heteroaryloxy group is a combination of a heteroaryl group such as pyridyl group, pyridazinyl group, pyrimidinyl group, pyrazinyl group, triazinyl group, tetrazinyl group, thienyl group, thiazolyl group, isothiazolyl group, thiadiazolyl group, furyl group, pyrrolyl group, imidazolyl group, pyrazolyl group, oxazolyl group, isoxazolyl group, triazolyl group, oxadiazolyl group, thiadiazolyl group or tetrazolyl group, and an oxygen atom as a bonding site. Specific examples of the heteroaryloxy groups include pyridyloxy group, pyridazinyloxy group, pyrimidinyloxy group, pyrazinyloxy group, triazinyloxy group, tetrazinyloxy group, thienyloxy group, thiazolyloxy group, isothiazolyloxy group, thiadiazolyloxy group, furyloxy group, pyrrolyloxy group, imidazolyloxy group, pyrazolyloxy group, oxazolyloxy group, isoxazolyloxy group, triazolyloxy group, oxadiazolyloxy group, thiadiazolyloxy group, tetrazolyloxy group, and the like.

The aralkyloxy group is a combination of an aralkyl group resulting from the substitution of a C1-C3 alkyl group with an aryl group such as phenyl group or naphthyl group in place of any hydrogen atom(s), and an oxygen atom as a bonding site. Specific examples of the aralkyloxy groups include benzyloxy group, phenethyloxy group, phenylpropyloxy group, naphthalenylmethoxy group, naphthalenylethoxy group, naphthalenylpropyloxy group, and the like.

Specific examples of the 3 to 6-membered ring groups containing 1 to 2 oxygen atoms include 1,2-epoxyethanyl group, oxetanyl group, oxolanyl group, oxanyl group, 1,3-dioxolanyl group, 1,3-dioxanyl group, 1,4-dioxanyl group, and the like.

The C2-C6 alkoxyalkoxy group is a group resulting from the substitution of any C1-C5 alkoxy group belonging to the C1-C6 alkoxy groups described hereinabove with one, or two or more C1-C5 alkoxy groups in place of any hydrogen atom(s). This alkoxyalkoxy group is not particularly limited as long as the total number of carbon atoms is as indicated. Specific examples of the C2-C6 alkoxyalkoxy groups include methoxymethoxy group, ethoxymethoxy group, propyloxymethoxy group, isopropyloxymethoxy group, methoxyethoxy group, ethoxyethoxy group, propyloxyethoxy group, isopropyloxyethoxy group, methoxypropyloxy group, ethoxypropyloxy group, propyloxypropyloxy group, isopropyloxypropyloxy group, and the like.

The pyridone compounds of the present invention include compounds represented by the following formula (1), and salts thereof (hereinafter, these compounds and salts are also written as the "inventive compounds").

[Chem. 3]

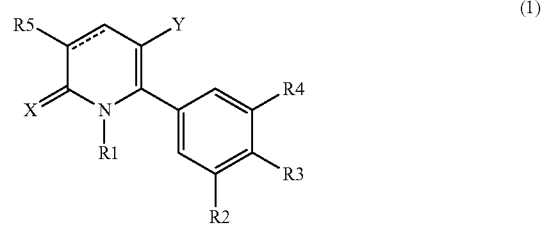

(1)

Hereinbelow, the formula (1) will be described.

In the formula (1), R1 represents a hydroxy group, a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group).

In particular, R1 is preferably a C1-C6 alkyl group optionally substituted with substituent(s) A, a C1-C6 haloalkyl group, a C2-C6 alkenyl group optionally substituted with substituent(s) A, or a C2-C6 haloalkenyl group;

R1 is more preferably a C1-C6 alkyl group optionally substituted with substituent(s) A, a C1-C6 haloalkyl group, or a C2-C6 haloalkenyl group; and R1 is particularly preferably a C1-C6 alkyl group optionally substituted with substituent(s) A, or a C1-C6 haloalkyl group.

In the formula (1), R1 may represent a hydroxy group or a cyano group.

In the "C1-C6 alkyl group optionally substituted with substituent(s) A" represented by R1 in the formula (1), the C1-C6 alkyl group is the same as defined hereinabove, and is preferably a methyl group, an ethyl group or a propyl group, and more preferably a methyl group or an ethyl group. When this group has substituent(s) A, the C1-C6 alkyl group is optionally substituted with substituent(s) A in place of any hydrogen atom(s).

The "C1-C6 haloalkyl group" represented by R1 in the formula (1) is the same as defined hereinabove, and is preferably a 2-fluoroethyl group, a 2,2-difluoroethyl group, a 2,2,2-trifluoroethyl group, a 3,3-difluoropropyl group or a 3,3,3-trifluoropropyl group, and more preferably a 2-fluoroethyl group, a 2,2-difluoroethyl group or a 2,2,2-trifluoroethyl group.

In the "C3-C8 cycloalkyl group optionally substituted with substituent(s) A" represented by R1 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) A, the C3-C8 cycloalkyl group is appropriately substituted with substituent(s) A in place of any hydrogen atom(s).

In the "C2-C6 alkenyl group optionally substituted with substituent(s) A" represented by R1 in the formula (1), the C2-C6 alkenyl group is the same as defined hereinabove, and is preferably a vinyl group, a 1-propenyl group or an allyl group, and more preferably a vinyl group or an allyl group. When this group has substituent(s) A, the C2-C6 alkenyl group is optionally substituted with substituent(s) A in place of any hydrogen atom(s).

The "C2-C6 haloalkenyl group" represented by R1 in the formula (1) is the same as defined hereinabove, and is preferably a 2-fluorovinyl group, a 2,2-difluorovinyl group, a 3-fluoroallyl group or a 3,3-difluoroallyl group, and more preferably a 2-fluorovinyl group or a 2,2-difluorovinyl group.

In the "C2-C6 alkynyl group optionally substituted with substituent(s) A" represented by R1 in the formula (1), the C2-C6 alkynyl group is the same as defined hereinabove, and is preferably a propargyl group, a 2-butynyl group or a 3-butynyl group, and more preferably a propargyl group. When this group has substituent(s) A, the C2-C6 alkynyl group is optionally substituted with substituent(s) A in place of any hydrogen atom(s).

The "C2-C6 haloalkynyl group" represented by R1 in the formula (1) is the same as defined hereinabove, and is preferably a 4,4-difluoro-2-butynyl group, a 4-chloro-4,4-difluoro-2-butynyl group, a 4-bromo-4,4-difluoro-2-butynyl group or a 4,4,4-trifluoro-2-butynyl group, and more preferably a 4,4-difluoro-2-butynyl group or a 4,4,4-trifluoro-2-butynyl group.

In the "C1-C6 alkoxy group optionally substituted with substituent(s) A" represented by R1 in the formula (1), the C1-C6 alkoxy group is the same as defined hereinabove, and is preferably a methoxy group, an ethoxy group or a propyloxy group, and more preferably a methoxy group or an ethoxy group. When this group has substituent(s) A, the C1-C6 alkoxy group is optionally substituted with substituent(s) A in place of any hydrogen atom(s).

The "C1-C6 haloalkoxy group" represented by R1 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

In the "C3-C8 cycloalkoxy group optionally substituted with substituent(s) A" represented by R1 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) A, the C3-C8 cycloalkoxy group is optionally substituted with substituent(s) A in place of any hydrogen atom(s).

In the "C2-C6 alkenyloxy group optionally substituted with substituent(s) A" represented by R1 in the formula (1), the C2-C6 alkenyloxy group is the same as defined hereinabove, and is preferably a vinyloxy group, a 1-propenyloxy group or an allyloxy group, and more preferably a vinyloxy group. When this group has substituent(s) A, the C2-C6 alkenyloxy group is optionally substituted with substituent(s) A in place of any hydrogen atom(s).

The "C2-C6 haloalkenyloxy group" represented by R1 in the formula (1) is the same as defined hereinabove, and is preferably a 2-fluorovinyloxy group, a 2,2-difluorovinyloxy group, a 3-fluoroallyloxy group or a 3,3-difluoroallyloxy group, and more preferably a 2-fluorovinyloxy group or a 2,2-difluorovinyloxy group.

In the "C3-C6 alkynyloxy group optionally substituted with substituent(s) A" represented by R1 in the formula (1), the C3-C6 alkynyloxy group is the same as defined hereinabove, and is preferably a propargyloxy group, a 2-butynyloxy group or a 3-butynyloxy group, and more preferably a propargyloxy group. When this group has substituent(s) A, the C3-C6 alkynyloxy group is optionally substituted with substituent(s) A in place of any hydrogen atom(s).

The "C3-C6 haloalkynyloxy group" represented by R1 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In "RaRbN—" (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group) represented by R1 in the formula (1), the terms are the same as defined hereinabove. When the "C1-C6 alkyl group optionally substituted with substituent(s) B" has substituent(s) B, the C1-C6 alkyl group is optionally substituted with substituent(s) B in place of any hydrogen atom(s). "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably an amino group, a dimethylamino group, an ethylmethylamino group or a diethylamino group.

In the formula (1), R2, R3 and R4 are independent of one another and each represent a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryloxy group optionally substituted with 0 to 5 substituents D, a heteroaryloxy group optionally substituted with 0 to 2 substituents D, an aralkyloxy group optionally substituted with 0 to 5 substituents D, Rx1C(=O)— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)), Rx1C(=O)O— (wherein Rx1 is the same as defined hereinabove), a 3 to 6-membered ring group containing 1 to 2 oxygen atoms, Rc-L- (wherein Rc represents a C1-C6 alkyl group or a C1-C6 haloalkyl group, and L represents S, SO or SO$_2$), RaRbN— (wherein Ra and Rb are the same as defined hereinabove) or Rx2C(=O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), and Rx3 represents a hydrogen atom, a C1-C6 alkyl group optionally substituted with substituent(s) B, a C1-C6 haloalkyl group or a C3-C8 cycloalkyl group).

In particular, it is preferable that R2, R3 and R4 are independent of one another and each represent a hydrogen atom, a halogen atom, a hydroxy group, a cyano group, a C1-C6 alkyl group optionally substituted with substituent(s) C, a C1-C6 haloalkyl group, a C2-C6 alkenyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aralkyloxy group optionally substituted with 0 to 5 substituents D, or Rx1C(=O)O— (wherein Rx1 is the same as defined hereinabove);

it is more preferable that R2, R3 and R4 are independent of one another and each represent a hydrogen atom, a halogen atom, a hydroxy group, a cyano group, a C1-C6 alkyl group optionally substituted with substituent(s) C, a C1-C6 haloalkyl group, a C2-C6 alkynyl group optionally substituted with substituent(s) C, a C1-C6 alkoxy group optionally substituted with substituent(s) C, a C1-C6 haloalkoxy group, a C2-C6 alkenyloxy group optionally substituted with substituent(s) C, a C3-C6 alkynyloxy group optionally substituted with substituent(s) C, an aralkyloxy group optionally substituted with 0 to 5 substituents D, or Rx1C(=O)O— (wherein Rx1 is the same as defined hereinabove); and it is particularly preferable that R2, R3 and R4 are independent of one another and each represent a hydrogen atom, a halogen atom, a hydroxy group, a cyano group, a C1-C6 alkyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C2-C6 alkenyloxy group optionally substituted with substituent(s) C, a C3-C6 alkynyloxy group optionally substituted with substituent(s) C, or Rx1C(=O)O— (wherein Rx1 is the same as defined hereinabove).

In the formula (1), R2 may represent a hydrogen atom, a hydroxy group, a cyano group or a nitro group.

The halogen atom represented by R2 in the formula (1) is the same as defined hereinabove, and is preferably a fluorine atom, a chlorine atom, a bromine atom or an iodine atom.

In the "C1-C6 alkyl group optionally substituted with substituent(s) C" represented by R2 in the formula (1), the C1-C6 alkyl group is the same as defined hereinabove, and is preferably a methyl group, an ethyl group, a propyl group, an isopropyl group, a butyl group or an isobutyl group, and more preferably a methyl group or an ethyl group. When this group has substituent(s) C, the C1-C6 alkyl group is optionally substituted with substituent(s) C in place of any hydrogen atom(s).

The "C1-C6 haloalkyl group" represented by R2 in the formula (1) is the same as defined hereinabove, and is preferably a difluoromethyl group, a trifluoromethyl group, a 2,2-difluoroethyl group or a 2,2,2-trifluoroethyl group, and more preferably a difluoromethyl group or a trifluoromethyl group.

In the "C3-C8 cycloalkyl group optionally substituted with substituent(s) C" represented by R2 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) C, the C3-C8 cycloalkyl group is optionally substituted with substituent(s) C in place of any hydrogen atom(s).

In the "C2-C6 alkenyl group optionally substituted with substituent(s) C" represented by R2 in the formula (1), the C2-C6 alkenyl group is the same as defined hereinabove, and is preferably a vinyl group, a 1-propenyl group, an allyl group, a 1-butenyl group, a 2-butenyl group or a 3-butenyl group, and more preferably a vinyl group, a 1-propenyl group or an allyl group. When this group has substituent(s) C, the C2-C6 alkenyl group is optionally substituted with substituent(s) C in place of any hydrogen atom(s).

The "C2-C6 haloalkenyl group" represented by R2 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

In the "C2-C6 alkynyl group optionally substituted with substituent(s) C" represented by R2 in the formula (1), the C2-C6 alkynyl group is the same as defined hereinabove, and is preferably an ethynyl group, a 1-propynyl group, a propargyl group, a 1-butynyl group, a 2-butynyl group or a 3-butyryl group, and more preferably an ethynyl group, a 1-propynyl group or a propargyl group. When this group has substituent(s) C, the C2-C6 alkynyl group is optionally substituted with substituent(s) C in place of any hydrogen atom(s).

The "C2-C6 haloalkynyl group" represented by R2 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

In the "C1-C6 alkoxy group optionally substituted with substituent(s) C" represented by R2 in the formula (1), the C1-C6 alkoxy group is the same as defined hereinabove, and is preferably a methoxy group, an ethoxy group, a propyloxy group, an isopropyloxy group, a butoxy group, an isobutoxy group or a pentyloxy group, and more preferably a methoxy group, an ethoxy group, a propyloxy group, an isopropyloxy group, a butoxy group or a pentyloxy group. When this group has substituent(s) C, the C1-C6 alkoxy group is optionally substituted with substituent(s) C in place of any hydrogen atom(s).

The "C1-C6 haloalkoxy group" represented by R2 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

In the "C3-C8 cycloalkoxy group optionally substituted with substituent(s) C" represented by R2 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R2 in the formula (1), the C2-C6 alkenyloxy group is the same as defined hereinabove, and is preferably a vinyloxy group, a 1-propenyloxy group, an allyloxy group, a 1-butenyloxy group, a 2-butenyloxy group or a 3-butenyloxy group, and more preferably a vinyloxy group, a 1-propenyloxy group or an allyloxy group. When this group has substituent(s) C, the C2-C6 alkenyloxy group is optionally substituted with substituent(s) C in place of any hydrogen atom(s).

The "C2-C6 haloalkenyloxy group" represented by R2 in the formula (1) is the same as defined hereinabove, and is preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

In the "C3-C6 alkynyloxy group optionally substituted with substituent(s) C" represented by R2 in the formula (1), the C3-C6 alkynyloxy group is the same as defined hereinabove, and is preferably a propargyloxy group, a 2-butynyloxy group or a 3-butynyloxy group, and more preferably a propargyloxy group or a 2-butynyloxy group. When this group has substituent(s) C, the C3-C6 alkynyloxy group is optionally substituted with substituent(s) C in place of any hydrogen atom(s).

The "C3-C6 haloalkynyloxy group" represented by R2 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In the "aryloxy group optionally substituted with 0 to 5 substituents D" represented by R2 in the formula (1), the aryloxy group is the same as defined hereinabove, and is preferably a phenoxy group or a naphthyloxy group, and more preferably a phenoxy group. When this group has substituent(s) D, the aryloxy group is optionally substituted with substituent(s) D in place of any hydrogen atom(s). Where there are two or more substituents D, they are independent of one another.

In the "heteroaryloxy group optionally substituted with 0 to 2 substituents D" represented by R2 in the formula (1), the heteroaryloxy group is the same as defined hereinabove, and is preferably a pyridyloxy group, a pyridazinyloxy group, a pyrimidinyloxy group, a pyrazinyloxy group, a triazinyloxy group, a tetrazinyloxy group, a thienyloxy group, a thiazolyloxy group, an isothiazolyloxy group or a thiadiazolyloxy group, and more preferably a pyridyloxy group, a pyridazinyloxy group, a pyrimidinyloxy group or a pyrazinyloxy group. When this group has substituent(s) D, the heteroaryloxy group is optionally substituted with substituent(s) D in place of any hydrogen atom(s). Where there are two substituents D, they are independent of one another.

In the "aralkyloxy group optionally substituted with 0 to 5 substituents D" represented by R2 in the formula (1), the aralkyloxy group is the same as defined hereinabove, and is preferably a benzyloxy group, a phenetyloxy group or a phenylpropyloxy group, and more preferably a benzyloxy group or a phenetyloxy group. When this group has substituent(s) D, the aralkyloxy group is optionally substituted with substituent(s) D in place of any hydrogen atom(s). Where there are two or more substituents D, they are independent of one another.

In "Rx1C(=O)—" (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)) represented by R2 in the formula (1), the terms are the same as defined hereinabove. Where the "C1-C6 alkyl group optionally substituted with substituent(s) B" has substituent(s) B, the C1-C6 alkyl group is optionally substituted with substituent(s) B in place of any hydrogen atom(s). Rx1 is preferably a C1-C6 alkyl group optionally substituted with substituent(s) B, or a C1-C6 alkoxy group, and more preferably a C1-C6 alkyl group optionally substituted with substituent(s) B. "Rx1C(=O)—" is preferably an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group or a piperidinylcarbonyl group, and more preferably an acetyl group, a methoxyacetyl group, a cyanoacetyl group, a propionyl group, a difluoroacetyl group, a trifluoroacetyl group, a methoxycarbonyl group or an ethoxycarbonyl group.

In "Rx1C(=O)O—" represented by R2 in the formula (1), Rx1 is the same as defined hereinabove. Rx1 is preferably a C1-C6 alkyl group optionally substituted with substituent(s) B, or a C1-C6 alkoxy group, and more preferably a C1-C6 alkyl group optionally substituted with substituent(s) B. "Rx1C(=O)O—" is preferably an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group, and more preferably an acetyloxy group, a methoxyacetyloxy group, a cyanoacetyloxy group or a propionyloxy group.

The "3 to 6-membered ring group containing 1 to 2 oxygen atoms" represented by R2 in the formula (1) is the same as defined hereinabove, and is preferably an oxolanyl group, an oxanyl group, a 1,3-dioxolanyl group or a 1,3-dioxanyl group, and more preferably a 1,3-dioxolanyl group or a 1,3-dioxanyl group.

In "Rc-L-" (wherein Rc represents a C1-C6 alkyl group or a C1-C6 haloalkyl group and L represents S, SO or $SO_2$) represented by R2 in the formula (1), the terms are the same as defined hereinabove. "Rc-L-" is preferably a methylthio group, a methanesulfinyl group, a methanesulfonyl group, a trifluoromethylthio group, a trifluoromethanesulfinyl group or a trifluoromethanesulfonyl group, and more preferably a methylthio group, a methanesulfinyl group or a methanesulfonyl group.

In "RaRbN—" represented by R2 in the formula (1), Ra and Rb are the same as defined hereinabove. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably an amino group, a methylamino group, an ethylamino group, a dimethylamino group, an ethylmethylamino group or a diethylamino group.

In "Rx2C(=O)N(Rx3)-" (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), and Rx3 represents a hydrogen atom, a C1-C6 alkyl group optionally substituted with substituent(s) B, a C1-C6 haloalkyl group or a C3-C8 cycloalkyl group) represented by R2 in the formula (1), the terms are the same as defined hereinabove. Where the "C1-C6 alkyl group optionally substituted with substituent(s) B" represented by Rx2 or Rx3 has substituent(s) B, the C1-C6 alkyl group is optionally substituted with substituent(s) B in place of any hydrogen atom(s). Rx2 is preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy, a 2,2,2-trifluoroethoxy group, a cyclopropyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably a hydrogen atom, a methyl group, a methoxymethyl group, a cyanomethyl group, a difluoromethyl group, a trifluoromethyl group, a methoxy group, an ethoxy group, an amino group, a dimethylamino group, an ethylmethylamino group or a diethylamino group. Rx3 is preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group or a cyclopropyl group, and more preferably a hydrogen atom, a methyl group, a methoxymethyl group, a cyanomethyl group, an ethyl group, a 2-methoxyethyl group, a 2,2-difluoroethyl group or a 2,2,2-trifluoroethyl group.

In the formula (1), R3 is defined the same as R2.
In the formula (1), R4 is defined the same as R2.
R2, R3 and R4 in the formula (1) are independent of one another and may be the same as or different from one another without limitation.
R5 in the formula (1) represents a hydrogen atom, a halogen atom, a cyano group, a nitro group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, Rc-L- (wherein Rc and L are the same as defined hereinabove), RaRbN— (wherein Ra and Rb are the same as defined hereinabove) or R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group).

In particular, R5 is preferably a hydrogen atom, a halogen atom, a C1-C6 alkyl group optionally substituted with substituent(s) A, a C1-C6 haloalkyl group, a C2-C6 alkenyl group optionally substituted with substituent(s) A, a C2-C6 alkynyl group optionally substituted with substituent(s) A, a C1-C6 alkoxy group optionally substituted with substituent (s) A, a C2-C6 alkenyloxy group optionally substituted with substituent(s) A, a C3-C6 alkynyloxy group optionally substituted with substituent(s) A, or R51C(=O)— (wherein R51 is the same as defined hereinabove);

R5 is more preferably a hydrogen atom, a halogen atom, a C1-C6 alkyl group optionally substituted with substituent (s) A, a C1-C6 haloalkyl group, a C2-C6 alkynyl group optionally substituted with substituent(s) A, a C1-C6 alkoxy group optionally substituted with substituent(s) A, or R51C (=O)— (wherein R51 is the same as defined hereinabove); and R5 is particularly preferably a hydrogen atom, a halogen atom, a C1-C6 alkyl group optionally substituted with substituent(s) A, or a C1-C6 alkoxy group optionally substituted with substituent(s) A.

In the formula (1), R5 may represent a hydrogen atom, a cyano group or a nitro group.

The halogen atom represented by R5 in the formula (1) is the same as defined hereinabove, and is preferably a fluorine atom, a chlorine atom, a bromine atom or an iodine atom.

In the "C1-C6 alkyl group optionally substituted with substituent(s) A" represented by R5 in the formula (1), the C1-C6 alkyl group is the same as defined hereinabove, and is preferably a methyl group, an ethyl group, a propyl group, an isopropyl group, a butyl group or an isobutyl group, and more preferably a methyl group or an ethyl group. When this group has substituent(s) A, the C1-C6 alkyl group is optionally substituted with substituent(s) A in place of any hydrogen atom(s).

The "C1-C6 haloalkyl group" represented by R5 in the formula (1) is the same as defined hereinabove, and is preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, and more preferably a difluoromethyl group or a trifluoromethyl group.

In the "C3-C8 cycloalkyl group optionally substituted with substituent(s) A" represented by R5 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) A, the C3-C8 cycloalkyl group is optionally substituted with substituent(s) A in place of any hydrogen atom(s).

In the "C2-C6 alkenyl group optionally substituted with substituent(s) A" represented by R5 in the formula (1), the C2-C6 alkenyl group is the same as defined hereinabove, and is preferably a vinyl group, a 1-propenyl group, an allyl group, a 1-butenyl group, a 2-butenyl group or a 3-butenyl group, and more preferably a vinyl group, a 1-propenyl group or an allyl group. When this group has substituent(s) A, the C2-C6 alkenyl group is optionally substituted with substituent(s) A in place of any hydrogen atom(s).

The "C2-C6 haloalkenyl group" represented by R5 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

In the "C2-C6 alkynyl group optionally substituted with substituent(s) A" represented by R5 in the formula (1), the C2-C6 alkynyl group is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When this group has substituent(s) A, the C2-C6 alkynyl group is optionally substituted with substituent(s) A in place of any hydrogen atom(s).

The "C2-C6 haloalkynyl group" represented by R5 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

In the "C1-C6 alkoxy group optionally substituted with substituent(s) A" represented by R5 in the formula (1), the C1-C6 alkoxy group is the same as defined hereinabove, and is preferably a methoxy group, an ethoxy group, a propyloxy group, an isopropyloxy group, a butoxy group or an isobutoxy group, and more preferably a methoxy group or an ethoxy group. When this group has substituent(s) A, the C1-C6 alkoxy group is optionally substituted with substituent(s) A in place of any hydrogen atom(s).

The "C1-C6 haloalkoxy group" represented by R5 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

In the "C3-C8 cycloalkoxy group optionally substituted with substituent(s) A" represented by R5 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) A, the C3-C8 cycloalkoxy group is optionally substituted with substituent(s) A in place of any hydrogen atom(s).

In the "C2-C6 alkenyloxy group optionally substituted with substituent(s) A" represented by R5 in the formula (1), the C2-C6 alkenyloxy group is the same as defined hereinabove, and is preferably a vinyloxy group, a 1-propenyloxy group, an allyloxy group, a 1-butenyloxy group, a 2-butenyloxy group or a 3-butenyloxy group, and more preferably a vinyloxy group, a 1-propenyloxy group or an allyloxy group. When this group has substituent(s) A, the C2-C6 alkenyloxy group is optionally substituted with substituent(s) A in place of any hydrogen atom(s).

The "C2-C6 haloalkenyloxy group" represented by R5 in the formula (1) is the same as defined hereinabove, and may be a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

In the "C3-C6 alkynyloxy group optionally substituted with substituent(s) A" represented by R5 in the formula (1), the C3-C6 alkynyloxy group is the same as defined hereinabove, and is preferably a propargyloxy group, a 2-butynyloxy group or a 3-butynyloxy group, and more preferably a propargyloxy group. When this group has substituent(s) A, the C3-C6 alkynyloxy group is optionally substituted with substituent(s) A in place of any hydrogen atom(s).

The "C3-C6 haloalkynyloxy group" represented by R5 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In "Rc-L-" represented by R5 in the formula (1), Rc and L are the same as defined hereinabove. "Rc-L-" is preferably a methylthio group, a methanesulfinyl group, a methanesulfonyl group, a trifluoromethylthio group, a trifluoromethanesulfinyl group or a trifluoromethanesulfonyl group, and more preferably a methylthio group, a methanesulfinyl group or a methanesulfonyl group.

In "RaRbN—" represented by R5 in the formula (1), Ra and Rb are the same as defined hereinabove. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably a dimethylamino group, an ethylmethylamino group or a diethylamino group.

In "R51C(=O)—" (wherein R51 represents a hydroxy group, a C1-C6 alkyl group optionally substituted with substituent(s) B, a C1-C6 haloalkyl group, a C3-C8 cycloalkyl group or a C1-C6 alkoxy group) represented by R5 in the formula (1), the terms are the same as defined hereinabove. Where the "C1-C6 alkyl group optionally substituted with substituent(s) B" has substituent(s) B, the C1-C6 alkyl group is optionally substituted with substituent(s) B in place of any hydrogen atom(s). R51 is preferably a C1-C6 alkyl group optionally substituted with substituent(s) B. "R51C(=O)—" is preferably a hydroxycarbonyl group, an acetyl group, a methoxyacetyl group, a cyanoacetyl group, a propionyl group, a difluoroacetyl group, a trifluoroacetyl group, a cyclopropanecarbonyl group, a methoxycarbonyl group or an ethoxycarbonyl group, and more preferably an acetyl group, a methoxyacetyl group, a cyanoacetyl group or a propionyl group.

In the formula (1), X represents an oxygen atom or a sulfur atom. Preferably, X represents an oxygen atom.

Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group. In particular, Y is preferably a phenyl group or a pyridyl group, and particularly preferably a phenyl group.

The phenyl group is substituted with R6 at an ortho position and is further optionally substituted with 0 to 4 substituents R7 independent of one another.

The pyridyl group, the pyrazinyl group, the pyrimidinyl group, the pyridazinyl group, the triazinyl group or the tetrazinyl group is substituted with R6 at an ortho position and is further optionally substituted with 0 to 3 substituents R7 independent of one another.

The thienyl group, the thiazolyl group, the isothiazolyl group or the thiadiazolyl group is substituted with R6 at an ortho position and is further optionally substituted with 0 to 2 substituents R7 independent of one another.

R6 represents a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryloxy group optionally substituted with 0 to 5 substituents D, a heteroaryloxy group optionally substituted with 0 to 2 substituents D, an aralkyloxy group optionally substituted with 0 to 5 substituents D, Rx1C(=O)— (wherein Rx1 is the same as defined hereinabove), Rx1C(=O)O— (wherein Rx1 is the same as defined hereinabove), a 3 to 6-membered ring group containing 1 to 2 oxygen atoms, Rc-L (wherein Rc and L are the same as defined hereinabove), RaRbN— (wherein Ra and Rb are the same as defined hereinabove) or Rx2C(=O)N(Rx3)- (wherein Rx2 and Rx3 are the same as defined hereinabove).

In particular, R6 is preferably a halogen atom, a hydroxy group, a cyano group, a C1-C6 alkyl group optionally substituted with substituent(s) C, a C1-C6 alkoxy group optionally substituted with substituent(s) C, a C2-C6 alkenyloxy group optionally substituted with substituent(s) C, or a C3-C6 alkynyloxy group optionally substituted with substituent(s) C;

R6 is more preferably a halogen atom, a cyano group, a C1-C6 alkyl group optionally substituted with substituent(s) C, or a C1-C6 alkoxy group optionally substituted with substituent(s) C; and R6 is particularly preferably a halogen atom or a C1-C6 alkyl group optionally substituted with substituent(s) C.

The halogen atom represented by R6 in the formula (1) is the same as defined hereinabove, and is preferably a fluorine atom, a chlorine atom, a bromine atom or an iodine atom.

R6 in the formula (1) may represent a hydroxy group, a cyano group or a nitro group.

In the "C1-C6 alkyl group optionally substituted with substituent(s) C" represented by R6 in the formula (1), the C1-C6 alkyl group is the same as defined hereinabove, and is preferably a methyl group, an ethyl group or a propyl group, and more preferably a methyl group or an ethyl group. When this group has substituent(s) C, the C1-C6 alkyl group is optionally substituted with substituent(s) C in place of any hydrogen atom(s).

The "C1-C6 haloalkyl group" represented by R6 in the formula (1) is the same as defined hereinabove, and is preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, and more preferably a difluoromethyl group or a trifluoromethyl group.

In the "C3-C8 cycloalkyl group optionally substituted with substituent(s) C" represented by R6 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) C, the C3-C8 cycloalkyl group is optionally substituted with substituent(s) C in place of any hydrogen atom(s).

In the "C2-C6 alkenyl group optionally substituted with substituent(s) C" represented by R6 in the formula (1), the C2-C6 alkenyl group is the same as defined hereinabove, and is preferably a vinyl group, a 1-propenyl group or an allyl group, and more preferably a vinyl group. When this group has substituent(s) C, the C2-C6 alkenyl group is optionally substituted with substituent(s) C in place of any hydrogen atom(s).

The "C2-C6 haloalkenyl group" represented by R6 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

In the "C2-C6 alkynyl group optionally substituted with substituent(s) C" represented by R6 in the formula (1), the C2-C6 alkynyl group is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When this group has substituent(s) C, the C2-C6 alkynyl group is optionally substituted with substituent(s) C in place of any hydrogen atom(s).

The "C2-C6 haloalkynyl group" represented by R6 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

In the "C1-C6 alkoxy group optionally substituted with substituent(s) C" represented by R6 in the formula (1), the C1-C6 alkoxy group is the same as defined hereinabove, and is preferably a methoxy group, an ethoxy group, a propyloxy group or an isopropyloxy group, and more preferably a methoxy group or an ethoxy group. When this group has substituent(s) C, the C1-C6 alkoxy group is optionally substituted with substituent(s) C in place of any hydrogen atom(s).

The "C1-C6 haloalkoxy group" represented by R6 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group or a trifluoromethoxy group.

In the "C3-C8 cycloalkoxy group optionally substituted with substituent(s) C" represented by R6 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R6 in the formula (1), the C2-C6 alkenyloxy group is the same as defined hereinabove, and is preferably a vinyloxy group, a 1-propenyloxy group or an allyloxy group, and more preferably a vinyloxy group. When this group has substituent(s) C, the C2-C6 alkenyloxy group is optionally substituted with substituent(s) C in place of any hydrogen atom(s).

The "C2-C6 haloalkenyloxy group" represented by R6 in the formula (1) is the same as defined hereinabove, and is preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

In the "C3-C6 alkynyloxy group optionally substituted with substituent(s) C" represented by R6 in the formula (1), the C3-C6 alkynyloxy group is the same as defined hereinabove, and is preferably a propargyloxy group, a 2-butynyloxy group or a 3-butynyloxy group, and more preferably a propargyloxy group. When this group has substituent(s) C, the C3-C6 alkynyloxy group is optionally substituted with substituent(s) C in place of any hydrogen atom(s).

The "C3-C6 haloalkynyloxy group" represented by R6 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In the "aryloxy group optionally substituted with 0 to 5 substituents D" represented by R6 in the formula (1), the aryloxy group is the same as defined hereinabove, and is preferably a phenoxy group or a naphthyloxy group, and more preferably a phenoxy group. When this group has substituent(s) D, the aryloxy group is optionally substituted with substituent(s) D in place of any hydrogen atom(s). Where there are two or more substituents D, they are independent of one another.

In the "heteroaryloxy group optionally substituted with 0 to 2 substituents D" represented by R6 in the formula (1), the heteroaryloxy group is the same as defined hereinabove, and is preferably a pyridyloxy group, a pyridazinyloxy group, a pyrimidinyloxy group, a pyrazinyloxy group, a triazinyloxy group, a tetrazinyloxy group, a thienyloxy group, a thiazolyloxy group, an isothiazolyloxy group or a thiadiazolyloxy group, and more preferably a pyridyloxy group, a pyridazinyloxy group, a pyrimidinyloxy group or a pyrazinyloxy group. When this group has substituent(s) D, the heteroaryloxy group is optionally substituted with substituent(s) D in place of any hydrogen atom(s). Where there are two substituents D, they are independent of one another.

In the "aralkyloxy group optionally substituted with 0 to 5 substituents D" represented by R6 in the formula (1), the aralkyloxy group is the same as defined hereinabove, and is preferably a benzyloxy group, a phenetyloxy group or a phenylpropyloxy group, and more preferably a benzyloxy group or a phenetyloxy group. When this group has substituent(s) D, the aralkyloxy group is optionally substituted with substituent(s) D in place of any hydrogen atom(s). Where there are two or more substituents D, they are independent of one another.

In "Rx1C(=O)—" represented by R6 in the formula (1), Rx1 is the same as defined hereinabove. Rx1 is preferably a C1-C6 alkyl group optionally substituted with substituent(s) B, or a C1-C6 alkoxy group. "Rx1C(=O)—" is preferably an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group or a piperidinylcarbonyl group, and more preferably an acetyl group, a methoxyacetyl group, a cyanoacetyl group, a propionyl group, a methoxycarbonyl group or an ethoxycarbonyl group.

In "Rx1C(=O)O—" represented by R6 in the formula (1), Rx1 is the same as defined hereinabove. Rx1 is preferably a C1-C6 alkyl group optionally substituted with substituent(s) B, or a C1-C6 alkoxy group. "Rx1C(=O)O—" is preferably an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group, and more preferably an acetyloxy group, a methoxyacetyloxy group, a cyanoacetyloxy group, a propionyloxy group, a methoxycarbonyloxy group or an ethoxycarbonyloxy group.

The "3 to 6-membered ring group containing 1 to 2 oxygen atoms" represented by R6 in the formula (1) is the same as defined hereinabove, and is preferably an oxolanyl group, an oxanyl group, a 1,3-dioxolanyl group or a 1,3-dioxanyl group, and more preferably a 1,3-dioxolanyl group or a 1,3-dioxanyl group.

In "Rc-L-" represented by R6 in the formula (1), Rc and L are the same as defined hereinabove. "Rc-L-" is preferably a methylthio group, a methanesulfinyl group, a methanesulfonyl group, a trifluoromethylthio group, a trifluoromethanesulfinyl group or a trifluoromethanesulfonyl group, and more preferably a methylthio group, a methanesulfinyl group or a methanesulfonyl group.

In "RaRbN—" represented by R6 in the formula (1), Ra and Rb are the same as defined hereinabove. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably a dimethylamino group, an ethylmethylamino group or a diethylamino group.

In "Rx2C(=O)N(Rx3)-" represented by R6 in the formula (1), Rx2 and Rx3 are the same as defined hereinabove. Rx2 is preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy, a 2,2,2-trifluoroethoxy group, a cyclopropyloxy group, an amino group, a methylamino group, an ethylamino group, a (methoxymethyl)amino group, a (2-methoxyethyl)amnino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably a hydrogen atom, a methyl group, a methoxymethyl group, a cyanomethyl group, a difluoromethyl group, a trifluoromethyl group, a methoxy group, an ethoxy group, an amino group, a dimethylamino group, an ethylmethylamino group or a diethylamino group. Rx3 is preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group or a cyclopropyl group, and more preferably a hydrogen atom, a methyl group, a methoxymethyl group, a cyanomethyl group, an ethyl group, a 2-methoxyethyl group, a 2,2-difluoroethyl group or a 2,2,2-trifluoroethyl group.

R7 is defined the same as R6 described hereinabove. That is, R7 represents a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryloxy group optionally substituted with 0 to 5 substituents D, a heteroaryloxy group optionally substituted with 0 to 2 substituents D, an aralkyloxy group optionally substituted with 0 to 5 substituents D, Rx1C(=O)— (wherein Rx1 is the same as defined hereinabove), Rx1C(=O)O— (wherein Rx1 is the same as defined hereinabove), a 3 to 6-membered ring group containing 1 to 2 oxygen atoms, Rc-L (wherein Rc and L are the same as defined hereinabove), RaRbN— (wherein Ra and Rb are the same as defined hereinabove) or Rx2C(=O)N(Rx3)- (wherein Rx2 and Rx3 are the same as defined hereinabove).

In particular, R7 is preferably a halogen atom, a hydroxy group, a cyano group, a C1-C6 alkyl group optionally substituted with substituent(s) C, a C1-C6 haloalkyl group, a C2-C6 alkenyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C2-C6 alkenyloxy group optionally substituted with substituent(s) C, a C3-C6 alkynyloxy group optionally substituted with substituent(s) C, a heteroaryloxy group optionally substituted with 0 to 2 substituents D, an aralkyloxy group optionally substituted with 0 to 5 substituents D, Rx1C(=O)— (wherein Rx1 is the same as defined hereinabove) or Rx1C(=O)O— (wherein Rx1 is the same as defined hereinabove);

R7 is more preferably a halogen atom, a hydroxy group, a C1-C6 alkyl group optionally substituted with substituent(s) C, a C1-C6 haloalkyl group, a C1-C6 alkoxy group optionally substituted with substituent(s) C, a C1-C6 haloalkoxy group, a C3-C6 alkynyloxy group optionally substituted with substituent(s) C, a heteroaryloxy group optionally substituted with 0 to 2 substituents D, an aralkyloxy group optionally substituted with 0 to 5 substituents D, Rx1C(=O)— (wherein Rx1 is the same as defined hereinabove) or Rx1C(=O)O— (wherein Rx1 is the same as defined hereinabove); and R7 is particularly preferably a halogen atom, a hydroxy group, a C1-C6 alkyl group optionally substituted with substituent(s) C, a C1-C6 alkoxy group optionally substituted with substituent(s) C, a C1-C6 haloalkoxy group, a C3-C6 alkynyloxy group optionally substituted with substituent(s) C, or Rx1C(=O)O— (wherein Rx1 is the same as defined hereinabove).

The halogen atom represented by R7 in the formula (1) is the same as defined hereinabove, and is preferably a fluorine atom, a chlorine atom, a bromine atom or an iodine atom.

In the formula (1), R7 may represent a hydroxy group, a cyano group or a nitro group.

In the "C1-C6 alkyl group optionally substituted with substituent(s) C" represented by R7 in the formula (1), the C1-C6 alkyl group is the same as defined hereinabove, and is preferably a methyl group, an ethyl group, a propyl group, an isopropyl group, a butyl group or an isobutyl group, and more preferably a methyl group, an ethyl group, a propyl group or an isopropyl group. When this group has substituent(s) C, the C1-C6 alkyl group is optionally substituted with substituent(s) C in place of any hydrogen atom(s).

The "C1-C6 haloalkyl group" represented by R7 in the formula (1) is the same as defined hereinabove, and is preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, and more preferably a difluoromethyl group, a trifluoromethyl group, a 2,2-difluoroethyl group or a 2,2,2-trifluoroethyl group.

In the "C3-C8 cycloalkyl group optionally substituted with substituent(s) C" represented by R7 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) C, the C3-C8 cycloalkyl group is optionally substituted with substituent(s) C in place of any hydrogen atom(s).

In the "C2-C6 alkenyl group optionally substituted with substituent(s) C" represented by R7 in the formula (1), the C2-C6 alkenyl group is the same as defined hereinabove, and is preferably a vinyl group, a 1-propenyl group, an allyl group, a 1-butenyl group, a 2-butenyl group or a 3-butenyl group, and more preferably a vinyl group, a 1-propenyl group or an allyl group. When this group has substituent(s) C, the C2-C6 alkenyl group is optionally substituted with substituent(s) C in place of any hydrogen atom(s).

The "C2-C6 haloalkenyl group" represented by R7 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

In the "C2-C6 alkynyl group optionally substituted with substituent(s) C" represented by R7 in the formula (1), the C2-C6 alkynyl group is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When this group has substituent(s) C, the C2-C6 alkynyl group is optionally substituted with substituent(s) C in place of any hydrogen atom(s).

The "C2-C6 haloalkynyl group" represented by R7 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

In the "C1-C6 alkoxy group optionally substituted with substituent(s) C" represented by R7 in the formula (1), the C1-C6 alkoxy group is the same as defined hereinabove, and is preferably a methoxy group, an ethoxy group, a propyloxy group, an isopropyloxy group, a butoxy group, an isobutoxy group or a pentyloxy group, and more preferably a methoxy group, an ethoxy group, a propyloxy group, an isopropyloxy group, a butoxy group or a pentyloxy group. When this group has substituent(s) C, the C1-C6 alkoxy group is optionally substituted with substituent(s) C in place of any hydrogen atom(s).

The "C1-C6 haloalkoxy group" represented by R7 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

In the "C3-C8 cycloalkoxy group optionally substituted with substituent(s) C" represented by R7 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R7 in the formula (1), the C2-C6 alkenyloxy group is the same as defined hereinabove, and is preferably a vinyloxy group, a 1-propenyloxy group, an allyloxy group, a 1-butenyloxy group, a 2-butenyloxy group or a 3-butenyloxy group, and more preferably a vinyloxy group, a 1-propenyloxy group or an allyloxy group. When this group has substituent(s) C, the C2-C6 alkenyloxy group is optionally substituted with substituent(s) C in place of any hydrogen atom(s).

The "C2-C6 haloalkenyloxy group" represented by R7 in the formula (1) is the same as defined hereinabove, and is preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

In the "C3-C6 alkynyloxy group optionally substituted with substituent(s) C" represented by R7 in the formula (1), the C3-C6 alkynyloxy group is the same as defined hereinabove, and is preferably a propargyloxy group, a 2-butynyloxy group or a 3-butynyloxy group, and more preferably a propargyloxy group or a 2-butynyloxy group. When this group has substituent(s) C, the C3-C6 alkynyloxy group is optionally substituted with substituent(s) C in place of any hydrogen atom(s).

The "C3-C6 haloalkynyloxy group" represented by R7 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In the "aryloxy group optionally substituted with 0 to 5 substituents D" represented by R7 in the formula (1), the aryloxy group is the same as defined hereinabove, and is preferably a phenoxy group or a naphthyloxy group, and more preferably a phenoxy group. When this group has substituent(s) D, the aryloxy group is optionally substituted with substituent(s) D in place of any hydrogen atom(s). Where there are two or more substituents D, they are independent of one another.

In the "heteroaryloxy group optionally substituted with 0 to 2 substituents D" represented by R7 in the formula (1), the heteroaryloxy group is the same as defined hereinabove, and is preferably a pyridyloxy group, a pyridazinyloxy group, a pyrimidinyloxy group, a pyrazinyloxy group, a triazinyloxy group, a tetrazinyloxy group, a thienyloxy group, a thiazolyloxy group, an isothiazolyloxy group or a thiadiazolyloxy group, and more preferably a pyridyloxy group, a pyridazinyloxy group, a pyrimidinyloxy group or a pyrazinyloxy group. When this group has substituent(s) D, the heteroaryloxy group is optionally substituted with substituent(s) D in place of any hydrogen atom(s). Where there are two or more substituents D, they are independent of one another.

In the "aralkyloxy group optionally substituted with 0 to 5 substituents D" represented by R7 in the formula (1), the aralkyloxy group is the same as defined hereinabove, and is preferably a benzyloxy group, a phenetyloxy group or a phenylpropyloxy group, and more preferably a benzyloxy group or a phenetyloxy group. When this group has substituent(s) D, the aralkyloxy group is optionally substituted with substituent(s) D in place of any hydrogen atom(s). Where there are two or more substituents D, they are independent of one another.

In "Rx1C(=O)—" represented by R7 in the formula (1), Rx1 is the same as defined hereinabove. Rx1 is preferably a C1-C6 alkyl group optionally substituted with substituent(s) B, or a C1-C6 alkoxy group. "Rx1C(=O)—" is preferably an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group or a piperidinylcarbonyl group, and more preferably an acetyl group, a methoxyacetyl group, a cyanoacetyl group, a propionyl group, a methoxycarbonyl group or an ethoxycarbonyl group.

In "Rx1C(=O)O—" represented by R7 in the formula (1), Rx1 is the same as defined hereinabove. Rx1 is preferably a C1-C6 alkyl group optionally substituted with substituent(s) B, or a C1-C6 alkoxy group. "Rx1C(=O)O—" is preferably an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group, and more preferably an acetyloxy group, a methoxyacetyloxy group, a cyanoacetyloxy group, a propionyloxy group, a methoxycarbonyloxy group or an ethoxycarbonyloxy group.

The "3 to 6-membered ring group containing 1 to 2 oxygen atoms" represented by R7 in the formula (1) is the same as defined hereinabove, and is preferably an oxolanyl group, an oxanyl group, a 1,3-dioxolanyl group or a 1,3-dioxanyl group, and more preferably a 1,3-dioxolanyl group or a 1,3-dioxanyl group.

In "Rc-L-" represented by R7 in the formula (1), Re and L are the same as defined hereinabove. "Rc-L-" is preferably a methylthio group, a methanesulfinyl group, a methanesulfonyl group, a trifluoromethylthio group, a trifluoromethanesulfinyl group or a trifluoromethanesulfonyl group, and more preferably a methylthio group, a methanesulfinyl group or a methanesulfonyl group.

In "RaRbN—" represented by R7 in the formula (1), Ra and Rb are the same as defined hereinabove. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably a dimethylamino group, an ethylmethylamino group or a diethylamino group.

In "Rx2C(=O)N(Rx3)-" represented by R7 in the formula (1), Rx2 and Rx3 are the same as defined hereinabove. Rx2 is preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy, a 2,2,2-trifluoroethoxy group, a cyclopropyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably a hydrogen atom, a methyl group, a methoxymethyl group, a cyanomethyl group, a difluoromethyl group, a trifluoromethyl group, a methoxy group, an ethoxy group, an amino group, a dimethylamino group, an ethylmethylamino group or a diethylamino group. Rx3 is preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group or a cyclopropyl group, and more preferably a hydrogen atom, a methyl group, a methoxymethyl group, a cyanomethyl group, an ethyl group, a 2-methoxyethyl group, a 2,2-difluoroethyl group or a 2,2,2-trifluoroethyl group.

Hereinbelow, Y in the formula (1) will be described in detail.

A) When Y is a phenyl group, Y represents a partial structure represented by the formula (a):

[Chem. 4]

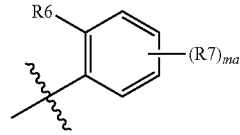

(a)

In the formula (a), R6 and R7 are the same as defined hereinabove.

In the formula (a), ma represents an integer of 0 to 4.

When ma in the formula (a) is 2 or greater, the two or more substituents R7 are independent of one another and may be selected appropriately to be the same as or different from one another.

When Y is a phenyl group in the present specification, the ortho position is the position on the phenyl group substituted with the substituent R6 as shown in the formula (a).

The phenyl group substituted with the substituent R6 at the ortho position satisfies the characteristics of the present invention.

B) When Y is a pyridyl group, a pyridazinyl group, a pyrimidinyl group, a pyrazinyl group, a triazinyl group or a tetrazinyl group, Y represents a partial structure represented by the formula (b):

[Chem. 5]

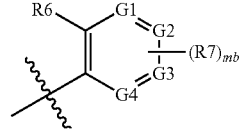

(b)

In the formula (b), R6 and R7 are the same as defined hereinabove.

In the formula (b), G1, G2, G3 and G4 are independent of one another and each represent a carbon atom or a nitrogen atom, with the proviso that at least one of G1, G2, G3 and G4 is a nitrogen atom. In a preferred embodiment of G1, G2, G3 and G4, at least one of G1, G2, G3 and G4 is a nitrogen atom, that is, the group is pyridyl.

In the formula (a), mb represents an integer of 0 to 3.

When mb in the formula (b) is 2 or greater, the two or more substituents R7 are independent of one another and may be selected appropriately to be the same as or different from one another.

When Y is a pyridyl group, a pyridazinyl group, a pyrimidinyl group, a pyrazinyl group, a triazinyl group or a tetrazinyl group in the present specification, the ortho position is the position on the 6-membered ring substituted with the substituent R6 as shown in the formula (b).

Specific examples of the partial structures represented by the formula (b) include those illustrated below.

[Chem. 6]

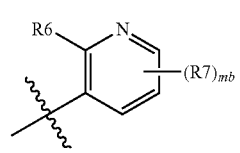 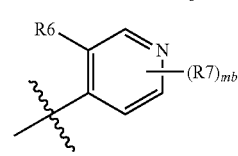

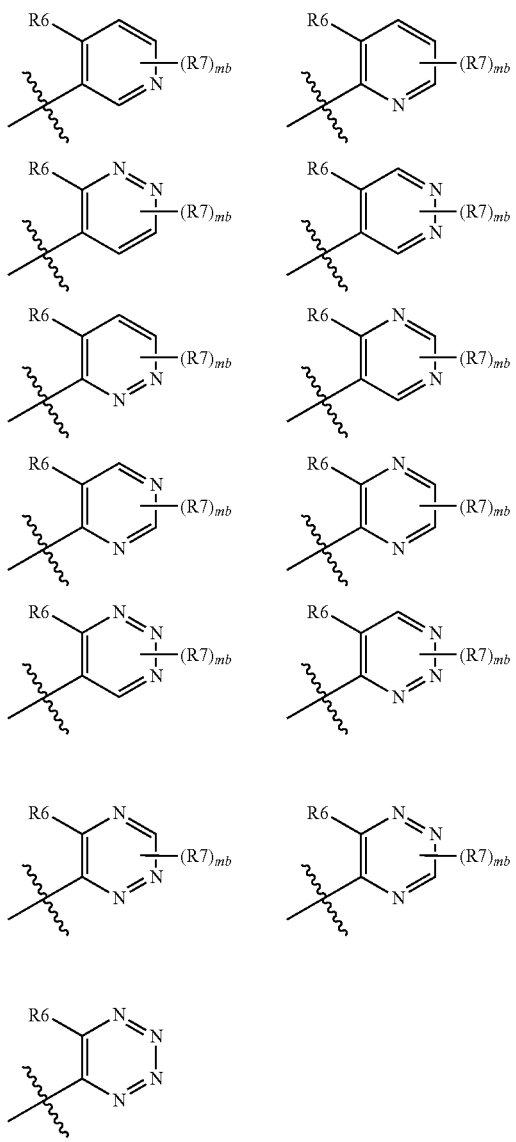

The pyridyl, pyridazinyl, pyrimidinyl, pyrazinyl, triazinyl or tetrazinyl group that is substituted with the substituent R6 at the ortho position satisfies the characteristics of the present invention.

C) When Y is a thienyl group, a thiazolyl group, an isothiazolyl group or a thiadiazolyl group, Y represents a partial structure represented by the formula (c-1):

[Chem. 7]

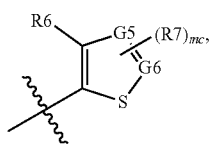

(c-1)

or the formula (c-2):

[Chem. 8]

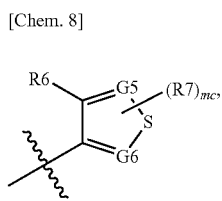

(c-2)

or the formula (c-3):

[Chem. 9]

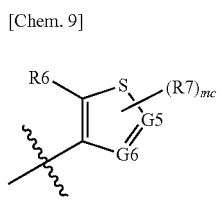

(c-3)

In the formula (c-1), the formula (c-2) and the formula (c-3), R6 and R7 are the same as defined hereinabove.

In the formula (c-1), the formula (c-2) and the formula (c-3), G5 and G6 are independent of one another and each represent a carbon atom or a nitrogen atom.

In the formula (c-1), the formula (c-2) and the formula (c-3), mc represents an integer of 0 to 2.

When mc in the formula (c-1), the formula (c-2) and the formula (c-3) is 2, the two substituents R7 are independent of one another and may be selected appropriately to be the same as or different from one another.

When Y is a thienyl group, a thiazolyl group, an isothiazolyl group or a thiadiazolyl group in the present specification, the ortho position is the position on the 5-membered ring substituted with the substituent R6 as shown in the formula (c-1), the formula (c-2) and the formula (c-3).

Specific examples of the partial structures represented by the formula (c-1) include those illustrated below.

[Chem. 10]

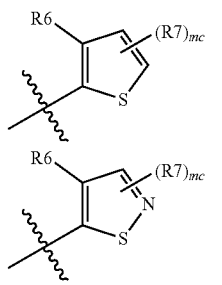
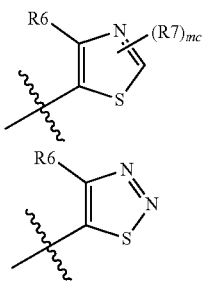

Specific examples of the partial structures represented by the formula (c-2) include those illustrated below.

[Chem. 11]

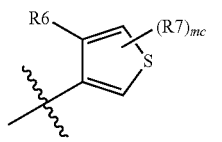
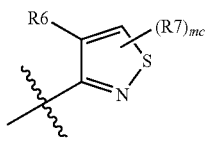

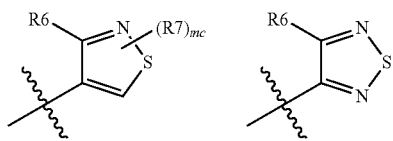

Specific examples of the partial structures represented by the formula (c-3) include those illustrated below.

[Chem. 11]

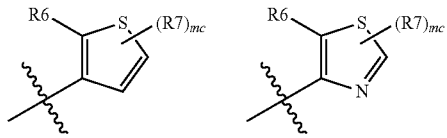

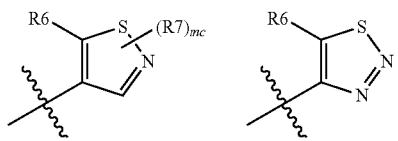

The thienyl, thiazolyl, isothiazolyl or thiadiazolyl group that is substituted with the substituent R6 at the ortho position satisfies the characteristics of the present invention.

The bond including the broken line in the formula (1) represents:

[Chem. 13]

The bond including the broken line in the formula (1) is a double bond or a single bond. It is preferable that the bond including the broken line is a double bond.

When the bond including the broken line is a double bond, the formula (1) represents a compound of the formula (1a) or a salt thereof:

[Chem. 14]

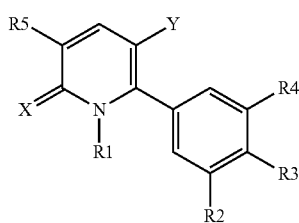

(In the formula, R1, R2, R3, R4, R5, X and Y are the same as defined in the formula (1)).

When the bond including the broken line is a single bond, the formula (1) represents a compound of the formula (1b) or a salt thereof:

[Chem. 15]

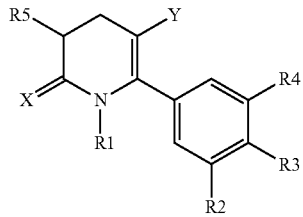

(In the formula, R1, R2, R3, R4, R5, X and Y are the same as defined in the formula (1)).

When R5 in the formula (1b) is a substituent other than hydrogen, the compound is R-isomer, S-isomer, or a mixture containing R-isomer and S-isomer in any proportions.

The compound represented by the formula (1) may have one or two chiral axes. In such a case, the compound may be any single isomer or a mixture of isomers in any proportions without limitation.

The compound represented by the formula (1) may have a chiral atom. In such a case, the compound may be any single isomer or a mixture of isomers in any proportions without limitation.

The compound represented by the formula (1) may have geometric isomeric forms. In such a case, the compound may be any single isomer or a mixture of isomers in any proportions without limitation.

The compound represented by the formula (1) may form a salt with, for example, an acid such as hydrochloric acid, sulfuric acid, acetic acid, fumaric acid or maleic acid, or a metal such as sodium, potassium or calcium. The form of the salt is not particularly limited as long as the salt may be used as an agricultural and horticultural fungicide.

The "substituent(s) A" in the formula (1) is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove).

In particular, the substituent(s) A is preferably a cyano group, a C1-C6 alkoxy group or Rc-L- (wherein Re and L are the same as defined hereinabove), and particularly preferably a cyano group or a C1-C6 alkoxy group.

The terms used in association with the substituent(s) A are the same as defined hereinabove.

Specifically, some preferred examples of the substituents A are hydroxy group; cyano group;

C3-C8 cycloalkyl groups such as cyclopropyl group, cyclobutyl group, cyclopentyl group and cyclohexyl group;

C1-C6 alkoxy groups such as methoxy group, ethoxy group, propyloxy group and isopropyloxy group;

C1-C6 haloalkoxy groups such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group;

C3-C8 cycloalkoxy groups such as cyclopropyloxy group, cyclobutoxy group, cyclopentyloxy group and cyclohexyloxy group;

RaRbN— (wherein Ra and Rb are the same as defined hereinabove) such as amino group, methylamino group, ethylamino group, (methoxymethyl)amino group, (2-methoxyethyl)amino group, (cyanomethyl)amino group, (2-cyanoethyl)amino group, dimethylamino group, ethylmethylamino group, diethylamino group, (methoxymethyl)methylamino group, (2-methoxyethyl)methylamino group, (cyanomethyl)methylamino group, (2-cyanoethyl)methylamino group, 2,2-difluoroethylamino group, 2,2,2-trifluoroethylamino group, cyclopropylamino group, (cyclopropyl)methylamino group, pyrrolidinyl group and piperidinyl group;

Rc-L- (wherein Rc and L are the same as defined hereinabove) such as methylthio group, methanesulfinyl group, methanesulfonyl group, trifluoromethylthio group, trifluoromethanesulfinyl group and trifluoromethanesulfonyl group; and the like.

Specifically, more preferred examples of the substituents A are hydroxy group; cyano group;

C3-C8 cycloalkyl groups such as cyclopropyl group and cyclobutyl group;

C1-C6 alkoxy groups such as methoxy group and ethoxy group;

C1-C6 haloalkoxy groups such as difluoromethoxy group, trifluoromethoxy group, 2,2-difluoroethoxy group and 2,2,2-trifluoroethoxy group;

C3-C8 cycloalkoxy groups such as cyclopropyloxy group and cyclobutoxy group;

RaRbN— (wherein Ra and Rb are the same as defined hereinabove) such as dimethylamino group, ethylmethylamino group and diethylamino group;

Rc-L- (wherein Rc and L are the same as defined hereinabove) such as methylthio group, methanesulfinyl group and methanesulfonyl group; and the like.

The "substituent(s) B" in the formula (1) is at least one selected from the group consisting of cyano group, C1-C6 alkoxy groups, C1-C6 haloalkoxy groups and C3-C8 cycloalkoxy groups.

In particular, the substituent(s) B is preferably a cyano group or a C1-C6 alkoxy group.

The terms used in association with the substituent(s) B are the same as defined hereinabove.

Specifically, some preferred examples of the substituents B are cyano group;

C1-C6 alkoxy groups such as methoxy group, ethoxy group, propyloxy group and isopropyloxy group;

C1-C6 haloalkoxy groups such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group;

C3-C8 cycloalkoxy groups such as cyclopropyloxy group, cyclobutoxy group, cyclopentyloxy group and cyclohexyloxy group; and the like.

Specifically, more preferred examples of the substituents B are cyano group;

C1-C6 alkoxy groups such as methoxy group and ethoxy group;

C1-C6 haloalkoxy groups such as difluoromethoxy group, trifluoromethoxy group, 2,2-difluoroethoxy group and 2,2,2-trifluoroethoxy group;

C3-C8 cycloalkoxy groups such as cyclopropyloxy group and cyclobutoxy group; and the like.

The "substituent(s) C" in the formula (1) is at least one selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— (wherein Ra and Rb are the same as defined hereinabove), Rc-L- (wherein Rc and L are the same as defined hereinabove), RdC(=O)— (wherein Rd is defined the same as Rx1 described hereinabove) and 3 to 6-membered ring groups containing 1 to 2 oxygen atoms.

In particular, it is preferable that the substituent(s) C is a cyano group, a C3-C8 cycloalkyl group, a C1-C6 alkoxy group, a C1-C6 haloalkoxy group, Rc-L- (wherein Rc and L are the same as defined hereinabove), RdC(=O)— (wherein Rd is defined the same as Rx1 described hereinabove) or a 3 to 6-membered ring group containing 1 to 2 oxygen atoms, and it is particularly preferable that the substituent(s) C is a cyano group, a C1-C6 alkoxy group, Rc-L- (wherein Rc and L are the same as defined hereinabove) or a 3 to 6-membered ring group containing 1 to 2 oxygen atoms.

The terms used in association with the substituent(s) C are the same as defined hereinabove.

Specifically, some preferred examples of the substituents C are hydroxy group; cyano group;

C3-C8 cycloalkyl groups such as cyclopropyl group, cyclobutyl group, cyclopentyl group and cyclohexyl group;

C1-C6 alkoxy groups such as methoxy group, ethoxy group, propyloxy group, isopropyloxy group, butoxy group, isobutoxy group and t-butoxy group;

C1-C6 haloalkoxy groups such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group;

C3-C8 cycloalkoxy groups such as cyclopropyloxy group, cyclobutoxy group, cyclopentyloxy group and cyclohexyloxy group;

C2-C6 alkoxyalkoxy groups such as methoxymethoxy group, ethoxymethoxy group, methoxyethoxy group, ethoxyethoxy group and methoxypropyloxy group;

RaRbN— (wherein Ra and Rb are the same as defined hereinabove) such as amino group, methylamino group, ethylamino group, (methoxymethyl)amino group, (2-methoxyethyl)amino group, (cyanomethyl)amino group, (2-cyanoethyl)amino group, dimethylamino group, ethylmethylamino group, diethylamino group, (methoxymethyl)methylamino group, (2-methoxyethyl)methylamino group, (cyanomethyl)methylamino group, (2-cyanoethyl)methylamino group, 2,2-difluoroethylamino group, 2,2,2-trifluoroethylamino group, cyclopropylamino group, (cyclopropyl)methylamino group, pyrrolidinyl group and piperidinyl group;

Rc-L- (wherein Rc and L are the same as defined hereinabove) such as methylthio group, methanesulfinyl group, methanesulfonyl group, trifluoromethylthio group, trifluoromethanesulfinyl group and trifluoromethanesulfonyl group;

RdC(=O)— (wherein Rd is defined the same as Rx1 described hereinabove) such as acetyl group, methoxyacetyl group, cyanoacetyl group, propionyl group, difluoroacetyl group, trifluoroacetyl group, cyclopropanecarbonyl group, methoxycarbonyl group, ethoxycarbonyl group, 2,2-difluoroethoxycarbonyl group, 2,2,2-trifluoroethoxycarbonyl group, 3,3,3-trifluoropropyloxycarbonyl group, cyclopropyloxycarbonyl group, aminocarbonyl group, methylaminocarbonyl group, ethylaminocarbonyl group, (methoxymethyl)aminocarbonyl group, (2-methoxyethyl)aminocarbonyl group, (cyanomethyl)aminocarbonyl group, (2-cyanoethyl)aminocarbonyl group, dimethylaminocarbonyl group, ethylmethylaminocarbonyl group, diethylaminocarbonyl group, (methoxymethyl)methylaminocarbonyl group, (2-methoxyethyl)methylaminocarbonyl group, (cyanomethyl)methylaminocarbonyl group, (2-cyanoethyl)methylaminocarbonyl group, 2,2-difluoroethylaminocarbonyl group, 2,2,2-trifluoroethylaminocarbonyl group, cyclopropylaminocarbonyl group, (cyclopropyl)methylaminocarbonyl group, pyrrolidinylcarbonyl group and piperidinylcarbonyl group;

3 to 6-membered ring groups containing 1 to 2 oxygen atoms such as oxolanyl group, oxanyl group, 1,3-dioxolanyl group and 1,3-dioxanyl group; and the like.

Specifically, more preferred examples of the substituents C are hydroxy group; cyano group;

C3-C8 cycloalkyl groups such as cyclopropyl group and cyclobutyl group;

C1-C6 alkoxy groups such as methoxy group and ethoxy group;

C1-C6 haloalkoxy groups such as difluoromethoxy group, trifluoromethoxy group, 2,2-difluoroethoxy group and 2,2,2-trifluoroethoxy group;

C3-C8 cycloalkoxy groups such as cyclopropyloxy group and cyclobutoxy group;

C2-C6 alkoxyalkoxy groups such as methoxymethoxy group, ethoxymethoxy group, methoxyethoxy group and ethoxyethoxy group;

RaRbN— (wherein Ra and Rb are the same as defined hereinabove) such as dimethylamino group, ethylmethylamino group and diethylamino group;

Rc-L- (wherein Rc and L are the same as defined hereinabove) such as methylthio group, methanesulfinyl group and methanesulfonyl group;

RdC(=O)— (wherein Rd is defined the same as Rx1 described hereinabove) such as acetyl group, methoxyacetyl group, cyanoacetyl group, difluoroacetyl group, trifluoroacetyl group, methoxycarbonyl group, ethoxycarbonyl group, aminocarbonyl group, dimethylaminocarbonyl group, ethylmethylaminocarbonyl group and diethylaminocarbonyl group;

3 to 6-membered ring groups containing 1 to 2 oxygen atoms such as 1,3-dioxolanyl group and 1,3-dioxanyl group; and the like.

The "substituent(s) D" in the formula (1) is at least one selected from the group consisting of halogen atoms, hydroxy group, cyano group, nitro group, C1-C6 alkyl groups optionally substituted with substituent(s) B, C1-C6 haloalkyl groups, C3-C8 cycloalkyl groups, C1-C6 alkoxy groups, C1-C6 haloalkoxy groups and C3-C8 cycloalkoxy groups.

In particular, it is preferable that the substituent(s) D is a halogen atom, a cyano group, a C1-C6 alkyl group optionally substituted with substituent(s) B, a C1-C6 haloalkyl group, a C1-C6 alkoxy group or a C1-C6 haloalkoxy group, and it is particularly preferable that the substituent(s) D is a halogen atom or a C1-C6 haloalkyl group.

The terms used in association with the substituent(s) D are the same as defined hereinabove. When the substituent(s) D is a "C1-C6 alkyl group optionally substituted with substituent(s) B" and when this group has substituent(s) B, the C1-C6 alkyl group is optionally substituted with substituent(s) B in place of any hydrogen atom(s).

Specifically, some preferred examples of the substituents D are:

halogen atoms such as fluorine atom, chlorine atom, bromine atom and iodine atom;

hydroxy group; cyano group; nitro group;

C1-C6 alkyl groups optionally substituted with substituent(s) B, such as methyl group, methoxymethyl group, ethoxymethyl group, cyanomethyl group, ethyl group, 2-methoxyethyl group, 2-ethoxyethyl group, 2-cyanoethyl group, propyl group, isopropyl group, butyl group and isobutyl group;

C1-C6 haloalkyl groups such as difluoromethyl group, trifluoromethyl group, 2,2-difluoroethyl group, 2,2,2-trifluoroethyl group, 3,3-difluoropropyl group and 3,3,3-trifluoropropyl group;

C3-C8 cycloalkyl groups such as cyclopropyl group, cyclobutyl group, cyclopentyl group and cyclohexyl group;

C1-C6 alkoxy groups such as methoxy group, ethoxy group, propyloxy group, isopropyloxy group, butoxy group, isobutoxy group and t-butoxy group;

C1-C6 haloalkoxy groups such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group;

C3-C8 cycloalkoxy groups such as cyclopropyloxy group, cyclobutoxy group, cyclopentyloxy group and cyclohexyloxy group; and the like.

Specifically, more preferred examples of the substituents D are:

halogen atoms such as fluorine atom, chlorine atom and bromine atom;

hydroxy group; cyano group; nitro group;

C1-C6 alkyl groups optionally substituted with substituent(s) B, such as methyl group, methoxymethyl group, ethoxymethyl group, cyanomethyl group, ethyl group, 2-methoxyethyl group, 2-ethoxyethyl group and 2-cyanoethyl group;

C1-C6 haloalkyl groups such as difluoromethyl group, trifluoromethyl group, 2,2-difluoroethyl group and 2,2,2-trifluoroethyl group;

C3-C8 cycloalkyl groups such as cyclopropyl group and cyclobutyl group;

C1-C6 alkoxy groups such as methoxy group, ethoxy group, propyloxy group and isopropyloxy group;

C1-C6 haloalkoxy groups such as difluoromethoxy group, trifluoromethoxy group, 2,2-difluoroethoxy group and 2,2,2-trifluoroethoxy group;

C3-C8 cycloalkoxy groups such as cyclopropyloxy group and cyclobutoxy group; and the like.

All the compounds resulting from any combination of preferred embodiments of R1, R2, R3, R4, R5, R6, R7, X, Y, the broken line, the substituents A, the substituents B, the substituents C and the substituents D described hereinabove are incorporated herein as the compounds of the formula (1) according to the present invention.

Next, some specific compounds of the present invention may be represented by combinations of the structural formulae shown in Table 1, Y shown in Table 2, and X that is an oxygen atom or a sulfur atom. Such compounds are only illustrative and do not limit the scope of the present invention thereto.

TABLE 1

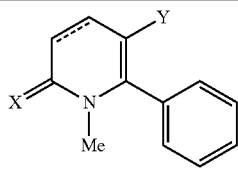

P-1

TABLE 1-continued
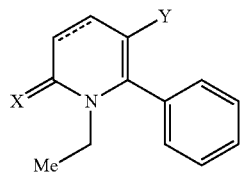 P-2
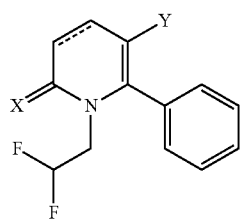 P-3
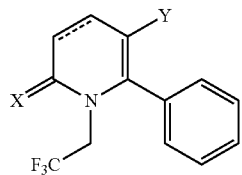 P-4
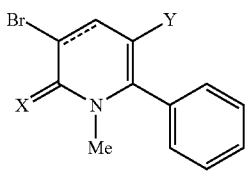 P-5
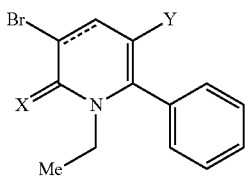 P-6
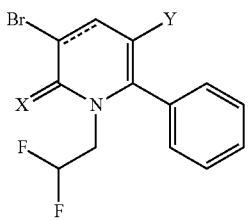 P-7
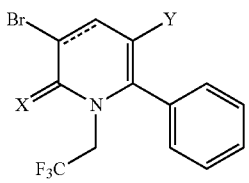 P-8
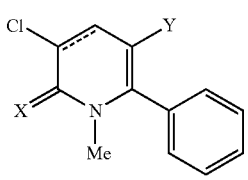 P-9
TABLE 1-continued
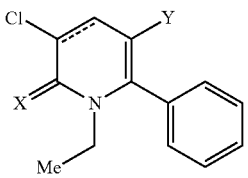 P-10
P-11
P-12
P-13
P-14
P-15
P-16
P-17

TABLE 1-continued
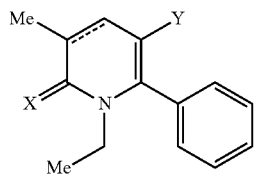 P-18
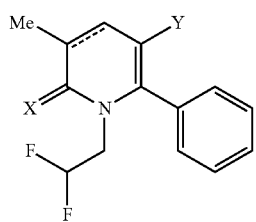 P-19
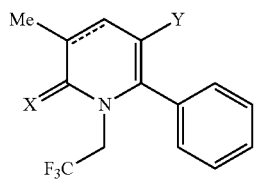 P-20
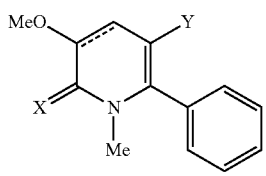 P-21
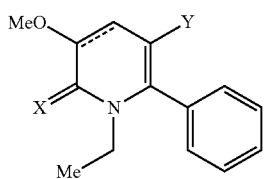 P-22
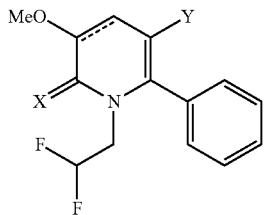 P-23
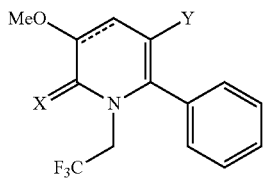 P-24
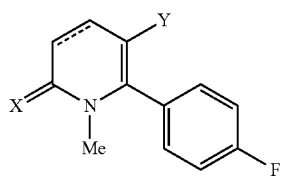 P-25
TABLE 1-continued
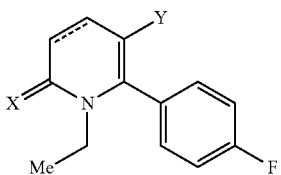 P-26
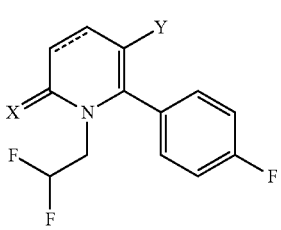 P-27
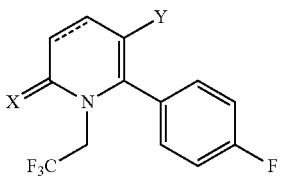 P-29
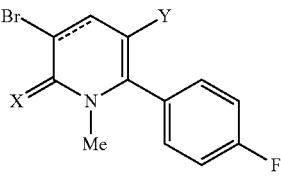 P-29
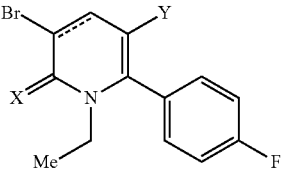 P-30
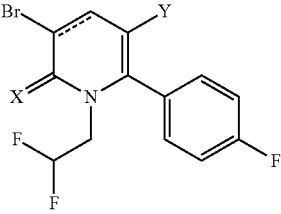 P-31
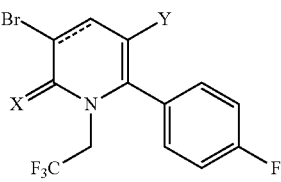 P-32
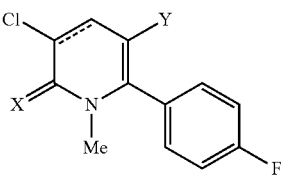 P-33

TABLE 1-continued
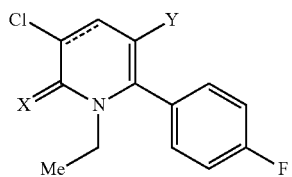 P-34
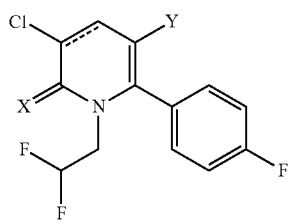 P-35
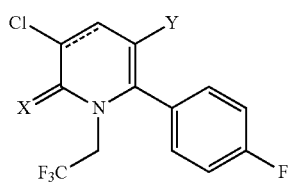 P-36
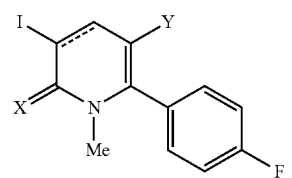 P-37
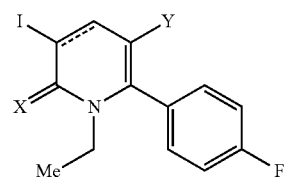 P-38
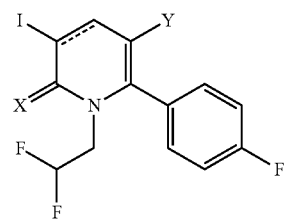 P-39
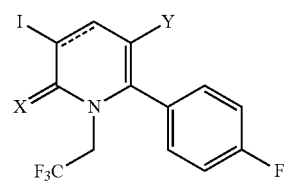 P-40
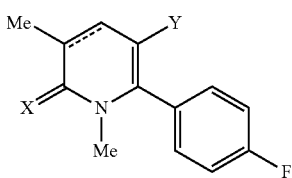 P-41
TABLE 1-continued
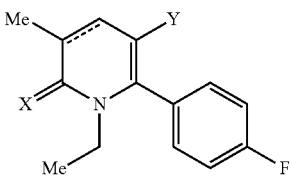 P-42
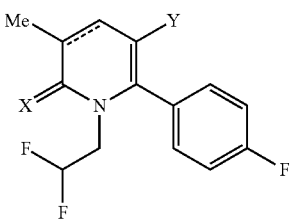 P-43
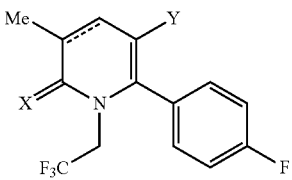 P-44
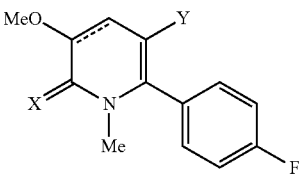 P-45
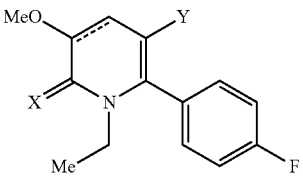 P-46
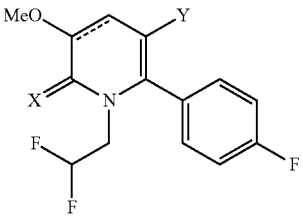 P-47
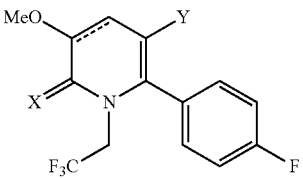 P-48
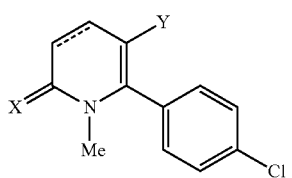 P-49

TABLE 1-continued
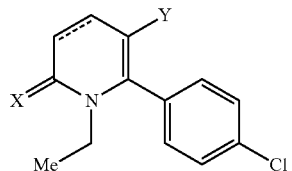 P-50
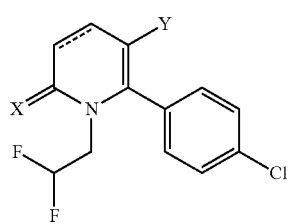 P-51
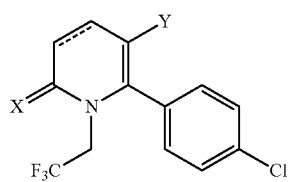 P-52
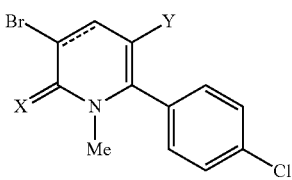 P-53
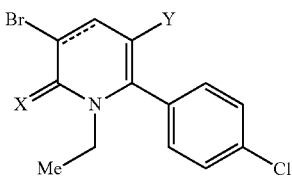 P-54
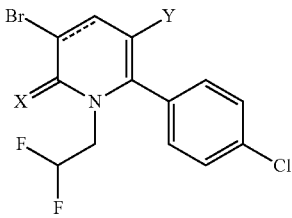 P-55
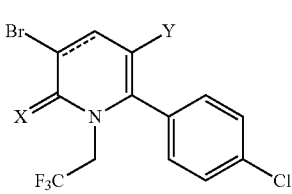 P-56
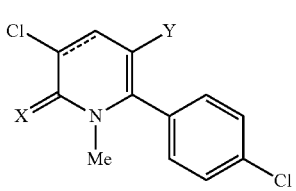 P-57
TABLE 1-continued
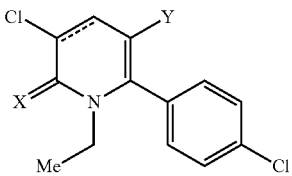 P-58
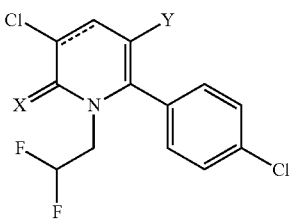 P-59
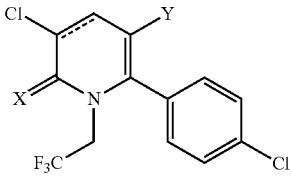 P-60
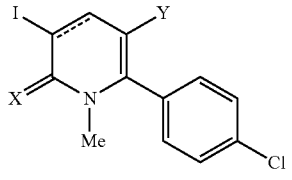 P-61
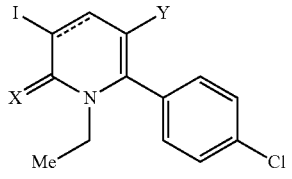 P-62
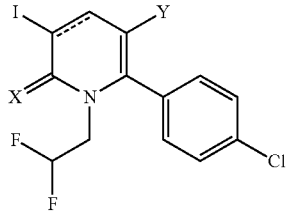 P-63
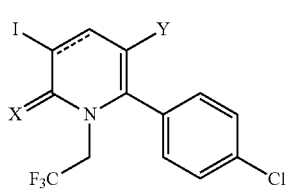 P-64
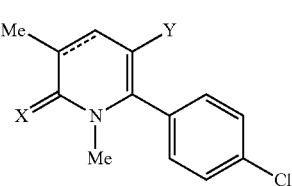 P-65

TABLE 1-continued
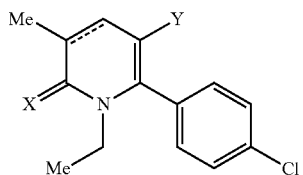 P-66
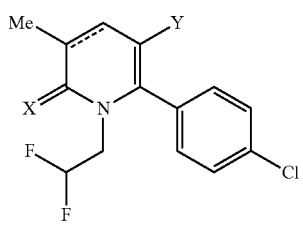 P-67
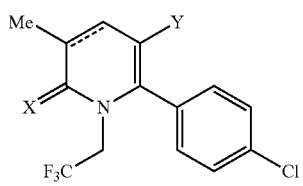 P-68
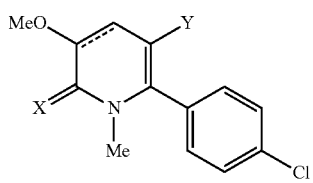 P-69
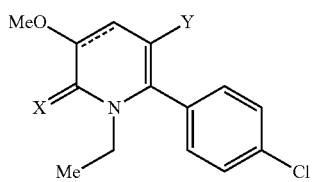 P-70
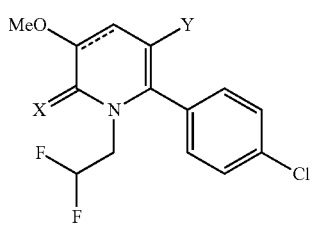 P-71
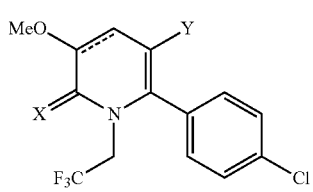 P-72
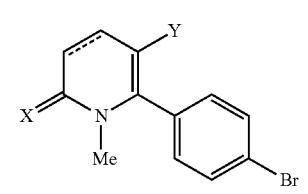 P-73
TABLE 1-continued
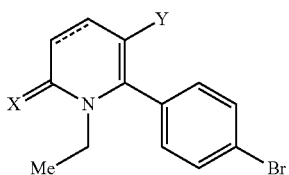 P-74
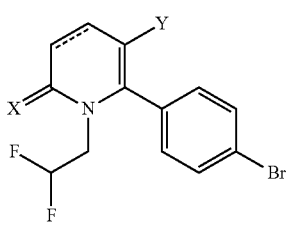 P-75
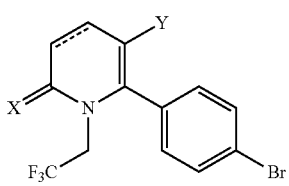 P-76
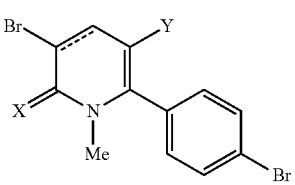 P-77
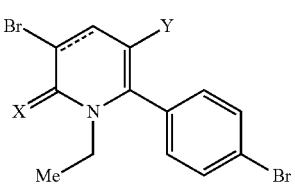 P-78
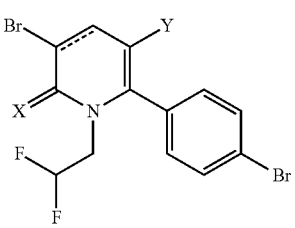 P-79
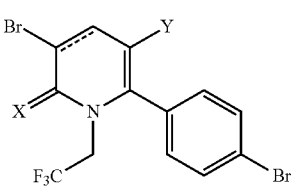 P-80
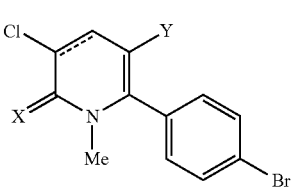 P-81

TABLE 1-continued
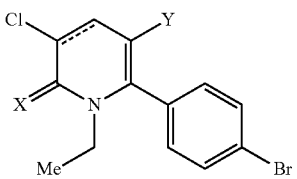 P-82
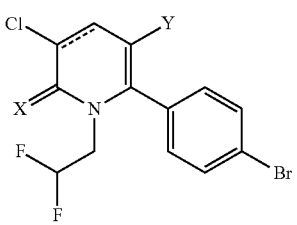 P-83
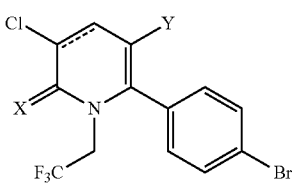 P-84
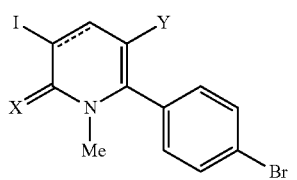 P-85
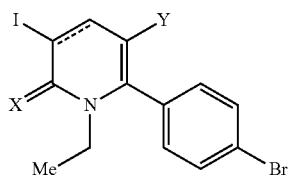 P-86
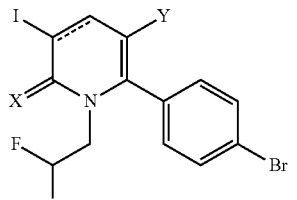 P-87
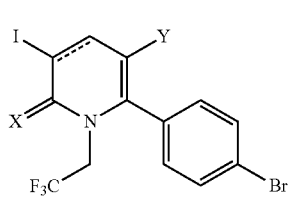 P-88
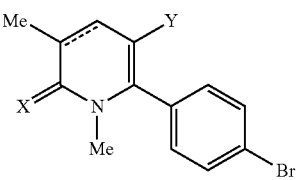 P-89
TABLE 1-continued
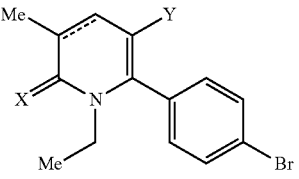 P-90
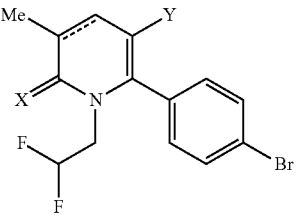 P-91
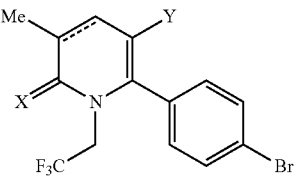 P-92
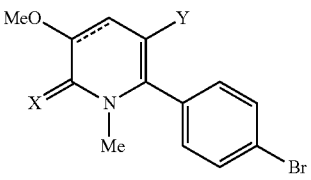 P-93
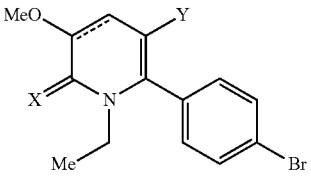 P-94
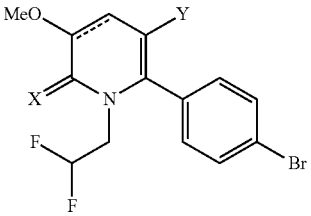 P-95
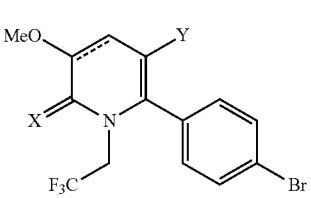 P-96
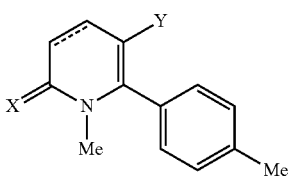 P-97

TABLE 1-continued
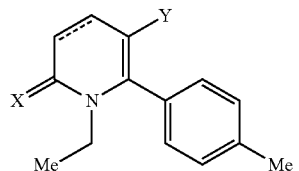 P-98
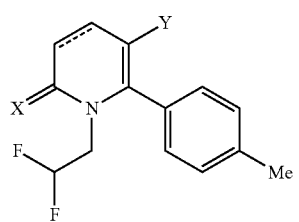 P-99
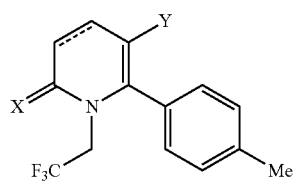 P-100
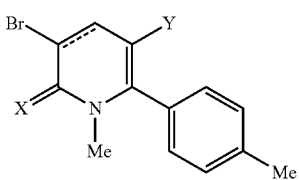 P-101
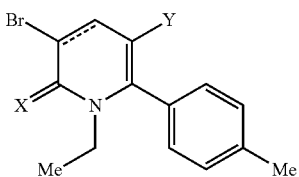 P-102
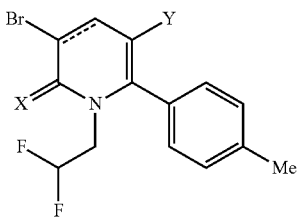 P-103
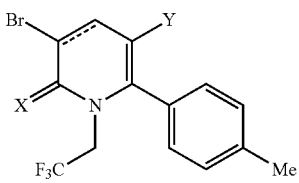 P-104
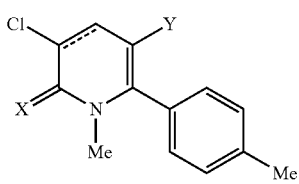 P-105
TABLE 1-continued
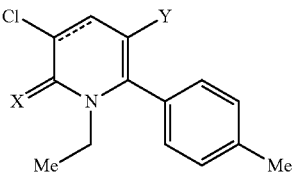 P-106
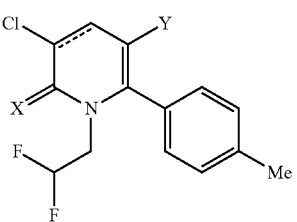 P-107
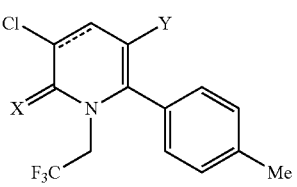 P-108
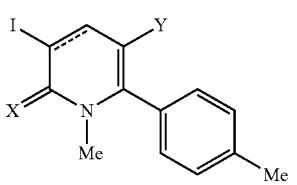 P-109
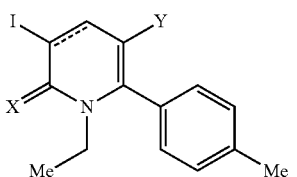 P-110
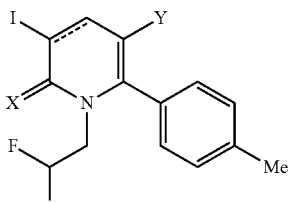 P-111
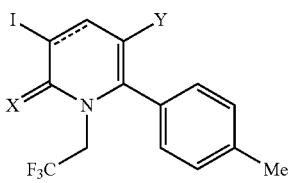 P-112
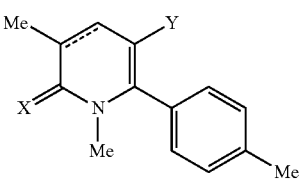 P-113

TABLE 1-continued

| Compound | Structure |
|---|---|
| P-114 | Pyridine with Me at 3, Y at 5, X at 2, N-Et, 4-methylphenyl at 6 |
| P-115 | Pyridine with Me at 3, Y at 5, X at 2, N-CH2CHF2, 4-methylphenyl at 6 |
| P-116 | Pyridine with Me at 3, Y at 5, X at 2, N-CH2CF3, 4-methylphenyl at 6 |
| P-117 | Pyridine with MeO at 3, Y at 5, X at 2, N-Me, 4-methylphenyl at 6 |
| P-118 | Pyridine with MeO at 3, Y at 5, X at 2, N-Et, 4-methylphenyl at 6 |
| P-119 | Pyridine with MeO at 3, Y at 5, X at 2, N-CH2CHF2, 4-methylphenyl at 6 |
| P-120 | Pyridine with MeO at 3, Y at 5, X at 2, N-CH2CF3, 4-methylphenyl at 6 |
| P-121 | Pyridine with Y at 5, X at 2, N-Me, 3,5-difluorophenyl at 6 |
| P-122 | Pyridine with Y at 5, X at 2, N-Et, 3,5-difluorophenyl at 6 |
| P-123 | Pyridine with Y at 5, X at 2, N-CH2CHF2, 3,5-difluorophenyl at 6 |
| P-124 | Pyridine with Y at 5, X at 2, N-CH2CF3, 3,5-difluorophenyl at 6 |
| P-125 | Pyridine with Br at 3, Y at 5, X at 2, N-Me, 3,5-difluorophenyl at 6 |
| P-126 | Pyridine with Br at 3, Y at 5, X at 2, N-Et, 3,5-difluorophenyl at 6 |
| P-127 | Pyridine with Br at 3, Y at 5, X at 2, N-CH2CHF2, 3,5-difluorophenyl at 6 |
| P-128 | Pyridine with Br at 3, Y at 5, X at 2, N-CH2CF3, 3,5-difluorophenyl at 6 |

TABLE 1-continued
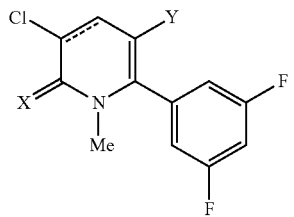 P-129
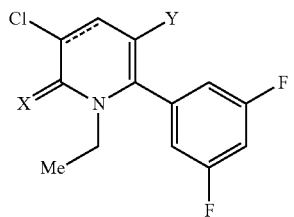 P-130
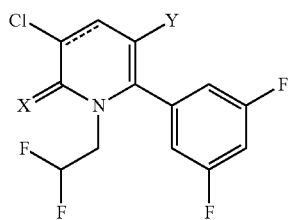 P-131
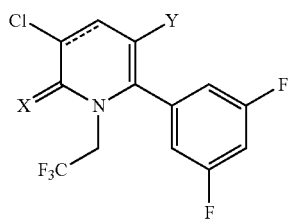 P-132
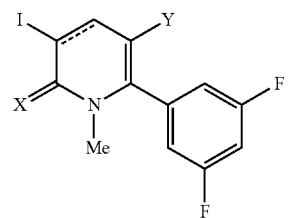 P-133
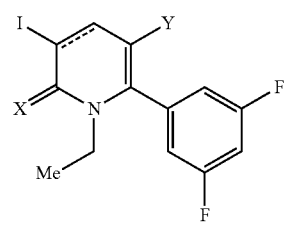 P-134
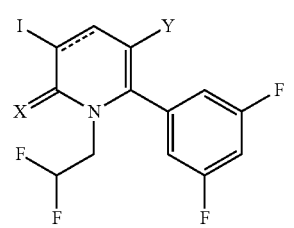 P-135
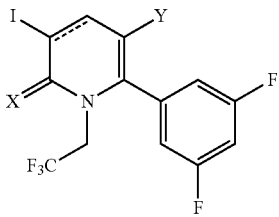 P-136
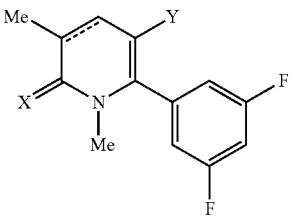 P-137
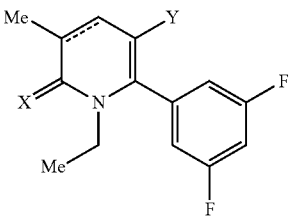 P-138
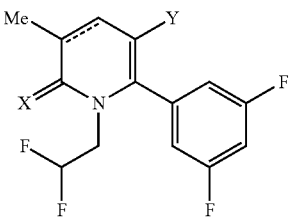 P-139
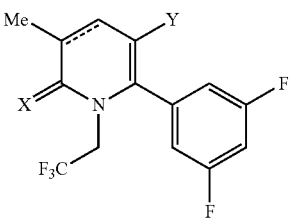 P-140
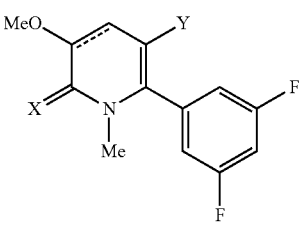 P-141
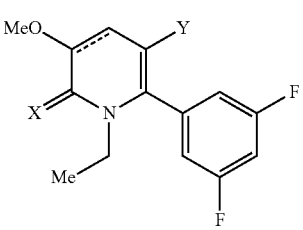 P-142

TABLE 1-continued
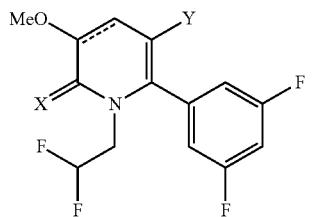
P-143
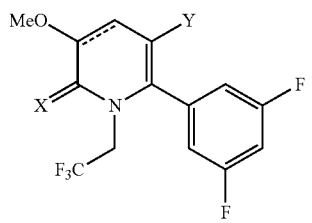
P-144
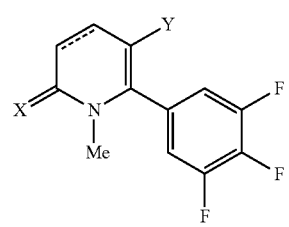
P-145
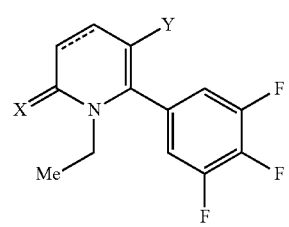
P-146
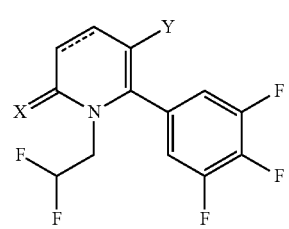
P-147
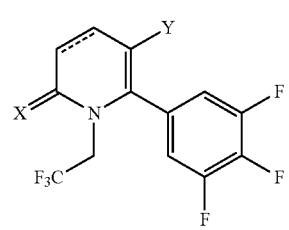
P-148
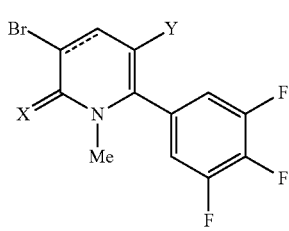
P-149
TABLE 1-continued
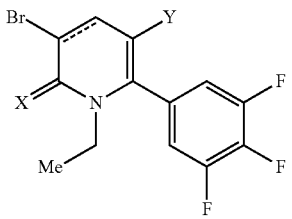
P-150
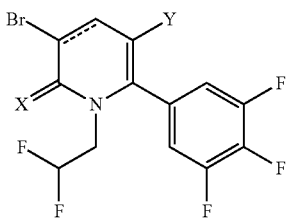
P-151
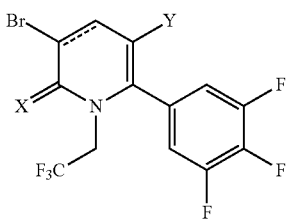
P-152
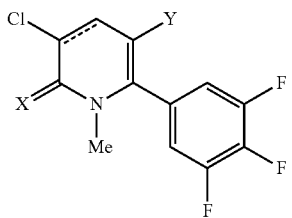
P-153
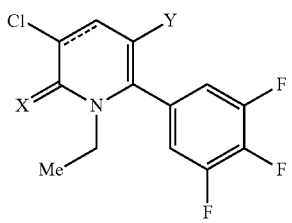
P-154
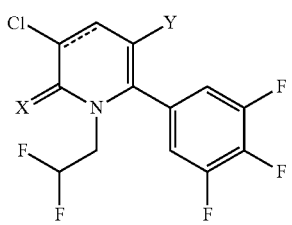
P-155
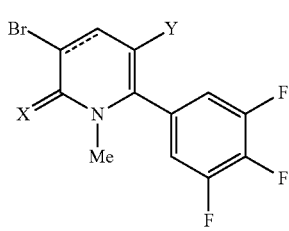
P-156

TABLE 1-continued
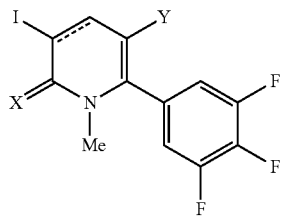 P-157
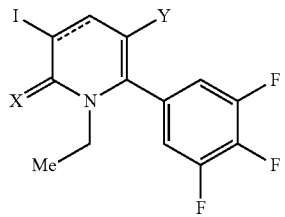 P-158
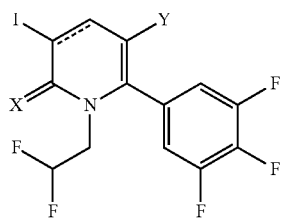 P-159
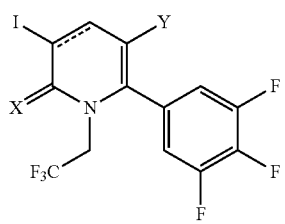 P-160
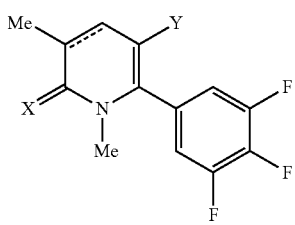 P-161
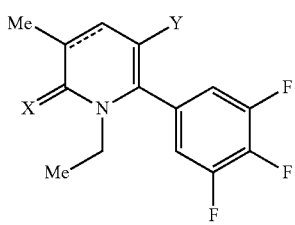 P-162
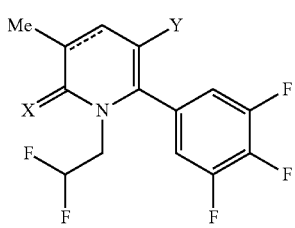 P-163
TABLE 1-continued
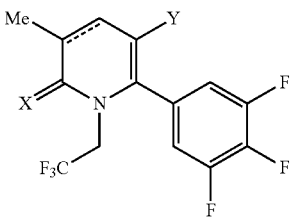 P-164
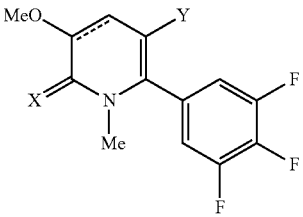 P-165
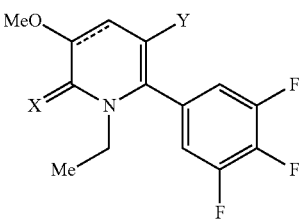 P-166
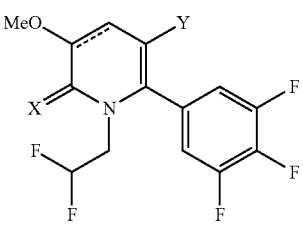 P-167
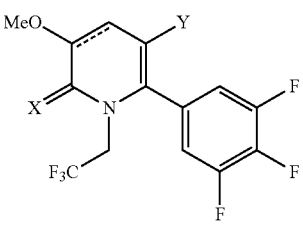 P-168
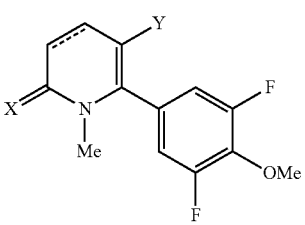 P-169
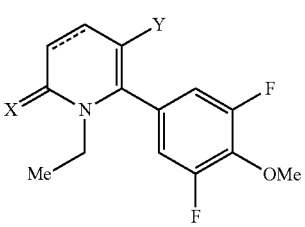 P-170

TABLE 1-continued
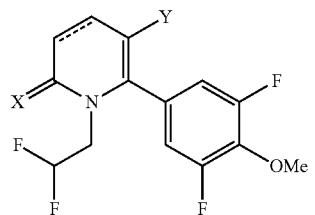 P-171
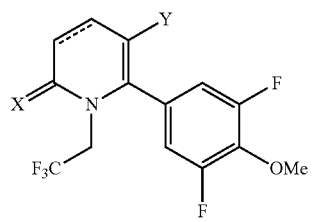 P-172
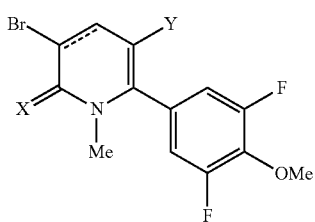 P-173
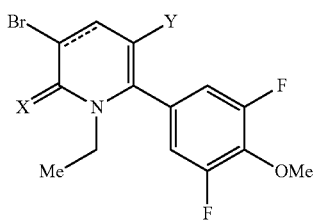 P-174
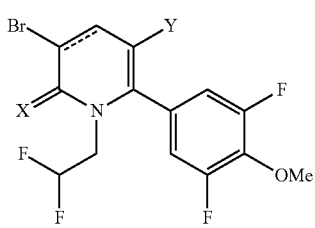 P-175
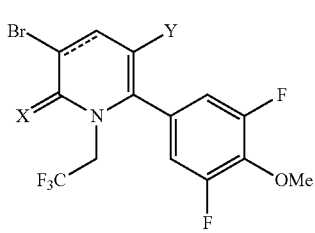 P-176
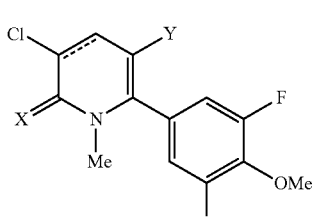 P-177
TABLE 1-continued
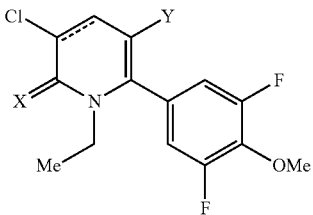 P-178
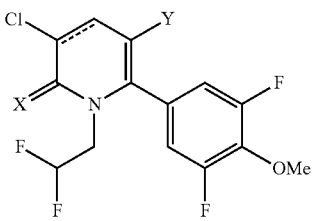 P-179
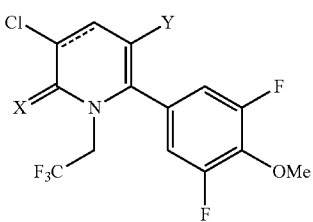 P-180
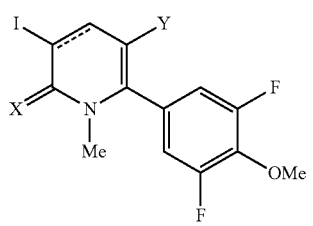 P-181
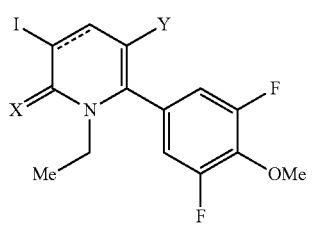 P-182
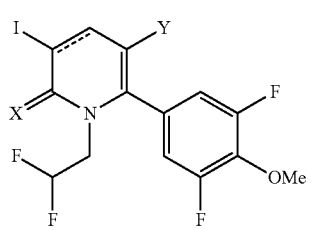 P-183
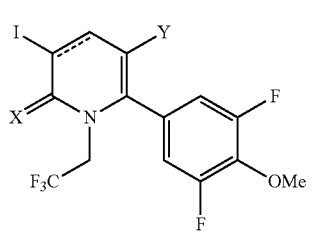 P-184

TABLE 1-continued

P-185, P-186, P-187, P-188, P-189, P-190, P-191, P-192, P-193, P-194, P-195, P-196, P-197, P-198, P-199

TABLE 1-continued
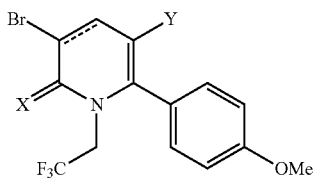 P-200
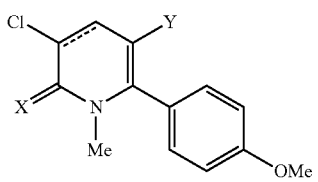 P-201
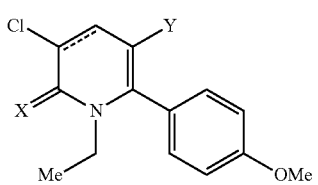 P-202
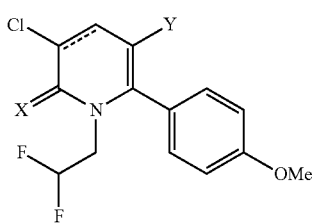 P-203
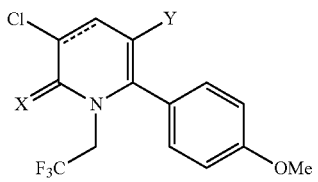 P-204
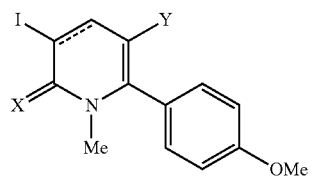 P-205
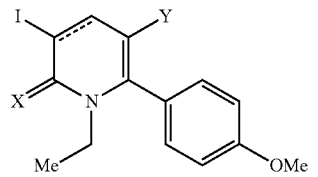 P-206
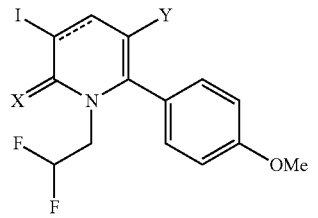 P-207
TABLE 1-continued
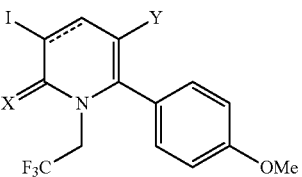 P-208
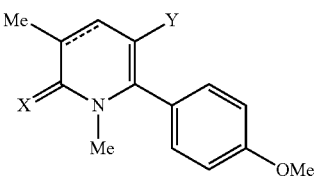 P-209
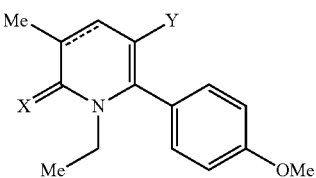 P-210
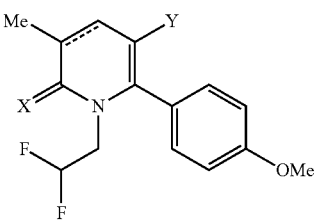 P-211
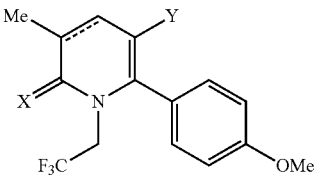 P-212
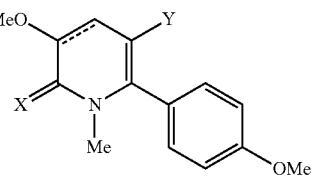 P-213
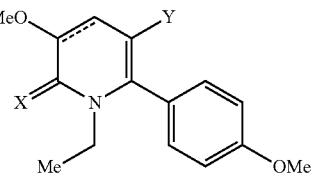 P-214
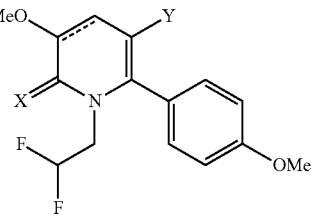 P-215

TABLE 1-continued
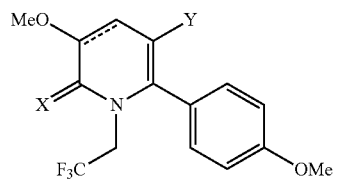 P-216
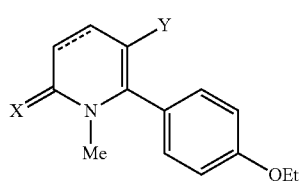 P-217
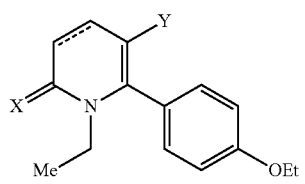 P-218
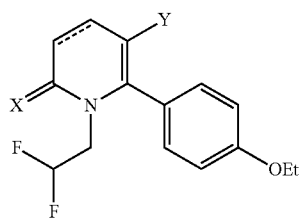 P-219
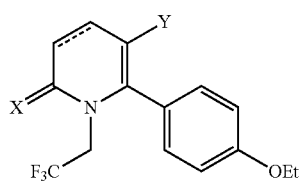 P-220
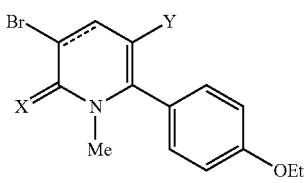 P-221
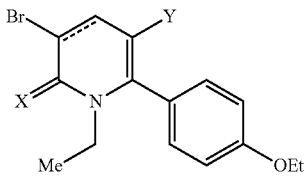 P-222
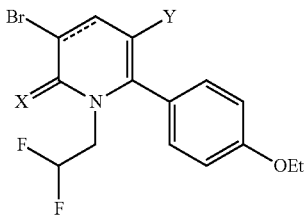 P-223
TABLE 1-continued
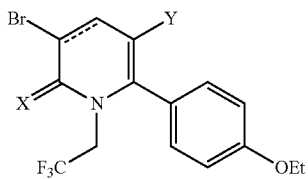 P-224
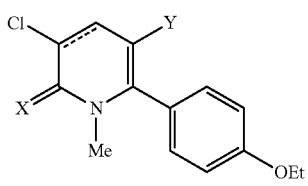 P-225
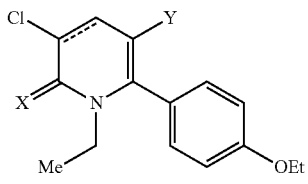 P-226
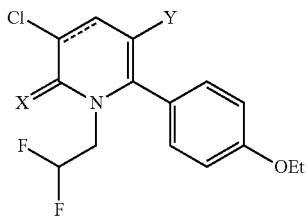 P-227
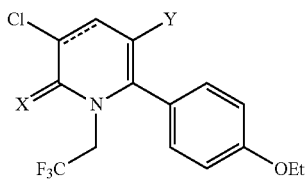 P-228
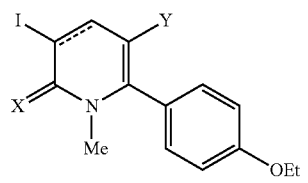 P-229
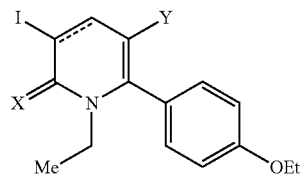 P-230
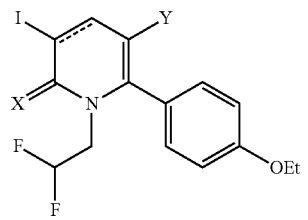 P-231

TABLE 1-continued
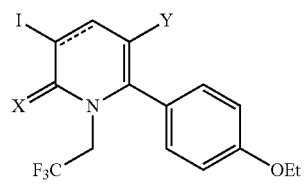 P-232
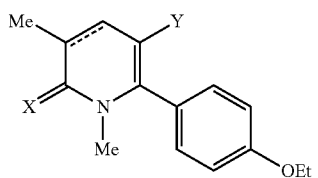 P-233
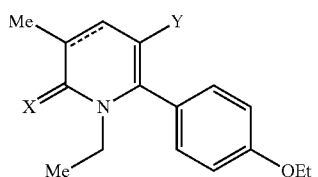 P-234
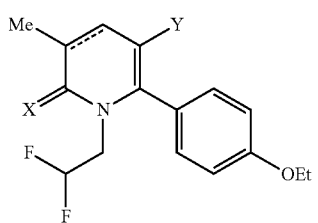 P-235
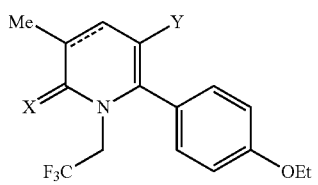 P-236
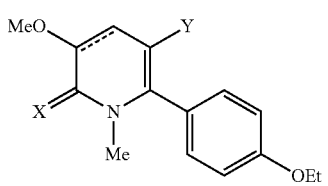 P-237
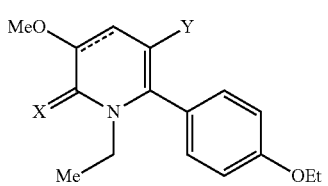 P-238
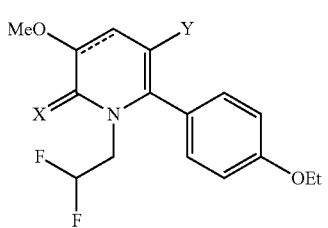 P-239
TABLE 1-continued
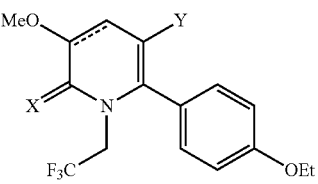 P-240
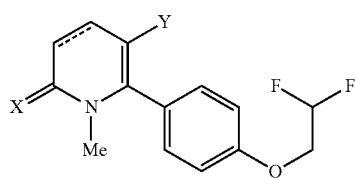 P-241
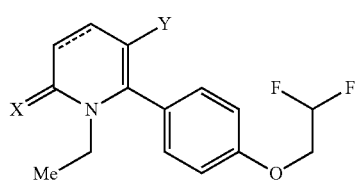 P-242
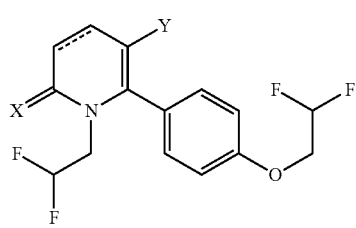 P-243
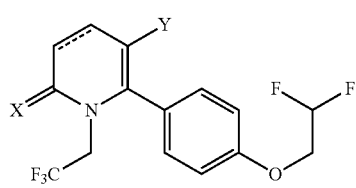 P-244
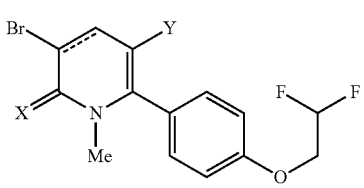 P-245
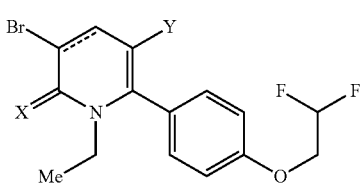 P-246
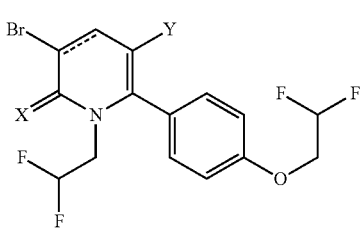 P-247

TABLE 1-continued
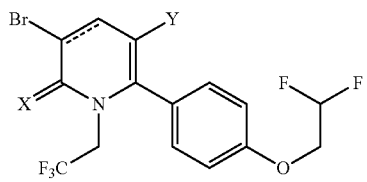 P-248
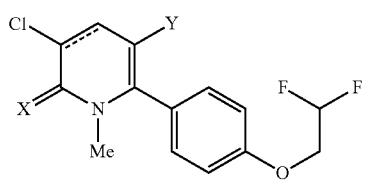 P-249
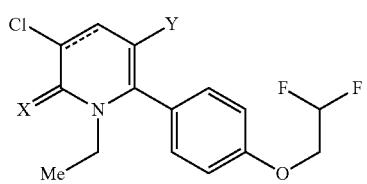 P-250
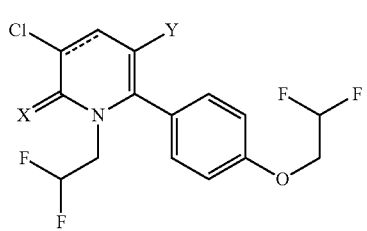 P-251
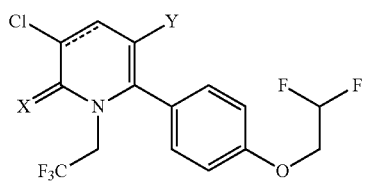 P-252
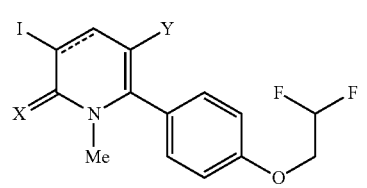 P-253
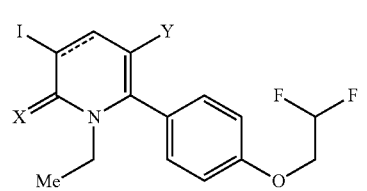 P-254
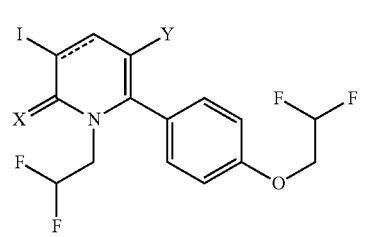 P-255
TABLE 1-continued
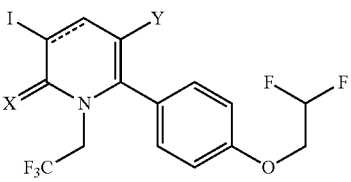 P-256
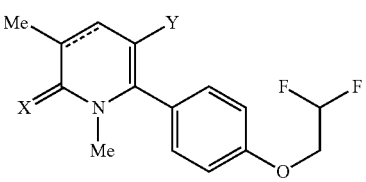 P-257
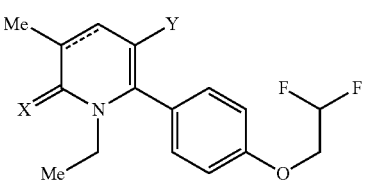 P-258
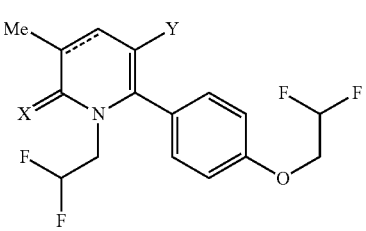 P-259
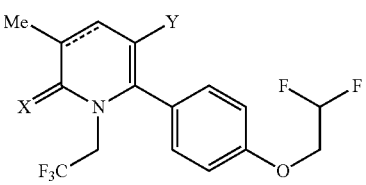 P-260
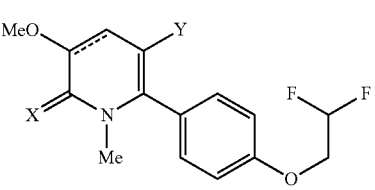 P-261
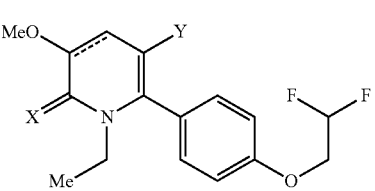 P-262
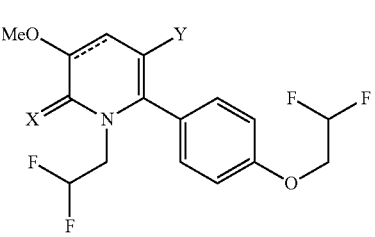 P-263

TABLE 1-continued
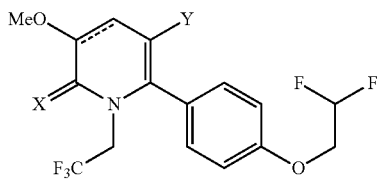
P-264
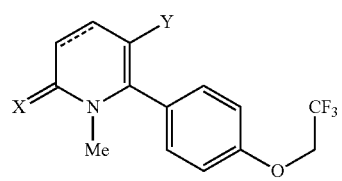
P-265
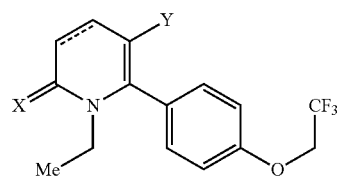
P-266
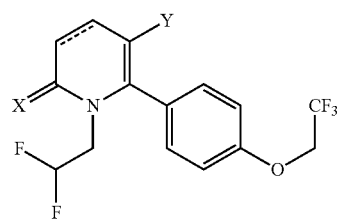
P-267
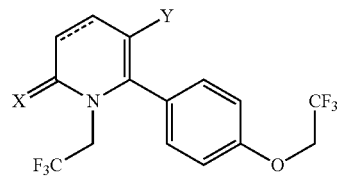
P-268
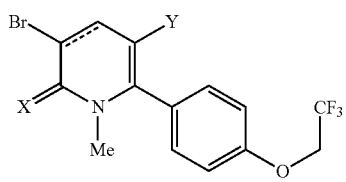
P-269
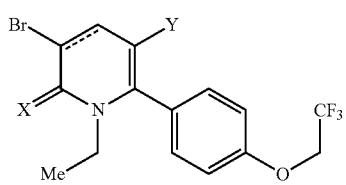
P-270
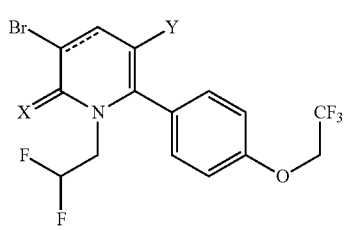
P-271
TABLE 1-continued
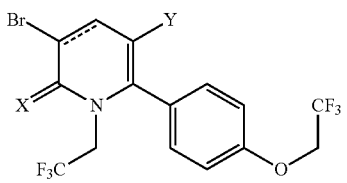
P-272
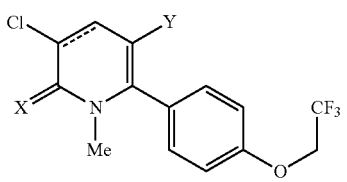
P-273
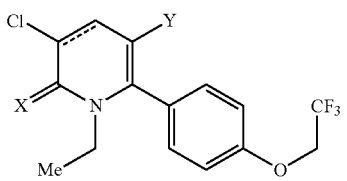
P-274
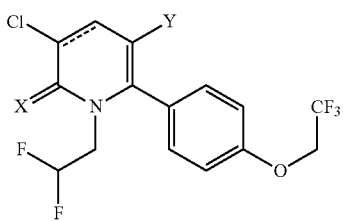
P-275
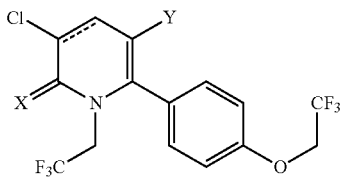
P-276
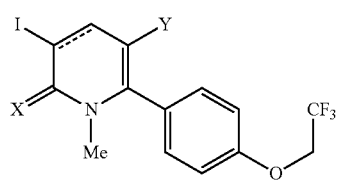
P-277
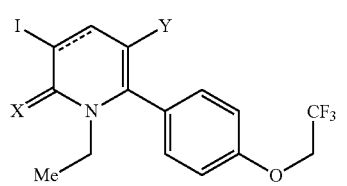
P-278
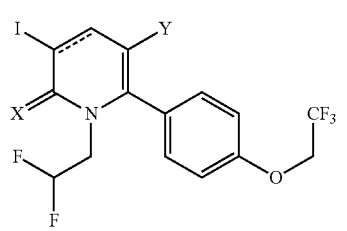
P-279

TABLE 1-continued
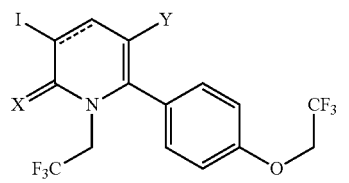 P-280
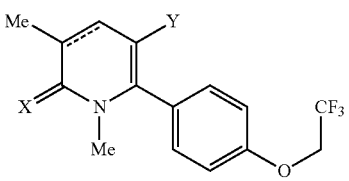 P-281
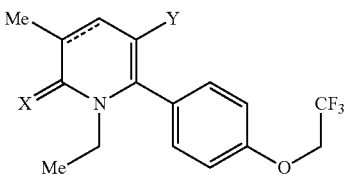 P-282
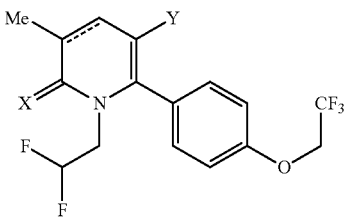 P-283
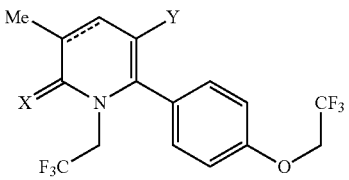 P-284
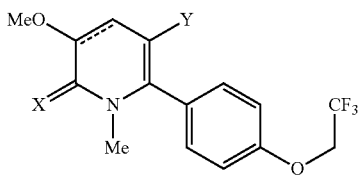 P-285
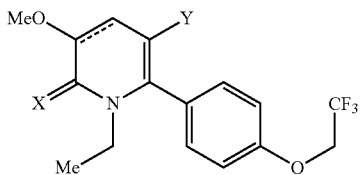 P-286
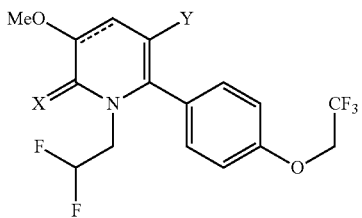 P-287
TABLE 1-continued
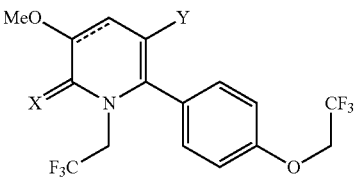 P-288
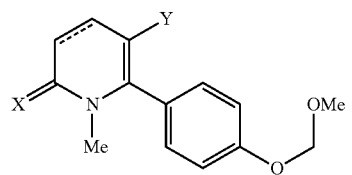 P-289
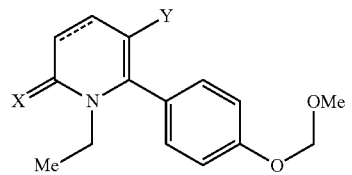 P-290
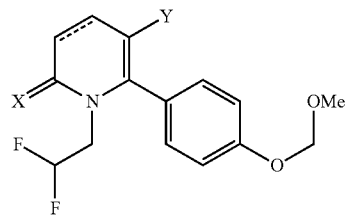 P-291
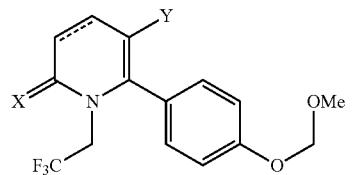 P-292
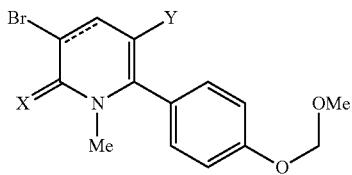 P-293
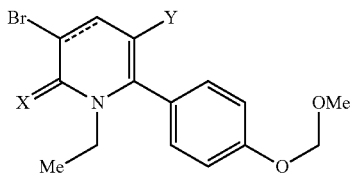 P-294
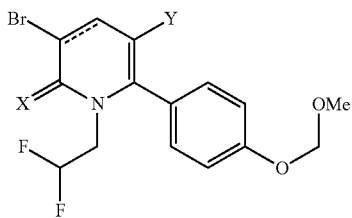 P-295

TABLE 1-continued
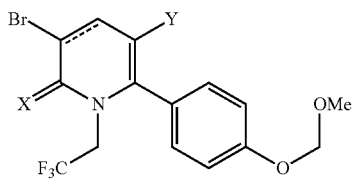 P-296
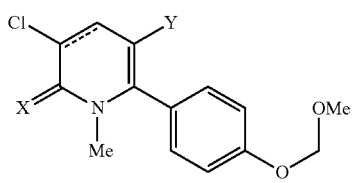 P-297
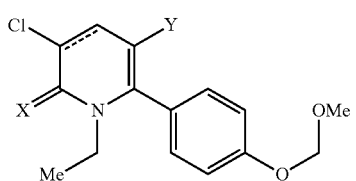 P-298
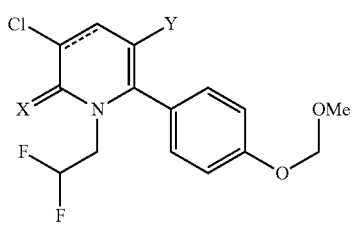 P-299
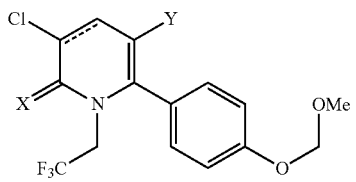 P-300
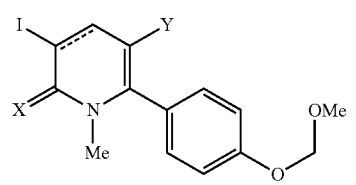 P-301
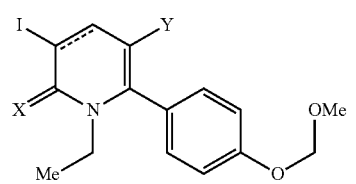 P-302
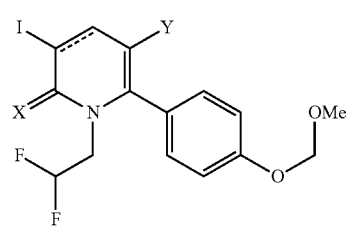 P-303
TABLE 1-continued
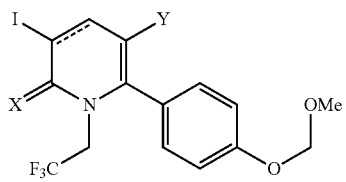 P-304
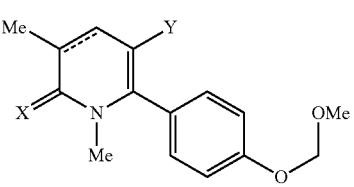 P-305
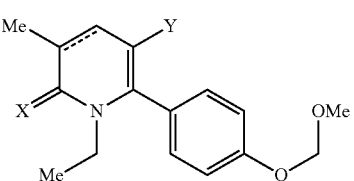 P-306
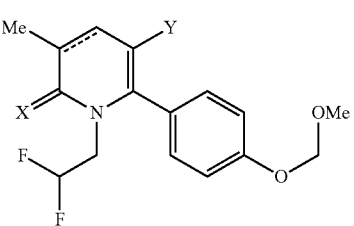 P-307
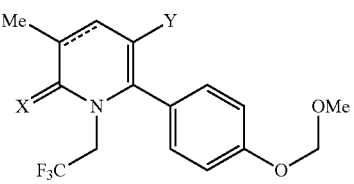 P-308
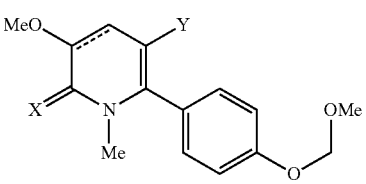 P-309
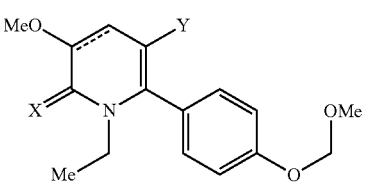 P-310
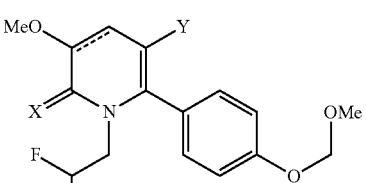 P-311

TABLE 1-continued
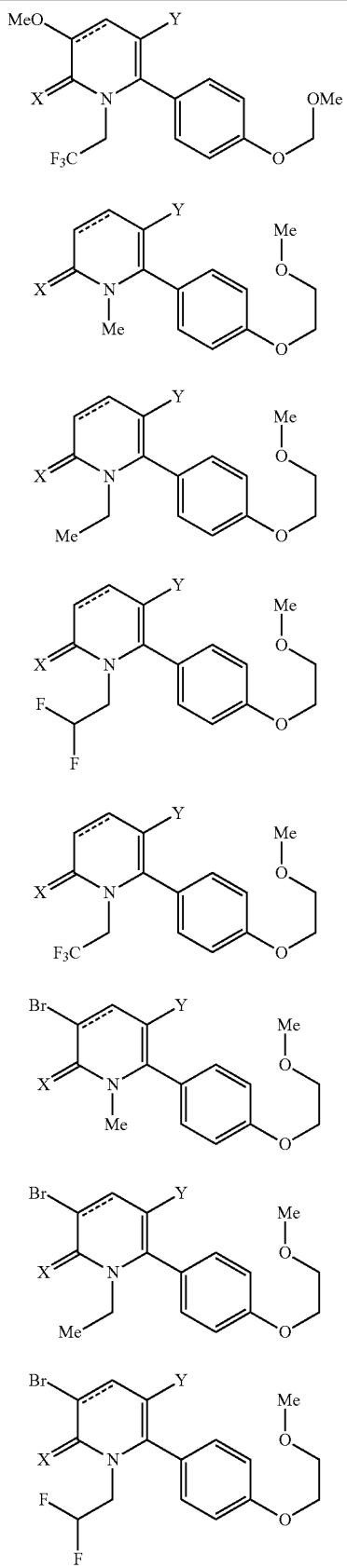
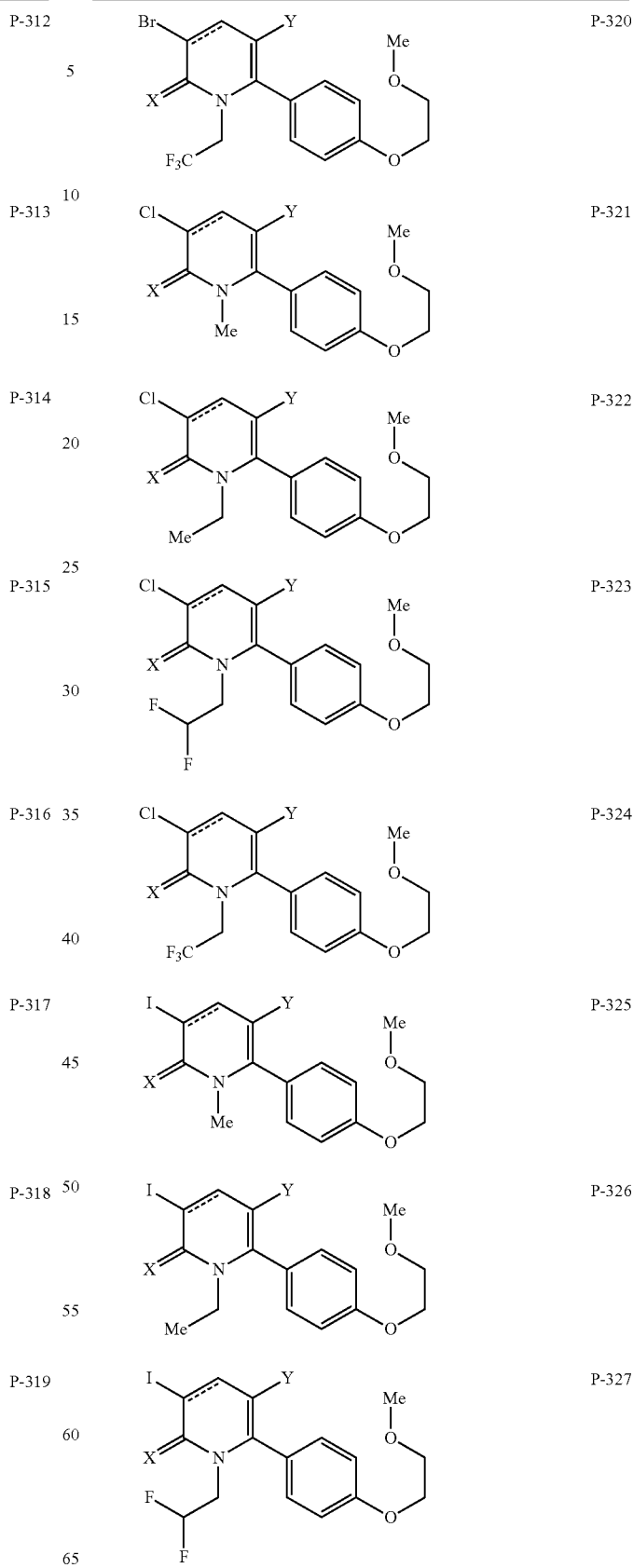

TABLE 1-continued
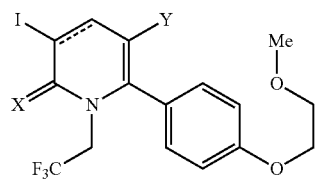 P-328
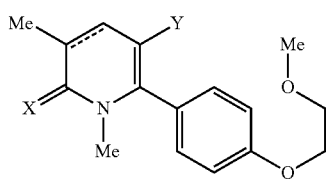 P-329
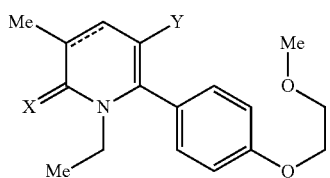 P-330
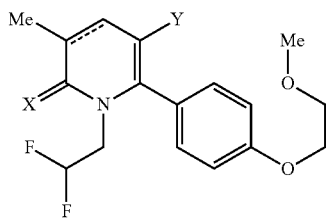 P-331
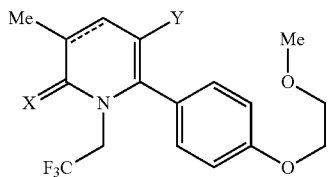 P-332
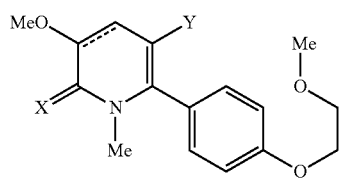 P-333
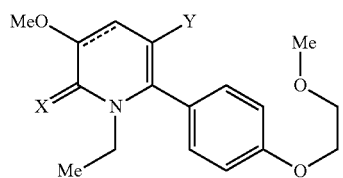 P-334
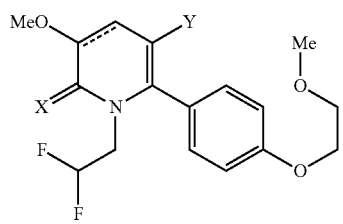 P-335
TABLE 1-continued
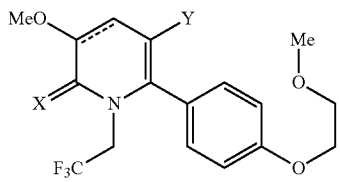 P-336
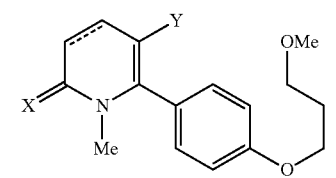 P-337
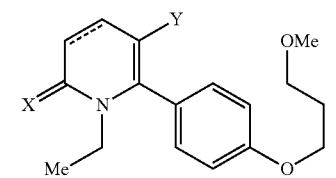 P-338
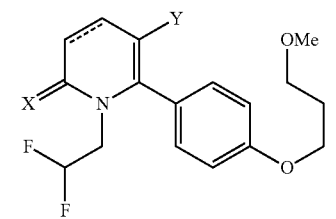 P-339
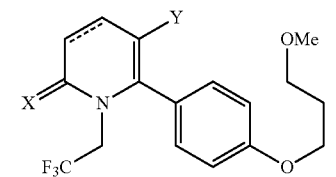 P-340
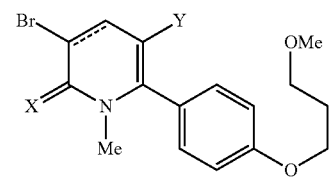 P-341
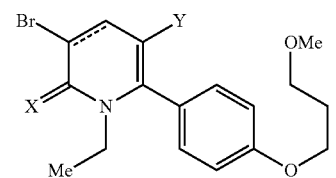 P-342
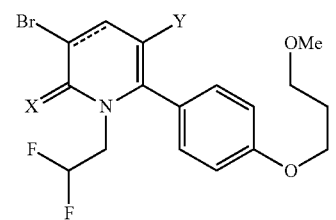 P-343

TABLE 1-continued
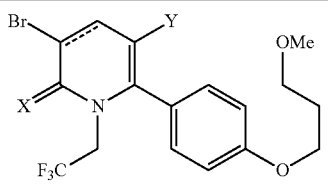 P-344
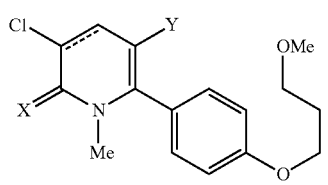 P-345
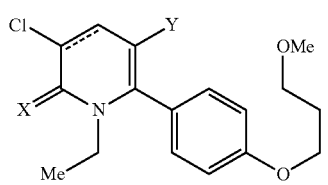 P-346
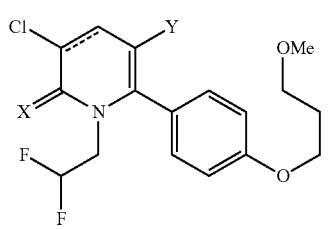 P-347
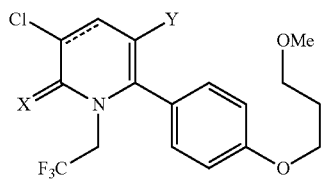 P-348
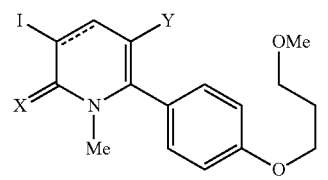 P-349
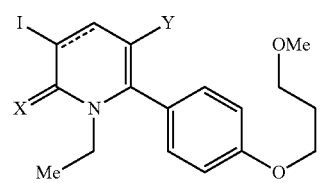 P-350
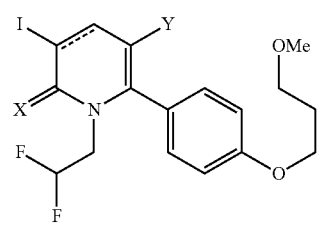 P-351
TABLE 1-continued
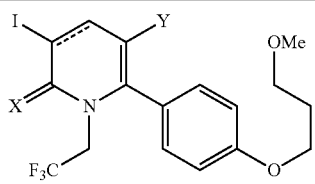 P-352
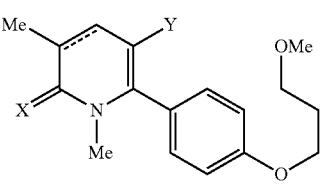 P-353
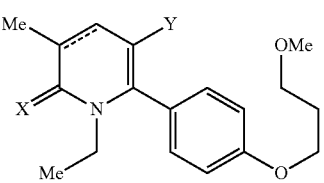 P-354
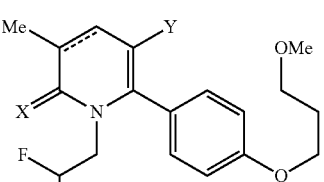 P-355
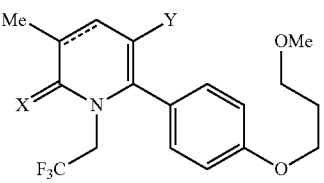 P-356
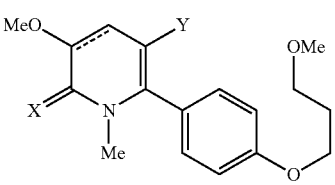 P-357
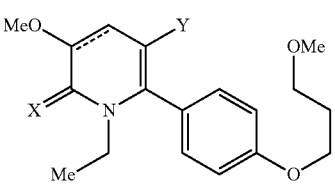 P-358
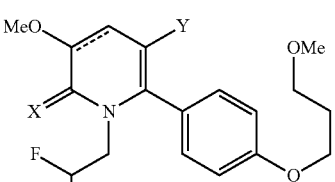 P-359

TABLE 1-continued

| Structure | ID |
|---|---|
| 3-OMe, N-CH2CF3, 6-(4-(3-methoxypropoxy)phenyl) pyridinone | P-360 |
| N-Me, 6-(4-(allyloxy)phenyl) pyridinone | P-361 |
| N-Et, 6-(4-(allyloxy)phenyl) pyridinone | P-362 |
| N-CHF2CH2, 6-(4-(allyloxy)phenyl) pyridinone | P-363 |
| N-CH2CF3, 6-(4-(allyloxy)phenyl) pyridinone | P-364 |
| 3-Br, N-Me, 6-(4-(allyloxy)phenyl) pyridinone | P-365 |
| 3-Br, N-Et, 6-(4-(allyloxy)phenyl) pyridinone | P-366 |
| 3-Br, N-CHF2CH2, 6-(4-(allyloxy)phenyl) pyridinone | P-367 |
| 3-Br, N-CH2CF3, 6-(4-(allyloxy)phenyl) pyridinone | P-368 |
| 3-Cl, N-Me, 6-(4-(allyloxy)phenyl) pyridinone | P-369 |
| 3-Cl, N-Et, 6-(4-(allyloxy)phenyl) pyridinone | P-370 |
| 3-Cl, N-CHF2CH2, 6-(4-(allyloxy)phenyl) pyridinone | P-371 |
| 3-Cl, N-CH2CF3, 6-(4-(allyloxy)phenyl) pyridinone | P-372 |
| 3-I, N-Me, 6-(4-(allyloxy)phenyl) pyridinone | P-373 |
| 3-I, N-Et, 6-(4-(allyloxy)phenyl) pyridinone | P-374 |
| 3-I, N-CHF2CH2, 6-(4-(allyloxy)phenyl) pyridinone | P-375 |

TABLE 1-continued
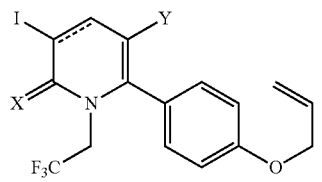 P-376
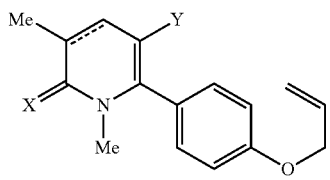 P-377
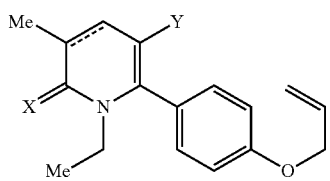 P-378
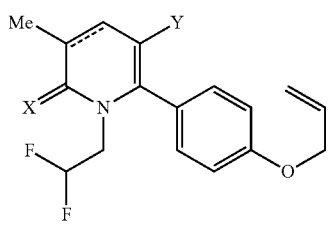 P-379
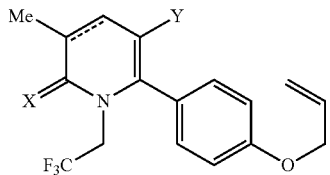 P-380
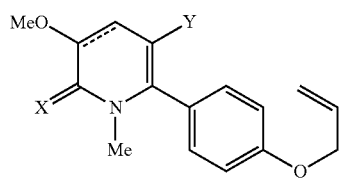 P-381
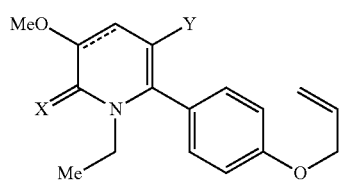 P-382
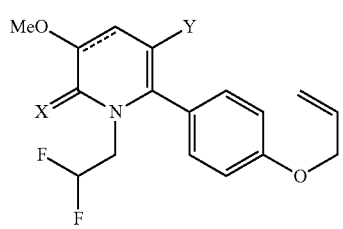 P-383
TABLE 1-continued
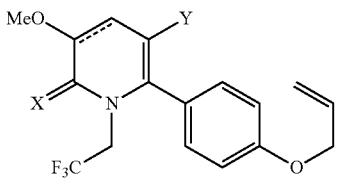 P-384
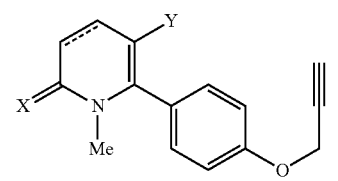 P-385
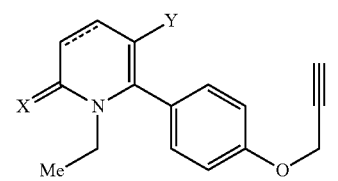 P-386
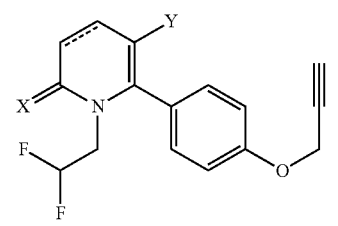 P-387
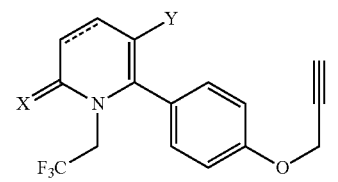 P-388
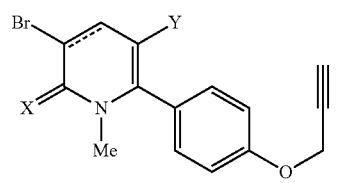 P-389
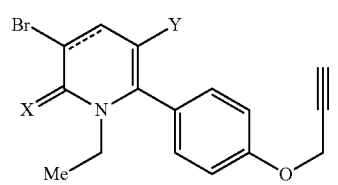 P-390
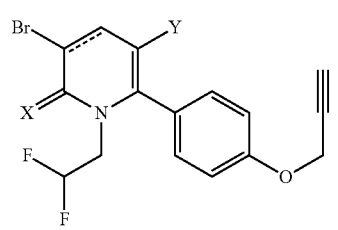 P-391

TABLE 1-continued
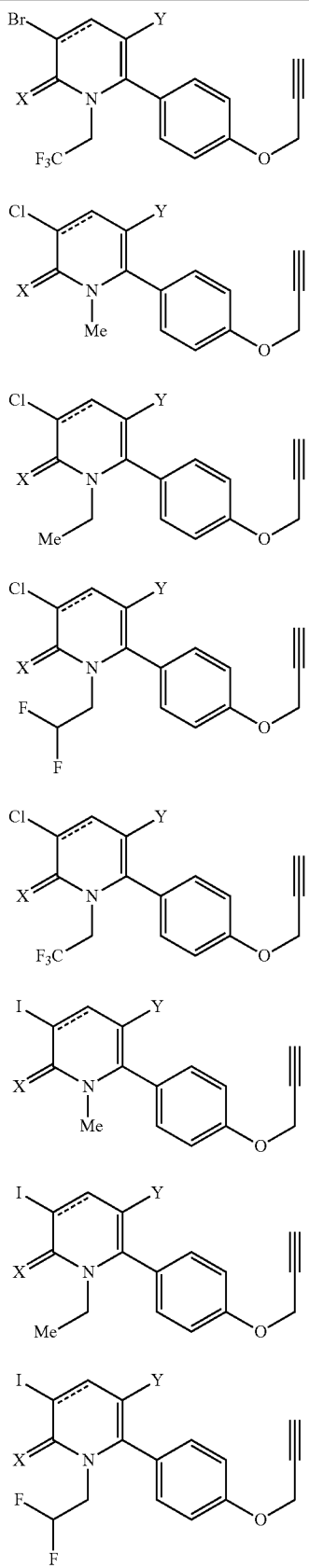
| | |
|---|---|
| P-392 | |
| P-393 | |
| P-394 | |
| P-395 | |
| P-396 | |
| P-397 | |
| P-398 | |
| P-399 | |
TABLE 1-continued
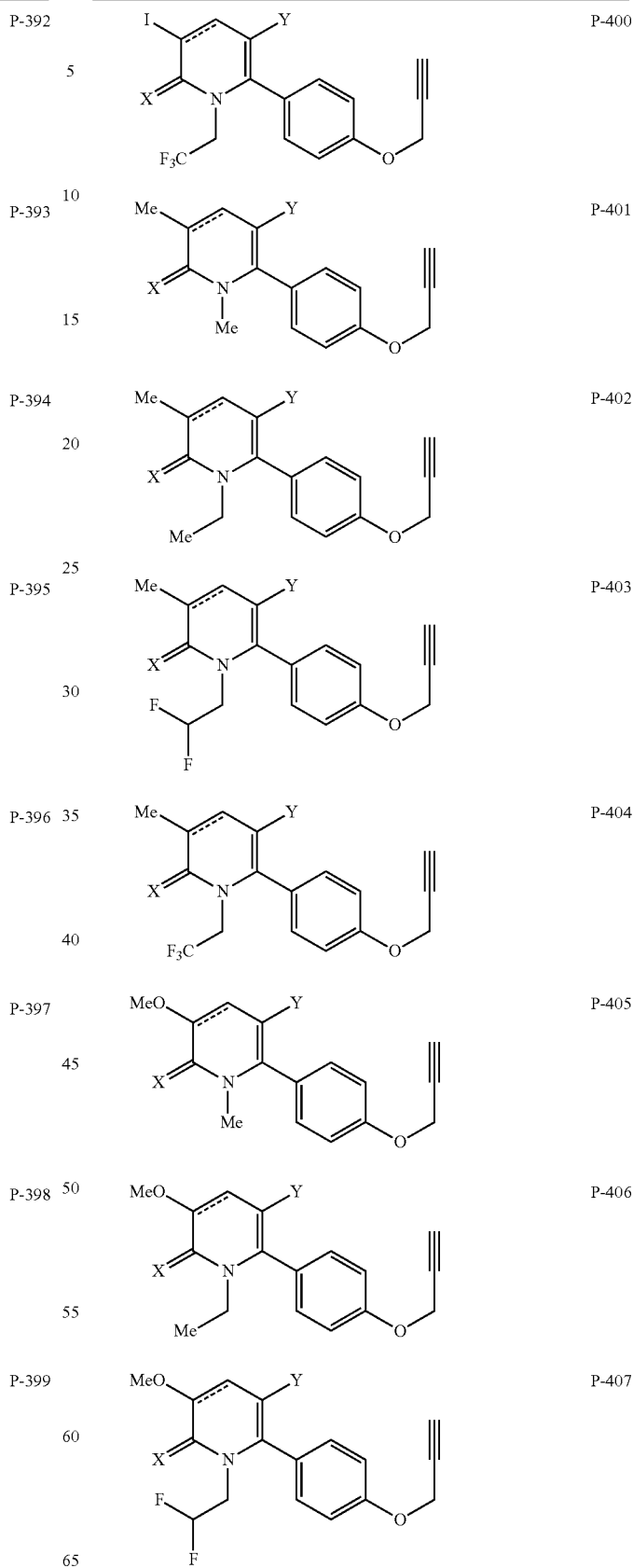
| | |
|---|---|
| P-400 | |
| P-401 | |
| P-402 | |
| P-403 | |
| P-404 | |
| P-405 | |
| P-406 | |
| P-407 | |

TABLE 1-continued
| | |
|---|---|
| 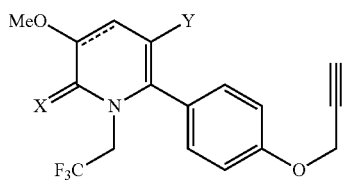 | P-408 |
| 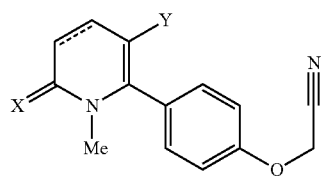 | P-409 |
| 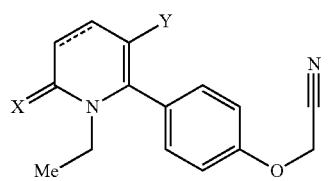 | P-410 |
| 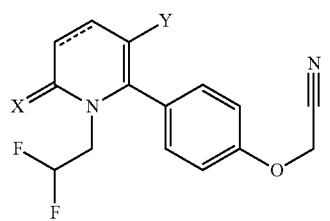 | P-411 |
| 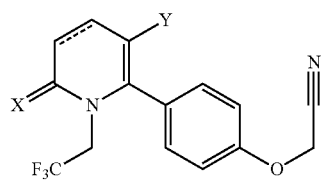 | P-412 |
| 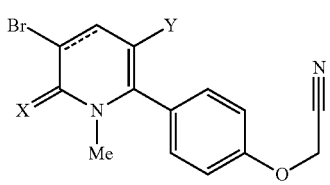 | P-413 |
| 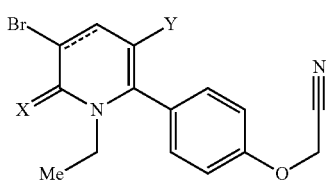 | P-414 |
| 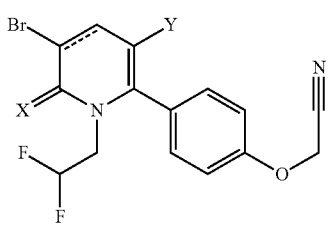 | P-415 |
TABLE 1-continued
| | |
|---|---|
| 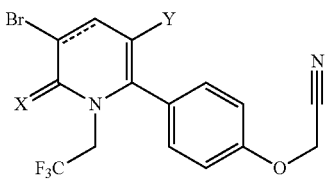 | P-416 |
| 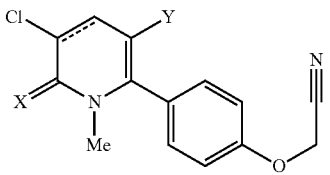 | P-417 |
| 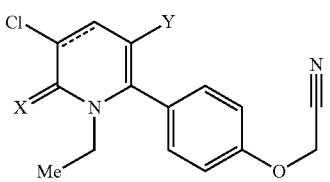 | P-418 |
| 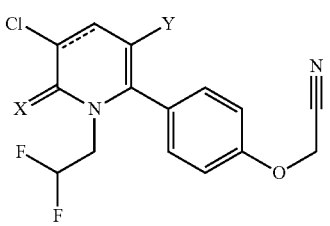 | P-419 |
| 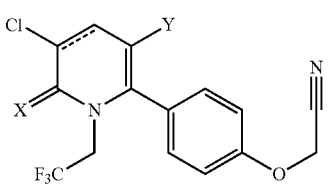 | P-420 |
| 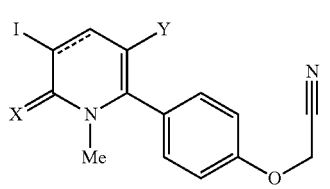 | P-421 |
| 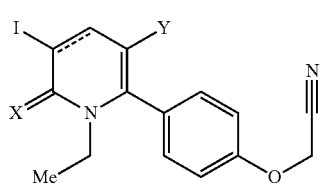 | P-422 |
| 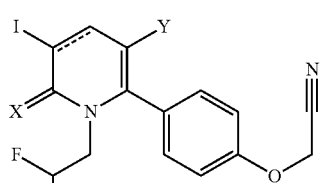 | P-423 |

TABLE 1-continued
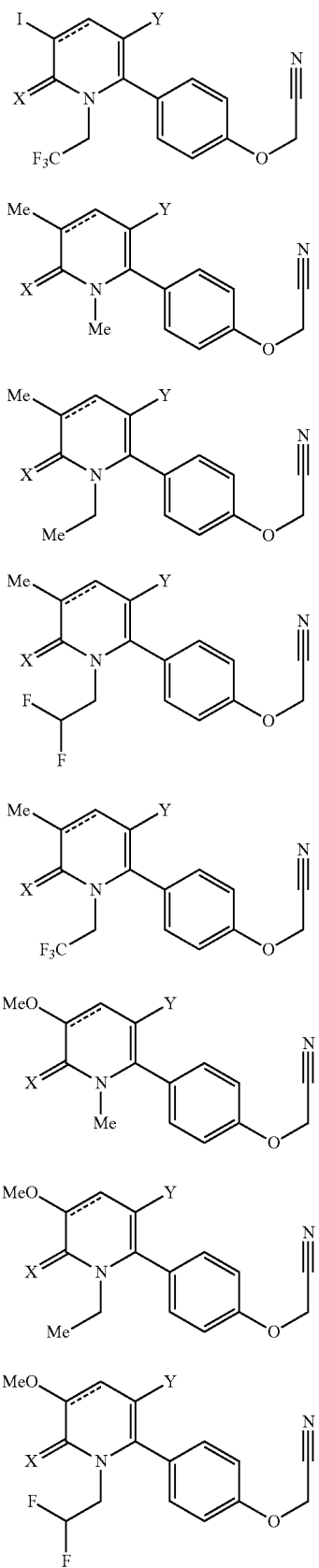
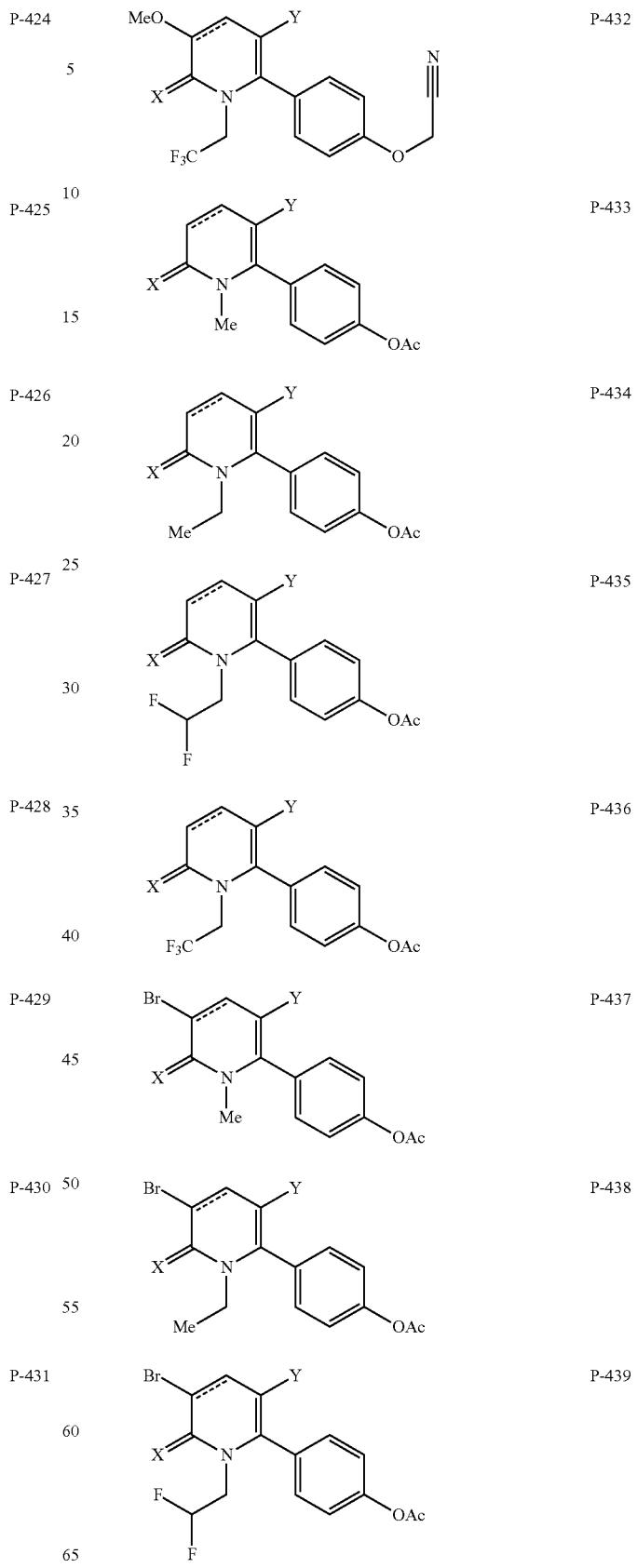

TABLE 1-continued
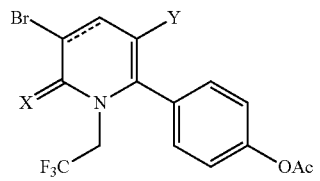 P-440
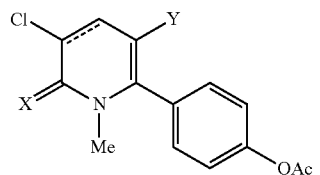 P-441
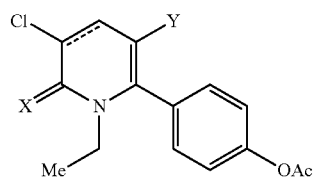 P-442
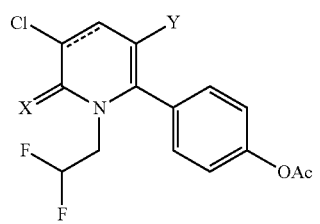 P-443
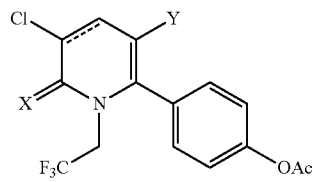 P-444
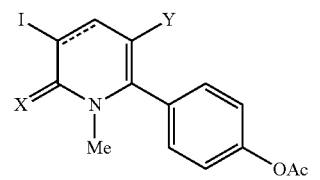 P-445
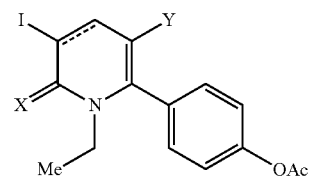 P-446
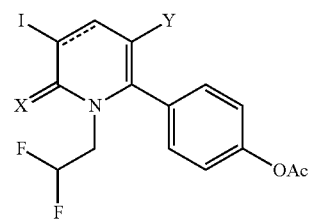 P-447
TABLE 1-continued
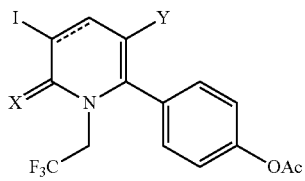 P-448
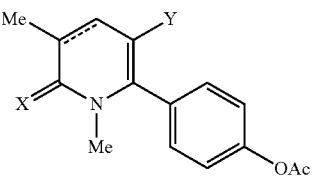 P-449
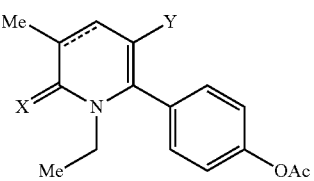 P-450
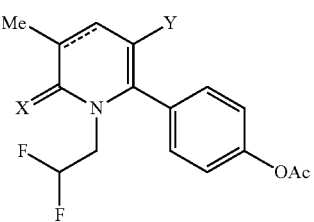 P-451
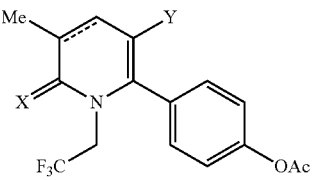 P-452
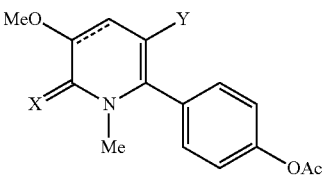 P-453
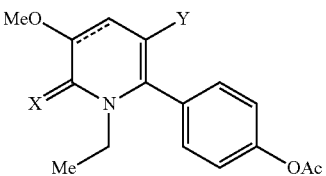 P-454
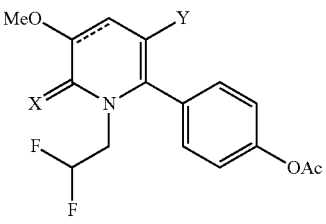 P-455

TABLE 1-continued
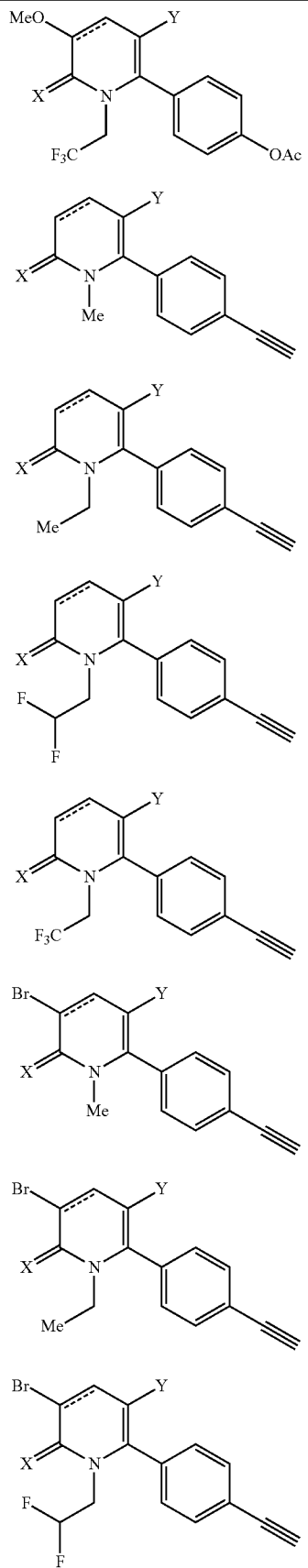
P-456
P-457
P-458
P-459
P-460
P-461
P-462
P-463
TABLE 1-continued
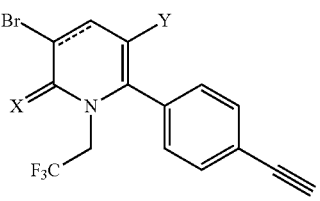
P-464
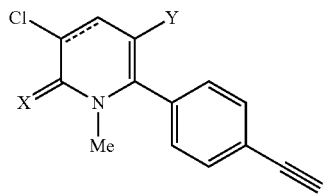
P-465
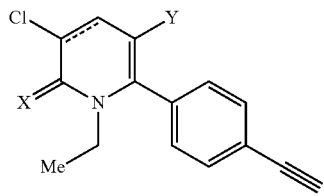
P-466
P-467
P-468
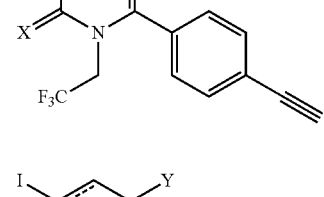
P-469
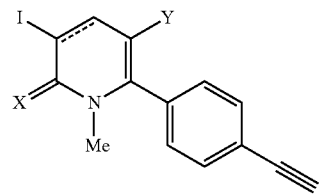
P-470
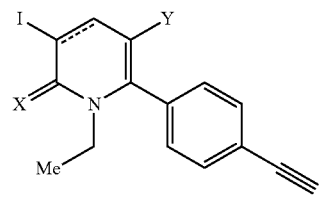

TABLE 1-continued
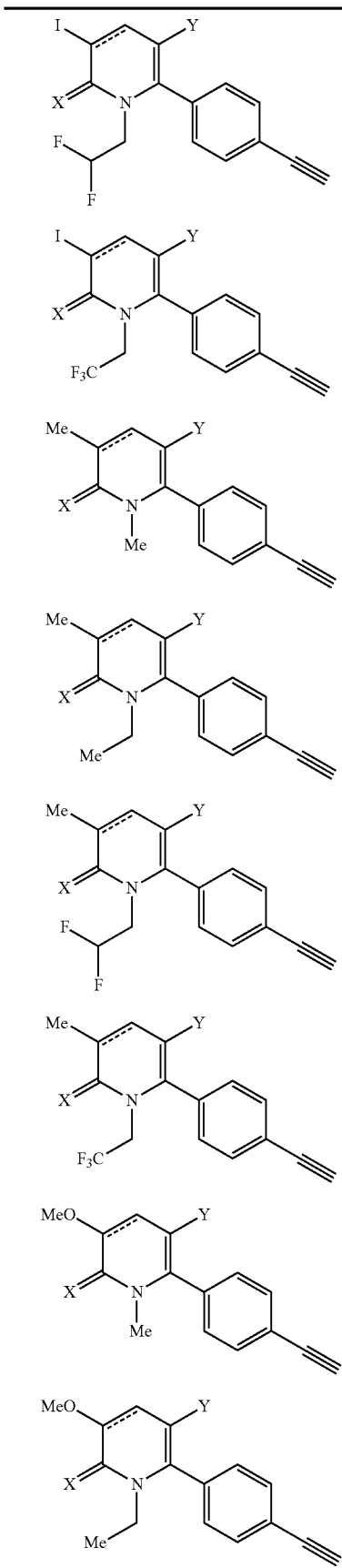
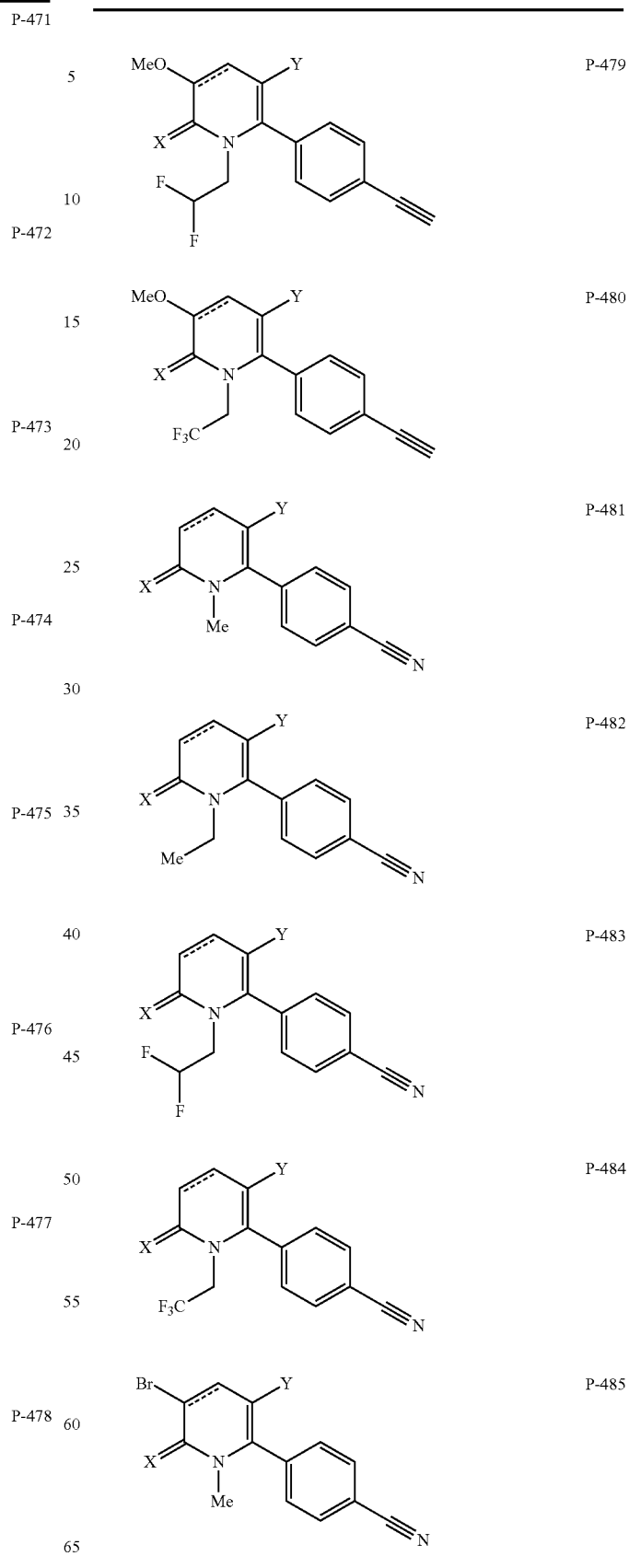

TABLE 1-continued
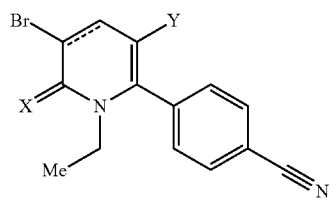 P-486
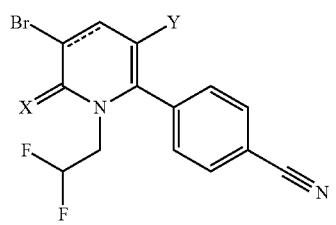 P-487
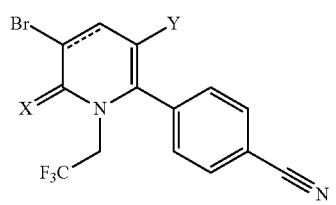 P-488
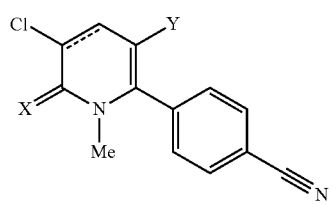 P-489
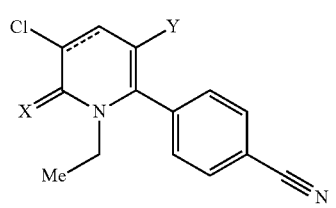 P-490
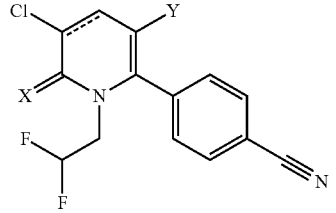 P-491
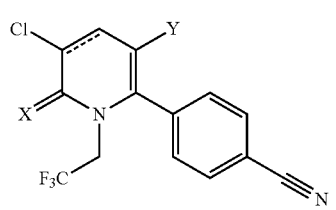 P-492
TABLE 1-continued
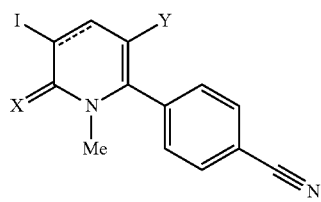 P-493
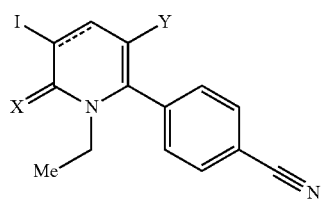 P-494
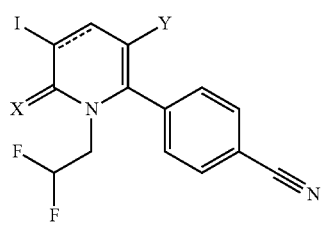 P-495
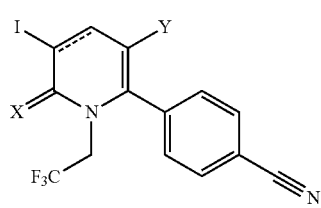 P-496
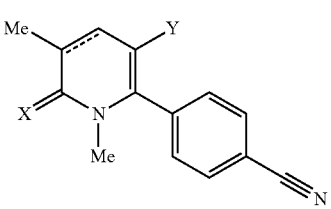 P-497
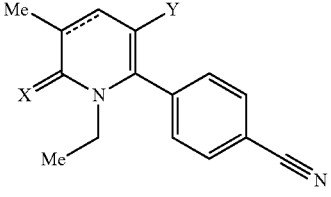 P-498
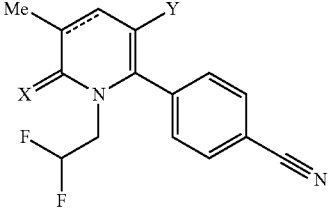 P-499

TABLE 1-continued

P-500, P-501, P-502, P-503, P-504, P-505, P-506, P-507, P-508, P-509, P-510, P-511, P-512, P-513

TABLE 1-continued
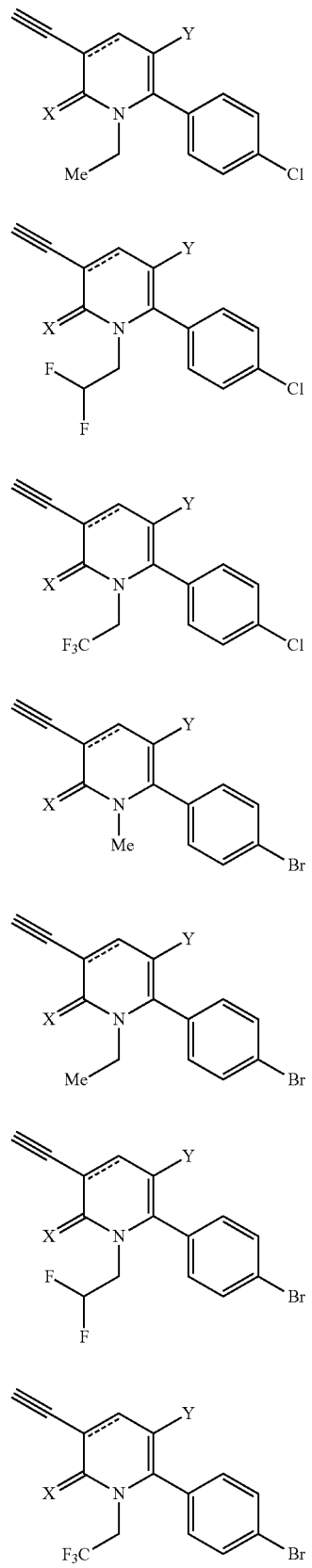
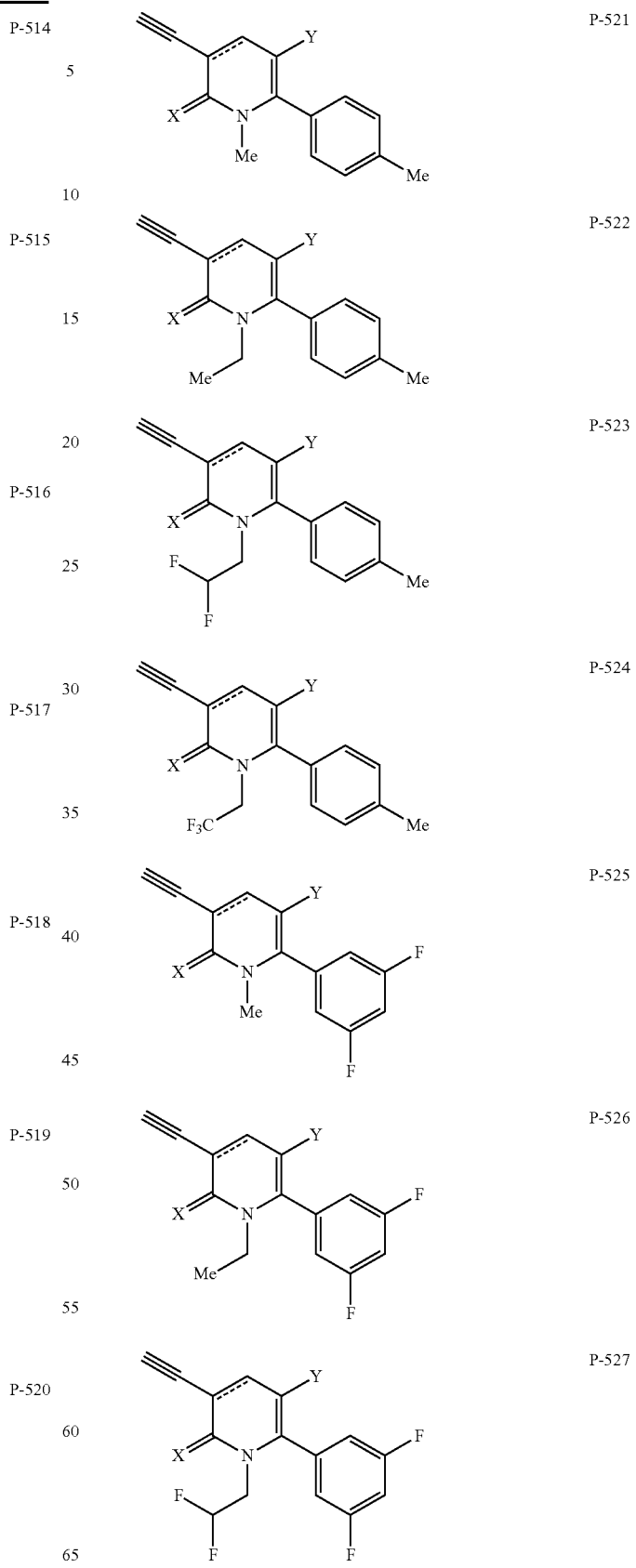

TABLE 1-continued
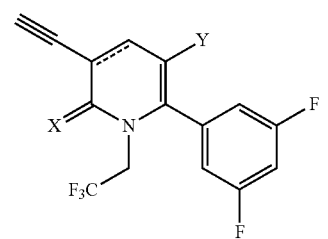 P-528
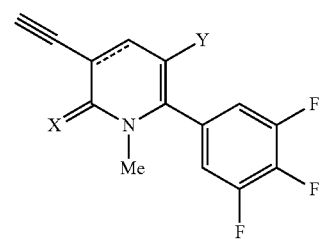 P-529
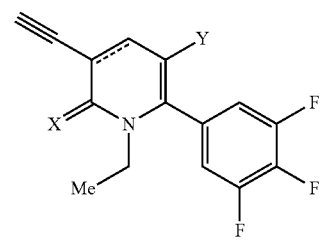 P-530
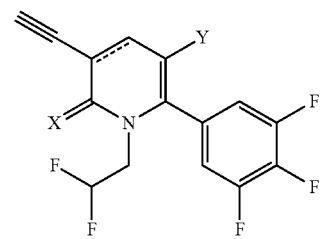 P-531
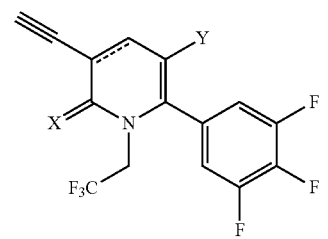 P-532
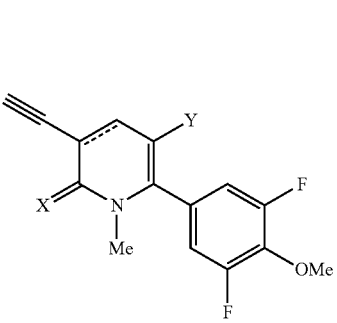 P-533
TABLE 1-continued
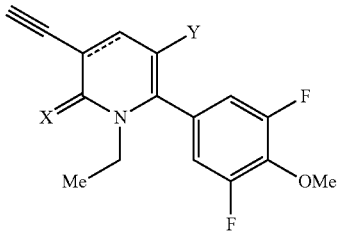 P-534
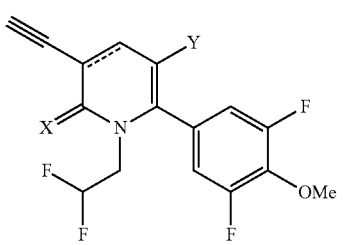 P-535
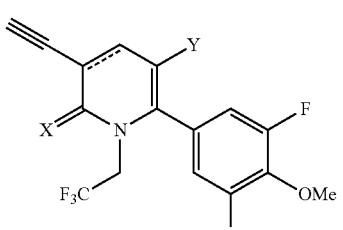 P-536
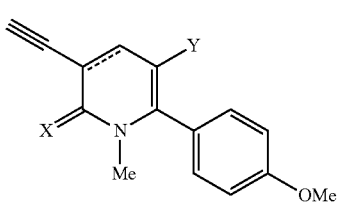 P-537
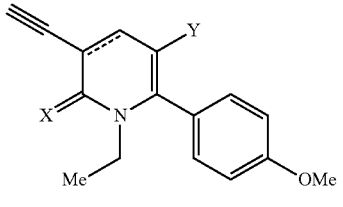 P-538
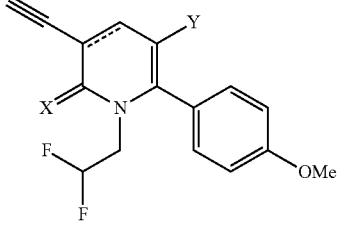 P-539
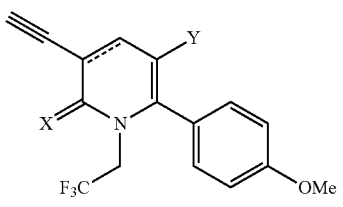 P-540

TABLE 1-continued
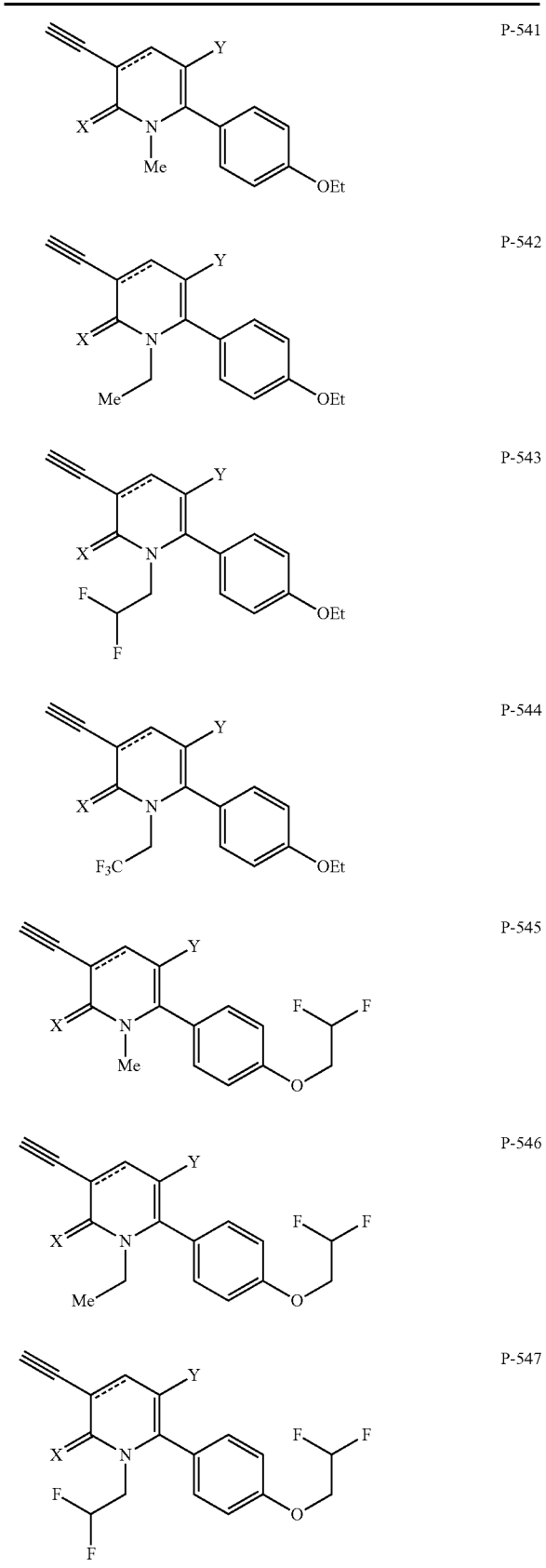
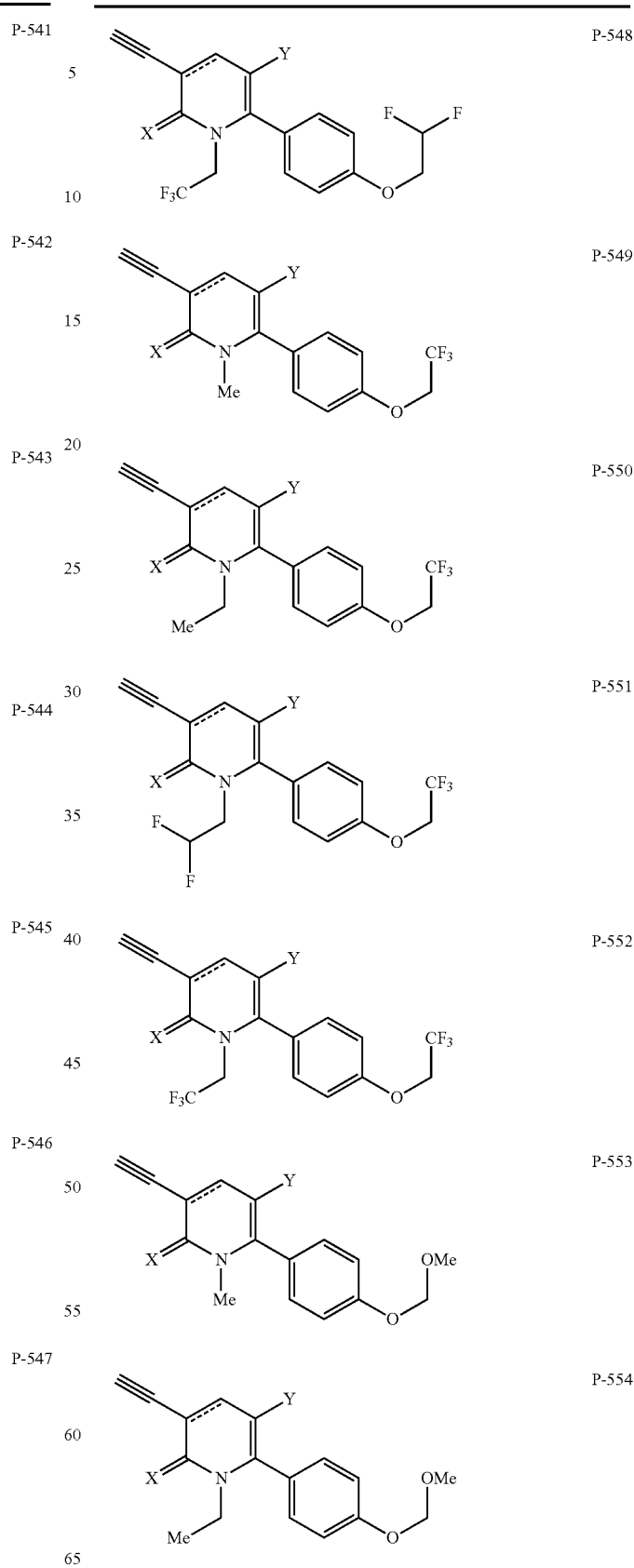

TABLE 1-continued
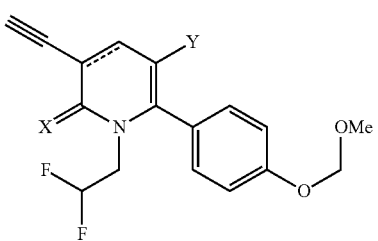 P-555
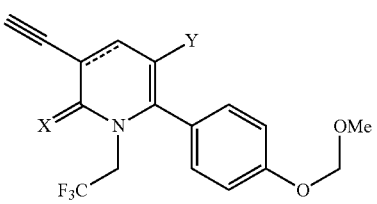 P-556
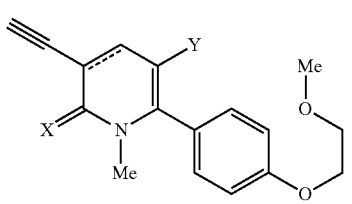 P-557
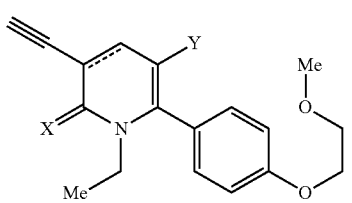 P-558
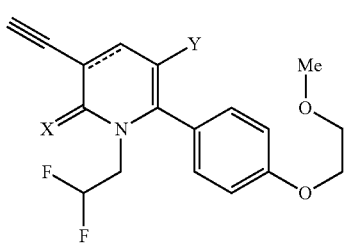 P-559
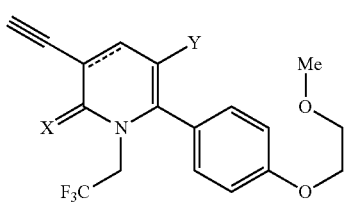 P-560
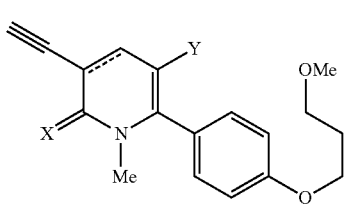 P-561
TABLE 1-continued
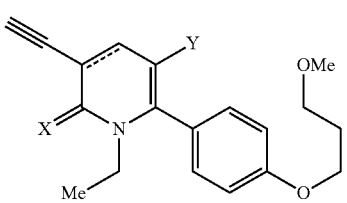 P-562
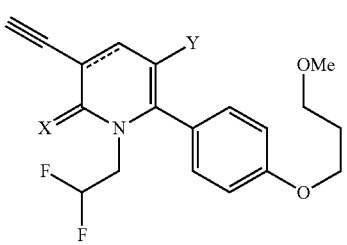 P-563
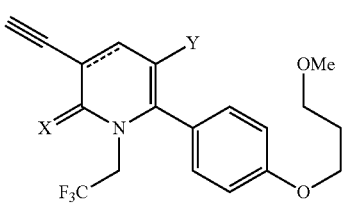 P-564
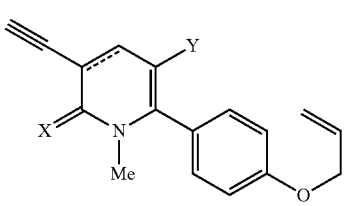 P-565
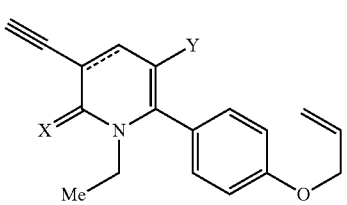 P-566
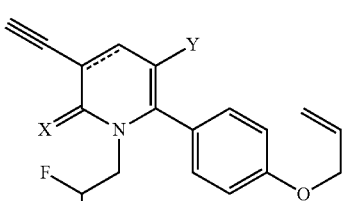 P-567
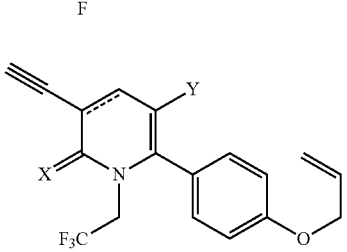 P-568

TABLE 1-continued
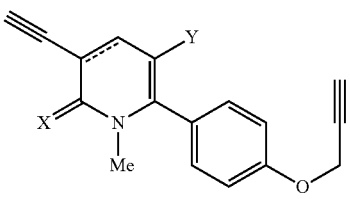 P-569
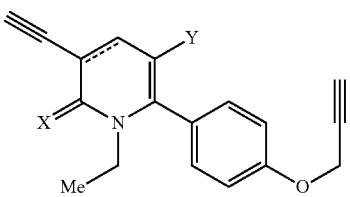 P-570
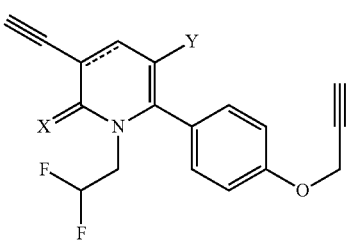 P-571
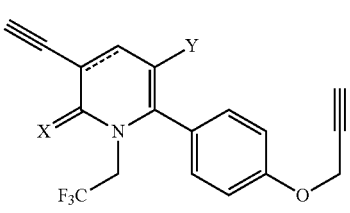 P-572
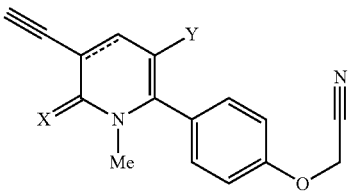 P-573
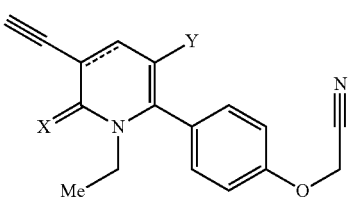 P-574
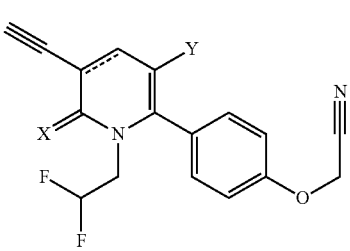 P-575
TABLE 1-continued
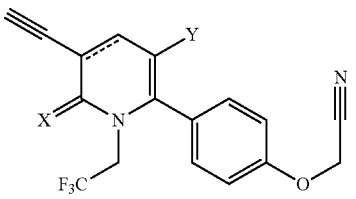 P-576
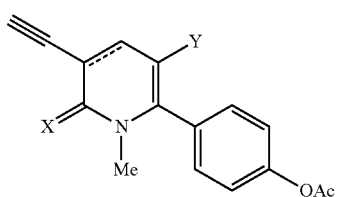 P-577
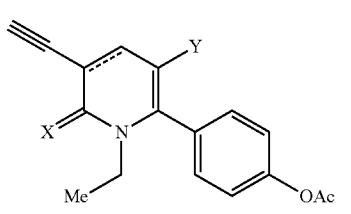 P-578
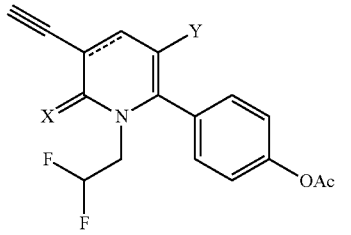 P-579
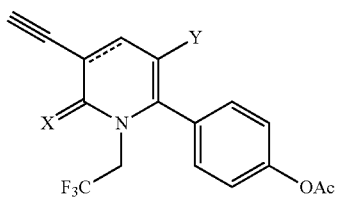 P-580
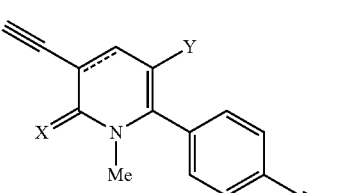 P-581
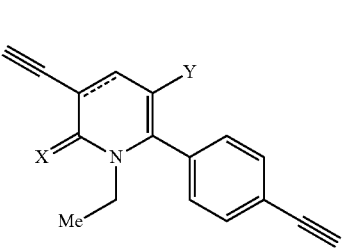 P-582

TABLE 1-continued
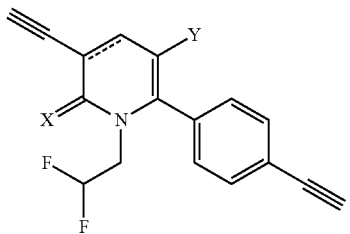 P-583
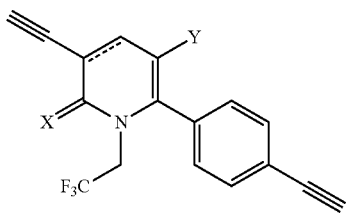 P-584
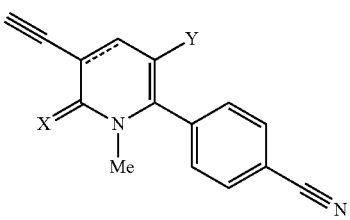 P-585
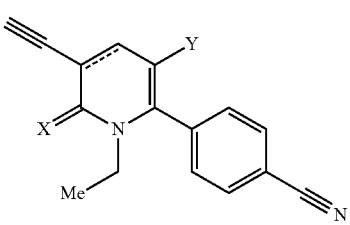 P-586
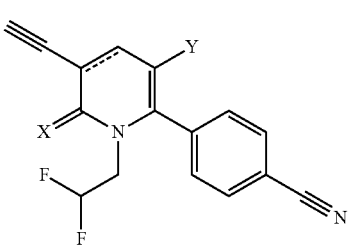 P-587
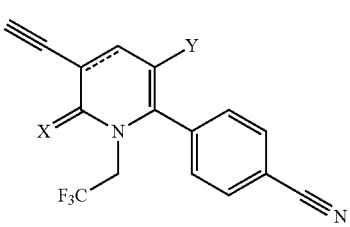 P-588
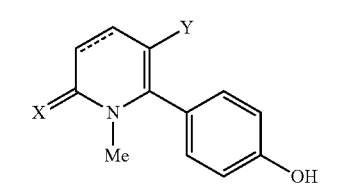 P-589
TABLE 1-continued
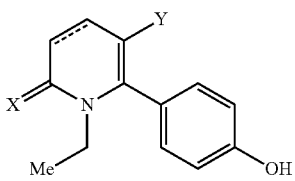 P-590
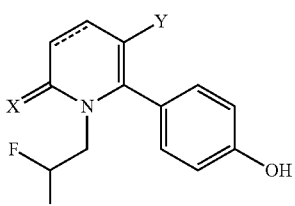 P-591
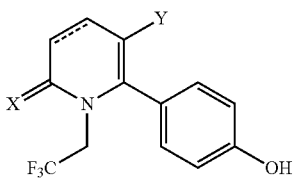 P-592
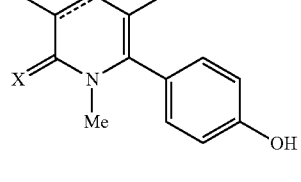 P-593
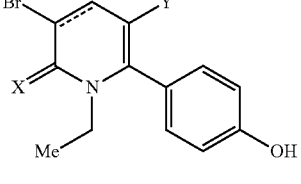 P-594
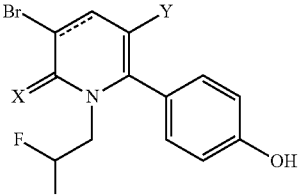 P-595
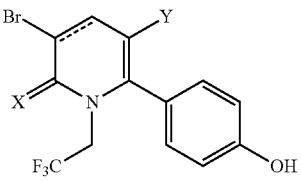 P-596
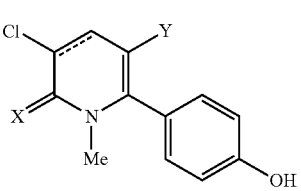 P-597

TABLE 1-continued
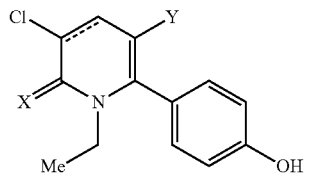 P-598
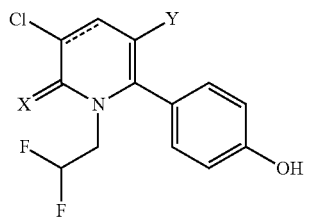 P-599
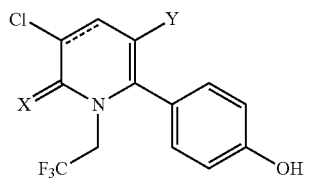 P-600
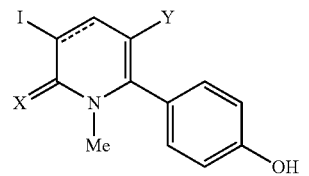 P-601
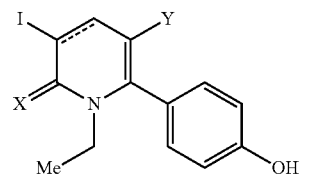 P-602
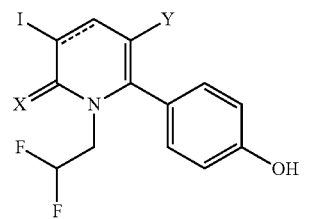 P-603
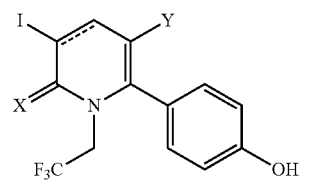 P-604
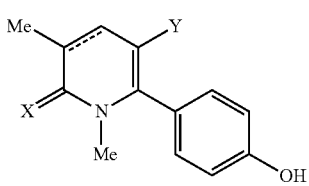 P-605
TABLE 1-continued
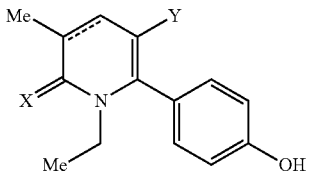 P-606
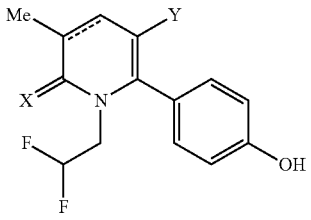 P-607
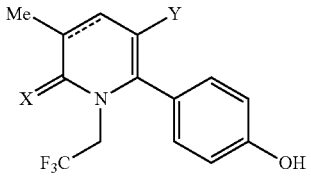 P-608
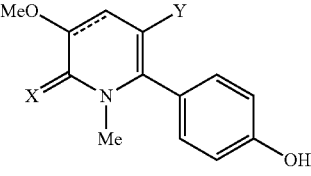 P-609
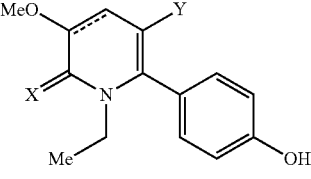 P-610
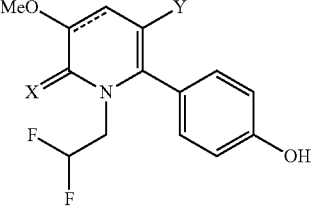 P-611
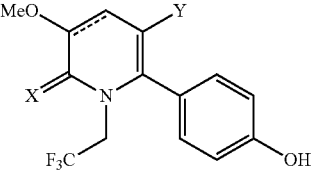 P-612
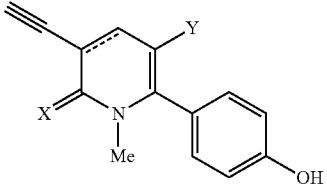 P-613

TABLE 1-continued

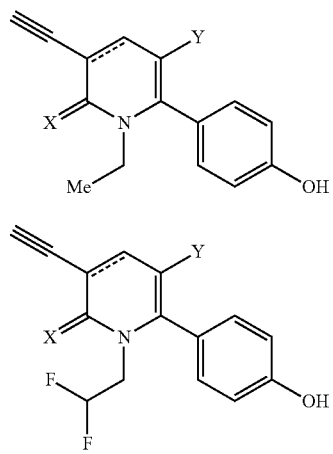

P-614

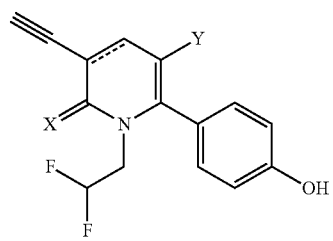

P-615

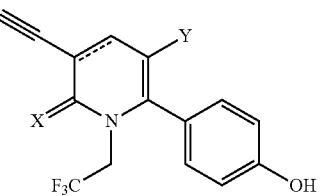

P-616

In Table 2, for example, the expression "2-F-Ph" means a phenyl group having a fluorine atom at 2-position; the expression "2-F-3-HO-Ph" means a phenyl group having a fluorine atom at 2-position and a hydroxy group at 3-position; the expression "2,3-di-F-Ph" means a phenyl group having fluorine atoms at 2-position and 3-position; and the expression "2-F-3-Py" means a pyridyl group having a fluorine atom at 2-position and being bonded to the pyrrolidone ring in the formula (1) at its 3-position. Other representations are understood in the similar manner.

TABLE 2

| No. | Y | No. | Y |
| --- | --- | --- | --- |
| 1 | Ph | 2 | 2-N≡C—Ph |
| 3 | 2-Me—Ph | 4 | 2-MeO—Ph |
| 5 | 2-F—Ph | 6 | 2-Cl—Ph |
| 7 | 2-Br—Ph | 8 | 2-I—Ph |
| 9 | 2-O2N—Ph | 10 | 2-HO—Ph |
| 11 | 3-F-2-Me—Ph | 12 | 4-F-2-Me—Ph |
| 13 | 5-F-2-Me—Ph | 14 | 6-F-2-Me—Ph |
| 15 | 3-Cl-2-Me—Ph | 16 | 4-Cl-2-Me—Ph |
| 17 | 5-Cl-2-Me—Ph | 18 | 6-Cl-2-Me—Ph |
| 19 | 3-Br-2-Me—Ph | 20 | 4-Br-2-Me—Ph |
| 21 | 5-Br-2-Me—Ph | 22 | 6-Br-2-Me—Ph |
| 23 | 3-I-2-Me—Ph | 24 | 4-I-2-Me—Ph |
| 25 | 5-I-2-Me—Ph | 26 | 6-I-2-Me—Ph |
| 27 | 2,3-di-F—Ph | 28 | 2,4-di-F—Ph |
| 29 | 2,5-di-F—Ph | 30 | 2,6-di-F—Ph |
| 31 | 3-Cl-2-F—Ph | 32 | 4-Cl-2-F—Ph |
| 33 | 5-Cl-2-F—Ph | 34 | 6-Cl-2-F—Ph |
| 35 | 3-Br-2-F—Ph | 36 | 4-Br-2-F—Ph |
| 37 | 5-Br-2-F—Ph | 38 | 6-Br-2-F—Ph |
| 39 | 2-F-3-I—Ph | 40 | 2-F-4-I—Ph |
| 41 | 2-F-5-I—Ph | 42 | 2-F-6-I—Ph |
| 43 | 2-Cl-3-F—Ph | 44 | 2-Cl-4-F—Ph |
| 45 | 2-Cl-5-F—Ph | 46 | 2-Cl-6-F—Ph |
| 47 | 2,3-di-Cl—Ph | 48 | 2,4-di-Cl—Ph |
| 49 | 2,5-di-Cl—Ph | 50 | 2,6-di-Cl—Ph |
| 51 | 3-Br-2-Cl—Ph | 52 | 4-Br-2-Cl—Ph |
| 53 | 5-Br-2-Cl—Ph | 54 | 6-Br-2-Cl—Ph |
| 55 | 2-Cl-3-I—Ph | 56 | 2-Cl-4-I—Ph |
| 57 | 2-Cl-5-I—Ph | 58 | 2-Cl-6-I—Ph |
| 59 | 2-Br-3-F—Ph | 60 | 2-Br-4-F—Ph |
| 61 | 2-Br-5-F—Ph | 62 | 2-Br-6-F—Ph |
| 63 | 2-Br-3-Cl—Ph | 64 | 2-Br-4-Cl—Ph |
| 65 | 2-Br-5-Cl—Ph | 66 | 2-Br-6-Cl—Ph |
| 67 | 2,3-di-Br—Ph | 68 | 2,4-di-Br—Ph |
| 69 | 2,5-di-Br—Ph | 70 | 2,6-di-Br—Ph |
| 71 | 2-Br-3-I—Ph | 72 | 2-Br-4-I—Ph |
| 73 | 2-Br-5-I—Ph | 74 | 2-Br-6-I—Ph |
| 75 | 3-F-2-I—Ph | 76 | 4-F-2-I—Ph |
| 77 | 5-F-2-I—Ph | 78 | 6-F-2-I—Ph |
| 79 | 3-Cl-2-I—Ph | 80 | 4-Cl-2-I—Ph |
| 81 | 5-Cl-2-I—Ph | 82 | 6-Cl-2-I—Ph |
| 83 | 3-Br-2-I—Ph | 84 | 4-Br-2-I—Ph |
| 85 | 5-Br-2-I—Ph | 86 | 6-Br-2-I—Ph |
| 87 | 2,3-di-I—Ph | 88 | 2,4-di-I—Ph |
| 89 | 2,5-di-I—Ph | 90 | 2,6-di-I—Ph |
| 91 | 2-Me-3-HO—Ph | 92 | 2-Me-4-HO—Ph |
| 93 | 2-Me-5-HO—Ph | 94 | 2-Me-6-HO—Ph |
| 95 | 2-F-3-HO—Ph | 96 | 2-F-4-HO—Ph |
| 97 | 2-F-5-HO—Ph | 98 | 2-F-6-HO—Ph |
| 99 | 2-Cl-3-HO—Ph | 100 | 2-Cl-4-HO—Ph |
| 101 | 2-Cl-5-HO—Ph | 102 | 2-Cl-6-HO—Ph |

TABLE 2-continued

| No. | Y | No. | Y |
|---|---|---|---|
| 103 | 2-Br-3-HO—Ph | 104 | 2-Br-4-HO—Ph |
| 105 | 2-Br-5-HO—Ph | 106 | 2-Br-6-HO—Ph |
| 107 | 2-I-3-HO—Ph | 108 | 2-I-4-HO—Ph |
| 109 | 2-I-5-HO—Ph | 110 | 2-I-6-HO—Ph |
| 111 | 2,3-di-Me—Ph | 112 | 2,4-di-Me—Ph |
| 113 | 2,5-di-Me—Ph | 114 | 2,6-di-Me—Ph |
| 115 | 2-F-3-Me—Ph | 116 | 2-F-4-Me—Ph |
| 117 | 2-F-5-Me—Ph | 118 | 2-F-6-Me—Ph |
| 119 | 2-Cl-3-Me—Ph | 120 | 2-Cl-4-Me—Ph |
| 121 | 2-Cl-5-Me—Ph | 122 | 2-Cl-6-Me—Ph |
| 123 | 2-Br-3-Me—Ph | 124 | 2-Br-4-Me—Ph |
| 125 | 2-Br-5-Me—Ph | 126 | 2-Br-6-Me—Ph |
| 127 | 2-I-3-Me—Ph | 128 | 2-I-4-Me—Ph |
| 129 | 2-I-5-Me—Ph | 130 | 2-I-6-Me—Ph |
| 131 | 2-Me-3-F3C—Ph | 132 | 2-Me-4-F3C—Ph |
| 133 | 2-Me-5-F3C—Ph | 134 | 2-Me-6-F3C—Ph |
| 135 | 2-F-3-F3C—Ph | 136 | 2-F-4-F3C—Ph |
| 137 | 2-F-5-F3C—Ph | 138 | 2-F-6-F3C—Ph |
| 139 | 2-Cl-3-F3C—Ph | 140 | 2-Cl-4-F3C—Ph |
| 141 | 2-Cl-5-F3C—Ph | 142 | 2-Cl-6-F3C—Ph |
| 143 | 2-Br-3-F3C—Ph | 144 | 2-Br-4-F3C—Ph |
| 145 | 2-Br-5-F3C—Ph | 146 | 2-Br-6-F3C—Ph |
| 147 | 2-I-3-F3C—Ph | 148 | 2-I-4-F3C—Ph |
| 149 | 2-I-5-F3C—Ph | 150 | 2-I-6-F3C—Ph |
| 151 | 2-Me-3-MeO—Ph | 152 | 2-Me-4-MeO—Ph |
| 153 | 2-Me-5-MeO—Ph | 154 | 2-Me-6-MeO—Ph |
| 155 | 2-F-3-MeO—Ph | 156 | 2-F-4-MeO—Ph |
| 157 | 2-F-5-MeO—Ph | 158 | 2-F-6-MeO—Ph |
| 159 | 2-Cl-3-MeO—Ph | 160 | 2-Cl-4-MeO—Ph |
| 161 | 2-Cl-5-MeO—Ph | 162 | 2-Cl-6-MeO—Ph |
| 163 | 2-Br-3-MeO—Ph | 164 | 2-Br-4-MeO—Ph |
| 165 | 2-Br-5-MeO—Ph | 166 | 2-Br-6-MeO—Ph |
| 167 | 2-I-3-MeO—Ph | 168 | 2-I-4-MeO—Ph |
| 169 | 2-I-5-MeO—Ph | 170 | 2-I-6-MeO—Ph |
| 171 | 2-Me-3-EtO—Ph | 172 | 2-Me-4-EtO—Ph |
| 173 | 2-Me-5-EtO—Ph | 174 | 2-Me-6-EtO—Ph |
| 175 | 2-F-3-EtO—Ph | 176 | 2-F-4-EtO—Ph |
| 177 | 2-F-5-EtO—Ph | 178 | 2-F-6-EtO—Ph |
| 179 | 2-Cl-3-EtO—Ph | 180 | 2-Cl-4-EtO—Ph |
| 181 | 2-Cl-5-EtO—Ph | 182 | 2-Cl-6-EtO—Ph |
| 183 | 2-Br-3-EtO—Ph | 184 | 2-Br-4-EtO—Ph |
| 185 | 2-Br-5-EtO—Ph | 186 | 2-Br-6-EtO—Ph |
| 187 | 2-I-3-EtO—Ph | 188 | 2-I-4-EtO—Ph |
| 189 | 2-I-5-EtO—Ph | 190 | 2-I-6-EtO—Ph |
| 191 | 2-Me-3-PrO—Ph | 192 | 2-Me-4-PrO—Ph |
| 193 | 2-Me-5-PrO—Ph | 194 | 2-Me-6-PrO—Ph |
| 195 | 2-F-3-PrO—Ph | 196 | 2-F-4-PrO—Ph |
| 197 | 2-F-5-PrO—Ph | 198 | 2-F-6-PrO—Ph |
| 199 | 2-Cl-3-PrO—Ph | 200 | 2-Cl-4-PrO—Ph |
| 201 | 2-Cl-5-PrO—Ph | 202 | 2-Cl-6-PrO—Ph |
| 203 | 2-Br-3-PrO—Ph | 204 | 2-Br-4-PrO—Ph |
| 205 | 2-Br-5-PrO—Ph | 206 | 2-Br-6-PrO—Ph |
| 207 | 2-I-3-PrO—Ph | 208 | 2-I-4-PrO—Ph |
| 209 | 2-I-5-PrO—Ph | 210 | 2-I-6-PrO—Ph |
| 211 | 2-Me-3-iPrO—Ph | 212 | 2-Me-4-iPrO—Ph |
| 213 | 2-Me-5-iPrO—Ph | 214 | 2-Me-6-iPrO—Ph |
| 215 | 2-F-3-iPrO—Ph | 216 | 2-F-4-iPrO—Ph |
| 217 | 2-F-5-iPrO—Ph | 218 | 2-F-6-iPrO—Ph |
| 219 | 2-Cl-3-iPrO—Ph | 220 | 2-Cl-4-iPrO—Ph |
| 221 | 2-Cl-5-iPrO—Ph | 222 | 2-Cl-6-iPrO—Ph |
| 223 | 2-Br-3-iPrO—Ph | 224 | 2-Br-4-iPrO—Ph |
| 225 | 2-Br-5-iPrO—Ph | 226 | 2-Br-6-iPrO—Ph |
| 227 | 2-I-3-iPrO—Ph | 228 | 2-I-4-iPrO—Ph |
| 229 | 2-I-5-iPrO—Ph | 230 | 2-I-6-iPrO—Ph |
| 231 | 2-Me-3-MeOCH2O—Ph | 232 | 2-Me-4-MeOCH2O—Ph |
| 233 | 2-Me-5-MeOCH2O—Ph | 234 | 2-Me-6-MeOCH2O—Ph |
| 235 | 2-F-3-MeOCH2O—Ph | 236 | 2-F-4-MeOCH2O—Ph |
| 237 | 2-F-5-MeOCH2O—Ph | 238 | 2-F-6-MeOCH2O—Ph |
| 239 | 2-Cl-3-MeOCH2O—Ph | 240 | 2-Cl-4-MeOCH2O—Ph |
| 241 | 2-Cl-5-MeOCH2O—Ph | 242 | 2-Cl-6-MeOCH2O—Ph |
| 243 | 2-Br-3-MeOCH2O—Ph | 244 | 2-Br-4-MeOCH2O—Ph |
| 245 | 2-Br-5-MeOCH2O—Ph | 246 | 2-Br-6-MeOCH2O—Ph |
| 247 | 2-I-3-MeOCH2O—Ph | 248 | 2-I-4-MeOCH2O—Ph |
| 249 | 2-I-5-MeOCH2O—Ph | 250 | 2-I-6-MeOCH2O—Ph |
| 251 | 2-Me-3-MeOCH2CH2O—Ph | 252 | 2-Me-4-MeOCH2CH2O—Ph |
| 253 | 2-Me-5-MeOCH2CH2O—Ph | 254 | 2-Me-6-MeOCH2CH2O—Ph |
| 255 | 2-F-3-MeOCH2CH2O—Ph | 256 | 2-F-4-MeOCH2CH2O—Ph |
| 257 | 2-F-5-MeOCH2CH2O—Ph | 258 | 2-F-6-MeOCH2CH2O—Ph |

TABLE 2-continued

| No. | Y | No. | Y |
|---|---|---|---|
| 259 | 2-Cl-3-MeOCH2CH2O—Ph | 260 | 2-Cl-4-MeOCH2CH2O—Ph |
| 261 | 2-Cl-5-MeOCH2CH2O—Ph | 262 | 2-Cl-6-MeOCH2CH2O—Ph |
| 263 | 2-Br-3-MeOCH2CH2O—Ph | 264 | 2-Br-4-MeOCH2CH2O—Ph |
| 265 | 2-Br-5-MeOCH2CH2O—Ph | 266 | 2-Br-6-MeOCH2CH2O—Ph |
| 267 | 2-I-3-MeOCH2CH2O—Ph | 268 | 2-I-4-MeOCH2CH2O—Ph |
| 269 | 2-I-5-MeOCH2CH2O—Ph | 270 | 2-I-6-MeOCH2CH2O—Ph |
| 271 | 2-Me-3-N≡CCH2O—Ph | 272 | 2-Me-4-N≡CCH2O—Ph |
| 273 | 2-Me-5-N≡CCH2O—Ph | 274 | 2-Me-6-N≡CCH2O—Ph |
| 275 | 2-F-3-N≡CCH2O—Ph | 276 | 2-F-4-N≡CCH2O—Ph |
| 277 | 2-F-5-N≡CCH2O—Ph | 278 | 2-F-6-N≡CCH2O—Ph |
| 279 | 2-Cl-3-N≡CCH2O—Ph | 280 | 2-Cl-4-N≡CCH2O—Ph |
| 281 | 2-Cl-5-N≡CCH2O—Ph | 282 | 2-Cl-6-N≡CCH2O—Ph |
| 283 | 2-Br-3-N≡CCH2O—Ph | 284 | 2-Br-4-N≡CCH2O—Ph |
| 285 | 2-Br-5-N≡CCH2O—Ph | 286 | 2-Br-6-N≡CCH2O—Ph |
| 287 | 2-I-3-N≡CCH2O—Ph | 288 | 2-I-4-N≡CCH2O—Ph |
| 289 | 2-I-5-N≡CCH2O—Ph | 290 | 2-I-6-N≡CCH2O—Ph |
| 291 | 2-Me-3-MeSCH2O—Ph | 292 | 2-Me-4-MeSCH2O—Ph |
| 293 | 2-Me-5-MeSCH2O—Ph | 294 | 2-Me-6-MeSCH2O—Ph |
| 295 | 2-F-3-MeSCH2O—Ph | 296 | 2-F-4-MeSCH2O—Ph |
| 297 | 2-F-5-MeSCH2O—Ph | 298 | 2-F-6-MeSCH2O—Ph |
| 299 | 2-Cl-3-MeSCH2O—Ph | 300 | 2-Cl-4-MeSCH2O—Ph |
| 301 | 2-Cl-5-MeSCH2O—Ph | 302 | 2-Cl-6-MeSCH2O—Ph |
| 303 | 2-Br-3-MeSCH2O—Ph | 304 | 2-Br-4-MeSCH2O—Ph |
| 305 | 2-Br-5-MeSCH2O—Ph | 306 | 2-Br-6-MeSCH2O—Ph |
| 307 | 2-I-3-MeSCH2O—Ph | 308 | 2-I-4-MeSCH2O—Ph |
| 309 | 2-I-5-MeSCH2O—Ph | 310 | 2-I-6-MeSCH2O—Ph |
| 311 | 2-Me-3-MeS(O)CH2O—Ph | 312 | 2-Me-4-MeS(O)CH2O—Ph |
| 313 | 2-Me-5-MeS(O)CH2O—Ph | 314 | 2-Me-6-MeS(O)CH2O—Ph |
| 315 | 2-F-3-MeS(O)CH2O—Ph | 316 | 2-F-4-MeS(O)CH2O—Ph |
| 317 | 2-F-5-MeS(O)CH2O—Ph | 318 | 2-F-6-MeS(O)CH2O—Ph |
| 319 | 2-Cl-3-MeS(O)CH2O—Ph | 320 | 2-Cl-4-MeS(O)CH2O—Ph |
| 321 | 2-Cl-5-MeS(O)CH2O—Ph | 322 | 2-Cl-6-MeS(O)CH2O—Ph |
| 323 | 2-Br-3-MeS(O)CH2O—Ph | 324 | 2-Br-4-MeS(O)CH2O—Ph |
| 325 | 2-Br-5-MeS(O)CH2O—Ph | 326 | 2-Br-6-MeS(O)CH2O—Ph |
| 327 | 2-I-3-MeS(O)CH2O—Ph | 328 | 2-I-4-MeS(O)CH2O—Ph |
| 329 | 2-I-5-MeS(O)CH2O—Ph | 330 | 2-I-6-MeS(O)CH2O—Ph |
| 331 | 2-Me-3-MeSO2CH2O—Ph | 332 | 2-Me-4-MeSO2CH2O—Ph |
| 333 | 2-Me-5-MeSO2CH2O—Ph | 334 | 2-Me-6-MeSO2CH2O—Ph |
| 335 | 2-F-3-MeSO2CH2O—Ph | 336 | 2-F-4-MeSO2CH2O—Ph |
| 337 | 2-F-5-MeSO2CH2O—Ph | 338 | 2-F-6-MeSO2CH2O—Ph |
| 339 | 2-Cl-3-MeSO2CH2O—Ph | 340 | 2-Cl-4-MeSO2CH2O—Ph |
| 341 | 2-Cl-5-MeSO2CH2O—Ph | 342 | 2-Cl-6-MeSO2CH2O—Ph |
| 343 | 2-Br-3-MeSO2CH2O—Ph | 344 | 2-Br-4-MeSO2CH2O—Ph |
| 345 | 2-Br-5-MeSO2CH2O—Ph | 346 | 2-Br-6-MeSO2CH2O—Ph |
| 347 | 2-I-3-MeSO2CH2O—Ph | 348 | 2-I-4-MeSO2CH2O—Ph |
| 349 | 2-I-5-MeSO2CH2O—Ph | 350 | 2-I-6-MeSO2CH2O—Ph |
| 351 | 2-Me-3-(1,3-dioxolan-2-yl)CH2O—Ph | 352 | 2-Me-4-(1,3-dioxolan-2-yl)CH2O—Ph |
| 353 | 2-Me-5-(1,3-dioxolan-2-yl)CH2O—Ph | 354 | 2-Me-6-(1,3-dioxolan-2-yl)CH2O—Ph |
| 355 | 2-F-3-(1,3-dioxolan-2-yl)CH2O—Ph | 356 | 2-F-4-(1,3-dioxolan-2-yl)CH2O—Ph |
| 357 | 2-F-5-(1,3-dioxolan-2-yl)CH2O—Ph | 358 | 2-F-6-(1,3-dioxolan-2-yl)CH2O—Ph |
| 359 | 2-Cl-3-(1,3-dioxolan-2-yl)CH2O—Ph | 360 | 2-Cl-4-(1,3-dioxolan-2-yl)CH2O—Ph |
| 361 | 2-Cl-5-(1,3-dioxolan-2-yl)CH2O—Ph | 362 | 2-Cl-6-(1,3-dioxolan-2-yl)CH2O—Ph |
| 363 | 2-Br-3-(1,3-dioxolan-2-yl)CH2O—Ph | 364 | 2-Br-4-(1,3-dioxolan-2-yl)CH2O—Ph |
| 365 | 2-Br-5-(1,3-dioxolan-2-yl)CH2O—Ph | 366 | 2-Br-6-(1,3-dioxolan-2-yl)CH2O—Ph |
| 367 | 2-I-3-(1,3-dioxolan-2-yl)CH2O—Ph | 368 | 2-I-4-(1,3-dioxolan-2-yl)CH2O—Ph |
| 369 | 2-I-5-(1,3-dioxolan-2-yl)CH2O—Ph | 370 | 2-I-6-(1,3-dioxolan-2-yl)CH2O—Ph |
| 371 | 2-Me-3-(1,3-dioxan-2-yl)CH2CH2O—Ph | 372 | 2-Me-4-(1,3-dioxan-2-yl)CH2CH2O—Ph |
| 373 | 2-Me-5-(1,3-dioxan-2-yl)CH2CH2O—Ph | 374 | 2-Me-6-(1,3-dioxan-2-yl)CH2CH2O—Ph |
| 375 | 2-F-3-(1,3-dioxan-2-yl)CH2CH2O—Ph | 376 | 2-F-4-(1,3-dioxan-2-yl)CH2CH2O—Ph |
| 377 | 2-F-5-(1,3-dioxan-2-yl)CH2CH2O—Ph | 378 | 2-F-6-(1,3-dioxan-2-yl)CH2CH2O—Ph |
| 379 | 2-Cl-3-(1,3-dioxan-2-yl)CH2CH2O—Ph | 380 | 2-Cl-4-(1,3-dioxan-2-yl)CH2CH2O—Ph |
| 381 | 2-Cl-5-(1,3-dioxan-2-yl)CH2CH2O—Ph | 382 | 2-Cl-6-(1,3-dioxan-2-yl)CH2CH2O—Ph |
| 383 | 2-Br-3-(1,3-dioxan-2-yl)CH2CH2O—Ph | 384 | 2-Br-4-(1,3-dioxan-2-yl)CH2CH2O—Ph |
| 385 | 2-Br-5-(1,3-dioxan-2-yl)CH2CH2O—Ph | 386 | 2-Br-6-(1,3-dioxan-2-yl)CH2CH2O—Ph |
| 387 | 2-I-3-(1,3-dioxan-2-yl)CH2CH2O—Ph | 388 | 2-I-4-(1,3-dioxan-2-yl)CH2CH2O—Ph |
| 389 | 2-I-5-(1,3-dioxan-2-yl)CH2CH2O—Ph | 390 | 2-I-6-(1,3-dioxan-2-yl)CH2CH2O—Ph |
| 391 | 2-Me-3-F2CHO—Ph | 392 | 2-Me-4-F2CHO—Ph |
| 393 | 2-Me-5-F2CHO—Ph | 394 | 2-Me-6-F2CHO—Ph |
| 395 | 2-F-3-F2CHO—Ph | 396 | 2-F-4-F2CHO—Ph |
| 397 | 2-F-5-F2CHO—Ph | 398 | 2-F-6-F2CHO—Ph |
| 399 | 2-Cl-3-F2CHO—Ph | 400 | 2-Cl-4-F2CHO—Ph |
| 401 | 2-Cl-5-F2CHO—Ph | 402 | 2-Cl-6-F2CHO—Ph |
| 403 | 2-Br-3-F2CHO—Ph | 404 | 2-Br-4-F2CHO—Ph |
| 405 | 2-Br-5-F2CHO—Ph | 406 | 2-Br-6-F2CHO—Ph |
| 407 | 2-I-3-F2CHO—Ph | 408 | 2-I-4-F2CHO—Ph |
| 409 | 2-I-5-F2CHO—Ph | 410 | 2-I-6-F2CHO—Ph |
| 411 | 2-Me-3-F3CO—Ph | 412 | 2-Me-4-F3CO—Ph |
| 413 | 2-Me-5-F3CO—Ph | 414 | 2-Me-6-F3CO—Ph |

TABLE 2-continued

| No. | Y | No. | Y |
|---|---|---|---|
| 415 | 2-F-3-F3CO—Ph | 416 | 2-F-4-F3CO—Ph |
| 417 | 2-F-5-F3CO—Ph | 418 | 2-F-6-F3CO—Ph |
| 419 | 2-Cl-3-F3CO—Ph | 420 | 2-Cl-4-F3CO—Ph |
| 421 | 2-Cl-5-F3CO—Ph | 422 | 2-Cl-6-F3CO—Ph |
| 423 | 2-Br-3-F3CO—Ph | 424 | 2-Br-4-F3CO—Ph |
| 425 | 2-Br-5-F3CO—Ph | 426 | 2-Br-6-F3CO—Ph |
| 427 | 2-I-3-F3CO—Ph | 428 | 2-I-4-F3CO—Ph |
| 429 | 2-I-5-F3CO—Ph | 430 | 2-I-6-F3CO—Ph |
| 431 | 2-Me-3-F2CHCH2O—Ph | 432 | 2-Me-4-F2CHCH2O—Ph |
| 433 | 2-Me-5-F2CHCH2O—Ph | 434 | 2-Me-6-F2CHCH2O—Ph |
| 435 | 2-F-3-F2CHCH2O—Ph | 436 | 2-F-4-F2CHCH2O—Ph |
| 437 | 2-F-5-F2CHCH2O—Ph | 438 | 2-F-6-F2CHCH2O—Ph |
| 439 | 2-Cl-3-F2CHCH2O—Ph | 440 | 2-Cl-4-F2CHCH2O—Ph |
| 441 | 2-Cl-5-F2CHCH2O—Ph | 442 | 2-Cl-6-F2CHCH2O—Ph |
| 443 | 2-Br-3-F2CHCH2O—Ph | 444 | 2-Br-4-F2CHCH2O—Ph |
| 445 | 2-Br-5-F2CHCH2O—Ph | 446 | 2-Br-6-F2CHCH2O—Ph |
| 447 | 2-I-3-F2CHCH2O—Ph | 448 | 2-I-4-F2CHCH2O—Ph |
| 449 | 2-I-5-F2CHCH2O—Ph | 450 | 2-I-6-F2CHCH2O—Ph |
| 451 | 2-Me-3-F3CCH2O—Ph | 452 | 2-Me-4-F3CCH2O—Ph |
| 453 | 2-Me-5-F3CCH2O—Ph | 454 | 2-Me-6-F3CCH2O—Ph |
| 455 | 2-F-3-F3CCH2O—Ph | 456 | 2-F-4-F3CCH2O—Ph |
| 457 | 2-F-5-F3CCH2O—Ph | 458 | 2-F-6-F3CCH2O—Ph |
| 459 | 2-Cl-3-F3CCH2O—Ph | 460 | 2-Cl-4-F3CCH2O—Ph |
| 461 | 2-Cl-5-F3CCH2O—Ph | 462 | 2-Cl-6-F3CCH2O—Ph |
| 463 | 2-Br-3-F3CCH2O—Ph | 464 | 2-Br-4-F3CCH2O—Ph |
| 465 | 2-Br-5-F3CCH2O—Ph | 466 | 2-Br-6-F3CCH2O—Ph |
| 467 | 2-I-3-F3CCH2O—Ph | 468 | 2-I-4-F3CCH2O—Ph |
| 469 | 2-I-5-F3CCH2O—Ph | 470 | 2-I-6-F3CCH2O—Ph |
| 471 | 2-Me-3-HC≡CCH2O—Ph | 472 | 2-Me-4-HC≡CCH2O—Ph |
| 473 | 2-Me-5-HC≡CCH2O—Ph | 474 | 2-Me-6-HC≡CCH2O—Ph |
| 475 | 2-F-3-HC≡CCH2O—Ph | 476 | 2-F-4-HC≡CCH2O—Ph |
| 477 | 2-F-5-HC≡CCH2O—Ph | 478 | 2-F-6-HC≡CCH2O—Ph |
| 479 | 2-Cl-3-HC≡CCH2O—Ph | 480 | 2-Cl-4-HC≡CCH2O—Ph |
| 481 | 2-Cl-5-HC≡CCH2O—Ph | 482 | 2-Cl-6-HC≡CCH2O—Ph |
| 483 | 2-Br-3-HC≡CCH2O—Ph | 484 | 2-Br-4-HC≡CCH2O—Ph |
| 485 | 2-Br-5-HC≡CCH2O—Ph | 486 | 2-Br-6-HC≡CCH2O—Ph |
| 487 | 2-I-3-HC≡CCH2O—Ph | 488 | 2-I-4-HC≡CCH2O—Ph |
| 489 | 2-I-5-HC≡CCH2O—Ph | 490 | 2-I-6-HC≡CCH2O—Ph |
| 491 | 2-Me-3-(3-Cl-5-F3C-2-Py)O—Ph | 492 | 2-Me-4-(3-Cl-5-F3C-2-Py)O—Ph |
| 493 | 2-Me-5-(3-Cl-5-F3C-2-Py)O—Ph | 494 | 2-Me-6-(3-Cl-5-F3C-2-Py)O—Ph |
| 495 | 2-F-3-(3-Cl-5-F3C-2-Py)O—Ph | 496 | 2-F-4-(3-Cl-5-F3C-2-Py)O—Ph |
| 497 | 2-F-5-(3-Cl-5-F3C-2-Py)O—Ph | 498 | 2-F-6-(3-Cl-5-F3C-2-Py)O—Ph |
| 499 | 2-Cl-3-(3-Cl-5-F3C-2-Py)O—Ph | 500 | 2-Cl-4-(3-Cl-5-F3C-2-Py)O—Ph |
| 501 | 2-Cl-5-(3-Cl-5-F3C-2-Py)O—Ph | 502 | 2-Cl-6-(3-Cl-5-F3C-2-Py)O—Ph |
| 503 | 2-Br-3-(3-Cl-5-F3C-2-Py)O—Ph | 504 | 2-Br-4-(3-Cl-5-F3C-2-Py)O—Ph |
| 505 | 2-Br-5-(3-Cl-5-F3C-2-Py)O—Ph | 506 | 2-Br-6-(3-Cl-5-F3C-2-Py)O—Ph |
| 507 | 2-I-3-(3-Cl-5-F3C-2-Py)O—Ph | 508 | 2-I-4-(3-Cl-5-F3C-2-Py)O—Ph |
| 509 | 2-I-5-(3-Cl-5-F3C-2-Py)O—Ph | 510 | 2-I-6-(3-Cl-5-F3C-2-Py)O—Ph |
| 511 | 2-Me-3-PhCH2O—Ph | 512 | 2-Me-4-PhCH2O—Ph |
| 513 | 2-Me-5-PhCH2O—Ph | 514 | 2-Me-6-PhCH2O—Ph |
| 515 | 2-F-3-PhCH2O—Ph | 516 | 2-F-4-PhCH2O—Ph |
| 517 | 2-F-5-PhCH2O—Ph | 518 | 2-F-6-PhCH2O—Ph |
| 519 | 2-Cl-3-PhCH2O—Ph | 520 | 2-Cl-4-PhCH2O—Ph |
| 521 | 2-Cl-5-PhCH2O—Ph | 522 | 2-Cl-6-PhCH2O—Ph |
| 523 | 2-Br-3-PhCH2O—Ph | 524 | 2-Br-4-PhCH2O—Ph |
| 525 | 2-Br-5-PhCH2O—Ph | 526 | 2-Br-6-PhCH2O—Ph |
| 527 | 2-I-3-PhCH2O—Ph | 528 | 2-I-4-PhCH2O—Ph |
| 529 | 2-I-5-PhCH2O—Ph | 530 | 2-I-6-PhCH2O—Ph |
| 531 | 2-Me-3-AcO—Ph | 532 | 2-Me-4-AcO—Ph |
| 533 | 2-Me-5-AcO—Ph | 534 | 2-Me-6-AcO—Ph |
| 535 | 2-F-3-AcO—Ph | 536 | 2-F-4-AcO—Ph |
| 537 | 2-F-5-AcO—Ph | 538 | 2-F-6-AcO—Ph |
| 539 | 2-Cl-3-AcO—Ph | 540 | 2-Cl-4-AcO—Ph |
| 541 | 2-Cl-5-AcO—Ph | 542 | 2-Cl-6-AcO—Ph |
| 543 | 2-Br-3-AcO—Ph | 544 | 2-Br-4-AcO—Ph |
| 545 | 2-Br-5-AcO—Ph | 546 | 2-Br-6-AcO—Ph |
| 547 | 2-I-3-AcO—Ph | 548 | 2-I-4-AcO—Ph |
| 549 | 2-I-5-AcO—Ph | 550 | 2-I-6-AcO—Ph |
| 551 | 2-Me-3-MeOC(=O)O—Ph | 552 | 2-Me-4-MeOC(=O)O—Ph |
| 553 | 2-Me-5-MeOC(=O)O—Ph | 554 | 2-Me-6-MeOC(=O)O—Ph |
| 555 | 2-F-3-MeOC(=O)O—Ph | 556 | 2-F-4-MeOC(=O)O—Ph |
| 557 | 2-F-5-MeOC(=O)O—Ph | 558 | 2-F-6-MeOC(=O)O—Ph |
| 559 | 2-Cl-3-MeOC(=O)O—Ph | 560 | 2-Cl-4-MeOC(=O)O—Ph |
| 561 | 2-Cl-5-MeOC(=O)O—Ph | 562 | 2-Cl-6-MeOC(=O)O—Ph |
| 563 | 2-Br-3-MeOC(=O)O—Ph | 564 | 2-Br-4-MeOC(=O)O—Ph |
| 565 | 2-Br-5-MeOC(=O)O—Ph | 566 | 2-Br-6-MeOC(=O)O—Ph |
| 567 | 2-I-3-MeOC(=O)O—Ph | 568 | 2-I-4-MeOC(=O)O—Ph |
| 569 | 2-I-5-MeOC(=O)O—Ph | 570 | 2-I-6-MeOC(=O)O—Ph |

TABLE 2-continued

| No. | Y | No. | Y |
|---|---|---|---|
| 571 | 2-Me-3-EtOC(=O)O—Ph | 572 | 2-Me-4-EtOC(=O)O—Ph |
| 573 | 2-Me-5-EtOC(=O)O—Ph | 574 | 2-Me-6-EtOC(=O)O—Ph |
| 575 | 2-F-3-EtOC(=O)O—Ph | 576 | 2-F-4-EtOC(=O)O—Ph |
| 577 | 2-F-5-EtOC(=O)O—Ph | 578 | 2-F-6-EtOC(=O)O—Ph |
| 579 | 2-Cl-3-EtOC(=O)O—Ph | 580 | 2-Cl-4-EtOC(=O)O—Ph |
| 581 | 2-Cl-5-EtOC(=O)O—Ph | 582 | 2-Cl-6-EtOC(=O)O—Ph |
| 583 | 2-Br-3-EtOC(=O)O—Ph | 584 | 2-Br-4-EtOC(=O)O—Ph |
| 585 | 2-Br-5-EtOC(=O)O—Ph | 586 | 2-Br-6-EtOC(=O)O—Ph |
| 587 | 2-I-3-EtOC(=O)O—Ph | 588 | 2-I-4-EtOC(=O)O—Ph |
| 589 | 2-I-5-EtOC(=O)O—Ph | 590 | 2-I-6-EtOC(=O)O—Ph |
| 591 | 2,3,5-tri-Me—Ph | 592 | 3,5-di-F-2-Me—Ph |
| 593 | 3,5-di-Cl-2-Me—Ph | 594 | 3,5-di-Br-2-Me—Ph |
| 595 | 3,5-di-I-2-Me—Ph | 596 | 2-F-3,5-di-Me—Ph |
| 597 | 2,3,5-tri-F—Ph | 598 | 3,5-di-Cl-2-F—Ph |
| 599 | 3,5-di-Br-2-F—Ph | 600 | 2-F-3,5-di-I—Ph |
| 601 | 2-Cl-3,5-di-Me—Ph | 602 | 2-Cl-3,5-di-F—Ph |
| 603 | 2,3,5-tri-Cl—Ph | 604 | 3,5-di-Br-2-Cl—Ph |
| 605 | 2-Cl-3,5-di-I—Ph | 606 | 2-Br-3,5-di-Me—Ph |
| 607 | 2-Br-3,5-di-F—Ph | 608 | 2-Br-3,5-di-Cl—Ph |
| 609 | 2,3,5-tri-Br—Ph | 610 | 2-Br-3,5-di-I—Ph |
| 611 | 2-I-3,5-di-Me—Ph | 612 | 3,5-di-F-2-I—Ph |
| 613 | 3,5-di-Cl-2-I—Ph | 614 | 3,5-di-Br-2-I—Ph |
| 615 | 2,3,5-tri-I—Ph | 616 | 2-Me-3,5-di-MeO—Ph |
| 617 | 2-F-3,5-di-MeO—Ph | 618 | 2-Cl-3,5-di-MeO—Ph |
| 619 | 2-Br-3,5-di-MeO—Ph | 620 | 2-I-3,5-di-MeO—Ph |
| 621 | 2-Me-3-Py | 622 | 3-Me-4-Py |
| 623 | 4-Me-3-Py | 624 | 3-Me-2-Py |
| 625 | 2-F-3-Py | 626 | 3-F-4-Py |
| 627 | 4-F-3-Py | 628 | 3-F-2-Py |
| 629 | 2-Cl-3-Py | 630 | 3-Cl-4-Py |
| 631 | 4-Cl-3-Py | 632 | 3-Cl-2-Py |
| 633 | 2-Br-3-Py | 634 | 3-Br-4-Py |
| 635 | 4-Br-3-Py | 636 | 3-Br-2-Py |
| 637 | 2-I-3-Py | 638 | 3-I-4-Py |
| 639 | 4-I-3-Py | 640 | 3-I-2-Py |
| 641 | 2,6-di-Me-3-Py | 642 | 2,5-di-Me-3-Py |
| 643 | 2,4-di-Me-3-Py | 644 | 4,6-di-Me-3-Py |
| 645 | 4,5-di-Me-3-Py | 646 | 2,3-di-Me-4-Py |
| 647 | 2,5-di-Me-4-Py | 648 | 3,5-di-Me-4-Py |
| 649 | 3,4-di-Me-2-Py | 650 | 3,5-di-Me-2-Py |
| 651 | 3,6-di-Me-2-Py | 652 | 2,6-di-F-3-Py |
| 653 | 2,5-di-F-3-Py | 654 | 2,4-di-F-3-Py |
| 655 | 4,6-di-F-3-Py | 656 | 4,5-di-F-3-Py |
| 657 | 2,3-di-F-4-Py | 658 | 2,5-di-F-4-Py |
| 659 | 3,5-di-F-4-Py | 660 | 3,4-di-F-2-Py |
| 661 | 3,5-di-F-2-Py | 662 | 3,6-di-F-2-Py |
| 663 | 2,6-di-Cl-3-Py | 664 | 2,5-di-Cl-3-Py |
| 665 | 2,4-di-Cl-3-Py | 666 | 4,6-di-Cl-3-Py |
| 667 | 4,5-di-Cl-3-Py | 668 | 2,3-di-Cl-4-Py |
| 669 | 2,5-di-Cl-4-Py | 670 | 3,5-di-Cl-4-Py |
| 671 | 3,4-di-F-2-Py | 672 | 3,5-di-F-2-Py |
| 673 | 3,6-di-Cl-2-Py | 674 | 2,6-di-Br-3-Py |
| 675 | 2,5-di-Br-3-Py | 676 | 2,4-di-Br-3-Py |
| 677 | 4,6-di-Br-3-Py | 678 | 4,5-di-Br-3-Py |
| 679 | 2,3-di-Br-4-Py | 680 | 2,5-di-Br-4-Py |
| 681 | 3,5-di-Br-4-Py | 682 | 3,4-di-F-2-Py |
| 683 | 3,5-di-F-2-Py | 684 | 3,6-di-Br-2-Py |
| 685 | 2,6-di-I-3-Py | 686 | 2,5-di-I-3-Py |
| 687 | 2,4-di-I-3-Py | 688 | 4,6-di-I-3-Py |
| 689 | 4,5-di-I-3-Py | 690 | 2,3-di-I-4-Py |
| 691 | 2,5-di-I-4-Py | 692 | 3,5-di-I-4-Py |
| 693 | 3,4-di-F-2-Py | 694 | 3,5-di-F-2-Py |
| 695 | 3,6-di-I-2-Py | 696 | 2-Me-6-MeO-3-Py |
| 697 | 4-Me-6-MeO-3-Py | 698 | 3-Me-5-MeO-2-Py |
| 699 | 2-Me-5-MeO-3-Py | 700 | 5-Me-2-MeO-4-Py |
| 701 | 3-Me-6-MeO-2-Py | 702 | 3-Me-2-MeO-4-Py |
| 703 | 4-Me-5-MeO-3-Py | 704 | 3-Me-4-MeO-2-Py |
| 705 | 2-F-6-MeO-3-Py | 706 | 4-F-6-MeO-3-Py |
| 707 | 3-F-5-MeO-2-Py | 708 | 2-F-5-MeO-3-Py |
| 709 | 5-F-2-MeO-4-Py | 710 | 3-F-6-MeO-2-Py |
| 711 | 3-F-2-MeO-4-Py | 712 | 4-F-5-MeO-3-Py |
| 713 | 3-F-4-MeO-2-Py | 714 | 2-Cl-6-MeO-3-Py |
| 715 | 4-Cl-6-MeO-3-Py | 716 | 3-Cl-5-MeO-2-Py |
| 717 | 2-Cl-5-MeO-3-Py | 718 | 5-Cl-2-MeO-4-Py |
| 719 | 3-Cl-6-MeO-2-Py | 720 | 3-Cl-2-MeO-4-Py |
| 721 | 4-Cl-5-MeO-3-Py | 722 | 3-Cl-4-MeO-2-Py |
| 723 | 2-Br-6-MeO-3-Py | 724 | 4-Br-6-MeO-3-Py |
| 725 | 3-Br-5-MeO-2-Py | 726 | 2-Br-5-MeO-3-Py |

TABLE 2-continued

| No. | Y | No. | Y |
|---|---|---|---|
| 727 | 5-Br-2-MeO-4-Py | 728 | 3-Br-6-MeO-2-Py |
| 729 | 3-Br-2-MeO-4-Py | 730 | 4-Br-5-MeO-3-Py |
| 731 | 3-Br-4-MeO-2-Py | 732 | 2-I-6-MeO-3-Py |
| 733 | 4-I-6-MeO-3-Py | 734 | 3-I-5-MeO-2-Py |
| 735 | 2-I-5-MeO-3-Py | 736 | 5-I-2-MeO-4-Py |
| 737 | 3-I-6-MeO-2-Py | 738 | 3-I-2-MeO-4-Py |
| 739 | 4-I-5-MeO-3-Py | 740 | 3-I-4-MeO-2-Py |
| 741 | 2-Me-3-Ac—Ph | 742 | 2-Me-4-Ac—Ph |
| 743 | 2-Me-5-Ac—Ph | 744 | 2-Me-6-Ac—Ph |
| 745 | 2-F-3-Ac—Ph | 746 | 2-F-4-Ac—Ph |
| 747 | 2-F-5-Ac—Ph | 748 | 2-F-6-Ac—Ph |
| 749 | 2-Cl-3-Ac—Ph | 750 | 2-Cl-4-Ac—Ph |
| 751 | 2-Cl-5-Ac—Ph | 752 | 2-Cl-6-Ac—Ph |
| 753 | 2-Br-3-Ac—Ph | 754 | 2-Br-4-Ac—Ph |
| 755 | 2-Br-5-Ac—Ph | 756 | 2-Br-6-Ac—Ph |
| 757 | 2-I-3-Ac—Ph | 758 | 2-I-4-Ac—Ph |
| 759 | 2-I-5-Ac—Ph | 760 | 2-I-6-Ac—Ph |

Hereinbelow, examples of the processes for producing the compounds of the formula (1) will be illustrated. The processes for producting the inventive compounds are not limited to Production Process A to Production Process V.

[Production Process A]

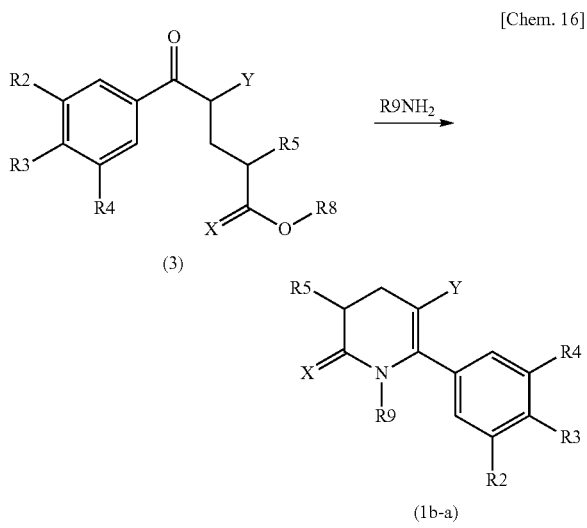

[Chem. 16]

In the formulae, R9 represents a hydrogen atom, a hydroxy group, a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group), R8 represents a hydrogen atom or a C1-C6 alkyl group, and R2, R3, R4, R5, X and Y are the same as defined hereinabove.

Production Process A is a method for obtaining a compound of the formula (1b-a) which is an inventive compound and also an intermediate of an inventive compound. The production process includes reacting a compound represented by the formula (3) with R9NH$_2$ in the presence of an acid.

R9NH$_2$ used in the reaction may be purchased from the market or may be produced by a known method. R9NH$_2$ may be in the form of a salt with an acidic compound such as hydrochloric acid or acetic acid, and is not particularly limited as long as the target reaction takes place.

The amount of R9NH$_2$ used in the reaction is at least 1 equivalent amount relative to the compound of the formula (3), and is not particularly limited as long as the above equivalent amount is satisfied and also the target reaction takes place. The amount is preferably 1 equivalent amount to 200 equivalent amounts.

Examples of the acids used in the reaction include inorganic acids such as hydrochloric acid and sulfuric acid, organic acids such as acetic acid, methanesulfonic acid and p-toluenesulfonic acid, and the like. The acid is not particularly limited as long as the target reaction takes place, but acetic acid is preferable. Where R9NH$_2$ is used as a salt with an acidic compound, the acid may not be used.

The amount of the acid used in the reaction is at least 1 equivalent amount relative to R9NH$_2$, and is not particularly limited as long as the above equivalent amount is satisfied and also the target reaction takes place. The amount is preferably 1 equivalent amount to 200 equivalent amounts. Where the acid used is liquid, it may also serve as a solvent.

The reaction may involve a solvent, but the use of a solvent is not indispensable.

The solvent used in the reaction is not particularly limited as long as the target reaction takes place. Examples of the solvents include acidic solvents such as acetic acid and methanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be used in combination in any ratio. The solvent is preferably an acidic solvent, and more preferably acetic acid.

The amount of the solvent used in the reaction is not particularly limited as long as the target reaction takes place, but is usually 3 to 200 times the weight of the compound represented by the formula (3).

The temperature at which the reaction is performed is not particularly limited as long as the target reaction takes place, but is usually from 50° C. to 180° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1b-a) may be dehydrated with a desiccant such as sodium sulfate or magnesium sulfate. This drying process may be omitted.

The reaction mixture including the compound of the formula (1b-a) may be distilled under reduced pressure to remove the solvent while avoiding the decomposition of the compound.

After the distillation, the reaction mixture including the compound of the formula (1b-a) may be purified by, for example, washing, reprecipitation, recrystallization or column chromatography using an appropriate solvent. The purification process may be selected appropriately in accordance with the desired purity.

According to Production Process A, a compound represented by the formula (1b-a) in which R9 is a hydrogen atom, specifically, a compound represented by the formula (2), may be produced. This compound may be a useful intermediate for the production of an inventive compound represented by the formula (1b).

Specific examples of the intermediates represented by the formula (2) may be represented by combinations of the structural formulae shown in Table 3, Y shown in Table 2, and X that is an oxygen atom or a sulfur atom. Such compounds are only illustrative and do not limit the scope of the present invention thereto.

TABLE 3

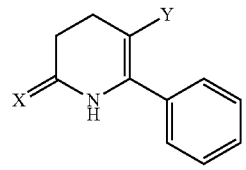

I-1

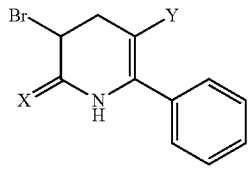

I-2

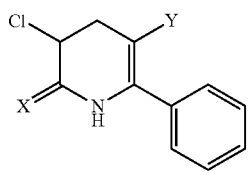

I-3

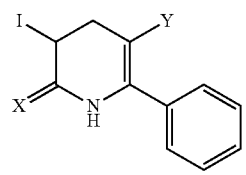

I-4

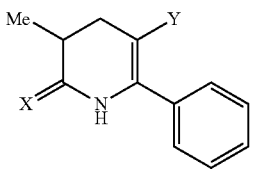

I-5

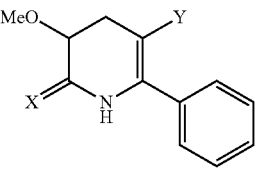

I-6

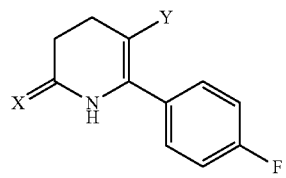

I-7

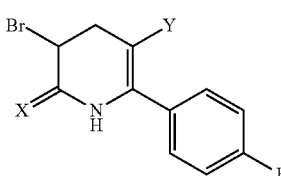

I-8

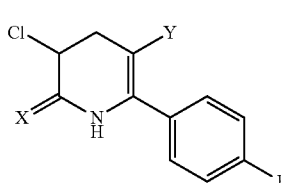

I-9

TABLE 3-continued

| Structure | ID |
|---|---|
| 3-iodo, 6-(4-fluorophenyl) dihydropyridinone | I-10 |
| 3-methyl, 6-(4-fluorophenyl) dihydropyridinone | I-11 |
| 3-methoxy, 6-(4-fluorophenyl) dihydropyridinone | I-12 |
| 6-(4-chlorophenyl) dihydropyridinone | I-13 |
| 3-bromo, 6-(4-chlorophenyl) dihydropyridinone | I-14 |
| 3-chloro, 6-(4-chlorophenyl) dihydropyridinone | I-15 |
| 3-iodo, 6-(4-chlorophenyl) dihydropyridinone | I-16 |
| 3-methyl, 6-(4-chlorophenyl) dihydropyridinone | I-17 |
| 3-methoxy, 6-(4-chlorophenyl) dihydropyridinone | I-18 |
| 6-(4-bromophenyl) dihydropyridinone | I-19 |
| 3-bromo, 6-(4-bromophenyl) dihydropyridinone | I-20 |
| 3-chloro, 6-(4-bromophenyl) dihydropyridinone | I-21 |
| 3-iodo, 6-(4-bromophenyl) dihydropyridinone | I-22 |
| 3-methyl, 6-(4-bromophenyl) dihydropyridinone | I-23 |
| 3-methoxy, 6-(4-bromophenyl) dihydropyridinone | I-24 |
| 6-(4-methylphenyl) dihydropyridinone | I-25 |
| 3-bromo, 6-(4-methylphenyl) dihydropyridinone | I-26 |

TABLE 3-continued

| Structure | No. |
|---|---|
| 3-Cl, 5-Y, 2-(4-Me-phenyl) dihydropyridinone | I-27 |
| 3-I, 5-Y, 2-(4-Me-phenyl) dihydropyridinone | I-28 |
| 3-Me, 5-Y, 2-(4-Me-phenyl) dihydropyridinone | I-29 |
| 3-MeO, 5-Y, 2-(4-Me-phenyl) dihydropyridinone | I-30 |
| 5-Y, 2-(3,5-diF-phenyl) dihydropyridinone | I-31 |
| 3-Br, 5-Y, 2-(3,5-diF-phenyl) dihydropyridinone | I-32 |
| 3-Cl, 5-Y, 2-(3,5-diF-phenyl) dihydropyridinone | I-33 |
| 3-I, 5-Y, 2-(3,5-diF-phenyl) dihydropyridinone | I-34 |
| 3-Me, 5-Y, 2-(3,5-diF-phenyl) dihydropyridinone | I-35 |
| 3-MeO, 5-Y, 2-(3,5-diF-phenyl) dihydropyridinone | I-36 |
| 5-Y, 2-(3,4,5-triF-phenyl) dihydropyridinone | I-37 |
| 3-Br, 5-Y, 2-(3,4,5-triF-phenyl) dihydropyridinone | I-38 |
| 3-Cl, 5-Y, 2-(3,4,5-triF-phenyl) dihydropyridinone | I-39 |
| 3-I, 5-Y, 2-(3,4,5-triF-phenyl) dihydropyridinone | I-40 |
| 3-Me, 5-Y, 2-(3,4,5-triF-phenyl) dihydropyridinone | I-41 |

TABLE 3-continued
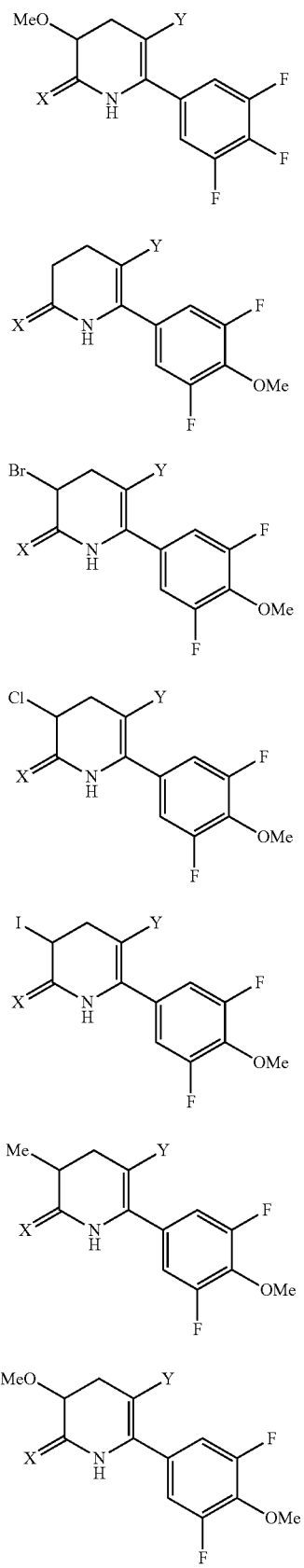
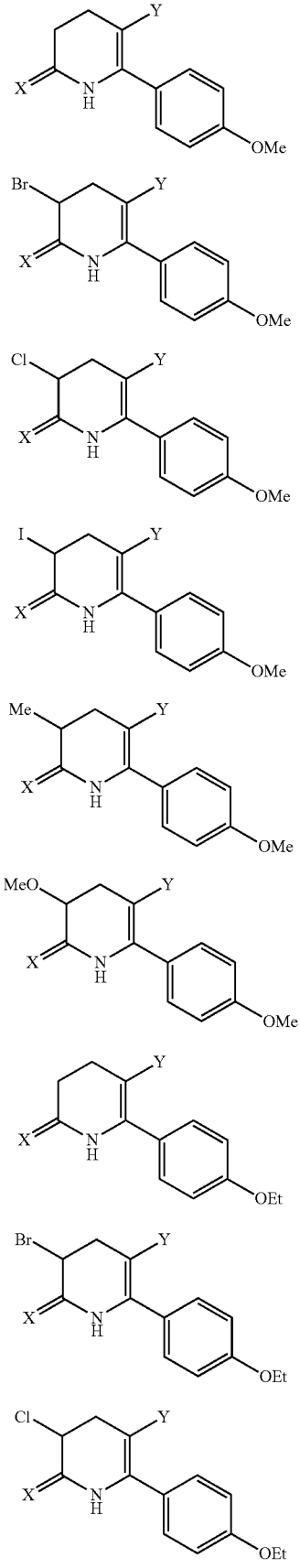

TABLE 3-continued

| Structure | ID |
|---|---|
| (3-iodo, 4-OEt phenyl) | I-58 |
| (3-Me, 4-OEt phenyl) | I-59 |
| (3-MeO, 4-OEt phenyl) | I-60 |
| (4-OCH₂CHF₂ phenyl) | I-61 |
| (3-Br, 4-OCH₂CHF₂ phenyl) | I-62 |
| (3-Cl, 4-OCH₂CHF₂ phenyl) | I-63 |
| (3-I, 4-OCH₂CHF₂ phenyl) | I-64 |
| (3-Me, 4-OCH₂CHF₂ phenyl) | I-65 |
| (3-MeO, 4-OCH₂CHF₂ phenyl) | I-66 |
| (4-OCH₂CF₃ phenyl) | I-67 |
| (3-Br, 4-OCH₂CF₃ phenyl) | I-68 |
| (3-Cl, 4-OCH₂CF₃ phenyl) | I-69 |
| (3-I, 4-OCH₂CF₃ phenyl) | I-70 |
| (3-Me, 4-OCH₂CF₃ phenyl) | I-71 |
| (3-MeO, 4-OCH₂CF₃ phenyl) | I-72 |
| (4-OCH₂OMe phenyl) | I-73 |
| (3-Br, 4-OCH₂OMe phenyl) | I-74 |

TABLE 3-continued
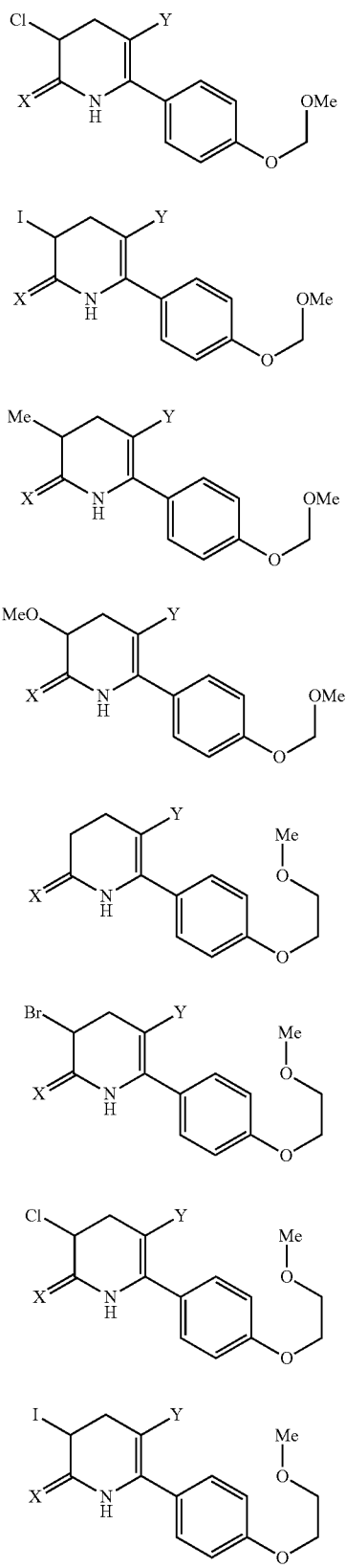
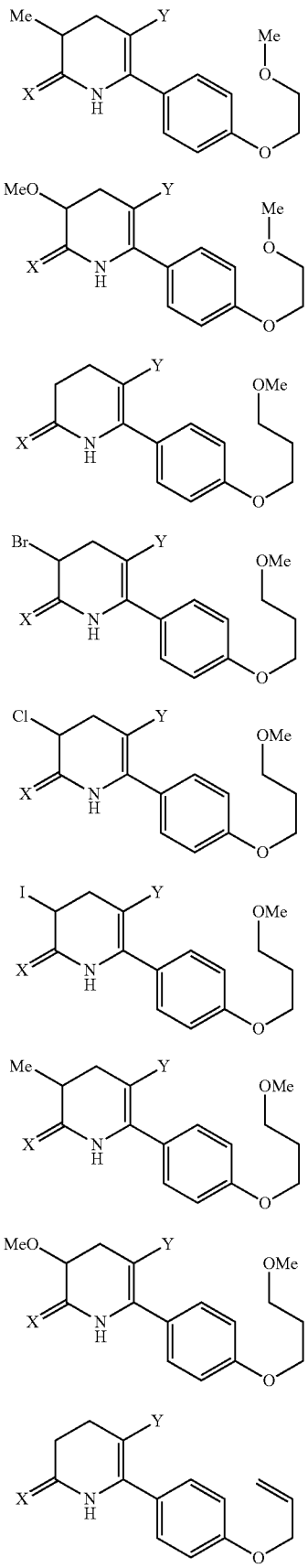

TABLE 3-continued
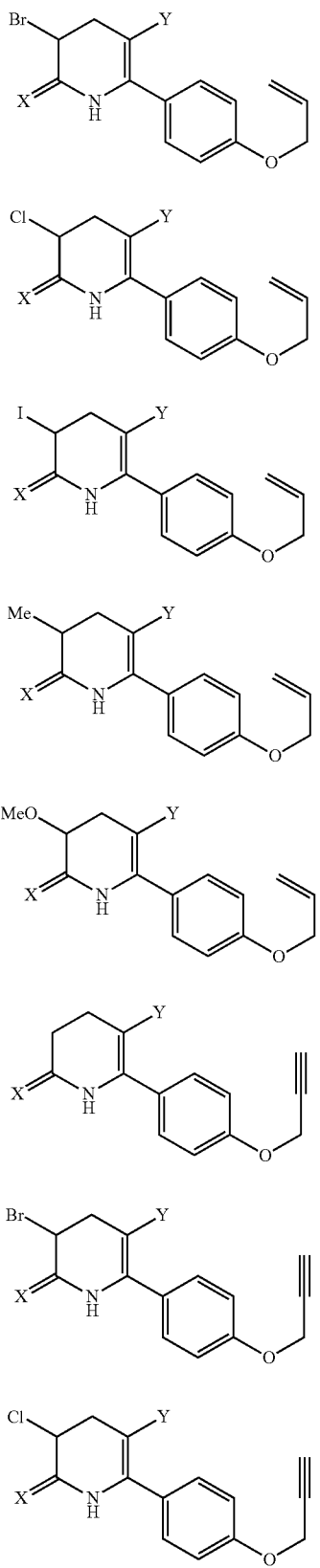
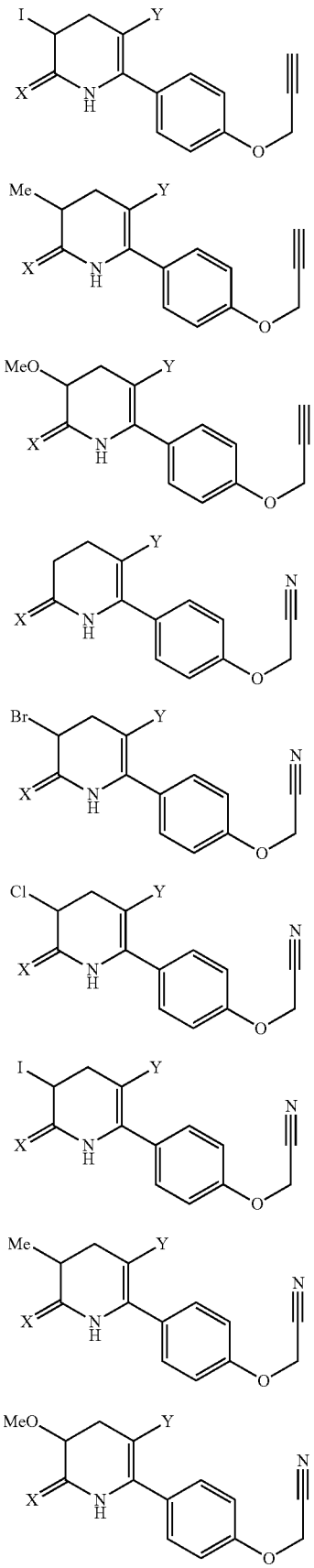

TABLE 3-continued
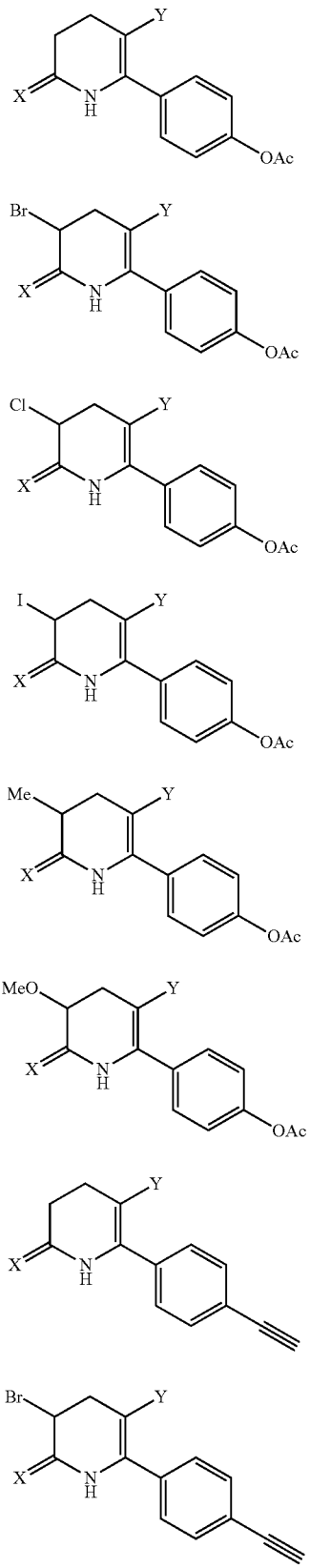
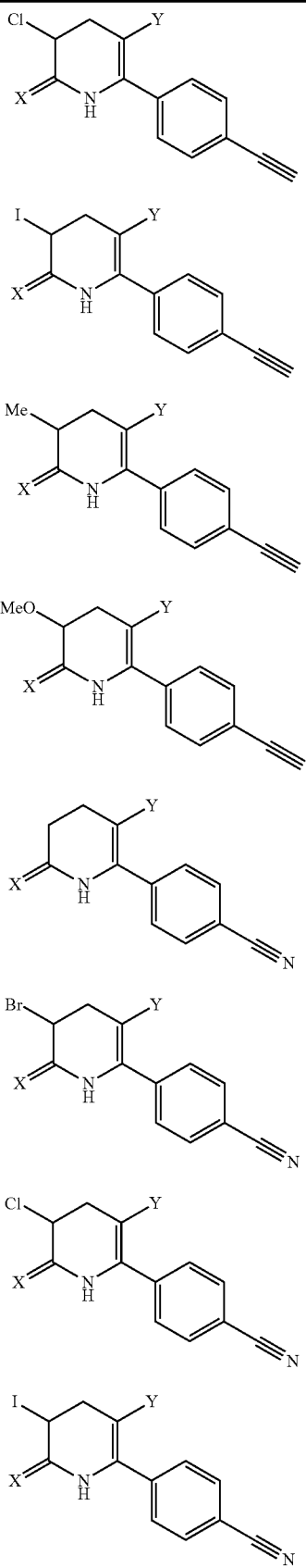

TABLE 3-continued
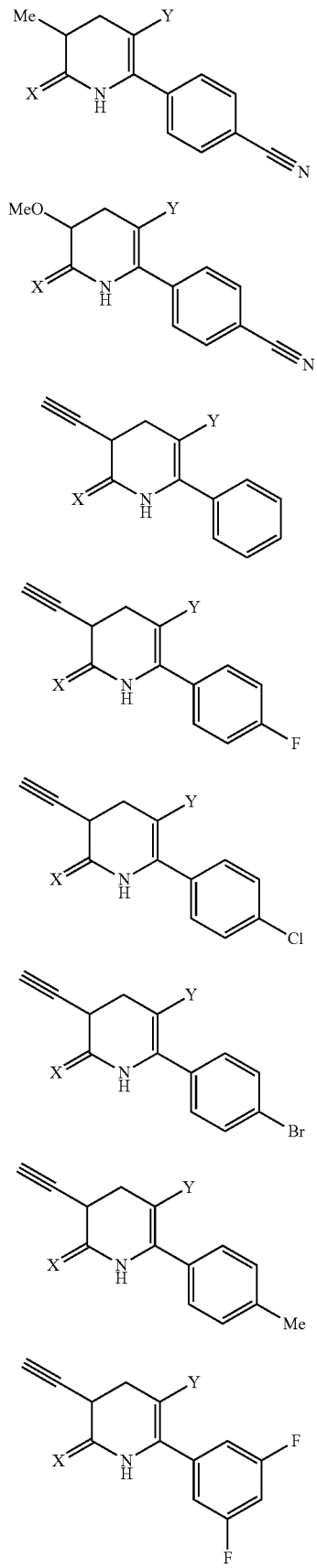
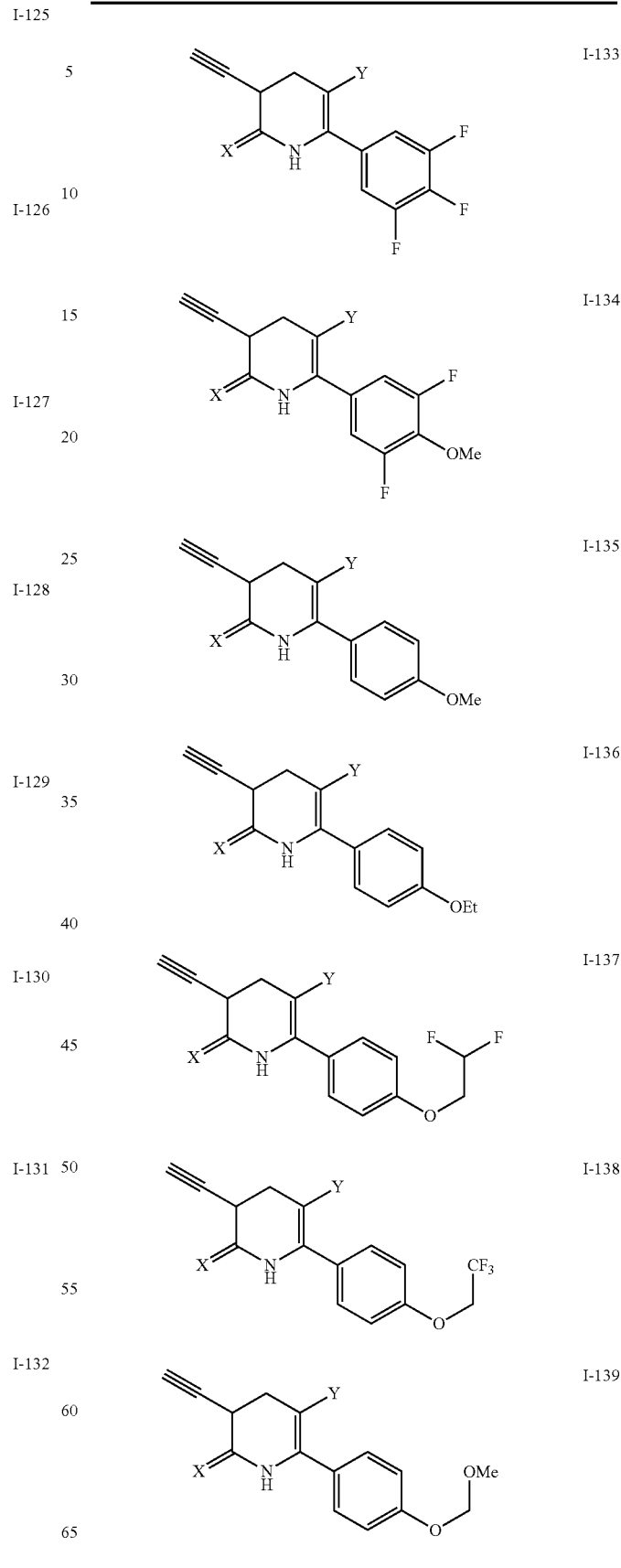

TABLE 3-continued
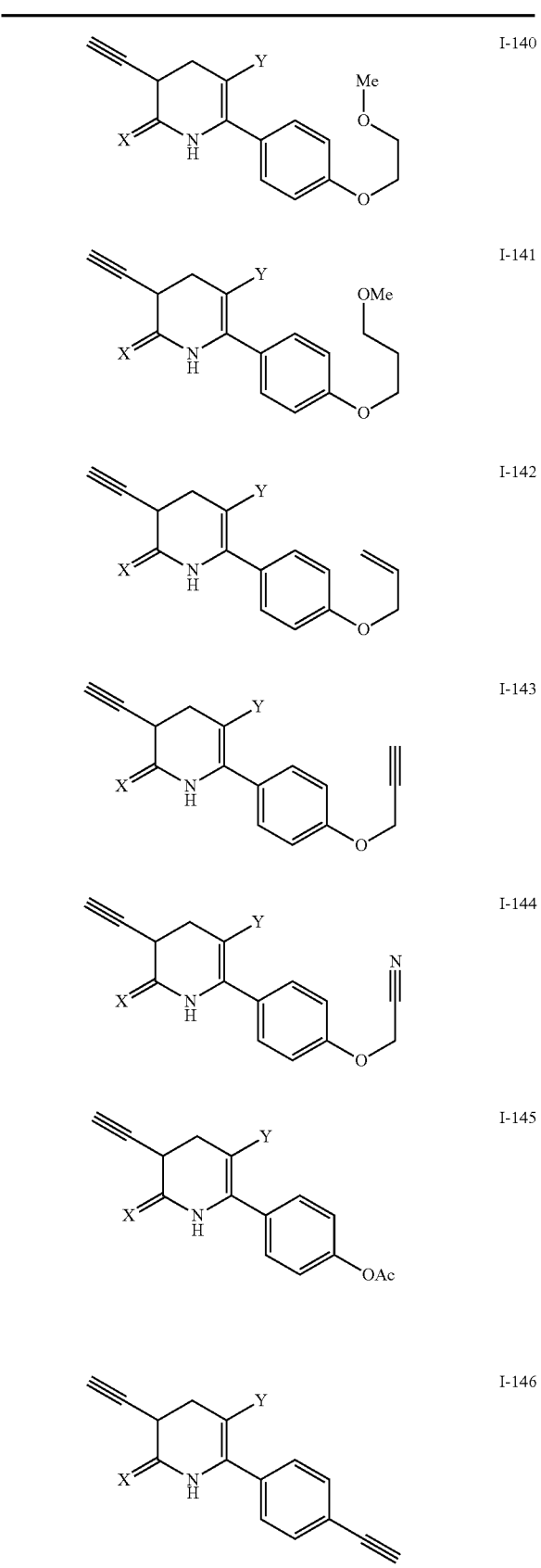
| | |
|---|---|
| I-140 | |
| I-141 | |
| I-142 | |
| I-143 | |
| I-144 | |
| I-145 | |
| I-146 | |
TABLE 3-continued
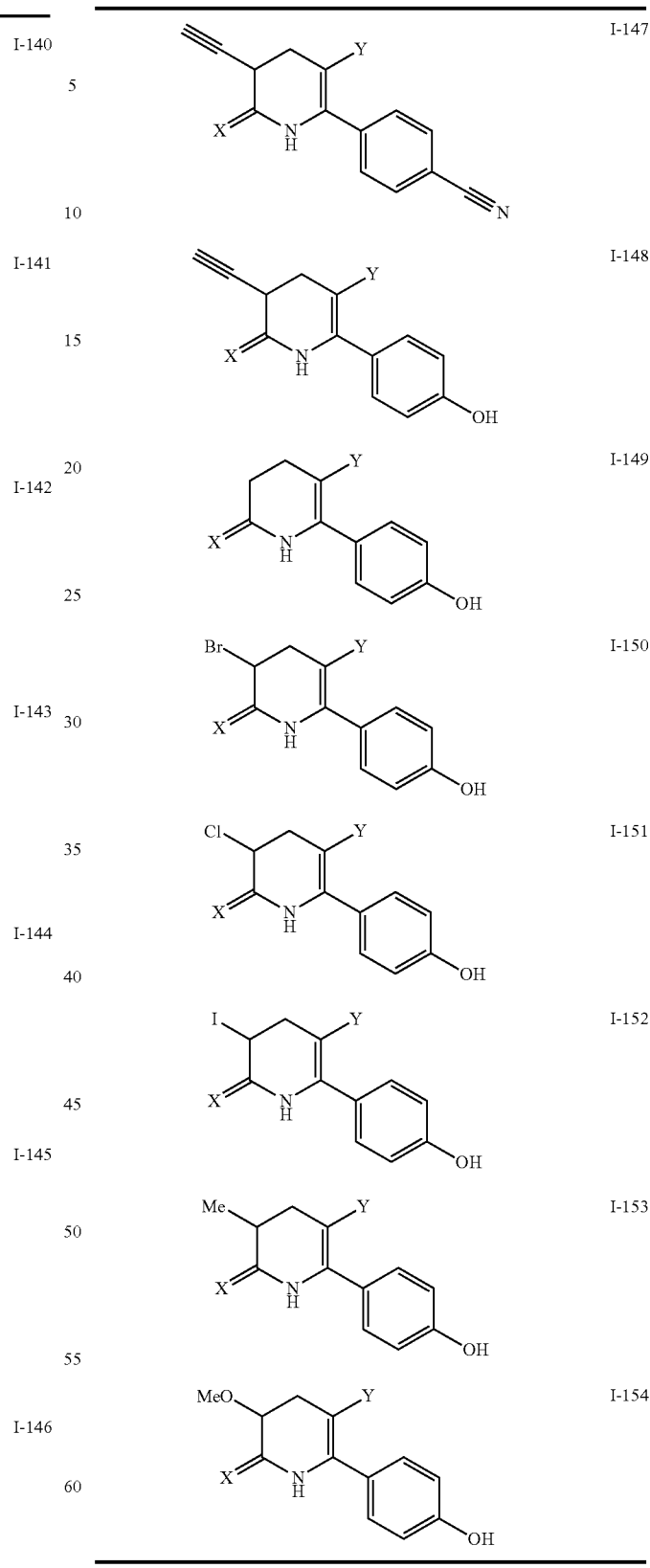
| | |
|---|---|
| I-147 | |
| I-148 | |
| I-149 | |
| I-150 | |
| I-151 | |
| I-152 | |
| I-153 | |
| I-154 | |
There will be described a process for obtaining an compound of the formula (1b) of the present invention using a compound represented by the formula (2) as an intermediate.

[Production Process B]

[Chem. 17]

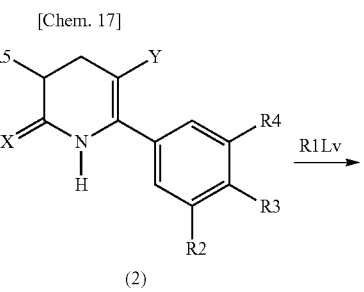

(2)

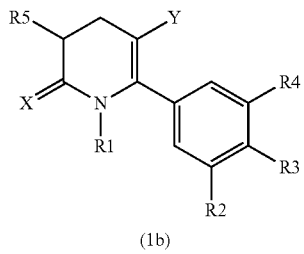

(1b)

In the formulae, Lv represents a leaving group such as a methanesulfonyl group, a trifluoromethanesulfonyl group, a p-toluenesulfonyl group or a halogen atom, and R1, R2, R3, R4, R5, X and Y are the same as defined hereinabove.

Production Process B is a method for obtaining a compound represented by the formula (1b), and includes reacting an intermediate of the formula (2) with R1Lv in a solvent in the presence of a base.

R1Lv used in the reaction may be purchased from the market or may be produced by a known method.

The amount of R1Lv used in the reaction is at least 1 equivalent amount relative to the compound of the formula (2) and is not particularly limited as long as the above equivalent amount is satisfied and also the target reaction takes place. The amount is preferably 1 equivalent amount to 10 equivalent amounts.

Examples of the bases used in the reaction include inorganic bases such as sodium hydroxide, potassium hydroxide, sodium carbonate, potassium carbonate, cesium carbonate, sodium hydride, and the like. The base is not particularly limited as long as the target reaction takes place.

The amount of the base used in the reaction is at least 1 equivalent amount relative to the compound of the formula (2) and is not particularly limited as long as the above equivalent amount is satisfied and also the target reaction takes place. The amount is preferably 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (2).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1b) may be dehydrated with a desiccant such as sodium sulfate or magnesium sulfate. This drying process may be omitted.

The reaction mixture including the compound of the formula (1b) may be distilled under reduced pressure to remove the solvent while avoiding the decomposition of the compound.

After the distillation, the reaction mixture including the compound of the formula (1b) may be purified by, for example, washing, reprecipitation, recrystallization or column chromatography using an appropriate solvent. The purification process may be selected appropriately in accordance with the desired purity.

[Production Process C]

[Chem. 18]

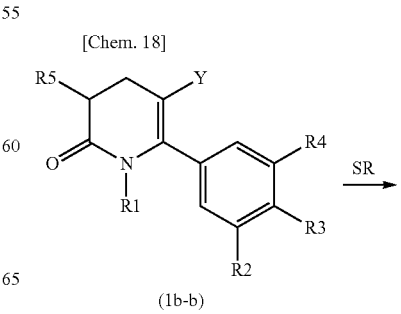

(1b-b)

-continued

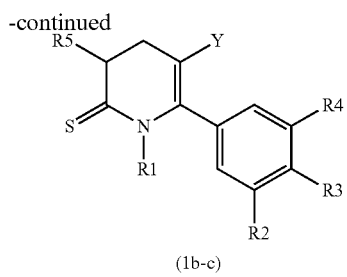

(1b-c)

In the formulae, SR represents a sulfurizing reagent, and R1, R2, R3, R4, R5 and Y are the same as defined hereinabove.

Production Process C is a method for producing a compound of the formula (1b-c) which belongs to the compounds represented by the formula (1b). This production process includes reacting a compound of the formula (1b-b) with a sulfurizing reagent (SR) in a solvent.

Examples of the sulfurizing reagents used in the reaction include Lawesson's reagent (2,4-bis(4-methoxyphenyl)-1,3-dithia-2,4-diphosphetane-2,4-disulfide), and the like.

The amount of the sulfurizing reagent used in the reaction is at least 0.5 equivalent amounts relative to the compound of the formula (1b-b) and is not particularly limited as long as the above equivalent amount is satisfied and also the target reaction takes place. The amount is preferably 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b-b).

The temperature at which the reaction is performed is not particularly limited as long as the target reaction takes place, but is usually from 50° C. to 180° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. In this reaction, the separation operations may be omitted.

The reaction mixture including the compound of the formula (1b-c) may be dehydrated with a desiccant such as sodium sulfate or magnesium sulfate. This drying process may be omitted.

The reaction mixture including the compound of the formula (1b-c) may be distilled under reduced pressure to remove the solvent while avoiding the decomposition of the compound.

After the distillation, the reaction mixture including the compound of the formula (1b-c) may be purified by, for example, washing, reprecipitation, recrystallization or column chromatography using an appropriate solvent. The purification process may be selected appropriately in accordance with the desired purity.

[Production Process D]

[Chem. 19]

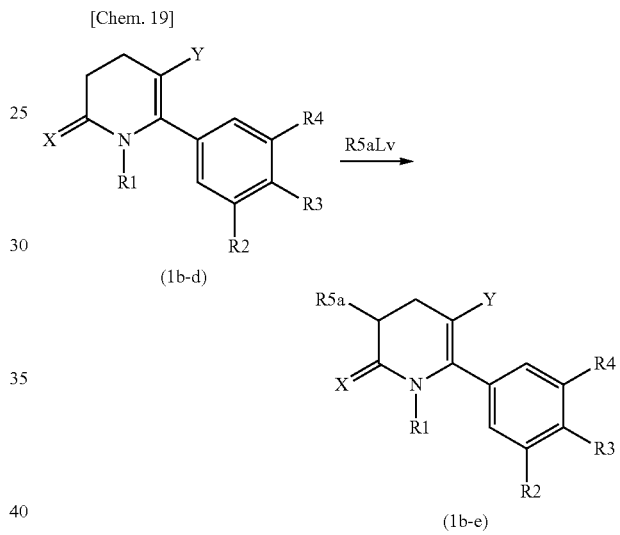

In the formulae, R5a represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, or a C2-C6 haloalkynyl group, and R1, R2, R3, R4, Lv, X and Y are the same as defined hereinabove.

Production Process D is a method for synthesizing a compound of the formula (1b-e), which belongs to the compounds represented by the formula (1b), in which R5a represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, or a C2-C6 haloalkynyl group. This production process includes reacting a compound of the formula (1b-d) with R5aLv in a solvent in the presence of a base.

R5aLv used in the reaction may be purchased from the market or may be produced by a known method.

The amount of R5aLv used in the reaction is at least 1 equivalent amount relative to the compound of the formula (1b-d) and is not particularly limited as long as the above equivalent amount is satisfied and also the target reaction takes place. The amount is preferably 1 equivalent amount to 1.8 equivalent amounts.

Examples of the bases used in the reaction include metal hydrides such as sodium hydride, organic lithiums such as methyllithium, butyllithium, sec-butyllithium, t-butyllithium and hexyllithium, metal amides such as lithium diisopropylamide, hexamethyldisilazane lithium, hexamethyldisilazane sodium and hexamethyldisilazane potassium, and the like.

The amount of the base used in the reaction is at least 1 equivalent amount relative to the compound of the formula (1b-d) and is not particularly limited as long as the above equivalent amount is satisfied and also the target reaction takes place. The amount is preferably 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, hydrocarbon solvents such as hexane, heptane, cyclohexane and methylcyclohexane, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b-d).

The temperature at which the reaction is performed is not particularly limited as long as the target reaction takes place, but is usually from −80° C. to 100° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid or sulfuric acid, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1b-e) may be dehydrated with a desiccant such as sodium sulfate or magnesium sulfate. This drying process may be omitted.

The reaction mixture including the compound of the formula (1b-e) may be distilled under reduced pressure to remove the solvent while avoiding the decomposition of the compound.

After the distillation, the reaction mixture including the compound of the formula (1b-e) may be purified by, for example, washing, reprecipitation, recrystallization or column chromatography using an appropriate solvent. The purification process may be selected appropriately in accordance with the desired purity.

[Production Process E]

[Chem. 20]

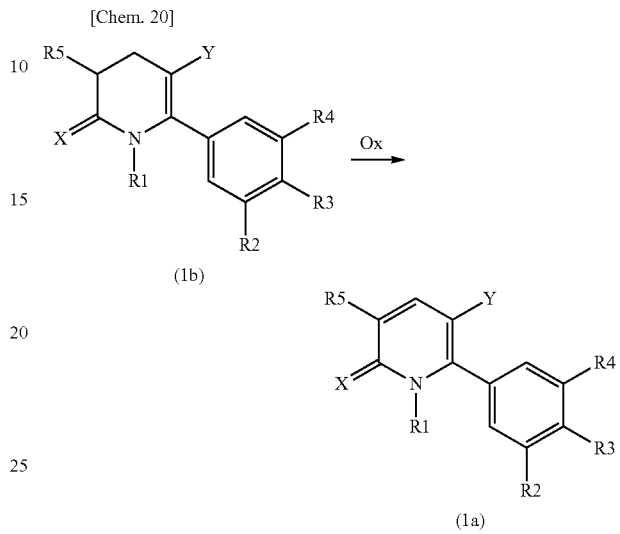

In the formulae, Ox represents an oxidizer, and R1, R2, R3, R4, R5, X and Y are the same as defined hereinabove.

Production Process E is a method for obtaining a compound represented by the formula (1a), and includes reacting a compound of the formula (1b) with an oxidizer (Ox) in a solvent.

The oxidizer used in the reaction may be a metal oxide such as manganese dioxide, a benzoquinone such as 2,3-dichloro-5,6-dicyano-p-benzoquinone, or a combination of a radical initiator such as azobisisobutyronitrile or benzoyl peroxide with a halogenating reagent such as N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin.

Hereinbelow, the process using a metal oxide as the oxidizer will be described.

The amount of the oxidizer used in the reaction is at least 1 equivalent amount relative to the compound of the formula (1b) and is not particularly limited as long as the above equivalent amount is satisfied and also the target reaction takes place. The amount is usually 1 equivalent amount to 200 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b).

The temperature at which the reaction is performed is not particularly limited as long as the target reaction takes place, but is usually from 0° C. to 150° C. or is not more than the boiling point of the solvent.

As post-treatment, insoluble metals may be removed by filtration. Further, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. In this reaction, the separation operations may be omitted.

The reaction mixture including the compound of the formula (1a) may be dehydrated with a desiccant such as sodium sulfate or magnesium sulfate. This drying process may be omitted.

The reaction mixture including the compound of the formula (1a) may be distilled under reduced pressure to remove the solvent while avoiding the decomposition of the compound.

After the distillation, the reaction mixture including the compound of the formula (1a) may be purified by, for example, washing, reprecipitation, recrystallization or column chromatography using an appropriate solvent. The purification process may be selected appropriately in accordance with the desired purity.

Hereinbelow, the process using a benzoquinone as the oxidizer will be described.

The amount of the oxidizer used in the reaction is at least 1 equivalent amount relative to the compound of the formula (1b) and is not particularly limited as long as the above equivalent amount is satisfied and also the target reaction takes place. The amount is usually 1 equivalent amount to 20 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. In this reaction, the separation operations may be omitted.

The reaction mixture including the compound of the formula (1a) may be dehydrated with a desiccant such as sodium sulfate or magnesium sulfate. This drying process may be omitted.

The reaction mixture including the compound of the formula (1a) may be distilled under reduced pressure to remove the solvent while avoiding the decomposition of the compound.

After the distillation, the reaction mixture including the compound of the formula (1a) may be purified by, for example, washing, reprecipitation, recrystallization or column chromatography using an appropriate solvent. The purification process may be selected appropriately in accordance with the desired purity.

Hereinbelow, the process using a combination of a radical initiator and a halogenating reagent as the oxidizer will be described.

The amount of the radical initiator and that of the halogenating reagent used in the reaction are at least 0.01 equivalent amount and at least 1.0 equivalent amount, respectively, relative to the compound of the formula (1b), and are not particularly limited as long as the above equivalent amounts are satisfied and also the target reaction takes place. Preferably, the amount of the radical initiator is 0.01 equivalent amount to 1 equivalent amount, and the amount of the halogenating reagent is 1 equivalent amount to 3 equivalent amounts.

The solvent used in the reaction is not particularly limited as long as the target reaction takes place. Examples of the solvents include halogenated benzene-based solvents such as chlorobenzene and dichlorobenzene, ester solvents such as ethyl acetate, isopropyl acetate and butyl acetate, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b).

The temperature at which the reaction is performed is not particularly limited as long as the target reaction takes place, but is usually from 20° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1a) may be dehydrated with a desiccant such as sodium sulfate or magnesium sulfate. This drying process may be omitted.

The reaction mixture including the compound of the formula (1a) may be distilled under reduced pressure to remove the solvent while avoiding the decomposition of the compound.

After the distillation, the reaction mixture including the compound of the formula (1a) may be purified by, for example, washing, reprecipitation, recrystallization or column chromatography using an appropriate solvent. The purification process may be selected appropriately in accordance with the desired purity.

[Production Process F]

[Chem. 21]

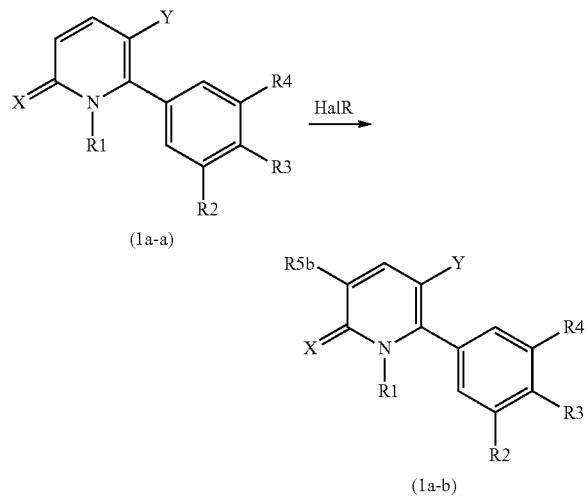

(1a-a)

(1a-b)

In the formulae, R5b represents a halogen atom, HalR represents a halogenating reagent, and R1, R2, R3, R4, X and Y are the same as defined hereinabove.

Production Process F is a method for obtaining a compound of the formula (1a-b), which belongs to the compound represented by the formula (1a), in which R5b is a halogen atom. This production process includes reacting a compound of the formula (1a-a) with a halogenating reagent (HalR) in a solvent.

Examples of the halogenating reagents used in the reaction include Selectfluor (N-fluoro-N'-triethylenediamine bis (tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine, and the like.

The amount of the halogenating reagent used in the reaction is at least 1 equivalent amount relative to the compound of the formula (1a-a), and is not particularly limited as long as the above equivalent amount is satisfied and also the target reaction takes place. The amount is preferably 1 equivalent amount to 10 equivalent amounts. Where the halogenating reagent contains hydantoin, the amount thereof is at least 0.5 equivalent amounts, and, although not particularly limited as long as the above equivalent amount is satisfied and also the target reaction takes place, is preferably 1 equivalent amount to 5 equivalent amounts.

When the halogenating reagent used in the reaction is an iodizing agent, an acid may be added, with examples including inorganic acids such as hydrochloric acid and sulfuric acid, organic acids such as acetic acid, trifluoroacetic acid, methanesulfonic acid and trifluoromethanesulfonic acid, and the like.

The amount of the acid used when the halogenating reagent in the reaction is an iodizing agent is at least 0.01 equivalent amount relative to the compound of the formula (1a-a), and is not particularly limited as long as the above equivalent amount is satisfied and also the target reaction takes place. The amount is preferably 0.1 equivalent amount to 3 equivalent amounts.

The solvent used in the reaction is not particularly limited as long as the target reaction takes place. Examples of the solvents include acidic solvents such as sulfuric acid, acetic acid, trifluoroacetic acid, methanesulfonic acid and trifluoromethanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-a).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1a-b) may be dehydrated with a desiccant such as sodium sulfate or magnesium sulfate. This drying process may be omitted.

The reaction mixture including the compound of the formula (1a-b) may be distilled under reduced pressure to remove the solvent while avoiding the decomposition of the compound.

After the distillation, the reaction mixture including the compound of the formula (1a-b) may be purified by, for example, washing, reprecipitation, recrystallization or column chromatography using an appropriate solvent. The purification process may be selected appropriately in accordance with the desired purity.

[Production Process G]

[Chem. 22]

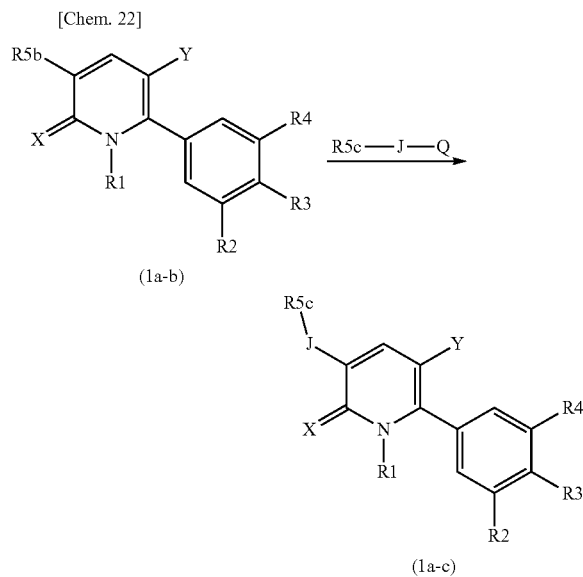

In the formulae, J represents an oxygen atom or a sulfur atom; when J is an oxygen atom, R5c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C3-C6 alkynyl group optionally substituted with substituent(s) A, or a C3-C6 haloalkynyl group; when J is a sulfur atom, R5c represents a C1-C6 alkyl group or a C1-C6 haloalkyl group; Q represents a hydrogen atom or a metal; and R1, R2, R3, R4, R5b, X and Y are the same as defined hereinabove.

Production Process G is a method for synthesizing a compound of the formula (1a-c), which belongs to the compounds represented by the formula (1a), in which J represents an oxygen atom or a sulfur atom; when J is an oxygen atom, R5c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C3-C6 alkynyl group optionally substituted with substituent(s) A, or a C3-C6 haloalkynyl group; and when J is a sulfur atom, R5c represents a C1-C6 alkyl group or a C1-C6 haloalkyl group. This production process includes reacting a compound of the formula (1a-b) with R5c-J-Q by a coupling reaction in the presence of a transition metal.

In the compound of the formula (1a-b), R5b is preferably a chlorine atom, a bromine atom or an iodine atom.

R5c-J-Q used in the reaction may be purchased from the market or may be produced by a known method. Q is preferably a hydrogen atom or an alkali metal such as sodium or potassium.

The amount of R5c-J-Q used in the reaction is at least 1 equivalent amount relative to the compound of the formula (1a-b), and is not particularly limited as long as the above equivalent amount is satisfied and also the target reaction takes place. Where Q is a hydrogen atom, this compound may be used also as a solvent.

The transition metal used in the reaction may have a ligand. Examples thereof include palladiums such as palladium acetate, [1,1'-bis(diphenylphosphino)ferrocene]palladium dichloride, tris(dibenzylideneacetone)dipalladium, tetrakis(triphenylphosphine)palladium, and bis(triphenylphosphine)palladium dichloride, and the like.

The amount of the transition metal used in the reaction is 0.001 equivalent amount to 1 equivalent amount relative to the compound of the formula (1a-b), but is not particularly limited thereto as long as the target reaction takes place.

To allow the reaction to proceed efficiently, a phosphine ligand may be added such as triphenylphosphine, 1,1'-bis (diphenylphosphino)ferrocene, 2-dicyclohexylphosphino-2', 4',6'-triisopropylbiphenyl or 2-di-t-butylphosphino-2',4,'6'-triisopropylbiphenyl.

The amount of the phosphine ligand used in the reaction is 0.001 equivalent amount to 1 equivalent amount relative to the compound of the formula (1a-b), but is not particularly limited thereto as long as the target reaction takes place.

The reaction may involve a base, for example, an inorganic base such as sodium carbonate, potassium carbonate or cesium carbonate, or an organic base such as triethylamine, tributylamine or diisopropylethylamine.

The amount of the base used in the reaction is at least 1 equivalent amount relative to the compound of the formula (1a-b) and is not particularly limited as long as the above equivalent amount is satisfied and also the target reaction takes place. The amount is preferably 1 equivalent amount to 50 equivalent amounts.

The solvent used in the reaction is not particularly limited as long as the target reaction takes place. Examples of the solvents include alcohol solvents represented by R5c-J-H (wherein R5c is the same as defined hereinabove, and J is an oxygen atom), ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-b).

The temperature at which the reaction is performed is not particularly limited as long as the target reaction takes place, but is usually from 30° C. to 200° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions.

The number of separation operations is not particularly limited and may be determined in accordance with the desired purity or yield. Further, insolubles may be removed by filtration, but this operation is not indispensable.

The reaction mixture including the compound of the formula (1a-c) may be dehydrated with a desiccant such as sodium sulfate or magnesium sulfate. This drying process may be omitted.

The reaction mixture including the compound of the formula (1a-c) may be distilled under reduced pressure to remove the solvent while avoiding the decomposition of the compound.

After the distillation, the reaction mixture including the compound of the formula (1a-c) may be purified by, for example, washing, reprecipitation, recrystallization or column chromatography using an appropriate solvent. The purification process may be selected appropriately in accordance with the desired purity.

[Production Process H]

[Chem. 23]

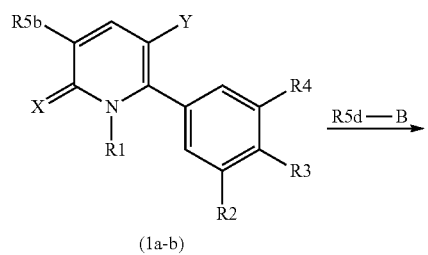

(1a-b)

-continued

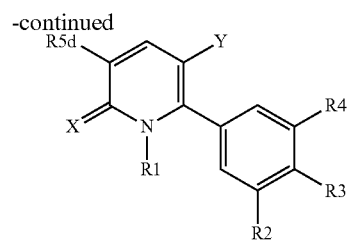

(1a-d)

In the formulae, R5d represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, or a C2-C6 haloalkenyl group, R5d-B represents an organoboronic acid, and R1, R2, R3, R4, R5b, X and Y are the same as defined hereinabove.

Production Process H is a method for synthesizing a compound of the formula (1a-d), which belongs to the compounds represented by the formula (1a), in which R5d represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent (s) A, or a C2-C6 haloalkenyl group. This production process includes reacting a compound of the formula (1a-b) with an organoboronic acid (R5d-B) by the Suzuki-Miyaura coupling reaction in the presence of a transition metal and a base.

In the formula (1a-b), R5b is preferably a chlorine atom, a bromine atom or an iodine atom.

R5d-B used in the reaction is an organoboronic acid such as an organic boronic acid or an organic boronate ester, and may be purchased from the market or may be produced by a known method.

The amount of R5d-B used in the reaction is at least 1 equivalent amount relative to the compound of the formula (1a-b), and is not particularly limited as long as the above equivalent amount is satisfied and also the target reaction takes place. The amount is preferably 1 equivalent amount to 10 equivalent amounts.

The transition metal used in the reaction may be, for example, palladium, nickel or ruthenium, and may have a ligand. Palladiums are preferable, with examples including palladium acetate, [1,1'-bis(diphenylphosphino)ferrocene] palladium dichloride, tris(dibenzylideneacetone)dipalladium, tetrakis(triphenylphosphine)palladium, bis(triphenylphosphine)palladium dichloride, and the like.

The amount of the transition metal used in the reaction is 0.001 equivalent amount to 1 equivalent amount relative to the compound of the formula (1a-b), but is not particularly limited thereto as long as the target reaction takes place.

To allow the reaction to proceed efficiently, a phosphine ligand such as triphenylphosphine or tricyclohexylphosphine may be added.

The amount of the phosphine ligand used in the reaction is 0.001 equivalent amount to 1 equivalent amount relative to the compound of the formula (1a-b), and is not particularly limited as long as the above equivalent amount is satisfied and also the target reaction takes place.

Examples of the bases used in the reaction include inorganic bases such as sodium carbonate, potassium carbonate, cesium carbonate and tripotassium phosphate, metal alkoxides such as sodium methoxide, sodium ethoxide and potassium t-butoxide, and the like.

The amount of the base used in the reaction is at least 1 equivalent amount relative to the compound of the formula (1a-b) and is not particularly limited as long as the above equivalent amount is satisfied and also the target reaction takes place. The amount is preferably 1 equivalent amount to 50 equivalent amounts.

The solvent used in the reaction is not particularly limited as long as the target reaction takes place. Examples of the solvents include water solvent, ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-b).

The temperature at which the reaction is performed is not particularly limited as long as the target reaction takes place, but is usually from 30° C. to 200° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. Further, insolubles may be removed by filtration, but this operation is not indispensable.

The reaction mixture including the compound of the formula (1a-d) may be dehydrated with a desiccant such as sodium sulfate or magnesium sulfate. This drying process may be omitted.

The reaction mixture including the compound of the formula (1a-d) may be distilled under reduced pressure to remove the solvent while avoiding the decomposition of the compound.

After the distillation, the reaction mixture including the compound of the formula (1a-d) may be purified by, for example, washing, reprecipitation, recrystallization or column chromatography using an appropriate solvent. The purification process may be selected appropriately in accordance with the desired purity.

[Production Process I]

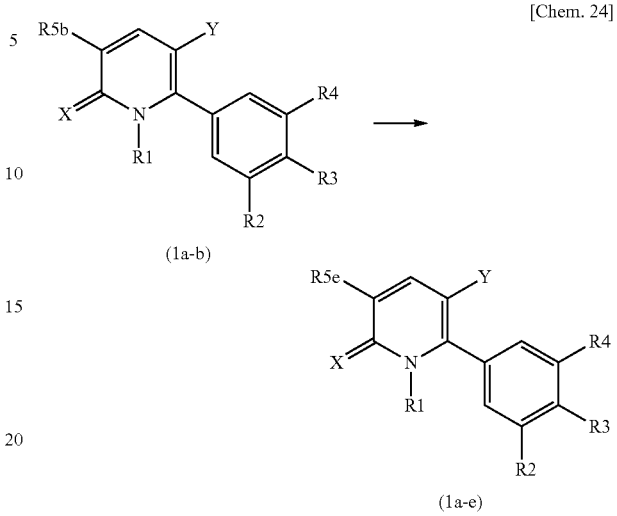

[Chem. 24]

In the formulae, R5e represents a C2-C6 alkynyl group optionally substituted with substituent(s) A, or a C2-C6 haloalkynyl group, and R1, R2, R3, R4, R5b, X and Y are the same as defined hereinabove.

Production Process I is a method for synthesizing a compound of the formula (1a-e), which belongs to the compounds represented by the formula (1a), in which R5e represents a C2-C6 alkynyl group optionally substituted with substituent(s) A, or a C2-C6 haloalkynyl group. This production process includes reacting a compound of the formula (1a-b) with an alkyne-terminated compound by the Sonogashira coupling reaction in the presence of transition metals and a base.

In the formula (1a-b), R5b is preferably a chlorine atom, a bromine atom or an iodine atom.

The alkyne-terminated compound used in the reaction may be purchased from the market or may be produced by a known method. Trimethylsilylacetylene is also usable as the alkyne-terminated compound. In this case, a trimethylsilylethynyl group is introduced into the compound of the formula (1a-b), and the compound is desilylated later. The desilylation may be performed with reference to non patent literature such as Journal of the American Chemical Society, vol. 131, No. 2, pp. 634-643 (2009) and Journal of Organometallic Chemistry, vol. 696, No. 25, pp. 4039-4045 (2011).

The amount of the alkyne-terminated compound used in the reaction is at least 1 equivalent amount relative to the compound of the formula (1a-b) and is not particularly limited as long as the above equivalent amount is satisfied and also the target reaction takes place. The amount is preferably 1 equivalent amount to 10 equivalent amounts.

The transition metals used in the reaction may have a ligand. Examples thereof include palladiums such as palladium acetate, [1,1'-bis(diphenylphosphino)ferrocene]palladium dichloride, tris(dibenzylideneacetone)dipalladium, tetrakis(triphenylphosphine)palladium and bis(triphenylphosphine)palladium dichloride, and the like. Coppers such as copper chloride, copper bromide and copper iodide are used concurrently.

The amounts of the transition metals used in the reaction are such that the amounts of the palladium and the copper are each at least 0.001 equivalent amount relative to the compound of the formula (1a-b), and are not particularly limited as long as the above equivalent amounts are satisfied and also the target reaction takes place. The amounts are preferably both 0.001 equivalent amount to 1 equivalent amount.

Examples of the bases used in the reaction include organic amines such as triethylamine, tributylamine, isopropylamine, diethylamine, diisopropylamine and diisopropylethylamine, inorganic bases such as sodium carbonate, potassium carbonate and cesium carbonate, and the like.

The amount of the base used in the reaction is at least 1 equivalent amount relative to the compound of the formula (1a-b) and is not particularly limited as long as the above equivalent amount is satisfied and also the target reaction takes place. The amount is preferably 1 equivalent amount to 50 equivalent amounts. A liquid organic base may also serve as a solvent.

To allow the reaction to proceed efficiently, a phosphine ligand such as tri-t-butylphosphine or 2-dicyclohexylphosphino-2',4',6'-triisopropylbiphenyl may be added, although the use of such a ligand is not indispensable.

The amount of the phosphine ligand used in the reaction is 0.001 equivalent amount to 1 equivalent amount relative to the compound of the formula (1a-b), but is not particularly limited thereto as long as the target reaction takes place.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, organic amine solvents such as triethylamine, tributylamine, isopropylamine, diethylamine, diisopropylamine and diisopropylethylamine, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-b).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. Further, insolubles may be removed by filtration, but this operation is not indispensable.

The reaction mixture including the compound of the formula (1a-e) may be dehydrated with a desiccant such as sodium sulfate or magnesium sulfate. This drying process may be omitted.

The reaction mixture including the compound of the formula (1a-e) may be distilled under reduced pressure to remove the solvent while avoiding the decomposition of the compound.

After the distillation, the reaction mixture including the compound of the formula (1a-e) may be purified by, for example, washing, reprecipitation, recrystallization or column chromatography using an appropriate solvent. The purification process may be selected appropriately in accordance with the desired purity.

[Production Process J]

[Chem. 25]

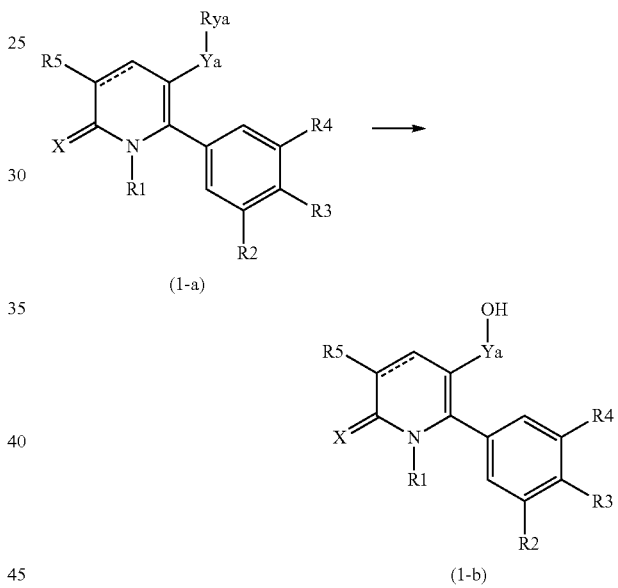

In the formulae, Rya-Ya- represents Y containing a C1-C6 alkoxy group as R6 or R7, Rya represents a C1-C6 alkoxy group, Ya represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, and R1, R2, R3, R4, R5, X and the broken line are the same as defined hereinabove.

Production Process J is a method for synthesizing a hydroxyl-containing compound of the formula (1-b) which belongs to the compounds represented by the formula (1). This production process includes reacting a compound of the formula (1-a) in which Rya is a C1-C6 alkoxy group with an acid.

Examples of the acids used in the reaction include boron halides such as boron trichloride and boron tribromide, and the like.

The amount of the acid used in the reaction is at least 1 equivalent amount relative to the compound of the formula (1-a) and is not particularly limited as long as the above equivalent amount is satisfied and also the target reaction takes place. The amount is preferably 1 equivalent amount to 10 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1-a).

The temperature at which the reaction is performed is not particularly limited as long as the target reaction takes place, but is usually from −80° C. to 100° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1-b) may be dehydrated with a desiccant such as sodium sulfate or magnesium sulfate. This drying process may be omitted.

The reaction mixture including the compound of the formula (1-b) may be distilled under reduced pressure to remove the solvent while avoiding the decomposition of the compound.

After the distillation, the reaction mixture including the compound of the formula (1-b) may be purified by, for example, washing, reprecipitation, recrystallization or column chromatography using an appropriate solvent. The purification process may be selected appropriately in accordance with the desired purity.

[Production Process K]

[Chem. 26]

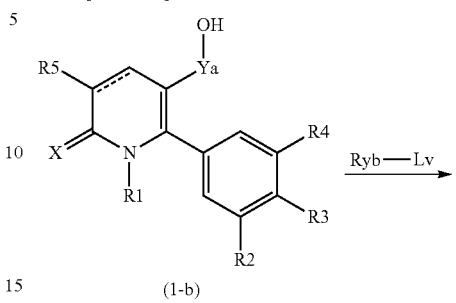

In the formulae, Ryb represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, a C3-C6 haloalkynyl group, an aryl group optionally substituted with 0 to 5 substituent(s) D, a heteroaryl group optionally substituted with 0 to 2 substituent(s) D, an aralkyl group optionally substituted with 0 to 5 substituent(s) D, or Rx1C(=O)—, and Lv, R1, R2, R3, R4, R5, Rx1, X, Ya and the broken line are the same as defined hereinabove.

Production Process K is a method for synthesizing a compound of the formula (1-c), which belongs to the compounds represented by the formula (1), in which Ryb represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, a C3-C6 haloalkynyl group, an awl group optionally substituted with 0 to 5 substituent(s) D, a heteroaryl group optionally substituted with 0 to 2 substituent(s) D, an aralkyl group optionally substituted with 0 to 5 substituent(s) D, or Rx1C(=O)— (wherein Rx1 is the same as defined hereinabove). This production process includes reacting a compound of the formula (1-b) with Ryb-Lv in a solvent in the presence of a base.

Ryb-Lv used in the reaction may be purchased from the market or may be produced by a known method.

The amount of Ryb-Lv used in the reaction is at least 1 equivalent amount relative to the compound of the formula (1-b) and is not particularly limited as long as the above equivalent amount is satisfied and also the target reaction takes place. The amount is preferably 1 equivalent amount to 10 equivalent amounts.

Examples of the bases used in the reaction include inorganic bases such as sodium carbonate, potassium carbonate, cesium carbonate and sodium hydride, organic bases such as triethylamine, tributylamine, diisopropylethylamine, pyridine, 4-dimethylaminopyridine, collidine and lutidine, and the like. The base is not particularly limited as long as the target reaction takes place.

The amount of the base used in the reaction is at least 1 equivalent amount relative to the compound of the formula (1-b) and is not particularly limited as long as the above equivalent amount is satisfied and also the target reaction takes place. The amount is preferably 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1-b).

The temperature at which the reaction is performed is not particularly limited as long as the target reaction takes place, but is usually from –20° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1-c) may be dehydrated with a desiccant such as sodium sulfate or magnesium sulfate. This drying process may be omitted.

The reaction mixture including the compound of the formula (1-c) may be distilled under reduced pressure to remove the solvent while avoiding the decomposition of the compound.

After the distillation, the reaction mixture including the compound of the formula (1-c) may be purified by, for example, washing, reprecipitation, recrystallization or column chromatography using an appropriate solvent. The purification process may be selected appropriately in accordance with the desired purity.

[Production Process L]

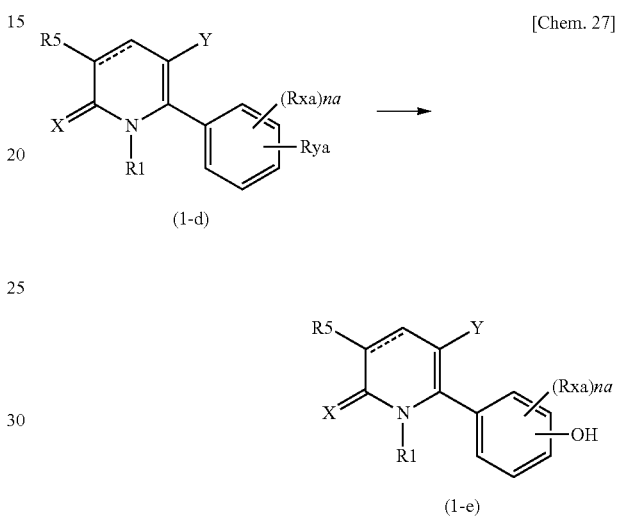

In the formulae, Rxa represents a hydrogen atom, a halogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, Rc-L- (wherein Rc and L are the same as defined hereinabove), RaRbN— (wherein Ra and Rb are the same as defined hereinabove), or Rx2C(=O)N(Rx3)- (wherein Rx2 and Rx3 are the same as defined hereinabove), na represents an integer of 1 to 2 (with the proviso that when na=2, the two substituents Rxa are independent of one another), and R1, R5, Rya, X, Y and the broken line are the same as defined hereinabove. Rxa in the compounds of the formula (1-d) and the formula (1-e), Rya in the compound of the formula (1-d), and the hydroxy group in the compound of the formula (1-e) are substituted at any of the positions in the compound of the formula (1) which correspond to R2, R3 and R4.

Production Process L is a method for synthesizing a hydroxyl-containing compound of the formula (1-e) which belongs to the compounds represented by the formula (1). This production process includes reacting a compound of the formula (1-d) with an acid.

Production Process L may be carried out in the same manner as Production

Process J, except that the compound of the formula (1-a) in Production Process J is replaced by the compound represented by the formula (1-d).

[Production Process M]

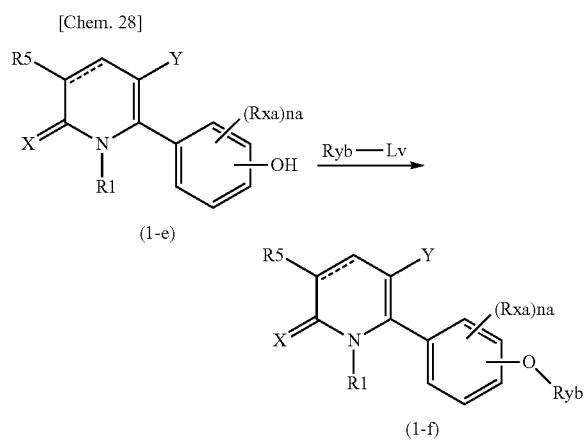

In the formulae, Lv, R1, R5, Rxa, Ryb, X, Y, na and the broken line are the same as defined hereinabove. Rxa in the compounds of the formula (1-e) and the formula (1-f), the hydroxy group in the compound of the formula (1-e), and Ryb-O— in the compound of the formula (1-f) are substituted at any of the positions in the compound of the formula (1) which correspond to R2, R3 and R4. When na=2, the two substituents Rxa are independent of one another.

Production Process M is a method for synthesizing a compound of the formula (1-f) which belongs to the compounds represented by the formula (1). This production process includes reacting a compound of the formula (1-e) with Ryb-Lv in a solvent in the presence of a base.

Production Process M may be carried out in the same manner as Production Process K, except that the compound of the formula (1-b) in Production Process K is replaced by the compound represented by the formula (1-e).

[Production Process N]

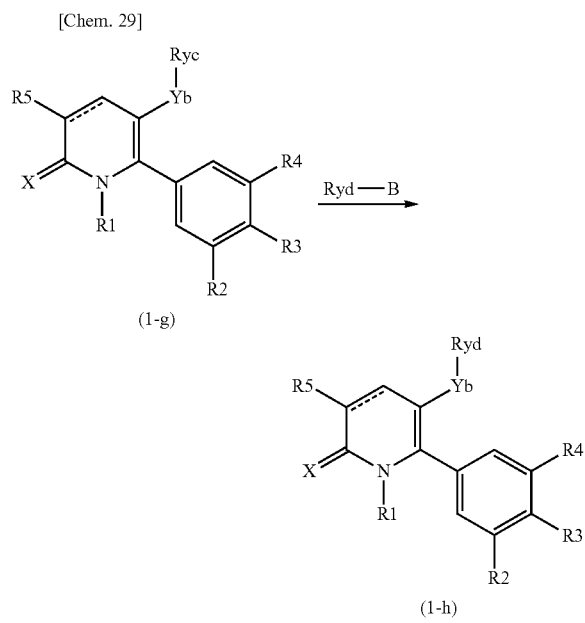

In the formulae, Ryc-Yb- represents Y containing a halogen atom as R6 or R7, Ryc represents a halogen atom, Ryd represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent (s) C, or a C2-C6 haloalkenyl group, Yb represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, Ryd-B represents an organoboronic acid, and R1, R2, R3, R4, R5, X and the broken line are the same as defined hereinabove.

Production Process N is a method for synthesizing a compound of the formula (1-h), which belongs to the compounds represented by the formula (1), in which Ryd represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent (s) C, or a C2-C6 haloalkenyl group. This production process includes reacting a compound of the formula (1-g) with an organoboronic acid (Ryd-B) by the Suzuki-Miyaura coupling reaction.

In the compound represented by the formula (1-g), Ryc is preferably a chlorine atom, a bromine atom or an iodine atom.

Ryd-B used in the reaction is an organoboronic acid such as an organic boronic acid or an organic boronate ester, and may be purchased from the market or may be produced by a known method.

Production Process N may be carried out in the same manner as Production Process H, except that the compound of the formula (1a-b) and R5d-B in Production Process H are replaced by the compound represented by the formula (1-g) and Ryd-B, respectively.

[Production Process O]

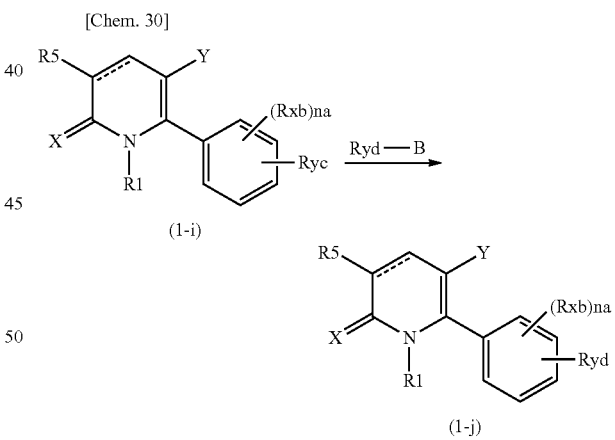

In the formulae, Rxb represents a hydrogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, an aryloxy group optionally substituted with 0 to 5 substituents D, a heteroaryloxy group optionally substituted with 0 to 2 substituents D, an aralkyloxy group optionally substituted with 0 to 5 substituents D, Rx1C(=O)— (wherein Rx1 is the same as defined hereinabove), Rx1C(=O)O— (wherein Rx1 is the same as defined hereinabove), a 3 to 6-membered ring group containing 1 to 2 oxygen atoms, Rc-L- (wherein Rc and L are the same as defined hereinabove), RaRbN— (wherein Ra and Rb are the same as defined hereinabove), or Rx2C(=O)N(Rx3)- (wherein Rx2 and Rx3 are the same as defined hereinabove), and Ryc, Ryd, Ryd-B, R1, R5, X, Y, na and the broken line are the same as defined hereinabove. Rxb in the compounds of the formula (1-i) and the formula (1-j), Ryc in the compound of the formula (1-i), and Ryd in the compound of the formula (1-j) are substituted at any of the positions in the compound of the formula (1) which correspond to R2, R3 and R4. When na=2, the two substituents Rxb are independent of one another.

Production Process O is a method for synthesizing a compound of the formula (1-j) which belongs to the compounds represented by the formula (1). This production process includes reacting a compound of the formula (1-i) with an organoboronic acid (Ryd-B) by the Suzuki-Miyaura coupling reaction.

In the compound represented by the formula (1-i), Ryc is preferably a chlorine atom, a bromine atom or an iodine atom.

Production Process O may be carried out in the same manner as Production Process H, except that the compound of the formula (1a-b) and R5d-B in Production Process H are replaced by the compound represented by the formula (1-i) and Ryd-B, respectively.

[Production Process P]

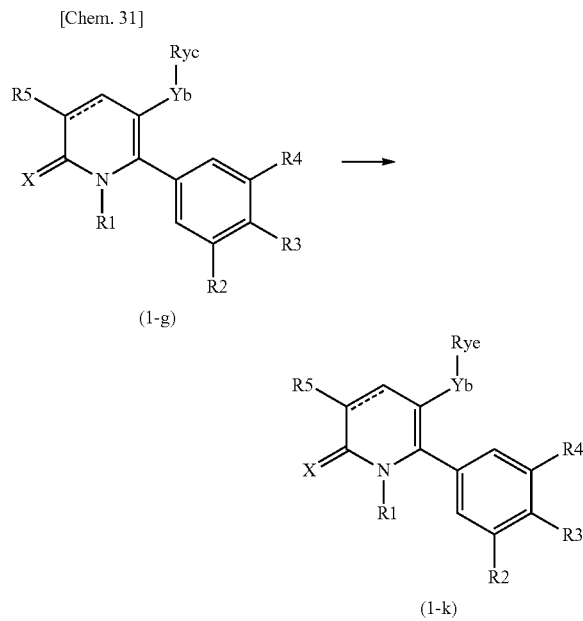

(1-g)

(1-k)

In the formulae, Rye represents a C2-C6 alkynyl group optionally substituted with substituent(s) C, or a C2-C6 haloalkynyl group, and Ryc, R1, R2, R3, R4, R5, X, Yb and the broken line are the same as defined hereinabove.

Production Process P is a method for synthesizing a compound of the formula (1-k), which belongs to the compounds represented by the formula (1), in which Rye represents a C2-C6 alkynyl group optionally substituted with substituent(s) C, or a C2-C6 haloalkynyl group. This production process includes reacting a compound of the formula (1-g) with an alkyne-terminated compound by the Sonogashira coupling reaction.

In the compound represented by the formula (1-g), Ryc is preferably a chlorine atom, a bromine atom or an iodine atom.

Production Process P may be carried out in the same manner as Production Process I, except that the compound of the formula (1a-b) in Production Process I is replaced by the compound represented by the formula (1-g).

[Production Process Q]

[Chem. 32]

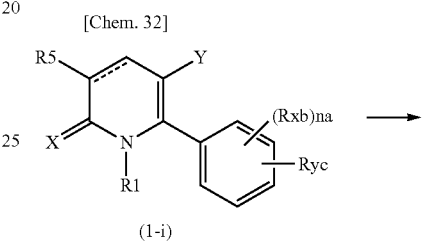

(1-i)

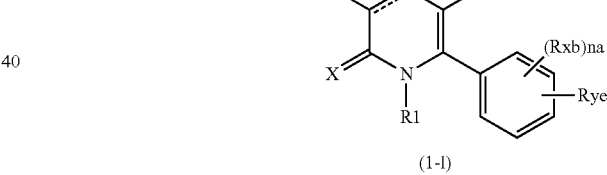

(1-l)

In the formulae, Rxb, Ryc, Rye, R1, R5, X, Y, na and the broken line are the same as defined hereinabove. Rxb in the compounds of the formula (1-i) and the formula (1-l), Ryc in the compound of the formula (1-i), and Rye in the compound of the formula (1-l) are substituted at any of the positions in the compound of the formula (1) which correspond to R2, R3 and R4. When na=2, the two substituents Rxb are independent of one another.

Production Process P is a method for synthesizing a compound of the formula (1-l) which belongs to the compounds represented by the formula (1). This production process includes reacting a compound of the formula (1-i) with an alkyne-terminated compound by the Sonogashira coupling reaction.

In the compound of the formula (1-i), Ryc is preferably a chlorine atom, a bromine atom or an iodine atom.

Production Process Q may be carried out in the same manner as Production Process I, except that the compound of the formula (1a-b) in Production Process I is replaced by the compound represented by the formula (1-i).

[Production Process R]

[Chem. 33]

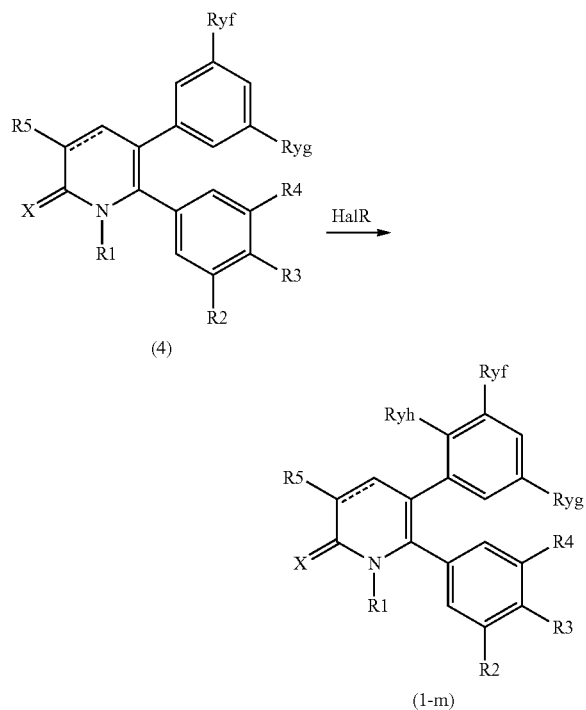

In the formulae, Ryf and Ryg each independently represent a C1-C6 alkoxy group optionally substituted with substituent(s) C, Ryh represents a halogen atom, and HalR, R1, R2, R3, R4, R5, X and the broken line are the same as defined hereinabove.

Production Process R is a method for producing a compound of the formula (1-m), which belongs to the compounds represented by the formula (1), in which Ryf and Ryg each independently represent a C1-C6 alkoxy group optionally substituted with substituent(s) C, and Ryh represents a halogen atom. This production process includes reacting a compound of the formula (4) with a halogenating reagent (HalR) in a solvent.

The compound represented by the formula (4) corresponds to a compound of the formula (1) except that R6 in Y is replaced by a hydrogen atom, and may be produced in accordance with the process for producing the compounds of the formula (1).

Examples of the halogenating reagents used in the reaction include Selectfluor (N-fluoro-M-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine, and the like.

The amount of the halogenating reagent used in the reaction is at least 1 equivalent amount relative to the compound of the formula (4), and is not particularly limited as long as the above equivalent amount is satisfied and also the target reaction takes place. The amount is preferably 1 equivalent amount to 10 equivalent amounts. Where the halogenating reagent contains hydantoin, the amount thereof is at least 0.5 equivalent amounts, and, although not particularly limited as long as the above equivalent amount is satisfied and also the target reaction takes place, is preferably 1 equivalent amount to 5 equivalent amounts.

When the halogenating reagent used in the reaction is an iodizing agent, an acid may be added, with examples including inorganic acids such as hydrochloric acid and sulfuric acid, organic acids such as acetic acid, trifluoroacetic acid, methanesulfonic acid and trifluoromethanesulfonic acid, and the like.

The amount of the acid used when the halogenating reagent in the reaction is an iodizing agent is at least 0.01 equivalent amount relative to the compound of the formula (4), and is not particularly limited as long as the above equivalent amount is satisfied and also the target reaction takes place. The amount is preferably 0.1 equivalent amount to 3 equivalent amounts.

The solvent used in the reaction is not particularly limited as long as the target reaction takes place. Examples of the solvents include acidic solvents such as sulfuric acid, acetic acid, trifluoroacetic acid, methanesulfonic acid and trifluoromethanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (4).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1-m) may be dehydrated with a desiccant such as sodium sulfate or magnesium sulfate. This drying process may be omitted.

The reaction mixture including the compound of the formula (1-m) may be distilled under reduced pressure to remove the solvent while avoiding the decomposition of the compound.

After the distillation, the reaction mixture including the compound of the formula (1-m) may be purified by, for example, washing, reprecipitation, recrystallization or column chromatography using an appropriate solvent. The purification process may be selected appropriately in accordance with the desired purity.

[Production Process S]

[Chem. 34]

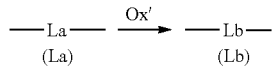

In the formulae, La represents S, Lb represents SO or $SO_2$, and Ox' represents an oxidizer.

Production Process S is a method for producing a compound of the formula (Lb), which belongs to compounds represented by the formula (1) in which any of R1, R2, R3, R4, R5, R6 and R7 includes Lb that is SO or $SO_2$. This production process includes reacting a compound of the formula (La), which belongs to compounds represented by the formula (1) in which any of R1, R2, R3, R4, R5, R6 or R7 includes La that is S, with an oxidizer (Ox') in a solvent.

The oxidizer used in the reaction may be a peroxide such as hydrogen peroxide solution or m-chloroperbenzoic acid. Transition metals such as sodium tungstate may be added.

When the target product is SO, the amount of the oxidizer used in the reaction is usually 1.0 equivalent amount to 1.2 equivalent amounts relative to the compound having the formula (La). When the target product is $SO_2$, the amount is usually 2 equivalent amounts to 10 equivalent amounts relative to the compound having the formula (La). When a transition metal is added, the amount thereof is usually 0.001 equivalent amount to 1 equivalent amount.

The solvent used in the reaction is not particularly limited as long as the target reaction takes place. Examples of the solvents include water solvent, acidic solvents such as acetic acid, benzene-based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound having the formula (La).

The temperature at which the reaction is performed is not particularly limited as long as the target reaction takes place, but is usually from −10° C. to 120° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be used in combination in any ratio. The number of separation operations is not particularly limited and may be determined in accordance with the desired purity or yield.

The reaction mixture including the compound with the formula (Lb) may be dehydrated with a desiccant such as sodium sulfate or magnesium sulfate. This drying process may be omitted.

The reaction mixture including the compound with the formula (Lb) may be distilled under reduced pressure to remove the solvent while avoiding the decomposition of the compound.

After the distillation, the reaction mixture including the compound with the formula (Lb) may be purified by, for example, washing, reprecipitation, recrystallization or column chromatography using an appropriate solvent. The purification process may be selected appropriately in accordance with the desired purity.

[Production Process T]

[Chem. 35]

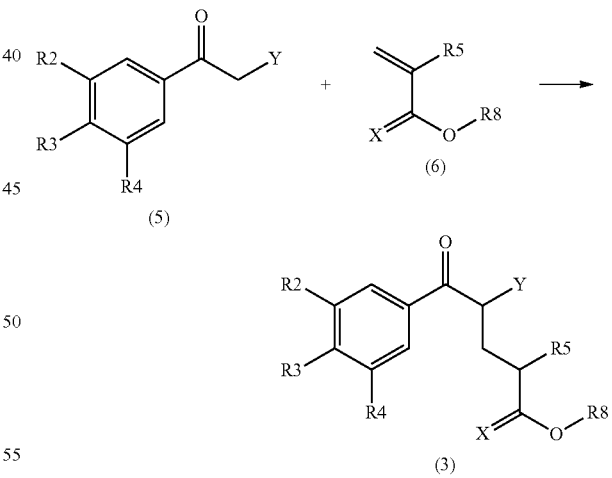

In the formulae, R2, R3, R4, R5, R8, X and Y are the same as defined hereinabove.

Production Process T is a method for producing an intermediate represented by the formula (3), and includes reacting a compound of the formula (5) with a compound of the formula (6) in a solvent in the presence of a base.

The compound of the formula (5) which is used in the reaction may be synthesized in accordance with Reference Example. Alternatively, the compound may be synthesized with reference to literature such as Green Chemistry, Vol. 41, pp. 580-585 or The Journal of Organic Chemistry, Vol. 65, No. 20, pp. 6458-6461 (2000).

The compound of the formula (6) which is used in the reaction may be purchased from the market or may be produced by a known method.

The amount of the compound of the formula (6) used in the reaction is at least 1 equivalent amount relative to the compound of the formula (5), and is not particularly limited as long as the above equivalent amount is satisfied and also the target reaction takes place. The amount is preferably 1 equivalent amount to 3 equivalent amounts.

Examples of the bases used in the reaction include inorganic bases such as sodium carbonate, potassium carbonate, cesium carbonate and tripotassium phosphate, metal alkoxides such as sodium methoxide, sodium ethoxide and potassium t-butoxide, and the like.

The amount of the base used in the reaction may be a catalytic amount and is not particularly limited as long as the target reaction takes place. The amount is preferably 0.01 equivalent amount to 3 equivalent amounts relative to the compound represented by the formula (5).

Examples of the solvents used in the reaction include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (5).

The temperature at which the reaction is performed is not particularly limited as long as the target reaction takes place, but is usually from −50° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like.

The solvents may be used singly, or two or more may be mixed in any proportions. The number of separation operations is not particularly limited and may be determined in accordance with the desired purity or yield.

The reaction mixture including the compound of the formula (3) may be dehydrated with a desiccant such as sodium sulfate or magnesium sulfate. This drying process may be omitted.

The reaction mixture including the compound of the formula (3) may be distilled under reduced pressure to remove the solvent while avoiding the decomposition of the compound.

After the distillation, the reaction mixture including the compound of the formula (3) may be purified by, for example, washing, reprecipitation, recrystallization or column chromatography using an appropriate solvent. The purification process may be selected appropriately in accordance with the desired purity.

[Production Process U]

[Chem. 36]

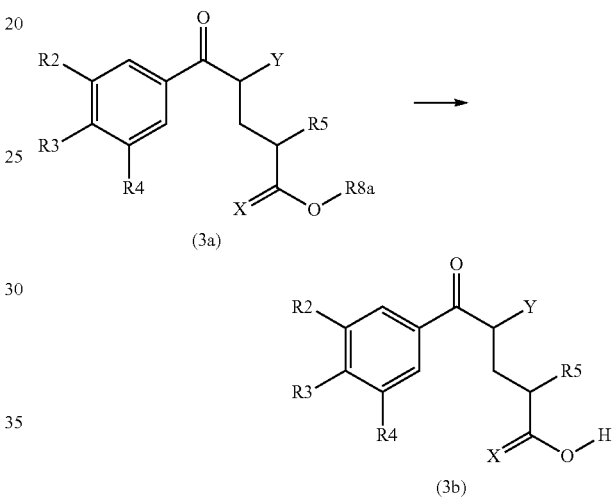

In the formulae, R8a represents a C1-C6 alkyl group, and R2, R3, R4, R5, X and Y are the same as defined hereinabove.

Production Process U is a method for producing an intermediate of the formula (3b) which belongs to the compounds represented by the formula (3). This production process includes reacting a compound of the formula (3a) under acidic conditions or basic conditions in a solvent.

First, the reaction under acidic conditions will be described.

Examples of the acids used in the reaction include inorganic acids such as hydrochloric acid, hydrobromic acid and phosphoric acid, organic acids such as acetic acid, methanesulfonic acid, p-toluenesulfonic acid and trifluoroacetic acid, and the like. The acid is not particularly limited as long as the target reaction takes place.

The amount of the acid used in the reaction may be a catalytic amount, and is not particularly limited as long as the target reaction takes place. The amount is preferably not less than 0.01 equivalent amount relative to the compound of the formula (3a). A liquid acid may also serve as a solvent.

The solvent used in the reaction is not particularly limited as long as the target reaction takes place. Examples of the solvents include water solvent, acidic solvents such as acetic acid and methanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (3a).

The temperature at which the reaction is performed is not particularly limited as long as the target reaction takes place, but is usually from 0° C. to 180° C. or is not more than the boiling point of the solvent.

Next, the reaction under basic conditions will be described.

Examples of the bases used in the reaction include inorganic bases such as lithium hydroxide, sodium hydroxide and potassium hydroxide, and the like. The base is not particularly limited as long as the target reaction takes place.

The amount of the base used in the reaction is at least 1 equivalent amount relative to the compound of the formula (3a) and is not particularly limited as long as the above equivalent amount is satisfied and also the target reaction takes place. The amount is preferably 1 equivalent amount to 30 equivalent amounts.

The solvent used in the reaction is not particularly limited as long as the target reaction takes place. Examples of the solvents include water solvent, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (3a).

The temperature at which the reaction is performed is not particularly limited as long as the target reaction takes place, but is usually from −20° C. to 180° C. or is not more than the boiling point of the solvent.

The type of post treatment may be common to the reaction under acidic conditions and the reaction under basic conditions. Water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (3b) may be dehydrated with a desiccant such as sodium sulfate or magnesium sulfate. This drying process may be omitted.

The reaction mixture including the compound of the formula (3b) may be distilled under reduced pressure to remove the solvent while avoiding the decomposition of the compound.

After the distillation, the reaction mixture including the compound of the formula (3b) may be purified by, for example, washing, reprecipitation, recrystallization or column chromatography using an appropriate solvent. The purification process may be selected appropriately in accordance with the desired purity.

The compounds represented by the formula (3b) include isomers represented by the formula (3b'):

[Chem. 37]

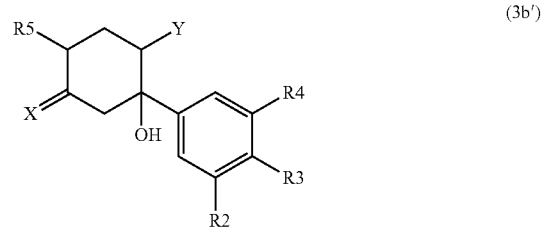

(3b')

wherein R2, R3, R4, R5, X and Y are the same as defined hereinabove.

The compounds represented by the formula (3b') may be handled similarly to the compounds of the formula (3b), and may be produced by Production Process A. The compound represented by the formula (3b') includes a chiral carbon atom, and may be any single isomer or a mixture of isomers in any proportions. Further, a mixture of a compound of the formula (3b) and a compound of the formula (3b') may be used, and each of the compounds may be any single isomer or a mixture of isomers in any proportions.

[Production Process V]

[Chem. 38]

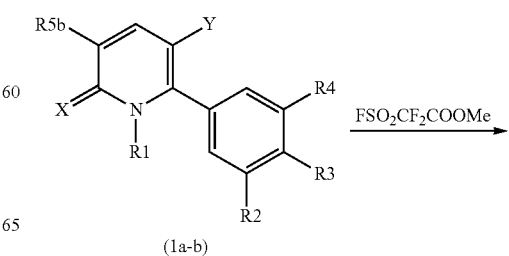

(1a-b)

-continued

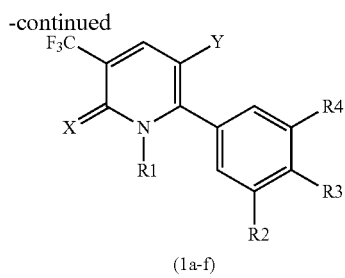

(1a-f)

In the formulae, R1, R2, R3, R4, R5b, X and Y are the same as defined hereinabove.

Production Process V is a method for synthesizing a trifluoromethyl-containing compound of the formula (1a-f) which belongs to the compounds represented by the formula (1a). This production process includes reacting a compound of the formula (1a-b) with methyl difluoro(fluorosulfonyl)acetate in the presence of a transition metal.

In the compound represented by the formula (1a-b), R5b is preferably a chlorine atom, a bromine atom or an iodine atom.

Methyl difluoro(fluorosulfonyl)acetate used in the reaction may be purchased from the market or may be produced by a known method.

The amount of methyl difluoro(fluorosulfonyl)acetate used in the reaction is at least 1 equivalent amount relative to the compound of the formula (1a-b), and is not particularly limited as long as the above equivalent amount is satisfied and also the target reaction takes place. The amount is preferably 1 equivalent amount to 50 equivalent amounts.

The transition metal used in the reaction may be, for example, a copper compound, and may be preferably copper bromide or copper iodide.

The amount of the transition metal used in the reaction is at least 1 equivalent amount relative to the compound of the formula (1a-b), and is not particularly limited as long as the above equivalent amount is satisfied and also the target reaction takes place. The amount is preferably 1 equivalent amount to 50 equivalent amounts.

To allow the reaction to proceed efficiently, additives such as ethyldiisopropylamine and hexamethylphosphoric triamide may be added, although the use of such additives is not indispensable.

The amount of the additives used in the reaction is not more than 50 equivalent amounts relative to the compound of the formula (1a-b), and is not particularly limited as long as the target reaction takes place.

The solvent used in the reaction is not particularly limited as long as the target reaction takes place. Examples of the solvents include amide solvents such as N-methylpyrrolidone, N,N-dimethylformamide and N,N-dimethylacetamide, sulfur solvents such as dimethylsulfoxide and sulfolane, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-b).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of ammonia, potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1a-f) may be dehydrated with a desiccant such as sodium sulfate or magnesium sulfate. This drying process may be omitted.

The reaction mixture including the compound of the formula (1a-f) may be distilled under reduced pressure to remove the solvent while avoiding the decomposition of the compound.

After the distillation, the reaction mixture including the compound of the formula (1a-f) may be purified by, for example, washing, reprecipitation, recrystallization or column chromatography using an appropriate solvent. The purification process may be selected appropriately in accordance with the desired purity.

The compounds represented by the formula (1) may be produced by an appropriate combination of Production Process A to Production Process V described hereinabove. The compounds of the formula (1) may be also produced by an appropriate combination of a known process and any of Production Process A to Production Process V.

The inventive compounds can protect plants from harmful organisms and thus may be used as agricultural chemicals, particularly as agricultural and horticultural pest control agents. Specific examples of such use include fungicides, insecticides, herbicides, plant growth regulators, and the like, with fungicides being preferable.

The inventive compounds may be used as agricultural and horticultural fungicides in farms, paddy fields, tea gardens, orchards, meadows, grasses, forests, gardens, roadside trees, etc. for the prevention and treatment of plant diseases.

Plant diseases in the present invention mean that systemic abnormal pathological symptoms such as wilting, damping-off, yellowing, dwarfism and spindly growth, or partial pathological symptoms such as spotting, leaf blight, mosaic pattern, leaf rolling, die back, root rot, clubroot and knotting, are induced in plants such as crops, flowering plants, flowering trees and shrubs, and trees. In other words, the term means that plants become or have become ill. Some main pathogens that cause plant diseases are fungi, bacteria, spiroplasmas, phytoplasmas, viruses, viroids, parasitic higher plants and nematodes. The inventive compounds are effective against fungi, which are not limitative.

Diseases caused by fungi are mainly fungal diseases. Examples of the fungi (pathogens) that cause fungal diseases include *Plasmodiophora, Oomycetes, Zygomycetes, Ascomycetes, Basidiomycetes, Deuteromycetes*, and the like.

Examples of the *Plasmodiophora* include clubroot fungus, potato powdery scab fungus, beet necrotic yellow vein virus, and the like. Examples of the *Oomycetes* include blight fungus, downy mildew fungus, *Pythium* species, *Aphanomyces* species, and the like. Examples of the *Zygomycetes* include *Rhizopus* species, and the like. Examples of the *Ascomycetes* include peach leaf curl fungus, corn southern leaf blight fungus, rice blast fungus, powdery mildew fungus, anthracnose fungus, *fusarium* head blight fungus, bakanae fungus, stem rot fungus, and the like. Examples of the Basidiomycetes include rust fungus, smut fungus, violet root rot fungus, blister blight fungus, rice sheath blight fungus, and the like. Examples of the *Deuteromycetes* include gray mold fungus, *Alternaria* species, *Fusarium* species, *Penicillium* species, *Rhizoctonia* species, southern blight fungus, and the like.

The inventive compounds are effective against various plant diseases. The following provides specific examples of disease names and pathogens thereof.

Rice: blast (*Magnaporthe grisea*), sheath blight (*Thanatephorus cucumeris*), brown sclerotial disease (*Ceratobasidium setariae*), brown small sclerotial disease (*Waitea circinata*), brown sheath blight (*Thanatephorus cucumeris*), globular sclerotial disease (*Sclerotium hydrophilum*), red sclerotial disease (*Waitea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), cercospora leaf spot (*Sphaerulina oryzina*), bakanae disease (*Gibberella fujikuroi*), seedling blight (*Pythium* spp., *Fusarium* spp., *Trichoderma* spp., *Rhizopus* spp., *Rhizoctonia solani, Mucor* sp., *Phoma* sp.), seedling rot (*Pythium* spp., *Achlya* spp., *Dictyuchus* spp.), rice false smut (*Claviceps virgins*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seeding blight (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus);

wheat and barley: powdery mildew (*Blumeria graminis* f. sp. *hordei*; f. sp. *tritici*), rust (*Puccinia striiformis, Puccinia graminis, Puccinia recondita, Puccinia hordei*), leaf blotch (*Pyrenophora graminea*), net blotch (*Pyrenophora teres*), *Fusarium* head blight (*Gibberella zeae, Fusarium culmorum, Fusarium avenaceum, Monographella nivalis*), *Typhula* snow blight (*Typhula incarnata, Typhula ishikariensis, Monographella nivalis*), loose smut (*Ustilago nuda*), stinking smut (*Tilletia caries, Tilletia controversa*), eye spot (*Pseudocercosporella herpotrichoides*), foot rot (*Ceratobasidium gramineum*), leaf scald (*Rhynchosporium secalis*), speckled leaf blotch (*Septoria tritici*), glume blotch (*Phaeosphaeria nodorum*), damping-off (*Fusarium* spp., *Pythium* spp., *Rhizoctonia* spp., *Septoria* spp., *Pyrenophora* spp.), take-all (*Gaeumannomyces graminis*), anthracnose (*Colletotrichum graminicola*), ergot (*Claviceps purpurea*), leaf spot (*Cochliobolus sativus*), bacterial black node (*Pseudomonas syringae* pv. *syringae*);

corn: *Fusarium* blight (*Gibberella zeae*, etc.), damping-off (*Fusarium avenaceum, Penicillium* spp., *Pythium* spp., *Rhizoctonia* spp.), rust (*Puccinia sorghi*), brown spot (*Cochliobolus heterostrophus*), smut (*Ustilago maydis*), anthracnose (*Colletotrichum graminicola*), northern leaf spot (*Cochliobolus carbonum*), bacterial brown stripe (*Acidovorax avenae* subsp. *avenae*), bacterial stripe (*Burkholderia andropogonis*), bacterial stalk rot (*Erwinia chrysanthemi* pv. *zeae*), bacterial wilt (*Erwinia stewartii*); grapes: downy mildew (*Plasmopara viticola*), rust (*Physopella ampelopsidis*), powdery mildew (*Uncinula necator*), scab (*Elsinoe ampelina*), ripe rot (*Glomerella cingulata, Colletotrichum acutatum*), black rot (*Guignardia bidwellii*), *Phomopsis* leaf spot (*Phomopsis viticola*), fly speck (*Zygophiala jamaicensis*), gray mold (*Botrytis cinerea*), twig blight (*Diaporthe medusaea*), violet root rot (*Helicobasidium mompa*), white root rot (*Rosellinia necatrix*), crown gall (*Agrobacterium vitis*); apples: powdery mildew (*Podosphaera leucotricha*), black spot disease (*Venturia inaequalis*), *Alternaria* leaf spot (*Alternaria mali*), rust (*Gymnosporangium yamadae*), blossom blight (*Monilinia mali*), apple canker (*Valsa ceratosperma*), ring spot (*Botryosphaeria berengeriana*), anthracnose (*Colletotrichum acutatum, Glomerella cingulata*), fly speck (*Zygophiala jamaicensis*), sooty spot (*Gloeodes pomigena*), fruit spot (*Mycosphaerella pomi*), violet root rot (*Helicobasidium mompa*), white root rot (*Rosellinia necatrix*), canker (*Phomopsis mali, Diaporthe tanakae*), apple blotch (*Diplocarpon mali*), fire blight (*Erwinia amylovora*), crown gall (*Agrobacterium tumefaciens*), hairy root disease (*Agrobacterium rhizogenes*);

Japanese pears: black spot (*Alternaria kikuchiana*), pear scab (*Venturia nashicola*), rust (*Gymnosporangium asiaticum*), ring spot (*Botryosphaeria berengeriana* f. sp. *piricola*), pear canker (*Phomopsis fukushii*), bacterial shoot blight (*Erwinia* sp.), crown gall (*Agrobacterium tumefaciens*), rusty canker (*Erwinia chrysanthemi* pv. *chrysanthemi*), bacterial petal blight (*Pseudomonas syringae* pv. *syringae*); European pears: blight (*Phytophthora cactorum, Phytophthora syringae*), bacterial shoot blight (*Erwinia* sp.); peaches: black spot (*Cladosporium carpophilum*), *Phomopsis* rot (*Phomopsis* sp.), blight (*Phytophthora* sp.), anthracnose (*Colletotrichum gloeosporioides*), leaf curl (*Taphrina deformans*), bacterial shot hole (*Xhanthomonas campestris* pv. *pruni*), crown gall (*Agrobacterium tumefaciens*); cherries: anthracnose (*Glomerella cingulata*), young fruit sclerotial disease (*Monilinia kusanoi*), gray spot (*Monilinia fructicola*), crown gall (*Agrobacterium tumefaciens*), bacterial gummosis (*Pseudomonas syringae* pv. *syringae*); persimmons: anthracnose (*Glomerella cingulata*), leaf spot (*Cercospora kaki; Mycosphaerella nawae*), powdery mildew (*Phyllactinia kakikora*), crown gall (*Agrobacterium tumefaciens*); citrus fruits: melanose (*Diaporthe citri*), green mold disease (*Penicillium digitatum*), blue mold disease (*Penicillium italicum*), scab (*Elsinoe fawcettii*), brown rot (*Phytophthora citrophthora*), canker (*Xhanthomonas campestris* pv. *citri*), bacterial brown spot (*Pseudomonas syringae* pv. *syringae*), greening disease (*Liberibactor asiaticus*), crown gall (*Agrobacterium tumefaciens*);

tomatoes, cucumbers, beans, strawberries, potatoes, cabbage, eggplants, lettuce and the like: gray mold (*Botrytis cinerea*); tomatoes, cucumbers, beans, strawberries, potatoes, rapeseed, cabbage, eggplants, lettuce and the like: sclerotial disease (*Sclerotinia sclerotiorum*); various vegetables such as tomatoes, cucumbers, beans, Japanese radishes, watermelons, eggplants, rapeseed, green peppers, spinach and beets: seedling damping-off (*Rhizoctonia* spp., *Pythium* spp., *Fusarium* spp., *Phythophthora* spp., *Sclerotinia sclerotiorum*, etc.); solanaceous plants: bacterial wilt (*Ralstonia solanacearum*); melons: downy mildew (*Pseudoperonospora cubensis*), powdery mildew (*Sphaerotheca fuliginea*), anthracnose (*Colletotrichum orbiculare*), gummy stem blight (*Didymella bryoniae*), stem rot (*Fusarium*

*oxysporum*), late blight (*Phytophthora parasitica, Phytophthora melonis, Phytophthora nicotianae, Phytophthora drechsleri, Phytophthora capsici*, etc.), bacterial brown spot (*Xhanthomonas campestris* pv. *cucurbitae*), soft rot (*Erwinia carotovora* subsp. *carotovora*), bacterial spot (*Pseudomonas syringae* pv. *lachrymans*), marginal blight (*Pseudomonas marginalis* pv. *marginalis*), canker (*Streptomyces* sp.), hairy root disease (*Agrobacterium rhizogenes*), cucumber mosaic virus (Cucumber mosaic virus);

tomatoes: ring spot (*Alternaria solani*), leaf mold (*Fulvia fulva*), late blight (*Phytophthora infestans*), wilt disease (*Fusarium oxysporum*), root rot (*Pythium myriotylum, Pythium dissotocum*), anthracnose (*Colletotrichum gloeosporioides*), canker (*Clavibacter michiganensis*), pith necrosis (*Pseudomonas corrugata*), bacterial black spot (*Pseudomonas viridijlava*), soft rot (*Erwinia carotovora* subsp. *carotovora*), bacterial leaf gall (*Crynebacterium* sp.), yellowing wilt (*Phytoplasma asteris*), yellow dwarfism (Tobacco leaf curl, subgroup III geminivirus); eggplants: powdery mildew (*Sphaerotheca fuliginea* etc.), leaf mold (*Mycovellosiella nattrassii*), blight (*Phytophthora infestans*), brown rot (*Phytophthora capsici*), bacterial brown spot (*Pseudomonas cichorii*), necrotic leaf spot (*Pseudomonas corrugata*), bacterial stem rot (*Erwinia chrysanthemi*), soft rot (*Erwinia carotovora* subsp. *carotovora*), bacterial spot (*Pseudomonas* sp.); rapeseed: black spot (*Alternaria brassicae*), black rot (*Xhanthomonas campestris* pv. *campestris*), bacterial black spot (*Pseudomonas syringae* pv. *maculicola*), soft rot (*Erwinia carotovora*); cruciferous vegetables: black spot (*Alternaria brassicae* etc.), white spot (*Cercosporella brassicae*), black leg (*Phoma lingam*), clubroot (*Plasmodiophora brassicae*), downy mildew (*Peronospora parasitica*), black rot (*Xanthomonas campestris* pv. *campestris*), bacterial black spot (*Pseudomonas syringae* pv. *maculicola*), soft rot (*Erwinia carotovora* subsp. *carotovora*);

cabbage: club foot (*Thanatephorus cucumeris*), yellowing wilt (*Fusarium oxysporum*), alternaria sooty spot (*Alternaria brassisicola*); Chinese cabbage: bottom rot (*Rhizoctonia solani*), yellowing (*Verticillium dahliae*); green onions: rust (*Puccinia allii*), black spot (*Alternaria porri*), southern blight (*Sclerotium rolfsii*), white rot (*Phytophthora porri*), black rot (*Sclerotium cepivorum*); onions: canker (*Curtobacterium flaccumfaciens*), soft rot (*Erwinia carotovora* subsp. *carotovora*), bacterial spot (*Pseudomonas syringae* pv. *syringae*), rot (*Erwinia rhapontici*), scale rot (*Burkholderia gladioli*), yellowing wilt (*Phytoplasma asteris*); garlic: soft rot (*Erwinia carotovora* subsp. *carotovora*), spring rot (*Pseudomonas marginalis* pv. *marginalis*); soybeans: purple seed stain (*Cercospora kikuchii*), scab (*Elsinoe glycines*), black spot (*Diaporthe phaseolorum*), *Rhizoctonia* root rot (*Rhizoctonia solani*), stem rot (*Phytophthora sojae*), downy mildew (*Peronospora manshurica*), rust (*Phakopsora pachyrhizi*), anthracnose (*Colletotrichum truncatum* etc.), leaf scald (*Xhanthomonas campestris* pv. *glycines*), bacterial spot (*Pseudomonas syringae* pv. *glycinea*); kidney beans: anthracnose (*Colletotrichum lindemuthianum*), bacterial wilt (*Ralstonia solanacearum*), halo blight (*Pseudomonas syringae* pv. *phaseolicola*), bacterial brown spot (*Pseudomonas viridiflava*), leaf scald (*Xhanthomonas campestris* pv. *phaseoli*);

peanuts: leaf spot (*Mycosphaerella berkeleyi*), brown spot (*Mycosphaerella arachidis*), bacterial wilt (*Ralstonia solanacearum*); garden peas: powdery mildew (*Erysiphe pisi*), downy mildew (*Peronospora pisi*), bacterial stem blight (*Pseudomonas syringae* pv. *pisi*), bacterial stem rot (*Xhanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solanacearum*), black foot disease (*Erwinia carotovora* subsp. *atroseptica*), common scab (*Streptomyces scabies, Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); sugar beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces scabies*), bacterial spot (*Pseudomonas syringae* pv. *aptata*);

carrots: leaf blight (*Alternaria dauci*), bacterial gall (*Rhizobacter dauci*), crown gall (*Agrobacterium tumefaciens*), Streptomyces scab (*Streptomyces* spp.), soft rot (*Erwinia carotovora* subsp. *carotovora*); strawberries: powdery mildew (*Sphaerotheca aphanis* var. *aphanis*), blight (*Phytophthora nicotianae* etc.), anthracnose (*Glomerella cingulata*), fruit rot (*Pythium ultimum*), bacterial wilt (*Ralstonia solanacearum*), angular leaf spot (*Xhanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xhanthomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), bacterial wilt (*Ralstonia solanacearum*), Tobacco mosaic virus (Tobacco mosaic virus);

coffee: rust (*Hemileia vastatrix*); banana: black sigatoka (*Mycosphaerella fijiensis*), panama disease (*Fusarium oxysporum* f. sp *cubense*); cotton: damping-off (*Fusarium oxysporum*), frosty mildew (*Ramularia areola*); sunflowers: sclerotial disease (*Sclerotinia sclerotiorum*), angular leaf spot (*Xhanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa* etc.), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (Erwinia carotovora subsp. carotovora), crown gall (*Agrobacterium tumefaciens*), hairy root disease (*Agrobacterium rhizogenes*), chrysanthemum virescence (*Phytoplasma aurantifolia*); grasses: brown patch disease (*Rhizoctonia solani*), dollar spot disease (*Sclerotinia homoeocarpa*), curvularia leaf blight (*Curvularia* sp.), rust (*Puccinia zoysiae*), helminthosporium leaf blight (*Cochliobolus* sp.), scald (*Rhynchosporium secalis*), take-all (*Gaeumannomyces graminis*), anthracnose (*Colletotrichum* sp.), typhula brown snow blight (*Typhula incarnata*), typhula black snow blight (*Typhula ishikariensis*), Sclerotinia (*Myriosclerotinia borealis*), fairy ring disease (*Marasmius oreades* etc.), *Pythium* blight (*Pythium aphanidermatum* etc.), blast (*Pyricularia grisea*).

The inventive compounds may be used singly, and may be preferably used as compositions such as powders, water-dispersible powders, water-dispersible granules, water-soluble powders, water-soluble granules, granules, emulsions, solutions, microemulsions, aqueous suspension preparations, aqueous emulsion preparations and suspoemulsion preparations by being mixed with solid carriers, liquid carriers, gas carriers, surfactants, binders, dispersants, stabilizers and the like. The form of use is not limited to such compositions as long as effects are obtained.

Some specific formulating examples will be described below without limiting the scope of the invention thereto.

PREPARATION EXAMPLE 1

Flowable

The inventive compound (10 parts by mass), a sodium salt of naphthalene sulfonate formaldehyde condensate (5 parts by mass), polyoxyethylene aryl phenyl ether (1 part by mass), propylene glycol (5 parts by mass), a silicone antifoaming agent (0.1 part by mass), xanthan gum (0.2 parts by mass), and ion exchanged water (78.7 parts by mass) are mixed to give a slurry. Further, the slurry is wet milled with Dyno-Mill KDL using glass beads having a diameter of 1.0 mm to give a flowable.

PREPARATION EXAMPLE 2

Emulsion

The inventive compound (5 parts by mass) is dissolved into a mixed solution of xylene (40 parts by mass) and cyclohexane (35 parts by mass). Tween 20 (20 parts by mass) is added to the resultant solution, and the mixture is mixed to give an emulsion.

PREPARATION EXAMPLE 3

Water-Dispersible Powder

The inventive compound (10 parts by mass), white carbon (10 parts by mass), polyvinyl alcohol (2 parts by mass), sodium dioctylsulfosuccinate (0.5 parts by mass), sodium alkylbenzenesulfonate (5 parts by mass), calcined diatomaceous earth (10 parts by mass), and kaolinite clay (62.5 parts by mass) are mixed thoroughly, and the mixture is milled with an air mill to give a water-dispersible powder.

The application of compositions (such as agricultural and horticultural pest control agents, and agricultural and horticultural fungicides) including the inventive compounds will be described hereinbelow.

For example, a composition containing the inventive compound may be applied by being brought into contact with a plant body or seeds, or by being added to cultivation soil and brought into contact with the roots or underground stem of a plant. Specific examples of the manners of application include spraying of the composition onto the stem and leaves of an individual plant, injection treatment, seedling nursery box treatment, cell tray treatment, spraying of the composition to plant seeds, plant seed coating treatment, plant seed immersion treatment, plant seed dressing treatment, spraying of the composition onto the surface of soil, spraying of the composition onto the surface of soil followed by mixing into the soil, injection into soil, injection and subsequent mixing into soil, irrigation to soil, irrigation and subsequent mixing into soil, and the like. The compositions offer sufficient effects when applied by any methods usually used by a person skilled in the art.

The term "plant" used in the present invention refers to one which thrives by photosynthesis without moving. Specific examples thereof include rice, wheat, barley, corn, coffee, bananas, grapes, apples, pears, peaches, cherries, persimmons, citrus fruits, soybeans, kidney beans, cotton, strawberries, potatoes, cabbage, lettuce, tomatoes, cucumbers, eggplants, watermelons, sugar beets, spinach, field peas, squash, sugar cane, tobacco, green peppers, sweet potatoes, taro potatoes, konjak, cotton, sunflowers, roses, tulips, chrysanthemums, grasses, etc., and F1 hybrids, etc. of the above plants. Examples further include gene recombinant crops that are created by genetic or other artificial manipulation and are inherently not present in nature, with specific examples including agricultural and horticultural crops such as soybeans, corn, cotton and the like which have been imparted with resistance to herbicides, rice, tobacco and the like acclimated to cold climates, and corn, cotton and the like which have been given the ability to produce insecticidal substances. Examples further include trees such as pines, ash trees, ginkgoes, maples, evergreen oaks, poplars, and zelkova trees, and the like. The term "plant body" used in the present invention is a generic term for all portions that constitute an individual plant, for example, stems, leaves, roots, seeds, flowers, fruits and the like.

The term "seed" used in the present invention refers to one which stores nutrients for the germination of seedlings and is used for agricultural production. Specific examples thereof include seeds of corn, soybeans, cotton, rice, sugar beets, wheat, barley, sunflowers, tomatoes, cucumbers, eggplants, spinach, field peas, squash, sugar cane, tobacco, green peppers, rape, etc., seeds of F1 hybrids, etc. of the above plants, seed tubers of taro potatoes, potatoes, sweet potatoes, konjak, etc., bulbs of edible lilies, tulips, etc., seed bulbs of scallions, etc., seeds and tubers of gene recombinant crops, and the like.

The amount and concentration in which the composition containing the inventive compound is applied may vary depending on factors such as the type of target crop, the type of target disease, the degree of progression of the disease, the formulation form of the compound, the application method and various environmental conditions. In the case of spraying or irrigation, the amount applied in terms of active ingredient may be suitably 0.1 to 10,000 g per hectare, and preferably 10 to 1,000 g per hectare. In the case of seed treatment, the amount used in terms of active ingredient may be 0.0001 to 1,000 g, and preferably 0.001 to 100 g per kg of seeds. Where the composition containing the inventive compound is sprayed to the stem and leaves of an individual plant, is sprayed to the surface of soil, is injected into the soil or is irrigated to the soil, the treatment may be carried out after the composition is diluted to an appropriate concentration with a suitable carrier. When the composition containing the inventive compound is brought into contact with plant seeds, the seeds may be immersed, dressed, sprayed or coated after the composition is diluted to an appropriate concentration. In the immersion, dressing, spraying or coating treatment, the amount of the composition in terms of active ingredient is usually about 0.05 to 50% of the dry weight of the plant seeds, and is preferably 0.1 to 30%, but is not limited thereto and may be determined appropriately depending on the form of the composition and the type of plant seeds to be treated.

Where necessary, the inventive compounds may be used as mixtures with other agricultural chemicals, for example, agricultural chemicals such as fungicides, insecticides (including miticides and nematicides), herbicides, biological pesticides and plant growth regulators, disease control agents containing nucleic acids as active ingredients (WO 2014/062775), soil improvers and fertilizing substances. A mixture of the inventive compound and the other agricultural chemical may be used in such a manner that the inventive compound and the other agricultural chemical are formulated into a single preparation, that each is formulated into separate preparations and the preparations are mixed together before use, that each is formulated into separate preparations and the preparations are used concurrently, or that each is formulated into separate preparations and the preparations are used successively.

Specific examples of the ingredients contained in fungicides which may be used as mixtures with the inventive compounds include those belonging to Group b below, and salts, isomers and N-oxides thereof. The fungicides are not limited thereto, and known fungicides may be used.

Group b:

b-1: Phenylamide Fungicides

Examples of the phenylamide fungicides include [b-1.1] benalaxyl, [b-1.2] benalaxyl-M or kiralaxyl, [b-1.3] furalaxyl, [b-1.4] metalaxyl, [b-1.5] metalaxyl-M or mefenoxam, [b-1.6] oxadixyl, [b-1.7] ofurace, and the like.

b-2: Mitosis Inhibitors and Cell Division Inhibitors

Examples of the mitosis inhibitors and cell division inhibitors include [b-2.1] benomyl, [b-2.2] carbendazim, [b-2.3] fuberidazole, [b-2.4] thiabendazole, [b-2.5] thiophanate, [b-2.6] thiophanate-methyl, [b-2.7] diethofencarb, [b-2,8] zoxamide, [b-2.9] ethaboxam, [b-2.10] pencycuron, [b-2.11] fluopicolide, [b-2.12] phenamacril, and the like.

b-3: Succinic Ddehydrogenase Inhibitors (SDHI)

Examples of the succinic dehydrogenase inhibitors (SDHI) include [b-3.1] benodanil, [b-3.2] benzovindiflupyr, [b-3.3] bixafen, [b-3.4] boscalid, [b-3.5] carboxin, [b-3.6] fenfuram, [b-3.7] fluopyram, [b-3.8] flutolanil, [b-3.9] fluxapyroxad, [b-3.10] furametpyr, [b-3.11] isofetamid, [b-3.12] isopyrazam, [b-3.13] mepronil, [b-3.14] oxycarboxin, [b-3.15] penthiopyrad, [b-3.16] penflufen, [b-3.17] pydiflumetofen, [b-3.18] sedaxane, [b-3.19] thifluzamide, [b-3.20] pyraziflumid, and the like.

b-4: Quinone oOtside Inhibitors (QoI)

Examples of the quinone outside inhibitors (QoI) include [b-4.1] azoxystrobin, [b-4.2] coumoxystrobin, [b-4.3] dimoxystrobin, [b-4.4] enoxastrobin, [b-4.5] famoxadone, [b-4.6] fenamidone, [b-4.7] fenaminstrobin, [b-4.8] flufenoxystrobin, [b-4.9] fluoxastrobin, [b-4.10] kresoximmethyl, [b-4.11] mandestrobin, [b-4.12] metominostrobin, [b-4.13] orysastrobin, [b-4.14] picoxystrobin, [b-4.15] pyraclostrobin, [b-4.16] pyrametostrobin, [b-4.17] pyraoxystrobin, [b-4.18] pyribencarb, [b-4.19] triclopyricarb, [b-4.20] trifloxystrobin, and the like.

b-5: Quinone Inside Inhibitors (QiI)

Examples of the quinone inside inhibitors (QiI) include [b-5.1] cyazofamid, [b-5.2] amisulbrom, and the like.

b-6: Oxidative Phosphorylation Uncoupling Inhibitors

Examples of the oxidative phosphorylation uncoupling inhibitors include [b-6.1] binapacryl, [b-6.2] meptyldinocap, [b-6.3] dinocap, [b-6.4] fluazinam, and the like.

b-7: Quinone Outside Stigmatellin Binding Subsite Inhibitors (QoSI)

Examples of the quinone outside stigmatellin binding subsite inhibitors (QoSI) include [b-7.1] ametoctradin, and the like.

b-8: Amino Acid Biosynthesis Inhibitors

Examples of the amino acid biosynthesis inhibitors include [b-8.1] cyprodinil, [b-8.2] mepanipyrim, [b-8.3] pyrimethanil, and the like.

b-9: Protein Biosynthesis Inhibitors

Examples of the protein biosynthesis inhibitors include [b-9.1] streptomycin, [b-9.2] blasticidin-S, [b-9.3] kasugamycin, [b-9.4] oxytetracycline, and the like.

b-10: Signal Transduction Inhibitors

Examples of the signal transduction inhibitors include [b-10.1] fenpiclonil, [b-10.2] fludioxonil, [b-10.3] quinoxyfen, [b-10.4] proquinazid, [b-10.5] chlozolinate, [b-10.6] dimethachlone, [b-10.7] iprodione, [b-10.8] procymidone, [b-10.9] vinclozolin, and the like.

b-11: Lipid and Cell Membrane Biosynthesis Inhibitors

Examples of the lipid and cell membrane biosynthesis inhibitors include [b-11.1] edifenphos, [b-11.2] iprobenfos, [b-11.3] pyrazophos, [b-11.4] isoprothiolane, [b-11.5] biphenyl, [b-11.6] chloroneb, [b-11.7] dicloran, [b-11.8] quintozene, [b-11.9] tecnazene, [b-11.10] tolclofos-methyl, [b-11.11] echlomezol or etridiazole, [b-11.12] iodocarb, [b-11.13] propamocarb, [b-11.14] prothiocarb, and the like.

b-12: Demethylation Inhibitors (DMI)

Examples of the demethylation inhibitors (DMI) include [b-12.1] azaconazole, [b-12.2] bitertanol, [b-12.3] bromuconazole, [b-12.4] cyproconazole, [b-12.5] difenoconazole, [b-12.6] diniconazole, [b-12.7] diniconazole-M, [b-12.8] epoxiconazole, [b-12.9] etaconazole, [b-12.10] fenarimol, [b-12.11] fenbuconazole, [b-12.12] fluquinconazole, [b-12.13] quinconazole, [b-12.14] flusilazole, [b-12.15] flutriafol, [b-12.16] hexaconazole, [b-12.17] imazalil, [b-12.18] imibenconazole, [b-12.19] ipconazole, [b-12.20] metconazole, [b-12.21] myclobutanil, [b-12.22] nuarimol, [b-12.23] oxpoconazole, [b-12.24] oxpoconazole fumarate, [b-12.25] pefurazoate, [b-12.26] penconazole, [b-12.27] prochloraz, [b-12.28] propiconazole, [b-12.29] prothioconazole, [b-12.30] pyrifenox, [b-12.31] pyrisoxazole, [b-12.32] simeconazole, [b-12.33] tebuconazole, [b-12.34] tetraconazole, [b-12.35] triadimefon, [b-12.36] triadimenol, [b-12.37] triflumizole, [b-12.38] triforine, [b-12.39] triticonazole, [b-12.40] mefentrifluconazole, [b-12.41] ipfentrifluconazole, and the like.

b-13: Amine Fungicides

Examples of the amine fungicides include [b-13.1] aldimorph, [b-13.2] dodemorph, [b-13.3] fenpropimorph, [b-13.4] tridemorph, [b-13.5] fenpropidin, [b-13.6] piperalin, [b-13.7] spiroxamine, and the like.

b-14: 3-Keto Reductase Inhibitors in C4-Demethylation in Sterol Biosynthesis

Examples of the 3-keto reductase inhibitors in C4-demethylation in sterol biosynthesis include [b-14.1] fenhexamid, [b-14.2] fenpyrazamine, and the like.

b-15: Squalene Epoxidase Inhibitors in Sterol Biosynthesis

Examples of the squalene epoxidase inhibitors in sterol biosynthesis include [b-15.1] pyributicarb, [b-15.2] naftifine, [b-15.3] terbinafine, and the like.

b-16: Cell Wall Biosynthesis Inhibitors

Examples of the cell wall biosynthesis inhibitors include [b-16.1] polyoxins, [b-16.2] dimethomorph, [b-16.3] flumorph, [b-16.4] pyrimorph, [b-16.5] benthiavalicarb, [b-16.6] benthiavalicarb-isopropyl, [b-16.7] iprovalicarb, [b-16.8] mandipropamid, [b-17.9] valifenalate, and the like.

b-17: Melanin Biosynthesis Inhibitors

Examples of the melanin biosynthesis inhibitors include [b-17.1] phthalide or fthalide, [b-17.2] pyroquilone, [b-17.3] tricyclazole, [b-17.4] carpropamid, [b-17.5] diclocymet, [b-17.6] fenoxanil, [b-17.7] tolprocarb, and the like.

b-18: Host Plant Resistance Inducers

Examples of the host plant resistance inducers include [b-18.1] acibenzolar-S-methyl, [b-18.2] probenazole, [b-18.3] tiadinil, [b-18.4] isotianil, [b-18.5] laminarin, and the like.

b-19: Dithiocarbamate Fungicides

Examples of the dithiocarbamate fungicides include [b-19.1] mancozeb or manzeb, [b-19.2] maneb, [b-19.3] metiram, [b-19.4] propineb, [b-19.5] thiram, [b-19.6] zineb, [b-19.7] ziram, [b-19.8] ferbam, and the like.

b-20: Phthalimide Fungicides

Examples of the phthalimide fungicides include [b-20.1] captan, [b-20.2] captafol, [b-20.3] folpet, [b-20.4] fluorofolpet, and the like.

b-21: Guanidine Fungicides

Examples of the guanidine fungicides include [b-21.1] guazatine, [b-21.2] iminoctadine, [b-21.3] iminoctadine albesilate, [b-21.4] iminoctadine triacetate, and the like.

b-22: Multi-Site Contact Active Fungicides

Examples of the multi-site contact active fungicides include [b-22.1] copper oxychloride, [b-22.2] copper (II) hydroxide, [b-22.3] copper hydroxide sulfate, [b-22.4] organocopper compound, [b-22.5] dodecylbenzenesulphonic acid bisethylenediamine copper [II] salt, DBEDC, [b-22.6] sulphur, [b-22.7] fluoroimide, [b-22.8] chlorothalonil, [b-22.9] dichlofluanid, [b-22.10] tolylfluanid, [b-22.11] anilazine, [b-22.12] dithianon, [b-22.13] chinomethionat or quinomethionate, [b-22.14] extract from lupine seedling cotyledons, and the like.

b-23: Other Fungicides

Examples of other fungicides include [b-23.1] dichlobentiazox, [b-23.2] fenpicoxamid, [b-23.3] dipymetitrone, [b-23.4] bupirimate, [b-23.5] dimethirimol, [b-23.6] ethirimol, [b-23.7] fentin acetate, [b-23.8] fentin chloride, [b-23.9] fentin hydroxide, [b-23.10] oxolinic acid, [b-23.11] hymexazol, [b-23.12] octhilinone, [b-23.13] fosetyl, [b-23.14] phosphorous acid, [b-23.15] sodium phosphite, [b-23.16] ammonium phosphite, [b-23.17] potassium phosphite, [b-23.18] tecloftalam, [b-23.19] triazoxide, [b-23.20] flusulfamide, [b-23.21] diclomezine, [b-23.22] silthiofam, [b-23.23] diflumetorim, [b-23.24] methasulfocarb, [b-23.25] cyflufenamid, [b-23.26] metrafenone, [b-23.27] pyriofenone, [b-23.28] dodine, [b-23.29] flutianil, [b-23.30] ferimzone, [b-23.31] oxathiapiprolin, [b-23.32] tebufloquin, [b-23.33] picarbutrazox, [b-23.34] validamycins, [b-23.35] cymoxanil, [b-23.36] quinofumelin,

[b-23.37] compound of the formula (s1):

[Chem. 39]

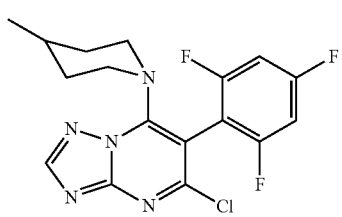

(s1)

(see WO 98/046607),

[b-23.38] compound of the formula (s2):

[Chem. 40]

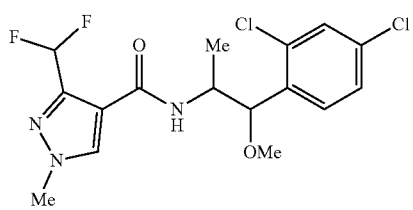

(s2)

(see WO 08/148570),

[b-23.39] compound of the formula (s3):

[Chem. 41]

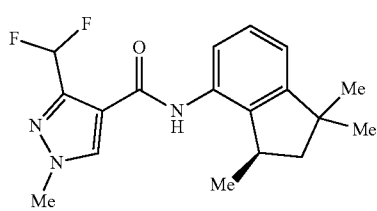

(s3)

(see WO 92/012970),

[b-23.40] compound of the formula (s4):

[Chem. 42]

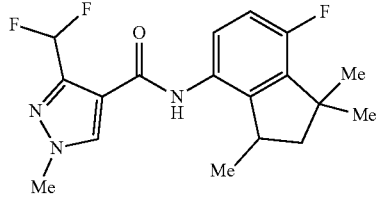

(s4)

(see WO 12/084812),

[b-23.41] compound of the formula (s5):

[Chem. 43]

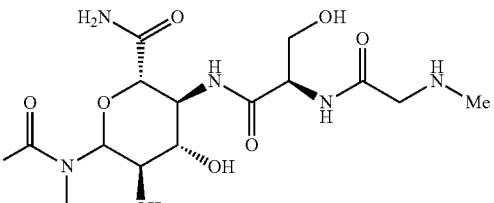

(s5)

(gougerotin),

[b-23.42] compound of the formula (s6):
[Chem. 44]
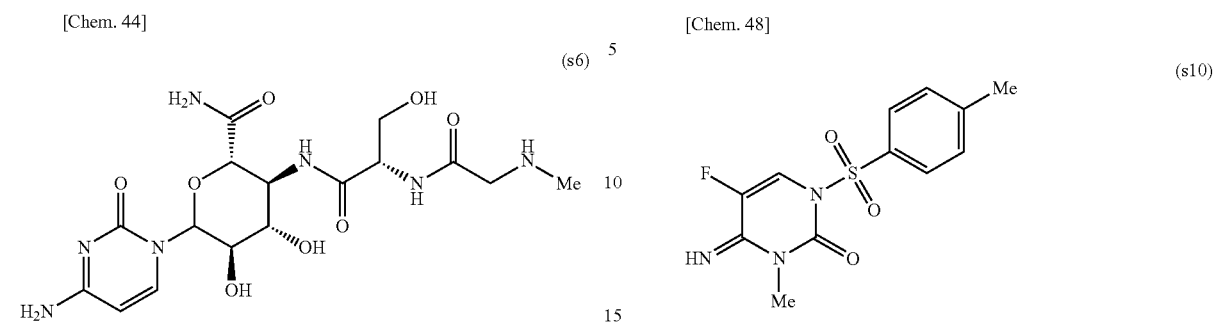
(ningnanmycin),
[b-23.43] compound of the formula (s7):
[Chem. 45]
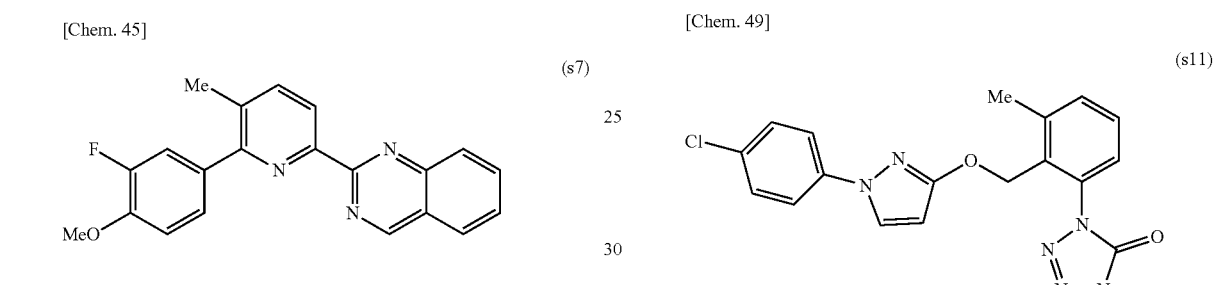
(see WO 10/136475),
[b-23.44] compound of the formula (s8):
[Chem. 46]
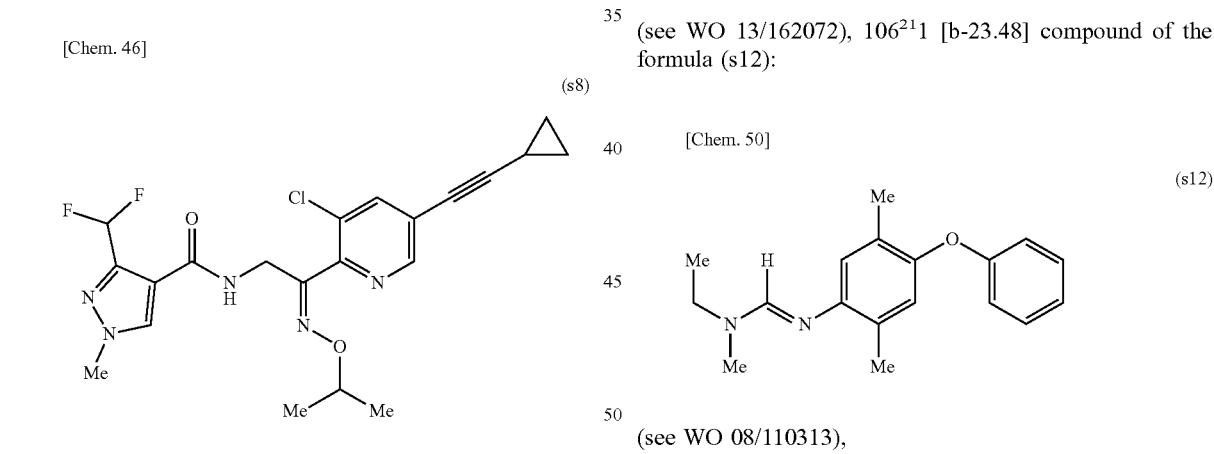
(see WO 14/010737),
[b-23.45] compound of the formula (s9):
[Chem. 47]
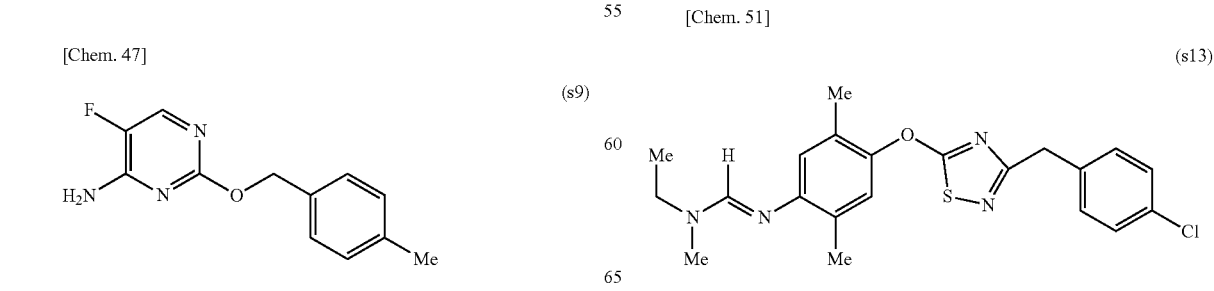
(see WO 11/085084),
[b-23.46] compound of the formula (s10):
[Chem. 48]
(see WO 11/137002),
[b-23.47] compound of the formula (s11):
[Chem. 49]
(see WO 13/162072), $106^{21}1$ [b-23.48] compound of the formula (s12):
[Chem. 50]
(see WO 08/110313),
[b-23.49] compound of the formula (s13):
[Chem. 51]
(see WO 09/156098),

[b-23.50] compound of the formula (s14):

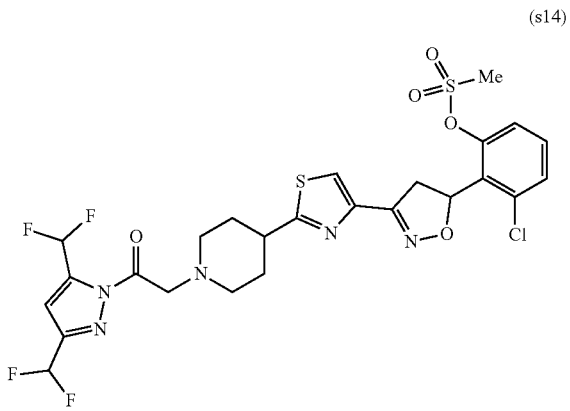

(see WO 12/025557),

[b-23.51] compound of the formula (s15):

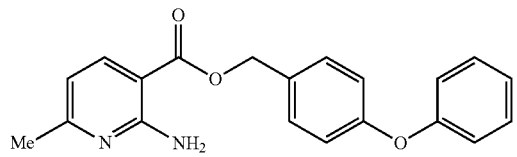

(see WO 14/006945),

[b-23.52] compounds of the formula (s16):

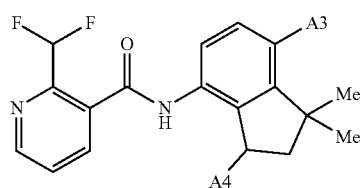

wherein A3 represents a hydrogen atom, a halogen atom, a C1-C6 alkyl group, a C1-C6 haloalkyl group or a cyano group, and A4 represents a hydrogen atom, a C1-C6 alkyl group, a C1-C6 haloalkyl group or a C3-C8 cycloalkyl group (see WO 14/095675),

[b-23.53] compounds of the formula (s17):

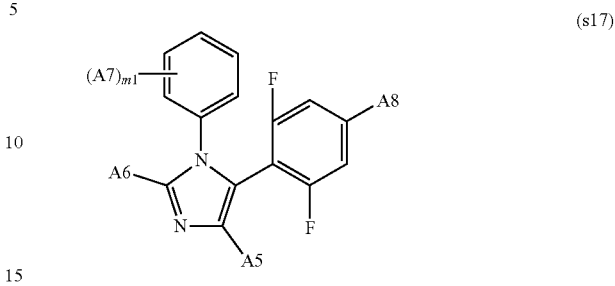

wherein m1 represents an integer of 0 to 3, A5 and A6 are independent of one another and each represent a halogen atom or a C1-C6 alkyl group, A7 and A8 are independent of one another and each represent a halogen atom or a C1-C6 alkoxy group, and when m1 is 2 or greater, the two or more substituents A7 are independent of one another and may be the same as or different from one another (see WO 09/137538 and International Patent No. 09/137651),

[b-23.54] compounds of the formula (s18):

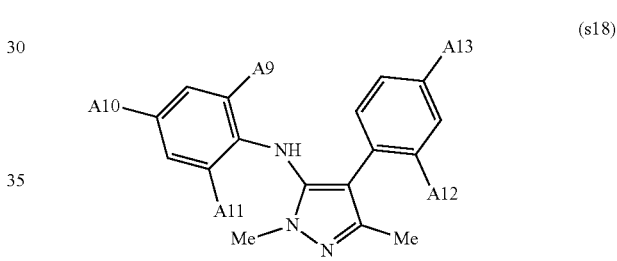

wherein A9 and A10 are independent of one another and each represent a hydrogen atom or a halogen atom, A11 represents a halogen atom, A12 represents a halogen atom or a C1-C6 alkyl group, and A13 represents a halogen atom, a cyano group, a C1-C6 alkyl group or a C1-C6 alkoxy group (see WO 12/031061),

[b-23.55] compounds of the formula (s19):

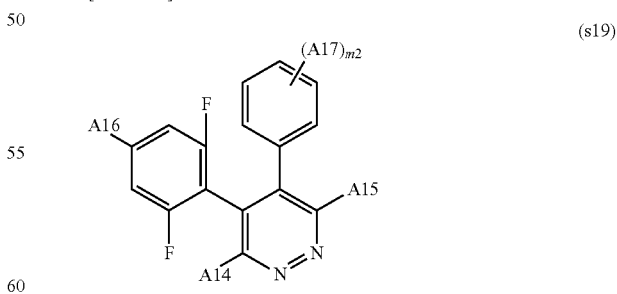

wherein m2 represents an integer of 0 to 6, A14 and A15 are independent of one another and each represent a halogen atom, a cyano group or a C1-C6 alkyl group, A16 represents a hydrogen atom, a halogen atom or a C1-C6 alkoxy group, A17 represents a halogen atom or a C1-C6 alkoxy group, and when m2 is 2 or greater, the two or more substituents A17 are independent of one another and may be the same as or different from one another (see WO 05/121104),

[b-23.56] compounds of the formula (s20):

[Chem. 58]

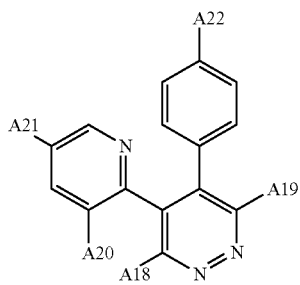

(s20)

wherein A18 and A19 are independent of one another and each represent a halogen atom, a cyano group or a C1-C6 alkyl group, and A20, A21 and A22 are independent of one another and each represent a hydrogen atom, a halogen atom or a C1-C6 alkoxy group (see WO 07/066601),

[b-23.57] compounds of the formula (s21):

[Chem. 59]

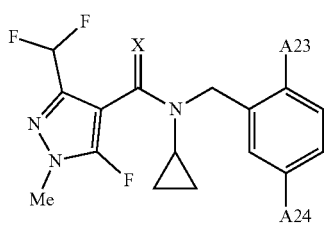

(s21)

wherein A23 and A24 are independent of one another and each represent a hydrogen atom, a halogen atom, a C1-C6 alkyl group or a C3-C8 cycloalkyl group, and X represents an oxygen atom or a sulfur atom (see WO 07/087906, International Patent No. 09/016220 and International Patent No. 10/130767),

[b-23.58] compounds of the formula (s22):

[Chem. 60]

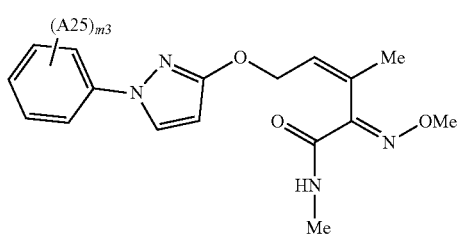

(s22)

wherein m3 represents an integer of 0 to 5, A25 represents a halogen atom, a C1-C6 alkyl group, a C1-C6 haloalkyl group, a C1-C6 alkoxy group, a C1-C6 haloalkoxy group or a C3-C8 cycloalkyl group, and when m3 is 2 or greater, the two or more substituents A25 are independent of one another and may be the same as or different from one another (see WO 13/092224),

[b-23.59] compounds of the formula (s23):

[Chem. 61]

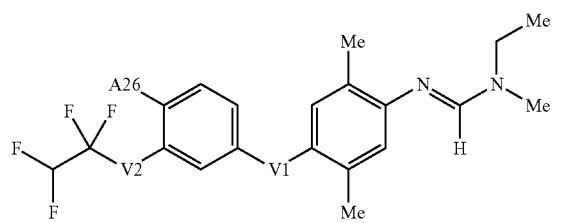

(s23)

wherein A26 represents a hydrogen atom or a halogen atom, and V1 and V2 are independent of one another and each represent an oxygen atom or a sulfur atom (see WO 12/025450),

[b-23.60] compounds of the formula (s24) or the formula (s25):

[Chem. 62]

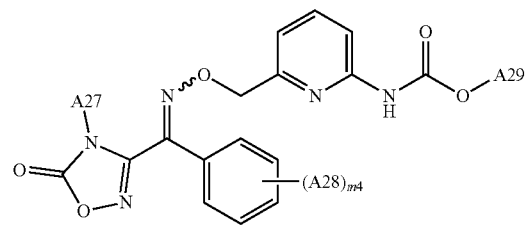

(s24)

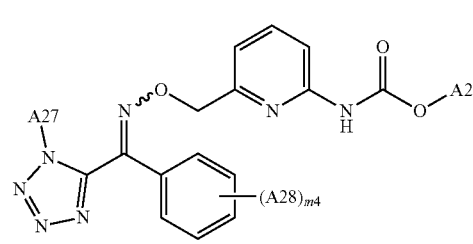

(s25)

wherein m4 represents an integer of 0 to 5, A27 represents a C1-C6 alkyl group, A28 represents a halogen atom, a cyano group, a C1-C6 alkyl group or a C1-C6 haloalkyl group wherein when m4 is 2 or greater, the two or more substituents A28 are independent of one another and may be the same as or different from one another, and A29 represents a C1-C6 alkyl group, a C2-C6 alkenyl group or a C3-C6 alkynyl group (see WO 13/037717),

[b-23.61] compounds of the formula (s26) or the formula (s27):

[Chem. 63]

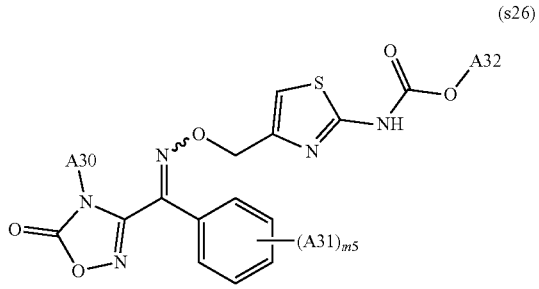

(s26)

(s27)

wherein m5 represents an integer of 0 to 5, A30 represents a C1-C6 alkyl group, A31 represents a halogen atom, a cyano group, a C1-C6 alkyl group or a C1-C6 haloalkyl group wherein when m5 is 2 or greater, the two or more substituents A31 are independent of one another and may be the same as or different from one another, and A32 represents a C1-C6 alkyl group, a C2-C6 alkenyl group or a C3-C6 alkynyl group (see WO 13/037717),

[b-23.62] compounds of the formula (s28):

[Chem. 64]

(s28)

wherein A33, A34, A35 and A36 are independent of one another and each represent a hydrogen atom or a halogen atom, and A37 represents a hydrogen atom, an acetyl group or a benzoyl group (see WO 06/031631 and International Patent No. 10/069882),

[b-23.63] compounds of the formula (s29):

[Chem. 65]

(s29)

wherein A38 represents a C1-C6 alkyl group or a C1-C6 haloalkyl group, and A39 and A40 are independent of one another and each represent a hydrogen atom or a halogen atom (see WO 14/043376),

[b-23.64] compounds of the formula (s30):

[Chem. 66]

(s30)

wherein A41 represents a hydrogen atom, a hydrosulfide group (—SH), a thiocyanate group (—SCN) or a C1-C6 alkylthio group, and A42, A43, A44 and A45 are independent of one another and each represent a hydrogen atom or a halogen atom (see WO 09/077443),

[b-23.65] compounds of the formula (s31) or the formula (s32):

[Chem. 67]

(s31)

(s32)

wherein A46 represents a hydrogen atom or a halogen atom, A47 represents a C1-C6 alkyl group, and A48 represents a halogen atom (see WO 11/070771),

[b-23.66] compounds of the formula (s33):

[Chem. 68]

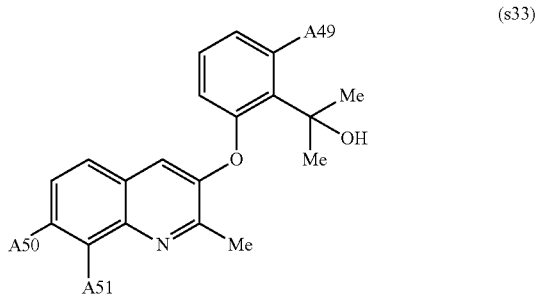

(s33)

wherein A49, A50 and A51 are independent of one another and each represent a hydrogen atom or a halogen atom (see WO 11/081174), and the like.

Specific examples of the ingredients contained in insecticides which may be used as mixtures with the inventive compounds include those belonging to Group c below, and salts, isomers and N-oxides thereof. The insecticides are not limited thereto, and known insecticides may be used.

Group c:

c-1: Carbamate-Based Acetylcholinesterase (AChE) Inhibitors

Examples of the carbamate-based acetylcholinesterase (AChE) inhibitors include [c-1.1] phosphocarb, [c-1.2] alanycarb, [c-1.3] butocarboxim, [c-1.4] butoxycarboxim, [c-1.5] thiodicarb, [c-1.6] thiofanox, [c-1.7] aldicarb, [c-1.8] bendiocarb, [c-1.9] benfuracarb, [c-1.10] carbaryl, [c-1.11] carbofuran, [c-1.12] carbosulfan, [c-1.13] ethiofencarb, [c-1.14] fenobucarb, [c-1.15] formetanate, [c-1.16] furathiocarb, [c-1.17] isoprocarb, [c-1.18] methiocarb, [c-1.19] methomyl, [c-1.20] oxamyl, [c-1.21] pirimicarb, [c-1.22] propoxur, [c-1.23] trimethacarb, [c-1.24] XMC (3,5-xylylmethylcarbamate), [c-1.25] allyxycarb, [c-1.26] aldoxycarb, [c-1.27] bufencarb, [c-1.28] butacarb, [c-1.29] carbanolate, [c-1.30] metolcarb, [c-1.31] xylylcarb, [c-1.32] fenothiocarb, [c-1.33] xylylcarb, [c-1.34] bendiocarb, and the like.

c-2: Organophosphorus-Based Acetylcholinesterase (AChE) Inhibitors

Examples of the organophosphorus-based acetylcholinesterase (AChE) inhibitors include [c-2.1] acephate, [c-2.2] azamethiphos, [c-2.3] azinphos-methyl, [c-2.4] azinphos-ethyl, [c-2.5] ethephon, [c-2.6] cadusafos, [c-2.7] chlorethoxyfos, [c-2.8] chlorfenvinphos, [c-2.9] chlormephos, [c-2.10] chlorpyrifos, [c-2.11] chlorpyrifos-methyl, [c-2.12] coumaphos, [c-2.13] cyanophos, [c-2.14] demeton-S-methyl, [c-2.15] diazinon, [c-2.16] dichlofenthion, [c-2.17] dichlorvos, [c-2.18] dicrotophos, [c-2.19] dimethoate, [c-2.20] dimethylvinphos, [c-2.21] disulfoton, [c-2.22] 0-ethyl 0-4-nitrophenyl phenylphosphonothioate, [c-2.23] ethion, [c-2.24] ethoprophos, [c-2.25] famphur, [c-2.26] fenamiphos, [c-2.27] fenitrothion, [c-2.28] fenthion, [c-2.29] fosthiazate, [c-2.30] heptenophos, [c-2.31] isofenphos-methyl, [c-2.32] isocarbophos, [c-2.33] isoxathion, [c-2.34] malathion, [c-2.35] mecarbam, [c-2.36] methamidophos, [c-2.37] methidathion, [c-2.38] mevinphos, [c-2.39] monocrotophos, [c-2.40] naled, [c-2.41] omethoate, [c-2.42] oxydemeton-methyl, [c-2.43] parathions, [c-2.44] parathion-methyl, [c-2.45] phenthoate, [c-2.46] phorate, [c-2.47] phosalone, [c-2.48] phosmet, [c-2.49] phosphamidon, [c-2.50] phoxim, [c-2.51] pirimiphos-methyl, [c-2.52] profenofos, [c-2.53] propetamphos, [c-2.54] prothiofos, [c-2.55] pyraclofos, [c-2.56] pyridaphenthion, [c-2.57] quinalphos, [c-2.58] sulfotep, [c-2.59] tebupirimfos, [c-2.60] temephos, [c-2.61] terbufos, [c-2.62] thiometon, [c-2.63] triazophos, [c-2.64] trichlorfon, [c-2.65] vamidothion, [c-2.66] chlorthion, [c-2.67] bromfenvinfos, [c-2.68] bromophos, [c-2.69] bromophos-ethyl, [c-2.70] butathiofos, [c-2.71] carbophenothion, [c-2.72] chlorphoxim, [c-2.73] sulprofos, [c-2.74] diamidafos, [c-2.75] tetrachlorvinphos, [c-2.76] propaphos, [c-2.77] mesulfenfos, [c-2.78] dioxabenzofos, [c-2.79] etrimfos, [c-2.80] oxydeprofos, [c-2.81] formothion, [c-2.82] fensulfothion, [c-2.83] isazofos, [c-2.84] imicyafos, [c-2.85] isamidofos, [c-2.86] thionazin, [c-2.87] fosthietan, and the like.

c-3: GABA-Gated Chloride Channel Blockers

Examples of the GABA-gated chloride channel blockers include [c-3.1] chlordane, [c-3.2] endosulfan, [c-3.3] lindane, [c-3.4] dienochlor, [c-3.5] ethiprole, [c-3.6] fipronil, [c-3.7] acetoprole, and the like.

c-4: Sodium Channel Modulators

Examples of the sodium channel modulators include [c-4.1] acrinathrin, [c-4.2] allethrin[(1R)-isomer], [c-4.3] bifenthrin, [c-4.4] bioallethrin, [c-4.5] bioallethrin S-cyclopentenyl isomer, [c-4.6] bioresmethrin, [c-4.7] cycloprothrin, [c-4.8] cyfluthrin, [c-4.9] beta-cyfluthrin, [c-4.10] cyhalothrin, [c-4.11] gamma-cyhalothrin, [c-4.12] lambda-cyhalothrin, [c-4.13] cypermethrin, [c-4.14] alpha-cypermethrin, [c-4.15] beta-cypermethrin, [c-4.16] theta-cypermethrin, [c-4.17] zeta-cypermethrin, [c-4.18] cyphenothrin [(1R)-trans-isomer], [c-4.19] deltamethrin, [c-4.20] empenthrin[(EZ)-(1R)-isomer], [c-4.21] esfenvalerate, [c-4.22] ethofenprox, [c-4.23] fenpropathrin, [c-4.24] fenvalerate, [c-4.25] flucythrinate, [c-4.26] flumethrin, [c-4.27] tau-fluvalinate, [c-4.28] halfenprox, [c-4.29] imiprothrin, [c-4.30] methothrin, [c-4.31] metofluthrin, [c-4.32] epsilon-metofluthrin, [c-4.33] momfluorothrin, [c-4.34] epsilon-momfluorothrin, [c-4.35] permethrin, [c-4.36] phenothrin [(1R)-trans-isomer], [c-4.37] prallethrin, [c-4.38] resmethrin, [c-4.39] kadethrin, [c-4.40] silafluofen, [c-4.41] tefluthrin, [c-4.42] tetramethrin, [c-4.43] tetramethrin[(1R)-isomer], [c-4.44] tralomethrin, [c-4.45] transfluthrin, [c-4.46] ZXI8901 (3-(4-bromophenoxy)phenyl]-cyanomethyl 4-(difluoromethoxy)-α-(1-methylethyl)benzeneacetate, [c-4.47] biopermethrin, [c-4.48] furamethrin, [c-4.49] profluthrin, [c-4.50] flubrocythrinate, [c-4.51] dimefluthrin, [c-4.52] DDT (dichloro-diphenyl-trichloroethane), [c-4.53] methoxychlor, [c-4.54] phenothrin, [c-4.55] fluvalinate, and the like.

c-5: Nicotinic Acetylcholine Receptor (nAChR) Competitive Modulators

Examples of the nicotinic acetylcholine receptor (nAChR) competitive modulators include [c-5.1] acetamiprid, [c-5.2] clothianidin, [c-5.3] dinotefuran, [c-5.4] imidacloprid, [c-5.5] nitenpyram, [c-5.6] thiacloprid, [c-5.7] thiamethoxam, [c-5.8] nicotine, [c-5.9] nicotine sulfate, [c-5.10] sulfoxaflor, [c-5.11] flupyradifurone, [c-5.12] triflumezopyrim, and the like.

c-6: Nicotinic Acetylcholine Receptor (nAChR) Allosteric Modulators

Examples of the nicotinic acetylcholine receptor (nAChR) allosteric modulators include [c-6.1] spinosad, [c-6.2] spinetoram, and the like.

c-7: Glutamate-Gated Chloride Channel (GluCl) Allosteric Modulators

Examples of the glutamate-gated chloride channel (GluCl) allosteric modulators include [c-7.1] abamectin, [c-7.2] emamectin benzoate, [c-7.3] lepimectin, [c-7.4] milbemectin, and the like.

c-8: Juvenile Hormone Analogues

Examples of the juvenile hormone analogues include [c-8.1] hydroprene, [c-8.2] kinoprene, [c-8.3] methoprene, [c-8.4] fenoxycarb, [c-8.5] pyriproxyfen, and the like.

c-9: Nonspecific (Multisite) Inhibitors

Examples of the nonspecific (multisite) inhibitors include [c-9.1] methyl bromide, [c-9.2] chloropicrin, [c-9.3] cryolite, [c-9.4] sulfuryl fluoride, [c-9.5] borax, [c-9.6] boric acid, [c-9.7] disodium octaborate, [c-9.8] sodium metaborate, [c-9.9] tartar emetic, [c-9.10] dazomet, [c-9.11] metam, [c-9.12] metam sodium, and the like.

c-10: Chordotonal Organ TRPV Channel Modulators

Examples of the chordotonal organ TRPV channel modulators include [c-10.1] pymetrozine, [c-10.2] pyrifluquinazon, and the like.

c-11: Mite Growth Inhibitors

Examples of the mite growth inhibitors include [c-11.1] clofentezine, [c-11.2] diflovidazin, [c-11.3] hexythiazox, [c-11.4] etoxazole, and the like.

c-12: Mitochondria ATP Synthase Inhibitors

Examples of the mitochondria ATP synthase inhibitors include [c-12.1] diafenthiuron, [c-12.2] azocyclotin, [c-12.3] cyhexatin, [c-12.4] fenbutatin oxide, [c-12.5] propargite, [c-12.6] tetradifon, and the like.

c-13: Uncouplers of Oxidative Phosphorylation via Disruption of Proton Gradient

Examples of the uncouplers of oxidative phosphorylation via disruption of the proton gradient include [c-13.1] chlorfenapyr, [c-13.2] DNOC (dinitro-ortho-cresol), [c-13.3] binapacryl, [c-13.4] sulfluramid, and the like.

c-14: Nicotinic Acetylcholine Receptor (nAChR) Channel Blockers

Examples of the nicotinic acetylcholine receptor (nAChR) channel blockers include [c-14.1] bensultap, [c-14.2] cartap hydrochloride, [c-14.3] thiocyclam, [c-14.4] monosultap, and the like.

c-15: Chitin Biosynthesis Inhibitors, Type 0

Examples of the chitin biosynthesis inhibitors, type 0, include [c-15.1] bistrifluron, [c-15.2] chlorfluazuron, [c-15.3] diflubenzuron, [c-15.4] flucycloxuron, [c-15.5] flufenoxuron, [c-15.6] hexaflumuron, [c-15.7] lufenuron, [c-15.8] novaluron, [c-15.9] noviflumuron, [c-15.10] teflubenzuron, [c-15.11] triflumuron, and the like.

c-16: Chitin Biosynthesis Inhibitors, Type 1

Examples of the chitin biosynthesis inhibitors, type 1, include [c-16.1] buprofezin, and the like.

c-17: Dipteran Molting Disruptors

Examples of the dipteran molting disruptors include [c-17.1] cyromazine, and the like.

c-18: Molting Hormone (Ecdysone) Receptor Agonists

Examples of the molting hormone (ecdysone) receptor agonists include [c-18.1] chromafenozide, [c-18.2] halofenozide, [c-18.3] methoxyfenozide, [c-18.4] tebufenozide, and the like.

c-19: Octopamine Receptor Agonists

Examples of the octopamine receptor agonists include [c-19.1] amitraz, and the like.

c-20: Mitochondrial Complex III Electron Transport Inhibitors

Examples of the mitochondrial complex III electron transport inhibitors include [c-20.1] hydramethylnon, [c-20.2] acequinocyl, [c-20.3] fluacrypyrim, [c-20.4] bifenazate, and the like.

c-21: Mitochondrial Complex I Electron Transport Inhibitors (METI)

Examples of the mitochondrial complex I electron transport inhibitors (METI) include [c-21.1] fenazaquin, [c-21.2] fenpyroximate, [c-21.3] pyridaben, [c-21.4] pylimidifen, [c-21.5] tebufenpyrad, [c-21.6] tolfenpyrad, [c-21.7] rotenone, and the like.

c-22: Voltage-Dependent Sodium Channel Blockers

Examples of the voltage-dependent sodium channel blockers include [c-22.1] indoxacarb, [c-22.2] metaflumizone, and the like.

c-23: Acetyl CoA Carboxylase Inhibitors

Examples of the acetyl CoA carboxylase inhibitors include [c-23.1] spirodiclofen, [c-23.2] spiromesifen, [c-23.3] spirotetramat, and the like.

c-24: Mitochondrial Complex IV Electron Transport Inhibitors

Examples of the mitochondrial complex IV electron transport inhibitors include [c-24.1] aluminum phosphide, [c-24.2] calcium phosphide, [c-24.3] phosphine, [c-24.4] zinc phosphide, [c-24.5] calcium cyanide, [c-24.6] potassium cyanide, [c-24.7] sodium cyanide, and the like.

c-25: Mitochondrial Complex II Electron Transport Inhibitors

Examples of the mitochondrial complex II electron transport inhibitors include [c-25.1] cyenopyrafen, [c-25.2] cyflumetofen, [c-25.3] pyflubumide, and the like.

c-26: Ryanodine Receptor Modulators

Examples of the ryanodine receptor modulators include [c-26.1] chlorantraniliprole, [c-26.2] cyantraniliprole, [c-26.3] flubendiamide, and the like.

c-27: Chordotonal Organ Modulators on Undefined Target Sites

Examples of the chordotonal organ modulators on undefined target sites include [c-27.1] flonicamid, and the like.

c-28: Other Insecticides

Examples of other insecticides include [c-28.1] azadirachtin, [c-28.2] benzoximate, [c-28.3] phenisobromolate, [c-28.4] chinomethionat, [c-28.5] dicofol, [c-28.6] pyridalyl, [c-28.7] bromopropylate, [c-28.8] triazamate, [c-28.9] dicyclanil, [c-28.10] dinobuton, [c-28.11] dinocap, [c-28.12] hydrogen cyanide, [c-28.13] methyl iodide, [c-28.14] karanjin, [c-28.15] mercury chloride, [c-28.16] methyl isothiocyanate, [c-28.17] pentachlorophenol, [c-28.18] phosphine, [c-28.19] piperonyl butoxide, [c-28.20] polynactins, [c-28.21] sabadilla, [c-28.22] sulcofuron-sodium, [c-28.23] tribufos, [c-28.24] aldrin, [c-28.25] amidithion, [c-28.26] amidothioate, [c-28.27] aminocarb, [c-28.28] amiton, [c-28.29] aramite, [c-28.30] athidathion, [c-28.31] azothoate, [c-28.32] barium polysulphide, [c-28.33] benclothiaz, [c-28.34] 5-(1,3-benzodioxole-5-yl)-3-hexylcyclohexa-2-enone, [c-28.35] 1,1-bis(4-chlorophenyl)-2-ethoxyethanol, [c-28.36] butonate, [c-28.37] butopyronoxyl, [c-28.38] 2-(2-butoxyethoxy)ethyl thiocyanate, [c-28.39] camphechlor, [c-28.40] chlorbenside, [c-28.41] chlordecone, [c-28.42] chlordimeform, [c-28.43] chlorfenethol, [c-28.44] chlorfenson, [c-28.45] fluazuron, [c-28.46] metaldehyde, [c-28.47] bialaphos, [c-28.48] levamisol, [c-28.49] amidoflumet, [c-28.50] pyrafluprole, [c-28.51] pyriprole, [c-28.52] tralopyril, [c-28.53] flupyrazofos, [c-28.54] diofenolan, [c-28.55] chlorobenzilate,

[c-28.56] flufenzine, [c-28.57] benzomate, [c-28.58] flufenerim, [c-28.59] albendazole, [c-28.60] oxibendazole, [c-28.61] fenbendazole, [c-28.62] metam-sodium, [c-28.63] 1,3-dichloropropene, [c-28.64] flometoquin, [c-28.65] cyclaniliprole, [c-28.66] tetraniliprole, [c-28.67] broflanilide, [c-28.68] dicloromezotiaz, [c-28.69] ethylene dibromide, [c-28.70] acrylonitrile, [c-28.71] bis(2-chloroethyl) ether, [c-28.72] 1-bromo-2-chloroethane, [c-28.73] 3-bromo-1-chloroprop-1-ene, [c-28.74] bromocyclen, [c-28.75] carbon disulfide, [c-28.76] tetrachloromethane, [c-28.77] nemadectin, [c-28.78] cymiazole, [c-28.79] calcium polysulfide, [c-28.80] cytokinin, [c-28.81] 2-(octylthio)ethanol, [c-28.82] potassium oleate, [c-28.83] sodium oleate, [c-28.84] machine oil, [c-28.85] tar oil, [c-28.86] anabasine, [c-28.87] morantel tartrate, [c-28.88] insect flower (pyrethrum), [c-28.89] rape seed oil, [c-28.90] soybean lecithin, [c-28.91] starch, [c-28.92] hydroxypropyl-starch, [c-28.93] decanoyloctanoylglycerol, [c-28.94] propylene glycol fatty acid ester, [c-28.95] diatomite, [c-28.96] afoxolaner, [c-28.97] fluazaindolizine, [c-28.98] afidopyropen, [c-28.99] cyhalodiamide, [c-28.100] tioxazafen, [c-28.101] fluhexafon, [c-28.102] fluralaner, [c-28.103] fluxametamide, [c-28.104] tetrachlorantraniliprole, [c-28.105] sarolaner, [c-28.106] lotilaner, [c-28.107] cycloxaprid, [c-28.108] fluensulfone, [c-28.109] TPIC (tripropyl isocyanurate), [c-28.110] D-D (1,3-dichloropropene), [c-28.111] peroxocarbonate, [c-28.112] MB-599 (verbutin), [c-28.113] bis(2,3,3,3-tetrachloropropyl) ether, [c-28.114] DCIP (bis(2-chloro-1-methylethyl)ether), [c-28.115] ENT-8184 (N-2-(ethylhexyl)bicyclo[2.2.1]hept-5-ene-2,3-dicarboximide), [c-28.116] Bayer 22408 (O,O-diethyl O-naphthalimido phosphorothioate), [c-28.117] Bayer 32394 (tris(1-dodecyl-3-methyl-2-phenylbenzimidazolium)hexacyanoferrate,

[c-28.118] compound of the formula (s34):

[Chem. 69]

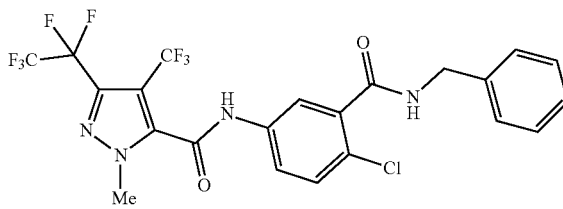

(s34)

(see WO 10/051926),

[c-28.119] compound of the formula (s35):

[Chem. 70]

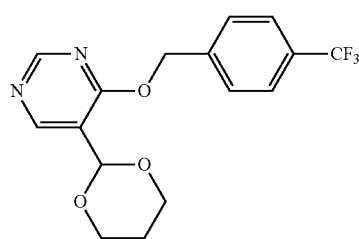

(s35)

(see WO 13/115391),

[c-28.120] compound of the formula (s36):

[Chem. 71]

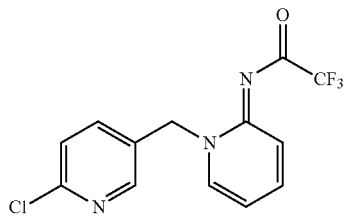

(s36)

(see WO 12/029672),

[c-28.121] compound of the formula (s37):

[Chem. 72]

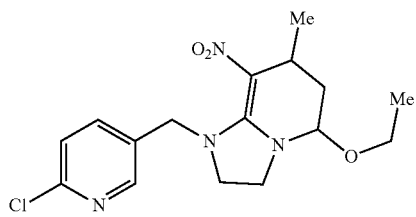

(s37)

(see WO 06/056108),

[c-28.122] compound of the formula (s38):

[Chem. 73]

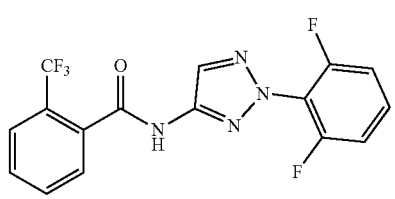

(s38)

(see WO 14/053450 and International Patent No. 15/144683),

[c-28.123] compound of the formula (s39):

[Chem. 74]

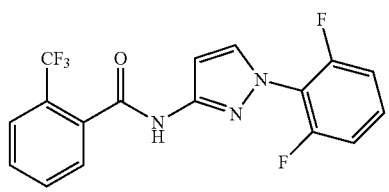

(s39)

(see WO 14/053450 and International Patent No. 15/144683),

[c-28.124] compound of the formula (s40):

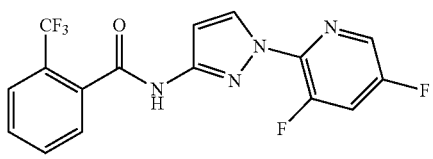

(see WO 14/053450 and International Patent No. 15/144683),

[c-28.125] compounds of the formula (s41):

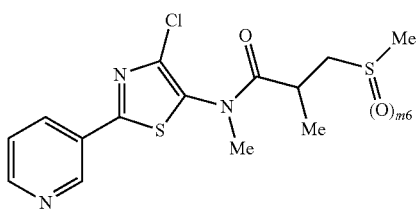

wherein m6 represents an integer of 0 to 2 (see WO 10/129497),

[c-28.126] compounds of the formula (s42):

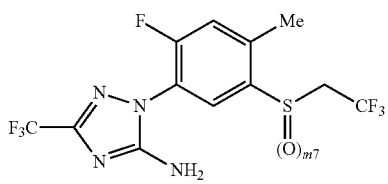

wherein m7 represents an integer of 0 to 2 (see WO 11/152320),

[c-28.127] compounds of the formula (s43):

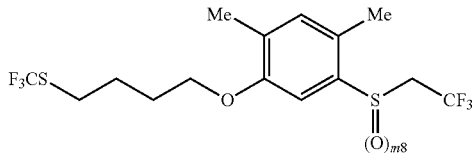

wherein m8 represents an integer of 0 to 2 (see Japanese Patent Application Kokai Publication No. H27-160813),

[c-28.128] compounds of the formula (s44):

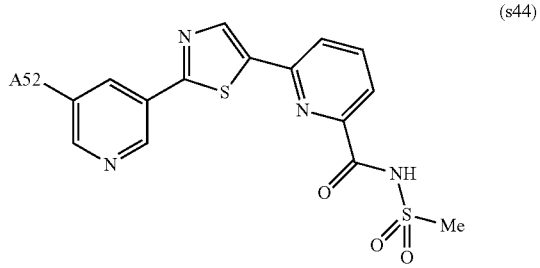

wherein A52 represents a hydrogen atom or a fluorine atom (see WO 11/134964 and International Patent No. 14/005982),

[c-28.129] compounds of the formula (s45):

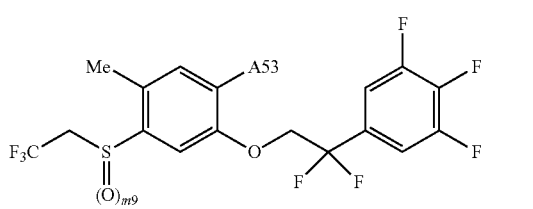

wherein m9 represents an integer of 0 to 2, and A53 represents a fluorine atom or a chlorine atom (see WO 15/025826),

[c-28.130] compounds of the formula (s46):

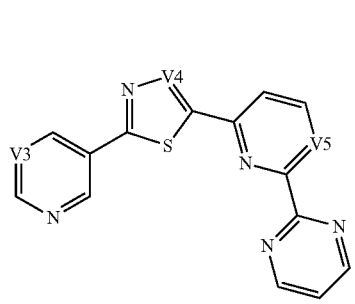

wherein V3 represents a nitrogen atom, a carbon atom or C—F, and V4 and V5 are independent of one another and each represent a nitrogen atom or a carbon atom (see WO 11/134964 and WO 14/005982),

[c-28.131] compounds of the formula (s47):

[Chem. 82]

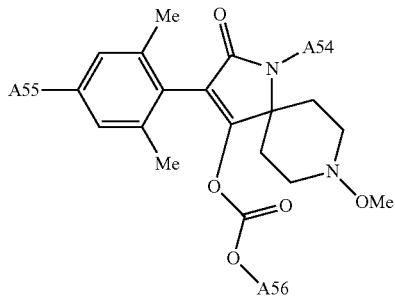

(s47)

wherein A54 represents a hydrogen atom, a methyl group, a methoxy group or an ethoxy group, A55 represents a chlorine atom or a methyl group, and A56 represents a methyl group or an ethyl group (see WO 09/049851),

[c-28.132] compounds of the formula (s48):

[Chem. 83]

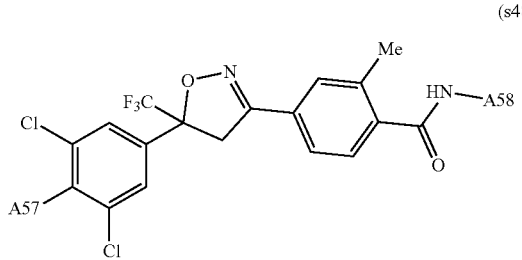

(s48)

wherein A57 represents a hydrogen atom, a fluorine atom or a chlorine atom, and A58 represents one partial structure selected from the group consisting of:

[Chem. 84]

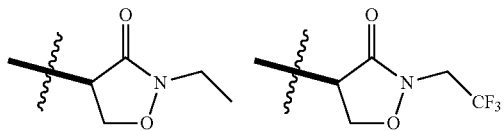

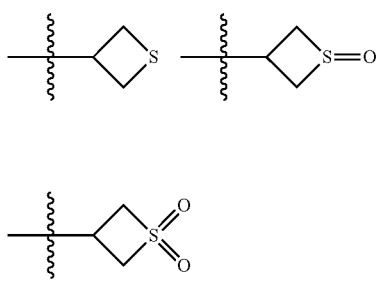

(see WO 11/067272),

[c-28.133] compounds of the formula (s49):

[Chem. 85]

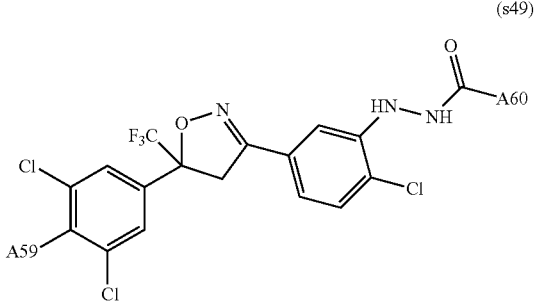

(s49)

wherein A59 represents a hydrogen atom, a fluorine atom or a chlorine atom, and A60 represents a partial structure selected from the group consisting of:

[Chem. 86]

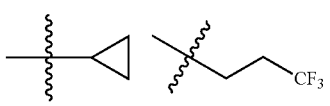

(see WO 10/090344),

[c-28.134] compounds of the formula (s50):

[Chem. 87]

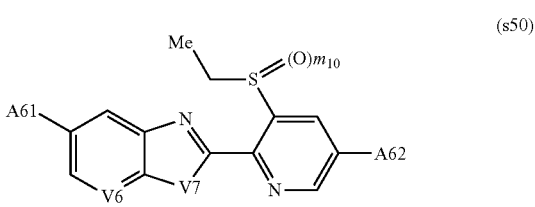

(s50)

wherein m10 represents an integer of 0 to 2, A61 represents a trifluoromethyl group, a trifluoromethylthio group, a trifluoromethylsulfinyl group or a trifluoromethylsulfonyl group, A62 represents a hydrogen atom or a trifluoromethyl group, V6 represents a nitrogen atom or a carbon atom, and V7 represents an oxygen atom or a N-methyl group (see WO 14/104407),

[c-28.135] compounds of the formula (s51):

[Chem. 88]

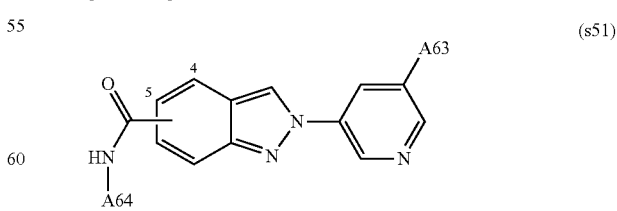

(s51)

wherein A63 represents a hydrogen atom or a fluorine atom, the amide group is bonded to 4-position or 5-position, and A64 represents a partial structure selected from the group consisting of:

[Chem. 89]

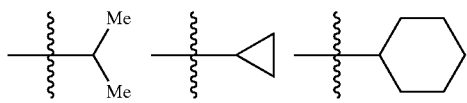

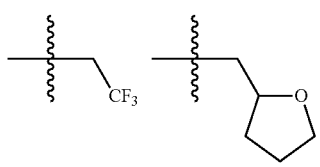

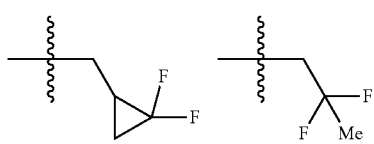

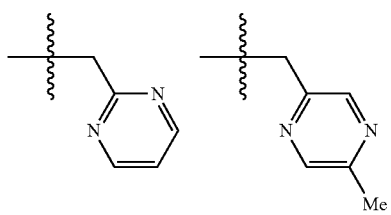

(see WO 15/038503, International Patent No. 16/144351 and International Patent No. 16/144678),

[c-28.136] compounds of the formula (s52):

[Chem. 90]

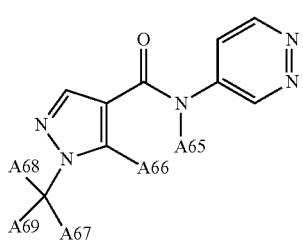

(s52)

wherein A65 represents a hydrogen atom, a C1-C6 alkyl group or a C1-C6 haloalkyl group, A66 represents a hydrogen atom, a halogen atom or a C1-C6 alkyl group, A67 and A68 are independent of one another and each represent a hydrogen atom, a C1-C6 alkyl group optionally substituted with a cyano group, an alkyl group optionally substituted with a methoxy group, an alkyl group optionally substituted with an ethoxy group, or a C3-C8 cycloalkyl group, and A69 represents a hydrogen atom, a cyano group, a C1-C6 haloalkyl group optionally substituted with a cyano group, a C1-C6 alkyl group, or a C3-C8 cycloalkyl group (see WO 12/143317 and International Patent No. 16/016369),

[c-28.137] compounds of the formula (s53) or the formula (s54):

[Chem. 91]

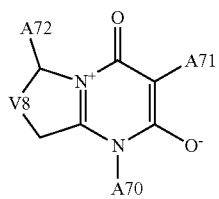

(s53)

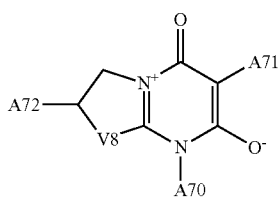

(s54)

wherein A70 represents a methyl group, an ethyl group, an isopropyl group, a 2,2,2-trifluoroethyl group or a phenyl group, A71 represents a partial structure selected from the group consisting of:

[Chem. 92]

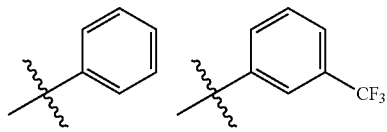

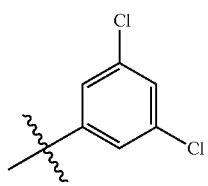

A72 represents a partial structure selected from the group consisting of:

[Chem. 93]

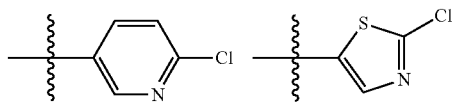

and V8 represents an oxygen atom, a sulfur atom, —CH$_2$— or —CH$_2$CH$_2$— (see WO 14/167084 and International Patent No. 16/055431),

[c-28.138] compounds of the formula (s55):

[Chem. 94]

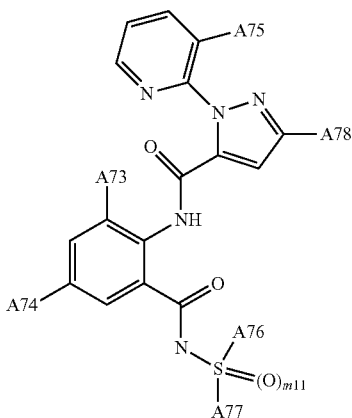

(s55)

wherein m11 represents an integer of 0 to 1, A73 represents a chlorine atom, a bromine atom, a methyl group or a trifluoromethyl group, A74 represents a hydrogen atom, a chlorine atom, a bromine atom, a cyano group or a trifluoromethyl group, A75 represents a hydrogen atom, a chlorine atom or a bromine atom, A76 and A77 are independent of one another and each represent a C1-C6 alkyl group or a C3-C8 cycloalkyl group, and A78 represents a chlorine atom, a bromine atom, a cyano group, a nitro group, a difluoromethyl group or a trifluoromethyl group (see WO 13/024009),

[c-28.139] compounds of the formula (s56):

[Chem. 95]

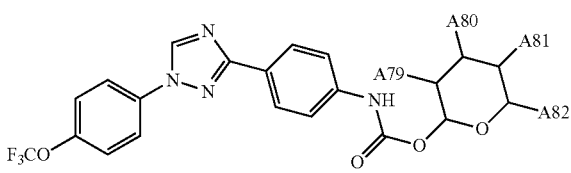

(s56)

wherein A79, A80, A81 and A82 are independent of one another and each represent a hydrogen atom, a halogen atom, a C1-C6 alkyl group, a C1-C6 haloalkyl group, a C1-C6 alkoxy group or a C3-C8 cycloalkoxy group (see WO 12/027521),

[c-28.140] compounds of the formula (s57):

[Chem. 96]

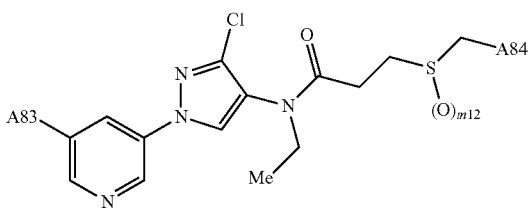

(s57)

wherein m12 represents an integer of 0 to 2, A83 represents a hydrogen atom or a fluorine atom, and A84 represents a partial structure selected from the group consisting of:

[Chem. 97]

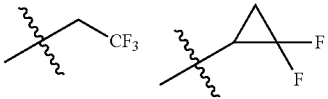

(see WO 13/162715),

[c-28.141] acynonapyr,

[c-28.142] compounds of the formula (s59):

[Chem. 98]

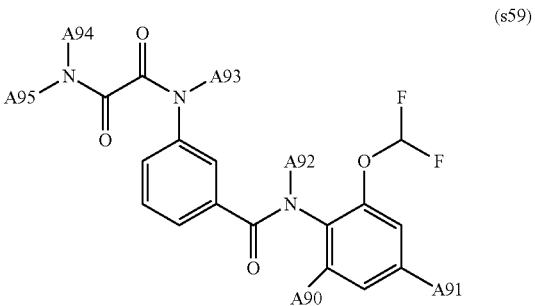

(s59)

wherein A90 represents a halogen atom, a C1-C6 alkyl group or a C1-C6 haloalkyl group, A91 represents a C1-C6 haloalkyl group, A92 and A93 are independent of one another and each represent a hydrogen atom, a C1-C6 alkyl group, an acetyl group, a propionoyl group, a methanesulfonylethyl group, a methoxycarbonyl group or an ethoxycarbonyl group, and A94 and A95 are independent of one another and each represent a hydrogen atom, a C1-C6 alkyl group or a C1-C6 haloalkyl group (see WO 12/164698), and the like.

The mixing ratio of the inventive compounds and the other agricultural chemicals described above which may be mixed therewith as necessary is not particularly limited as long as effects are obtained. Usually, the weight ratio of the other agricultural chemical to the inventive compound is 0.001 to 1000, and preferably 0.01 to 100.

EXAMPLES

The present invention will be described in greater detail hereinbelow based on Synthetic Examples, Reference Examples and Test Examples. However, it should be construed that the scope of the invention is not limited thereto.

Synthetic Example 1

Step 1: Synthesis of 5-(2-chloro-3,5-difluorophenyl)-6-(4-fluorophenyl)-3,4-dihydropyridin-2(1H)-one

[Chem. 99]

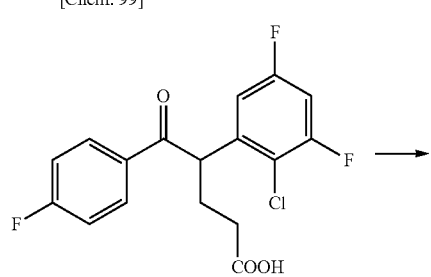

33.80 g of ammonium acetate and 33 ml of acetic acid were added to 3.30 g of 4-(2-chloro-3,5-difluorophenyl)-5-(4-fluorophenyl)-5-oxopentanoic acid obtained in Reference Example 3, and the mixture was stirred at 120° C. for 1 hour. After the mixture was cooled to room temperature, water and ethyl acetate were added to the reaction mixture, and the resultant liquid mixture was separated. The obtained organic layer was sequentially washed with saturated aqueous sodium hydrogen carbonate solution and saturated brine, and was dried over sodium sulfate. The solvent was distilled off under reduced pressure, and the resultant solid was washed by the addition of a mixed solution of isopropyl ether and hexane. The title compound was obtained as a white solid weighing 2.40 g.

$^1$H-NMR(CDCl$_3$)δ:7.11-7.09(2H, m),6.96-6.92(3H,m), 6.76(1H,ddd,J=8.9,8.3, 2.8 Hz),6.49(1H,ddd,J=8.9,2.8,1.8 Hz),2.83-2.67(4H,m).

Step 2: Synthesis of 5-(2-chloro-3,5-difluorophenyl)-1-ethyl-6-(4-fluorophenyl)-3,4-dihydropyridin-2(1H)-one (Compound No. 11)

[Chem. 100]

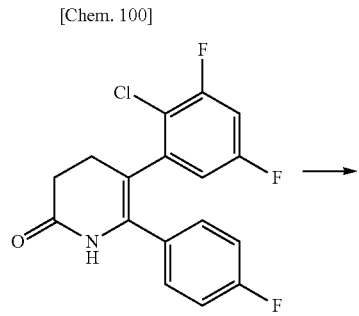

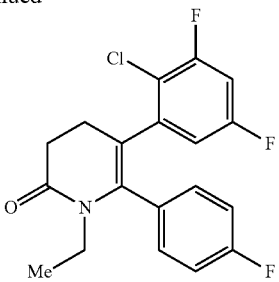

7 ml of DMF containing 700 mg of 5-(2-chloro-3,5-difluorophenyl)-6-(4-fluorophenyl)-3,4-dihydropyridin-2(1H)-one, 497 μl of ethyl iodide and 2.03 g of cesium carbonate was stirred at 80° C. for 2 hours. After the mixture was cooled to room temperature, water and ethyl acetate were added to the reaction mixture, and the resultant liquid mixture was separated. The obtained organic layer was sequentially washed with aqueous sodium thiosulfate solution and saturated brine, and was dried over sodium sulfate. The solvent was distilled off under reduced pressure, and the resultant residue was purified by silica gel column chromatography. The title compound was obtained as a light yellow solid weighing 644 mg.

Synthetic Example 2

Synthesis of 5-(2-chloro-3,5-difluorophenyl)-1-ethyl-6-(4-fluorophenyl)pyridin-2(1H)-one (Compound No. 12)

[Chem. 101]

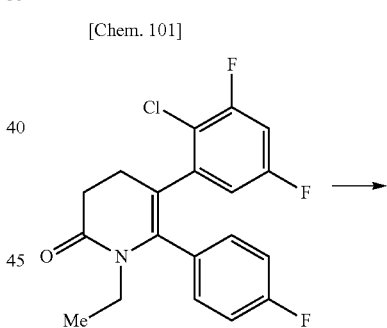

308 mg of N-bromosuccinimide and 27 mg of azobisisobutyronitrile were added to 12 ml of carbon tetrachloride solution containing 602 mg of 5-(2-chloro-3,5-difluorophenyl)-1-ethyl-6-(4-fluorophenyl)-3,4-dihydropyridin-2(1H)-one, and the mixture was stirred at 80° C. for 2 hours. After the mixture was cooled to room temperature, dichloromethane and aqueous sodium thiosulfate solution were added to the reaction mixture, and the resultant liquid mixture was separated. The obtained organic layer was washed with saturated brine and was dried over sodium sulfate. The solvent was distilled off under reduced pressure, and the resultant residue was purified by silica gel column chromatography. The title compound was obtained as a white solid weighing 541 mg.

Synthetic Example 3

Synthesis of 3-chloro-5-(2-chloro-3,5-difluorophenyl)-1-ethyl-6-(4-fluorophenyl)pyridin-2(1H)-one (Compound No. 13)

[Chem. 102]

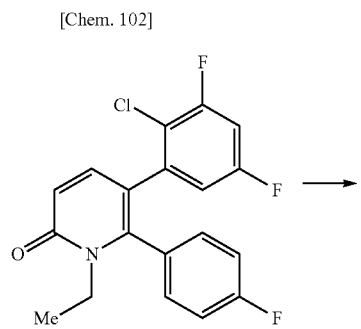

5 ml of DMF solution containing 200 mg of 5-(2-chloro-3,5-difluorophenyl)-1-ethyl-6-(4-fluorophenyl)pyridin-2(1H)-one and 88 mg of N-chlorosuccinimide was stirred at 80° C. for 2 hours. After the mixture was cooled to room temperature, water and ethyl acetate were added to the reaction mixture, and the resultant liquid mixture was separated. The obtained organic layer was sequentially washed with aqueous sodium thiosulfate solution and saturated brine, and was dried over sodium sulfate. The solvent was distilled off under reduced pressure, and the resultant residue was purified by silica gel column chromatography. The title compound was obtained as a white solid weighing 211 mg.

Synthetic Example 4

Synthesis of 5-(2-chloro-3,5-difluorophenyl)-1-(2,2-difluoroethyl)-6-(4-fluorophenyl)-3,4-dihydropyridin-2(1H)-one (Compound No. 29)

[Chem. 103]

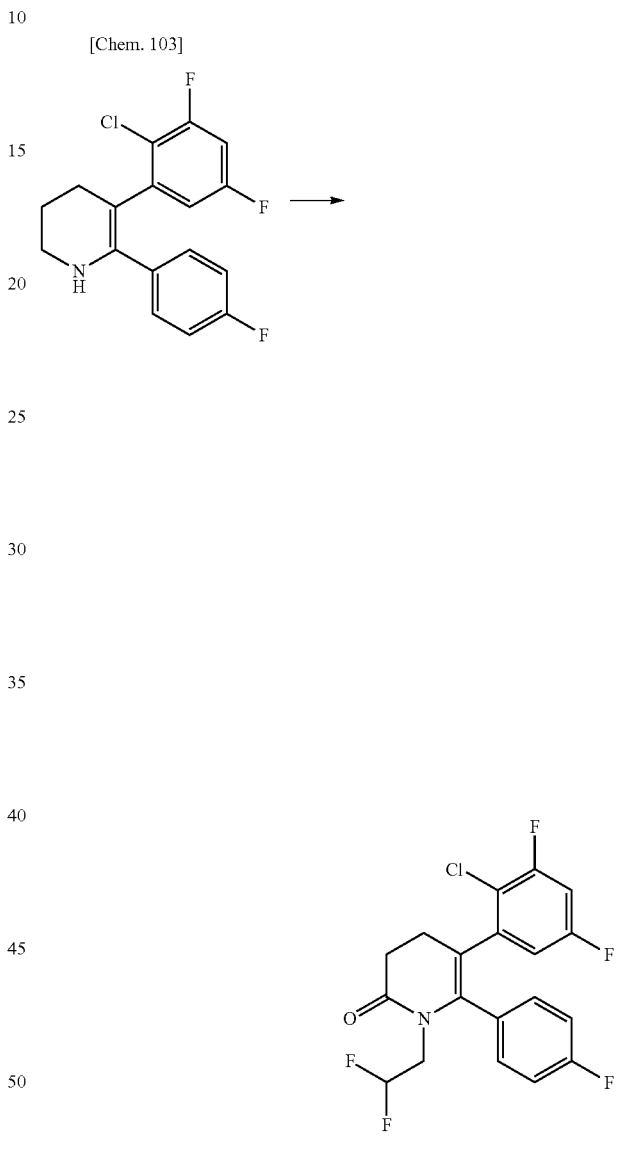

10 ml of DMF solution containing 600 mg of 5-(2-chloro-3,5-difluorophenyl)-6-(4-fluorophenyl)-3,4-dihydropyridin-2(1H)-one, 629 mg of 2,2-difluoroethyl p-toluenesulfonate and 1.74 g of cesium carbonate was stirred at 70° C. for 4 hours and was further stirred at 90° C. for 4 hours. After the mixture was cooled to room temperature, water and ethyl acetate were added to the reaction mixture, and the resultant liquid mixture was separated. The obtained organic layer was washed with saturated brine and dried over sodium sulfate. The solvent was distilled off under reduced pressure, and the resultant residue was purified by silica gel column chromatography. The title compound was obtained as a white solid weighing 542 mg.

Synthetic Example 5

Synthesis of 5-(2-chloro-3,5-difluorophenyl)-1-(2,2-difluoroethyl)-6-(4-fluorophenyl)pyridin-2(1H)-one (Compound No. 30)

[Chem. 104]

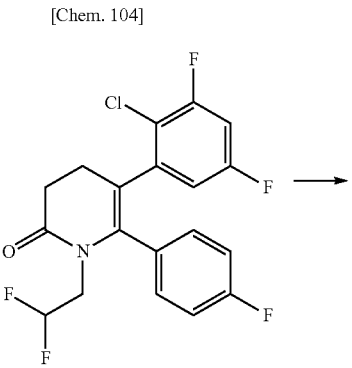

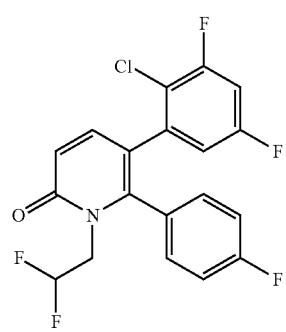

233 mg of N-bromosuccinimide and 20 mg of azobisisobutyronitrile were added to 10 ml of carbon tetrachloride solution containing 500 mg of 5-(2-chloro-3,5-difluorophenyl)-1-(2,2-difluoroethyl)-6-(4-fluorophenyl)-3,4-dihydropyridin-2(1H)-one, and the mixture was stirred at 85° C. for 3 hours. After the mixture was cooled to room temperature, dichloromethane and water were added to the reaction mixture, and the resultant liquid mixture was separated. The obtained organic layer was sequentially washed with aqueous sodium thiosulfate solution and saturated brine, and was dried over sodium sulfate. The solvent was distilled off under reduced pressure, and the resultant residue was purified by silica gel column chromatography. The title compound was obtained as a white solid weighing 380 mg.

Synthetic Example 6

Synthesis of 3-chloro-5-(2-chloro-3,5-difluorophenyl)-1-(2,2-difluoroethyl)-6-(4-fluorophenyl)pyridin-2(1H)-one (Compound No. 31)

[Chem. 105]

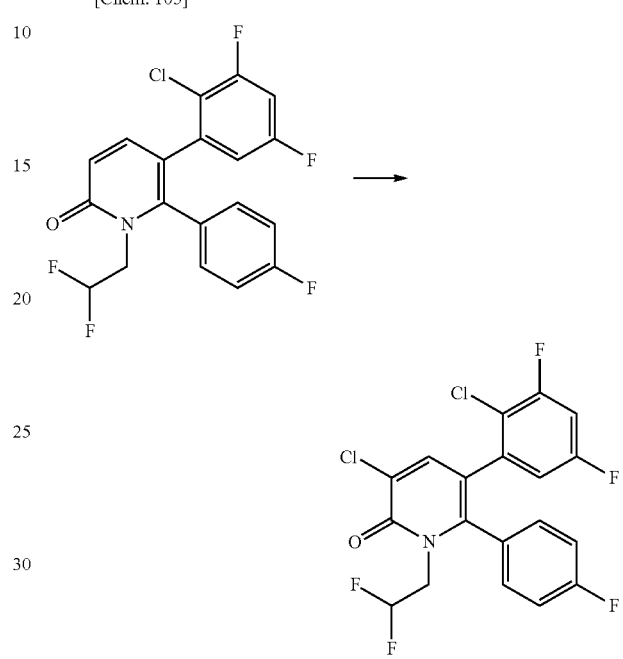

3 ml of DMF solution containing 150 mg of 5-(2-chloro-3,5-difluorophenyl)-1-(2,2-difluoroethyl)-6-(4-fluorophenyl)pyridin-2(1H)-one and 55 mg of N-chlorosuccinimide was stirred at 75° C. for 3 hours. After the mixture was cooled to room temperature, water and ethyl acetate were added to the reaction mixture, and the resultant liquid mixture was separated. The obtained organic layer was washed with saturated brine and was dried over sodium sulfate. The solvent was distilled off under reduced pressure, and the resultant residue was purified by silica gel column chromatography. The title compound was obtained as a white solid weighing 131 mg.

Synthetic Example 7

Synthesis of 3-bromo-5-(2-chloro-3,5-difluorophenyl)-1-ethyl-6-(4-fluorophenyl)pyridin-2(1H)-one (Compound No. 14)

[Chem. 106]

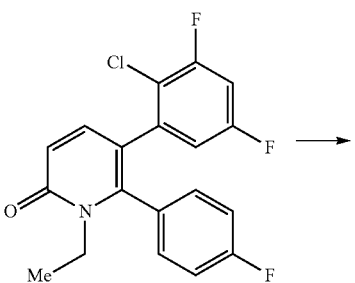

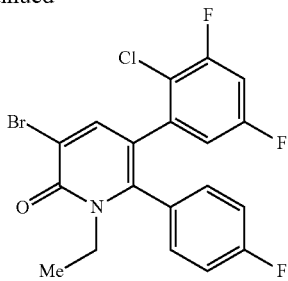

6 ml of DMF solution containing 235 mg of 5-(2-chloro-3,5-difluorophenyl)-1-ethyl-6-(4-fluorophenyl)pyridin-2(1H)-one and 127 mg of N-bromosuccinimide was stirred at 80° C. for 2 hours. After the mixture was cooled to room temperature, water and ethyl acetate were added to the reaction mixture, and the resultant liquid mixture was separated. The obtained organic layer was sequentially washed with aqueous sodium thiosulfate solution and saturated brine, and was dried over sodium sulfate. The solvent was distilled off under reduced pressure, and the resultant residue was purified by silica gel column chromatography. The title compound was obtained as a white solid weighing 252 mg.

Synthetic Example 8

5-(2-Chloro-3,5-difluorophenyl)-1-ethyl-6-(4-fluorophenyl)-3-methylpyridin-2(1H)-one (Compound No. 27)

[Chem. 107]

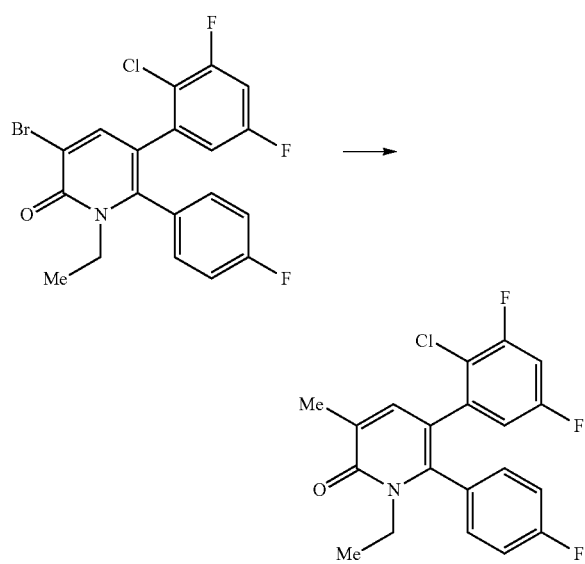

A solution of 125 mg 3-bromo-5-(2-chloro-3,5-difluorophenyl)-1-ethyl-6-(4-fluorophenyl)pyridin-2(1H)-one, 51 mg methylboronic acid, 3 mg palladium (II) acetate, 210 mg tripotassium phosphate and 8 mg tricyclohexylphosphine in a mixed solvent containing 5 ml toluene and 0.5 ml water was stirred at 90° C. for 8 hours. After the mixture was cooled to room temperature, water and ethyl acetate were added to the reaction mixture, and the resultant liquid mixture was separated. The obtained organic layer was washed with saturated brine, and was dried over sodium sulfate. The solvent was distilled off under reduced pressure, and the resultant residue was purified by silica gel column chromatography. The title compound was obtained as a light yellow solid weighing 66 mg.

Synthetic Example 9

Step 1: Synthesis of 5-(2-chloro-5-methoxyphenyl)-6-(4-fluorophenyl)-3,4-dihydropyridin-2(1H)-one

[Chem. 108]

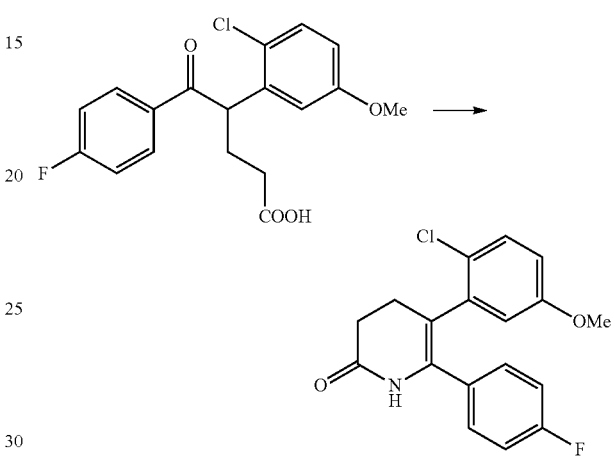

50 ml of acetic acid solution containing 8.62 g of 4-(2-chloro-5-methoxyphenyl)-5-(4-fluorophenyl)-5-oxopentanoic acid obtained in Reference Example 6 and 95.00 g of ammonium acetate was stirred at 130° C. for 2 hours. After the mixture was cooled to room temperature, ethyl acetate and water were added to the reaction mixture, and the resultant liquid mixture was separated. Water was added to the organic layer, and potassium carbonate was further added until the generation of bubbles stopped. Thereafter, the liquid mixture was separated. Next, the obtained organic layer was washed with saturated brine and was dried over sodium sulfate. The solvent was distilled off under reduced pressure, and the precipitate was washed with diisopropyl ether. The title compound was obtained as a gray solid weighing 5.25 g.

$^1$H-NMR(CDCl$_3$)δ:7.22(1H,d,J=8.6 Hz),7.14-7.10(2H,m),6.96(1H,brs),6.93-6.88(2H,m),6.67(1H,dd,J=8.6,3.1 Hz),6.44(1H,d,J=3.1 Hz),3.61(3H,s),2.98-2.53(4H,brm).

Step 2: Synthesis of 5-(2-chloro-5-methoxyphenyl)-1-ethyl-6-(4-fluorophenyl)-3,4-dihydropyridin-2(1H)-one

[Chem. 109]

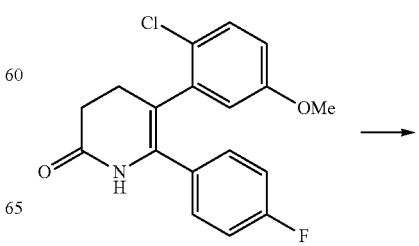

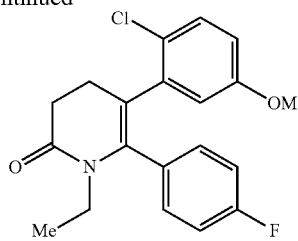

3.50 g of ethyl iodide and 7.37 g of cesium carbonate were added to 30 ml of DMF solution containing 2.50 g of 5-(2-chloro-5-methoxyphenyl)-6-(4-fluorophenyl)-3,4-dihydropyridin-2(1H)-one, and the mixture was stirred at 55° C. for 90 minutes. After the mixture was cooled to room temperature, water and ethyl acetate were added to the reaction mixture, and the resultant liquid mixture was separated. The obtained organic layer was sequentially washed with aqueous sodium thiosulfate solution and saturated brine, and was dried over sodium sulfate. The solvent was distilled off under reduced pressure, and the resultant residue was purified by silica gel column chromatography. The title compound was obtained as a light brown oil weighing 2.33 g.

$^1$H-NMR(CDCl$_3$)δ:7.19-7.04(3H,m),6.92-6.87(2H,brm), 6.60(1H,dd,J=8.8,2.9 Hz),6.36(1H,d,J=2.9 Hz),3.68-3.55 (4H,m),3.32-3.23(1H,m),2.90-2.63(3H,m),2.46-2.39(1H, m),0.96(3H,t,J=7.1 Hz).

Synthetic Example 10

Synthesis of 5-(2-chloro-5-methoxyphenyl)-1-ethyl-6-(4-fluorophenyl)pyridin-2(1H)-one (Compound No. 33)

[Chem. 110]

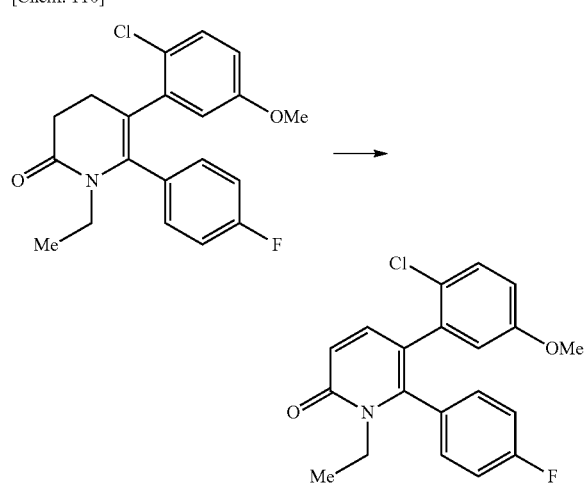

1.21 g of N-bromosuccinimide and 106 mg of azobisisobutyronitrile were added to 140 ml of carbon tetrachloride solution containing 2.33 g of 5-(2-chloro-5-methoxyphenyl)-1-ethyl-6-(4-fluorophenyl)-3,4-dihydropyridin-2 (1H)-one, and the mixture was stirred at 90° C. for 90 minutes. After the mixture was cooled to room temperature, aqueous sodium thiosulfate solution was added to the reaction mixture, and the resultant liquid mixture was separated. The obtained organic layer was combined with ethyl acetate, washed with saturated brine, and dried over sodium sulfate. The solvent was distilled off under reduced pressure, and the resultant residue was purified by silica gel column chromatography. The title compound was obtained as a white solid weighing 1.77 g.

Synthetic Example 11

3-Chloro-5-(2-chloro-5-methoxyphenyl)-1-ethyl-6-(4-fluorophenyl)pyridin-2(1H)-one (Compound No. 44)

[Chem. 111]

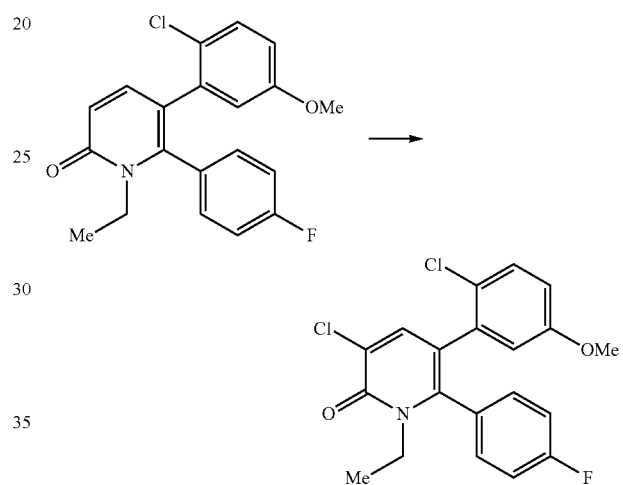

6 ml of DMF solution containing 0.30 g of 5-(2-chloro-5-methoxyphenyl)-1-ethyl-6-(4-fluorophenyl)pyridin-2 (1H)-one and 0.13 g of N-chlorosuccinimide was stirred at 75° C. for 2 hours. After the mixture was cooled to room temperature, water and ethyl acetate were added to the reaction mixture, and the resultant liquid mixture was separated. The obtained organic layer was washed with saturated brine, and was dried over sodium sulfate. The solvent was distilled off under reduced pressure, and the resultant residue was purified by silica gel column chromatography. The title compound was obtained as a white solid weighing 0.23 g.

[Synthetic Example 12] Synthesis of 3-chloro-5-(2-chloro-5-hydroxyphenyl)-1-ethyl-6-(4-fluorophenyl)pyridin-2(1H)-one (Compound No. 340)

[Chem. 112]

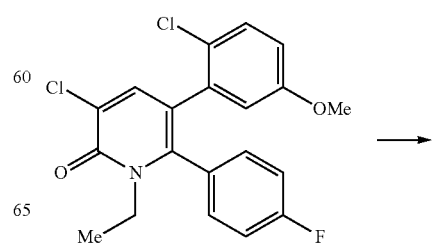

-continued

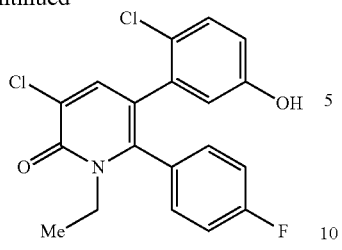

35 ml of dichloromethane solution containing 3.50 g of 3-chloro-5-(2-chloro-5-methoxyphenyl)-1-ethyl-6-(4-fluorophenyl)pyridin-2(1H)-one was cooled with ice, and 19.67 ml of 1.0 mol/l solution of boron tribromide in dichloromethane was added dropwise. The mixture was stirred for 2 hours while performing ice cooling. Thereafter, water and ethyl acetate were added to the reaction mixture, and the resultant liquid mixture was separated. The obtained organic layer was sequentially washed with saturated aqueous sodium hydrogen carbonate solution and saturated brine, and was dried over sodium sulfate. The solvent was distilled off under reduced pressure, and the precipitate was washed with a mixture of ethyl acetate and hexane (mixing ratio 1/3). The title compound was obtained as a white solid weighing 2.85 g.

Synthetic Example 13

Synthesis of 3-chloro-5-(2-chloro-5-(methoxymethoxy)phenyl)-1-ethyl-6-(4-fluorophenyl)pyridin-2(1H)-one (Compound No. 248)

[Chem. 113]

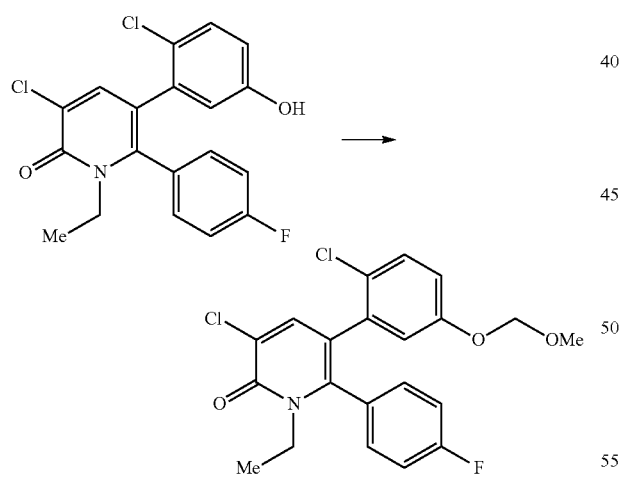

3 ml of acetonitrile solution containing 0.10 g of 3-chloro-5-(2-chloro-5-hydroxyphenyl)-1-ethyl-6-(4-fluorophenyl)pyridin-2(1H)-one, 0.17 g of cesium carbonate and 24 μl of chloromethyl methyl ether was stirred at 60° C. for 2 hours. After the mixture was cooled to room temperature, water and ethyl acetate were added to the reaction mixture, and the resultant liquid mixture was separated.

The obtained organic layer was washed with saturated brine and was dried over sodium sulfate. The solvent was distilled off under reduced pressure, and the resultant residue was purified by silica gel column chromatography. The title compound was obtained as a white solid weighing 0.11 g.

Synthetic Example 14

Synthesis of 2'-chloro-2-(4-fluorophenyl)-4,5-dihydro-[3,3'-bipyridin]-6(1H)-one

[Chem. 114]

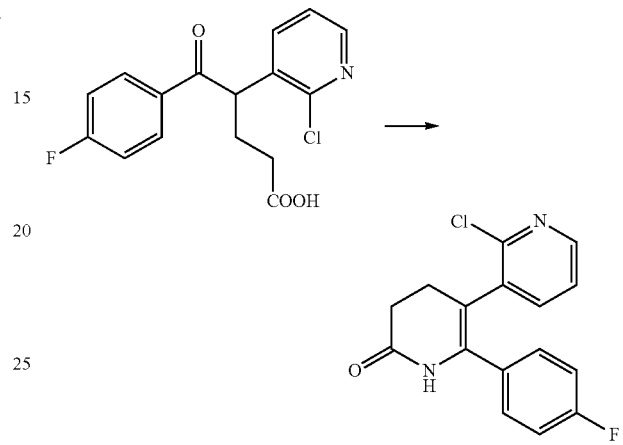

10 ml of acetic acid solution containing 1.16 g of 4-(2-chloropyridin-3-yl)-5-(4-fluorophenyl)-5-oxopentanoic acid obtained in Reference Example 9 and 13.90 g of ammonium acetate was stirred at 100° C. for 2 hours. After the mixture was cooled to room temperature, ethyl acetate and water were added to the reaction mixture, and the resultant liquid mixture was separated. Water was added to the obtained organic layer, and potassium carbonate was further added until the generation of bubbles stopped. Thereafter, the liquid mixture was separated. Next, the organic layer was washed with saturated brine and was dried over sodium sulfate. The solvent was distilled off under reduced pressure, and the precipitate was washed with diisopropyl ether. The brown solid obtained was identified to be the title compound, and the yield was 0.72 g.

$^1$H-NMR(CDCl$_3$)δ:8.23(1H,dd,J=4.7,2.0 Hz),7.21(1H,dd,J=7.6,2.0 Hz),7.13-7.09(3H,m),7.02(1H,dd,J=7.6,4.7 Hz),6.94-6.89(2H,m),3.02(1H,brs),2.81-2.66(2H,brm),2.57 (1H,brs).

Synthetic Example 15

Synthesis of 2'-chloro-1-ethyl-2-(4-fluorophenyl)-4,5-dihydro-[3,3'-bipyridin]-6(1H)-one

[Chem. 115]

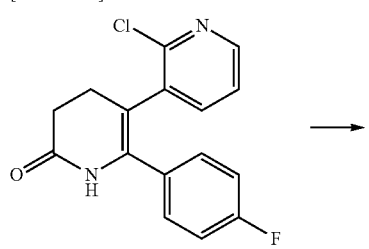

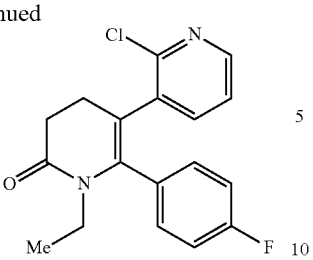

282 µl of ethyl iodide and 1.16 g of cesium carbonate were added to 5 ml of DMF solution containing 0.36 g of 2'-chloro-2-(4-fluorophenyl)-4,5-dihydro-[3,3'-bipyridin]-6(1H)-one, and the mixture was stirred at 60° C. for 1 hour. After the mixture was cooled to room temperature, water and ethyl acetate were added to the reaction mixture, and the resultant liquid mixture was separated. The obtained organic layer was washed with saturated brine and was dried over sodium sulfate. The solvent was distilled off under reduced pressure, and the resultant residue was purified by silica gel column chromatography. The title compound was obtained as a white oil weighing 0.33 g.

$^1$H-NMR(CDCl$_3$)δ:8.15(1H,dd,J=4.7,2.0 Hz),7.14(1H,dd,J=7.4,2.0 Hz),7.12-7.06(2H,brm),6.96(1H,dd,J=7.4,4.7 Hz),6.94-6.88(2H,brm),3.70-3.63(1H,m),3.29-3.22(1H,m),2.94-2.87(1H,m),2.82-2.76(1H,m),2.72-2.66(1H,m),2.46-2.40(1H,m),0.97(3H,t,J=7.0 Hz).

Synthetic Example 16

Synthesis of 2'-chloro-1-ethyl-2-(4-fluorophenyl)-[3,3'-bipyridin]-6(1H)-one (Compound No. 288)

[Chem. 116]

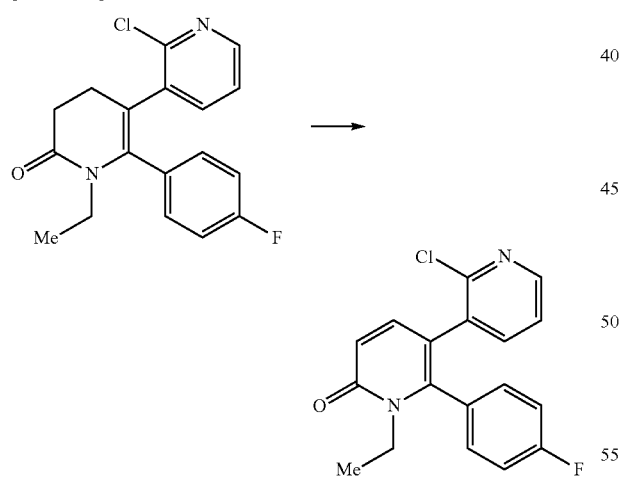

0.19 g of N-bromosuccinimide and 16 mg of azobisisobutyronitrile were added to 10 ml of carbon tetrachloride solution containing 0.33 g of 2'-chloro-1-ethyl-2-(4-fluorophenyl)-4,5-dihydro-[3,3'-bipyridin]-6(1H)-one, and the mixture was stirred at 80° C. for 2 hours. After the mixture was cooled to room temperature, ethyl acetate and aqueous sodium thiosulfate solution were added to the reaction mixture, and the resultant liquid mixture was separated. The obtained organic layer was washed with saturated brine and was dried over sodium sulfate. The solvent was distilled off under reduced pressure, and the resultant residue was purified by silica gel column chromatography. The title compound was obtained as a white solid weighing 0.20 g.

Synthetic Example 17

Synthesis of 2',5-dichloro-1-ethyl-2-(4-fluorophenyl)-[3,3'-bipyridin]-6(1H)-one (Compound No. 291)

[Chem. 117]

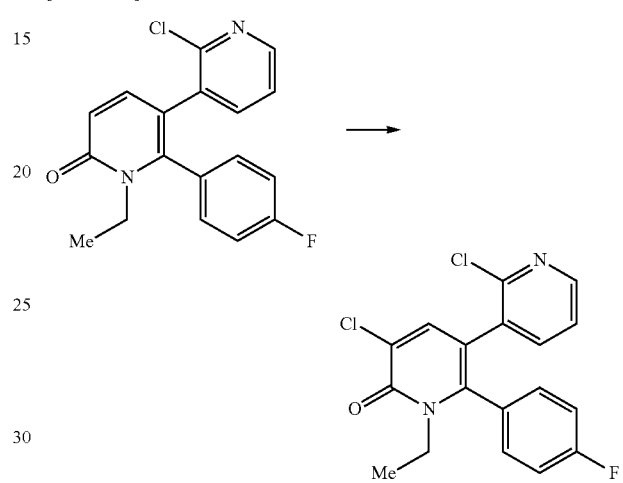

5 ml of DMF solution containing 164 mg of 2'-chloro-1-ethyl-2-(4-fluorophenyl)-[3,3'-bipyridin]-6(1H)-one and 80 mg of N-chlorosuccinimide was stirred at 60° C. for 13 hours. After the mixture was cooled to room temperature, water and ethyl acetate were added to the reaction mixture, and the resultant liquid mixture was separated. The obtained organic layer was washed with saturated brine and was dried over sodium sulfate. The solvent was distilled off under reduced pressure, and the resultant residue was purified by silica gel column chromatography. The title compound was obtained as a white solid weighing 151 mg.

Reference Example 1

Synthesis of 2-(2-chloro-3,5-difluorophenyl)-1-(4-fluorophenyl)ethan-1-one

[Chem. 118]

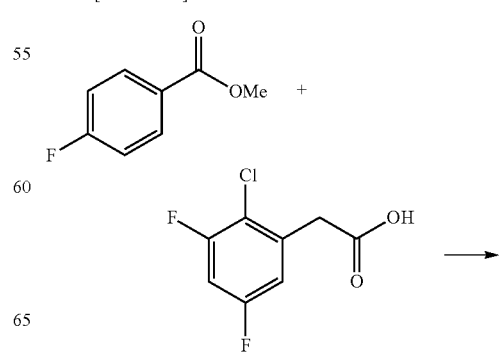

-continued

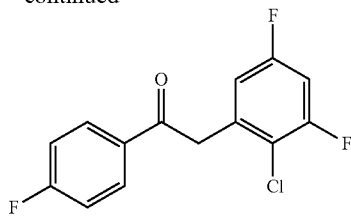

At −78° C., 16.4 ml of 1.9 mol/L solution of hexamethyldisilazane sodium in THF was added dropwise to 50 ml of THF solution containing 2.00 g of 2-(2-chloro-3,5-difluorophenyl)acetic acid, and the mixture was stirred for 10 minutes. Next, 1.50 g of methyl p-fluorobenzoate was added dropwise, and the mixture was brought from −78° C. to ice-cooled conditions and was stirred for 30 minutes. Saturated aqueous ammonium chloride solution was added thereto, and the mixture was stirred. Thereafter, ethyl acetate was added, and the resultant liquid mixture was separated. The obtained organic layer was washed with saturated brine and was dried over sodium sulfate. The solvent was distilled off under reduced pressure, and 2.60 g of a light yellow solid including the title compound was obtained. This product was used for the next reaction without further purification.

$^1$H-NMR(CDCl$_3$)δ:8.08-8.04(2H,m),7.20-7.18(2H,m), 6.89(1H,td,J=8.6,2.8 Hz),6.85(1H,ddd,J=8.6,2.8,1.8 Hz), 4.42(2H,s).

Reference Example 2

Synthesis of ethyl 4-(2-chloro-3,5-difluorophenyl)-5-(4-fluorophenyl)-5-oxopentanoate

[Chem. 119]

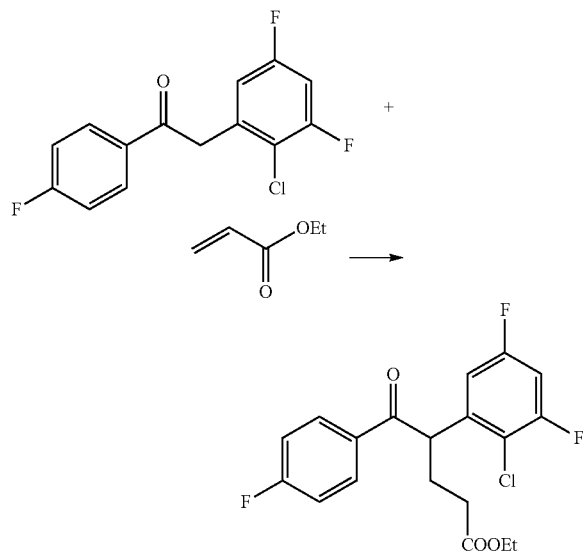

103 mg of potassium t-butoxide and 1.09 ml of ethyl acrylate were added to 40 ml of THF solution containing 2.60 g of 2-(2-chloro-3,5-difluorophenyl)-1-(4-fluorophenyl)ethan-1-one obtained in Reference Example 1, and the mixture was stirred for 4 hours while performing cooling with ice. Saturated ammonium chloride solution and ethyl acetate were added thereto, and the resultant liquid mixture was separated. The obtained organic layer was washed with saturated brine and was dried over sodium sulfate. The solvent was distilled off under reduced pressure. Thus, 3.37 g of a yellow oil including the title compound was obtained. This product was used for the next reaction without further purification.

$^1$H-NMR(CDCl$_3$)δ:8.00-7.97(2H,m),7.13-7.09(2H,m), 6.83-6.82(2H,m),5.21(1H,td,J=7.2,1.0 Hz),4.13(2H,q,J=7.2 Hz),2.47-2.27(3H,m),2.09-2.07(1H,m),1.24(3H,t,J=7.2 Hz).

Reference Example 3

Synthesis of 4-(2-chloro-3,5-difluorophenyl)-5-(4-fluorophenyl)-5-oxopentanoic acid

[Chem. 120]

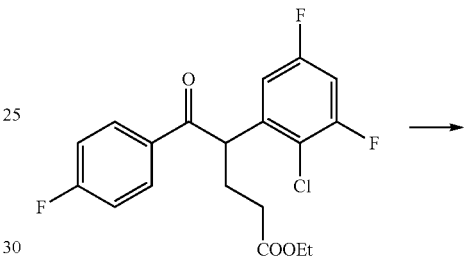

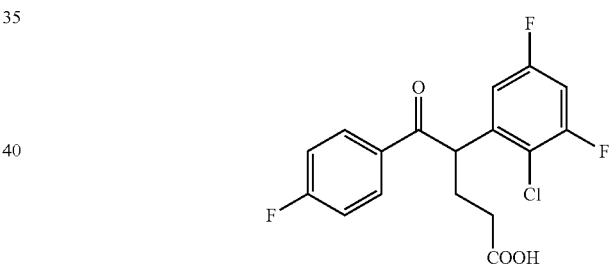

1.84 g of lithium hydroxide monohydrate was added to a solution of 3.37 g ethyl 4-(2-chloro-3,5-difluorophenyl)-5-(4-fluorophenyl)-5-oxopentanoate obtained in Reference Example 2 in a mixed solvent containing 20 ml THF and 10 ml water. The mixture was stirred at 70° C. for 1.5 hours. After the mixture was cooled to room temperature, the solvent of the reaction mixture was distilled off to approximately half volume. Water and diethyl ether were added thereto, and the resultant liquid mixture was separated. Concentrated hydrochloric acid and ethyl acetate were added to the obtained aqueous layer, and the resultant liquid mixture was separated. The organic layer thus obtained was washed with saturated brine and was dried over sodium sulfate. Next, the solvent was distilled off under reduced pressure. Thus, 3.30 g of a yellow gum including the title compound was obtained. This product was used for the next reaction without further purification.

$^1$H-NMR(CDCl$_3$)δ:7.97-7.96(2H,m),7.12-7.08(2H,m), 6.85-6.78(2H,m),5.19-5.18(1H,m),2.48-2.36(3H,m),2.09-2.06(2H,m).

Reference Example 4

Step 1: Synthesis of 1-(4-fluorophenyl)-2-(3-methoxyphenyl)ethan-1-one

[Chem. 121]

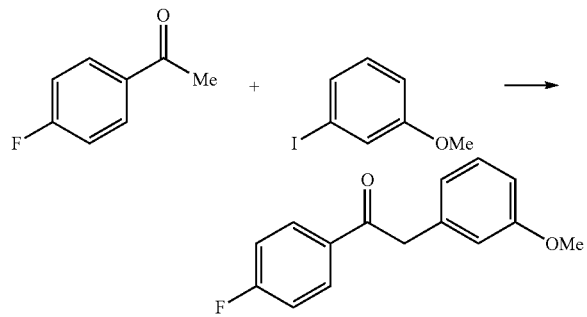

0.66 g of palladium (II) acetate, 3.42 g of xantphos (4,5'-bis(diphenylphosphino)-9,9'-dimethylxanthene), 9.00 g of 4'-fluoroacetophenone and 8.63 g of potassium t-butoxide were sequentially added to 100 ml of toluene solution containing 13.84 g of 1-iodo-3-methoxybenzene, and the mixture was stirred at room temperature for 90 minutes. Saturated aqueous ammonium chloride solution was added to the reaction mixture, and the resultant mixture was filtered through Celite. Ethyl acetate was added to the filtrate, and the resultant liquid mixture was separated. Thereafter, the obtained organic layer was sequentially washed with water and saturated brine, and was dried over sodium sulfate. The solvent was distilled off under reduced pressure, and the resultant residue was purified by silica gel column chromatography. The title compound was obtained as a white solid weighing 9.81 g.

$^1$H-NMR(CDCl$_3$)δ:8.05-8.01(2H,m),7.25-7.23(1H,m), 7.15-7.10(2H,m),6.85-6.83(1H,m),6.82-6.79(2H,m),4.23 (2H,s),3.79(3H,s).

Step 2: Synthesis of 2-(2-chloro-5-methoxyphenyl)-1-(4-fluorophenyl)ethan-1-one

[Chem. 122]

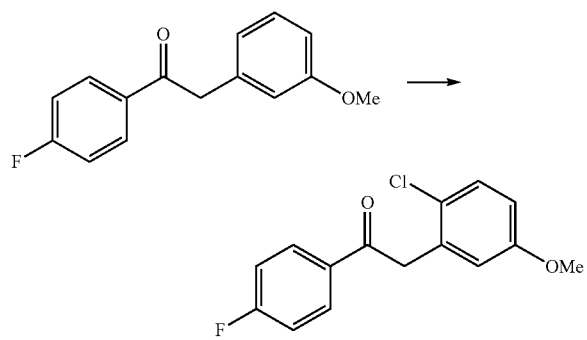

110 ml of DMF solution containing 9.81 g of 1-(4-fluorophenyl)-2-(3-methoxyphenyl)ethan-1-one and 6.40 g of N-chlorosuccinimide was stirred at 75° C. for 2 hours. After the mixture was cooled to room temperature, ethyl acetate and water were added to the reaction mixture, and the resultant liquid mixture was separated. The obtained organic layer was sequentially washed with water and saturated brine, and was dried over sodium sulfate. The solvent was distilled off under reduced pressure, and the precipitate was washed with hexane. The title compound was obtained as a white solid weighing 7.15 g.

$^1$H-NMR(CDCl$_3$)δ:8.09-8.05(2H,m),7.32-7.30(1H,m), 7.18-7.13(2H,m),6.81-6.77(2H,m),4.36(2H,s),3.77(3H,s).

Reference Example 5

Synthesis of ethyl 4-(2-chloro-5-methoxyphenyl)-5-(4-fluorophenyl)-5-oxopentanoate

[Chem. 123]

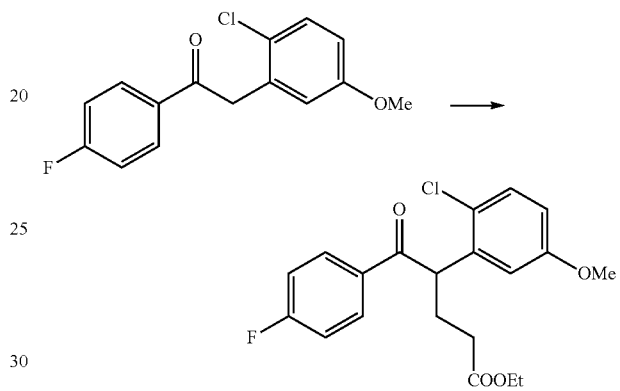

While performing cooling with ice, 0.43 g of potassium t-butoxide and 2.80 g of ethyl acrylate were added to 80 ml of THF solution containing 7.13 g of 2-(2-chloro-5-methoxyphenyl)-1-(4-fluorophenyl)ethan-1-one, and the mixture was stirred for 1 hour. The reaction mixture was brought to room temperature and was stirred for 5.5 hours. 1 N hydrochloric acid and ethyl acetate were added thereto, and the resultant liquid mixture was separated. The obtained organic layer was sequentially washed with saturated aqueous sodium hydrogen carbonate solution and saturated brine, and was dried over sodium sulfate. The solvent was distilled off under reduced pressure. Thus, 9.66 g of an orange oil including the title compound was obtained. This product was used for the next reaction without further purification.

$^1$H-NMR(CDCl$_3$)δ:8.01-7.96(2H,m),7.31(1H,dd,J=8.3, 0.5 Hz),7.09-7.03(2H,m), 6.73-6.68(2H,m),5.10-5.07(1H, m),4.15-4.09(2H,m),3.70(3H,s),2.48-2.24(3H-m),2.14-2.05 (1H,m),1.25-1.22(3H,m).

Reference Example 6

Synthesis of 4-(2-chloro-5-methoxyphenyl)-5-(4-fluorophenyl)-5-oxopentanoic acid

[Chem. 124]

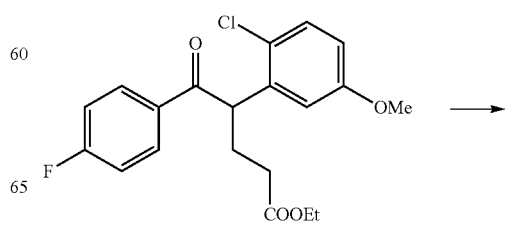

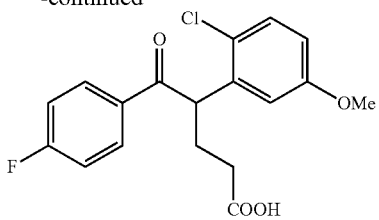

5.30 g of lithium hydroxide monohydrate was added to a solution of 9.66 g ethyl 4-(2-chloro-5-methoxyphenyl)-5-(4-fluorophenyl)-5-oxopentanoate obtained in Reference Example 5 in a mixed solvent containing 100 ml THF and 50 ml water, and the mixture was stirred at 60° C. for 2 hours. After the mixture was cooled to room temperature, the solvent of the reaction mixture was distilled off to approximately half volume. Water and diethyl ether were added to the reaction mixture, and the resultant liquid mixture was separated. Concentrated hydrochloric acid and ethyl acetate were added to the obtained aqueous layer, and the resultant liquid mixture was separated. The organic layer thus obtained was washed with saturated brine and was dried over sodium sulfate. Next, the solvent was distilled off under reduced pressure. Thus, 8.62 g of a yellow gum including the title compound was obtained. This product was used for the next reaction without further purification.

$^1$H-NMR(CDCl$_3$)δ:7.99-7.94(2H,m),7.32(1H,d,J=8.6 Hz),7.08-7.04(2H,m),6.72(1H,dd,J=8.6,3.1 Hz),6.67(1H,d, J=3.1 Hz),5.09-5.06(1H,m),3.69(3H,s),2.47-2.40(2H,m), 2.38-2.30(1H,m),2.14-2.08(1H,m).

Reference Example 7

Synthesis of 2-(2-chloropyridin-3-yl)-1-(4-fluoro-phenyl)ethan-1-one

[Chem. 125]

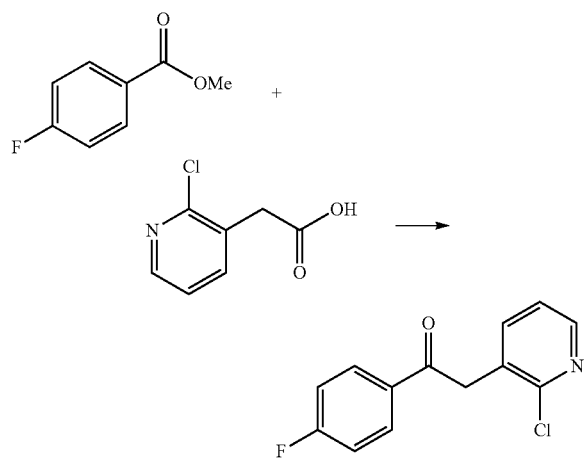

At −78° C., 19.6 ml of 1.9 mol/L solution of hexamethyldisilazane sodium in THF was added dropwise to 100 ml of THF solution containing 2.00 g of 2-(2-chloropyridin-3-yl)acetic acid, and the mixture was stirred for 10 minutes. Next, 1.50 ml of methyl p-fluorobenzoate was added dropwise. The mixture was then brought from −78° C. to room temperature and was stirred for 1 hour. Saturated aqueous ammonium chloride solution was added thereto, and the mixture was stirred.

Thereafter, ethyl acetate was added, and the resultant liquid mixture was separated. The obtained organic layer was washed with saturated brine and was dried over sodium sulfate. The solvent was distilled off under reduced pressure, and the resultant residue was purified by silica gel column chromatography. The title compound was obtained as a colorless amorphous compound weighing 1.45 g.

$^1$H-NMR(CDCl$_3$)δ:8.36(1H,dd,J=4.6,1.9 Hz),8.11-8.07 (2H,m),7.62(1H,dd,J=7.4,1.9 Hz),7.27-7.24(1H,m),7.21-7.17(2H,m),4.42(2H,s).

Reference Example 8

Synthesis of ethyl 4-(2-chloropyridin-3-yl)-5-(4-fluorophenyl)-5-oxopentanoate

[Chem. 126]

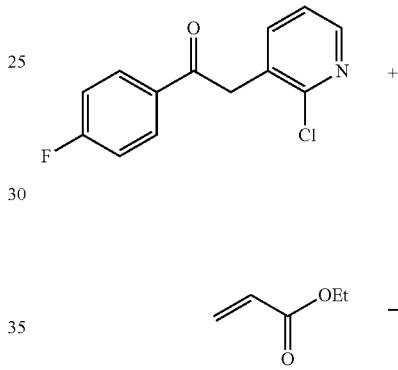

94 mg of potassium t-butoxide and 638 μl of ethyl acrylate were added to 28 ml of THF solution containing 1.40 g of 2-(2-chloro-3,5-difluorophenyl)-1-(4-fluorophenyl)ethan-1-one obtained in Reference Example 7, and the mixture was stirred for 4 hours while performing cooling with ice. 1 N hydrochloric acid and ethyl acetate were added thereto, and the resultant liquid mixture was separated. The obtained organic layer was washed with saturated brine, and was dried over sodium sulfate. The solvent was distilled off under reduced pressure. Thus, 1.60 g of a yellow oil including the title compound was obtained. This product was used for the next reaction without further purification.

$^1$H-NMR(CDCl$_3$)δ:8.30(1H,dd,J=4.6,2.0 Hz),8.07-8.02 (2H,m),7.64(1H,dd,J=7.8,2.0 Hz),7.20(1H,dd,J=7.8,4.6 Hz),7.14-7.08(2H,m),5.19(1H,t,J=7.3 Hz),4.15-4.10(2H,m), 2.52-2.28(3H,m),2.16-2.07(1H,m),1.26-1.21(3H,m).

Reference Example 9

Synthesis of 4-(2-chloropyridin-3-yl)-5-(4-fluorophenyl)-5-oxopentanoic acid

[Chem. 127]

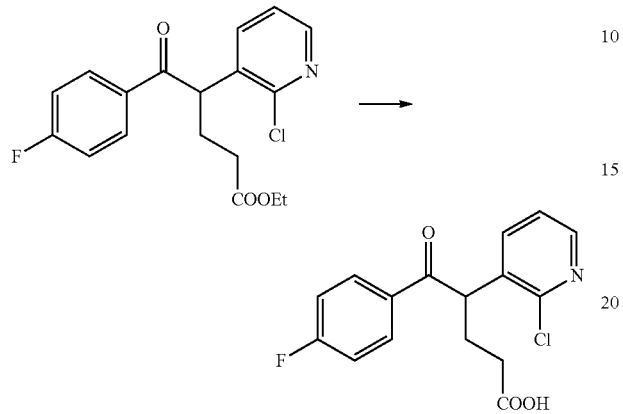

0.90 g of lithium hydroxide monohydrate was added to a solution of 1.50 g ethyl 4-(2-chloropyridin-3-yl)-5-(4-fluorophenyl)-5-oxopentanoate obtained in Reference Example 8 in a mixed solvent containing 25 ml THF and 25 ml water, and the mixture was stirred at 60° C. for 1 hour. After the mixture was cooled to room temperature, the solvent of the reaction mixture was distilled off to approximately half volume. Water and diethyl ether were added to the reaction mixture, and the resultant liquid mixture was separated. Concentrated hydrochloric acid and ethyl acetate were added to the obtained aqueous layer, and the resultant liquid mixture was separated. The organic layer thus obtained was washed with saturated brine, and was dried over sodium sulfate. Next, the solvent was distilled off under reduced pressure. Thus, 1.16 g of a yellow gum including the title compound was obtained. This product was used for the next reaction without further purification.

$^1$H-NMR(CDCl$_3$)δ:8.31(1H,dd,J=4.6,2.0 Hz),8.03-8.01 (2H,m),7.61(1H,dd,J=7.8,2.0 Hz),7.20(1H,dd,J=7.8,4.6 Hz),7.13-7.10(2H,m),5.18(1H,t,J=7.2 Hz),2.50-2.37(3H,m), 2.17-2.11(1H,m).

Table 4 lists compounds synthesized in accordance with Examples described hereinabove. The compounds according to the present invention are not limited thereto.

In Table 4, Structure A is the following.

[Chem. 128]

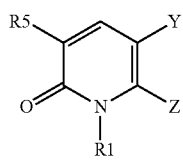

In Table 4, Structure B is the following.

[Chem. 129]

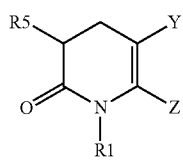

In Table 4, Structure C is the following.

[Chem. 130]

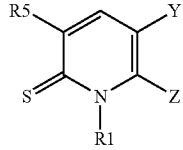

In Table 4, Structure D is the following.

[Chem. 131]

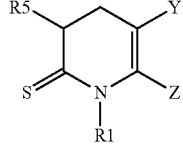

TABLE 4

| Compound | Structure | R1 | Z | Y | R5 |
|---|---|---|---|---|---|
| 1 | A | Me | Ph | 2-Br-3,5-di-MeO—Ph | H |
| 2 | A | Me | Ph | 2-Cl-3,5-di-MeO—Ph | H |
| 3 | A | Et | Ph | 2-Br-3,5-di-MeO—Ph | H |
| 4 | A | Et | Ph | 2-Cl-3,5-di-MeO—Ph | H |
| 5 | A | Et | 4-F—Ph | 2-Cl-5-F—Ph | H |
| 6 | A | Et | 4-F—Ph | 2-Cl-5-F—Ph | Cl |
| 7 | A | Et | 4-F—Ph | 2-Cl-5-F—Ph | Br |
| 8 | A | Me | 4-F—Ph | 2-Cl-5-F—Ph | H |
| 9 | A | Me | 4-F—Ph | 2-Cl-5-F—Ph | Cl |
| 10 | A | Me | 4-F—Ph | 2-Cl-5-F—Ph | Br |
| 11 | B | Et | 4-F—Ph | 2-Cl-3,5-di-F—Ph | H |
| 12 | A | Et | 4-F—Ph | 2-Cl-3,5-di-F—Ph | H |
| 13 | A | Et | 4-F—Ph | 2-Cl-3,5-di-F—Ph | Cl |
| 14 | A | Et | 4-F—Ph | 2-Cl-3,5-di-F—Ph | Br |
| 15 | B | Et | Ph | 2-Cl-3,5-di-F—Ph | H |
| 16 | A | Et | Ph | 2-Cl-3,5-di-F—Ph | H |

TABLE 4-continued

| Compound | Structure | R1 | Z | Y | R5 |
|---|---|---|---|---|---|
| 17 | A | Et | Ph | 2-Cl-3,5-di-F—Ph | Cl |
| 18 | A | Et | Ph | 2-Cl-3,5-di-F—Ph | Br |
| 19 | B | Me | Ph | 2-Cl-3,5-di-F—Ph | H |
| 20 | A | Me | Ph | 2-Cl-3,5-di-F—Ph | H |
| 21 | A | Me | Ph | 2-Cl-3,5-di-F—Ph | Cl |
| 22 | A | Me | Ph | 2-Cl-3,5-di-F—Ph | Br |
| 23 | B | Me | 4-F—Ph | 2-Cl-3,5-di-F—Ph | H |
| 24 | A | Me | 4-F—Ph | 2-Cl-3,5-di-F—Ph | H |
| 25 | A | Me | 4-F—Ph | 2-Cl-3,5-di-F—Ph | Cl |
| 26 | A | Me | 4-F—Ph | 2-Cl-3,5-di-F—Ph | Br |
| 27 | A | Et | 4-F—Ph | 2-Cl-3,5-di-F—Ph | Me |
| 28 | A | Et | 4-MeO—Ph | 2-Cl-3,5-di-F—Ph | H |
| 29 | B | F2CHCH2 | 4-F—Ph | 2-Cl-3,5-di-F—Ph | H |
| 30 | A | F2CHCH2 | 4-F—Ph | 2-Cl-3,5-di-F—Ph | H |
| 31 | A | F2CHCH2 | 4-F—Ph | 2-Cl-3,5-di-F—Ph | Cl |
| 32 | A | F2CHCH2 | 4-F—Ph | 2-Cl-3,5-di-F—Ph | Br |
| 33 | A | Et | 4-F—Ph | 2-Cl-5-MeO—Ph | H |
| 34 | A | Me | 4-F—Ph | 2-Cl-5-MeO—Ph | H |
| 35 | A | Et | 4-MeO—Ph | 2-Cl-3,5-di-F—Ph | Cl |
| 36 | A | Et | 4-MeO—Ph | 2-Cl-3,5-di-F—Ph | Br |
| 37 | A | Me | 4-MeO—Ph | 2-Cl-3,5-di-F—Ph | H |
| 38 | A | Me | 4-MeO—Ph | 2-Cl-3,5-di-F—Ph | Cl |
| 39 | A | Me | 4-MeO—Ph | 2-Cl-3,5-di-F—Ph | Br |
| 40 | A | Et | 4-MeO—Ph | 2-Cl-5-F—Ph | H |
| 41 | A | Et | 4-MeO—Ph | 2-Cl-5-F—Ph | Br |
| 42 | D | Et | 4-F—Ph | 2-Cl-3,5-di-F—Ph | H |
| 43 | C | Et | 4-F—Ph | 2-Cl-3,5-di-F—Ph | H |
| 44 | A | Et | 4-F—Ph | 2-Cl-5-MeO—Ph | Cl |
| 45 | A | Me | 4-F—Ph | 2-Cl-5-MeO—Ph | Cl |
| 46 | A | Et | 4-F—Ph | 2-Cl-5-MeO—Ph | Br |
| 47 | A | Me | 4-F—Ph | 2-Cl-5-MeO—Ph | Br |
| 48 | A | Et | 4-F—Ph | 2-Cl-3-F—Ph | H |
| 49 | A | Et | 4-F—Ph | 2-Cl-3-F—Ph | Cl |
| 50 | A | Et | 4-MeO—Ph | 2-Cl-5-F—Ph | Cl |
| 51 | A | Me | 4-MeO—Ph | 2-Cl-5-F—Ph | H |
| 52 | A | Me | 4-MeO—Ph | 2-Cl-5-F—Ph | Cl |
| 53 | A | Me | 4-MeO—Ph | 2-Cl-5-F—Ph | Br |
| 54 | A | Et | 4-MeO—Ph | 2-Cl-3-F—Ph | H |
| 55 | A | Et | 4-MeO—Ph | 2-Cl-3-F—Ph | Cl |
| 56 | B | F2CHCH2 | Ph | 2-Cl-3,5-di-F—Ph | H |
| 57 | A | Et | 4-F—Ph | 2-Cl-3-F—Ph | Br |
| 58 | A | Me | 4-F—Ph | 2-Cl-3-F—Ph | H |
| 59 | A | Me | 4-F—Ph | 2-Cl-3-F—Ph | Cl |
| 60 | A | Me | 4-F—Ph | 2-Cl-3-F—Ph | Br |
| 61 | A | Et | 4-MeO—Ph | 2-Cl-3-F—Ph | Br |
| 62 | A | Me | 4-MeO—Ph | 2-Cl-3-F—Ph | H |
| 63 | A | Me | 4-MeO—Ph | 2-Cl-3-F—Ph | Cl |
| 64 | A | Me | 4-MeO—Ph | 2-Cl-3-F—Ph | Br |
| 65 | B | Et | 4-F—Ph | 2,3,5-tri-F—Ph | H |
| 66 | A | Et | 4-F—Ph | 2,3,5-tri-F—Ph | H |
| 67 | A | Et | 4-F—Ph | 2,3,5-tri-F—Ph | Cl |
| 68 | A | Et | 4-F—Ph | 2,3,5-tri-F—Ph | Br |
| 69 | A | F2CHCH2 | Ph | 2-Cl-3,5-di-F—Ph | H |
| 70 | A | F2CHCH2 | Ph | 2-Cl-3,5-di-F—Ph | Br |
| 71 | A | F2CHCH2 | Ph | 2-Cl-3,5-di-F—Ph | Cl |
| 72 | A | Et | 4-MeO—Ph | 2-Cl-5-MeO—Ph | H |
| 73 | A | Et | 4-MeO—Ph | 2-Cl-5-MeO—Ph | Cl |
| 74 | A | Et | 4-MeO—Ph | 2-Cl-5-MeO—Ph | Br |
| 75 | A | Me | 4-MeO—Ph | 2-Cl-5-MeO—Ph | H |
| 76 | A | Me | 4-MeO—Ph | 2-Cl-5-MeO—Ph | Cl |
| 77 | A | Me | 4-MeO—Ph | 2-Cl-5-MeO—Ph | Br |
| 78 | A | Et | Ph | 2-Cl-5-F—Ph | H |
| 79 | A | Et | Ph | 2-Cl-5-F—Ph | Cl |
| 80 | A | Et | Ph | 2-Cl-5-F—Ph | Br |
| 81 | A | Me | Ph | 2-Cl-5-F—Ph | H |
| 82 | A | Me | Ph | 2-Cl-5-F—Ph | Cl |
| 83 | A | Me | Ph | 2-Cl-5-F—Ph | Br |
| 84 | A | Et | Ph | 2-Cl-5-MeO—Ph | H |
| 85 | A | Et | Ph | 2-Cl-5-MeO—Ph | Cl |
| 86 | A | Et | Ph | 2-Cl-5-MeO—Ph | Br |
| 87 | A | Et | Ph | 2-Cl-3-F—Ph | H |
| 88 | A | Et | Ph | 2-Cl-3-F—Ph | Cl |
| 89 | A | Et | Ph | 2-Cl-3-F—Ph | Br |
| 90 | A | Me | Ph | 2-Cl-5-MeO—Ph | H |
| 91 | A | Me | Ph | 2-Cl-5-MeO—Ph | Cl |
| 92 | A | Me | Ph | 2-Cl-5-MeO—Ph | Br |
| 93 | A | Me | Ph | 2-Cl-3-F—Ph | H |
| 94 | A | Et | 4-F—Ph | 2-Cl-3-MeO—Ph | H |

TABLE 4-continued

| Compound | Structure | R1 | Z | Y | R5 |
|---|---|---|---|---|---|
| 95 | A | Et | 4-F—Ph | 2-Cl-3-MeO—Ph | Br |
| 96 | A | Et | 4-F—Ph | 2-Cl-3-MeO—Ph | Cl |
| 97 | A | Me | Ph | 2-Cl-3-F—Ph | Cl |
| 98 | A | Me | Ph | 2-Cl-3-F—Ph | Br |
| 99 | A | Me | 4-F—Ph | 2-Cl-3-MeO—Ph | H |
| 100 | A | Me | 4-F—Ph | 2-Cl-3-MeO—Ph | Br |
| 101 | A | Me | 4-F—Ph | 2-Cl-3-MeO—Ph | Cl |
| 102 | A | Et | 4-MeO—Ph | 2-Cl-3,5-di-MeO—Ph | H |
| 103 | A | Me | 4-MeO—Ph | 2-Cl-3,5-di-MeO—Ph | H |
| 104 | A | Et | Ph | 2-Cl-3-MeO—Ph | H |
| 105 | A | Et | Ph | 2-Cl-3-MeO—Ph | Br |
| 106 | A | Me | Ph | 2-Cl-3-MeO—Ph | Br |
| 107 | A | Et | Ph | 2-Cl-3-MeO—Ph | Cl |
| 108 | A | Me | Ph | 2-Cl—Ph | H |
| 109 | A | Et | Ph | 2-Cl—Ph | H |
| 110 | A | Me | 4-F—Ph | 2-Cl—Ph | H |
| 111 | A | Et | 4-F—Ph | 2-Cl—Ph | H |
| 112 | A | Me | 4-MeO—Ph | 2-Cl—Ph | H |
| 113 | A | Et | 4-MeO—Ph | 2-Cl—Ph | H |
| 114 | A | Me | 4-Cl—Ph | 2-Cl—Ph | H |
| 115 | A | Et | 4-Cl—Ph | 2-Cl—Ph | H |
| 116 | B | Me | 4-Me—Ph | 2-Cl—Ph | H |
| 117 | B | Et | 4-Me—Ph | 2-Cl—Ph | H |
| 118 | A | Me | Ph | 2-Cl-3-MeO—Ph | Cl |
| 119 | A | Et | 4-MeO—Ph | 2-Cl-3-MeO—Ph | H |
| 120 | A | Me | Ph | 2-Cl-3-MeO—Ph | H |
| 121 | A | Et | 4-MeO—Ph | 2-Cl-3-MeO—Ph | Cl |
| 122 | A | Et | 4-MeO—Ph | 2-Cl-3-MeO—Ph | Br |
| 123 | A | Me | 4-MeO—Ph | 2-Cl-3-MeO—Ph | H |
| 124 | A | Et | 3,5-di-F—Ph | 2-Cl-5-F—Ph | H |
| 125 | A | Et | 4-F—Ph | 2-Cl-3,5-di-MeO—Ph | H |
| 126 | A | Me | 4-F—Ph | 2-Cl-3,5-di-MeO—Ph | H |
| 127 | A | Et | Ph | 2-Cl—Ph | Cl |
| 128 | A | Et | Ph | 2-Cl—Ph | Br |
| 129 | A | Me | Ph | 2-Cl—Ph | Cl |
| 130 | A | Me | Ph | 2-Cl—Ph | Br |
| 131 | A | Et | 4-F—Ph | 2-Br-3,5-di-F—Ph | H |
| 132 | A | Et | 4-F—Ph | 2-Br-3,5-di-F—Ph | Cl |
| 133 | A | Et | 4-F—Ph | 2-Br-3,5-di-F—Ph | Br |
| 134 | A | Me | 4-MeO—Ph | 2-Cl-3-MeO—Ph | Cl |
| 135 | A | Et | 4-Cl—Ph | 2-Cl—Ph | Cl |
| 136 | A | Me | 4-MeO—Ph | 2-Cl-3-MeO—Ph | Br |
| 137 | A | Et | 4-Cl—Ph | 2-Cl—Ph | Br |
| 138 | A | Et | 3,5-di-F—Ph | 2-Cl-5-F—Ph | Cl |
| 139 | A | Et | 3,5-di-F—Ph | 2-Cl-5-F—Ph | Br |
| 140 | A | Me | 3,5-di-F—Ph | 2-Cl-5-F—Ph | H |
| 141 | A | Me | 4-Cl—Ph | 2-Cl—Ph | Cl |
| 142 | A | Me | 4-Cl—Ph | 2-Cl—Ph | Br |
| 143 | A | Et | 4-Me—Ph | 2-Cl—Ph | H |
| 144 | A | Me | 3,5-di-F—Ph | 2-Cl-5-F—Ph | Cl |
| 145 | A | Me | 3,5-di-F—Ph | 2-Cl-5-F—Ph | Br |
| 146 | A | Me | 4-Me—Ph | 2-Cl—Ph | H |
| 147 | A | Et | 4-F—Ph | 2-Cl—Ph | Cl |
| 148 | A | Et | 4-F—Ph | 2-Cl—Ph | Br |
| 149 | A | Me | 4-F—Ph | 2-Cl—Ph | Cl |
| 150 | A | Me | 4-F—Ph | 2-Cl—Ph | Br |
| 151 | A | Et | 4-MeO—Ph | 2-Cl—Ph | Cl |
| 152 | A | Et | 4-MeO—Ph | 2-Cl—Ph | Br |
| 153 | A | Me | 4-F—Ph | 2-Br-3,5-di-F—Ph | H |
| 154 | A | Me | 4-F—Ph | 2-Br-3,5-di-F—Ph | Cl |
| 155 | A | Me | 4-F—Ph | 2-Br-3,5-di-F—Ph | Br |
| 156 | A | Et | 4-Me—Ph | 2-Cl—Ph | Cl |
| 157 | A | Et | 4-Me—Ph | 2-Cl—Ph | Br |
| 158 | A | Me | 4-Me—Ph | 2-Cl—Ph | Cl |
| 159 | A | Me | 4-Me—Ph | 2-Cl—Ph | Br |
| 160 | A | Me | 3,4,5-tri-F—Ph | 2-Cl-5-F—Ph | H |
| 161 | A | Me | 3,4,5-tri-F—Ph | 2-Cl-5-F—Ph | Cl |
| 162 | A | Me | 4-MeO—Ph | 2-Cl—Ph | Cl |
| 163 | A | Me | 4-MeO—Ph | 2-Cl—Ph | Br |
| 164 | A | Et | 4-HO—Ph | 2-Cl-3,5-di-F—Ph | H |
| 165 | A | Et | 4-HO—Ph | 2-Cl-3,5-di-F—Ph | Cl |
| 166 | A | Et | 4-EtO—Ph | 2-Cl-3,5-di-F—Ph | Cl |
| 167 | A | Et | 4-EtO—Ph | 2-Cl-3,5-di-F—Ph | Br |
| 168 | A | Me | 3,4,5-tri-F—Ph | 2-Cl-5-F—Ph | Br |
| 169 | A | Et | 3,4,5-tri-F—Ph | 2-Cl-5-F—Ph | H |
| 170 | A | Me | 3,5-di-F-4-MeO—Ph | 2-Cl-5-F—Ph | H |
| 171 | A | Et | 3,4,5-tri-F—Ph | 2-Cl-5-F—Ph | Cl |
| 172 | A | Et | 3,4,5-tri-F—Ph | 2-Cl-5-F—Ph | Br |

TABLE 4-continued

| Compound | Structure | R1 | Z | Y | R5 |
|---|---|---|---|---|---|
| 173 | A | Et | 4-BuO—Ph | 2-Cl-3,5-di-F—Ph | H |
| 174 | A | Et | 4-BuO—Ph | 2-Cl-3,5-di-F—Ph | Cl |
| 175 | A | Et | 4-BuO—Ph | 2-Cl-3,5-di-F—Ph | Br |
| 176 | A | Et | 3,5-di-F—Ph | 2-Cl-5-MeO—Ph | H |
| 177 | A | Et | 3,5-di-F—Ph | 2-Cl-5-MeO—Ph | Cl |
| 178 | A | Et | 3,5-di-F—Ph | 2-Cl-5-MeO—Ph | Br |
| 179 | A | Me | 3,5-di-F-4-MeO—Ph | 2-Cl-5-F—Ph | Cl |
| 180 | A | Me | 3,4-di-F-5-MeO—Ph | 2-Cl-5-F—Ph | Cl |
| 181 | A | Me | 3,5-di-F-4-MeO—Ph | 2-Cl-5-F—Ph | Br |
| 182 | A | Me | 3,4-di-F-5-MeO—Ph | 2-Cl-5-F—Ph | Br |
| 183 | B | Et | 3,5-di-F3C—Ph | 2-Cl—Ph | H |
| 184 | A | Et | 3,5-di-F-4-MeO—Ph | 2-Cl-5-F—Ph | H |
| 185 | A | Et | 3,4-di-F-5-MeO—Ph | 2-Cl-5-F—Ph | H |
| 186 | A | Et | 3,5-di-F-4-MeO—Ph | 2-Cl-5-F—Ph | Cl |
| 187 | A | Et | 3,4-di-F-5-MeO—Ph | 2-Cl-5-F—Ph | Cl |
| 188 | A | Et | 3,5-di-F-4-MeO—Ph | 2-Cl-5-F—Ph | Br |
| 189 | A | Et | 3,4-di-F-5-MeO—Ph | 2-Cl-5-F—Ph | Br |
| 190 | B | Et | 3,5-di-F—Ph | 2-Cl—Ph | H |
| 191 | A | Et | 3,5-di-F3C—Ph | 2-Cl—Ph | H |
| 192 | A | Et | 3,5-di-F3C—Ph | 2-Cl—Ph | Cl |
| 193 | A | Et | 4-iPrO—Ph | 2-Cl-3,5-di-F—Ph | H |
| 194 | A | Et | 4-iPrO—Ph | 2-Cl-3,5-di-F—Ph | Cl |
| 195 | A | Et | 4-iPrO—Ph | 2-Cl-3,5-di-F—Ph | Br |
| 196 | B | Me | 3,5-di-F3C—Ph | 2-Cl—Ph | H |
| 197 | A | Me | 3,5-di-F3C—Ph | 2-Cl—Ph | H |
| 198 | B | Pr | 3,5-di-F—Ph | 2-Cl—Ph | H |
| 199 | A | Et | 3,5-di-F3C—Ph | 2-Cl—Ph | Br |
| 200 | A | Me | 3,5-di-F3C—Ph | 2-Cl—Ph | Cl |
| 201 | A | Me | 3,5-di-F3C—Ph | 2-Cl—Ph | Br |
| 202 | A | Et | 3,5-di-F—Ph | 2-Cl—Ph | H |
| 203 | A | Pr | 3,5-di-F—Ph | 2-Cl—Ph | H |
| 204 | A | Et | 3,5-di-F—Ph | 2-Cl—Ph | Cl |
| 205 | A | Et | 3,5-di-F—Ph | 2-Cl—Ph | Br |
| 206 | A | Et | 3,5-di-Cl—Ph | 2-Cl—Ph | H |
| 207 | A | Pr | 3,5-di-F—Ph | 2-Cl—Ph | Cl |
| 208 | A | Et | 4-CH2=CHCH2O—Ph | 2-Cl-3,5-di-F—Ph | Cl |
| 209 | A | Et | 4-AcO—Ph | 2-Cl-3,5-di-F—Ph | Cl |
| 210 | A | Et | 4-PhCH2O—Ph | 2-Cl-3,5-di-F—Ph | H |
| 211 | A | Et | 4-F—Ph | 2-Br—Ph | H |
| 212 | A | Et | 4-F—Ph | 2-Br—Ph | Cl |
| 213 | A | Pr | 3,5-di-F—Ph | 2-Cl—Ph | Br |
| 214 | A | Me | 3,5-di-Cl—Ph | 2-Cl—Ph | H |
| 215 | A | Et | 3,5-di-Cl—Ph | 2-Cl—Ph | Cl |
| 216 | A | Et | 3,5-di-Cl—Ph | 2-Cl—Ph | Br |
| 217 | A | Me | 3,5-di-Cl—Ph | 2-Cl—Ph | Cl |
| 218 | A | Me | 3,5-di-Cl—Ph | 2-Cl—Ph | Br |
| 219 | A | Et | 4-PrO—Ph | 2-Cl-3,5-di-F—Ph | H |
| 220 | A | Et | 4-PrO—Ph | 2-Cl-3,5-di-F—Ph | Cl |
| 221 | A | Et | 4-F2CHCH2O—Ph | 2-Cl-3,5-di-F—Ph | H |
| 222 | A | Et | 4-F2CHCH2O—Ph | 2-Cl-3,5-di-F—Ph | Cl |
| 223 | A | Et | 4-MeOCH2O—Ph | 2-Cl-3,5-di-F—Ph | H |
| 224 | A | Et | 4-F3CCH2O—Ph | 2-Cl-3,5-di-F—Ph | H |
| 225 | A | Et | 4-PhCH2O—Ph | 2-Cl-3,5-di-F—Ph | Cl |
| 226 | A | Et | 4-MeOCH2O—Ph | 2-Cl-3,5-di-F—Ph | Cl |
| 227 | A | Et | 4-N≡CCH2O—Ph | 2-Cl-3,5-di-F—Ph | H |
| 228 | A | Et | 4-MeOCH2CH2O—Ph | 2-Cl-3,5-di-F—Ph | H |
| 229 | A | Et | 4-MeOCH2CH2O—Ph | 2-Cl-3,5-di-F—Ph | Cl |
| 230 | A | Et | 3,5-di-Me—Ph | 2-Cl—Ph | H |
| 231 | A | Et | 3,5-di-Me—Ph | 2-Cl—Ph | Cl |
| 232 | A | Et | 3,5-di-Me—Ph | 2-Cl—Ph | Br |
| 233 | A | Et | 4-F—Ph | 2-Br—Ph | Br |
| 234 | A | Et | 4-F3CCH2O—Ph | 2-Cl-3,5-di-F—Ph | Cl |
| 235 | A | Et | 4-N≡CCH2O—Ph | 2-Cl-3,5-di-F—Ph | Cl |
| 236 | A | Me | 3,5-di-Me—Ph | 2-Cl—Ph | H |
| 237 | A | Me | 3,5-di-Me—Ph | 2-Cl—Ph | Cl |
| 238 | A | Me | 3,5-di-Me—Ph | 2-Cl—Ph | Br |
| 239 | A | Me | 4-F—Ph | 2-Br—Ph | H |
| 240 | A | Me | 4-F—Ph | 2-Br—Ph | Cl |
| 241 | A | Me | 4-F—Ph | 2-Br—Ph | Br |
| 242 | A | Et | 4-F—Ph | 2-Cl-5-EtO—Ph | Cl |
| 243 | A | Et | 4-F—Ph | 2-Cl-5-PrO—Ph | Cl |
| 244 | A | Et | 4-F—Ph | 2-Cl-5-N≡CCH2O—Ph | Cl |
| 245 | A | Et | 4-F—Ph | 2-Cl-5-F3CCH2O—Ph | Cl |
| 246 | A | Et | 4-F—Ph | 2-Cl-5-MeOCH2CH2O—Ph | Cl |
| 247 | A | Et | 4-F—Ph | 2-Cl-5-F2CHCH2O—Ph | Cl |
| 248 | A | Et | 4-F—Ph | 2-Cl-5-MeOCH2O—Ph | Cl |
| 249 | A | Et | 4-F—Ph | 2-Cl-5-AcO—Ph | Cl |
| 250 | A | Et | 4-F—Ph | 2-Cl-5-PhCH2O—Ph | Cl |

TABLE 4-continued

| Compound | Structure | R1 | Z | Y | R5 |
|---|---|---|---|---|---|
| 251 | A | Et | 4-F—Ph | 2-Cl-5-HC≡CCH2O—Ph | Cl |
| 252 | A | Et | 4-F—Ph | 2-Cl-5-MeOC(=O)O—Ph | Cl |
| 253 | A | Et | 4-F—Ph | 2-Cl-5-EtOC(=O)O—Ph | Cl |
| 254 | A | Et | 4-MeO—Ph | 2-Br-3,5-di-F—Ph | H |
| 255 | A | Et | 4-MeO—Ph | 2-Br-3,5-di-F—Ph | Br |
| 256 | A | Et | 4-MeO—Ph | 2-Br-3,5-di-F—Ph | Cl |
| 257 | A | Et | 4-F—Ph | 2-Cl-5-MeSCH2O—Ph | Cl |
| 258 | A | Et | 4-F—Ph | 2-Cl-5-(1,3-dioxolan-2-yl)CH2O—Ph | Cl |
| 259 | A | Et | 4-F—Ph | 2-Cl-5-(1,3-dioxan-2-yl)CH2CH2O—Ph | Cl |
| 260 | A | Me | 4-MeO—Ph | 2-Br-3,5-di-F—Ph | H |
| 261 | A | Me | 4-MeO—Ph | 2-Br-3,5-di-F—Ph | Cl |
| 262 | A | Me | 4-MeO—Ph | 2-Br-3,5-di-F—Ph | Br |
| 263 | A | Et | 4-F—Ph | 2-Cl-5-(3-Cl-5-F3C-2-Py)O—Ph | Cl |
| 264 | A | Et | 4-F—Ph | 2-Cl-3-N≡CCH2O—Ph | Cl |
| 265 | A | Et | 4-F—Ph | 2-Cl-3-EtO—Ph | Cl |
| 266 | A | Et | 4-F—Ph | 2-Cl-5-MeSO2CH2O—Ph | Cl |
| 267 | A | Et | 4-F—Ph | 2-Cl-3-MeOCH2O—Ph | Cl |
| 268 | A | Et | 4-F—Ph | 2-Cl-3-F2CHCH2O—Ph | Cl |
| 269 | A | Et | 4-F—Ph | 2-Cl-3-F3CCH2O—Ph | Cl |
| 270 | A | Et | 4-MeOCH2CH2CH2O—Ph | 2-Cl-3,5-di-F—Ph | Cl |
| 271 | A | Et | 4-F—Ph | 2-Cl-3-HC≡CCH2O—Ph | Cl |
| 272 | A | Et | 4-F—Ph | 2-Cl-3-PrO—Ph | Cl |
| 273 | A | Et | 4-F—Ph | 2-Cl-3-MeSCH2O—Ph | Cl |
| 274 | A | Et | 4-F—Ph | 2-F—Ph | H |
| 275 | A | Et | 4-F—Ph | 2-F—Ph | Cl |
| 276 | A | Et | 4-F—Ph | 2-F—Ph | Br |
| 277 | A | Me | 4-F—Ph | 2,6-di-F—Ph | Br |
| 278 | A | Me | 4-F—Ph | 2,6-di-F—Ph | H |
| 279 | A | Et | 4-F—Ph | 2,6-di-F—Ph | Br |
| 280 | A | Et | 4-F—Ph | 2,6-di-F—Ph | H |
| 281 | A | Et | 4-F—Ph | 2,6-di-F—Ph | Cl |
| 282 | A | Me | 4-F—Ph | 2,6-di-F—Ph | Cl |
| 283 | A | Et | 4-F—Ph | 2-I—Ph | H |
| 284 | A | Et | 4-F—Ph | 2-I—Ph | Br |
| 285 | A | Et | 4-F—Ph | 2-I—Ph | Cl |
| 286 | A | Et | 4-F—Ph | 2-Cl-3-MeSO2CH2O—Ph | Cl |
| 287 | A | Me | 4-F—Ph | 2-Cl-3-Py | H |
| 288 | A | Et | 4-F—Ph | 2-Cl-3-Py | H |
| 289 | A | Et | 4-F—Ph | 2-Cl-3-Py | Br |
| 290 | A | Me | 4-F—Ph | 2-Cl-3-Py | Br |
| 291 | A | Et | 4-F—Ph | 2-Cl-3-Py | Cl |
| 292 | A | Me | 4-F—Ph | 2-Cl-3-Py | Cl |
| 293 | A | Et | 4-F—Ph | 2-Me—Ph | H |
| 294 | A | Et | 4-F—Ph | 2-Me—Ph | Br |
| 295 | A | Et | 4-F—Ph | 2-Me—Ph | Cl |
| 296 | A | Et | 4-F—Ph | 2-Cl-3-iPrO—Ph | Cl |
| 297 | A | Et | 4-F—Ph | 2-Cl-5-iPrO—Ph | Cl |
| 298 | A | Et | 4-F—Ph | 2-N≡C—Ph | H |
| 299 | A | Et | 4-F—Ph | 2-N≡C—Ph | Cl |
| 300 | A | Me | 4-F3C—Ph | 2-Cl-3,5-di-F—Ph | H |
| 301 | A | Et | 4-F3C—Ph | 2-Cl-3,5-di-F—Ph | H |
| 302 | A | Et | 4-F3C—Ph | 2-Cl-3,5-di-F—Ph | Cl |
| 303 | A | Et | 4-F3C—Ph | 2-Cl-3,5-di-F—Ph | Br |
| 304 | A | Me | 4-F3C—Ph | 2-Cl-3,5-di-F—Ph | Cl |
| 305 | A | Me | 4-F3C—Ph | 2-Cl-3,5-di-F—Ph | Br |
| 306 | A | Et | 4-F—Ph | 2-MeO—Ph | H |
| 307 | A | Et | 4-F—Ph | 2-MeO—Ph | Cl |
| 308 | A | Et | 4-Br—Ph | 2-Cl-3,5-di-F—Ph | H |
| 309 | A | Me | 4-Br—Ph | 2-Cl-3,5-di-F—Ph | H |
| 310 | A | Et | 4-Br—Ph | 2-Cl-3,5-di-F—Ph | Cl |
| 311 | A | Et | 4-Br—Ph | 2-Cl-3,5-di-F—Ph | Br |
| 312 | A | Me | 4-Br—Ph | 2-Cl-3,5-di-F—Ph | Br |
| 313 | A | Me | 4-Br—Ph | 2-Cl-3,5-di-F—Ph | Cl |
| 314 | A | Me | 4-F—Ph | 2-N≡C—Ph | H |
| 315 | A | Me | 4-F—Ph | 2-N≡C—Ph | Cl |
| 316 | A | Me | 4-F—Ph | 2-N≡C—Ph | Br |
| 317 | A | Et | 4-N≡C—Ph | 2-Cl-3,5-di-F—Ph | H |
| 318 | A | Me | 4-N≡C—Ph | 2-Cl-3,5-di-F—Ph | H |
| 319 | A | Et | 4-N≡C—Ph | 2-Cl-3,5-di-F—Ph | Cl |
| 320 | A | Et | 4-N≡C—Ph | 2-Cl-3,5-di-F—Ph | Br |
| 321 | A | Me | 4-N≡C—Ph | 2-Cl-3,5-di-F—Ph | Cl |
| 322 | A | Me | 4-N≡C—Ph | 2-Cl-3,5-di-F—Ph | Br |
| 323 | A | Et | 4-HC≡C—Ph | 2-Cl-3,5-di-F—Ph | H |
| 324 | A | Et | 4-HC≡C—Ph | 2-Cl-3,5-di-F—Ph | Cl |
| 325 | A | Et | 4-HC≡C—Ph | 2-Cl-3,5-di-F—Ph | Br |
| 326 | A | Me | 4-HC≡C—Ph | 2-Cl-3,5-di-F—Ph | Br |
| 327 | A | Me | 4-HC≡C—Ph | 2-Cl-3,5-di-F—Ph | Cl |
| 328 | A | Me | 4-HC≡C—Ph | 2-Cl-3,5-di-F—Ph | H |

TABLE 4-continued

| Compound | Structure | R1 | Z | Y | R5 |
|---|---|---|---|---|---|
| 329 | A | Et | 4-N≡C—Ph | 2-Cl—Ph | Br |
| 330 | A | Et | 4-N≡C—Ph | 2-Cl—Ph | H |
| 331 | A | Me | 4-N≡C—Ph | 2-Cl—Ph | Br |
| 332 | A | Me | 4-N≡C—Ph | 2-Cl—Ph | H |
| 333 | A | Et | 4-N≡C—Ph | 2-Cl—Ph | Cl |
| 334 | A | Me | 4-N≡C—Ph | 2-Cl—Ph | Cl |
| 335 | A | Et | 4-N≡C—Ph | 2-Cl—Ph | I |
| 336 | A | Me | 4-N≡C—Ph | 2-Cl—Ph | I |
| 337 | A | F2CHCH2 | 4-N≡C—Ph | 2-Cl—Ph | H |
| 338 | A | F2CHCH2 | 4-N≡C—Ph | 2-Cl—Ph | Cl |
| 339 | A | F2CHCH2 | 4-N≡C—Ph | 2-Cl—Ph | Br |
| 340 | A | Et | 4-F—Ph | 2-Cl-5-HO—Ph | Cl |
| 341 | A | Et | 4-F—Ph | 2-Cl-3-HO—Ph | Cl |
| 342 | A | Et | 4-N≡C—Ph | 2-Cl—Ph | Me |
| 343 | A | Et | 4-N≡C—Ph | 2-Cl—Ph | HC≡C— |
| 344 | B | Me | 4-F—Ph | 2-Cl-4-F—Ph | H |
| 345 | A | Me | 4-F—Ph | 2-Cl-4-F—Ph | H |
| 346 | A | Me | 4-F—Ph | 2-Cl-4-F—Ph | Cl |
| 347 | A | Me | 4-F—Ph | 2-Cl-4-F—Ph | Br |
| 348 | A | Me | 4-F—Ph | 2-Cl-4-F—Ph | I |
| 349 | B | Et | 4-F—Ph | 2-Cl-4-F—Ph | H |
| 350 | A | Et | 4-F—Ph | 2-Cl-4-F—Ph | H |
| 351 | A | Et | 4-F—Ph | 2-Cl-4-F—Ph | Cl |
| 352 | A | Et | 4-F—Ph | 2-Cl-4-F—Ph | Br |
| 353 | A | Et | 4-N≡C—Ph | 2-Cl—Ph | MeO |
| 354 | B | Me | 4-F—Ph | 2,4-di-Cl—Ph | H |
| 355 | A | Me | 4-F—Ph | 2,4-di-Cl—Ph | H |
| 356 | A | Me | 4-F—Ph | 2,4-di-Cl—Ph | Cl |
| 357 | A | Me | 4-F—Ph | 2,4-di-Cl—Ph | Br |
| 358 | B | Et | 4-F—Ph | 2,4-di-Cl—Ph | H |
| 359 | A | Et | 4-F—Ph | 2,4-di-Cl—Ph | H |
| 360 | A | Et | 4-F—Ph | 2,4-di-Cl—Ph | Cl |
| 361 | A | Et | 4-F—Ph | 2,4-di-Cl—Ph | Br |
| 362 | A | Et | 4-F—Ph | 2,4-di-Cl—Ph | I |
| 363 | A | Et | 4-F—Ph | 2,4-di-Cl—Ph | Me |
| 364 | A | Et | 4-F—Ph | 2,4-di-Cl—Ph | MeO |
| 365 | A | Et | 4-F—Ph | 2,4-di-Cl—Ph | HC≡C— |
| 366 | B | F3CCH2 | 4-F—Ph | 2,4-di-F—Ph | H |
| 367 | A | F3CCH2 | 4-F—Ph | 2,4-di-F—Ph | H |
| 368 | A | Et | 4-HC≡CCH2O—Ph | 2-Cl-3,5-di-F—Ph | H |
| 369 | A | Et | 4-HC≡CCH2O—Ph | 2-Cl-3,5-di-F—Ph | Cl |
| 370 | A | F3CCH2 | 4-N≡C—Ph | 2-Cl—Ph | H |
| 371 | A | F3CCH2 | 4-N≡C—Ph | 2-Cl—Ph | Cl |
| 372 | A | F3CCH2 | 4-N≡C—Ph | 2-Cl—Ph | Br |
| 373 | A | F3CCH2 | 4-F—Ph | 2,4-di-F—Ph | Cl |
| 374 | A | F3CCH2 | 4-F—Ph | 2,4-di-F—Ph | Br |
| 375 | B | Me | 4-F—Ph | 2-Cl-5-F3C—Ph | H |
| 376 | A | Me | 4-F—Ph | 2-Cl-5-F3C—Ph | H |
| 377 | A | Me | 4-F—Ph | 2-Cl-5-F3C—Ph | Cl |
| 378 | A | Me | 4-F—Ph | 2-Cl-5-F3C—Ph | Br |
| 379 | B | Et | 4-F—Ph | 2-Cl-5-F3C—Ph | H |
| 380 | A | Et | 4-F—Ph | 2-Cl-5-F3C—Ph | H |
| 381 | B | Me | 4-F—Ph | 4-Br-2-Cl—Ph | H |
| 382 | A | Me | 4-F—Ph | 4-Br-2-Cl—Ph | H |
| 383 | A | Me | 4-F—Ph | 4-Br-2-Cl—Ph | Cl |
| 384 | A | Me | 4-F—Ph | 4-Br-2-Cl—Ph | Br |
| 385 | B | Et | 4-F—Ph | 4-Br-2-Cl—Ph | H |
| 386 | A | Et | 4-F—Ph | 4-Br-2-Cl—Ph | H |
| 387 | A | Et | 4-F—Ph | 4-Br-2-Cl—Ph | Cl |
| 388 | A | Et | 4-F—Ph | 4-Br-2-Cl—Ph | Br |
| 389 | A | Et | 4-F—Ph | 2-Cl-5-F3C—Ph | Cl |
| 390 | A | Et | 4-F—Ph | 2-Cl-5-F3C—Ph | Br |
| 391 | A | Me | 4-F—Ph | 2-Cl-4-Me—Ph | H |
| 392 | A | Me | 4-F—Ph | 2-Cl-4-Ac—Ph | H |
| 393 | B | Me | 4-F—Ph | 2-Cl-4-Me—Ph | H |
| 394 | A | Et | 4-F—Ph | 2-Cl-5-F3C—Ph | Ac |
| 395 | A | Me | 4-F—Ph | 2-Cl-4-Me—Ph | Cl |
| 396 | A | Me | 4-F—Ph | 2-Cl-4-Me—Ph | Br |
| 397 | A | Et | 4-F—Ph | 2-Cl-4-Me—Ph | H |
| 398 | A | Et | 4-F—Ph | 2-Cl-4-Me—Ph | Cl |
| 399 | A | Et | 4-F—Ph | 2-Cl-4-Me—Ph | Br |
| 400 | A | Me | 4-F—Ph | 4-Br-2-Cl—Ph | F |
| 401 | A | Et | 4-F—Ph | 4-Br-2-Cl—Ph | F |
| 402 | A | Et | 4-N≡C—Ph | 2-Cl-3-Py | Br |
| 403 | A | Et | 4-N≡C—Ph | 2-Cl-3-Py | H |
| 404 | A | Et | 4-N≡C—Ph | 2-Cl-3-Py | Cl |
| 405 | B | F2CHCH2 | 4-F—Ph | 2-Cl—Ph | H |
| 406 | A | F2CHCH2 | 4-F—Ph | 2-Cl—Ph | H |

TABLE 4-continued

| Compound | Structure | R1 | Z | Y | R5 |
| --- | --- | --- | --- | --- | --- |
| 407 | A | F2CHCH2 | 4-F—Ph | 2-Cl—Ph | Cl |
| 408 | A | F2CHCH2 | 4-F—Ph | 2-Cl—Ph | Br |
| 409 | B | F3CCH2 | 4-F—Ph | 2-Cl—Ph | H |
| 410 | A | F2CHCH2 | 4-F—Ph | 2-Cl—Ph | MeO |
| 411 | A | F3CCH2 | 4-F—Ph | 2-Cl—Ph | H |
| 412 | A | F3CCH2 | 4-F—Ph | 2-Cl—Ph | Br |
| 413 | A | F3CCH2 | 4-F—Ph | 2-Cl—Ph | Cl |
| 414 | B | Et | 4-F—Ph | 2,5-di-Cl—Ph | H |
| 415 | B | F2CHCH2 | 4-F—Ph | 2,5-di-Cl—Ph | H |
| 416 | A | Et | 4-F—Ph | 2,5-di-Cl—Ph | H |
| 417 | A | Et | 4-F—Ph | 2,5-di-Cl—Ph | Cl |
| 418 | A | Et | 4-F—Ph | 2,5-di-Cl—Ph | Br |
| 419 | A | F2CHCH2 | 4-F—Ph | 2,5-di-Cl—Ph | H |
| 420 | A | F2CHCH2 | 4-F—Ph | 2,5-di-Cl—Ph | Br |
| 421 | B | Et | 4-N≡C—Ph | 2,5-di-Cl—Ph | H |
| 422 | A | F2CHCH2 | 4-F—Ph | 2,5-di-Cl—Ph | Cl |
| 423 | A | Et | 4-N≡C—Ph | 2,5-di-Cl—Ph | H |
| 424 | A | Et | 4-N≡C—Ph | 2,5-di-Cl—Ph | Br |
| 425 | A | Et | 4-N≡C—Ph | 2,5-di-Cl—Ph | Cl |
| 426 | A | F2CHCH2 | 4-N≡C—Ph | 2,5-di-Cl—Ph | H |
| 427 | A | Et | Ph | 2-Br-3,5-di-F—Ph | H |
| 428 | A | Et | Ph | 2-Br-3,5-di-F—Ph | Cl |
| 429 | A | Et | Ph | 2-Br-3,5-di-F—Ph | Br |
| 430 | A | F2CHCH2 | Ph | 2-Br-3,5-di-F—Ph | H |
| 431 | A | F2CHCH2 | Ph | 2-Br-3,5-di-F—Ph | Cl |
| 432 | A | F2CHCH2 | Ph | 2-Br-3,5-di-F—Ph | Br |
| 433 | A | Et | 4-F—Ph | 2-Cl-5-MeOCH2CH2O—Ph | Br |
| 434 | A | Et | 4-F—Ph | 2-Cl-5-MeSCH2O—Ph | Br |
| 435 | A | F2CHCH2 | 4-F—Ph | 2-Cl-5-MeOCH2CH2O—Ph | Br |
| 436 | A | F2C=CH | 4-F—Ph | 2-Cl—Ph | Br |
| 437 | A | F2CHCH2 | 4-N≡C—Ph | 2,5-di-Cl—Ph | Cl |
| 438 | A | F2CHCH2 | 4-N≡C—Ph | 2,5-di-Cl—Ph | Br |
| 439 | A | F2CHCH2 | 4-F—Ph | 2-Cl-5-MeOCH2CH2O—Ph | Cl |
| 440 | A | Et | 4-N≡C—Ph | 2-Cl-5-MeOCH2CH2O—Ph | Cl |
| 441 | A | Et | 4-N≡C—Ph | 2-Cl-5-MeSCH2O—Ph | Br |
| 442 | A | F2CHCH2 | 4-F—Ph | 2-Cl-5-MeSCH2O—Ph | Cl |
| 443 | A | F2CHCH2 | Ph | 2-Cl-5-F—Ph | H |
| 444 | A | F2CHCH2 | Ph | 2-Cl-5-F—Ph | Cl |
| 445 | A | F2CHCH2 | Ph | 2-Cl-5-F—Ph | Br |
| 446 | A | F2CHCH2 | 4-N≡C—Ph | 2-Cl-5-MeOCH2CH2O—Ph | Cl |
| 447 | A | F2CHCH2 | 4-N≡C—Ph | 2-Cl-5-MeOCH2CH2O—Ph | Br |
| 448 | A | Et | 4-N≡C—Ph | 2-Cl-5-MeSCH2O—Ph | Cl |
| 449 | A | F2CHCH2 | 4-F—Ph | 2-Cl-5-F—Ph | H |
| 450 | A | F2CHCH2 | 4-F—Ph | 2-Cl-5-F—Ph | Cl |
| 451 | A | F2CHCH2 | 4-F—Ph | 2-Cl-5-F—Ph | Br |
| 452 | A | Et | 4-F—Ph | 2-Cl-5-F3C—Ph | F3C |
| 453 | A | Et | 4-N≡C—Ph | 2-Cl-5-MeSCH2O—Ph | Br |
| 454 | A | F2CHCH2 | 4-N≡C—Ph | 2-Cl-5-MeSCH2O—Ph | Cl |
| 455 | A | F2CHCH2 | 4-N≡C—Ph | 2-Cl-5-MeSCH2O—Ph | Br |
| 456 | A | Et | 4-HC≡CCH2O—Ph | 2-Cl-3,5-di-F—Ph | Br |
| 457 | A | F2CHCH2 | Ph | 2-Cl-3-F—Ph | H |
| 458 | A | F2CHCH2 | Ph | 2-Cl-3-F—Ph | Br |
| 459 | A | F2CHCH2 | Ph | 2-Cl-3-F—Ph | Cl |
| 460 | A | F2CHCH2 | 4-F—Ph | 2-Cl-3-F—Ph | H |
| 461 | A | F2CHCH2 | 4-F—Ph | 2-Cl-3-F—Ph | Cl |
| 462 | A | F2CHCH2 | 4-F—Ph | 2-Cl-3-F—Ph | Br |
| 463 | A | F3CCH2 | 4-F—Ph | 2-Cl—Ph | I |
| 464 | A | Et | Ph | 2,5-di-Me—Ph | H |
| 465 | B | Et | Ph | 5-F-2-Me—Ph | H |
| 466 | A | Et | Ph | 5-F-2-Me—Ph | H |
| 467 | A | Et | Ph | 5-F-2-Me—Ph | Cl |
| 468 | A | Et | Ph | 5-F-2-Me—Ph | Br |
| 469 | A | F2CHCH2 | Ph | 5-F-2-Me—Ph | H |
| 470 | A | F2CHCH2 | Ph | 5-F-2-Me—Ph | Cl |
| 471 | A | F2CHCH2 | Ph | 5-F-2-Me—Ph | Br |
| 472 | A | Et | 4-F—Ph | 5-F-2-Me—Ph | H |
| 473 | A | F2CHCH2 | 4-F—Ph | 5-F-2-Me—Ph | H |
| 474 | A | Et | 4-F—Ph | 5-F-2-Me—Ph | Br |
| 475 | A | F2CHCH2 | 4-F—Ph | 5-F-2-Me—Ph | Cl |
| 476 | A | F2CHCH2 | 4-F—Ph | 5-F-2-Me—Ph | Br |
| 477 | A | Et | 4-F—Ph | 2,5-di-Me—Ph | H |
| 478 | A | Et | 4-F—Ph | 2,5-di-Me—Ph | Cl |
| 479 | A | Et | 4-F—Ph | 2,5-di-Me—Ph | Br |
| 480 | A | F2CHCH2 | 4-F—Ph | 2,5-di-Me—Ph | H |
| 481 | A | F2CHCH2 | 4-F—Ph | 2,5-di-Me—Ph | Br |
| 482 | A | F2CHCH2 | 4-F—Ph | 2,5-di-Me—Ph | Cl |
| 483 | A | F2CHCH2 | Ph | 2,5-di-Me—Ph | H |
| 484 | A | Et | Ph | 2,5-di-Me—Ph | Cl |

TABLE 4-continued

| Compound | Structure | R1 | Z | Y | R5 |
|---|---|---|---|---|---|
| 485 | A | Et | Ph | 2,5-di-Me—Ph | Br |
| 486 | A | F2CHCH2 | Ph | 2,5-di-Me—Ph | Cl |
| 487 | A | F2CHCH2 | Ph | 2,5-di-Me—Ph | Br |
| 488 | A | F2CHCH2 | Ph | 2-Cl—Ph | H |
| 489 | B | F2CHCH2 | Ph | 2-Me—Ph | H |
| 490 | A | F2CHCH2 | Ph | 2-Cl—Ph | Cl |
| 491 | A | F2CHCH2 | Ph | 2-Cl—Ph | Br |
| 492 | A | F2CHCH2 | Ph | 2-Me—Ph | H |
| 493 | A | F2CHCH2 | Ph | 2-Me—Ph | Cl |
| 494 | A | F2CHCH2 | Ph | 2-Me—Ph | Br |
| 495 | A | Et | 4-F—Ph | 5-F-2-Me—Ph | Cl |
| 496 | A | F2CHCH2 | Ph | 2-Br-5-F—Ph | H |
| 497 | A | F2CHCH2 | 4-F—Ph | 2-Cl-4-F—Ph | H |
| 498 | A | F2CHCH2 | 4-F—Ph | 2-Cl-4-F—Ph | Cl |
| 499 | A | F2CHCH2 | 4-F—Ph | 2-Cl-4-F—Ph | Br |
| 500 | A | F2CHCH2 | Ph | 2-Br-5-F—Ph | Cl |
| 501 | A | F2CHCH2 | Ph | 2-Br-5-F—Ph | Br |
| 502 | B | Et | Ph | 2-Br-5-F—Ph | H |
| 503 | A | Et | Ph | 2-Br-5-F—Ph | H |
| 504 | A | Et | Ph | 2-Br-5-F—Ph | Cl |
| 505 | A | Et | Ph | 2-Br-5-F—Ph | Br |
| 506 | A | F2CHCH2 | Ph | 2-Cl-4-F—Ph | H |
| 507 | A | F2CHCH2 | 4-F—Ph | 2-Cl-4-F—Ph | I |
| 508 | A | F2CHCH2 | Ph | 2-Br-5-F—Ph | I |
| 509 | A | F2CHCH2 | Ph | 2-Cl-4-F—Ph | Br |
| 510 | A | F2CHCH2 | Ph | 2-Cl-4-F—Ph | Cl |
| 511 | B | Et | 4-F—Ph | 2-Br-5-F—Ph | H |
| 512 | A | F2CHCH2 | 4-F—Ph | 2-Br-5-F—Ph | H |
| 513 | A | Et | 4-F—Ph | 2-Br-5-F—Ph | H |
| 514 | A | F2CHCH2 | Ph | 2-Cl-4-F—Ph | I |
| 515 | A | F2CHCH2 | 4-F—Ph | 2-Br-5-F—Ph | Br |
| 516 | A | F2CHCH2 | 4-F—Ph | 2-Br-5-F—Ph | Cl |
| 517 | A | Et | 4-F—Ph | 2-Br-5-F—Ph | Cl |
| 518 | A | Et | 4-F—Ph | 2-Br-5-F—Ph | Br |
| 519 | B | Et | 4-F—Ph | 2-Br—Ph | H |
| 520 | A | F2CHCH2 | 4-F—Ph | 2-Br—Ph | H |
| 521 | A | F2CHCH2 | 4-F—Ph | 2-Br—Ph | Cl |
| 522 | A | F2CHCH2 | 4-F—Ph | 2-Br—Ph | Br |
| 523 | A | F2CHCH2 | 4-F—Ph | 2-Br—Ph | I |
| 524 | A | Et | 4-F—Ph | 2-Cl—Ph | I |
| 525 | A | F2CHCH2 | Ph | 2-Cl—Ph | I |
| 526 | A | F2CHCH2 | Ph | 2-Me—Ph | I |
| 527 | A | F2CHCH2 | 4-F—Ph | 2-Me—Ph | H |
| 528 | A | F2CHCH2 | 4-F—Ph | 2-Me—Ph | Cl |
| 529 | A | F2CHCH2 | 4-F—Ph | 2-Me—Ph | Br |
| 530 | A | F2CHCH2 | Ph | 2-Br—Ph | H |
| 531 | A | Et | Ph | 2-Br-5-F—Ph | I |
| 532 | A | F2CHCH2 | 4-F—Ph | 2-Br-5-F—Ph | I |
| 533 | A | F2CHCH2 | Ph | 2-Br—Ph | Cl |
| 534 | A | F2CHCH2 | Ph | 2-Br—Ph | Br |
| 535 | A | Et | Ph | 2-Br—Ph | H |
| 536 | A | Et | Ph | 2-Br—Ph | Cl |
| 537 | A | Et | Ph | 2-Br—Ph | Br |
| 538 | A | Et | Ph | 2-Me—Ph | H |
| 539 | A | Et | Ph | 2-Me—Ph | Cl |
| 540 | A | Et | Ph | 2-Me—Ph | Br |

Table 5 describes the $^1$H-NMR data of the compounds listed in Table 4.

TABLE 5

| Compound | $^1$H-NMR |
|---|---|
| 1 | 1H-NMR (CDCl3) δ: 7.35-7.33 (1H, m), 7.30-7.20 (4H, m), 7.12-7.11 (1H, m), 6.67 (1H, d, J = 9.5 Hz), 6.26 (1H, d, J = 2.7 Hz), 6.04 (1H, d, J = 2.7 Hz), 3.81 (3H, s), 3.56 (3H, s), 3.33 (3H, s). |
| 2 | 1H-NMR (CDCl3) δ: 7.36-7.28 (3H, m), 7.27-7.21 (2H, m), 7.10-7.08 (1H, m), 6.68 (1H, d, J = 9.5 Hz), 6.29 (1H, d, J = 2.7 Hz), 6.01 (1H, d, J = 2.7 Hz), 3.81 (3H, s), 3.56 (3H, s), 3.33 (3H, s). |
| 3 | 1H-NMR (CDCl3) δ: 7.32-7.17 (6H, m), 6.65 (1H, d, J = 9.2 Hz), 6.24 (1H, d, J = 2.8 Hz), 6.08 (1H, d, J = 2.8 Hz), 3.92-3.86 (2H, m), 3.81 (3H, s), 3.59 (3H, s), 1.17 (3H, t, J = 7.0 Hz). |

TABLE 5-continued

| Compound | ¹H-NMR |
|---|---|
| 4 | 1H-NMR (CDCl3) δ: 7.34-7.21 (5H, m), 7.15-7.14 (1H, m), 6.65 (1H, d, J = 9.5 Hz), 6.28 (1H, d, J = 2.8 Hz), 6.05 (1H, d, J = 2.8 Hz), 3.92-3.87 (2H, m), 3.80 (3H, s), 3.59 (3H, s), 1.17 (3H, t, J = 7.0 Hz). |
| 5 | 1H-NMR (CDCl3) δ: 7.25-7.20 (3H, m), 7.19-7.15 (1H, m), 7.05 (1H, td, J = 8.5, 2.7 Hz), 6.95 (1H, td, J = 8.5, 2.7 Hz), 6.82 (1H, ddd, J = 8.9, 7.6, 3.1 Hz), 6.69-6.65 (2H, m), 3.96-3.81 (2H, m), 1.16 (3H, t, J = 7.0 Hz). |
| 6 | 1H-NMR (CDCl3) δ: 7.46 (1H, s), 7.25-7.15 (3H, m), 7.05 (1H, td, J = 8.4, 2.6 Hz), 6.96 (1H, td, J = 8.4, 2.6 Hz), 6.84 (1H, ddd, J = 8.9, 7.9, 3.1 Hz), 6.67 (1H, dd, J = 8.5, 3.1 Hz), 4.00-3.86 (2H, m), 1.19 (3H, t, J = 7.0 Hz). |
| 7 | 1H-NMR (CDCl3) δ: 7.66 (1H, s), 7.24-7.16 (3H, m), 7.07-7.02 (1H, m), 6.99-6.93 (1H, m), 6.84 (1H, ddd, J = 8.9, 7.9, 3.1 Hz), 6.67 (1H, dd, J = 8.5, 3.1 Hz), 3.99-3.86 (2H, m), 1.18 (3H, t, J = 7.0 Hz). |
| 8 | 1H-NMR (CDCl3) δ: 7.27-7.22 (2H, m), 7.19-7.16 (1H, m), 7.13-7.10 (1H, m), 7.05 (1H, td, J = 8.5, 2.5 Hz), 6.95 (1H, td, J = 8.5, 2.5 Hz), 6.83 (1H, ddd, J = 8.9, 7.9, 3.1 Hz), 6.69 (1H, d, J = 9.5 Hz), 6.64 (1H, dd, J = 8.9, 3.1 Hz), 3.32 (3H, s). |
| 9 | 1H-NMR (CDCl3) δ: 7.49 (1H, s), 7.27-7.23 (1H, m), 7.18-7.10 (2H, m), 7.06 (1H, td, J = 8.5, 2.5 Hz), 6.97 (1H, td, J = 8.5, 2.5 Hz), 6.86 (1H, ddd, J = 8.9, 7.9, 3.1 Hz), 6.66 (1H, dd, J = 8.5, 3.1 Hz), 3.38 (3H, s). |
| 10 | 1H-NMR (CDCl3) δ: 7.70 (1H, s), 7.26-7.23 (1H, m), 7.18-7.10 (2H, m), 7.06 (1H, td, J = 8.5, 2.7 Hz), 6.97 (1H, td, J = 8.5, 2.7 Hz), 6.86 (1H, ddd, J = 8.9, 7.6, 3.1 Hz), 6.66 (1H, dd, J = 8.5, 3.1 Hz), 3.39 (3H, s). |
| 11 | 1H-NMR (CDCl3) δ: 7.08-7.05 (2H, br m), 6.94-6.92 (1H, m), 6.69 (1H, ddd, J = 8.9, 8.3, 2.8 Hz), 6.42 (1H, ddd, J = 8.9, 2.8, 1.8 Hz), 3.62-3.57 (1H, m), 3.33-3.27 (1H, m), 2.83-2.65 (3H, m), 2.44-2.41 (1H, m), 0.96 (3H, t, J = 7.0 Hz). |
| 12 | 1H-NMR (CDCl3) δ: 7.23 (1H, m), 7.20 (1H, d, J = 9.2 Hz), 7.16-7.13 (1H, m), 7.06 (1H, td, J = 8.4, 2.8 Hz), 6.98 (1H, td, J = 8.4, 2.8 Hz), 6.76-6.72 (1H, m), 6.68 (1H, d, J = 9.2 Hz), 6.52 (1H, ddd, J = 8.6, 2.8, 1.8 Hz), 3.92-3.83 (2H, m), 1.16 (3H, t, J = 7.0 Hz). |
| 13 | 1H-NMR (CDCl3) δ: 7.44 (1H, s), 7.21-7.19 (1H, m), 7.17-7.13 (1H, m), 7.07 (1H, td, J = 8.4, 2.6 Hz), 6.99 (1H, td, J = 8.4, 2.6 Hz), 6.77 (1H, td, J = 8.4, 2.8 Hz), 6.54 (1H, ddd, J = 8.4, 2.8, 1.8 Hz), 3.98-3.87 (2H, m), 1.19 (3H, t, J = 7.0 Hz). |
| 14 | 1H-NMR (CDCl3) δ: 7.65 (1H, s), 7.22-7.14 (2H, m), 7.06 (1H, td, J = 8.4, 2.6 Hz), 6.99 (1H, td, J = 8.4, 2.6 Hz), 6.77 (1H, td, J = 8.4, 2.8 Hz), 6.54 (1H, ddd, J = 8.4, 2.8, 1.8 Hz), 3.98-3.87 (2H, m), 1.19 (3H, t, J = 7.1 Hz). |
| 15 | 1H-NMR (CDCl3) δ: 7.26-7.21 (3H, br m), 7.12-7.04 (2H, br m), 6.66 (1H, td, J = 8.6, 3.0 Hz), 6.42-6.41 (1H, m), 3.64-3.61 (1H, m), 3.30-3.27 (1H, m), 2.86-2.66 (3H, m), 2.44-2.39 (1H, m), 0.97 (3H, t, J = 7.0 Hz). |
| 16 | 1H-NMR (CDCl3) δ: 7.37-7.35 (1H, m), 7.33-7.31 (1H, m), 7.27-7.25 (2H, m), 7.21 (1H, d, J = 9.2 Hz), 7.13-7.12 (1H, m), 6.72-6.68 (1H, m), 6.68 (1H, d, J = 9.2 Hz), 6.52-6.50 (1H, m), 3.90-3.88 (2H, m), 1.17 (3H, t, J = 7.0 Hz). |
| 17 | 1H-NMR (CDCl3) δ: 7.45 (1H, s), 7.37-7.32 (2H, m), 7.29-7.26 (1H, m), 7.23-7.22 (1H, m), 7.14-7.12 (1H, m), 6.73-6.72 (1H, m), 6.54-6.52 (1H, m), 3.95-3.92 (2H, m), 1.19 (3H, t, J = 7.0 Hz). |
| 18 | 1H-NMR (CDCl3) δ: 7.66 (1H, s), 7.37-7.32 (2H, m), 7.29-7.27 (1H, m), 7.22-7.21 (1H, m), 7.14-7.13 (1H, m), 6.73 (1H, td, J = 8.5, 2.9 Hz), 6.54-6.52 (1H, m), 3.95-3.92 (2H, m), 1.19 (3H, t, J = 7.0 Hz). |
| 19 | 1H-NMR (CDCl3) δ: 7.24-7.23 (3H, m), 7.07-7.05 (2H, br m), 6.69-6.65 (1H, m), 6.42-6.40 (1H, m), 2.89-2.85 (1H, m), 2.85 (3H, s), 2.81-2.77 (1H, m), 2.72-2.69 (1H, m), 2.45-2.42 (1H, m). |
| 20 | 1H-NMR (CDCl3) δ: 7.39-7.24 (3H, m), 7.26 (1H, d, J = 9.3 Hz), 7.21-7.19 (1H, m), 7.08-7.07 (1H, m), 6.74-6.71 (1H, m), 6.70 (1H, d, J = 9.3 Hz), 6.50-6.48 (1H, m), 3.32 (3H, s). |
| 21 | 1H-NMR (CDCl3) δ: 7.49 (1H, s), 7.37-7.34 (2H, m), 7.29-7.28 (1H, m), 7.18-7.17 (1H, m), 7.08-7.07 (1H, m), 6.76-6.73 (1H, m), 6.51-6.50 (1H, m), 3.39 (3H, s). |
| 22 | 1H-NMR (CDCl3) δ: 7.69 (1H, s), 7.38-7.32 (2H, m), 7.31-7.26 (1H, m), 7.19-7.16 (1H, m), 7.09-7.08 (1H, m), 6.74 (1H, td, J = 8.4, 3.0 Hz), 6.51-6.49 (1H, m), 3.39 (3H, s). |
| 23 | 1H-NMR (CDCl3) δ: 7.05-7.04 (2H, m), 6.95-6.92 (2H, m), 6.70 (1H, td, J = 8.4, 2.8 Hz), 6.42 (1H, ddd, J = 8.4, 2.8, 1.8 Hz), 2.85 (3H, s), 2.84-2.76 (2H, m), 2.73-2.68 (1H, m), 2.46-2.43 (1H, m). |
| 24 | 1H-NMR (CDCl3) δ: 7.24 (1H, d, J = 9.5 Hz), 7.20-7.17 (1H, m), 7.11-7.05 (2H, m), 6.99 (1H, td, J = 8.5, 2.7 Hz), 6.76 (1H, td, J = 8.5, 2.8 Hz), 6.70 (1H, d, J = 9.5 Hz), 6.50 (1H, ddd, J = 8.5, 2.8, 1.8 Hz), 3.32 (3H, s). |
| 25 | 1H-NMR (CDCl3) δ: 7.47 (1H, s), 7.18-7.14 (1H, m), 7.12-7.05 (2H, m), 7.00 (1H, td, J = 8.4, 2.7 Hz), 6.78 (1H, td, J = 8.4, 2.8 Hz), 6.52 (1H, ddd, J = 8.4, 2.8, 1.8 Hz), 3.38 (3H, s). |
| 26 | 1H-NMR (CDCl3) δ: 7.68 (1H, s), 7.18-7.14 (1H, m), 7.12-7.06 (2H, m), 7.00 (1H, td, J = 8.5, 2.7 Hz), 6.78 (1H, td, J = 8.4, 2.8 Hz), 6.52 (1H, ddd, J = 8.4, 2.8, 1.8 Hz), 3.39 (3H, s). |
| 27 | 1H-NMR (CDCl3) δ: 7.22-7.18 (1H, m), 7.17-7.13 (1H, m), 7.09 (1H, q, J = 1.1 Hz), 7.04 (1H, td, J = 8.4, 2.6 Hz), 6.96 (1H, td, J = 8.4, 2.6 Hz), 6.73 (1H, td, J = 8.4, 2.8 Hz), 6.52 (1H, ddd, J = 8.4, 2.8, 1.8 Hz), 3.92-3.85 (2H, m), 2.23 (3H, d, J = 1.1 Hz), 1.16 (3H, t, J = 7.1 Hz). |
| 28 | 1H-NMR (CDCl3) δ: 7.19 (1H, d, J = 9.5 Hz), 7.14 (1H, dd, J = 8.4, 2.3 Hz), 7.04 (1H, dd, J = 8.4, 2.3 Hz), 6.86 (1H, dd, J = 8.4, 2.7 Hz), 6.76 (2H, dd, J = 8.4, |

TABLE 5-continued

| Compound | ¹H-NMR |
|---|---|
| | 2.7 Hz), 6.74-6.69 (2H, m), 6.65 (1H, d, J = 9.5 Hz), 6.52 (1H, m), 3.95-3.85 (2H, m), 3.79 (3H, s), 1.16 (3H, t, J = 7.1 Hz). |
| 29 | 1H-NMR (CDCl3) δ: 7.07-7.05 (2H, m), 6.97-6.95 (2H, m), 6.71 (1H, td, J = 8.4, 3.2 Hz), 6.47 (1H, ddd, J = 8.4, 3.2, 1.8 Hz), 5.93 (1H, tt, J = 56.6, 4.4 Hz), 3.79-3.76 (1H, m), 3.70-3.61 (1H, m), 2.89-2.71 (3H, m), 2.54-2.51 (1H, m). |
| 30 | 1H-NMR (CDCl3) δ: 7.29 (1H, d, J = 9.2 Hz), 7.24-7.21 (1H, m), 7.13-7.11 (1H, m), 7.08 (1H, td, J = 8.4, 2.8 Hz), 6.99 (1H, td, J = 8.4, 2.8 Hz), 6.76 (1H, td, J = 8.4, 3.2 Hz), 6.72 (1H, d, J = 9.2 Hz), 6.53 (1H, ddd, J = 8.4, 3.2, 1.8 Hz), 6.30 (1H, tt, J = 57.2, 4.6 Hz), 4.15-4.09 (2H, m). |
| 31 | 1H-NMR (CDCl3) δ: 7.52 (1H, s), 7.22-7.19 (1H, m), 7.15-7.07 (2H, m), 7.00 (1H, td, J = 8.5, 2.7 Hz), 6.79 (1H, td, J = 8.4, 3.2 Hz), 6.55 (1H, ddd, J = 8.4, 3.2, 1.8 Hz), 6.32 (1H, tt, J = 57.0, 4.6 Hz), 4.24-4.08 (2H, m). |
| 32 | 1H-NMR (CDCl3) δ: 7.72 (1H, s), 7.22-7.20 (1H, m), 7.15-7.06 (2H, m), 7.00 (1H, td, J = 8.4, 2.7 Hz), 6.79 (1H, td, J = 8.4, 3.2 Hz), 6.55 (1H, ddd, J = 8.4, 3.2, 1.8 Hz), 6.32 (1H, tt, J = 57.0, 4.7 Hz), 4.23-4.10 (2H, m). |
| 33 | 1H-NMR (CDCl3) δ: 7.25-7.22 (2H, m), 7.20-7.14 (2H, m), 7.02 (1H, td, J = 8.5, 2.7 Hz), 6.94 (1H, td, J = 8.5, 2.7 Hz), 6.67 (1H, d, J = 9.0 Hz), 6.64 (1H, dd, J = 9.0, 3.1 Hz), 6.45 (1H, d, J = 3.1 Hz), 3.93-3.85 (2H, m), 3.64 (3H, s), 1.16 (3H, t, J = 7.0 Hz). |
| 34 | 1H-NMR (CDCl3) δ: 7.29 (1H, d, J = 9.2 Hz), 7.21-7.18 (1H, m), 7.17 (1H, d, J = 8.9 Hz), 7.14-7.11 (1H, m), 7.04 (1H, td, J = 8.6, 2.8 Hz), 6.95 (1H, td, J = 8.6, 2.8 Hz), 6.68 (1H, d, J = 9.2 Hz), 6.65 (1H, dd, J = 8.9, 3.1 Hz), 6.43 (1H, d, J = 3.1 Hz), 3.63 (3H, s), 3.32 (3H, s). |
| 35 | 1H-NMR (CDCl3) δ: 7.43 (1H, s), 7.11 (1H, dd, J = 8.5, 2.2 Hz), 7.05 (1H, dd, J = 8.5, 2.2 Hz), 6.86 (1H, dd, J = 8.5, 2.6 Hz), 6.78-6.71 (2H, m), 6.55-6.52 (1H, m), 4.00-3.90 (2H, m), 3.79 (3H, s), 1.19 (3H, t, J = 7.1 Hz). |
| 36 | 1H-NMR (CDCl3) δ: 7.63 (1H, s), 7.11 (1H, dd, J = 8.5, 2.2 Hz), 7.05 (1H, dd, J = 8.5, 2.2 Hz), 6.86 (1H, dd, J = 8.5, 2.7 Hz), 6.79-6.72 (2H, m), 6.55-6.51 (1H, m), 3.99-3.91 (2H, m), 3.79 (3H, s), 1.18 (3H, t, J = 7.0 Hz). |
| 37 | 1H-NMR, (CDCl3) δ: 7.24 (1H, d, J = 9.2 Hz), 7.10 (1H, dd, J = 8.6, 2.1 Hz), 6.99 (1H, dd, J = 8.4, 2.3 Hz), 6.87 (1H, dd, J = 8.6, 2.1 Hz), 6.79-6.72 (2H, m), 6.67 (1H, d, J = 9.2 Hz), 6.51-6.48 (1H, m), 3.79 (3H, s), 3.33 (3H, s). |
| 38 | 1H-NMR (CDCl3) δ: 7.47 (1H, s), 7.07 (1H, dd, J = 8.4, 2.3 Hz), 7.00 (1H, dd, J = 8.4, 2.3 Hz), 6.87 (1H, dd, J = 8.5, 2.7 Hz), 6.80-6.74 (2H, m), 6.53-6.49 (1H, m), 3.79 (3H, s), 3.39 (3H, s). |
| 39 | 1H-NMR, (CDCl3) δ: 7.67 (1H, s), 7.07 (1H, dd, J = 8.6, 2.1 Hz), 7.00 (1H, dd, J = 8.4, 2.3 Hz), 6.87 (1H, dd, J = 8.6, 2.1 Hz), 6.78 (1H, dd, J = 8.4, 2.3 Hz), 6.75 (1H, td, J = 8.7, 2.9 Hz), 6.52-6.50 (1H, m), 3.79 (3H, s), 3.40 (3H, s). |
| 40 | 1H-NMR, (CDCl3) δ: 7.23-7.20 (2H, m), 7.15 (1H, dd, J = 8.6, 2.1 Hz), 7.06 (1H, dd, J = 8.6, 2.1 Hz), 6.85 (1H, dd, J = 8.4, 2.6 Hz), 6.81-6.77 (1H, m), 6.74 (1H, dd, J = 8.6, 2.8 Hz), 6.68-6.64 (2H, m), 3.95-3.86 (2H, m), 3.78 (3H, s), 1.16 (3H, t, J = 7.0 Hz). |
| 41 | 1H-NMR (CDCl3) δ: 7.66 (1H, s), 7.22 (1H, dd, J = 8.9, 5.2 Hz), 7.12 (1H, dd, J = 8.5, 2.2 Hz), 7.07 (1H, dd, J = 8.5, 2.2 Hz), 6.86-6.79 (2H, m), 6.75 (1H, dd, J = 8.4, 2.6 Hz), 6.67 (1H, dd, J = 8.7, 3.1 Hz), 4.00-3.90 (2H, m), 3.78 (3H, s), 1.18 (3H, t, J = 7.0 Hz). |
| 42 | 1H-NMR (CDCl3) δ: 7.12-7.09 (2H, br m), 7.00-6.96 (2H, br m), 6.71 (1H, td, J = 8.4, 3.2 Hz), 6.43 (1H, ddd, J = 8.4, 3.2, 1.8 Hz), 4.28 (1H, dq, J = 13.7, 7.0 Hz), 3.87 (1H, dq, J = 13.7, 7.0 Hz), 3.41-3.37 (1H, m), 3.23-3.15 (1H, m), 2.71-2.63 (1H, m), 2.34-2.30 (1H, m), 1.08 (3H, t, J = 7.0 Hz). |
| 43 | 1H-NMR (CDCl3) δ: 7.81 (1H, d, J = 8.8 Hz), 7.25-7.17 (2H, m), 7.08 (1H, td, J = 8.4, 2.8 Hz), 7.03-6.98 (2H, m), 6.77 (1H, td, J = 8.4, 2.8 Hz), 6.52 (1H, ddd, J = 8.4, 2.8, 1.8 Hz), 4.55-4.54 (2H, m), 1.28 (3H, t, J = 7.0 Hz). |
| 44 | 1H-NMR (CDCl3) δ: 7.49 (1H, s), 7.22-7.14 (3H, m), 7.02 (1H, td, J = 8.3, 2.8 Hz), 6.95 (1H, td, J = 8.3, 2.8 Hz), 6.66 (1H, dd, J = 8.9, 3.1 Hz), 6.46 (1H, d, J = 3.1 Hz), 3.99-3.89 (2H, m), 3.65 (3H, s), 1.19 (3H, t, J = 6.9 Hz). |
| 45 | 1H-NMR (CDCl3) δ: 7.52 (1H, s), 7.18-7.13 (3H, m), 7.04 (1H, td, J = 8.4, 2.7 Hz), 6.96 (1H, td, J = 8.4, 2.7 Hz), 6.67 (1H, dd, J = 8.8, 3.2 Hz), 6.44 (1H, d, J = 3.2 Hz), 3.64 (3H, s), 3.39 (3H, s). |
| 46 | 1H-NMR (CDCl3) δ: 7.69 (1H, s), 7.23-7.18 (2H, m), 7.15 (1H, d, J = 8.9 Hz), 7.03-7.02 (1H, m), 6.96-6.94 (1H, m), 6.65 (1H, dd, J = 8.9, 3.1 Hz), 6.46 (1H, d, J = 3.1 Hz), 3.99-3.88 (2H, m), 3.65 (3H, s), 1.18 (3H, t, J = 7.0 Hz). |
| 47 | 1H-NMR (CDCl3) δ: 7.72 (1H, s), 7.17-7.14 (3H, m), 7.04 (1H, td, J = 8.4, 2.7 Hz), 6.96 (1H, td, J = 8.4, 2.7 Hz), 6.67 (1H, dd, J = 8.8, 2.9 Hz), 6.44 (1H, d, J = 2.9 Hz), 3.64 (3H, s), 3.39 (3H, s). |
| 48 | 1H-NMR (CDCl3) δ: 7.24-7.20 (2H, m), 7.16-7.13 (1H, m), 7.03-6.92 (4H, m), 6.74-6.72 (1H, m), 6.68 (1H, d, J = 9.2 Hz), 3.93-3.85 (2H, m), 1.17 (3H, t, J = 7.1 Hz). |
| 49 | 1H-NMR (CDCl3) δ: 7.47 (1H, s), 7.21-7.13 (2H, m), 7.04-6.93 (4H, m), 6.76-6.73 (1H, m), 3.98-3.89 (2H, m), 1.19 (3H, t, J = 7.1 Hz). |
| 50 | 1H-NMR (CDCl3) δ: 7.46 (1H, s), 7.23 (1H, dd, J = 8.9, 5.2 Hz), 7.12 (1H, dd, J = 8.4, 2.3 Hz), 7.06 (1H, dd, J = 8.6, 2.1 Hz), 6.86-6.80 (2H, m), 6.75 (1H, dd, J = 8.4, 2.3 Hz), 6.68 (1H, dd, J = 8.9, 3.1 Hz), 3.99-3.88 (2H, m), 3.78 (3H, s), 1.19 (3H, t, J = 7.0 Hz). |
| 51 | 1H-NMR (CDCl3) δ: 7.27-7.22 (2H, m), 7.11 (1H, dd, J = 8.4, 2.3 Hz), 7.01 (1H, dd, J = 8.6, 2.1 Hz), 6.86 (1H, dd, J = 8.6, 2.8 Hz), 6.83-6.79 (1H, m), 6.75 (1H, dd, J = 8.6, 2.1 Hz), 6.60-6.62 (2H, m), 3.78 (3H, s), 3.33 (3H, s). |

TABLE 5-continued

| Compound | ¹H-NMR |
|---|---|
| 52 | 1H-NMR (CDCl3) δ: 7.49 (1H, s), 7.25 (1H, dd, J = 8.9, 5.2 Hz), 7.08 (1H, dd, J = 8.4, 2.3 Hz), 7.01 (1H, dd, J = 8.6, 2.1 Hz), 6.87-6.82 (2H, m), 6.76 (1H, dd, J = 8.6, 2.1 Hz), 6.65 (1H, dd, J = 8.6, 2.1 Hz), 3.78 (3H, s), 3.40 (3H, s). |
| 53 | 1H-NMR (CDCl3) δ: 7.69 (1H, s), 7.25-7.22 (1H, m), 7.08 (1H, dd, J = 8.5, 2.2 Hz), 7.01 (1H, dd, J = 8.5, 2.2 Hz), 6.87-6.81 (2H, m), 6.76 (1H, dd, J = 8.4, 2.6 Hz), 6.65 (1H, dd, J = 8.8, 2.9 Hz), 3.78 (3H, s), 3.40 (3H, s). |
| 54 | 1H-NMR (CDCl3) δ: 7.22 (1H, d, J = 9.5 Hz), 7.13 (1H, dd, J = 8.6, 2.1 Hz), 7.05 (1H, dd, J = 8.6, 2.1 Hz), 6.99-6.95 (1H, m), 6.94-6.90 (1H, m), 6.81 (1H, dd, J = 8.6, 2.8 Hz), 6.74-6.72 (2H, m), 6.65 (1H, d, J = 9.5 Hz), 3.94-3.88 (2H, m), 3.76 (3H, s), 1.16 (3H, t, J = 7.0 Hz). |
| 55 | 1H-NMR (CDCl3) δ: 7.46 (1H, s), 7.10 (1H, dd, J = 8.5, 2.2 Hz), 7.05 (1H, dd, J = 8.5, 2.2 Hz), 7.02-6.93 (2H, m), 6.81 (1H, dd, J = 8.4, 2.6 Hz), 6.75-6.73 (2H, m), 3.99-3.91 (2H, m), 3.77 (3H, s), 1.19 (3H, t, J = 7.0 Hz). |
| 56 | 1H-NMR (CDCl3) δ: 7.28-7.24 (3H, br m), 7.09-7.06 (2H, br m), 6.68 (1H, td, J = 8.5, 2.9 Hz), 6.46 (1H, ddd, J = 8.5, 2.9, 1.9 Hz), 5.92 (1H, tt, J = 56.6, 4.4 Hz), 3.86-3.79 (1H, m), 3.67-3.60 (1H, m), 2.85-2.74 (3H, m), 2.53-2.49 (1H, m). |
| 57 | 1H-NMR (CDCl3) δ: 7.67 (1H, s), 7.20-7.14 (2H, m), 7.04-6.93 (4H, m), 6.76-6.73 (1H, m), 4.00-3.87 (2H, m), 1.19 (3H, t, J = 7.1 Hz). |
| 58 | 1H-NMR (CDCl3) δ: 7.27 (1H, d, J = 9.5 Hz), 7.19-7.15 (1H, m), 7.11-7.07 (1H, m), 7.05-6.92 (4H, m), 6.72-6.69 (2H, m), 3.33 (3H, s). |
| 59 | 1H-NMR (CDCl3) δ: 7.50 (1H, s), 7.16-7.13 (1H, m), 7.11-7.08 (1H, m), 7.05-6.94 (4H, m), 6.74-6.72 (1H, m), 3.39 (3H, s). |
| 60 | 1H-NMR (CDCl3) δ: 7.71 (1H, s), 7.16-7.13 (1H, m), 7.12-7.09 (1H, m), 7.04-6.94 (4H, m), 6.73-6.71 (1H, m), 3.39 (3H, s). |
| 61 | 1H-NMR (CDCl3) δ: 7.66 (1H, s), 7.10 (1H, dd, J = 8.5, 2.2 Hz), 7.05 (1H, dd, J = 8.5, 2.2 Hz), 7.02-6.92 (2H, m), 6.81 (1H, dd, J = 8.4, 2.6 Hz), 6.75-6.73 (2H, m), 4.00-3.91 (2H, m), 3.76 (3H, s), 1.19 (3H, t, J = 7.0 Hz). |
| 62 | 1H-NMR (CDCl3) δ: 7.27 (1H, d, J = 9.5 Hz), 7.09 (1H, dd, J = 8.5, 2.2 Hz), 7.01-6.92 (3H, m), 6.83 (1H, dd, J = 8.5, 2.7 Hz), 6.76-6.70 (2H, m), 6.67 (1H, d, J = 9.5 Hz), 3.77 (3H, s), 3.34 (3H, s). |
| 63 | 1H-NMR (CDCl3) δ: 7.49 (1H, s), 7.06 (1H, dd, J = 8.6, 2.1 Hz), 7.03-6.95 (3H, m), 6.83 (1H, dd, J = 8.4, 2.6 Hz), 6.76-6.71 (2H, m), 3.77 (3H, s), 3.40 (3H, s). |
| 64 | 1H-NMR (CDCl3) δ: 7.70 (1H, s), 7.06 (1H, dd, J = 8.4, 2.3 Hz), 7.02-6.95 (3H, m), 6.83 (1H, dd, J = 8.4, 2.6 Hz), 6.76-6.71 (2H, m), 3.77 (3H, s), 3.40 (3H, s). |
| 65 | 1H-NMR (CDCl3) δ: 7.11-7.08 (2H, m), 6.98-6.95 (2H, m), 6.68-6.66 (1H, m), 6.28-6.26 (1H, m), 3.45 (2H, q, J = 7.0 Hz), 2.72-2.64 (4H, m), 0.95 (3H, t, J = 7.0 Hz). |
| 66 | 1H-NMR (CDCl3) δ: 7.26 (1H, d, J = 9.3 Hz), 7.21-7.18 (2H, m), 7.05-7.04 (2H, m), 6.77-6.71 (1H, m), 6.69 (1H, d, J = 9.3 Hz), 6.47-6.45 (1H, m), 3.89 (2H, q, J = 7.0 Hz), 1.15 (3H, t, J = 7.0 Hz). |
| 67 | 1H-NMR (CDCl3) δ: 7.51 (1H, d, J = 0.7 Hz), 7.19-7.17 (2H, m), 7.07-7.04 (2H, m), 6.80-6.73 (1H, m), 6.49-6.47 (1H, m), 3.93 (2H, q, J = 7.1 Hz), 1.18 (3H, t, J = 7.1 Hz). |
| 68 | 1H-NMR (CDCl3) δ: 7.71 (1H, d, J = 0.5 Hz), 7.20-7.16 (2H, m), 7.07-7.03 (2H, m), 6.80-6.73 (1H, m), 6.49-6.47 (1H, m), 3.93 (2H, q, J = 7.0 Hz), 1.18 (3H, t, J = 7.0 Hz). |
| 69 | 1H-NMR (CDCl3) δ: 7.40-7.23 (5H, m), 7.10 (1H, d, J = 7.6 Hz), 6.75-6.69 (1H, m), 6.70 (1H, d, J = 9.5 Hz), 6.53-6.51 (1H, m), 6.30 (1H, tt, J = 57.1, 4.7 Hz), 4.20-4.08 (2H, m). |
| 70 | 1H-NMR (CDCl3) δ: 7.73 (1H, s), 7.40-7.34 (2H, m), 7.31-7.27 (1H, m), 7.23-7.21 (1H, m), 7.11-7.10 (1H, m), 6.75 (1H, td, J = 8.5, 2.9 Hz), 6.55-6.53 (1H, m), 6.33 (1H, tt, J = 57.0, 4.6 Hz), 4.23-4.13 (2H, m). |
| 71 | 1H-NMR (CDCl3) δ: 7.53 (1H, s), 7.41-7.34 (2H, m), 7.31-7.27 (1H, m), 7.22 (1H, d, J = 7.3 Hz), 7.10 (1H, d, J = 7.6 Hz), 6.77-6.73 (1H, m), 6.55-6.53 (1H, m), 6.32 (1H, tt, J = 57.0, 4.7 Hz), 4.22-4.15 (2H, m). |
| 72 | 1H-NMR (CDCl3) δ: 7.25 (1H, d, J = 9.5 Hz), 7.17-7.14 (2H, m), 7.08 (1H, dd, J = 8.6, 2.2 Hz), 6.83 (1H, dd, J = 8.6, 2.8 Hz), 6.74 (1H, dd, J = 8.6, 2.8 Hz), 6.65-6.61 (2H, m), 6.46 (1H, d, J = 3.1 Hz), 3.95-3.87 (2H, m), 3.77 (3H, s), 3.62 (3H, s), 1.16 (3H, t, J = 7.0 Hz). |
| 73 | 1H-NMR (CDCl3) δ: 7.48 (1H, s), 7.15-7.13 (2H, m), 7.08 (1H, dd, J = 8.5, 2.1 Hz), 6.83 (1H, dd, J = 8.5, 2.6 Hz), 6.75 (1H, dd, J = 8.5, 2.6 Hz), 6.64 (1H, dd, J = 8.6, 3.1 Hz), 6.46 (1H, d, J = 3.1 Hz), 3.99-3.91 (2H, m), 3.77 (3H, s), 3.63 (3H, s), 1.18 (3H, t, J = 7.0 Hz). |
| 74 | 1H-NMR (CDCl3) δ: 7.68 (1H, s), 7.16-7.07 (3H, m), 6.83 (1H, dd, J = 8.4, 2.6 Hz), 6.75 (1H, dd, J = 8.5, 2.6 Hz), 6.64 (1H, dd, J = 8.9, 3.2 Hz), 6.46 (1H, d, J = 3.2 Hz), 3.98-3.93 (2H, m), 3.77 (3H, s), 3.63 (3H, s), 1.18 (3H, t, J = 7.0 Hz). |
| 75 | 1H-NMR (CDCl3) δ: 7.29 (1H, d, J = 9.2 Hz), 7.16 (1H, d, J = 8.9 Hz), 7.12 (1H, dd, J = 8.6, 2.1 Hz), 7.02 (1H, dd, J = 8.6, 2.1 Hz), 6.85 (1H, dd, J = 8.6, 2.8 Hz), 6.75 (1H, dd, J = 8.6, 2.8 Hz), 6.67-6.63 (2H, m), 6.43 (1H, d, J = 2.8 Hz), 3.77 (3H, s), 3.61 (3H, s), 3.34 (3H, s). |
| 76 | 1H-NMR (CDCl3) δ: 7.52 (1H, s), 7.17 (1H, d, J = 8.8 Hz), 7.09 (1H, dd, J = 8.5, 2.2 Hz), 7.03 (1H, dd, J = 8.3, 2.2 Hz), 6.84 (1H, dd, J = 8.3, 2.7 Hz), 6.76 (1H, dd, J = 8.5, 2.7 Hz), 6.66 (1H, dd, J = 8.8, 3.2 Hz), 6.44 (1H, d, J = 3.2 Hz), 3.77 (3H, s), 3.62 (3H, s), 3.40 (3H, s). |
| 77 | 1H-NMR (CDCl3) δ: 7.72 (1H, s), 7.16 (1H, d, J = 8.9 Hz), 7.09 (1H, dd, J = 8.6, 2.3 Hz), 7.03 (1H, dd, J = 8.6, 2.3 Hz), 6.84 (1H, dd, J = 8.6, 2.8 Hz), 6.76 (1H, dd, J = 8.6, 2.8 Hz), 6.66 (1H, dd, J = 8.9, 3.1 Hz), 6.44 (1H, d, J = 3.1 Hz), 3.77 (3H, s), 3.62 (3H, s), 3.40 (3H, s). |

TABLE 5-continued

| Compound | ¹H-NMR |
|---|---|
| 78 | 1H-NMR (CDCl3) δ: 7.36-7.33 (1H, m), 7.31-7.27 (1H, m), 7.26-7.23 (3H, m), 7.21 (1H, dd, J = 8.9, 5.2 Hz), 7.16-7.14 (1H, m), 6.80-6.76 (1H, m), 6.67-6.64 (2H, m), 3.94-3.83 (2H, m), 1.17 (3H, t, J = 7.0 Hz). |
| 79 | 1H-NMR (CDCl3) δ: 7.48 (1H, s), 7.37-7.34 (1H, m), 7.32-7.29 (1H, m), 7.25-7.20 (3H, m), 7.16-7.14 (1H, m), 6.82-6.78 (1H, m), 6.67 (1H, dd, J = 8.9, 3.1 Hz), 3.99-3.88 (2H, m), 1.19 (3H, t, J = 6.9 Hz). |
| 80 | 1H-NMR (CDCl3) δ: 7.68 (1H, s), 7.37-7.33 (1H, m), 7.32-7.29 (1H, m), 7.25-7.20 (3H, m), 7.16-7.14 (1H, m), 6.82-6.78 (1H, m), 6.67 (1H, dd, J = 8.7, 2.9 Hz), 3.98-3.89 (2H, m), 1.19 (3H, t, J = 7.0 Hz). |
| 81 | 1H-NMR (CDCl3) δ: 7.37-7.34 (1H, m), 7.32-7.27 (2H, m), 7.26-7.20 (3H, m), 7.11-7.08 (1H, m), 6.82-6.78 (1H, m), 6.69 (1H, d, J = 9.2 Hz), 6.63 (1H, dd, J = 8.7, 2.9 Hz), 3.33 (3H, s). |
| 82 | 1H-NMR (CDCl3) δ: 7.51 (1H, s), 7.38-7.35 (1H, m), 7.33-7.29 (1H, m), 7.27-7.22 (2H, m), 7.19-7.17 (1H, m), 7.10-7.09 (1H, m), 6.84-6.80 (1H, m), 6.64 (1H, dd, J = 8.7, 2.9 Hz), 3.39 (3H, s). |
| 83 | 1H-NMR (CDCl3) δ: 7.71 (1H, s), 7.38-7.35 (1H, m), 7.33-7.29 (1H, m), 7.28-7.22 (2H, m), 7.17-7.16 (1H, m), 7.11-7.09 (1H, m), 6.84-6.79 (1H, m), 6.64 (1H, dd, J = 8.7, 3.1 Hz), 3.39 (3H, s). |
| 84 | 1H-NMR (CDCl3) δ: 7.35-7.21 (5H, m), 7.15-7.13 (2H, m), 6.66 (1H, d, J = 9.3 Hz), 6.60 (1H, dd, J = 8.8, 2.9 Hz), 6.44 (1H, d, J = 2.9 Hz), 3.95-3.85 (2H, m), 3.60 (3H, s), 1.17 (3H, t, J = 7.0 Hz). |
| 85 | 1H-NMR (CDCl3) δ: 7.50 (1H, s), 7.35-7.28 (2H, m), 7.25-7.23 (2H, m), 7.16-7.14 (2H, m), 6.62 (1H, dd, J = 8.9, 3.1 Hz), 6.45 (1H, d, J = 3.1 Hz), 3.97-3.91 (2H, m), 3.61 (3H, s), 1.19 (3H, t, J = 7.0 Hz). |
| 86 | 1H-NMR (CDCl3) δ: 7.71 (1H, s), 7.35-7.23 (4H, m), 7.16-7.13 (2H, m), 6.62 (1H, dd, J = 8.8, 2.9 Hz), 6.45 (1H, d, J = 2.9 Hz), 3.99-3.89 (2H, m), 3.61 (3H, s), 1.19 (3H, t, J = 7.1 Hz). |
| 87 | 1H-NMR (CDCl3) δ: 7.33-7.21 (5H, m), 7.15-7.12 (1H, m), 6.97-6.89 (2H, m), 6.74-6.71 (1H, m), 6.67 (1H, d, J = 9.3 Hz), 3.94-3.86 (2H, m), 1.17 (3H, t, J = 7.0 Hz). |
| 88 | 1H-NMR (CDCl3) δ: 7.48 (1H, s), 7.34-7.19 (4H, m), 7.15-7.12 (1H, m), 6.99-6.91 (2H, m), 6.75-6.73 (1H, m), 3.99-3.89 (2H, m), 1.19 (3H, t, J = 7.0 Hz). |
| 89 | 1H-NMR (CDCl3) δ: 7.68 (1H, s), 7.33-7.19 (4H, m), 7.15-7.12 (1H, m), 6.99-6.91 (2H, m), 6.75-6.72 (1H, m), 3.98-3.89 (2H, m), 1.19 (3H, t, J = 7.1 Hz). |
| 90 | 1H-NMR (CDCl3) δ: 7.36-7.22 (5H, m), 7.15 (1H, d, J = 8.8 Hz), 7.11-7.09 (1H, m), 6.68 (1H, d, J = 9.3 Hz), 6.62 (1H, dd, J = 8.9, 2.9 Hz), 6.41 (1H, d, J = 2.9 Hz), 3.58 (3H, s), 3.33 (3H, s). |
| 91 | 1H-NMR, (CDCl3) δ: 7.54 (1H, s), 7.37-7.23 (3H, m), 7.21-7.20 (1H, m), 7.16 (1H, d, J = 8.8 Hz), 7.11-7.10 (1H, m), 6.64 (1H, dd, J = 8.9, 3.1 Hz), 6.42 (1H, d, J = 2.9 Hz), 3.59 (3H, s), 3.39 (3H, s). |
| 92 | 1H-NMR (CDCl3) δ: 7.74 (1H, s), 7.36-7.23 (3H, m), 7.21-7.18 (1H, m), 7.15 (1H, d, J = 8.8 Hz), 7.12-7.09 (1H, m), 6.64 (1H, dd, J = 8.8, 3.2 Hz), 6.42 (1H, d, J = 3.2 Hz), 3.59 (3H, s), 3.40 (3H, s). |
| 93 | 1H-NMR (CDCl3) δ: 7.35-7.18 (5H, m), 7.09-7.06 (1H, m), 6.98-6.90 (2H, m), 6.71-6.68 (2H, m), 3.33 (3H, s). |
| 94 | 1H-NMR (CDCl3) δ: 7.25-7.20 (2H, m), 7.18-7.14 (1H, m), 7.02-6.95 (2H, m), 6.93-6.88 (1H, m), 6.73 (1H, dd, J = 8.3, 1.5 Hz), 6.66 (1H, d, J = 9.3 Hz), 6.54 (1H, dd, J = 7.7, 1.3 Hz), 3.92-3.84 (5H, m), 1.16 (3H, t, J = 7.1 Hz). |
| 95 | 1H-NMR (CDCl3) δ: 7.67 (1H, s), 7.21-7.15 (2H, m), 7.02-6.90 (3H, m), 6.74 (1H, dd, J = 8.3, 1.4 Hz), 6.54 (1H, dd, J = 7.7, 1.4 Hz), 3.97-3.88 (2H, m), 3.84 (3H, s), 1.18 (3H, t, J = 7.1 Hz). |
| 96 | 1H-NMR (CDCl3) δ: 7.47 (1H, s), 7.21-7.15 (2H, m), 7.02-6.90 (3H, m), 6.74 (1H, dd, J = 8.4, 1.4 Hz), 6.54 (1H, dd, J = 7.8, 1.4 Hz), 3.97-3.88 (2H, m), 3.84 (3H, s), 1.18 (3H, t, J = 7.1 Hz). |
| 97 | 1H-NMR (CDCl3) δ: 7.51 (1H, s), 7.35-7.23 (3H, m), 7.18-7.15 (1H, m), 7.09-7.06 (1H, m), 7.00-6.92 (2H, m), 6.73-6.70 (1H, m), 3.39 (3H, s). |
| 98 | 1H-NMR (CDCl3) δ: 7.71 (1H, s), 7.35-7.23 (3H, m), 7.18-7.15 (1H, m), 7.09-7.07 (1H, m), 7.00-6.93 (2H, m), 6.73-6.70 (1H, m), 3.39 (3H, s). |
| 99 | 1H-NMR (CDCl3) δ: 7.29-7.26 (1H, m), 7.20-7.16 (1H, m), 7.13-7.09 (1H, m), 7.03-6.96 (2H, m), 6.91 (1H, td, J = 8.5, 2.7 Hz), 6.74 (1H, dd, J = 8.3, 1.5 Hz), 6.68 (1H, d, J = 9.3 Hz), 6.51 (1H, dd, J = 7.8, 1.5 Hz), 3.86 (3H, s), 3.32 (3H, s). |
| 100 | 1H-NMR (CDCl3) δ: 7.70 (1H, s), 7.17-7.10 (2H, m), 7.03-6.97 (2H, m), 6.93 (1H, td, J = 8.5, 2.6 Hz), 6.76 (1H, dd, J = 8.3, 1.2 Hz), 6.52 (1H, dd, J = 7.7, 1.2 Hz), 3.85 (3H, s), 3.38 (3H, s). |
| 101 | 1H-NMR (CDCl3) δ: 7.50 (1H, s), 7.17-7.09 (2H, m), 7.03-6.97 (2H, m), 6.93 (1H, td, J = 8.5, 2.6 Hz), 6.76 (1H, dd, J = 8.3, 1.4 Hz), 6.52 (1H, dd, J = 7.7, 1.4 Hz), 3.85 (3H, s), 3.38 (3H, s). |
| 102 | 1H-NMR (CDCl3) δ: 7.23 (1H, d, J = 9.3 Hz), 7.18 (1H, dd, J = 8.3, 2.2 Hz), 7.07 (1H, dd, J = 8.3, 2.2 Hz), 6.83 (1H, dd, J = 8.3, 2.7 Hz), 6.73 (1H, dd, J = 8.3, 2.7 Hz), 6.64 (1H, d, J = 9.3 Hz), 6.29 (1H, d, J = 2.7 Hz), 6.07 (1H, d, J = 2.7 Hz), 3.93-3.87 (2H, m), 3.81 (3H, s), 3.77 (3H, s), 3.61 (3H, s), 1.16 (3H, t, J = 7.1 Hz). |
| 103 | 1H-NMR (CDCl3) δ: 7.28 (1H, d, J = 9.5 Hz), 7.14 (1H, dd, J = 8.5, 2.2 Hz), 7.02 (1H, dd, J = 8.5, 2.2 Hz), 6.85 (1H, dd, J = 8.5, 2.7 Hz), 6.74 (1H, dd, J = 8.5, 2.7 Hz), 6.66 (1H, d, J = 9.5 Hz), 6.31 (1H, d, J = 2.9 Hz), 6.03 (1H, d, J = 2.9 Hz), 3.82 (3H, s), 3.77 (3H, s), 3.59 (3H, s), 3.33 (3H, s). |

TABLE 5-continued

| Compound | ¹H-NMR |
|---|---|
| 104 | 1H-NMR (CDCl3) δ: 7.32-7.18 (5H, m), 7.16-7.14 (1H, m), 6.93 (1H, dd, J = 8.3, 7.9 Hz), 6.70 (1H, dd, J = 8.3, 1.2 Hz), 6.66 (1H, d, J = 9.3 Hz), 6.54 (1H, dd, J = 7.7, 1.2 Hz), 3.93-3.83 (5H, m), 1.16 (3H, t, J = 7.1 Hz). |
| 105 | 1H-NMR (CDCl3) δ: 7.68 (1H, s), 7.32-7.20 (4H, m), 7.17-7.14 (1H, m), 6.95 (1H, dd, J = 8.3, 7.9 Hz), 6.71 (1H, dd, J = 8.3, 1.5 Hz), 6.54 (1H, dd, J = 7.9, 1.5 Hz), 3.98-3.88 (2H, m), 3.83 (3H, s), 1.18 (3H, t, J = 7.1 Hz). |
| 106 | 1H-NMR (CDCl3) δ: 7.72 (1H, s), 7.34-7.25 (2H, m), 7.24-7.20 (1H, m), 7.19-7.16 (1H, m), 7.11-7.09 (1H, m), 6.95 (1H, dd, J = 8.3, 7.8 Hz), 6.73 (1H, dd, J = 8.3, 1.5 Hz), 6.52 (1H, dd, J = 7.8, 1.5 Hz), 3.84 (3H, s), 3.39 (3H, s). |
| 107 | 1H-NMR (CDCl3) δ: 7.48 (1H, s), 7.32-7.25 (2H, m), 7.23-7.20 (2H, m), 7.16-7.14 (1H, m), 6.95 (1H, dd, J = 8.3, 7.6 Hz), 6.71 (1H, dd, J = 8.3, 1.2 Hz), 6.55 (1H, dd, J = 7.6, 1.2 Hz), 3.98-3.89 (2H, m), 3.83 (3H, s), 1.19 (3H, t, J = 7.0 Hz). |
| 108 | 1H-NMR (CDCl3) δ: 7.33-7.19 (6H, m), 7.11-7.05 (2H, m), 6.99-6.97 (1H, m), 6.89 (1H, dd, J = 7.6, 1.7 Hz), 6.69 (1H, d, J = 9.5 Hz), 3.33 (3H, s). |
| 109 | 1H-NMR (CDCl3) δ: 7.30-7.14 (7H, m), 7.06-7.04 (1H, m), 6.98-6.96 (1H, m), 6.93-6.91 (1H, m), 6.66 (1H, d, J = 9.5 Hz), 3.92-3.88 (2H, m), 1.17 (3H, t, J = 7.0 Hz). |
| 110 | 1H-NMR (CDCl3) δ: 7.31-7.27 (2H, m), 7.19-7.15 (1H, m), 7.12-7.10 (2H, m), 7.02-7.00 (2H, m), 6.93-6.90 (2H, m), 6.69 (1H, d, J = 9.5 Hz), 3.33 (3H, s). |
| 111 | 1H-NMR (CDCl3) δ: 7.27-7.15 (4H, m), 7.09 (1H, td, J = 7.7, 1.9 Hz), 7.03-6.97 (2H, m), 6.92-6.91 (2H, m), 6.67 (1H, d, J = 9.3 Hz), 3.91-3.87 (2H, m), 1.16 (3H, t, J = 7.0 Hz). |
| 112 | 1H-NMR (CDCl3) δ: 7.30-7.26 (2H, m), 7.10-7.08 (2H, m), 7.02-6.99 (2H, m), 6.90 (1H, dd, J = 7.6, 1.7 Hz), 6.82 (1H, dd, J = 8.5, 2.7 Hz), 6.72 (1H, dd, J = 8.5, 2.7 Hz), 6.66 (1H, d, J = 9.3 Hz), 3.76 (3H, s), 3.34 (3H, s). |
| 113 | 1H-NMR (CDCl3) δ: 7.26-7.24 (2H, m), 7.15-7.13 (1H, m), 7.09-7.04 (2H, m), 7.01-6.98 (1H, m), 6.93-6.91 (1H, m), 6.81 (1H, dd, J = 8.5, 2.7 Hz), 6.71 (1H, dd, J = 8.5, 2.7 Hz), 6.64 (1H, d, J = 9.3 Hz), 3.93-3.89 (2H, m), 3.75 (3H, s), 1.16 (3H, t, J = 7.0 Hz). |
| 114 | 1H-NMR (CDCl3) δ: 7.30-7.28 (3H, m), 7.21 (1H, dd, J = 8.3, 2.2 Hz), 7.13-7.11 (2H, m), 7.08-7.06 (1H, m), 7.04-7.02 (1H, m), 6.90 (1H, dd, J = 7.8, 1.7 Hz), 6.69 (1H, d, J = 9.3 Hz), 3.32 (3H, s). |
| 115 | 1H-NMR (CDCl3) δ: 7.30-7.24 (3H, m), 7.22-7.20 (1H, m), 7.18-7.16 (1H, m), 7.12-7.10 (2H, m), 7.03-7.01 (1H, m), 6.92 (1H, dd, J = 7.6, 1.7 Hz), 6.67 (1H, d, J = 9.3 Hz), 3.89-3.86 (2H, m), 1.16 (3H, t, J = 7.0 Hz). |
| 116 | 1H-NMR (CDCl3) δ: 7.27-7.25 (1H, m), 7.04-7.02 (1H, m), 6.96-6.94 (5H, m), 6.85 (1H, dd, J = 7.6, 1.7 Hz), 2.91-2.67 (3H, m), 2.85 (3H, s), 2.44-2.40 (1H, m), 2.25 (3H, s). |
| 117 | 1H-NMR (CDCl3) δ: 7.27-7.25 (1H, m), 7.04-7.02 (1H, m), 6.97-6.94 (5H, m), 6.84 (1H, dd, J = 7.6, 1.7 Hz), 3.67-3.60 (1H, m), 3.29-3.25 (1H, m), 2.88-2.66 (3H, m), 2.42-2.38 (1H, m), 2.24 (3H, s), 0.96 (3H, t, J = 7.0 Hz). |
| 118 | 1H-NMR (CDCl3) δ: 7.52 (1H, s), 7.34-7.26 (2H, m), 7.24-7.20 (1H, m), 7.19-7.17 (1H, m), 7.11-7.09 (1H, m), 6.95 (1H, dd, J = 8.3, 7.6 Hz), 6.73 (1H, dd, J = 8.3, 1.2 Hz), 6.52 (1H, dd, J = 7.6, 1.2 Hz), 3.84 (3H, s), 3.38 (3H, s). |
| 119 | 1H-NMR (CDCl3) δ: 7.23 (1H, d, J = 9.5 Hz), 7.14 (1H, dd, J = 8.4, 2.2 Hz), 7.07 (1H, dd, J = 8.4, 2.2 Hz), 6.96 (1H, dd, J = 8.3, 7.6 Hz), 6.81 (1H, dd, J = 8.4, 2.6 Hz), 6.72-6.70 (2H, m), 6.64 (1H, d, J = 9.5 Hz), 6.55 (1H, dd, J = 7.6, 1.5 Hz), 3.93-3.86 (2H, m), 3.84 (3H, s), 3.76 (3H, s), 1.16 (3H, t, J = 7.0 Hz). |
| 120 | 1H-NMR (CDCl3) δ: 7.34-7.19 (5H, m), 7.11-7.08 (1H, m), 6.96-6.92 (1H, m), 6.71 (1H, dd, J = 8.3, 1.5 Hz), 6.68 (1H, d, J = 9.3 Hz), 6.51 (1H, dd, J = 7.6, 1.5 Hz), 3.84 (3H, s), 3.32 (3H, s). |
| 121 | 1H-NMR (CDCl3) δ: 7.46 (1H, s), 7.11 (1H, dd, J = 8.4, 2.1 Hz), 7.07 (1H, dd, J = 8.4, 2.1 Hz), 6.97 (1H, dd, J = 8.4, 7.8 Hz), 6.80 (1H, dd, J = 8.4, 2.7 Hz), 6.74-6.71 (2H, m), 6.55 (1H, dd, J = 7.8, 1.3 Hz), 3.99-3.90 (2H, m), 3.84 (3H, s), 3.76 (3H, s), 1.18 (3H, t, J = 7.0 Hz). |
| 122 | 1H-NMR (CDCl3) δ: 7.66 (1H, s), 7.12-7.06 (2H, m), 6.99-6.95 (1H, m), 6.80 (1H, dd, J = 8.5, 2.7 Hz), 6.74-6.71 (2H, m), 6.55 (1H, dd, J = 7.6, 1.5 Hz), 3.99-3.90 (2H, m), 3.84 (3H, s), 3.76 (3H, s), 1.18 (3H, t, J = 7.0 Hz). |
| 123 | 1H-NMR (CDCl3) δ: 7.28-7.26 (1H, m), 7.10 (1H, dd, J = 8.4, 2.3 Hz), 7.01 (1H, dd, J = 8.4, 2.3 Hz), 6.96 (1H, dd, J = 8.3, 7.6 Hz), 6.82 (1H, dd, J = 8.4, 2.4 Hz), 6.74-6.70 (2H, m), 6.66 (1H, d, J = 9.2 Hz), 6.52 (1H, dd, J = 7.6, 1.4 Hz), 3.85 (3H, s), 3.76 (3H, s), 3.33 (3H, s). |
| 124 | 1H-NMR (CDCl3) δ: 7.29-7.25 (1H, m), 7.22 (1H, d, J = 9.3 Hz), 6.87 (1H, ddd, J = 8.8, 7.8, 2.9 Hz), 6.83-6.75 (3H, m), 6.72-6.68 (2H, m), 3.95-3.80 (2H, m), 1.20 (3H, t, J = 7.0 Hz). |
| 125 | 1H-NMR (CDCl3) δ: 7.27-7.22 (2H, m), 7.19-7.15 (1H, m), 7.02 (1H, td, J = 8.4, 2.7 Hz), 6.93 (1H, td, J = 8.4, 2.7 Hz), 6.66 (1H, d, J = 9.3 Hz), 6.31 (1H, d, J = 2.7 Hz), 6.06 (1H, d, J = 2.7 Hz), 3.91-3.85 (2H, m), 3.82 (3H, s), 3.63 (3H, s), 1.16 (3H, t, J = 7.0 Hz). |
| 126 | 1H-NMR (CDCl3) δ: 7.28 (1H, d, J = 9.5 Hz), 7.23-7.19 (1H, m), 7.14-7.10 (1H, m), 7.03 (1H, td, J = 8.5, 2.7 Hz), 6.94 (1H, td, J = 8.5, 2.7 Hz), 6.68 (1H, d, J = 9.5 Hz), 6.32 (1H, d, J = 2.7 Hz), 6.03 (1H, d, J = 2.7 Hz), 3.83 (3H, s), 3.61 (3H, s), 3.32 (3H, s). |
| 127 | 1H-NMR (CDCl3) δ: 7.50 (1H, s), 7.33-7.20 (5H, m), 7.17-7.13 (1H, m), 7.07 (1H, td, J = 7.5, 1.9 Hz), 6.99 (1H, td, J = 7.5, 1.9 Hz), 6.93 (1H, dd, J = 7.5, 1.9 Hz), 3.99-3.89 (2H, m), 1.19 (3H, t, J = 7.1 Hz). |
| 128 | 1H-NMR (CDCl3) δ: 7.70 (1H, s), 7.32-7.20 (5H, m), 7.17-7.15 (1H, m), 7.07 (1H, td, J = 7.7, 1.8 Hz), 6.99 (1H, td, J = 7.7, 1.8 Hz), 6.92 (1H, dd, J = 7.7, 1.8 Hz), 3.99-3.89 (2H, m), 1.19 (3H, t, J = 7.0 Hz). |

TABLE 5-continued

| Compound | ¹H-NMR |
|---|---|
| 129 | 1H-NMR (CDCl3) δ: 7.54 (1H, s), 7.32-7.21 (4H, m), 7.18-7.15 (1H, m), 7.11-7.07 (2H, m), 7.00 (1H, td, J = 7.5, 1.3 Hz), 6.90 (1H, dd, J = 7.5, 1.3 Hz), 3.39 (3H, s). |
| 130 | 1H-NMR (CDCl3) δ: 7.74 (1H, s), 7.33-7.30 (1H, m), 7.29-7.25 (2H, m), 7.24-7.21 (1H, m), 7.17-7.15 (1H, m), 7.11-7.07 (2H, m), 6.99 (1H, td, J = 7.6, 1.3 Hz), 6.90 (1H, dd, J = 7.6, 1.5 Hz), 3.40 (3H, s). |
| 131 | 1H-NMR (CDCl3) δ: 7.26-7.22 (1H, m), 7.20-7.15 (2H, m), 7.06 (1H, td, J = 8.4, 2.7 Hz), 6.97 (1H, td, J = 8.4, 2.7 Hz), 6.74-6.67 (2H, m), 6.54 (1H, dq, J = 8.5, 1.5 Hz), 3.93-3.82 (2H, m), 1.16 (3H, t, J = 7.1 Hz). |
| 132 | 1H-NMR (CDCl3) δ: 7.42 (1H, s), 7.23-7.16 (2H, m), 7.07 (1H, td, J = 8.4, 2.7 Hz), 6.98 (1H, td, J = 8.4, 2.7 Hz), 6.74 (1H, td, J = 8.3, 2.8 Hz), 6.55 (1H, m), 3.98-3.86 (2H, m), 1.19 (3H, t, J = 7.0 Hz). |
| 133 | 1H-NMR (CDCl3) δ: 7.63 (1H, s), 7.21-7.19 (2H, m), 7.07 (1H, td, J = 8.4, 2.7 Hz), 6.98 (1H, td, J = 8.4, 2.7 Hz), 6.74 (1H, td, J = 8.3, 2.9 Hz), 6.55 (1H, m), 3.96-3.89 (2H, m), 1.19 (3H, t, J = 7.1 Hz). |
| 134 | 1H-NMR (CDCl3) δ: 7.69 (1H, s), 7.07 (1H, dd, J = 8.6, 2.1 Hz), 7.02 (1H, dd, J = 8.6, 2.1 Hz), 6.98 (1H, dd, J = 8.4, 7.6 Hz), 6.82 (1H, dd, J = 8.4, 2.6 Hz), 6.75-6.72 (2H, m), 6.52 (1H, dd, J = 7.8, 1.4 Hz), 3.85 (3H, s), 3.76 (3H, s), 3.39 (3H, s). |
| 135 | 1H-NMR (CDCl3) δ: 7.49 (1H, s), 7.30-7.26 (2H, m), 7.23-7.21 (1H, m), 7.15-7.10 (3H, m), 7.04 (1H, td, J = 7.6, 1.3 Hz), 6.93 (1H, dd, J = 7.6, 1.5 Hz), 3.98-3.87 (2H, m), 1.19 (3H, t, J = 7.0 Hz). |
| 136 | 1H-NMR (CDCl3) δ: 7.69 (1H, s), 7.07 (1H, dd, J = 8.4, 2.3 Hz), 7.03-6.96 (2H, m), 6.82 (1H, dd, J = 8.5, 2.7 Hz), 6.75-6.71 (2H, m), 6.52 (1H, dd, J = 7.7, 1.3 Hz), 3.85 (3H, s), 3.76 (3H, s), 3.39 (3H, s). |
| 137 | 1H-NMR (CDCl3) δ: 7.69 (1H, s), 7.29-7.27 (2H, m), 7.23-7.21 (1H, m), 7.15-7.10 (3H, m), 7.04 (1H, td, J = 7.5, 1.3 Hz), 6.93 (1H, dd, J = 7.6, 1.7 Hz), 3.99-3.86 (2H, m), 1.19 (3H, t, J = 7.1 Hz). |
| 138 | 1H-NMR (CDCl3) δ: 7.46 (1H, s), 7.28 (1H, dd, J = 8.7, 5.0 Hz), 6.89 (1H, ddd, J = 8.9, 7.6, 3.1 Hz), 6.82-6.75 (3H, m), 6.71 (1H, dd, J = 8.4, 2.9 Hz), 3.98-3.86 (2H, m), 1.23 (3H, t, J = 7.0 Hz). |
| 139 | 1H-NMR (CDCl3) δ: 7.66 (1H, s), 7.30-7.26 (1H, m), 6.91-6.86 (1H, m), 6.83-6.75 (3H, m), 6.71 (1H, dd, J = 8.4, 3.1 Hz), 3.99-3.85 (2H, m), 1.22 (3H, t, J = 7.0 Hz). |
| 140 | 1H-NMR (CDCl3) δ: 7.29-7.27 (2H, m), 6.88 (1H, ddd, J = 8.8, 7.8, 2.9 Hz), 6.82-6.76 (2H, m), 6.72-6.67 (3H, m), 3.33 (3H, s). |
| 141 | 1H-NMR (CDCl3) δ: 7.52 (1H, s), 7.31-7.28 (2H, m), 7.23 (1H, dd, J = 8.0, 2.1 Hz), 7.16-7.03 (4H, m), 6.91 (1H, dd, J = 7.6, 1.5 Hz), 3.38 (3H, s). |
| 142 | 1H-NMR (CDCl3) δ: 7.72 (1H, s), 7.31-7.28 (2H, m), 7.24-7.22 (1H, m), 7.15-7.03 (4H, m), 6.91 (1H, dd, J = 7.6, 1.2 Hz), 3.39 (3H, s). |
| 143 | 1H-NMR (CDCl3) δ: 7.27-7.24 (2H, m), 7.12-6.97 (6H, m), 6.92 (1H, dd, J = 7.6, 1.7 Hz), 6.65 (1H, d, J = 9.3 Hz), 3.96-3.83 (2H, m), 2.27 (3H, s), 1.16 (3H, t, J = 7.0 Hz). |
| 144 | 1H-NMR (CDCl3) δ: 7.49 (1H, s), 7.30 (1H, dd, J = 8.9, 5.2 Hz), 6.91 (1H, ddd, J = 8.9, 7.6, 3.1 Hz), 6.80 (1H, tt, J = 8.9, 2.4 Hz), 6.77-6.68 (3H, m), 3.40 (3H, s). |
| 145 | 1H-NMR (CDCl3) δ: 7.69 (1H, s), 7.30 (1H, dd, J = 8.9, 5.2 Hz), 6.91 (1H, ddd, J = 8.9, 7.6, 3.1 Hz), 6.80 (1H, tt, J = 8.9, 2.3 Hz), 6.76-6.74 (1H, m), 6.72-6.68 (2H, m), 3.40 (3H, s). |
| 146 | 1H-NMR (CDCl3) δ: 7.31-7.26 (2H, m), 7.12-7.05 (3H, m), 7.02-6.96 (3H, m), 6.90 (1H, dd, J = 7.7, 1.8 Hz), 6.67 (1H, d, J = 9.3 Hz), 3.32 (3H, s), 2.28 (3H, s). |
| 147 | 1H-NMR (CDCl3) δ: 7.49 (1H, s), 7.28-7.26 (1H, m), 7.21-7.15 (2H, m), 7.11 (1H, td, J = 7.7, 1.7 Hz), 7.04-6.97 (2H, m), 6.95-6.90 (2H, m), 3.98-3.89 (2H, m), 1.19 (3H, t, J = 7.1 Hz). |
| 148 | 1H-NMR (CDCl3) δ: 7.69 (1H, s), 7.28-7.25 (1H, m), 7.20-7.15 (2H, m), 7.11 (1H, td, J = 7.7, 1.7 Hz), 7.04-6.97 (2H, m), 6.95-6.90 (2H, m), 3.98-3.87 (2H, m), 1.19 (3H, t, J = 7.1 Hz). |
| 149 | 1H-NMR (CDCl3) δ: 7.52 (1H, s), 7.29 (1H, dd, J = 8.1, 1.2 Hz), 7.17-7.09 (3H, m), 7.06-6.99 (2H, m), 6.96-6.89 (2H, m), 3.39 (3H, s). |
| 150 | 1H-NMR (CDCl3) δ: 7.73 (1H, s), 7.28 (1H, dd, J = 8.1, 1.2 Hz), 7.16-7.10 (3H, m), 7.06-6.99 (2H, m), 6.96-6.89 (2H, m), 3.39 (3H, s). |
| 151 | 1H-NMR (CDCl3) δ: 7.48 (1H, s), 7.27-7.26 (1H, m), 7.11-7.05 (3H, m), 7.01 (1H, td, J = 7.6, 1.5 Hz), 6.93 (1H, dd, J = 7.6, 1.5 Hz), 6.81 (1H, dd, J = 8.6, 2.8 Hz), 6.72 (1H, dd, J = 8.6, 2.8 Hz), 3.99-3.92 (2H, m), 3.75 (3H, s), 1.19 (3H, t, J = 7.0 Hz). |
| 152 | 1H-NMR (CDCl3) δ: 7.68 (1H, s), 7.27-7.25 (1H, m), 7.12-7.06 (3H, m), 7.01 (1H, td, J = 7.5, 1.3 Hz), 6.93 (1H, dd, J = 7.7, 1.8 Hz), 6.80 (1H, dd, J = 8.4, 2.6 Hz), 6.72 (1H, dd, J = 8.4, 2.6 Hz), 4.00-3.91 (2H, m), 3.75 (3H, s), 1.19 (3H, t, J = 7.0 Hz). |
| 153 | 1H-NMR (CDCl3) δ: 7.22-7.20 (2H, m), 7.13-7.06 (2H, m), 6.98 (1H, td, J = 8.5, 2.5 Hz), 6.75-6.69 (2H, m), 6.51 (1H, dq, J = 8.5, 1.5 Hz), 3.32 (3H, s). |
| 154 | 1H-NMR (CDCl3) δ: 7.46 (1H, s), 7.20-7.16 (1H, m), 7.12-7.08 (2H, m), 6.99 (1H, td, J = 8.4, 2.7 Hz), 6.75 (1H, td, J = 8.4, 2.7 Hz), 6.53 (1H, m), 3.38 (3H, s). |
| 155 | 1H-NMR (CDCl3) δ: 7.66 (1H, s), 7.19-7.16 (1H, m), 7.14-7.11 (1H, m), 7.08 (1H, td, J = 8.4, 2.5 Hz), 6.99 (1H, td, J = 8.4, 2.5 Hz), 6.75 (1H, td, J = 8.3, 2.8 Hz), 6.53 (1H, m), 3.38 (3H, s). |

TABLE 5-continued

| Compound | ¹H-NMR |
|---|---|
| 156 | 1H-NMR (CDCl3) δ: 7.48 (1H, s), 7.27-7.25 (1H, m), 7.11-7.06 (3H, m), 7.04-6.98 (3H, m), 6.93 (1H, dd, J = 7.6, 1.7 Hz), 4.00-3.87 (2H, m), 2.28 (3H, s), 1.18 (3H, t, J = 7.0 Hz). |
| 157 | 1H-NMR (CDCl3) δ: 7.69 (1H, s), 7.27-7.25 (1H, m), 7.10-6.98 (6H, m), 6.93 (1H, dd, J = 7.7, 1.8 Hz), 4.00-3.87 (2H, m), 2.28 (3H, s), 1.18 (3H, t, J = 7.0 Hz). |
| 158 | 1H-NMR (CDCl3) δ: 7.52 (1H, s), 7.29-7.27 (1H, m), 7.12-7.08 (2H, m), 7.05-6.96 (4H, m), 6.91 (1H, dd, J = 7.6, 1.7 Hz), 3.38 (3H, s), 2.28 (3H, s). |
| 159 | 1H-NMR (CDCl3) δ: 7.72 (1H, s), 7.29-7.26 (1H, m), 7.12-7.08 (2H, m), 7.04-6.96 (4H, m), 6.91 (1H, dd, J = 7.6, 1.5 Hz), 3.39 (3H, s), 2.28 (3H, s). |
| 160 | 1H-NMR (CDCl3) δ: 7.30 (1H, dd, J = 8.9, 4.9 Hz), 7.25 (1H, d, J = 9.5 Hz), 6.94-6.82 (3H, m), 6.73-6.68 (2H, m), 3.32 (3H, s). |
| 161 | 1H-NMR (CDCl3) δ: 7.48 (1H, s), 7.31 (1H, dd, J = 8.9, 5.2 Hz), 6.94 (1H, ddd, J = 8.9, 7.6, 3.1 Hz), 6.87-6.83 (2H, m), 6.71 (1H, dd, J = 8.3, 3.1 Hz), 3.39 (3H, s). |
| 162 | 1H-NMR (CDCl3) δ: 7.52 (1H, s), 7.28 (1H, dd, J = 7.7, 1.1 Hz), 7.11 (1H, td, J = 7.7, 1.7 Hz), 7.08-7.00 (3H, m), 6.91 (1H, dd, J = 7.7, 1.7 Hz), 6.82 (1H, dd, J = 8.5, 2.7 Hz), 6.73 (1H, dd, J = 8.5, 2.7 Hz), 3.76 (3H, s), 3.40 (3H, s). |
| 163 | 1H-NMR (CDCl3) δ: 7.72 (1H, s), 7.28 (1H, dd, J = 8.1, 1.2 Hz), 7.10 (1H, td, J = 7.7, 1.7 Hz), 7.07-7.00 (3H, m), 6.91 (1H, dd, J = 7.7, 1.7 Hz), 6.82 (1H, dd, J = 8.5, 2.7 Hz), 6.73 (1H, dd, J = 8.5, 2.7 Hz), 3.76 (3H, s), 3.40 (3H, s). |
| 164 | 1H-NMR (CDCl3) δ: 7.22 (1H, d, J = 9.3 Hz), 7.10 (1H, dd, J = 8.4, 2.3 Hz), 7.01-6.98 (1H, m), 6.84 (1H, dd, J = 8.4, 2.3 Hz), 6.75-6.70 (2H, m), 6.67 (1H, d, J = 9.3 Hz), 6.53-6.50 (1H, m), 5.93 (1H, s), 3.95-3.89 (2H, m), 1.17 (3H, t, J = 7.0 Hz). |
| 165 | 1H-NMR (CDCl3) δ: 7.44 (1H, s), 7.07 (1H, dd, J = 8.4, 2.3 Hz), 7.00 (1H, dd, J = 8.4, 2.3 Hz), 6.83 (1H, dd, J = 8.3, 2.7 Hz), 6.77-6.72 (2H, m), 6.54-6.51 (1H, m), 5.33 (1H, s), 3.99-3.91 (2H, m), 1.19 (3H, t, J = 7.1 Hz). |
| 166 | 1H-NMR (CDCl3) δ: 7.43 (1H, s), 7.09 (1H, dd, J = 8.5, 2.2 Hz), 7.04-7.00 (1H, m), 6.84 (1H, dd, J = 8.5, 2.2 Hz), 6.78-6.71 (2H, m), 6.54-6.51 (1H, m), 4.02-3.92 (4H, m), 1.40 (3H, t, J = 7.1 Hz), 1.18 (3H, t, J = 7.1 Hz). |
| 167 | 1H-NMR (CDCl3) δ: 7.63 (1H, s), 7.09 (1H, dd, J = 8.4, 2.3 Hz), 7.03 (1H, dd, J = 8.4, 2.3 Hz), 6.84 (1H, dd, J = 8.4, 2.6 Hz), 6.76-6.71 (2H, m), 6.54-6.51 (1H, m), 4.02-3.92 (4H, m), 1.40 (3H, t, J = 7.0 Hz), 1.18 (3H, t, J = 7.0 Hz). |
| 168 | 1H-NMR (CDCl3) δ: 7.68 (1H, s), 7.31 (1H, dd, J = 8.9, 5.2 Hz), 6.94 (1H, ddd, J = 8.9, 8.0, 3.1 Hz), 6.87-6.83 (2H, m), 6.71 (1H, dd, J = 8.3, 3.1 Hz), 3.39 (3H, s). |
| 169 | 1H-NMR (CDCl3) δ: 7.30-7.27 (1H, m), 7.20 (1H, d, J = 9.3 Hz), 6.94-6.87 (3H, m), 6.72-6.68 (2H, m), 3.94-3.79 (2H, m), 1.20 (3H, t, J = 7.0 Hz). |
| 170 | 1H-NMR (CDCl3) δ: 7.29 (1H, dd, J = 8.9, 5.2 Hz), 7.24 (1H, d, J = 9.2 Hz), 6.89 (1H, ddd, J = 8.9, 7.6, 3.1 Hz), 6.78 (1H, dt, J = 10.4, 1.8 Hz), 6.73-6.67 (3H, m), 4.01 (3H, t, J = 1.4 Hz), 3.34 (3H, s). |
| 171 | 1H-NMR (CDCl3) δ: 7.45 (1H, s), 7.30 (1H, dd, J = 8.8, 5.1 Hz), 6.95-6.87 (3H, m), 6.72 (1H, dd, J = 8.4, 3.1 Hz), 3.99-3.84 (2H, m), 1.22 (3H, t, J = 7.1 Hz). |
| 172 | 1H-NMR (CDCl3) δ: 7.65 (1H, s), 7.29 (1H, dd, J = 8.8, 5.1 Hz), 6.95-6.86 (3H, m), 6.72 (1H, dd, J = 8.4, 3.1 Hz), 3.97-3.86 (2H, m), 1.22 (3H, t, J = 7.1 Hz). |
| 173 | 1H-NMR (CDCl3) δ: 7.19 (1H, d, J = 9.2 Hz), 7.12 (1H, dd, J = 8.4, 2.3 Hz), 7.02 (1H, dd, J = 8.4, 2.3 Hz), 6.84 (1H, dd, J = 8.4, 2.4 Hz), 6.76-6.70 (2H, m), 6.65 (1H, d, J = 9.2 Hz), 6.53-6.50 (1H, m), 3.94-3.86 (4H, m), 1.79-1.72 (2H, m), 1.51-1.44 (2H, m), 1.16 (3H, t, J = 6.9 Hz), 0.97 (3H, t, J = 7.3 Hz). |
| 174 | 1H-NMR (CDCl3) δ: 7.43 (1H, s), 7.09 (1H, dd, J = 8.4, 2.3 Hz), 7.02 (1H, dd, J = 8.4, 2.3 Hz), 6.84 (1H, dd, J = 8.6, 2.8 Hz), 6.76-6.72 (2H, m), 6.54-6.52 (1H, m), 3.98-3.90 (4H, m), 1.77-1.72 (2H, m), 1.51-1.44 (2H, m), 1.18 (3H, t, J = 7.0 Hz), 0.97 (3H, t, J = 7.3 Hz). |
| 175 | 1H-NMR (CDCl3) δ: 7.63 (1H, s), 7.09 (1H, dd, J = 8.3, 2.2 Hz), 7.02 (1H, dd, J = 8.3, 2.2 Hz), 6.84 (1H, dd, J = 8.3, 2.7 Hz), 6.76-6.71 (2H, m), 6.55-6.51 (1H, m), 3.98-3.90 (4H, m), 1.78-1.71 (2H, m), 1.51-1.43 (2H, m), 1.18 (3H, t, J = 7.1 Hz), 0.97 (3H, t, J = 7.4 Hz). |
| 176 | 1H-NMR (CDCl3) δ: 7.24 (1H, d, J = 9.5 Hz), 7.19 (1H, d, J = 8.9 Hz), 6.85-6.82 (1H, m), 6.79-6.75 (2H, m), 6.68 (2H, dd, J = 8.9, 3.1 Hz), 6.48 (1H, d, J = 3.1 Hz), 3.90-3.85 (2H, m), 3.66 (3H, s), 1.20 (3H, t, J = 7.0 Hz). |
| 177 | 1H-NMR (CDCl3) δ: 7.48 (1H, s), 7.19 (1H, d, J = 8.9 Hz), 6.80-6.78 (3H, m), 6.69 (1H, dd, J = 8.9, 2.8 Hz), 6.49 (1H, d, J = 2.8 Hz), 3.99-3.87 (2H, m), 3.67 (3H, s), 1.23 (3H, t, J = 7.0 Hz). |
| 178 | 1H-NMR (CDCl3) δ: 7.68 (1H, s), 7.19 (1H, d, J = 8.8 Hz), 6.82-6.75 (3H, m), 6.69 (1H, dd, J = 8.8, 3.2 Hz), 6.49 (1H, d, J = 3.2 Hz), 3.95-3.90 (2H, m), 3.67 (3H, s), 1.22 (3H, t, J = 7.1 Hz). |
| 179 | 1H-NMR (CDCl3) δ: 7.47 (1H, s), 7.30 (1H, dd, J = 8.8, 5.1 Hz), 6.92 (1H, ddd, J = 8.8, 7.8, 2.9 Hz), 6.77-6.68 (3H, m), 4.01 (3H, t, J = 1.5 Hz), 3.40 (3H, s). |
| 180 | "Major isomer: 1H-NMR (CDCl3) δ: 7.47 (1H, s), 7.30 (1H, dd, J = 8.8, 5.1 Hz), 6.92 (1H, ddd, J = 8.8, 7.8, 3.2 Hz), 6.74-6.61 (2H, m), 6.57-6.52 (1H, m), 3.75 (3H, s), 3.42 (3H, s). Minor isomer: 1H-NMR (CDCl3) δ: 7.48 (1H, s), 7.30 (1H, dd, J = 8.8, 5.1 Hz), 6.92 (1H, ddd, J = 8.8, 7.8, 3.2 Hz), 6.74-6.61 (2H, m), 6.57-6.52 (1H, m), 3.85 (3H, s), 3.41 (3H, s). (Ratio ≈ 60/40)" |
| 181 | 1H-NMR (CDCl3) δ: 7.69 (1H, s), 7.31 (1H, dd, J = 8.9, 5.2 Hz), 6.93 (1H, ddd, J = 8.9, 8.0, 3.1 Hz), 6.78-6.69 (3H, m), 3.75 (3H, s), 3.42 (3H, s). |
| 182 | "Major isomer: 1H-NMR (CDCl3) δ: 7.68 (1H, s), 7.30 (1H, dd, J = 8.9, 5.2 Hz), 6.94-6.90 (1H, m), 6.74-6.62 (2H, m), 6.57-6.52 (1H, m), 3.75 (3H, s), 3.42 (3H, s). Minor isomer: 1H-NMR (CDCl3) δ: 7.69 (1H, s), 7.30 (1H, dd, J = 8.9, |

TABLE 5-continued

| Compound | ¹H-NMR |
|---|---|
| | 5.2 Hz), 6.94-6.90 (1H, m), 6.74-6.62 (2H, m), 6.57-6.52 (1H, m), 3.84 (3H, s), 3.41 (3H, s). (Ratio ≈ 59/41)" |
| 183 | 1H-NMR (CDCl3) δ: 7.67 (1H, s), 7.53 (2H, s), 7.27-7.24 (1H, m), 7.08 (1H, ddd, J = 7.8, 7.6, 1.7 Hz), 7.02 (1H, ddd, J = 7.6, 7.5, 1.2 Hz), 6.86 (1H, dd, J = 7.6, 1.7 Hz), 3.60-3.51 (1H, m), 3.40-3.31 (1H, m), 2.85-2.66 (3H, m), 2.60-2.52 (1H, m), 0.99 (3H, t, J = 7.1 Hz). |
| 184 | 1H-NMR (CDCl3) δ: 7.28 (1H, dd, J = 8.8, 5.1 Hz), 7.20 (1H, d, J = 9.3 Hz), 6.88 (1H, ddd, J = 8.8, 7.8, 2.9 Hz), 6.82 (1H, dt, J = 10.5, 1.8 Hz), 6.77 (1H, dt, J = 10.7, 1.8 Hz), 6.71-6.66 (2H, m), 4.01 (3H, t, J = 1.3 Hz), 3.95-3.81 (2H, m), 1.20 (3H, t, J = 7.1 Hz). |
| 185 | "Major isomer: 1H-NMR (CDCl3) δ: 7.29-7.24 (1H, m), 7.20 (1H, d, J = 3.9 Hz), 6.88 (1H, ddd, J = 8.8, 7.8, 3.2 Hz), 6.74-6.65 (3H, m), 6.62-6.59 (1H, m), 3.76 (3H, s) 4.00-3.79 (2H, m), 1.24-1.20 (3H, m). Minor isomer: 1H-NMR (CDCl3) δ: 7.29-7.24 (1H, m), 7.22 (1H, d, J = 3.9 Hz), 6.88 (1H, ddd, J = 8.8, 7.8, 3.2 Hz), 6.74-6.65 (3H, m), 6.62-6.59 (1H, m), 4.00-3.79 (2H, m), 3.87 (3H, s), 1.24-1.20 (3H, m). (Ratio ≈ 52/48)" |
| 186 | 1H-NMR (CDCl3) δ: 7.44 (1H, s), 7.29 (1H, dd, J = 8.9, 4.9 Hz), 6.90 (1H, ddd, J = 8.9, 8.0, 3.1 Hz), 6.81-6.75 (2H, m), 6.71 (1H, dd, J = 8.4, 2.9 Hz), 4.01 (3H, t, J = 1.4 Hz), 3.99-3.87 (2H, m), 1.23 (3H, t, J = 7.0 Hz). |
| 187 | Major isomer: 1H-NMR (CDCl3) δ: 7.45 (1H, s), 7.30-7.26 (1H, m), 6.91 (1H, ddd, J = 8.9, 8.0, 3.1 Hz), 6.74-6.66 (2H, m), 6.62-6.57 (1H, m), 4.05-3.85 (2H, m), 3.77 (3H, s), 1.26-1.23 (3H, m). Minor isomer: 1H-NMR, (CDCl3) δ: 7.45 (1H, s), 7.30-7.26 (1H, m), 6.91 (1H, ddd, J = 8.9, 8.0, 3.1 Hz), 6.74-6.66 (2H, m), 6.62-6.57 (1H, m), 4.05-3.85 (2H, m), 3.86 (3H, s), 1.26-1.23 (3H, m). (Ratio ≈ 58/42) |
| 188 | 1H-NMR (CDCl3) δ: 7.65 (1H, s), 7.29 (1H, dd, J = 8.9, 5.2 Hz), 6.90 (1H, ddd, J = 8.9, 8.0, 3.1 Hz), 6.80-6.76 (2H, m), 6.71 (1H, dd, J = 8.3, 3.1 Hz), 4.01 (3H, t, J = 1.4 Hz), 3.99-3.87 (2H, m), 1.23 (3H, t, J = 7.0 Hz). |
| 189 | "Major isomer: 1H-NMR (CDCl3) δ: 7.65 (1H, s), 7.30-7.26 (1H, m), 6.90 (1H, ddd, J = 8.9, 7.6, 3.1 Hz), 6.74-6.66 (2H, m), 6.62-6.57 (1H, m), 4.05-3.84 (2H, m), 3.77 (3H, s), 1.26-1.23 (3H, m). Minor isomer: 1H-NMR (CDCl3) δ: 7.66 (1H, s), 7.30-7.26 (1H, m), 6.90 (1H, ddd, J = 8.9, 7.6, 3.1 Hz), 6.74-6.66 (2H, m), 6.62-6.57 (1H, m), 4.05-3.84 (2H, m), 3.86 (3H, s), 1.26-1.23 (3H, m). (Ratio ≈ 58/42)" |
| 190 | 1H-NMR (CDCl3) δ: 7.30 (1H, dd, J = 8.0, 0.9 Hz), 7.11-7.08 (1H, m), 7.04-7.01 (1H, m), 6.87 (1H, dd, J = 7.5, 1.7 Hz), 6.66-6.62 (1H, m), 3.68-3.61 (1H, m), 3.32-3.25 (1H, m), 2.86-2.74 (2H, m), 2.71-2.64 (1H, m), 2.47-2.42 (1H, m), 1.00 (3H, t, J = 7.0 Hz). |
| 191 | 1H-NMR (CDCl3) δ: 7.78 (1H, s), 7.74 (1H, s), 7.66 (1H, s), 7.28 (1H, d, J = 9.3 Hz), 7.26-7.24 (1H, m), 7.13-7.09 (1H, m), 7.07-7.03 (1H, m), 6.95 (1H, dd, J = 7.6, 1.7 Hz), 6.73 (1H, d, J = 9.3 Hz), 3.95-3.79 (2H, m), 1.20 (3H, t, J = 7.1 Hz). |
| 192 | 1H-NMR (CDCl3) δ: 7.79 (1H, s), 7.74 (1H, s), 7.63 (1H, s), 7.53 (1H, s), 7.26-7.24 (1H, m), 7.13 (1H, ddd, J = 7.8, 7.6, 1.8 Hz), 7.07 (1H, ddd, J = 7.6, 7.5, 1.2 Hz), 6.96 (1H, dd, J = 7.6, 1.8 Hz), 3.99-3.85 (2H, m), 1.23 (3H, t, J = 7.2 Hz). |
| 193 | 1H-NMR (CDCl3) δ: 7.19 (1H, d, J = 9.3 Hz), 7.12 (1H, dd, J = 8.4, 2.3 Hz), 7.00 (1H, dd, J = 8.4, 2.3 Hz), 6.83 (1H, dd, J = 8.4, 2.7 Hz), 6.74-6.69 (2H, m), 6.65 (1H, d, J = 9.3 Hz), 6.52-6.49 (1H, m), 4.54-4.48 (1H, m), 3.96-3.88 (2H, m), 1.31 (6H, d, J = 5.9 Hz), 1.17 (3H, t, J = 7.0 Hz). |
| 194 | 1H-NMR (CDCl3) δ: 7.43 (1H, s), 7.09 (1H, dd, J = 8.4, 2.3 Hz), 7.00 (1H, dd, J = 8.4, 2.3 Hz), 6.83 (1H, dd, J = 8.4, 2.6 Hz), 6.76-6.71 (2H, m), 6.54-6.50 (1H, m), 4.54-4.48 (1H, m), 3.99-3.93 (2H, m), 1.31 (6H, d, J = 6.1 Hz), 1.19 (3H, t, J = 7.0 Hz). |
| 195 | 1H-NMR (CDCl3) δ: 7.63 (1H, s), 7.08 (1H, dd, J = 8.4, 2.3 Hz), 7.01 (1H, dd, J = 8.4, 2.3 Hz), 6.83 (1H, dd, J = 8.4, 2.6 Hz), 6.76-6.71 (2H, m), 6.53-6.50 (1H, m), 4.54-4.48 (1H, m), 4.00-3.93 (2H, m), 1.31 (6H, d, J = 5.9 Hz), 1.19 (3H, t, J = 7.0 Hz). |
| 196 | 1H-NMR (CDCl3) δ: 7.69-7.67 (1H, m), 7.52-7.50 (2H, m), 7.28-7.26 (1H, m), 7.12-7.09 (1H, m), 7.04 (1H, ddd, J = 7.5, 7.3, 1.2 Hz), 6.88 (1H, dd, J = 7.3, 1.5 Hz), 2.89 (3H, s), 2.88-2.78 (2H, m), 2.76-2.70 (1H, m), 2.63-2.56 (1H, m). |
| 197 | 1H-NMR (CDCl3) δ: 7.78 (1H, s), 7.69 (1H, s), 7.61 (1H, s), 7.32 (1H, d, J = 9.3 Hz), 7.27-7.26 (1H, m), 7.13 (1H, ddd, J = 8.0, 7.3, 1.8 Hz), 7.07 (1H, ddd, J = 7.6, 7.3, 1.5 Hz), 6.94 (1H, dd, J = 7.6, 1.8 Hz), 6.75 (1H, d, J = 9.3 Hz), 3.36 (3H, s). |
| 198 | 1H-NMR (CDCl3) δ: 7.31 (1H, dd, J = 8.0, 1.2 Hz), 7.10 (1H, ddd, J = 8.0, 7.6, 1.7 Hz), 7.02 (1H, ddd, J = 7.6, 7.5, 1.2 Hz), 6.85 (1H, dd, J = 7.5, 1.7 Hz), 6.66-6.62 (3H, m), 3.68-3.62 (1H, m), 3.17-3.11 (1H, m), 2.89-2.83 (1H, m), 2.79-2.74 (1H, m), 2.71-2.64 (1H, m), 2.46-2.40 (1H, m), 1.48-1.40 (2H, m), 0.79 (3H, t, J = 7.3 Hz). |
| 199 | 1H-NMR (CDCl3) δ: 7.79 (1H, br s), 7.74 (1H, br s), 7.73 (1H, s), 7.63 (1H, br s), 7.26-7.24 (1H, m), 7.13 (1H, ddd, J = 8.0, 7.5, 1.8 Hz), 7.07 (1H, ddd, J = 7.6, 7.5, 1.5 Hz), 6.96 (1H, dd, J = 7.6, 1.8 Hz), 3.99-3.85 (2H, m), 1.23 (3H, t, J = 7.0 Hz). |
| 200 | 1H-NMR (CDCl3) δ: 7.80-7.78 (1H, m), 7.69-7.68 (1H, m), 7.59 (1H, br s), 7.56 (1H, s), 7.28-7.26 (1H, m), 7.17-7.14 (1H, m), 7.09 (1H, ddd, J = 7.6, 7.5, 1.4 Hz), 6.96 (1H, dd, J = 7.6, 1.5 Hz), 3.43 (3H, s). |
| 201 | 1H-NMR (CDCl3) δ: 7.79 (1H, br s), 7.76 (1H, s), 7.69 (1H, br s), 7.58 (1H, br s), 7.28-7.26 (1H, m), 7.17-7.14 (1H, m), 7.09 (1H, ddd, J = 7.7, 7.5, 1.2 Hz), 6.96 (1H, dd, J = 7.5, 1.7 Hz), 3.43 (3H, s). |

TABLE 5-continued

| Compound | ¹H-NMR |
|---|---|
| 202 | 1H-NMR (CDCl3) δ: 7.30 (1H, dd, J = 8.0, 1.5 Hz), 7.25 (1H, d, J = 9.5 Hz), 7.13 (1H, ddd, J = 8.0, 7.6, 1.8 Hz), 7.06 (1H, td, J = 7.6, 1.5 Hz), 6.95 (1H, dd, J = 7.6, 1.8 Hz), 6.82-6.79 (1H, m), 6.77-6.71 (2H, m), 6.69 (1H, d, J = 9.5 Hz), 3.94-3.82 (2H, m), 1.20 (3H, t, J = 7.0 Hz). |
| 203 | 1H-NMR (CDCl3) δ: 7.32-7.29 (1H, m), 7.25-7.22 (1H, m), 7.16-7.11 (1H, m), 7.08-7.04 (1H, m), 6.95-6.93 (1H, m), 6.79-6.67 (4H, m), 3.81-3.69 (2H, m), 1.71-1.56 (2H, m), 0.78 (3H, t, J = 7.4 Hz). |
| 204 | 1H-NMR (CDCl3) δ: 7.49 (1H, s), 7.31 (1H, dd, J = 8.0, 1.2 Hz), 7.17-7.14 (1H, m), 7.08 (1H, ddd, J = 7.6, 7.5, 1.2 Hz), 6.96 (1H, dd, J = 7.6, 1.5 Hz), 6.79-6.73 (3H, m), 3.99-3.87 (2H, m), 1.23 (3H, t, J = 7.0 Hz). |
| 205 | 1H-NMR (CDCl3) δ: 7.69 (1H, s), 7.31 (1H, dd, J = 8.1, 1.3 Hz), 7.17-7.14 (1H, m), 7.08 (1H, td, J = 7.6, 1.3 Hz), 6.96 (1H, dd, J = 7.6, 1.5 Hz), 6.79-6.73 (3H, m), 3.99-3.87 (2H, m), 1.23 (3H, t, J = 7.0 Hz). |
| 206 | 1H-NMR (CDCl3) δ: 7.31 (1H, dd, J = 7.9, 1.3 Hz), 7.27-7.23 (2H, m), 7.16-7.06 (4H, m), 6.96 (1H, dd, J = 7.6, 1.7 Hz), 6.69 (1H, d, J = 9.3 Hz), 3.95-3.82 (2H, m), 1.20 (3H, t, J = 7.0 Hz). |
| 207 | 1H-NMR (CDCl3) δ: 7.48 (1H, s), 7.31 (1H, dd, J = 8.0, 1.3 Hz), 7.17-7.14 (1H, m), 7.08 (1H, td, J = 7.6, 1.3 Hz), 6.95 (1H, dd, J = 7.6, 1.5 Hz), 6.77-6.73 (3H, m), 3.84-3.75 (2H, m), 1.72-1.58 (2H, m), 0.79 (3H, t, J = 7.5 Hz). |
| 208 | 1H-NMR (CDCl3) δ: 7.43 (1H, s), 7.11 (1H, dd, J = 8.5, 2.2 Hz), 7.03 (1H, dd, J = 8.5, 2.2 Hz), 6.87 (1H, dd, J = 8.5, 2.7 Hz), 6.80-6.72 (2H, m), 6.54-6.51 (1H, m), 6.07-5.97 (1H, m), 5.42-5.36 (1H, m), 5.31-5.28 (1H, m), 4.50 (2H, dt, J = 5.4, 1.5 Hz), 3.99-3.91 (2H, m), 1.19 (3H, t, J = 7.0 Hz). |
| 209 | 1H-NMR (CDCl3) δ: 7.44 (1H, s), 7.23 (1H, dd, J = 8.4, 2.1 Hz), 7.16-7.12 (2H, m), 7.04 (1H, dd, J = 8.4, 2.1 Hz), 6.75 (1H, td, J = 8.4, 2.9 Hz), 6.54-6.51 (1H, m), 4.00-3.89 (2H, m), 2.29 (3H, s), 1.20 (3H, t, J = 7.1 Hz). |
| 210 | 1H-NMR (CDCl3) δ: 7.41-7.33 (5H, m), 7.20 (1H, d, J = 9.5 Hz), 7.15 (1H, dd, J = 8.6, 2.4 Hz), 7.04 (1H, dd, J = 8.6, 2.1 Hz), 6.94 (1H, dd, J = 8.6, 2.1 Hz), 6.84 (1H, dd, J = 8.6, 2.4 Hz), 6.74-6.70 (1H, m), 6.66 (1H, d, J = 9.5 Hz), 6.52-6.50 (1H, m), 5.02 (2H, s), 3.95-3.88 (2H, m), 1.17 (3H, t, J = 7.0 Hz). |
| 211 | 1H-NMR (CDCl3) δ: 7.46 (1H, dd, J = 7.8, 1.5 Hz), 7.27-7.19 (3H, m), 7.08-6.97 (3H, m), 6.93-6.90 (2H, m), 6.67 (1H, d, J = 9.3 Hz), 3.91-3.86 (2H, m), 1.17 (3H, t, J = 7.1 Hz). |
| 212 | 1H-NMR (CDCl3) δ: 7.48-7.46 (2H, m), 7.22-7.19 (2H, m), 7.05-6.95 (5H, m), 3.99-3.86 (2H, m), 1.19 (3H, t, J = 7.0 Hz). |
| 213 | 1H-NMR (CDCl3) δ: 7.68 (1H, s), 7.31 (1H, dd, J = 8.0, 1.2 Hz), 7.17-7.13 (1H, m), 7.08 (1H, ddd, J = 7.6, 7.5, 1.2 Hz), 6.95 (1H, dd, J = 7.6, 1.5 Hz), 6.77-6.73 (3H, m), 3.84-3.75 (2H, m), 1.72-1.59 (2H, m), 0.78 (3H, t, J = 7.5 Hz). |
| 214 | 1H-NMR (CDCl3) δ: 7.33 (1H, dd, J = 8.0, 1.2 Hz), 7.29-7.26 (2H, m), 7.16 (1H, ddd, J = 8.0, 7.3, 1.8 Hz), 7.11-7.06 (3H, m), 6.94 (1H, dd, J = 7.6, 1.8 Hz), 6.71 (1H, d, J = 9.2 Hz), 3.34 (3H, s). |
| 215 | 1H-NMR (CDCl3) δ: 7.48 (1H, s), 7.32 (1H, dd, J = 8.0, 1.5 Hz), 7.28 (1H, t, J = 2.0 Hz), 7.16 (1H, ddd, J = 8.0, 7.6, 1.8 Hz), 7.12-7.08 (3H, m), 6.97 (1H, dd, J = 7.6, 1.8 Hz), 3.99-3.87 (2H, m), 1.22 (3H, t, J = 7.0 Hz). |
| 216 | 1H-NMR (CDCl3) δ: 7.70 (1H, s), 7.33 (1H, dd, J = 8.0, 0.9 Hz), 7.30 (1H, t, J = 1.8 Hz), 7.18 (1H, ddd, J = 8.0, 7.6, 1.8 Hz), 7.13-7.10 (3H, m), 6.98 (1H, dd, J = 7.6, 1.8 Hz), 4.00-3.89 (2H, m), 1.23 (3H, t, J = 7.0 Hz). |
| 217 | 1H-NMR (CDCl3) δ: 7.51 (1H, s), 7.33 (1H, dd, J = 8.1, 1.2 Hz), 7.29 (1H, t, J = 1.8 Hz), 7.18 (1H, ddd, J = 8.1, 7.3, 1.8 Hz), 7.11 (1H, ddd, J = 7.6, 7.3, 1.2 Hz), 7.07-7.06 (2H, m), 6.96 (1H, dd, J = 7.6, 1.8 Hz), 3.40 (3H, s). |
| 218 | 1H-NMR (CDCl3) δ: 7.72 (1H, s), 7.33 (1H, dd, J = 8.1, 1.2 Hz), 7.29 (1H, t, J = 2.0 Hz), 7.18 (1H, ddd, J = 8.1, 7.6, 1.8 Hz), 7.11 (1H, td, J = 7.6, 1.2 Hz), 7.07-7.06 (2H, m), 6.95 (1H, dd, J = 7.6, 1.8 Hz), 3.41 (3H, s). |
| 219 | 1H-NMR (CDCl3) δ: 7.19 (1H, d, J = 9.2 Hz), 7.12 (1H, dd, J = 8.6, 2.1 Hz), 7.02 (1H, dd, J = 8.6, 2.1 Hz), 6.85 (1H, dd, J = 8.6, 2.8 Hz), 6.76-6.70 (2H, m), 6.65 (1H, d, J = 9.2 Hz), 6.52 (1H, ddd, J = 8.6, 2.8, 1.8 Hz), 3.94-3.87 (4H, m), 1.83-1.76 (2H, m), 1.16 (3H, t, J = 7.0 Hz), 1.03 (3H, t, J = 7.5 Hz). |
| 220 | 1H-NMR (CDCl3) δ: 7.43 (1H, s), 7.09 (1H, dd, J = 8.5, 2.4 Hz), 7.02 (1H, dd, J = 8.5, 2.4 Hz), 6.85 (1H, dd, J = 8.5, 2.4 Hz), 6.77-6.72 (2H, m), 6.55-6.52 (1H, m), 4.00-3.91 (2H, m), 3.88 (2H, t, J = 6.6 Hz), 1.84-1.75 (2H, m), 1.18 (3H, t, J = 6.8 Hz), 1.03 (3H, t, J = 7.6 Hz). |
| 221 | 1H-NMR (CDCl3) δ: 7.20-7.17 (2H, m), 7.09 (1H, dd, J = 8.6, 2.1 Hz), 6.89 (1H, dd, J = 8.6, 2.8 Hz), 6.79 (1H, dd, J = 8.6, 2.8 Hz), 6.73 (1H, td, J = 8.6, 2.8 Hz), 6.67 (1H, d, J = 9.2 Hz), 6.54-6.51 (1H, m), 6.08 (1H, tt, J = 55.0, 4.0 Hz), 4.15 (2H, td, J = 12.8, 4.0 Hz), 3.93-3.84 (2H, m), 1.16 (3H, t, J = 7.0 Hz). |
| 222 | 1H-NMR (CDCl3) δ: 7.43 (1H, s), 7.15 (1H, dd, J = 8.5, 2.2 Hz), 7.10 (1H, dd, J = 8.5, 2.2 Hz), 6.89 (1H, dd, J = 8.5, 2.7 Hz), 6.81 (1H, dd, J = 8.5, 2.7 Hz), 6.75 (1H, td, J = 8.5, 2.7 Hz), 6.56-6.52 (1H, m), 6.08 (1H, tt, J = 54.9, 4.1 Hz), 4.16 (2H, td, J = 12.9, 4.1 Hz), 3.97-3.90 (2H, m), 1.18 (3H, t, J = 6.8 Hz). |
| 223 | 1H-NMR (CDCl3) δ: 7.19 (1H, d, J = 9.3 Hz), 7.15 (1H, dd, J = 8.5, 2.2 Hz), 7.05-6.98 (2H, m), 6.90 (1H, dd, J = 8.5, 2.4 Hz), 6.75-6.70 (1H, m), 6.66 (1H, d, J = 9.3 Hz), 6.53-6.50 (1H, m), 5.15 (2H, s), 3.97-3.83 (2H, m), 3.47 (3H, s), 1.17 (3H, t, J = 7.1 Hz). |
| 224 | 1H-NMR (CDCl3) δ: 7.21-7.18 (2H, m), 7.12 (1H, dd, J = 8.5, 2.2 Hz), 6.92 (1H, dd, J = 8.5, 2.7 Hz), 6.82 (1H, dd, J = 8.5, 2.7 Hz), 6.76-6.71 (1H, m), 6.67 (1H, d, J = 9.3 Hz), 6.54-6.51 (1H, m), 4.33 (2H, q, J = 8.0 Hz), 3.93-3.83 (2H, m), 1.16 (3H, t, J = 7.1 Hz). |

TABLE 5-continued

| Compound | ¹H-NMR |
|---|---|
| 225 | 1H-NMR (CDCl3) δ: 7.44 (1H, s), 7.41-7.33 (5H, m), 7.12 (1H, dd, J = 8.4, 2.1 Hz), 7.05 (1H, dd, J = 8.4, 2.1 Hz) 6.94 (1H, dd, J = 8.4, 2.6 Hz), 6.85 (1H, dd, J = 8.4, 2.6 Hz), 6.75 (1H, td, J = 8.5, 3.0 Hz), 6.54-6.51 (1H, m), 5.02 (2H, s), 4.00-3.90 (2H, m), 1.19 (3H, t, J = 6.9 Hz). |
| 226 | 1H-NMR (CDCl3) δ: 7.43 (1H, s), 7.12 (1H, dd, J = 8.6, 2.1 Hz), 7.05-7.03 (1H, m), 7.00 (1H, dd, J = 8.6, 2.4 Hz), 6.91 (1H, dd, J = 8.6, 2.4 Hz), 6.75 (1H, td, J = 8.6, 3.1 Hz), 6.55-6.52 (1H, m), 5.15 (2H, s), 3.99-3.90 (2H, m), 3.47 (3H, s), 1.19 (3H, t, J = 7.0 Hz). |
| 227 | 1H-NMR (CDCl3) δ: 7.23 (1H, dd, J = 8.6, 2.1 Hz), 7.20 (1H, d, J = 9.5 Hz), 7.15 (1H, dd, J = 8.6, 2.1 Hz), 6.96 (1H, dd, J = 8.6, 2.8 Hz), 6.87 (1H, dd, J = 8.6, 2.8 Hz), 6.76-6.72 (1H, m), 6.68 (1H, d, J = 9.5 Hz), 6.54-6.51 (1H, m), 4.76 (2H, s), 3.93-3.84 (2H, m), 1.17 (3H, t, J = 7.0 Hz). |
| 228 | 1H-NMR (CDCl3) δ: 7.19 (1H, d, J = 9.2 Hz), 7.13 (1H, dd, J = 8.6, 2.4 Hz), 7.03 (1H, dd, J = 8.6, 2.4 Hz), 6.89 (1H, dd, J = 8.4, 2.6 Hz), 6.79 (1H, dd, J = 8.4, 2.6 Hz), 6.72 (1H, td, J = 8.5, 2.9 Hz), 6.65 (1H, d, J = 9.2 Hz), 6.53-6.50 (1H, m), 4.09-4.07 (2H, m), 3.94-3.85 (2H, m), 3.75-3.73 (2H, m), 3.45 (3H, s), 1.15 (3H, t, J = 7.0 Hz). |
| 229 | 1H-NMR (CDCl3) δ: 7.44 (1H, s), 7.10 (1H, dd, J = 8.6, 2.1 Hz), 7.04 (1H, dd, J = 8.6, 2.1 Hz), 6.89 (1H, dd, J = 8.6, 2.8 Hz), 6.80 (1H, dd, J = 8.6, 2.8 Hz), 6.74 (1H, td, J = 8.5, 3.1 Hz), 6.54-6.52 (1H, m), 4.09-4.07 (2H, m), 4.00-3.89 (2H, m), 3.75-3.73 (2H, m), 3.45 (3H, s), 1.18 (3H, t, J = 7.0 Hz). |
| 230 | 1H-NMR (CDCl3) δ: 7.27-7.23 (2H, m), 7.06 (1H, ddd, J = 8.1, 7.4, 1.7 Hz), 6.98 (1H, ddd, J = 7.6, 7.4, 1.2 Hz), 6.93 (1H, dd, J = 7.6, 1.7 Hz), 6.86-6.83 (2H, m), 6.75 (1H, br s), 6.64 (1H, d, J = 9.3 Hz), 3.96-3.83 (2H, m), 2.26 (3H, s), 2.16 (3H, s), 1.17 (3H, t, J = 7.1 Hz). |
| 231 | 1H-NMR (CDCl3) δ: 7.48 (1H, s), 7.27-7.25 (1H, m), 7.08 (1H, td, J = 7.7, 1.8 Hz), 7.00 (1H, td, J = 7.7, 1.2 Hz), 6.93 (1H, dd, J = 7.7, 1.8 Hz), 6.87 (1H, br s), 6.80 (1H, br s), 6.74 (1H, br s), 4.01-3.88 (2H, m), 2.26 (3H, s), 2.16 (3H, s), 1.19 (3H, t, J = 7.1 Hz). |
| 232 | 1H-NMR (CDCl3) δ: 7.68 (1H, s), 7.27-7.25 (1H, m), 7.08 (1H, td, J = 7.6, 1.7 Hz), 7.00 (1H, td, J = 7.6, 1.2 Hz), 6.93 (1H, dd, J = 7.6, 1.7 Hz), 6.87 (1H, s), 6.80 (1H, s), 6.75 (1H, s), 4.01-3.88 (2H, m), 2.25 (3H, s), 2.16 (3H, s), 1.19 (3H, t, J = 7.0 Hz). |
| 233 | 1H-NMR (CDCl3) δ: 7.68 (1H, s), 7.46 (1H, dd, J = 7.8, 1.4 Hz), 7.23-7.18 (2H, m), 7.07 (1H, m), 7.04-6.98 (2H, m), 6.94-6.92 (2H, m), 3.96-3.91 (2H, m), 1.19 (3H, t, J = 7.0 Hz). |
| 234 | 1H-NMR (CDCl3) δ: 7.44 (1H, s), 7.17 (1H, dd, J = 8.6, 2.1 Hz), 7.12 (1H, dd, J = 8.6, 2.1 Hz), 6.92 (1H, dd, J = 8.6, 2.8 Hz), 6.83 (1H, dd, J = 8.6, 2.8 Hz), 6.76 (1H, td, J = 8.6, 2.8 Hz), 6.55-6.53 (1H, m), 4.33 (2H, q, J = 8.0 Hz), 3.97-3.88 (2H, m), 1.18 (3H, t, J = 7.0 Hz). |
| 235 | 1H-NMR (CDCl3) δ: 7.44 (1H, s), 7.21 (1H, dd, J = 8.5, 2.2 Hz), 7.16 (1H, dd, J = 8.5, 2.2 Hz), 6.97 (1H, dd, J = 8.5, 2.7 Hz), 6.88 (1H, dd, J = 8.5, 2.7 Hz), 6.76 (1H, td, J = 8.4, 2.9 Hz), 6.56-6.52 (1H, m), 4.76 (2H, s), 3.98-3.88 (2H, m), 1.19 (3H, t, J = 7.0 Hz). |
| 236 | 1H-NMR (CDCl3) δ: 7.30-7.27 (2H, m), 7.08 (1H, ddd, J = 8.0, 7.3, 1.5 Hz), 6.99 (1H, ddd, J = 7.6, 7.3, 1.5 Hz), 6.91 (1H, dd, J = 7.6, 1.5 Hz), 6.87 (1H, br s), 6.79 (1H, br s), 6.69 (1H, br s), 6.66 (1H, d, J = 9.5 Hz), 3.33 (3H, s), 2.26 (3H, s), 2.15 (3H, s). |
| 237 | 1H-NMR (CDCl3) δ: 7.51 (1H, s), 7.28 (1H, dd, J = 8.0, 1.3 Hz), 7.09 (1H, ddd, J = 8.0, 7.3, 1.8 Hz), 7.00 (1H, ddd, J = 7.5, 7.3, 1.3 Hz), 6.91 (1H, dd, J = 7.5, 1.8 Hz), 6.88 (1H, br s), 6.76 (1H, br s), 6.69 (1H, br s), 3.39 (3H, s), 2.25 (3H, s), 2.15 (3H, s). |
| 238 | 1H-NMR (CDCl3) δ: 7.71 (1H, s), 7.28 (1H, dd, J = 8.3, 1.2 Hz), 7.09 (1H, ddd, J = 8.3, 7.6, 1.8 Hz), 7.00 (1H, ddd, J = 7.8, 7.6, 1.2 Hz), 6.91 (1H, dd, J = 7.8, 1.8 Hz), 6.88 (1H, br s), 6.76 (1H, br s), 6.69 (1H, br s), 3.39 (3H, s), 2.25 (3H, s), 2.15 (3H, s). |
| 239 | 1H-NMR (CDCl3) δ: 7.48 (1H, dd, J = 7.9, 1.3 Hz), 7.28 (1H, d, J = 9.5 Hz), 7.20-7.12 (2H, m), 7.09-6.99 (3H, m), 6.93-6.91 (2H, m), 6.69 (1H, d, J = 9.5 Hz), 3.32 (3H, s). |
| 240 | 1H-NMR (CDCl3) δ: 7.51 (1H, s), 7.48 (1H, dd, J = 7.6, 1.5 Hz), 7.16-7.14 (2H, m), 7.10-7.00 (3H, m), 6.94-6.92 (2H, m), 3.39 (3H, s). |
| 241 | 1H-NMR (CDCl3) δ: 7.71 (1H, s), 7.48 (1H, dd, J = 8.0, 1.2 Hz), 7.16-7.14 (2H, m), 7.10-7.00 (3H, m), 6.95-6.9 0 (2H, m), 3.39 (3H, s). |
| 242 | 1H-NMR (CDCl3) δ: 7.48 (1H, s), 7.22-7.18 (2H, m), 7.13 (1H, d, J = 8.8 Hz), 7.04-6.93 (2H, m), 6.64 (1H, dd, J = 8.8, 2.9 Hz), 6.45 (1H, d, J = 2.9 Hz), 3.96-3.75 (4H, m), 1.33 (3H, t, J = 7.0 Hz), 1.18 (3H, t, J = 7.0 Hz). |
| 243 | 1H-NMR (CDCl3) δ: 7.48 (1H, s), 7.22-7.18 (2H, m), 7.13 (1H, d, J = 8.8 Hz), 7.02 (1H, td, J = 8.8, 2.4 Hz), 6.95 (1H, td, J = 8.8, 2.4 Hz), 6.65 (1H, dd, J = 8.8, 2.9 Hz), 6.45 (1H, d, J = 2.9 Hz), 3.98-3.88 (2H, m), 3.77 (1H, dt, J = 9.3, 6.7 Hz), 3.67 (1H, dt, J = 9.3, 6.7 Hz), 1.75-166 (2H, m), 1.18 (3H, t, J = 7.1 Hz), 0.97 (3H, t, J = 7.3 Hz). |
| 244 | 1H-NMR (CDCl3) δ: 7.47 (1H, s), 7.25-7.22 (2H, m), 7.20-7.16 (1H, m), 7.05 (1H, td, J = 8.5, 2.6 Hz), 6.96 (1H, td, J = 8.5, 2.6 Hz), 6.76 (1H, dd, J = 8.9, 3.1 Hz), 6.62 (1H, d, J = 3.1 Hz), 4.65 (1H, d, J = 15.9 Hz), 4.60 (1H, d, J = 15.9 Hz), 4.01-3.86 (2H, m), 1.19 (3H, t, J = 7.0 Hz). |
| 245 | 1H-NMR (CDCl3) δ: 7.47 (1H, s), 7.23-7.16 (3H, m), 7.04 (1H, td, J = 8.5, 2.7 Hz), 6.96 (1H, td, J = 8.5, 2.7 Hz), 6.71 (1H, dd, J = 8.9, 3.1 Hz), 6.55 (1H, d, J = 3.1 Hz), 4.25-4.10 (2H, m), 4.00-3.86 (2H, m), 1.19 (3H, t, J = 7.0 Hz). |

TABLE 5-continued

| Compound | ¹H-NMR |
|---|---|
| 246 | 1H-NMR (CDCl3) δ: 7.47 (1H, s), 7.22-7.16 (2H, m), 7.14 (1H, d, J = 8.9 Hz), 7.01 (1H, td, J = 8.6, 2.4 Hz), 6.95 (1H, td, J = 8.6, 2.4 Hz), 6.69 (1H, dd, J = 8.9, 3.1 Hz), 6.51 (1H, d, J = 3.1 Hz), 3.99-3.86 (4H, m), 3.68-3.66 (2H, m), 3.42 (3H, s), 1.18 (3H, t, J = 7.0 Hz). |
| 247 | 1H-NMR (CDCl3) δ: 7.47 (1H, s), 7.23-7.17 (3H, m), 7.04 (1H, td, J = 8.6, 2.8 Hz), 6.96 (1H, td, J = 8.6, 2.8 Hz), 6.68 (1H, dd, J = 8.9, 3.1 Hz), 6.51 (1H, d, J = 3.1 Hz), 5.98 (1H, tt, J = 55.0, 4.0 Hz), 4.08-3.89 (4H, m), 1.19 (3H, t, J = 7.0 Hz). |
| 248 | 1H-NMR (CDCl3) δ: 7.50 (1H, s), 7.25-7.22 (1H, m), 7.17-7.12 (2H, m), 7.02 (1H, td, J = 8.5, 2.8 Hz), 6.94 (1H, td, J = 8.5, 2.8 Hz), 6.77 (1H, dd, J = 8.8, 2.9 Hz), 6.62 (1H, d, J = 2.9 Hz), 5.02 (1H, d, J = 6.8 Hz), 4.93 (1H, d, J = 6.8 Hz), 3.99-3.88 (2H, m), 3.37 (3H, s), 1.19 (3H, t, J = 7.1 Hz). |
| 249 | 1H-NMR (CDCl3) δ: 7.49 (1H, s), 7.25 (1H, d, J = 8.8 Hz), 7.20-7.16 (2H, m), 7.03 (1H, td, J = 8.4, 2.5 Hz), 6.96 (1H, td, J = 8.4, 2.5 Hz), 6.86 (1H, dd, J = 8.8, 2.7 Hz), 6.75 (1H, d, J = 2.7 Hz), 3.99-3.88 (2H, m), 2.24 (3H, s), 1.18 (3H, t, J = 7.0 Hz). |
| 250 | 1H-NMR (CDCl3) δ: 7.47 (1H, s), 7.41-7.30 (5H, m), 7.20-7.16 (1H, m), 7.14 (1H, d, J = 8.9 Hz), 7.08-7.04 (1H, m), 6.97-6.92 (2H, m), 6.72 (1H, dd, J = 8.9, 3.1 Hz), 6.53 (1H, d, J = 3.1 Hz), 4.95 (1H, d, J = 11.9 Hz), 4.86 (1H, d, J = 11.9 Hz), 3.95-3.88 (2H, m), 1.17 (3H, t, J = 7.0 Hz). |
| 251 | 1H-NMR (CDCl3) δ: 7.48 (1H, s), 7.22-7.16 (3H, m), 7.01 (1H, td, J = 8.6, 2.8 Hz), 6.95 (1H, td, J = 8.6, 2.8 Hz), 6.74 (1H, dd, J = 8.9, 3.1 Hz), 6.57 (1H, d, J = 3.1 Hz), 4.53 (2H, d, J = 2.4 Hz), 3.97-3.89 (2H, m), 2.51 (1H, t, J = 2.4 Hz), 1.19 (3H, t, J = 7.0 Hz). |
| 252 | 1H-NMR (CDCl3) δ: 7.49 (1H, s), 7.27-7.25 (1H, m), 7.19-7.16 (2H, m), 7.05-7.00 (1H, m), 6.98-6.93 (2H, m), 6.84 (1H, d, J = 2.9 Hz), 4.01-3.84 (5H, m), 1.18 (3H, t, J = 7.0 Hz). |
| 253 | 1H-NMR (CDCl3) δ: 7.50 (1H, s), 7.27-7.25 (1H, m), 7.19-7.16 (2H, m), 7.04-7.00 (1H, m), 6.97-6.94 (2H, m), 6.84 (1H, d, J = 2.8 Hz), 4.29 (2H, q, J = 7.1 Hz), 4.00-3.87 (2H, m), 1.37 (3H, t, J = 7.1 Hz), 1.18 (3H, t, J = 7.0 Hz). |
| 254 | 1H-NMR (CDCl3) δ: 7.18-7.15 (2H, m), 7.07 (1H, dd, J = 8.6, 2.1 Hz), 6.86 (1H, dd, J = 8.6, 2.8 Hz), 6.76 (1H, dd, J = 8.6, 2.8 Hz), 6.70-6.66 (2H, m), 6.55-6.53 (1H, m), 3.94-3.85 (2H, m), 3.78 (3H, s), 1.16 (3H, t, J = 7.0 Hz). |
| 255 | 1H-NMR (CDCl3) δ: 7.62 (1H, s), 7.12 (1H, dd, J = 8.6, 2.1 Hz), 7.07 (1H, dd, J = 8.6, 2.1 Hz), 6.86 (1H, dd, J = 8.6, 2.4 Hz), 6.77 (1H, dd, J = 8.6, 2.4 Hz), 6.71 (1H, td, J = 8.3, 2.8 Hz), 6.55 (1H, m), 4.00-3.88 (2H, m), 3.79 (3H, s), 1.18 (3H, t, J = 7.0 Hz). |
| 256 | 1H-NMR (CDCl3) δ: 7.42 (1H, s), 7.12 (1H, dd, J = 8.4, 2.2 Hz), 7.07 (1H, dd, J = 8.5, 2.2 Hz), 6.86 (1H, dd, J = 8.5, 2.7 Hz), 6.77 (1H, dd, J = 8.5, 2.7 Hz), 6.71 (1H, td, J = 8.3, 2.9 Hz), 6.55 (1H, m), 4.01-3.87 (2H, m), 3.79 (3H, s), 1.19 (3H, t, J = 7.0 Hz). |
| 257 | 1H-NMR (CDCl3) δ: 7.49 (1H, s), 7.25-7.21 (1H, m), 7.17 (2H, d, J = 8.8 Hz), 7.02 (1H, td, J = 8.5, 2.4 Hz), 6.95 (1H, td, J = 8.5, 2.4 Hz), 6.71 (1H, dd, J = 8.8, 3.0 Hz), 6.53 (1H, d, J = 3.0 Hz), 4.97 (2H, s), 3.98-3.88 (2H, m), 2.16 (3H, s), 1.19 (3H, t, J = 7.0 Hz). |
| 258 | 1H-NMR (CDCl3) δ: 7.47 (1H, s), 7.22-7.17 (2H, m), 7.15 (1H, d, J = 8.8 Hz), 7.02 (1H, td, J = 8.5, 2.5 Hz), 6.95 (1H, td, J = 8.5, 2.5 Hz), 6.70 (1H, dd, J = 8.8, 3.1 Hz), 6.51 (1H, d, J = 3.1 Hz), 5.17 (1H, t, J = 3.9 Hz), 4.04-3.78 (8H, m), 1.18 (3H, t, J = 7.0 Hz). |
| 259 | "1H-NMR (CDCl3) δ: 7.48 (1H, s), 7.23-7.16 (2H, m), 7.13 (1H, d, J = 8.8 Hz), 7.03 (1H, td, J = 8.5, 2.7 Hz), 6.95 (1H, td, J = 8.5, 2.7 Hz), 6.65 (1H, dd, J = 8.8, 3.1 Hz), 6.46 (1H, d, J = 3.1 Hz), 4.68 (1H, t, J = 5.2 Hz), 4.15-4.09 (2H, m), 3.98-3.88 (3H, m), 3.86-3.73 (3H, m), 2.15-2.03 (1H, m), 1.98 (2H, td, J = 6.5, 5.3 Hz), 1.39-1.35 (1H, m), 1.18 (3H, t, J = 7.1 Hz)." |
| 260 | 1H-NMR (CDCl3) δ: 7.22 (1H, d, J = 9.5 Hz), 7.11 (1H, dd, J = 8.6, 2.3 Hz), 7.01 (1H, dd, J = 8.6, 2.3 Hz), 6.88 (1H, dd, J = 8.6, 2.4 Hz), 6.77 (1H, dd, J = 8.6, 2.4 Hz), 6.73-6.70 (1H, m), 6.68 (1H, d, J = 9.5 Hz), 6.52-6.50 (1H, m), 3.79 (3H, s), 3.33 (3H, s). |
| 261 | 1H-NMR (CDCl3) δ: 7.45 (1H, s), 7.08 (1H, dd, J = 8.5, 2.2 Hz), 7.01 (1H, dd, J = 8.5, 2.2 Hz), 6.88 (1H, dd, J = 8.4, 2.6 Hz), 6.79-6.71 (2H, m), 6.54-6.52 (1H, m), 3.79 (3H, s), 3.39 (3H, s). |
| 262 | 1H-NMR (CDCl3) δ: 7.65 (1H, s), 7.08 (1H, dd, J = 8.6, 2.4 Hz), 7.02 (1H, dd, J = 8.6, 2.4 Hz), 6.87 (1H, dd, J = 8.6, 2.8 Hz), 6.77 (1H, dd, J = 8.6, 2.8 Hz), 6.73 (1H, td, J = 8.3, 2.9 Hz), 6.54-6.52 (1H, m), 3.79 (3H, s), 3.40 (3H, s). |
| 263 | 1H-NMR (CDCl3) δ: 8.20-8.19 (1H, m), 7.97 (1H, d, J = 2.2 Hz), 7.54 (1H, s), 7.34 (1H, d, J = 8.8 Hz), 7.23-7.15 (2H, m), 7.03-6.94 (3H, m), 6.76 (1H, d, J = 2.7 Hz), 3.99-3.88 (2H, m), 1.18 (3H, t, J = 7.1 Hz). |
| 264 | 1H-NMR (CDCl3) δ: 7.47 (1H, s), 7.21-7.13 (2H, m), 7.06 (1H, t, J = 7.8 Hz), 7.01 (1H, td, J = 8.5, 2.6 Hz), 6.95 (1H, td, J = 8.5, 2.6 Hz), 6.90 (1H, dd, J = 8.5, 1.3 Hz), 6.73 (1H, dd, J = 7.8, 1.3 Hz), 4.78 (2H, s), 3.98-3.88 (2H, m), 1.19 (3H, t, J = 7.1 Hz). |
| 265 | 1H-NMR (CDCl3) δ: 7.47 (1H, s), 7.21-7.14 (2H, m), 7.02-6.90 (3H, m), 6.73 (1H, dd, J = 8.3, 1.3 Hz), 6.51 (1H, dd, J = 7.7, 1.3 Hz), 4.07-4.00 (2H, m), 3.97-3.88 (2H, m), 1.44 (3H, t, J = 7.0 Hz), 1.18 (3H, t, J = 7.1 Hz). |
| 266 | 1H-NMR (CDCl3) δ: 7.47 (1H, s), 7.26-7.21 (2H, m), 7.18-7.14 (1H, m), 7.05 (1H, td, J = 8.5, 2.7 Hz), 6.96 (1H, td, J = 8.5, 2.7 Hz), 6.83 (1H, dd, J = 8.8, 2.9 Hz), 6.73 (1H, d, J = 2.9 Hz), 4.82 (1H, d, J = 12.5 Hz), 4.75 (1H, d, J = 12.5 Hz), 4.01-3.85 (2H, m), 2.95 (3H, s), 1.19 (3H, t, J = 7.1 Hz). |

TABLE 5-continued

| Compound | ¹H-NMR |
|---|---|
| 267 | 1H-NMR (CDCl3) δ: 7.48 (1H, s), 7.20-7.16 (2H, m), 7.02-6.90 (4H, m), 6.61 (1H, dd, J = 6.8, 2.2 Hz), 5.20 (1H, d, J = 6.8 Hz), 5.17 (1H, d, J = 6.8 Hz), 3.98-3.88 (2H, m), 3.47 (3H, s), 1.18 (3H, t, J = 7.0 Hz). |
| 268 | 1H-NMR (CDCl3) δ: 7.46 (1H, s), 7.21-7.14 (2H, m), 7.03-6.98 (2H, m), 6.94 (1H, td, J = 8.5, 2.5 Hz), 6.75 (1H, dd, J = 8.5, 1.4 Hz), 6.63 (1H, dd, J = 8.0, 1.4 Hz), 6.12 (1H, tt, J = 55.0, 4.0 Hz), 4.17 (2H, td, J = 12.8, 4.0 Hz), 3.97-3.89 (2H, m), 1.19 (3H, t, J = 7.0 Hz) |
| 269 | 1H-NMR (CDCl3) δ: 7.47 (1H, s), 7.20-7.14 (2H, m), 7.01-7.00 (2H, m), 6.94 (1H, td, J = 8.5, 2.5 Hz), 6.78 (1H, dd, J = 8.5, 1.5 Hz), 6.67 (1H, dd, J = 7.6, 1.5 Hz), 4.33 (2H, q, J = 8.1 Hz), 3.99-3.87 (2H, m), 1.19 (3H, t, J = 7.0 Hz). |
| 270 | 1H-NMR (CDCl3) δ: 7.43 (1H, s), 7.09 (1H, dd, J = 8.5, 2.4 Hz), 7.03 (1H, dd, J = 8.5, 2.4 Hz), 6.85 (1H, dd, J = 8.5, 2.4 Hz), 6.78-6.73 (2H, m), 6.55-6.52 (1H, m), 4.02 (2H, t, J = 6.2 Hz), 3.99-3.89 (2H, m), 3.54 (2H, t, J = 6.2 Hz), 3.35 (3H, s), 2.06-2.01 (2H, m), 1.18 (3H, t, J = 7.0 Hz). |
| 271 | 1H-NMR (CDCl3) δ: 7.47 (1H, s), 7.21-7.14 (2H, m), 7.02-6.97 (2H, m), 6.95-6.88 (2H, m), 6.60 (1H, dd, J = 7.7, 1.3 Hz), 4.74 (1H, dd, J = 16.0, 2.2 Hz), 4.69 (1H, dd, J = 16.0, 2.2 Hz), 3.97-3.88 (2H, m), 2.53 (1H, t, J = 2.2 Hz), 1.18 (3H, t, J = 7.0 Hz). |
| 272 | 1H-NMR (CDCl3) δ: 7.47 (1H, s), 7.22-7.15 (2H, m), 7.02-6.90 (3H, m), 6.72 (1H, dd, J = 8.3, 1.5 Hz), 6.51 (1H, dd, J = 7.8, 1.5 Hz), 3.97-3.87 (4H, m), 1.88-1.78 (2H, m), 1.18 (3H, t, J = 7.1 Hz), 1.04 (3H, t, J = 7.4 Hz). |
| 273 | 1H-NMR (CDCl3) δ: 7.49 (1H, s), 7.19-7.16 (2H, m), 7.02-6.97 (2H, m), 6.95-6.90 (1H, m), 6.82 (1H, dd, J = 8.3, 1.5 Hz), 6.62 (1H, dd, J = 7.7, 1.5 Hz), 5.16 (2H, s), 3.98-3.88 (2H, m), 2.24 (3H, s), 1.19 (3H, t, J = 7.1 Hz). |
| 274 | 1H-NMR (CDCl3) δ: 7.31 (1H, dd, J = 9.5, 0.8 Hz), 7.18-7.17 (2H, m), 7.15-7.11 (1H, m), 6.99-6.96 (2H, m), 6.93-6.91 (2H, m), 6.88-6.87 (1H, m), 6.67 (1H, d, J = 9.5 Hz), 3.90 (2H, q, J = 7.0 Hz), 1.15 (3H, t, J = 7.0 Hz). |
| 275 | 1H-NMR (CDCl3) δ: 7.54 (1H, d, J = 0.6 Hz), 7.17-7.14 (3H, m), 6.96-6.91 (5H, m), 3.94 (2H, q, J = 7.0 Hz), 1.18 (3H, t, J = 7.0 Hz). |
| 276 | 1H-NMR (CDCl3) δ: 7.75 (1H, d, J = 0.5 Hz), 7.19-7.12 (3H, m), 6.97-6.90 (5H, m), 3.94 (2H, q, J = 7.0 Hz), 1.18 (3H, t, J = 7.0 Hz). |
| 277 | 1H-NMR (CDCl3) δ: 7.71 (1H, s), 7.18-7.14 (3H, m), 7.02-6.98 (2H, m), 6.74 (2H, dd, J = 8.4, 7.0 Hz), 3.39 (3H, s). |
| 278 | 1H-NMR (CDCl3) δ: 7.29-7.26 (1H, m), 7.19-7.10 (3H, m), 7.02-6.96 (2H, m), 6.75-6.70 (3H, m), 3.32 (3H, s). |
| 279 | 1H-NMR (CDCl3) δ: 7.68 (1H, s), 7.22-7.19 (2H, m), 7.16-7.12 (1H, m), 7.01-6.96 (2H, m), 6.76-6.70 (2H, m), 3.93 (2H, q, J = 7.2 Hz), 1.18 (3H, t, J = 7.2 Hz). |
| 280 | 1H-NMR (CDCl3) δ: 7.25-7.20 (3H, m), 7.15-7.09 (1H, m), 6.99-6.96 (2H, m), 6.74-6.68 (3H, m), 3.88 (2H, q, J = 7.1 Hz), 1.16 (3H, t, J = 7.1 Hz). |
| 281 | 1H-NMR (CDCl3) δ: 7.48 (1H, s), 7.22-7.18 (2H, m), 7.17-7.12 (1H, m), 7.01-6.96 (2H, m), 6.73 (2H, dd, J = 8.3, 7.1 Hz), 3.93 (2H, q, J = 7.0 Hz), 1.18 (3H, t, J = 7.0 Hz). |
| 282 | 1H-NMR (CDCl3) δ: 7.51 (1H, s), 7.20-7.12 (3H, m), 7.03-6.97 (2H, m), 6.77-6.71 (2H, m), 3.38 (3H, s). |
| 283 | 1H-NMR (CDCl3) δ: 7.74 (1H, dd, J = 8.0, 1.2 Hz), 7.29-7.28 (1H, m), 7.22-7.20 (2H, m), 7.10 (1H, td, J = 7.5, 1.2 Hz), 7.00 (1H, td, J = 8.6, 2.8 Hz), 6.93-6.91 (2H, m), 6.84-6.81 (1H, m), 6.68 (1H, d, J = 9.2 Hz), 3.94-3.83 (2H, m), 1.17 (3H, t, J = 7.0 Hz). |
| 284 | 1H-NMR (CDCl3) δ: 7.74 (1H, dd, J = 8.0, 0.9 Hz), 7.63 (1H, s), 7.29-7.28 (1H, m), 7.20-7.19 (1H, m), 7.11 (1H, td, J = 7.5, 1.2 Hz), 7.00 (1H, td, J = 8.5, 2.5 Hz), 6.94-6.93 (2H, m), 6.85-6.84 (1H, m), 3.96-3.90 (2H, m), 1.19 (3H, t, J = 7.0 Hz). |
| 285 | 1H-NMR (CDCl3) δ: 7.74 (1H, dd, J = 8.1, 1.2 Hz), 7.43 (1H, s), 7.29-7.28 (1H, m), 7.21-7.17 (1H, m), 7.11 (1H, td, J = 7.4, 1.2 Hz), 7.00 (1H, td, J = 8.4, 2.7 Hz), 6.95-6.92 (2H, m), 6.85 (1H, td, J = 7.7, 1.8 Hz), 3.95-3.90 (2H, m), 1.19 (3H, t, J = 7.1 Hz). |
| 286 | 1H-NMR (CDCl3) δ: 7.47 (1H, s), 7.21-7.12 (2H, m), 7.06-6.92 (4H, m), 6.71 (1H, dd, J = 7.6, 1.5 Hz), 4.93 (2H, s), 3.98-3.88 (2H, m), 3.07 (3H, s), 1.19 (3H, t, J = 7.0 Hz). |
| 287 | 1H-NMR (CDCl3) δ: 8.22 (1H, dd, J = 4.7, 2.0 Hz), 7.31 (1H, d, J = 9.2 Hz), 7.22 (1H, dd, J = 7.6, 2.0 Hz), 7.20-7.17 (1H, m), 7.14-7.11 (1H, m), 7.07-7.01 (2H, m), 6.96 (1H, td, J = 8.4, 2.5 Hz), 6.72 (1H, d, J = 9.2 Hz), 3.33 (3H, s). |
| 288 | 1H-NMR (CDCl3) δ: 8.20 (1H, dd, J = 4.7, 2.0 Hz), 7.28-7.17 (4H, m), 7.06-7.00 (2H, m), 6.95 (1H, td, J = 8.4, 2.7 Hz), 6.70 (1H, d, J = 9.5 Hz), 3.93-3.85 (2H, m), 1.17 (3H, t, J = 7.0 Hz). |
| 289 | 1H-NMR (CDCl3) δ: 8.22 (1H, dd, J = 4.6, 2.0 Hz), 7.71 (1H, s), 7.27-7.25 (1H, m), 7.21-7.17 (2H, m), 7.06-6.94 (3H, m), 3.98-3.89 (2H, m), 1.19 (3H, t, J = 7.1 Hz). |
| 290 | 1H-NMR (CDCl3) δ: 8.24 (1H, dd, J = 4.6, 2.0 Hz), 7.74 (1H, s), 7.24 (1H, dd, J = 7.6, 2.0 Hz), 7.17-7.12 (2H, m), 7.08-7.03 (2H, m), 6.97 (1H, td, J = 8.5, 2.6 Hz), 3.40 (3H, s). |
| 291 | 1H-NMR (CDCl3) δ: 8.22 (1H, dd, J = 4.7, 2.0 Hz), 7.50 (1H, s), 7.27-7.25 (1H, m), 7.20-7.18 (2H, m), 7.06-7.02 (2H, m), 6.99-6.95 (1H, m), 3.96-3.91 (2H, m), 1.20 (3H, t, J = 7.0 Hz). |
| 292 | 1H-NMR (CDCl3) δ: 8.24 (1H, dd, J = 4.9, 2.0 Hz), 7.54 (1H, s), 7.24 (1H, dd, J = 7.6, 2.0 Hz), 7.17-7.11 (2H, m), 7.08-6.95 (3H, m), 3.39 (3H, s). |
| 293 | 1H-NMR (CDCl3) δ: 7.23-7.19 (2H, m), 6.99-6.93 (6H, m), 6.84 (1H, d, J = 7.3 Hz), 6.66 (1H, d, J = 9.2 Hz), 3.91-3.88 (2H, m), 2.10 (3H, s), 1.16 (3H, t, J = 7.0 Hz). |
| 294 | 1H-NMR (CDCl3) δ: 7.67 (1H, s), 7.20-7.17 (1H, m), 7.08-6.89 (6H, m), 6.84 (1H, d, J = 7.6 Hz), 3.97-3.91 (2H, m), 2.11 (3H, s), 1.18 (3H, t, J = 7.0 Hz). |

TABLE 5-continued

| Compound | ¹H-NMR |
|---|---|
| 295 | 1H-NMR (CDCl3) δ: 7.46 (1H, s), 7.20-7.17 (1H, m), 7.08-6.89 (6H, m), 6.84 (1H, d, J = 7.3 Hz), 3.97-3.91 (2H, m), 2.11 (3H, s), 1.18 (3H, t, J = 7.0 Hz). |
| 296 | 1H-NMR (CDCl3) δ: 7.48 (1H, s), 7.20-7.15 (2H, m), 7.02-6.89 (3H, m), 6.76 (1H, dd, J = 8.3, 1.5 Hz), 6.52 (1H, dd, J = 7.6, 1.5 Hz), 4.49-4.43 (1H, m), 3.98-3.88 (2H, m), 1.33 (3H, d, J = 6.1 Hz), 1.31 (3H, d, J = 6.1 Hz), 1.18 (3H, t, J = 7.0 Hz). |
| 297 | 1H-NMR (CDCl3) δ: 7.49 (1H, s), 7.22-7.18 (2H, m), 7.13 (1H, d, J = 8.9 Hz), 7.01 (1H, td, J = 8.6, 2.5 Hz), 6.96 (1H, td, J = 8.6, 2.5 Hz), 6.64 (1H, dd, J = 8.9, 3.1 Hz), 6.44 (1H, d, J = 3.1 Hz), 4.32-4.27 (1H, m), 3.97-3.89 (2H, m), 1.23 (3H, d, J = 6.1 Hz), 1.20-1.16 (6H, m). |
| 298 | 1H-NMR (CDCl3) δ: 7.52 (1H, dd, J = 7.8, 1.5 Hz), 7.38 (1H, m), 7.29-7.27 (4H, m), 7.09-7.08 (1H, m), 7.00-6.96 (2H, m), 6.71 (1H, d, J = 9.3 Hz), 3.90 (2H, q, J = 7.0 Hz), 1.17 (3H, t, J = 7.0 Hz). |
| 299 | 1H-NMR (CDCl3) δ: 7.53-7.51 (2H, m), 7.44-6.97 (7H, m), 3.95 (2H, q, J = 7.0 Hz), 1.19 (3H, t, J = 7.0 Hz). |
| 300 | 1H-NMR (CDCl3) δ: 7.65 (1H, d, J = 8.5 Hz), 7.58 (1H, d, J = 8.5 Hz), 7.35 (1H, d, J = 7.8 Hz), 7.30-7.24 (2H, m), 6.80-6.72 (2H, m), 6.53-6.50 (1H, m), 3.29 (3H, s). |
| 301 | 1H-NMR (CDCl3) δ: 7.64 (1H, d, J = 8.0 Hz), 7.57 (1H, d, J = 8.4 Hz), 7.40 (1H, d, J = 8.0 Hz), 7.32 (1H, d, J = 8.4 Hz), 7.21 (1H, d, J = 9.2 Hz), 6.75 (1H, td, J = 8.4, 3.1 Hz), 6.71 (1H, d, J = 9.2 Hz), 6.55-6.52 (1H, m), 3.90-3.77 (2H, m), 1.17 (3H, t, J = 7.0 Hz). |
| 302 | 1H-NMR (CDCl3) δ: 7.64 (1H, d, J = 8.2 Hz), 7.58 (1H, d, J = 8.2 Hz), 7.45 (1H, s), 7.37 (1H, d, J = 8.5 Hz), 7.33 (1H, d, J = 8.5 Hz), 6.78 (1H, td, J = 8.5, 2.9 Hz), 6.57-6.54 (1H, m), 3.96-3.81 (2H, m), 1.19 (3H, t, J = 7.1 Hz). |
| 303 | 1H-NMR (CDCl3) δ: 7.66-7.64 (2H, m), 7.58 (1H, d, J = 8.0 Hz), 7.37 (1H, d, J = 8.3 Hz), 7.33 (1H, d, J = 8.0 Hz), 6.78 (1H, td, J = 8.5, 3.0 Hz), 6.56-6.54 (1H, m), 3.95-3.84 (2H, m), 1.19 (3H, t, J = 7.0 Hz). |
| 304 | 1H-NMR (CDCl3) δ: 7.66 (1H, d, J = 8.1 Hz), 7.59 (1H, d, J = 8.1 Hz), 7.49 (1H, s), 7.33 (1H, d, J = 8.5 Hz), 7.29-7.26 (1H, m), 6.80 (1H, td, J = 8.5, 2.8 Hz), 6.55-6.52 (1H, m), 3.38 (3H, s). |
| 305 | 1H-NMR (CDCl3) δ: 7.69 (1H, s), 7.65 (1H, d, J = 8.1 Hz), 7.59 (1H, d, J = 8.1 Hz), 7.33 (1H, d, J = 8.4 Hz), 7.29-7.27 (1H, m), 6.79 (1H, td, J = 8.4, 2.8 Hz), 6.55-6.52 (1H, m), 3.36 (3H, s). |
| 306 | 1H-NMR (CDCl3) δ: 7.28 (1H, d, J = 9.2 Hz), 7.16-7.10 (3H, m), 6.95-6.91 (2H, m), 6.86 (1H, J = 7.6, 1.8 Hz), 6.74 (1H, m), 6.68 (1H, m), 6.65 (1H, d, J = 9.2 Hz), 3.89 (2H, q, J = 7.0 Hz), 3.65 (3H, s), 1.15 (3H, t, J = 7.0 Hz). |
| 307 | 1H-NMR (CDCl3) δ: 7.51 (1H, s), 7.15-7.11 (3H, m), 6.96-6.92 (2H, m), 6.86 (1H, dd, J = 7.5, 1.7 Hz), 6.74 (1H, m), 6.68 (1H, m), 3.94 (2H, q, J = 7.0 Hz), 3.66 (3H, s), 1.18 (3H, t, J = 7.0 Hz). |
| 308 | 1H-NMR (CDCl3) δ: 7.50 (1H, dd, J = 8.3, 2.1 Hz), 7.43 (1H, dd, J = 8.3, 2.1 Hz), 7.20 (1H, d, J = 9.3 Hz), 7.12 (1H, dd, J = 8.3, 2.1 Hz), 7.05 (1H, dd, J = 8.3, 2.1 Hz), 6.76 (1H, td, J = 8.5, 2.8 Hz), 6.68 (1H, d, J = 9.3 Hz), 6.55-6.52 (1H, m), 3.93-3.79 (2H, m), 1.16 (3H, t, J = 7.1 Hz). |
| 309 | 1H-NMR (CDCl3) δ: 7.52 (1H, dd, J = 8.2, 2.1 Hz), 7.44 (1H, dd, J = 8.2, 2.1 Hz), 7.24 (1H, d, J = 9.3 Hz), 7.07 (1H, dd, J = 8.2, 2.1 Hz), 7.00 (1H, dd, J = 8.2, 2.1 Hz), 6.78 (1H, td, J = 8.4, 2.9 Hz), 6.70 (1H, d, J = 9.3 Hz), 6.53-6.50 (1H, m), 3.31 (3H, s). |
| 310 | 1H-NMR (CDCl3) δ: 7.51 (1H, dd, J = 8.2, 2.1 Hz), 7.45-7.43 (2H, m), 7.09 (1H, dd, J = 8.2, 2.1 Hz), 7.05 (1H, dd, J = 8.2, 2.1 Hz), 6.79 (1H, td, J = 8.5, 2.8 Hz), 6.57-6.53 (1H, m), 3.98-3.84 (2H, m), 1.18 (3H, t, J = 7.1 Hz). |
| 311 | 1H-NMR (CDCl3) δ: 7.64 (1H, s), 7.51 (1H, dd, J = 8.1, 2.0 Hz), 7.44 (1H, dd, J = 8.1, 2.0 Hz), 7.10-7.04 (2H, m), 6.78 (1H, td, J = 8.4, 3.0 Hz), 6.56-6.53 (1H, m), 3.98-3.84 (2H, m), 1.18 (3H, t, J = 7.0 Hz). |
| 312 | 1H-NMR (CDCl3) δ: 7.67 (1H, s), 7.52 (1H, dd, J = 8.2, 2.0 Hz), 7.45 (1H, dd, J = 8.2, 2.0 Hz), 7.04 (1H, dd, J = 8.2, 2.0 Hz), 7.00 (1H, dd, J = 8.2, 2.0 Hz), 6.80 (1H, td, J = 8.4, 3.0 Hz), 6.55-6.52 (1H, m), 3.37 (3H, s). |
| 313 | 1H-NMR (CDCl3) δ: 7.52 (1H, dd, J = 8.2, 2.1 Hz), 7.47-7.44 (2H, m), 7.05 (1H, dd, J = 8.2, 2.1 Hz), 7.00 (1H, dd, J = 8.2, 2.1 Hz), 6.80 (1H, td, J = 8.3, 2.7 Hz), 6.55-6.52 (1H, m), 3.37 (3H, s). |
| 314 | 1H-NMR (CDCl3) δ: 7.55-7.53 (1H, m), 7.40-7.39 (1H, m), 7.35 (1H, d, J = 9.2 Hz), 7.29-7.07 (4H, m), 7.00-6.99 (2H, m), 6.73 (1H, d, J = 9.2 Hz), 3.34 (3H, s). |
| 315 | 1H-NMR (CDCl3) δ: 7.57 (1H, s), 7.54-7.53 (1H, m), 7.43 (1H, td, J = 7.7, 1.4 Hz), 7.32-7.00 (6H, m), 3.40 (3H, s). |
| 316 | 1H-NMR (CDCl3) δ: 7.77 (1H, s), 7.54-7.52 (1H, m), 7.44-7.42 (1H, m), 7.32-6.98 (6H, m), 3.40 (3H, s). |
| 317 | 1H-NMR (CDCl3) δ: 7.67 (1H, dd, J = 8.0, 1.7 Hz), 7.61 (1H, dd, J = 8.0, 1.7 Hz), 7.38 (1H, dd, J = 8.0, 1.7 Hz), 7.33 (1H, dd, J = 8.0, 1.7 Hz), 7.21 (1H, d, J = 9.5 Hz), 6.77 (1H, td, J = 8.3, 2.7 Hz), 6.72 (1H, d, J = 9.5 Hz), 6.54-6.51 (1H, m), 3.89-3.78 (2H, m), 1.16 (3H, t, J = 7.1 Hz). |
| 318 | 1H-NMR (CDCl3) δ: 7.69 (1H, dd, J = 8.1, 1.7 Hz), 7.62 (1H, dd, J = 8.1, 1.7 Hz), 7.35 (1H, dd, J = 8.1, 1.7 Hz), 7.29-7.24 (2H, m), 6.79 (1H, td, J = 8.5, 2.8 Hz), 6.74 (1H, d, J = 9.3 Hz), 6.52-6.49 (1H, m), 3.30 (3H, s). |
| 319 | 1H-NMR (CDCl3) δ: 7.69-7.67 (1H, m), 7.63-7.61 (1H, m), 7.46 (1H, s), 7.37-7.32 (2H, m), 6.80 (1H, td, J = 8.4, 2.8 Hz), 6.56-6.53 (1H, m), 3.93-3.83 (2H, m), 1.19 (3H, t, J = 7.0 Hz). |

TABLE 5-continued

| Compound | ¹H-NMR |
|---|---|
| 320 | 1H-NMR (CDCl3) δ: 7.69-7.66 (2H, m), 7.63-7.61 (1H, m), 7.37-7.32 (2H, m), 6.80 (1H, td, J = 8.4, 3.0 Hz), 6.56-6.53 (1H, m), 3.94-3.82 (2H, m), 1.19 (3H, t, J = 7.1 Hz). |
| 321 | 1H-NMR (CDCl3) δ: 7.70-7.68 (1H, m), 7.64-7.62 (1H, m), 7.49 (1H, s), 7.33-7.31 (1H, m), 7.29-7.27 (1H, m), 6.82 (1H, td, J = 8.3, 2.8 Hz), 6.54-6.51 (1H, m), 3.36 (3H, s). |
| 322 | 1H-NMR (CDCl3) δ: 7.70-7.68 (2H, m), 7.63 (1H, dd, J = 8.0, 1.7 Hz), 7.32 (1H, dd, J = 8.0, 1.7 Hz), 7.29 (1H, dd, J = 8.0, 1.7 Hz), 6.81 (1H, td, J = 8.4, 2.8 Hz), 6.54-6.51 (1H, m), 3.36 (3H, s). |
| 323 | 1H-NMR (CDCl3) δ: 7.48 (1H, dd, J = 7.8, 1.6 Hz), 7.40 (1H, dd, J = 7.8, 1.6 Hz), 7.22-7.19 (2H, m), 7.12 (1H, dd, J = 7.8, 1.6 Hz), 6.74 (1H, td, J = 8.5, 3.1 Hz), 6.68 (1H, d, J = 9.3 Hz), 6.54-6.51 (1H, m), 3.91-3.81 (2H, m), 3.14 (1H, s), 1.16 (3H, t, J = 7.1 Hz). |
| 324 | 1H-NMR (CDCl3) δ: 7.48 (1H, dd, J = 7.8, 1.5 Hz), 7.44 (1H, s), 7.41 (1H, dd, J = 7.8, 1.5 Hz), 7.18 (1H, dd, J = 8.1, 1.7 Hz), 7.13 (1H, dd, J = 8.1, 1.7 Hz), 6.76 (1H, td, J = 8.5, 2.9 Hz), 6.56-6.52 (1H, m), 3.98-3.84 (2H, m), 3.15 (1H, s), 1.18 (3H, t, J = 7.1 Hz). |
| 325 | 1H-NMR (CDCl3) δ: 7.65 (1H, s), 7.48 (1H, dd, J = 8.0, 1.5 Hz), 7.41 (1H, dd, J = 8.0, 1.5 Hz), 7.18 (1H, dd, J = 8.0, 1.5 Hz), 7.13 (1H, dd, J = 8.0, 1.5 Hz), 6.76 (1H, td, J = 8.5, 2.9 Hz), 6.55-6.53 (1H, m), 3.97-3.85 (2H, m), 3.16 (1H, s), 1.18 (3H, t, J = 7.0 Hz). |
| 326 | 1H-NMR (CDCl3) δ: 7.68 (1H, s), 7.49 (1H, dd, J = 8.0, 1.5 Hz), 7.42 (1H, dd, J = 8.0, 1.5 Hz), 7.14 (1H, dd, J = 8.0, 1.5 Hz), 7.08 (1H, dd, J = 8.0, 1.5 Hz), 6.78 (1H, td, J = 8.4, 2.8 Hz), 6.53-6.51 (1H, m), 3.38 (3H, s), 3.16 (1H, s). |
| 327 | 1H-NMR (CDCl3) δ: 7.50-7.48 (2H, m), 7.41 (1H, dd, J = 8.0, 1.4 Hz), 7.14 (1H, dd, J = 8.0, 1.4 Hz), 7.07 (1H, dd, J = 8.0, 1.4 Hz), 6.78 (1H, td, J = 8.3, 2.9 Hz), 6.54-6.50 (1H, m), 3.37 (3H, s), 3.16 (1H, s). |
| 328 | 1H-NMR (CDCl3) δ: 7.49 (1H, dd, J = 8.0, 1.7 Hz), 7.40 (1H, dd, J = 8.0, 1.7 Hz), 7.24 (1H, d, J = 9.5 Hz), 7.17 (1H, dd, J = 8.0, 1.7 Hz), 7.07 (1H, dd, J = 8.0, 1.7 Hz), 6.76 (1H, td, J = 8.6, 3.1 Hz), 6.70 (1H, d, J = 9.5 Hz), 6.51-6.49 (1H, m), 3.31 (3H, s), 3.15 (1H, s). |
| 329 | 1H-NMR (CDCl3) δ: 7.71 (1H, s), 7.62-7.60 (1H, m), 7.56-7.54 (1H, m), 7.36-7.33 (2H, m), 7.28-7.26 (1H, m), 7.13 (1H, td, J = 7.6, 1.5 Hz), 7.04 (1H, td, J = 7.6, 1.5 Hz), 6.92 (1H, dd, J = 7.6, 1.5 Hz), 3.94-3.85 (2H, m), 1.19 (3H, t, J = 7.0 Hz). |
| 330 | 1H-NMR (CDCl3) δ: 7.62-7.59 (1H, m), 7.55-7.53 (1H, m), 7.38-7.33 (2H, m), 7.28-7.25 (2H, m), 7.11 (1H, td, J = 7.7, 1.7 Hz), 7.02 (1H, td, J = 7.7, 1.7 Hz), 6.91 (1H, dd, J = 7.7, 1.7 Hz), 6.70 (1H, d, J = 9.3 Hz), 3.92-3.78 (2H, m), 1.17 (3H, t, J = 6.8 Hz). |
| 331 | 1H-NMR (CDCl3) δ: 7.74 (1H, s), 7.63-7.61 (1H, m), 7.57-7.55 (1H, m), 7.31-7.28 (3H, m), 7.15 (1H, td, J = 7.6, 1.2 Hz), 7.05 (1H, td, J = 7.6, 1.2 Hz), 6.90 (1H, dd, J = 7.6, 1.2 Hz), 3.38 (3H, s). |
| 332 | 1H-NMR (CDCl3) δ: 7.63-7.61 (1H, m), 7.56-7.54 (1H, m), 7.34-7.27 (4H, m), 7.15-7.12 (1H, m), 7.03 (1H, td, J = 7.6, 1.3 Hz), 6.89 (1H, dd, J = 7.6, 1.3 Hz), 6.72 (1H, d, J = 9.2 Hz), 3.31 (3H, s). |
| 333 | 1H-NMR (CDCl3) δ: 7.63-7.59 (1H, m), 7.57-7.54 (1H, m), 7.50 (1H, s), 7.35-7.33 (2H, m), 7.29-7.26 (1H, m), 7.14 (1H, td, J = 7.3, 1.7 Hz), 7.04 (1H, td, J = 7.6, 1.2 Hz), 6.92 (1H, dd, J = 7.3, 1.7 Hz), 3.95-3.85 (2H, m), 1.19 (3H, t, J = 7.0 Hz). |
| 334 | 1H-NMR (CDCl3) δ: 7.63-7.61 (1H, m), 7.57-7.54 (2H, m), 7.31-7.28 (3H, m), 7.16 (1H, td, J = 7.7, 1.6 Hz), 7.05 (1H, td, J = 7.5, 1.3 Hz), 6.91 (1H, dd, J = 7.7, 1.6 Hz), 3.37 (3H, s). |
| 335 | 1H-NMR (CDCl3) δ: 7.94 (1H, s), 7.61-7.59 (1H, m), 7.56-7.54 (1H, m), 7.36-7.32 (2H, m), 7.27-7.26 (1H, m), 7.15-7.11 (1H, m), 7.04 (1H, td, J = 7.5, 1.2 Hz), 6.91 (1H, dd, J = 7.5, 1.5 Hz), 3.95-3.83 (2H, m), 1.18 (3H, t, J = 7.0 Hz). |
| 336 | 1H-NMR (CDCl3) δ: 7.97 (1H, s), 7.61 (1H, dt, J = 7.3, 1.6 Hz), 7.56 (1H, dt, J = 7.3, 1.6 Hz), 7.30-7.27 (3H, m), 7.15 (1H, td, J = 7.6, 1.5 Hz), 7.05 (1H, td, J = 7.6, 1.2 Hz), 6.90 (1H, dd, J = 7.6, 1.5 Hz), 3.38 (3H, s). |
| 337 | 1H-NMR (CDCl3) δ: 7.62 (1H, ddd, J = 8.0, 1.8, 0.6 Hz), 7.55 (1H, ddd, J = 8.0, 1.8, 0.6 Hz), 7.38-7.35 (2H, m), 7.32-7.27 (2H, m), 7.15-7.12 (1H, m), 7.04 (1H, td, J = 7.6, 1.3 Hz), 6.91 (1H, dd, J = 7.6, 1.8 Hz), 6.73 (1H, d, J = 9.2 Hz), 6.30 (1H, tt, J = 57.0, 4.6 Hz), 4.18-3.98 (2H, m). |
| 338 | 1H-NMR (CDCl3) δ: 7.64-7.61 (1H, m), 7.58 (1H, s), 7.57-7.55 (1H, m), 7.36-7.28 (3H, m), 7.16 (1H, td, J = 7.6, 1.6 Hz), 7.05 (1H, td, J = 7.6, 1.2 Hz), 6.93 (1H, dd, J = 7.6, 1.6 Hz), 6.32 (1H, tt, J = 57.0, 4.6 Hz), 4.24-4.01 (2H, m). |
| 339 | 1H-NMR (CDCl3) δ: 7.79 (1H, s), 7.62 (1H, ddd, J = 7.8, 1.7, 0.7 Hz), 7.56 (1H, ddd, J = 7.8, 1.7, 0.7 Hz), 7.36-7.27 (3H, m), 7.15 (1H, td, J = 7.8, 1.7 Hz), 7.05 (1H, td, J = 7.8, 1.2 Hz), 6.92 (1H, dd, J = 7.8, 1.7 Hz), 6.32 (1H, tt, J = 56.9, 4.6 Hz), 4.24-4.01 (2H, m). |
| 340 | 1H-NMR (CDCl3) δ: 7.51 (1H, s), 7.24-7.20 (1H, m), 7.18-7.14 (1H, m), 7.09 (1H, d, J = 8.6 Hz), 7.04-6.95 (2H, m), 6.64 (1H, dd, J = 8.6, 3.1 Hz), 6.43 (1H, d, J = 3.1 Hz), 6.10 (1H, br s), 3.98-3.88 (2H, m), 1.17 (3H, t, J = 7.1 Hz). |
| 341 | 1H-NMR (CDCl3) δ: 7.48 (1H, s), 7.21-7.17 (1H, m), 7.15-7.12 (1H, m), 7.01 (1H, td, J = 8.4, 2.7 Hz), 6.95 (2H, td, J = 8.4, 2.7 Hz), 6.85 (1H, dd, J = 8.4, 1.5 Hz), 6.52 (1H, dd, J = 7.6, 1.5 Hz), 5.66 (1H, s), 3.98-3.89 (2H, m), 1.19 (3H, t, J = 7.0 Hz). |

TABLE 5-continued

| Compound | ¹H-NMR |
|---|---|
| 342 | 1H-NMR (CDCl3) δ: 7.59-7.56 (1H, m), 7.54-7.52 (1H, m), 7.35-7.33 (2H, m), 7.27-7.25 (1H, m), 7.16-7.15 (1H, m), 7.10 (1H, td, J = 7.6, 1.7 Hz), 7.02 (1H, td, J = 7.6, 1.2 Hz), 6.91 (1H, dd, J = 7.6, 1.7 Hz), 3.92-3.79 (2H, m), 2.24 (3H, d, J = 1.2 Hz), 1.16 (3H, t, J = 7.1 Hz). |
| 343 | 1H-NMR (CDCl3) δ: 7.62-7.54 (3H, m), 7.36-7.32 (2H, m), 7.28-7.25 (1H, m), 7.13 (1H, td, J = 7.7, 1.6 Hz), 7.04 (1H, td, J = 7.4, 1.2 Hz), 6.91 (1H, dd, J = 7.7, 1.6 Hz), 3.92-3.82 (2H, m), 3.39 (1H, s), 1.18 (3H, t, J = 7.1 Hz). |
| 344 | 1H-NMR, (CDCl3) δ: 7.04-7.02 (3H, m), 6.91-6.89 (2H, m), 6.81 (1H, dd, J = 8.5, 6.1 Hz), 6.73-6.69 (1H, m), 2.84 (3H, s), 2.82-2.67 (3H, m), 2.43 (1H, ddd, J = 15.7, 7.6, 5.7 Hz). |
| 345 | 1H-NMR (CDCl3) δ: 7.26-7.25 (1H, m), 7.17-7.13 (1H, m), 7.11-7.07 (1H, m), 7.04-7.02 (2H, m), 6.95 (1H, td, J = 8.5, 2.7 Hz), 6.88 (1H, dd, J = 8.5, 6.1 Hz), 6.77-6.74 (1H, m), 6.69 (1H, d, J = 9.3 Hz), 3.32 (3H, s). |
| 346 | 1H-NMR (CDCl3) δ: 7.49 (1H, s), 7.15-7.08 (2H, m), 7.04-7.03 (2H, m), 6.97 (1H, td, J = 8.6, 2.5 Hz), 6.89 (1H, dd, J = 8.6, 6.1 Hz), 6.77 (1H, ddd, J = 9.6, 6.9, 1.7 Hz), 3.38 (3H, s). |
| 347 | 1H-NMR (CDCl3) δ: 7.69 (1H, s), 7.15-7.09 (2H, m), 7.06-7.01 (2H, m), 6.97 (1H, td, J = 8.6, 2.5 Hz), 6.89 (1H, dd, J = 8.6, 5.8 Hz), 6.79-6.76 (1H, m), 3.38 (3H, s). |
| 348 | 1H-NMR (CDCl3) δ: 7.92 (1H, s), 7.14-7.08 (2H, m), 7.05-7.03 (2H, m), 6.99-6.96 (1H, m), 6.89 (1H, dd, J = 8.5, 6.1 Hz), 6.77 (1H, td, J = 8.5, 2.7 Hz), 3.39 (3H, s). |
| 349 | 1H-NMR (CDCl3) δ: 7.07-7.06 (2H, m), 7.02 (1H, dd, J = 8.5, 2.4 Hz), 6.90-6.88 (2H, m), 6.81 (1H, dd, J = 8.5, 6.1 Hz), 6.72-6.69 (1H, m), 3.62 (1H, td, J = 14.0, 7.0 Hz), 3.28 (1H, td, J = 14.0, 7.0 Hz), 2.78-2.68 (3H, m), 2.43-2.39 (1H, m), 0.96 (3H, t, J = 7.0 Hz). |
| 350 | 1H-NMR (CDCl3) δ: 7.22 (1H, d, J = 9.5 Hz), 7.20-7.19 (1H, m), 7.17-7.13 (1H, m), 7.03-7.00 (2H, m), 6.95 (1H, td, J = 8.6, 2.8 Hz), 6.90 (1H, dd, J = 8.6, 6.0 Hz), 6.77-6.73 (1H, m), 6.67 (1H, d, J = 9.5 Hz), 3.91-3.85 (2H, m), 1.16 (3H, t, J = 7.0 Hz) |
| 351 | 1H-NMR (CDCl3) δ: 7.46 (1H, s), 7.17-7.15 (2H, m), 7.03-7.01 (2H, m), 6.97-6.95 (1H, m), 6.91 (1H, dd, J = 8.6, 6.1 Hz), 6.78-6.75 (1H, m), 3.96-3.90 (2H, m), 1.18 (3H, t, J = 7.0 Hz). |
| 352 | 1H-NMR (CDCl3) δ: 7.66 (1H, s), 7.19-7.14 (2H, m), 7.03-7.01 (2H, m), 6.96 (1H, td, J = 8.6, 2.4 Hz), 6.91 (1H, dd, J = 8.5, 6.1 Hz), 6.79-6.74 (1H, m), 3.94-3.91 (2H, m), 1.18 (3H, t, J = 7.0 Hz). |
| 353 | 1H-NMR (CDCl3) δ: 7.59-7.56 (1H, m), 7.53-7.50 (1H, m), 7.35-7.32 (2H, m), 7.29-7.26 (1H, m), 7.12 (1H, td, J = 7.6, 1.7 Hz), 7.04 (1H, td, J = 7.6, 1.3 Hz), 6.95 (1H, dd, J = 7.6, 1.7 Hz), 6.55 (1H, s), 3.92-3.85 (5H, m), 1.16 (3H, t, J = 7.0 Hz). |
| 354 | 1H-NMR (CDCl3) δ: 7.29 (1H, d, J = 2.1 Hz), 7.04-7.02 (2H, m), 6.96 (1H, dd, J = 8.3, 2.1 Hz), 6.92-6.90 (2H, m), 6.76 (1H, d, J = 8.3 Hz), 2.84 (3H, s), 2.84-2.74 (2H, m), 2.71-2.67 (1H, m), 2.43-2.40 (1H, m). |
| 355 | 1H-NMR (CDCl3) δ: 7.31 (1H, d, J = 2.2 Hz), 7.25 (1H, d, J = 9.3 Hz), 7.18-7.14 (1H, m), 7.09-7.07 (1H, m), 7.04-7.00 (2H, m), 6.96 (1H, td, J = 8.5, 2.6 Hz), 6.83 (1H, d, J = 8.3 Hz), 6.69 (1H, d, J = 9.3 Hz), 3.31 (3H, s). |
| 356 | 1H-NMR (CDCl3) δ: 7.48 (1H, s), 7.32 (1H, d, J = 2.1 Hz), 7.15-7.12 (1H, m), 7.10-7.08 (1H, m), 7.05-7.03 (2H, m), 6.98 (1H, td, J = 8.5, 2.5 Hz), 6.84 (1H, d, J = 8.3 Hz), 3.38 (3H, s). |
| 357 | 1H-NMR (CDCl3) δ: 7.68 (1H, s), 7.32 (1H, d, J = 2.1 Hz), 7.15-7.08 (2H, m), 7.06-7.02 (2H, m), 6.98 (1H, td, J = 8.5, 2.5 Hz), 6.84 (1H, d, J = 8.3 Hz), 3.38 (3H, s). |
| 358 | 1H-NMR (CDCl3) δ: 7.29 (1H, d, J = 2.1 Hz), 7.08-7.06 (2H, m), 6.96 (1H, dd, J = 8.3, 2.1 Hz), 6.92-6.90 (2H, m), 6.76 (1H, d, J = 8.3 Hz), 3.64-3.61 (1H, m), 3.28-3.25 (1H, m), 2.82-2.73 (2H, m), 2.70-2.66 (1H, m), 2.43-2.38 (1H, m), 0.96 (3H, t, J = 7.0 Hz). |
| 359 | 1H-NMR (CDCl3) δ: 7.29 (1H, d, J = 2.1 Hz), 7.21-7.19 (2H, m), 7.16-7.13 (1H, m), 7.03-7.01 (2H, m), 6.95 (1H, td, J = 8.5, 2.7 Hz), 6.85 (1H, d, J = 8.3 Hz), 6.67 (1H, d, J = 9.2 Hz), 3.90-3.85 (2H, m), 1.16 (3H, t, J = 7.0 Hz). |
| 360 | 1H-NMR (CDCl3) δ: 7.44 (1H, s), 7.30 (1H, d, J = 2.1 Hz), 7.19-7.13 (2H, m), 7.04-7.02 (2H, m), 6.97 (1H, td, J = 8.4, 2.5 Hz), 6.86 (1H, d, J = 8.3 Hz), 3.95-3.91 (2H, m), 1.18 (3H, t, J = 7.0 Hz). |
| 361 | 1H-NMR (CDCl3) δ: 7.65 (1H, s), 7.30 (1H, d, J = 2.1 Hz), 7.19-7.13 (2H, m), 7.04-7.02 (2H, m), 6.97 (1H, td, J = 8.5, 2.4 Hz), 6.86 (1H, d, J = 8.3 Hz), 3.98-3.87 (2H, m), 1.18 (3H, t, J = 6.9 Hz). |
| 362 | 1H-NMR (CDCl3) δ: 7.88 (1H, s), 7.29 (1H, d, J = 2.1 Hz), 7.19-7.14 (2H, m), 7.03-7.02 (2H, m), 6.98-6.96 (1H, m), 6.85 (1H, d, J = 8.3 Hz), 3.93-3.90 (2H, m), 1.17 (3H, t, J = 7.0 Hz). |
| 363 | 1H-NMR (CDCl3) δ: 7.28 (1H, d, J = 2.1 Hz), 7.18-7.13 (2H, m), 7.09-7.09 (1H, m), 7.01-6.99 (2H, m), 6.96-6.93 (1H, m), 6.86 (1H, d, J = 8.3 Hz), 3.89-3.88 (2H, m), 2.23 (3H, d, J = 0.9 Hz), 1.15 (3H, t, J = 7.0 Hz). |
| 364 | 1H-NMR (CDCl3) δ: 7.29 (1H, d, J = 2.1 Hz), 7.21-7.19 (2H, m), 7.16-7.13 (1H, m), 7.03-7.01 (2H, m), 6.95 (1H, td, J = 8.5, 2.7 Hz), 6.85 (1H, d, J = 8.3 Hz), 6.67 (1H, d, J = 9.2 Hz), 3.90-3.85 (2H, m), 1.16 (3H, t, J = 7.0 Hz). |

TABLE 5-continued

| Compound | ¹H-NMR |
|---|---|
| 365 | 1H-NMR (CDCl3) δ: 7.49 (1H, s), 7.29 (1H, d, J = 1.8 Hz), 7.18-7.13 (2H, m), 7.04-7.01 (2H, m), 6.97 (1H, td, J = 8.5, 2.2 Hz), 6.85 (1H, d, J = 8.3 Hz), 3.93-3.87 (2H, m), 3.37 (1H, d, J = 0.6 Hz), 1.18 (3H, t, J = 7.0 Hz). |
| 366 | 1H-NMR (CDCl3) δ: 7.04-7.03 (2H, m), 6.97-6.93 (2H, m), 6.77-6.74 (1H, m), 6.70-6.67 (1H, m), 6.62 (1H, dq, J = 13.1, 2.7 Hz), 4.13-4.12 (2H, m), 2.78-2.76 (2H, m), 2.71-2.68 (2H, m). |
| 367 | 1H-NMR (CDCl3) δ: 7.32 (1H, dd, J = 9.5, 0.7 Hz), 7.14-7.12 (2H, m), 7.05-6.98 (2H, m), 6.92-6.90 (1H, m), 6.74-6.63 (3H, m), 4.66-4.63 (2H, br m). |
| 368 | 1H-NMR (CDCl3) δ: 7.20 (1H, d, J = 9.3 Hz), 7.16 (1H, dd, J = 8.5, 2.2 Hz), 7.06 (1H, dd, J = 8.3, 2.2 Hz), 6.94 (1H, dd, J = 8.3, 2.7 Hz), 6.85 (1H, dd, J = 8.5, 2.7 Hz), 6.73-6.71 (1H, m), 6.66 (1H, d, J = 9.3 Hz), 6.52-6.50 (1H, m), 4.67 (2H, d, J = 2.3 Hz), 3.91-3.89 (2H, m), 2.53 (1H, t, J = 2.3 Hz), 1.17 (3H, t, J = 7.0 Hz). |
| 369 | 1H-NMR (CDCl3) δ: 7.45 (1H, s), 7.15 (1H, dd, J = 8.4, 2.3 Hz), 7.07 (1H, dd, J = 8.6, 2.3 Hz), 6.96 (1H, dd, J = 8.4, 2.8 Hz), 6.87 (1H, dd, J = 8.6, 2.8 Hz), 6.76-6.74 (1H, m), 6.54-6.53 (1H, m), 4.68 (2H, d, J = 2.4 Hz), 3.97-3.94 (2H, m), 2.55 (1H, t, J = 2.4 Hz), 1.20 (3H, t, J = 7.0 Hz). |
| 370 | 1H-NMR (CDCl3) δ: 7.62-7.54 (2H, m), 7.33-7.27 (4H, m), 7.14 (1H, td, J = 7.8, 1.5 Hz), 7.07-7.04 (1H, m), 6.94-6.92 (1H, m), 6.76 (1H, d, J = 9.5 Hz), 4.61 (2H, br s). |
| 371 | 1H-NMR (CDCl3) δ: 7.62-7.52 (3H, m), 7.33-7.27 (3H, m), 7.17 (1H, td, J = 7.8, 1.7 Hz), 7.07 (1H, td, J = 7.4, 1.2 Hz), 6.94 (1H, dd, J = 7.8, 1.7 Hz), 4.65 (2H, br s). |
| 372 | 1H-NMR (CDCl3) δ: 7.76 (1H, s), 7.62-7.60 (1H, m), 7.58-7.56 (1H, m), 7.33-7.27 (3H, m), 7.17 (1H, td, J = 7.8, 1.7 Hz), 7.07 (1H, td, J = 7.5, 1.1 Hz), 6.94 (1H, d, J = 7.5 Hz), 4.67 (2H, br s). |
| 373 | 1H-NMR (CDCl3) δ: 7.56 (1H, s), 7.13-7.11 (2H, m), 7.03-7.01 (2H, m), 6.96-6.90 (1H, m), 6.74-6.64 (2H, m), 4.68 (2H, br s). |
| 374 | 1H-NMR (CDCl3) δ: 7.76 (1H, s), 7.13-7.11 (2H, m), 7.03-7.01 (2H, m), 6.93 (1H, td, J = 8.4, 6.3 Hz), 6.74-6.64 (2H, m), 4.69 (2H, br s). |
| 375 | 1H-NMR (CDCl3) δ: 7.39 (1H, d, J = 8.3 Hz), 7.31-7.29 (1H, m), 7.09 (1H, d, J = 2.2 Hz), 7.04-7.01 (2H, m), 6.91-6.89 (2H, m), 2.91-2.70 (6H, m), 2.52-2.45 (1H, m). |
| 376 | 1H-NMR (CDCl3) δ: 7.42 (1H, d, J = 8.3 Hz), 7.37-7.35 (1H, m), 7.30 (1H, d, J = 9.2 Hz), 7.22-7.19 (1H, m), 7.16 (1H, d, J = 2.4 Hz), 7.07-7.04 (2H, m), 6.93 (1H, td, J = 8.6, 2.8 Hz), 6.71 (1H, d, J = 9.2 Hz), 3.34 (3H, s). |
| 377 | 1H-NMR (CDCl3) δ: 7.53 (1H, s), 7.43 (1H, dd, J = 9.2, 0.6 Hz), 7.39-7.37 (1H, m), 7.20-7.16 (2H, m), 7.07-7.05 (2H, m), 6.97-6.93 (1H, m), 3.40 (3H, s). |
| 378 | 1H-NMR (CDCl3) δ: 7.73 (1H, s), 7.43 (1H, d, J = 8.3 Hz), 7.39-7.37 (1H, m), 7.18-7.17 (2H, m), 7.07-7.05 (2H, m), 6.95 (1H, td, J = 8.4, 2.8 Hz), 3.40 (3H, s). |
| 379 | 1H-NMR (CDCl3) δ: 7.38 (1H, d, J = 8.3 Hz), 7.30-7.29 (1H, m), 7.09-7.05 (3H, m), 6.92-6.90 (2H, m), 3.62-3.57 (1H, m), 3.36-3.30 (1H, m), 2.86-2.67 (3H, m), 2.48-2.45 (1H, m), 0.98 (3H, t, J = 7.0 Hz). |
| 380 | 1H-NMR (CDCl3) δ: 7.40 (1H, d, J = 8.3 Hz), 7.35-7.33 (1H, m), 7.26-7.25 (2H, m), 7.19 (1H, d, J = 2.1 Hz), 7.12-7.09 (1H, m), 7.04 (1H, td, J = 8.5, 2.7 Hz), 6.92 (1H, td, J = 8.5, 2.7 Hz), 6.69 (1H, d, J = 9.5 Hz), 3.92-3.88 (2H, m), 1.17 (3H, t, J = 7.0 Hz). |
| 381 | 1H-NMR (CDCl3) δ: 7.44 (1H, d, J = 2.0 Hz), 7.11 (1H, dd, J = 8.3, 2.0 Hz), 7.04-7.02 (2H, m), 6.92-6.90 (2H, m), 6.70 (1H, d, J = 8.3 Hz), 2.81-2.73 (6H, m), 2.45-2.38 (1H, m). |
| 382 | 1H-NMR (CDCl3) δ: 7.46 (1H, d, J = 1.8 Hz), 7.24 (1H, d, J = 9.5 Hz), 7.17-7.16 (2H, m), 7.04 (1H, td, J = 8.5, 2.5 Hz), 6.96 (1H, td, J = 8.5, 2.5 Hz), 6.77 (1H, d, J = 8.3 Hz), 6.69 (1H, d, J = 9.5 Hz), 3.31 (3H, s). |
| 383 | 1H-NMR (CDCl3) δ: 7.47-7.47 (2H, m), 7.18 (1H, dd, J = 8.3, 1.8 Hz), 7.15-7.12 (1H, m), 7.11-7.07 (1H, m), 7.07-7.03 (1H, m), 6.98 (1H, td, J = 8.5, 2.5 Hz), 6.78 (1H, d, J = 8.3 Hz), 3.38 (3H, s). |
| 384 | 1H-NMR (CDCl3) δ: 7.68 (1H, s), 7.47 (1H, d, J = 1.8 Hz), 7.18 (1H, dd, J = 8.3, 1.8 Hz), 7.15-7.08 (2H, m), 7.04 (1H, dt, J = 10.0, 4.3 Hz), 7.00-6.96 (1H, m), 6.78 (1H, d, J = 8.3 Hz), 3.38 (3H, s). |
| 385 | 1H-NMR (CDCl3) δ: 7.44 (1H, d, J = 2.1 Hz), 7.10-7.06 (3H, m), 6.92-6.91 (2H, br m), 6.70 (1H, d, J = 8.3 Hz), 3.64-3.61 (1H, m), 3.28-3.25 (1H, m), 2.78-2.69 (3H, m), 2.42-2.38 (1H, m), 0.96 (3H, t, J = 7.0 Hz). |
| 386 | 1H-NMR (CDCl3) δ: 7.45 (1H, d, J = 1.8 Hz), 7.21-7.19 (2H, m), 7.16-7.13 (2H, m), 7.03 (1H, td, J = 8.5, 2.7 Hz), 6.96 (1H, td, J = 8.5, 2.5 Hz), 6.79 (1H, d, J = 8.3 Hz), 6.67 (1H, d, J = 9.5 Hz), 3.90-3.85 (2H, m), 1.16 (3H, t, J = 7.0 Hz). |
| 387 | 1H-NMR (CDCl3) δ: 7.45 (1H, d, J = 2.1 Hz), 7.44 (1H, s), 7.19-7.13 (3H, m), 7.03 (1H, td, J = 8.3, 2.5 Hz), 6.97 (1H, td, J = 8.5, 2.5 Hz), 6.80 (1H, d, J = 8.3 Hz), 3.94-3.91 (2H, m), 1.18 (3H, t, J = 7.0 Hz). |
| 388 | 1H-NMR (CDCl3) δ: 7.64 (1H, s), 7.45 (1H, d, J = 1.8 Hz), 7.18-7.15 (3H, m), 7.03 (1H, td, J = 8.3, 2.5 Hz), 6.97 (1H, td, J = 8.4, 2.5 Hz), 6.80 (1H, d, J = 8.0 Hz), 3.96-3.89 (2H, m), 1.18 (3H, t, J = 7.0 Hz). |

TABLE 5-continued

| Compound | ¹H-NMR |
|---|---|
| 389 | 1H-NMR (CDCl3) δ: 7.50 (1H, s), 7.42-7.36 (2H, m), 7.25-7.20 (2H, m), 7.13-7.10 (1H, m), 7.07-7.03 (1H, m), 6.94 (1H, td, J = 8.4, 2.7 Hz), 3.99-3.91 (2H, m), 1.20 (3H, t, J = 7.0 Hz). |
| 390 | 1H-NMR (CDCl3) δ: 7.70 (1H, s), 7.40-7.37 (2H, m), 7.24-7.20 (2H, m), 7.14-7.10 (1H, m), 7.06-7.02 (1H, m), 6.94 (1H, td, J = 8.5, 2.7 Hz), 3.98-3.93 (2H, m), 1.20 (3H, t, J = 7.0 Hz). |
| 391 | 1H-NMR (CDCl3) δ: 7.28-7.26 (1H, m), 7.18-7.09 (3H, m), 7.01 (1H, td, J = 8.4 2.5 Hz), 6.93 (1H, td, J = 8.5, 2.5 Hz), 6.83-6.80 (1H, m), 6.76 (1H, d, J = 7.8 Hz), 6.67 (1H, d, J = 9.3 Hz), 3.31 (3H, s), 2.24 (3H, s). |
| 392 | 1H-NMR (CDCl3) δ: 7.88 (1H, d, J = 1.8 Hz), 7.59 (1H, dd, J = 8.0, 1.8 Hz), 7.27-7.27 (1H, m), 7.21-7.19 (1H, m), 7.11-7.07 (1H, m), 7.04-7.01 (2H, m), 6.93 (1H, td, J = 8.4, 2.7 Hz), 6.71 (1H, d, J = 9.5 Hz), 3.33 (3H, s), 2.54 (3H, s). |
| 393 | 1H-NMR (CDCl3) δ: 7.10-7.08 (1H, m), 7.05-7.03 (2H, m), 6.90-6.89 (1H, m), 6.78-6.77 (1H, m), 6.71-6.70 (1H, m), 2.82-2.78 (5H, m), 2.70-2.67 (1H, m), 2.45-2.43 (1H, m), 2.23 (3H, s). |
| 394 | 1H-NMR (CDCl3) δ: 8.06 (1H, s), 7.41 (1H, d, J = 8.3 Hz), 7.38-7.36 (1H, m), 7.24-7.13 (3H, m), 7.06 (1H, td, J = 8.4, 2.6 Hz), 6.97 (1H, td, J = 8.4, 2.6 Hz), 4.03-3.91 (2H, m), 2.79 (3H, s), 1.22 (3H, t, J = 7.1 Hz). |
| 395 | 1H-NMR (CDCl3) δ: 7.50 (1H, s), 7.15-7.09 (3H, m), 7.03-6.99 (1H, m), 6.96-6.94 (1H, m), 6.83 (1H, dd, J = 7.8, 1.0 Hz), 6.77 (1H, d, J = 7.8 Hz), 3.38 (3H, s), 2.24 (3H, s). |
| 396 | 1H-NMR (CDCl3) δ: 7.70 (1H, s), 7.15-7.10 (3H, m), 7.03-7.01 (1H, m), 6.96-6.93 (1H, m), 6.83 (1H, dd, J = 7.8, 0.8 Hz), 6.77 (1H, d, J = 7.8 Hz), 3.38 (3H, s), 2.24 (3H, s). |
| 397 | 1H-NMR (CDCl3) δ: 7.24-7.14 (3H, m), 7.08-7.08 (1H, m), 7.02-6.97 (1H, m), 6.92 (1H, td, J = 8.5, 2.6 Hz), 6.82-6.80 (1H, m), 6.78 (1H, d, J = 7.3 Hz), 6.65 (1H, d, J = 9.5 Hz), 3.91-3.85 (2H, m), 2.23 (3H, s), 1.16 (3H, t, J = 7.1 Hz). |
| 398 | 1H-NMR (CDCl3) δ: 7.46 (1H, s), 7.20-7.15 (2H, m), 7.08-7.08 (1H, m), 7.00 (1H, td, J = 8.6, 2.8 Hz), 6.94 (1H, td, J = 8.6, 2.5 Hz), 6.83-6.81 (1H, m), 6.79 (1H, d, J = 7.8 Hz), 3.95-3.90 (2H, m), 2.23 (3H, s), 1.18 (3H, t, J = 7.1 Hz). |
| 399 | 1H-NMR (CDCl3) δ: 7.67 (1H, s), 7.19-7.15 (2H, m), 7.08-7.08 (1H, m), 7.00 (1H, td, J = 8.4, 2.4 Hz), 6.94 (1H, td, J = 8.4, 2.8 Hz), 6.83-6.81 (1H, m), 6.79 (1H, d, J = 8.0 Hz), 3.95-3.90 (2H, m), 2.23 (3H, s), 1.18 (3H, t, J = 7.0 Hz). |
| 400 | 1H-NMR (CDCl3) δ: 7.47 (1H, d, J = 2.0 Hz), 7.19-7.13 (2H, m), 7.07-7.04 (3H, m), 6.99-6.97 (1H, m), 6.78 (1H, d, J = 8.3 Hz), 3.36 (3H, s) |
| 401 | 1H-NMR (CDCl3) δ: 7.45 (1H, d, J = 2.1 Hz), 7.21-7.16 (2H, m), 7.15-7.12 (1H, m), 7.05-7.01 (2H, m), 6.96 (1H, td, J = 8.4, 2.7 Hz), 6.81 (1H, d, J = 8.3 Hz), 3.95-3.89 (2H, m), 1.18-1.16 (3H, m). |
| 402 | 1H-NMR (CDCl3) δ: 8.25 (1H, dd, J = 4.9, 2.0 Hz), 7.72 (1H, s), 7.66-7.64 (1H, m), 7.61-7.59 (1H, m), 7.39-7.34 (2H, m), 7.28-7.26 (1H, m), 7.06 (1H, dd, J = 7.6, 4.9 Hz), 3.95-3.85 (2H, m), 1.20 (3H, t, J = 7.0 Hz). |
| 403 | 1H-NMR (CDCl3) δ: 8.23 (1H, dd, J = 4.9, 2.0 Hz), 7.66-7.63 (1H, m), 7.59-7.57 (1H, m), 7.39-7.36 (2H, m), 7.28-7.27 (1H, m), 7.26-7.24 (1H, m), 7.03 (1H, dd, J = 7.6, 4.9 Hz), 6.73 (1H, d, J = 9.5 Hz), 3.91-3.79 (2H, m), 1.17 (3H, t, J = 7.1 Hz). |
| 404 | 1H-NMR (CDCl3) δ: 8.25 (1H, dd, J = 4.6, 2.0 Hz), 7.66-7.64 (1H, m), 7.62-7.59 (1H, m), 7.51 (1H, s), 7.39-7.33 (2H, m), 7.28-7.26 (1H, m), 7.06 (1H, dd, J = 7.6, 4.6 Hz), 3.96-3.83 (2H, m), 1.20 (3H, t, J = 7.1 Hz). |
| 405 | 1H-NMR (CDCl3) δ: 7.27-7.25 (1H, m), 7.08-7.05 (3H, m), 7.00 (1H, td, J = 7.5, 1.4 Hz), 6.90-6.88 (3H, m), 5.93 (1H, tt, J = 56.6, 4.5 Hz), 3.78 (1H, td, J = 14.0, 4.5 Hz), 3.67 (1H, td, J = 14.0, 4.5 Hz), 2.89-2.79 (2H, m), 2.76-2.70 (1H, m), 2.55-2.52 (1H, m). |
| 406 | 1H-NMR (CDCl3) δ: 7.34 (1H, d, J = 9.3 Hz), 7.28-7.26 (1H, m), 7.23-7.19 (1H, m), 7.14-7.10 (2H, m), 7.03-7.01 (2H, m), 6.95-6.90 (2H, m), 6.70 (1H, d, J = 9.3 Hz), 6.32 (1H, tt, J = 57.1, 4.7 Hz), 4.20-4.07 (2H, m). |
| 407 | 1H-NMR (CDCl3) δ: 7.57 (1H, s), 7.29-7.27 (1H, m), 7.18-7.14 (3H, m), 7.04-7.01 (2H, m), 6.95-6.92 (2H, m), 6.34 (1H, tt, J = 57.0, 4.6 Hz), 4.24-4.11 (2H, m). |
| 408 | 1H-NMR (CDCl3) δ: 7.77 (1H, s), 7.29-7.27 (1H, m), 7.21-7.10 (3H, m), 7.06-6.99 (2H, m), 6.95-6.92 (2H, m), 6.34 (1H, tt, J = 57.1, 4.7 Hz), 4.24-4.11 (2H, m). |
| 409 | 1H-NMR (CDCl3) δ: 7.28-7.26 (1H, m), 7.11-6.99 (4H, m), 6.92-6.87 (3H, m), 4.32-4.19 (1H, m), 4.07-3.94 (1H, m), 2.87-2.74 (3H, m), 2.56-2.52 (1H, m). |
| 410 | 1H-NMR (CDCl3) δ: 7.29-7.27 (1H, m), 7.21-7.17 (1H, m), 7.15-7.09 (2H, m), 7.05-7.03 (1H, m), 6.99-6.97 (2H, m), 6.90 (1H, td, J = 8.5, 2.7 Hz), 6.61 (1H, s), 6.33 (1H, tt, J = 57.1, 4.7 Hz), 4.26-4.04 (2H, m), 3.86 (3H, s). |
| 411 | 1H-NMR (CDCl3) δ: 7.30 (1H, d, J = 9.5 Hz), 7.28-7.27 (1H, m), 7.16-7.12 (3H, m), 7.06-6.90 (4H, m), 6.72 (1H, d, J = 9.5 Hz), 4.75-4.54 (2H, br m). |

TABLE 5-continued

| Compound | ¹H-NMR |
|---|---|
| 412 | 1H-NMR (CDCl3) δ: 7.74 (1H, s), 7.29-7.27 (1H, m), 7.15-7.13 (3H, m), 7.07-6.92 (4H, m), 4.77-4.56 (2H, br m). |
| 413 | 1H-NMR (CDCl3) δ: 7.54 (1H, s), 7.29-7.27 (1H, m), 7.15-7.14 (3H, m), 7.06-7.05 (1H, m), 7.03-6.93 (3H, m), 4.76-4.60 (2H, br m). |
| 414 | 1H-NMR (CDCl3) δ: 7.29 (1H, d, J = 2.1 Hz), 7.07 (2H, s), 6.96 (1H, dd, J = 8.3, 2.1 Hz), 6.92-6.89 (2H, m), 6.76 (1H, d, J = 8.3 Hz), 3.66-3.59 (1H, m), 3.30-3.23 (1H, m), 2.83-2.73 (2H, m), 2.70-2.64 (1H, m), 2.43-2.37 (1H, m), 0.96 (3H, t, J = 7.0 Hz). |
| 415 | 1H-NMR (CDCl3) δ: 7.29 (1H, d, J = 2.1 Hz), 7.05 (2H, br s), 6.98 (1H, dd, J = 8.3, 2.1 Hz), 6.94-6.91 (2H, m), 6.81 (1H, d, J = 8.3 Hz), 5.92 (1H, tt, J = 56.6, 4.4 Hz), 3.79 (1H, ddd, J = 27.4, 14.2, 4.4 Hz), 3.66-3.61 (1H, m), 2.87-2.69 (3H, m), 2.54-2.47 (1H, m). |
| 416 | 1H-NMR (CDCl3) δ: 7.29 (1H, d, J = 2.1 Hz), 7.22-7.19 (2H, m), 7.16-7.13 (1H, m), 7.05-6.99 (2H, m), 6.95 (1H, td, J = 8.5, 2.7 Hz), 6.85 (1H, d, J = 8.3 Hz), 6.67 (1H, d, J = 9.5 Hz), 3.93-3.82 (2H, m), 1.16 (3H, t, J = 7.0 Hz). |
| 417 | 1H-NMR (CDCl3) δ: 7.44 (1H, s), 7.30 (1H, d, J = 2.1 Hz), 7.19-7.13 (2H, m), 7.05-7.01 (2H, m), 6.99-6.95 (1H, m), 6.86 (1H, d, J = 8.3 Hz), 3.98-3.87 (2H, m), 1.18 (3H, t, J = 7.0 Hz). |
| 418 | 1H-NMR (CDCl3) δ: 7.65 (1H, s), 7.30 (1H, d, J = 2.1 Hz), 7.19-7.13 (2H, m), 7.05-7.01 (2H, m), 6.99-6.95 (1H, m), 6.86 (1H, d, J = 8.3 Hz), 3.98-3.87 (2H, m), 1.18 (3H, t, J = 7.0 Hz). |
| 419 | 1H-NMR (CDCl3) δ: 7.31-7.28 (2H, m), 7.23-7.19 (1H, m), 7.13-7.09 (1H, m), 7.07-7.01 (2H, m), 6.99-6.94 (1H, m), 6.86 (1H, d, J = 8.1 Hz), 6.70 (1H, d, J = 9.5 Hz), 6.30 (1H, tt, J = 57.1, 4.7 Hz), 4.22-4.02 (2H, m). |
| 420 | 1H-NMR (CDCl3) δ: 7.72 (1H, s), 7.31 (1H, d, J = 2.2 Hz), 7.20-7.16 (1H, m), 7.14-7.10 (1H, m), 7.07-7.02 (2H, m), 6.98 (1H, td, J = 8.5, 2.6 Hz), 6.87 (1H, d, J = 8.3 Hz), 6.32 (1H, tt, J = 57.1, 4.7 Hz), 4.26-4.06 (2H, m). |
| 421 | 1H-NMR (CDCl3) δ: 7.53-7.51 (2H, m), 7.30 (1H, d, J = 2.2 Hz), 7.22-7.20 (1H, m), 6.99 (1H, dd, J = 8.3, 2.2 Hz), 6.76 (1H, d, J = 8.3 Hz), 3.65-3.56 (1H, m), 3.29-3.20 (1H, m), 2.86-2.64 (3H, m), 2.49-2.42 (1H, m), 0.96 (3H, t, J = 7.1 Hz). |
| 422 | 1H-NMR (CDCl3) δ: 7.52 (1H, s), 7.31 (1H, d, J = 2.2 Hz), 7.20-7.17 (1H, m), 7.14-7.10 (1H, m), 7.07-7.02 (2H, m), 7.00-6.95 (1H, m), 6.87 (1H, d, J = 8.1 Hz), 6.32 (1H, tt, J = 57.1, 4.7 Hz), 4.26-4.06 (2H, m). |
| 423 | 1H-NMR (CDCl3) δ: 7.65-7.62 (1H, m), 7.59-7.57 (1H, m), 7.37-7.31 (2H, m), 7.30 (1H, d, J = 2.1 Hz), 7.22 (1H, d, J = 9.5 Hz), 7.02 (1H, dd, J = 8.3, 2.1 Hz), 6.85 (1H, d, J = 8.3 Hz), 6.70 (1H, d, J = 9.5 Hz), 3.90-3.76 (2H, m), 1.16 (3H, t, J = 7.0 Hz). |
| 424 | 1H-NMR (CDCl3) δ: 7.66 (1H, s), 7.65-7.58 (2H, m), 7.35-7.30 (3H, m), 7.04 (1H, dd, J = 8.2, 2.1 Hz), 6.86 (1H, d, J = 8.2 Hz), 3.95-3.81 (2H, m), 1.18 (3H, t, J = 7.1 Hz). |
| 425 | 1H-NMR (CDCl3) δ: 7.65-7.63 (1H, m), 7.60-7.59 (1H, m), 7.46 (1H, s), 7.35-7.30 (3H, m), 7.04 (1H, dd, J = 8.3, 2.1 Hz), 6.86 (1H, d, J = 8.3 Hz), 3.94-3.82 (2H, m), 1.18 (3H, t, J = 7.0 Hz). |
| 426 | 1H-NMR (CDCl3) δ: 7.65 (1H, dd, J = 8.0, 1.2 Hz), 7.59 (1H, dd, J = 8.0, 1.2 Hz), 7.36 (1H, dd, J = 8.0, 1.5 Hz), 7.32-7.28 (3H, m), 7.04 (1H, dd, J = 8.3, 1.8 Hz), 6.86 (1H, d, J = 8.3 Hz), 6.73 (1H, d, J = 9.2 Hz), 6.29 (1H, tt, J = 57.0, 4.6 Hz), 4.17-4.08 (1H, m), 4.04-3.96 (1H, m). |
| 427 | 1H-NMR (CDCl3) δ: 7.37-7.35 (1H, m), 7.31 (1H, tt, J = 7.5, 1.4 Hz), 7.27-7.24 (2H, m), 7.20 (1H, d, J = 9.5 Hz), 7.16-7.14 (1H, m), 6.69-6.66 (2H, m), 6.53 (1H, ddd, J = 8.6, 3.1, 1.5 Hz), 3.91-3.86 (2H, m), 1.17 (3H, t, J = 7.0 Hz). |
| 428 | 1H-NMR (CDCl3) δ: 7.43 (1H, s), 7.39-7.31 (2H, m), 7.26-7.24 (2H, m), 7.16-7.15 (1H, m), 6.70 (1H, td, J = 8.5, 2.9 Hz), 6.54 (1H, ddd, J = 8.5, 2.9, 1.5 Hz), 3.96-3.90 (2H, m), 1.19 (3H, t, J = 7.0 Hz). |
| 429 | 1H-NMR (CDCl3) δ: 7.64 (1H, s), 7.38-7.30 (2H, m), 7.29-7.21 (2H, m), 7.17-7.15 (1H, m), 6.69 (1H, td, J = 8.4, 2.9 Hz), 6.54 (1H, ddd, J = 8.4, 2.9, 1.6 Hz), 3.96-3.90 (2H, m), 1.19 (3H, t, J = 7.0 Hz). |
| 430 | 1H-NMR (CDCl3) δ: 7.39-7.38 (1H, m), 7.33 (1H, tt, J = 7.5, 1.4 Hz), 7.30-7.24 (3H, m), 7.12 (1H, d, J = 7.6 Hz), 6.71-6.67 (2H, m), 6.54 (1H, ddd, J = 8.6, 2.9, 1.5 Hz), 6.30 (1H, tt, J = 57.2, 4.7 Hz), 4.21-4.06 (2H, m). |
| 431 | 1H-NMR (CDCl3) δ: 7.51 (1H, s), 7.41-7.33 (2H, m), 7.30-7.28 (1H, m), 7.23-7.21 (1H, m), 7.14-7.12 (1H, m), 6.72 (1H, td, J = 8.3, 2.8 Hz), 6.56 (1H, ddd, J = 8.3, 2.8, 1.5 Hz), 6.32 (1H, tt, J = 57.0, 4.7 Hz), 4.27-4.09 (2H, m). |
| 432 | 1H-NMR (CDCl3) δ: 7.71 (1H, s), 7.41-7.33 (2H, m), 7.30-7.28 (1H, m), 7.23-7.22 (1H, m), 7.14-7.12 (1H, m), 6.71 (1H, td, J = 8.3, 2.8 Hz), 6.55 (1H, ddd, J = 8.3, 2.8, 1.5 Hz), 6.32 (1H, tt, J = 57.1, 4.6 Hz), 4.27-4.09 (2H, m). |
| 433 | 1H-NMR (CDCl3) δ: 7.67 (1H, s), 7.23-7.17 (2H, m), 7.14 (1H, d, J = 8.9 Hz), 7.01 (1H, td, J = 8.4, 2.4 Hz), 6.96 (1H, td, J = 8.4, 2.4 Hz), 6.69 (1H, dd, J = 8.9, 3.1 Hz), 6.51 (1H, d, J = 3.1 Hz), 4.00-3.86 (4H, m), 3.68-3.66 (2H, m), 3.42 (3H, s), 1.18 (3H, t, J = 7.0 Hz). |

TABLE 5-continued

| Compound | ¹H-NMR |
|---|---|
| 434 | 1H-NMR (CDCl3) δ: 7.70 (1H, s), 7.25-7.21 (1H, m), 7.19-7.15 (2H, m), 6.99 (2H, dtd, J = 27.2, 8.5, 2.9 Hz), 6.71 (1H, dd, J = 8.5, 2.9 Hz), 6.54 (1H, d, J = 2.9 Hz), 4.98 (2H, s), 4.01-3.87 (2H, m), 2.16 (3H, s), 1.19 (3H, t, J = 7.0 Hz). |
| 435 | 1H-NMR (CDCl3) δ: 7.75 (1H, s), 7.21-7.14 (3H, m), 7.06-6.94 (2H, m), 6.70 (1H, dd, J = 8.9, 3.0 Hz), 6.51 (1H, d, J = 3.0 Hz), 6.33 (1H, tt, J = 57.3, 4.7 Hz), 4.27-4.06 (2H, m), 4.00-3.95 (1H, m), 3.90-3.85 (1H, m), 3.68-3.65 (2H, m), 3.42 (3H, s). |
| 436 | 1H-NMR (CDCl3) δ: 7.77 (1H, s), 7.31 (1H, dd, J = 8.0, 1.2 Hz), 7.17-7.13 (1H, m), 7.12-7.02 (3H, m), 7.02-6.88 (3H, m), 5.55 (1H, dd, J = 19.1, 2.9 Hz). |
| 437 | 1H-NMR (CDCl3) δ: 7.67-7.65 (1H, m), 7.62-7.59 (1H, m), 7.53 (1H, s), 7.35-7.28 (3H, m), 7.05 (1H, dd, J = 8.3, 2.2 Hz), 6.87 (1H, d, J = 8.3 Hz), 6.31 (1H, tt, J = 57.0, 4.6 Hz), 4.23-3.99 (2H, m). |
| 438 | 1H-NMR (CDCl3) δ: 7.75 (1H, s), 7.68-7.66 (1H, m), 7.62-7.60 (1H, m), 7.36-7.30 (3H, m), 7.06 (1H, dd, J = 8.3, 2.1 Hz), 6.88 (1H, d, J = 8.3 Hz), 6.32 (1H, tt, J = 56.9, 4.6 Hz), 4.22-4.02 (2H, m). |
| 439 | 1H-NMR (CDCl3) δ: 7.54 (1H, s), 7.21-7.14 (3H, m), 7.06-6.94 (2H, m), 6.71 (1H, dd, J = 8.8, 3.0 Hz), 6.51 (1H, d, J = 3.0 Hz), 6.33 (1H, tt, J = 57.1, 4.7 Hz), 4.27-4.06 (2H, m), 4.00-3.85 (2H, m), 3.68-3.65 (2H, m), 3.42 (3H, s). |
| 440 | 1H-NMR (CDCl3) δ: 7.63-7.61 (1H, m), 7.59-7.57 (1H, m), 7.47 (1H, s), 7.40-7.38 (1H, m), 7.35-7.33 (1H, m), 7.14 (1H, d, J = 8.9 Hz), 6.70 (1H, dd, J = 8.9, 3.0 Hz), 6.53 (1H, d, J = 3.0 Hz), 4.02-3.83 (4H, m), 3.68 (2H, t, J = 4.7 Hz), 3.42 (3H, s), 1.18 (3H, t, J = 7.0 Hz). |
| 441 | 1H-NMR (CDCl3) δ: 7.68 (1H, s), 7.63-7.57 (2H, m), 7.40 (1H, dd, J = 8.0, 1.7 Hz), 7.33 (1H, dd, J = 8.0, 1.7 Hz), 7.13 (1H, d, J = 8.8 Hz), 6.70 (1H, dd, J = 8.8, 3.0 Hz), 6.52 (1H, d, J = 3.0 Hz), 4.01-3.83 (4H, m), 3.68 (2H, t, J = 4.6 Hz), 3.42 (3H, s), 1.18 (3H, t, J = 7.1 Hz). |
| 442 | 1H-NMR (CDCl3) δ: 7.57 (1H, s), 7.26-7.22 (1H, m), 7.19 (1H, d, J = 8.8 Hz), 7.16-7.12 (1H, m), 7.04 (1H, td, J = 8.5, 2.7 Hz), 6.96 (1H, td, J = 8.5, 2.7 Hz), 6.73 (1H, dd, J = 8.8, 2.9 Hz), 6.54 (1H, d, J = 2.9 Hz), 6.33 (1H, tt, J = 57.0, 4.6 Hz), 4.98 (2H, s), 4.28-4.07 (2H, m), 2.16 (3H, s). |
| 443 | 1H-NMR (CDCl3) δ: 7.38-7.35 (1H, m), 7.34-7.29 (2H, m), 7.24-7.21 (3H, m), 7.12 (1H, d, J = 7.8 Hz), 6.80 (1H, ddd, J = 9.0, 8.0, 3.1 Hz), 6.70 (1H, d, J = 9.5 Hz), 6.67 (1H, dd, J = 8.8, 3.1 Hz), 6.30 (1H, tt, J = 57.1, 4.6 Hz), 4.20-4.09 (2H, m). |
| 444 | 1H-NMR (CDCl3) δ: 7.56 (1H, s), 7.40-7.31 (2H, m), 7.28-7.21 (3H, m), 7.12 (1H, d, J = 7.8 Hz), 6.83 (1H, ddd, J = 9.0, 8.0, 3.1 Hz), 6.68 (1H, dd, J = 8.8, 3.1 Hz), 6.33 (1H, tt, J = 57.1, 4.7 Hz), 4.24-4.13 (2H, m). |
| 445 | 1H-NMR (CDCl3) δ: 7.76 (1H, s), 7.40-7.31 (2H, m), 7.27-7.23 (3H, m), 7.12 (1H, d, J = 7.6 Hz), 6.82 (1H, ddd, J = 8.9, 8.0, 3.1 Hz), 6.68 (1H, dd, J = 8.8, 3.1 Hz), 6.33 (1H, tt, J = 57.1, 4.6 Hz), 4.24-4.14 (2H, m). |
| 446 | 1H-NMR (CDCl3) δ: 7.65-7.63 (1H, m), 7.60-7.58 (1H, m), 7.55 (1H, s), 7.37-7.33 (2H, m), 7.15 (1H, d, J = 8.9 Hz), 6.72 (1H, dd, J = 8.9, 3.1 Hz), 6.53 (1H, d, J = 3.1 Hz), 6.31 (1H, tt, J = 56.9, 4.7 Hz), 4.22-3.88 (4H, m), 3.68 (2H, t, J = 4.7 Hz), 3.43 (3H, s). |
| 447 | 1H-NMR (CDCl3) δ: 7.65-7.63 (1H, m), 7.60-7.58 (1H, m), 7.38-7.33 (2H, m), 7.15 (1H, d, J = 8.9 Hz), 6.72 (1H, dd, J = 8.9, 3.0 Hz), 6.53 (1H, d, J = 3.0 Hz), 6.31 (1H, tt, J = 57.0, 4.6 Hz), 4.22-3.87 (4H, m), 3.68 (2H, t, J = 4.7 Hz), 3.42 (3H, s). |
| 448 | 1H-NMR (CDCl3) δ: 7.63 (1H, dd, J = 7.8, 1.2 Hz), 7.58 (1H, dd, J = 7.8, 1.2 Hz), 7.50 (1H, s), 7.39 (1H, dd, J = 8.0, 1.2 Hz), 7.35 (1H, dd, J = 8.0, 1.2 Hz), 7.18 (1H, d, J = 8.8 Hz), 6.73 (1H, dd, J = 8.8, 3.2 Hz), 6.52 (1H, d, J = 3.2 Hz), 5.00 (2H, s), 3.97-3.82 (2H, m), 2.17 (3H, s), 1.19 (3H, t, J = 7.0 Hz). |
| 449 | 1H-NMR (CDCl3) δ: 7.31 (1H, d, J = 9.5 Hz), 7.25-7.20 (2H, m), 7.16-7.12 (1H, m), 7.06 (1H, td, J = 8.4, 2.7 Hz), 6.96 (1H, td, J = 8.4, 2.7 Hz), 6.85-6.83 (1H, m), 6.70 (1H, d, J = 9.5 Hz), 6.67 (1H, dd, J = 8.7, 3.1 Hz), 6.30 (1H, tt, J = 57.3, 4.7 Hz), 4.22-4.03 (2H, m). |
| 450 | 1H-NMR (CDCl3) δ: 7.55 (1H, s), 7.25 (1H, dd, J = 8.9, 5.2 Hz), 7.22-7.19 (1H, m), 7.16-7.13 (1H, m), 7.07 (1H, td, J = 8.5, 2.7 Hz), 6.97 (1H, td, J = 8.5, 2.7 Hz), 6.87-6.85 (1H, m), 6.68 (1H, dd, J = 8.6, 3.1 Hz), 6.33 (1H, tt, J = 57.0, 4.6 Hz), 4.25-4.09 (2H, m). |
| 451 | 1H-NMR (CDCl3) δ: 7.75 (1H, s), 7.24-7.24 (1H, m), 7.22-7.19 (1H, m), 7.17-7.13 (1H, m), 7.07 (1H, td, J = 8.6, 2.8 Hz), 6.97 (1H, td, J = 8.6, 2.8 Hz), 6.87-6.85 (1H, m), 6.68 (1H, dd, J = 8.6, 3.1 Hz), 6.33 (1H, tt, J = 57.0, 4.7 Hz), 4.26-4.08 (2H, m). |
| 452 | H-NMR (CDCl3) δ: 7.68 (1H, d, J = 0.7 Hz), 7.44-7.42 (1H, m), 7.40-7.37 (1H, m), 7.25-7.23 (1H, m), 7.21-7.20 (1H, m), 7.12-7.07 (2H, m), 6.96 (1H, td, J = 8.4, 2.7 Hz), 4.01-3.88 (2H, m), 1.21 (3H, t, J = 7.1 Hz). |
| 453 | 1H-NMR (CDCl3) δ: 7.70 (1H, s), 7.64-7.62 (1H, m), 7.59-7.56 (1H, m), 7.40-7.34 (2H, m), 7.17 (1H, d, J = 9.0 Hz), 6.73 (1H, dd, J = 9.0, |

TABLE 5-continued

| Compound | ¹H-NMR |
|---|---|
| | 3.0 Hz), 6.52 (1H, d, J = 3.0 Hz), 4.99 (2H, s), 3.97-3.82 (2H, m), 2.17 (3H, s), 1.19 (3H, t, J = 7.0 Hz). |
| 454 | 1H-NMR (CDCl3) δ: 7.66-7.64 (1H, m), 7.60-7.57 (2H, m), 7.40 (1H, dd, J = 7.9, 1.6 Hz), 7.32 (1H, dd, J = 7.9, 1.6 Hz), 7.19 (1H, d, J = 8.8 Hz), 6.75 (1H, dd, J = 8.8, 2.9 Hz), 6.53 (1H, d, J = 2.9 Hz), 6.31 (1H, tt, J = 56.9, 4.6 Hz), 5.00 (2H, s), 4.25-4.02 (2H, m), 2.17 (3H, s). |
| 455 | 1H-NMR (CDCl3) δ: 7.78 (1H, s), 7.65-7.63 (1H, m), 7.59-7.57 (1H, m), 7.40-7.38 (1H, m), 7.33-7.31 (1H, m), 7.20-7.18 (1H, m), 6.76-6.73 (1H, m), 6.53 (1H, d, J = 2.9 Hz), 6.32 (1H, tt, J = 57.1, 4.3 Hz), 5.00 (2H, s), 4.24-4.01 (2H, m), 2.17 (3H, s). |
| 456 | 1H-NMR (CDCl3) δ: 7.64 (1H, s), 7.14 (1H, dd, J = 8.6, 2.1 Hz), 7.07 (1H, dd, J = 8.6, 2.1 Hz), 6.94 (1H, dd, J = 8.6, 2.8 Hz), 6.86 (1H, dd, J = 8.6, 2.8 Hz), 6.74 (1H, td, J = 8.4, 2.8 Hz), 6.53-6.52 (1H, m), 4.67 (2H, d, J = 2.4 Hz), 3.97-3.93 (2H, m), 2.54 (1H, t, J = 2.4 Hz), 1.19 (3H, t, J = 7.0 Hz). |
| 457 | 1H-NMR (CDCl3) δ: 7.35-7.22 (5H, m), 7.10 (1H, d, J = 7.3 Hz), 6.99-6.91 (2H, m), 6.74 (1H, ddd, J = 7.3, 2.2, 1.2 Hz), 6.70 (1H, d, J = 9.5 Hz), 6.31 (1H, tt, J = 57.3, 4.7 Hz), 4.21-4.09 (2H, m). |
| 458 | 1H-NMR (CDCl3) δ: 7.76 (1H, s), 7.35-7.29 (1H, m), 7.26 (2H, tt, J = 6.6, 2.1 Hz), 7.21-7.20 (1H, m), 7.12-7.10 (1H, m), 7.00-6.93 (2H, m), 6.75 (1H, ddd, J = 7.3, 2.4, 1.2 Hz), 6.33 (1H, tt, J = 57.0, 4.7 Hz), 4.27-4.11 (2H, m). |
| 459 | 1H-NMR (CDCl3) δ: 7.56 (1H, s), 7.35-7.28 (2H, m), 7.28-7.24 (1H, m), 7.21-7 20 (11-1, m), 7.11-7.10 (1H, m), 7.00-6.93 (2H, m), 6.75 (1H, ddd, J = 7.3, 2.1, 1.2 Hz), 6.33 (1H, tt, J = 57.0, 4.7 Hz), 4.27-4.10 (2H, m). |
| 460 | 1H-NMR (CDCl3) δ: 7.32 (1H, d, J = 9.2 Hz), 7.23-7.20 (1H, m), 7.13-7.10 (1H, m), 7.05-6.93 (4H, m), 6.75-6.73 (1H, m), 6.71 (1H, d, J = 9.2 Hz), 6.31 (1H, tt, J = 57.0, 4.7 Hz), 4.18-4.08 (2H, m). |
| 461 | 1H-NMR (CDCl3) δ: 7.55 (1H, s), 7.21-7.18 (1H, m), 7.14-7.11 (1H, m), 7.05-6.95 (4H, m), 6.76-6.74 (1H, m), 6.33 (1H, tt, J = 57.0, 4.7 Hz), 4.25-4.09 (2H, m). |
| 462 | 1H-NMR (CDCl3) δ: 7.75 (1H, s), 7.21-7.17 (1H, m), 7.15-7.11 (1H, m), 7.05-6.94 (4H, m), 6.76-6.74 (1H, m), 6.33 (1H, tt, J = 57.0, 4.7 Hz), 4.21-4.12 (2H, m). |
| 463 | 1H-NMR (CDCl3) δ: 7.98 (1H, s), 7.28-7.27 (1H, m), 7.17-7.11 (3H, m), 7.07-6.93 (4H, m), 4.69-4.67 (2H, br m). |
| 464 | 1H-NMR (CDCl3) δ: 7.30-7.18 (5H, m), 7.03-7.01 (1H, m), 6.90 (1H, d, J = 7.6 Hz), 6.82 (1H, dd, J = 7.6, 1.5 Hz), 6.67 (1H, d, J = 1.5 Hz), 6.65 (1H, d, J = 9.5 Hz), 3.96-3.83 (2H, m), 2.12 (3H, s), 2.06 (3H, s), 1.16 (3H, t, J = 7.0 Hz). |
| 465 | 1H-NMR (CDCl3) δ: 7.19-7.16 (3H, m), 7.03-7.01 (2H, m), 6.96 (1H, dd, J = 8.3, 5.9 Hz), 6.70 (1H, td, J = 8.3, 2.8 Hz), 6.55 (1H, dd, J = 9.5, 2.8 Hz), 3.56-3.49 (1H, m), 3.46-3.39 (1H, m), 2.72-2.49 (4H, m), 2.12 (3H, s), 0.96 (3H, t, J = 7.1 Hz). |
| 466 | 1H-NMR (CDCl3) δ: 7.34-7.31 (1H, m), 7.28-7.26 (1H, m), 7.23-7.20 (3H, m), 7.02 (1H, d, J = 7.6 Hz), 6.97 (1H, dd, J = 8.4, 5.8 Hz), 6.72 (1H, td, J = 8.4, 2.8 Hz), 6.66 (1H, d, J = 9.5 Hz), 6.58 (1H, dd, J = 9.3, 2.8 Hz), 3.92-3.87 (2H, m), 2.07 (3H, s), 1.16 (3H, t, J = 7.0 Hz). |
| 467 | 1H-NMR (CDCl3) δ: 7.44 (1H, s), 7.35-7.20 (4H, m), 7.02 (1H, d, J = 7.3 Hz), 6.98 (1H, dd, J = 8.4, 6.0 Hz), 6.74 (1H, td, J = 8.4, 2.8 Hz), 6.59 (1H, dd, J = 9.4, 2.8 Hz), 3.98-3.91 (2H, m), 2.08 (3H, s), 1.19 (3H, t, J = 7.0 Hz). |
| 468 | 1H-NMR (CDCl3) δ: 7.65 (1H, s), 7.35-7.26 (2H, m), 7.24-7.21 (2H, m), 7.02-6.98 (2H, m), 6.74 (1H, td, J = 8.5, 2.8 Hz), 6.59 (1H, dd, J = 9.2, 2.8 Hz), 3.96-3.92 (2H, m), 2.08 (3H, s), 1.18 (3H, t, J = 7.0 Hz). |
| 469 | 1H-NMR (CDCl3) δ: 7.36-7.20 (5H, m), 7.00-6.98 (2H, m), 6.74 (1H, td, J = 8.5, 2.7 Hz), 6.69 (1H, d, J = 9.5 Hz), 6.59 (1H, dd, J = 9.3, 2.7 Hz), 6.30 (1H, tt, J = 57.3, 4.7 Hz), 4.15 (2H, td, J = 12.6, 4.7 Hz), 2.08 (3H, s). |
| 470 | 1H-NMR (CDCl3) δ: 7.52 (1H, s), 7.37-7.23 (3H, m), 7.18 (1H, d, J = 7.3 Hz), 7.01-6.98 (2H, m), 6.76 (1H, td, J = 8.5, 2.8 Hz), 6.60 (1H, dd, J = 9.3, 2.8 Hz), 6.32 (1H, tt, J = 57.1, 4.7 Hz), 4.20 (2H, td, J = 12.5, 4.7 Hz), 2.09 (3H, s). |
| 471 | 1H-NMR (CDCl3) δ: 7.72 (1H, s), 7.37-7.23 (3H, m), 7.18 (1H, d, J = 7.1 Hz), 7.01-6.99 (2H, m), 6.76 (1H, td, J = 8.4, 2.7 Hz), 6.60 (1H, dd, J = 9.3, 2.7 Hz), 6.32 (1H, tt, J = 57.1, 4.7 Hz), 4.20 (2H, td, J = 12.4, 4.7 Hz), 2.09 (3H, s). |
| 472 | 1H-NMR (CDCl3) δ: 7.24-7.19 (2H, m), 7.05-6.98 (3H, m), 6.92 (1H, td, J = 8.4, 2.8 Hz), 6.75 (1H, td, J = 8.4, 2.8 Hz), 6.67 (1H, d, J = 9.2 Hz), 6.57 (1H, dd, J = 9.2, 2.8 Hz), 3.94-3.83 (2H, m), 2.06 (3H, s), 1.16 (3H, t, J = 7.0 Hz). |
| 473 | 1H-NMR (CDCl3) δ: 7.28 (1H, d, J = 9.3 Hz), 7.22-7.18 (1H, m), 7.08-6.90 (4H, m), 6.80-6.74 (1H, m), 6.69 (1H, d, J = 9.3 Hz), 6.61-6.56 (1H, m), 6.30 (1H, tt, J = 57.1, 4.7 Hz), 4.14 (2H, td, J = 12.6, 4.7 Hz), 2.06 (3H, s). |

TABLE 5-continued

| Compound | ¹H-NMR |
|---|---|
| 474 | 1H-NMR (CDCl3) δ: 7.64 (1H, s), 7.21-7.18 (1H, m), 7.05-6.99 (3H, m), 6.94 (1H, td, J = 8.4, 2.8 Hz), 6.77 (1H, td, J = 8.4, 2.8 Hz), 6.58 (1H, dd, J = 9.2, 2.8 Hz), 4.00-3.87 (2H, m), 2.07 (3H, s), 1.18 (3H, t, J = 7.0 Hz). |
| 475 | 1H-NMR (CDCl3) δ: 7.52 (1H, s), 7.21-7.15 (1H, m), 7.07-6.94 (4H, m), 6.79 (1H, td, J = 8.4, 2.7 Hz), 6.59 (1H, dd, J = 9.0, 2.7 Hz), 6.32 (1H, tt, J = 56.9, 4.6 Hz), 4.18 (2H, td, J = 12.3, 4.6 Hz), 2.07 (3H, s). |
| 476 | 1H-NMR (CDCl3) δ: 7.72 (1H, s), 7.20-7.16 (1H, m), 7.07-6.93 (4H, m), 6.79 (1H, td, J = 8.4, 2.7 Hz), 6.59 (1H, dd, J = 9.2, 2.7 Hz), 6.32 (1H, tt, J = 57.4, 4.6 Hz), 4.18 (2H, td, J = 12.5, 4.6 Hz), 2.07 (3H, s). |
| 477 | 1H-NMR (CDCl3) δ: 7.23-7.19 (2H, m), 7.04-6.96 (2H, m), 6.93-6.88 (2H, m), 6.86-6.84 (1H, m), 6.66-6.64 (2H, m), 3.96-3.83 (2H, m), 2.14 (3H, s), 2.05 (3H, s), 1.16 (3H, t, J = 7.1 Hz). |
| 478 | 1H-NMR (CDCl3) δ: 7.45 (1H, s), 7.20-7.17 (1H, m), 7.04-6.97 (2H, m), 6.94-6.90 (2H, m), 6.86 (1H, dd, J = 8.0, 1.5 Hz), 6.66 (1H, s), 4.01-3.87 (2H, m), 2.15 (3H, s), 2.05 (3H, s), 1.18 (3H, t, J = 7.0 Hz). |
| 479 | 1H-NMR (CDCl3) δ: 7.66 (1H, s), 7.20-7.16 (1H, m), 7.05-6.97 (2H, m), 6.94-6.90 (2H, m), 6.86 (1H, dd, J = 7.6, 1.5 Hz), 6.66 (1H, s), 3.99-3.88 (2H, m), 2.15 (3H, s), 2.05 (3H, s), 1.18 (3H, t, J = 7.0 Hz). |
| 480 | 1H-NMR (CDCl3) δ: 7.30 (1H, d, J = 9.5 Hz), 7.21-7.17 (1H, m), 7.02-6.98 (2H, m), 6.94-6.90 (2H, m), 6.86 (1H, dd, J = 7.8, 1.4 Hz), 6.69-6.66 (2H, m), 6.31 (1H, tt, J = 57.2, 4.6 Hz), 4.21-4.07 (2H, m), 2.15 (3H, s), 2.05 (3H, s). |
| 481 | 1H-NMR (CDCl3) δ: 7.74 (1H, s), 7.18-7.15 (1H, m), 7.04-6.98 (2H, m), 6.96-6.92 (2H, m), 6.89-6.87 (1H, m), 6.67 (1H, s), 6.33 (1H, tt, J = 57.2, 4.7 Hz), 4.22-4.15 (2H, m), 2.15 (3H, s), 2.05 (3H, s). |
| 482 | 1H-NMR (CDCl3) δ: 7.53 (1H, s), 7.18-7.14 (1H, m), 7.03-6.87 (5H, m), 6.67 (1H, s), 6.33 (1H, tt, J = 57.1, 4.7 Hz), 4.23-4.14 (2H, m), 2.15 (3H, s), 2.05 (3H, s). |
| 483 | 1H-NMR (CDCl3) δ: 7.32-7.19 (5H, m), 7.02-6.99 (1H, m), 6.91 (1H, d, J = 7.8 Hz), 6.84 (1H, dd, J = 7.8, 1.6 Hz), 6.68-6.66 (2H, m), 6.30 (1H, tt, J = 57.3, 4.7 Hz), 4.24-4.08 (2H, m), 2.13 (3H, s), 2.06 (3H, s). |
| 484 | 1H-NMR (CDCl3) δ: 7.46 (1H, s), 7.31-7.18 (4H, m), 7.04-7.02 (1H, m), 6.90 (1H, d, J = 7.8 Hz), 6.83 (1H, dd, J = 7.8, 1.5 Hz), 6.68 (1H, d, J = 1.5 Hz), 4.02-3.87 (2H, m), 2.13 (3H, s), 2.06 (3H, s), 1.18 (3H, t, J = 7.1 Hz). |
| 485 | 1H-NMR (CDCl3) δ: 7.67 (1H, s), 7.30-7.18 (4H, m), 7.05-7.02 (1H, m), 6.90 (1H, d, J = 8.0 Hz), 6.83 (1H, dd, J = 8.0, 1.2 Hz), 6.68 (1H, d, J = 1.2 Hz), 4.01-3.88 (2H, m), 2.13 (3H, s), 2.06 (3H, s), 1.18 (3H, t, J = 7.0 Hz). |
| 486 | 1H-NMR (CDCl3) δ: 7.54 (1H, s), 7.32-7.21 (3H, m), 7.18-7.16 (1H, m), 7.03-7.00 (1H, m), 6.91 (1H, d, J = 7.8 Hz), 6.85 (1H, dd, J = 7.8, 1.7 Hz), 6.68 (1H, s), 6.68 (1H, d, J = 1.7 Hz), 6.33 (1H, tt, J = 57.1, 4.7 Hz), 4.27-4.16 (2H, m), 2.13 (3H, s), 2.06 (3H, s). |
| 487 | 1H-NMR (CDCl3) δ: 7.54 (1H, s), 7.32-7.21 (3H, m), 7.18-7.16 (1H, m), 7.03-7.00 (1H, m), 6.91 (1H, d, J = 7.8 Hz), 6.85 (1H, dd, J = 7.8, 1.5 Hz), 6.68 (1H, d, J = 1.5 Hz), 6.33 (1H, tt, J = 57.1, 4.7 Hz), 4.28-4.11 (2H, m), 2.13 (3H, s), 2.06 (3H, s). |
| 488 | 1H-NMR (CDCl3) δ: 7.35 (1H, d, J = 9.5 Hz), 7.33-7.31 (1H, m), 7.29-7.20 (4H, m), 7.12 (1H, d, J = 7.6 Hz), 7.07 (1H, ddd, J = 8.0, 7.6, 1.8 Hz), 6.99 (1H, td, J = 7.6, 1.2 Hz), 6.93 (1H, dd, J = 7.6, 1.8 Hz), 6.69 (1H, d, J = 9.5 Hz), 6.32 (1H, tt, J = 57.2, 4.6 Hz), 4.23-4.07 (2H, m). |
| 489 | 1H-NMR (CDCl3) δ: 7.17-7.17 (3H, m), 7.04-7.02 (4H, m), 6.92 (1H, td, J = 7.3, 1.5 Hz), 6.82-6.81 (1H, m), 5.92 (1H, tt, J = 56.7, 4.4 Hz), 3.92-3.61 (2H, m), 2.77-2.52 (4H, m), 2.19 (3H, s). |
| 490 | 1H-NMR (CDCl3) δ: 7.58 (1H, s), 7.34-7.20 (5H, m), 7.13-7.08 (2H, m), 7.00 (1H, td, J = 7.6, 1.3 Hz), 6.93 (1H, dd, J = 7.6, 1.8 Hz), 6.34 (1H, tt, J = 57.2, 4.6 Hz), 4.25-4.14 (2H, m). |
| 491 | 1H-NMR (CDCl3) δ: 7.78 (1H, s), 7.35-7.20 (5H, m), 7.11-7.09 (2H, m), 7.00 (1H, td, J = 7.6, 1.3 Hz), 6.93 (1H, dd, J = 7.6, 1.8 Hz), 6.34 (1H, tt, J = 57.1, 4.6 Hz), 4.25-4.13 (2H, m). |
| 492 | 1H-NMR (CDCl3) δ: 7.32 (1H, d, J = 9.5 Hz), 7.30-7.28 (1H, m), 7.26-7.24 (1H, m), 7.22-7.19 (2H, m), 7.05-7.03 (2H, m), 7.01-7.00 (1H, m), 6.94-6.92 (1H, m), 6.86 (1H, d, J = 7.3 Hz), 6.68 (1H, d, J = 9.5 Hz), 6.31 (1H, tt, J = 57.3, 4.7 Hz), 4.18-4.15 (2H, m), 2.12 (3H, s). |
| 493 | 1H-NMR (CDCl3) δ: 7.55 (1H, s), 7.32-7.17 (4H, m), 7.07-7.00 (3H, m), 6.96-6.92 (1H, m), 6.86 (1H, d, J = 7.6 Hz), 6.33 (1H, tt, J = 57.1, 4.6 Hz), 4.22-4.19 (2H, m), 2.13 (3H, s). |
| 494 | 1H-NMR (CDCl3) δ: 7.75 (1H, s), 7.32-7.16 (4H, m), 7.05-7.03 (3H, m), 6.95-6.93 (1H, m), 6.86 (1H, d, J = 7.3 Hz), 6.33 (1H, tt, J = 57.1, 4.6 Hz), 4.22-4.18 (2H, m), 2.13 (3H, s). |
| 495 | 1H-NMR (CDCl3) δ: 7.44 (1H, s), 7.21-7.18 (1H, m), 7.05-6.99 (3H, m), 6.94 (1H, td, J = 8.4, 2.8 Hz), 6.77 (1H, td, J = 8.4, 2.8 Hz), |

TABLE 5-continued

| Compound | ¹H-NMR |
|---|---|
|  | 6.58 (1H, dd, J = 9.2, 2.8 Hz), 4.00-3.87 (2H, m), 2.07 (3H, s), 1.18 (3H, t, J = 7.0 Hz). |
| 496 | 1H-NMR (CDCl3) δ: 7.41 (1H, dd, J = 8.8, 5.4 Hz), 7.37-7.35 (1H, m), 7.33-7.29 (2H, m), 7.25-7.24 (2H, m), 7.16-7.15 (1H, m), 6.74 (1H, ddd, J = 8.8, 7.8, 3.1 Hz), 6.71-6.66 (2H, m), 6.30 (1H, tt, J = 57.1, 4.7 Hz), 4.22-4.09 (2H, m). |
| 497 | 1H-NMR (CDCl3) δ: 7.30 (1H, d, J = 9.5 Hz), 7.22-7.18 (1H, m), 7.14-7.10 (1H, m), 7.05-7.02 (2H, m), 6.95 (1H, td, J = 8.5, 2.7 Hz), 6.91 (1H, dd, J = 8.5, 5.9 Hz), 6.78-6.74 (1H, m), 6.69 (1H, d, J = 9.5 Hz), 6.31 (1H, tt, J = 57.3, 4.6 Hz), 4.17-4.07 (2H, m). |
| 498 | 1H-NMR (CDCl3) δ: 7.54 (1H, s), 7.20-7.16 (1H, m), 7.14-7.10 (1H, m), 7.07-7.02 (2H, m), 6.97 (1H, td, J = 8.5, 2.8 Hz), 6.92 (1H, dd, J = 8.5, 5.9 Hz), 6.78 (1H, ddd, J = 8.5, 7.8, 2.7 Hz), 6.33 (1H, tt, J = 57.1, 4.7 Hz), 4.20-4.14 (2H, m). |
| 499 | 1H-NMR (CDCl3) δ: 7.74 (1H, s), 7.20-7.16 (1H, m), 7.15-7.11 (1H, m), 7.06-7.02 (2H, m), 6.97 (1H, td, J = 8.5, 2.7 Hz), 6.92 (1H, dd, J = 8.5, 6.0 Hz), 6.78 (1H, ddd, J = 8.5, 7.8, 2.7 Hz), 6.33 (1H, tt, J = 57.1, 4.7 Hz), 4.27-4.06 (2H, m). |
| 500 | 1H-NMR (CDCl3) δ: 7.54 (1H, s), 7.42 (1H, dd, J = 8.9, 5.2 Hz), 7.39-7.37 (1H, m), 7.33 (1H, tt, J = 7.5, 1.3 Hz), 7.28-7.25 (1H, m), 7.24-7.22 (1H, m), 7.17-7.15 (1H, m), 6.76 (1H, ddd, J = 8.9, 7.8, 3.1 Hz), 6.69 (1H, dd, J = 8.7, 3.1 Hz), 6.33 (1H, tt, J = 57.2, 4.7 Hz), 4.25-4.10 (2H, m). |
| 501 | 1H-NMR (CDCl3) δ: 7.74 (1H, s), 7.42 (1H, dd, J = 8.8, 5.4 Hz), 7.38-7.31 (2H, m), 7.28-7.22 (2H, m), 7.17-7.15 (1H, m), 6.76 (1H, ddd, J = 8.9, 7.8, 3.1 Hz), 6.69 (1H, dd, J = 8.8, 3.1 Hz), 6.33 (1H, tt, J = 57.0, 4.6 Hz), 4.26-4.12 (2H, m). |
| 502 | 1H-NMR (CDCl3) δ: 7.38 (1H, dd, J = 8.8, 5.4 Hz), 7.21-7.20 (3H, m), 7.13-7.12 (2H, m), 6.68 (1H, ddd, J = 8.9, 7.8, 3.1 Hz), 6.60 (1H, dd, J = 9.2, 3.1 Hz), 3.62 (1H, dq, J = 13.8, 7.0 Hz), 3.29 (1H, dq, J = 13.8, 7.0 Hz), 2.88-2.78 (2H, m), 2.73-2.66 (1H, m), 2.43-2.40 (1H, m), 0.97 (3H, t, J = 7.0 Hz). |
| 503 | 1H-NMR (CDCl3) δ: 7.39 (1H, dd, J = 8.9, 5.2 Hz), 7.36-7.34 (1H, m), 7.31-7.17 (5H, m), 6.72 (1H, ddd, J = 8.9, 7.8, 3.1 Hz), 6.68-6.66 (2H, m), 3.94-3.83 (2H, m), 1.17 (3H, t, J = 7.0 Hz). |
| 504 | 1H-NMR (CDCl3) δ: 7.46 (1H, s), 7.41 (1H, dd, J = 8.9, 5.5 Hz), 7.38-7.34 (1H, m), 7.32-7.30 (1H, m), 7.24-7.23 (2H, m), 7.20-7.18 (1H, m), 6.74 (1H, ddd, J = 8.9, 7.8, 3.1 Hz), 6.68 (1H, dd, J = 9.2, 3.1 Hz), 3.96-3.91 (2H, m), 1.19 (3H, t, J = 7.0 Hz). |
| 505 | 1H-NMR (CDCl3) δ: 7.66 (1H, s), 7.40 (1H, dd, J = 8.9, 5.4 Hz), 7.37-7.35 (1H, m), 7.32-7.30 (1H, m), 7.24-7.23 (2H, m), 7.20-7.18 (1H, m), 6.74 (1H, ddd, J = 8.9, 7.8, 3.1 Hz), 6.68 (1H, dd, J = 8.9, 3.1 Hz), 3.96-3.90 (2H, m), 1.19 (3H, t, J = 7.0 Hz). |
| 506 | 1H-NMR (CDCl3) δ: 7.36-7.28 (3H, m), 7.24 (2H, ddd, J = 13.7, 6.8, 4.2 Hz), 7.10 (1H, d, J = 7.3 Hz), 7.02 (1H, dd, J = 8.6, 2.6 Hz), 6.90 (1H, dd, J = 8.6, 6.1 Hz), 6.72 (1H, ddd, J = 8.6, 8.0, 2.7 Hz), 6.69 (1H, d, J = 9.5 Hz), 6.31 (1H, tt, J = 57.2, 4.7 Hz), 4.19-4.09 (2H, m). |
| 507 | 1H-NMR (CDCl3) δ: 7.97 (1H, s), 7.19-7.16 (1H, m), 7.15-7.11 (1H, m), 7.05-7.03 (2H, m), 6.97 (1H, td, J = 8.6, 2.8 Hz), 6.91 (1H, dd, J = 8.6, 6.1 Hz), 6.78 (1H, ddd, J = 8.6, 8.0, 2.8 Hz), 6.32 (1H, tt, J = 57.2, 4.7 Hz), 4.25-4.08 (2H, m). |
| 508 | 1H-NMR (CDCl3) δ: 7.97 (1H, s), 7.43-7.35 (2H, m), 7.32 (1H, tt, J = 7.4, 1.4 Hz), 7.28-7.25 (1H, m), 7.23-7.22 (1H, m), 7.17-7.15 (1H, m), 6.76 (1H, ddd, J = 8.8, 8.0, 3.1 Hz), 6.68 (1H, dd, J = 8.8, 3.1 Hz), 6.32 (1H, tt, J = 57.1, 4.7 Hz), 4.23-4.12 (2H, m). |
| 509 | 1H-NMR (CDCl3) δ: 7.75 (1H, s), 7.37-7.29 (2H, m), 7.28-7.24 (1H, m), 7.20-7.18 (1H, m), 7.12-7.10 (1H, m), 7.02 (1H, dd, J = 8.4, 2.7 Hz), 6.92 (1H, dd, J = 8.6, 5.9 Hz), 6.73 (1H, ddd, J = 8.6, 8.0, 2.7 Hz), 6.33 (1H, tt, J = 57.1, 4.7 Hz), 4.24-4.12 (2H, m). |
| 510 | 1H-NMR (CDCl3) δ: 7.55 (1H, s), 7.37-7.29 (2H, m), 7.27-7.25 (1H, m), 7.20-7.18 (1H, m), 7.11-7.09 (1H, m), 7.03 (1H, dd, J = 8.4, 2.7 Hz), 6.92 (1H, dd, J = 8.6, 5.9 Hz), 6.74 (1H, ddd, J = 8.6, 8.0, 2.7 Hz), 6.33 (1H, tt, J = 57.1, 4.7 Hz), 4.22-4.14 (2H, m). |
| 511 | 1H-NMR (CDCl3) δ: 7.39 (1H, dd, J = 8.8, 5.4 Hz), 7.12-7.10 (2H, m), 6.92-6.89 (2H, m), 6.71 (1H, ddd, J = 8.8, 7.8, 2.9 Hz), 6.61 (1H, dd, J = 9.0, 2.9 Hz), 3.62-3.55 (1H, m), 3.34-3.27 (1H, m), 2.83-2.80 (2H, m), 2.73-2.64 (1H, m), 2.46-2.39 (1H, m), 0.97 (3H, t, J = 7.1 Hz). |
| 512 | 1H-NMR (CDCl3) δ: 7.42 (1H, dd, J = 8.9, 5.2 Hz), 7.30 (1H, d, J = 9.5 Hz), 7.25-7.22 (1H, m), 7.19-7.16 (1H, m), 7.07 (1H, td, J = 8.5, 2.7 Hz), 6.96 (1H, td, J = 8.5, 2.7 Hz), 6.78 (1H, ddd, J = 8.9, 7.8, 3.1 Hz), 6.70 (1H, d, J = 9.5 Hz), 6.68 (1H, dd, J = 8.9, 3.1 Hz), 6.31 (1H, tt, J = 57.2, 4.6 Hz), 4.21-4.03 (2H, m). |
| 513 | 1H-NMR (CDCl3) δ: 7.41 (1H, dd, J = 8.9, 5.2 Hz), 7.24-7.20 (3H, m), 7.05 (1H, td, J = 8.5, 2.7 Hz), 6.95 (1H, td, J = 8.5, 2.7 Hz), 6.76 (1H, ddd, J = 8.9, 7.8, 3.1 Hz), 6.68-6.66 (2H, m), 3.91-3.85 (2H, m), 1.16 (3H, t, J = 7.0 Hz). |

TABLE 5-continued

| Compound | ¹H-NMR |
|---|---|
| 514 | 1H-NMR (CDCl3) δ: 7.98 (1H, s), 7.36-7.29 (2H, m), 7.27-7.24 (1H, m), 7.19-7.18 (1H, m), 7.12-7.10 (1H, m), 7.02 (1H, dd, J = 8.6, 2.6 Hz), 6.91 (1H, dd, J = 8.6, 6.1 Hz), 6.73 (1H, ddd, J = 8.6, 8.0, 2.6 Hz), 6.32 (1H, tt, J = 57.2, 4.6 Hz), 4.23-4.13 (2H, m). |
| 515 | 1H-NMR (CDCl3) δ: 7.73 (1H, s), 7.43 (1H, dd, J = 8.8, 5.1 Hz), 7.23-7.17 (2H, m), 7.07 (1H, td, J = 8.4, 2.5 Hz), 6.97 (1H, td, J = 8.4, 2.5 Hz), 6.80 (1H, ddd, J = 8.9, 7.8, 2.9 Hz), 6.69 (1H, dd, J = 8.8, 2.9 Hz), 6.33 (1H, tt, J = 57.0, 4.7 Hz), 4.23-4.10 (2H, m). |
| 516 | 1H-NMR (CDCl3) δ: 7.53 (1H, d, J = 3.7 Hz), 7.43 (1H, dd, J = 8.9 5.2 Hz), 7.24-7.17 (2H, m), 7.09-7.06 (1H, m), 6.99-6.94 (1H, m), 6.80 (1H, ddd, J = 8.9, 7.8, 3.1 Hz), 6.69 (1H, dd, J = 8.9, 3.1 Hz), 6.33 (1H, tt, J = 57.0, 4.7 Hz), 4.21-4.12 (2H, m). |
| 517 | 1H-NMR (CDCl3) δ: 7.45 (1H, s), 7.42 (1H, dd, J = 8.9, 5.2 Hz), 7.23-7.19 (2H, m), 7.08-7.03 (1H, m), 6.98-6.93 (1H, m), 6.78 (1H, ddd, J = 8.9, 7.8, 2.9 Hz), 6.68 (1H, dd, J = 8.9, 2.9 Hz), 3.98-3.87 (2H, m), 1.19 (3H, t, J = 7.0 Hz). |
| 518 | 1H-NMR (CDCl3) δ: 7.65 (1H, s), 7.42 (1H, dd, J = 8.9, 5.4 Hz), 7.23-7.19 (2H, m), 7.08-7.03 (1H, m), 6.97-6.95 (1H, m), 6.78 (1H, ddd, J = 8.9, 7.8, 2.9 Hz), 6.68 (1H, dd, J = 8.9, 2.9 Hz), 3.98-3.87 (2H, m), 1.19 (3H, t, J = 7.0 Hz). |
| 519 | 1H-NMR (CDCl3) δ: 7.45 (1H, dd, J = 7.8, 1.5 Hz), 7.11-7.09 (2H, m), 7.04 (1H, td, J = 7.4, 1.8 Hz), 6.97 (1H, td, J = 7.4, 1.8 Hz), 6.89-6.85 (3H, m), 3.62 (1H, dq, J = 13.9, 7.0 Hz), 3.29 (1H, dq, J = 13.9, 7.0 Hz), 2.88-2.77 (2H, m), 2.73-2.64 (1H, m), 2.45-2.41 (1H, m), 0.97 (3H, t, J = 7.0 Hz). |
| 520 | 1H-NMR (CDCl3) δ: 7.48-7.46 (1H, m), 7.33 (1H, d, J = 9.5 Hz), 7.24-7.15 (2H, m), 7.09-6.99 (3H, m), 6.94-6.91 (2H, m), 6.70 (1H, d, J = 9.5 Hz), 6.32 (1H, tt, J = 57.3, 4.7 Hz), 4.20-4.06 (2H, m). |
| 521 | 1H-NMR (CDCl3) δ: 7.55 (1H, s), 7.49-7.47 (1H, m), 7.22-7.16 (2H, m), 7.11-7.00 (3H, m), 6.96-6.91 (2H, m), 6.34 (1H, tt, J = 57.1, 4.7 Hz), 4.28-4.07 (2H, m). |
| 522 | 1H-NMR (CDCl3) δ: 7.76 (1H, s), 7.49-7.46 (1H, m), 7.21-7.18 (2H, m), 7.11-7.00 (3H, m), 6.96-6.91 (2H, m), 6.34 (1H, tt, J = 57.1, 4.6 Hz), 4.24-4.11 (2H, m). |
| 523 | 1H-NMR (CDCl3) δ: 7.99 (1H, s), 7.48-7.46 (1H, m), 7.20-7.18 (2H, m), 7.08-7.02 (3H, m), 6.94-6.92 (2H, m), 6.33 (1H, tt, J = 57.1, 4.8 Hz), 4.27-4.07 (2H, m). |
| 524 | 1H-NMR (CDCl3) δ: 7.92 (1H, s), 7.26 (1H, dd, J = 8.1, 1.2 Hz), 7.20-7.16 (2H, m), 7.10 (1H, td, J = 7.7, 1.6 Hz), 7.04-6.90 (4H, m), 3.95-3.91 (2H, m), 1.18 (3H, t, J = 7.1 Hz). |
| 525 | 1H-NMR (CDCl3) δ: 8.01 (1H, s), 7.34-7.20 (5H, m), 7.14-7.12 (1H, m), 7.10-7.08 (1H, m), 7.01-6.99 (1H, m), 6.92 (1H, dd, J = 7.6, 1.7 Hz), 6.33 (1H, tt, J = 57.1, 4.7 Hz), 4.25-4.13 (2H, m). |
| 526 | 1H-NMR (CDCl3) δ: 7.99 (1H, s), 7.31-7.21 (3H, m), 7.17 (1H, d, J = 7.0 Hz), 7.05-7.03 (3H, m), 6.96-6.92 (1H, m), 6.86-6.85 (1H, m), 6.33 (1H, tt, J = 57.2, 4.7 Hz), 4.21-4.19 (2H, m), 2.12 (3H, s). |
| 527 | 1H-NMR (CDCl3) δ: 7.31 (1H, d, J = 9.2 Hz), 7.21-7.17 (1H, m), 7.07-7.06 (2H, m), 7.01-6.89 (4H, m), 6.84 (1H, d, J = 7.3 Hz), 6.69 (1H, d, J = 9.2 Hz), 6.31 (1H, tt, J = 57.2, 4.8 Hz), 4.16-4.13 (2H, m), 2.11 (3H, s). |
| 528 | 1H-NMR (CDCl3) δ: 7.54 (1H, s), 7.18-7.15 (1H, m), 7.07 (2H, ddd, J = 13.5, 6.8, 2.4 Hz), 7.02-6.91 (4H, m), 6.85-6.84 (1H, m), 6.33 (1H, tt, J = 57.2, 4.8 Hz), 4.22-4.14 (2H, m), 2.11 (3H, s). |
| 529 | 1H-NMR (CDCl3) δ: 7.75 (1H, s), 7.18-7.15 (1H, m), 7.10-7.04 (2H, m), 7.03-6.91 (4H, m), 6.85-6.84 (1H, m), 6.34 (1H, tt, J = 57.2, 4.6 Hz), 4.20-4.17 (2H, m), 2.11 (3H, s). |
| 530 | 1H-NMR (CDCl3) δ: 7.46 (1H, dd, J = 7.9, 1.3 Hz), 7.35-7.20 (5H, m), 7.17-7.15 (1H, m), 7.06-6.97 (2H, m), 6.93 (1H, dd, J = 7.3, 2.0 Hz), 6.69 (1H, d, J = 9.5 Hz), 6.31 (1H, tt, J = 57.3, 4.7 Hz), 4.21-4.09 (2H, m). |
| 531 | 1H-NMR (CDCl3) δ: 7.89 (1H, s), 7.41-7.18 (6H, m), 6.73 (1H, ddd, J = 8.9, 7.8, 2.9 Hz), 6.67 (1H, dd, J = 8.9, 2.9 Hz), 3.99-3.89 (2H, m), 1.21 (3H, t, J = 7.0 Hz). |
| 532 | 1H-NMR (CDCl3) δ: 7.96 (1H, s), 7.43 (1H, dd, J = 8.9, 5.2 Hz), 7.22-7.18 (2H, m), 7.09-7.05 (1H, m), 6.98-6.96 (1H, m), 6.79 (1H, ddd, J = 8.9, 7.8, 3.0 Hz), 6.68 (1H, dd, J = 8.9, 3.1 Hz), 6.32 (1H, tt, J = 57.1, 4.7 Hz), 4.22-4.09 (2H, m). |
| 533 | 1H-NMR (CDCl3) δ: 7.57 (1H, s), 7.47-7.45 (1H, m), 7.35-7.21 (4H, m), 7.17-7.15 (1H, m), 7.07-6.99 (2H, m), 6.95-6.93 (1H, m), 6.34 (1H, tt, J = 57.1, 4.6 Hz), 4.28-4.09 (2H, m). |
| 534 | 1H-NMR (CDCl3) δ: 7.77 (1H, s), 7.46 (1H, dd, J = 7.6, 1.5 Hz), 7.34-7.31 (1H, m), 7.30-7.26 (1H, m), 7.24-7.22 (2H, m), 7.17-7.16 (1H, m), 7.06-7.04 (1H, m), 7.01 (1H, td, J = 7.5, 1.8 Hz), 6.95-6.93 (1H, m), 6.34 (1H, tt, J = 57.4, 4.6 Hz), 4.24-4.13 (2H, m). |
| 535 | 1H-NMR (CDCl3) δ: 7.45 (1H, dd, J = 7.6, 1.4 Hz), 7.32-7.18 (6H, m), 7.03-7.01 (1H, m), 6.97 (1H, td, J = 7.6, 1.8 Hz), 6.93 (1H, dd, J = 7.6, 2.0 Hz), 6.66 (1H, d, J = 9.2 Hz), 3.94-3.85 (2H, m), 1.17 (3H, t, J = 7.0 Hz). |

TABLE 5-continued

| Compound | 1H-NMR |
|---|---|
| 536 | 1H-NMR (CDCl3) δ: 7.48 (1H, s), 7.45 (1H, dd, J = 7.7, 1.4 Hz), 7.33-7.18 (5H, m), 7.03-6.99 (2H, m), 6.93 (1H, dd, J = 7.3, 2.0 Hz), 3.97-3.91 (2H, m), 1.19 (3H, t, J = 7.1 Hz). |
| 537 | 1H-NMR (CDCl3) δ: 7.69 (1H, s), 7.46-7.44 (1H, m), 7.33-7.18 (5H, m), 7.03 (1H, td, J = 7.6, 1.4 Hz), 6.99 (1H, td, J = 7.6, 2.0 Hz), 6.93 (1H, dd, J = 7.6, 2.0 Hz), 3.97-3.91 (2H, m), 1.19 (3H, t, J = 7.1 Hz). |
| 538 | 1H-NMR (CDCl3) δ: 7.29-7.18 (5H, m), 7.03-7.00 (3H, m), 6.93-6.90 (1H, m), 6.85 (1H, d, J = 7.3 Hz), 6.66 (1H, d, J = 9.2 Hz), 3.92-3.88 (2H, m), 2.12 (3H, s), 1.16 (3H, t, J = 7.0 Hz). |
| 539 | 1H-NMR (CDCl3) δ: 7.47 (1H, s), 7.27-7.22 (4H, m), 7.03-7.02 (3H, m), 6.95-6.91 (1H, m), 6.87-6.85 (1H, m), 3.96-3.93 (2H, m), 2.12 (3H, s), 1.19 (3H, t, J = 7.0 Hz). |
| 540 | 1H-NMR (CDCl3) δ: 7.67 (1H, s), 7.30-7.19 (4H, m), 7.04-7.02 (3H, m), 6.95-6.91 (1H, m), 6.86-6.85 (1H, m), 3.98-3.91 (2H, m), 2.12 (3H, s), 1.19 (3H, t, J = 7.1 Hz). |

The following specifically illustrates the effectiveness of the inventive compounds on plant diseases without limiting the scope of the invention to such examples.

Disease development in Test Examples described below was evaluated in increments of 0.05 by setting 0 as no incidence of disease and 3 as disease development in a plant of untreated group. Further, control values were calculated using the following equation based on disease development.

<Control Value>

Control value=$100\{1-(n/3)\}$ n=Disease development of each treated group

TEST EXAMPLE A

Blast on Rice

Seeds of a test plant (rice variety: Sachikaze) were planted and cultivated until the second leaves appeared. In the test, the inventive compounds were dissolved into a dimethyl sulfoxide-methanol mixture solution (volume ratio: 9/1), and the resultant solutions were diluted with well water to a concentration of 250 ppm. The dilutions thus obtained were sprayed to the test plant (2.5 ml/pot). After the dilutions dried, a conidial suspension ($1-2\times10^5$ conidia/ml) of *Magnaporthe grisea* was inoculated to the plant by spraying. After the inoculation, the plant was kept in a mist chamber at room temperature of 20 to 23° C. for about 24 hours to promote the onset of disease. The disease development was investigated 6 to 10 days after the inoculation, and the effectiveness of the dilutions was evaluated.

The following compounds attained more than 50% control values.

Compounds Nos.: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 107, 109, 110, 111, 112, 113, 114, 115, 116, 117, 118, 119, 120, 121, 122, 123, 124, 125, 126, 127, 128, 129, 130, 131, 132, 133, 134, 136, 137, 138, 139, 140, 141, 142, 143, 144, 145, 147, 148, 149, 151, 152, 153, 154, 156, 157, 163, 164, 165, 166, 167, 169, 171, 172, 173, 174, 176, 177, 178, 183, 184, 185, 186, 187, 188, 189, 190, 192, 193, 194, 195, 196, 199, 200, 201, 202, 204, 205, 206, 208, 209, 211, 212, 215, 220, 221, 222, 223, 227, 228, 229, 233, 235, 238, 239, 240, 241, 242, 243, 244, 245, 246, 247, 248, 249, 250, 251, 252, 253, 254, 255, 256, 257, 258, 261, 262, 264, 265, 266, 267, 268, 269, 270, 271, 272, 273, 274, 275, 276, 278, 279, 280, 281, 283, 285, 288, 289, 291, 292, 293, 294, 295, 297, 299, 300, 308, 309, 310, 311, 318, 319, 320, 321, 323, 324, 325, 326, 327, 329, 330, 331, 332, 333, 334, 335, 337, 338, 339, 340, 341, 342, 344, 345, 346, 347, 348, 349, 350, 351, 352, 353, 354, 355, 359, 360, 362, 363, 364, 368, 369, 381, 382, 385, 386, 387, 388, 391, 395, 396, 397, 398, 399, 400, 401, 402, 403, 404, 406, 407, 408, 409, 410, 411, 412, 413, 414, 416, 417, 420, 422, 423, 426, 427, 428, 429, 430, 431, 432, 433, 434, 435, 436, 438, 439, 443, 444, 445, 446, 448, 449, 450, 451, 453, 454, 455, 456, 457, 458, 459, 460, 461, 462, 464, 466, 467, 468, 469, 470, 471, 473, 474, 475, 476, 478, 479, 480, 481, 483, 484, 488, 490, 491, 492, 493, 494, 495, 496, 497, 498, 499, 500, 501, 504, 505, 506, 508, 509, 510, 511, 512, 513, 515, 516, 517, 518, 520, 521, 522, 523, 524, 526, 527, 528, 529, 531, 532, 533, 534, 535, 536, 537, 538, 539 and 540.

TEST EXAMPLE B

Gray Mold on Tomato

Seeds of a test plant (tomato variety: Oogata Fukuju) were planted and cultivated until three to five first leaves (true leaves) appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension ($4-8\times10^5$ conidia/ml) of *Botrytis cinerea* was inoculated to the plant by spraying. After the inoculation, the plant was kept in a mist chamber at room temperature of 20 to 23° C. for about 48 hours to promote the onset of disease. The disease development was investigated 2 to 3 days after the inoculation, and the effectiveness of the dilutions was evaluated.

The following compounds attained more than 50% control values.

Compounds Nos.: 1, 2, 3, 4, 5, 6, 7, 8, 9, 10, 11, 12, 13, 14, 15, 16, 17, 18, 19, 20, 21, 22, 23, 24, 25, 26, 27, 28, 30, 31, 32, 33, 34, 35, 36, 37, 38, 39, 40, 41, 42, 43, 44, 45, 46, 47, 48, 49, 50, 51, 52, 53, 54, 55, 57, 58, 59, 60, 61, 62, 63, 64, 66, 69, 70, 71, 72, 73, 74, 75, 76, 77, 78, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 118, 119, 120, 123, 124, 125, 126, 127, 128, 129, 130, 131, 132, 133, 134, 136, 138, 139, 140, 141, 142, 143, 144, 145, 146, 147, 148, 149, 150, 151, 152, 153, 154, 155, 156, 157, 158, 160, 161, 162, 163, 165, 166, 167, 168, 169, 170, 171, 172, 174, 176, 177, 178, 179, 180, 181, 182, 184, 185, 186, 187, 188, 189, 190, 202, 203, 204, 205, 206, 208, 209, 211, 212, 214, 216, 218, 222, 223, 226, 227, 228, 229, 230, 231, 232, 233, 234, 235, 239, 240, 241, 242, 243, 244, 245, 246, 247, 248, 249, 251, 252, 253, 254, 255, 256, 257, 258, 259, 260, 261, 262, 263, 264, 265, 266, 267, 269, 270, 271, 272, 273, 274, 275, 276, 278, 279, 280, 281, 282, 283, 284, 285, 286, 288, 289, 291, 292, 293, 294, 295, 298, 299, 301, 302, 303, 308, 310, 313, 314, 315, 316, 317, 318, 319, 320, 321, 322, 323, 324, 325, 327, 328, 329, 331, 333, 334, 335, 336, 337, 338, 339, 340, 341, 342, 344, 345, 346, 347, 348, 349, 350, 351, 352, 354, 359, 360, 361, 363, 368, 369, 371, 373, 375, 376, 379, 380, 387, 391, 392, 395, 397, 398, 399, 400, 401, 402, 404, 406, 407, 408, 410, 412, 416, 417, 418, 419, 427, 428, 429, 430, 431, 432, 433, 434, 435, 436, 437, 438, 439, 441, 443, 444, 445, 446, 447, 448, 449, 450, 451, 453, 454, 455, 456, 457, 458, 459, 460, 461, 462, 464, 465, 466, 467, 469, 470, 471, 473, 474, 475, 476, 477, 478, 479, 484, 485, 486, 488, 490, 491, 492, 493, 494, 495, 496, 497, 498, 499, 500, 501, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539 and 540.

TEST EXAMPLE C

*Alternaria* Sooty Spot on Cabbage

Seeds of a test plant (cabbage variety: Shikidori) were planted and cultivated until the cotyledons extended. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (4-8×10$^5$ conidia/ml) of *Alternaia brassicicola* was inoculated to the plant by spraying. After the inoculation, the plant was kept in a mist chamber at room temperature of 20 to 23° C. for about 48 hours to promote the onset of disease. The disease development was investigated 2 to 3 days after the inoculation, and the effectiveness of the dilutions was evaluated.

The following compounds attained more than 50% control values.

Compounds Nos.: 1, 3, 4, 5, 6, 7, 8, 9, 10, 11, 12, 13, 14, 16, 17, 18, 20, 21, 22, 23, 24, 25, 26, 27, 28, 30, 31, 32, 33, 34, 35, 36, 37, 38, 39, 40, 41, 43, 44, 45, 46, 47, 48, 49, 50, 51, 52, 53, 54, 55, 57, 58, 59, 60, 61, 62, 63, 64, 66, 67, 69, 70, 71, 72, 73, 74, 75, 76, 77, 78, 80, 81, 82, 84, 85, 86, 87, 88, 89, 90, 91, 92, 93, 94, 95, 96, 97, 99, 100, 101, 102, 103, 104, 105, 110, 111, 112, 113, 114, 115, 119, 123, 124, 125, 126, 127, 128, 131, 132, 133, 134, 136, 141, 142, 147, 148, 149, 151, 152, 153, 154, 155, 156, 157, 161, 162, 163, 165, 166, 167, 169, 170, 176, 177, 178, 184, 186, 188, 202, 208, 209, 211, 212, 219, 221, 222, 223, 224, 227, 228, 229, 230, 233, 234, 235, 236, 237, 238, 239, 240, 242, 243, 244, 245, 246, 247, 248, 249, 251, 252, 253, 254, 255, 256, 257, 258, 259, 260, 261, 262, 264, 266, 267, 268, 270, 271, 272, 273, 274, 275, 276, 278, 279, 280, 281, 282, 283, 284, 285, 286, 287, 288, 289, 291, 293, 294, 295, 296, 298, 299, 304, 305, 306, 307, 308, 310, 311, 314, 315, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 350, 351, 352, 355, 356, 358, 359, 360, 361, 362, 363, 364, 365, 368, 369, 370, 377, 386, 387, 391, 395, 397, 398, 399, 401, 402, 404, 406, 407, 408, 411, 412, 416, 417, 419, 422, 425, 427, 428, 429, 430, 431, 432, 433, 434, 436, 439, 442, 443, 444, 445, 446, 447, 448, 449, 450, 451, 452, 453, 454, 455, 456, 457, 458, 459, 460, 461, 462, 464, 466, 467, 469, 470, 471, 472, 473, 474, 475, 476, 477, 478, 484, 485, 488, 490, 491, 492, 493, 494, 495, 496, 497, 498, 499, 500, 501, 503, 505, 506, 508, 509, 510, 512, 513, 515, 516, 517, 518, 520, 521, 522, 523, 524, 525, 527, 528, 529, 530, 531, 532, 533, 534, 535, 536, 537, 538, 539 and 540.

TEST EXAMPLE D

Powdery Mildew on Barley

Seeds of a test plant (barley variety: Akashinriki) were planted and cultivated until the first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, conidia of *Blumeria graminis* f. sp. *hordei* were inoculated to the plant by shaking off. The disease development was investigated 6 to 10 days after the inoculation, and the effectiveness of the dilutions was evaluated.

The following compounds attained more than 50% control values.

Compounds Nos. 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 38, 40, 41, 42, 43, 44, 48, 49, 50, 51, 54, 55, 56, 57, 58, 61, 66, 69, 70, 71, 73, 78, 80, 84, 85, 89, 90, 94, 96, 99, 103, 104, 109, 111, 113, 116, 117, 119, 124, 125, 126, 131, 132, 133, 143, 146, 147, 166, 167, 168, 169, 170, 174, 175, 184, 190, 194, 198, 202, 208, 209, 211, 212, 229, 244, 245, 246, 247, 248, 251, 252, 253, 254, 255, 256, 261, 262, 266, 270, 271, 274, 275, 278, 279, 280, 281, 283, 288, 291, 293, 295, 298, 306, 309, 310, 319, 324, 333, 337, 338, 340, 341, 342, 344, 349, 351, 352, 354, 358, 359, 360, 363, 367, 368, 369, 373, 380, 385, 391, 393, 397, 398, 399, 405, 406, 407, 408, 411, 414, 415, 416, 419, 427, 428, 429, 430, 431, 432, 435, 436, 443, 444, 445, 449, 450, 451, 457, 458, 459, 460, 461, 462, 464, 465, 466, 469, 470, 471, 473, 475, 476, 477, 480, 482, 486, 487, 488, 489, 490, 491, 492, 493, 494, 495, 496, 497, 498, 499, 500, 501, 504, 505, 506, 508, 509, 510, 511, 512, 514, 515, 516, 517, 518, 519, 520, 521, 522, 523, 524, 525, 526, 527, 528, 529, 530, 531, 532, 533 and 534.

TEST EXAMPLE E

Brown Rust on Wheat

Seeds of a test plant (wheat variety: Norin 61) were planted and cultivated until the first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a urediniospore suspension (1-2×10$^5$ urediniospores/ml) of *Puccinia recondita* was inoculated to the plant by spraying. After the inoculation, the plant was kept in a mist chamber at room temperature of 20 to 23° C. for about 24 hours to promote the onset of disease. The disease development was investigated 7 to 10 days after the inoculation, and the effectiveness of the dilutions was evaluated.

The following compounds attained more than 50% control values.

Compounds Nos.: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 57, 58, 59, 60, 61, 62, 63, 64, 65, 66, 69, 70, 71, 72, 73, 74, 75, 76, 77, 78, 80, 81, 82, 83, 84, 85, 86, 87, 88, 89, 90, 91, 92, 93, 94, 95, 96, 97, 98, 99, 100, 101, 102, 103, 104, 105, 107, 108, 109, 110, 111, 112, 113, 114, 117, 118, 119, 120, 121, 122, 123, 124, 125, 126, 127, 128, 129, 131, 132, 133, 134, 135, 136, 138, 139, 140, 141, 142, 143, 144, 145, 146, 147, 148, 149, 150, 151, 152, 153, 154, 155, 156, 157, 160, 161, 162, 163, 165, 166, 167, 168, 169, 170, 172, 176, 177, 178, 184, 186, 188, 190, 202, 203, 204, 205, 206, 208, 209, 210, 211, 212, 221, 223, 225, 229, 230, 233, 234, 235, 239, 240, 241, 242, 243, 244, 245, 246, 247, 248, 249, 251, 252, 253, 254, 255, 256, 257, 258, 259, 260, 261, 262, 264, 265, 266, 267, 269, 270, 271, 272, 273, 274, 275, 276, 277, 278, 279, 280, 281, 282, 283, 284, 285, 286, 287, 288, 289, 290, 291, 292, 293, 294, 295, 298, 299, 306, 307, 308, 309, 310, 311, 312, 313, 314, 315, 316, 317, 318, 319, 320, 321, 322, 323, 324, 325, 326, 327, 328, 329, 331, 333, 334, 335, 336, 337, 338, 339, 340, 341, 342, 344, 345, 346, 347, 348, 349, 350, 351, 352, 354, 356, 357, 358, 359, 360, 361, 362, 363, 365, 367, 368, 369, 370, 376, 379, 380, 381, 382, 383, 384, 386, 387, 388, 391, 392, 393, 395, 396, 397, 398, 399, 400, 401, 402, 404, 406, 407, 408, 409, 411, 412, 414, 415, 416, 417, 418, 419, 421, 422, 424, 425, 426, 427, 428, 429, 430, 431, 432, 433, 434, 435, 436, 443, 444, 445, 446, 447, 448, 449, 450, 451, 453, 454, 455, 456, 457, 458, 459, 460, 461, 462, 464, 465, 466, 467, 469, 470, 471, 473, 474, 476, 477, 481, 484, 488, 490, 491, 492, 493, 494, 495, 496, 497, 498, 499, 500, 501, 503, 504, 505, 506, 508, 509, 510, 511, 512, 513, 514, 515, 516, 517, 518, 519, 520, 521, 522, 523, 524, 525, 526, 527, 528, 529, 530, 531, 532, 533, 534, 535, 536 and 537.

TEST EXAMPLE F

Late Blight on Tomato

Seeds of a test plant (tomato variety: Oogata Fukuju) were planted and cultivated until three to five first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a zoosporangia suspension (4-8× $10^3$ zoosporangia/ml) of Phytophthora infestans was inoculated to the plant by spraying. After the inoculation, the plant was kept in a mist chamber at room temperature of 20° C. for about 24 hours to promote the onset of disease. The disease development was investigated 5 to 10 days after the inoculation, and the effectiveness of the dilutions was evaluated.

The following compounds attained more than 50% control values.

Compounds Nos.: 1, 2, 4, 11, 75, 81, 103, 110, 197, 349, 389, 390, 397, 409, 449, 459, 464, 465, 466, 506, 519, 520 and 527.

TEST EXAMPLE G

Downy Mildew on Vine

Seeds of a test plant (grape variety: Neomuscat) were planted and cultivated until three to four first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a zoosporangia suspension (1-2× $10^4$ zoosporangia/ml) of Plasmopara viticola was inoculated to the plant by spraying. After the inoculation, the plant was kept in a mist chamber at room temperature of 20° C. for about 24 hours to promote the onset of disease. The disease development was investigated 7 to 10 days after the inoculation, and the effectiveness of the dilutions was evaluated.

The following compounds attained more than 50% control values.

Compounds Nos. 1, 3, 4, 8, 11, 16, 20, 23, 27, 34, 36, 39, 40, 41, 43, 48, 50, 51, 52, 53, 55, 56, 65, 72, 73, 75, 76, 77, 81, 82, 84, 85, 87, 90, 91, 93, 94, 103, 108, 109, 110, 111, 113, 114, 116, 117, 125, 129, 132, 133, 134, 136, 142, 143, 146, 149, 152, 159, 162, 168, 169, 184, 191, 197, 198, 203, 209, 211, 213, 217, 235, 239, 247, 251, 252, 253, 258, 259, 263, 264, 266, 270, 271, 273, 286, 287, 293, 310, 314, 315, 319, 331, 334, 335, 338, 339, 340, 341, 345, 348, 351, 352, 363, 366, 367, 368, 369, 371, 375, 378, 386, 387, 393, 397, 400, 401, 406, 407, 409, 410, 411, 414, 415, 416, 417, 433, 449, 450, 459, 460, 463, 465, 466, 473, 474, 483, 484, 488, 489, 490, 492, 494, 501, 506, 509, 511, 513, 519, 520, 524, 525, 527, 533 and 538.

TEST EXAMPLE H

Anthracnose on Cucumber

Seeds of a test plant (cucumber variety: Sagami Hanjiro) were planted and cultivated until the first leaf appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (2-4×$10^5$ conidia/ml) of Colletotrichum orbiculare was inoculated to the plant by spraying. After the inoculation, the plant was kept in a mist chamber at room temperature of 20 to 23° C. for about 24 hours to promote the onset of disease. The disease development was investigated 6 to 10 days after the inoculation, and the effectiveness of the dilutions was evaluated.

The following compounds attained more than 50% control values.

Compounds Nos. 3, 4, 5, 6, 7, 8, 9, 10, 11, 12, 13, 14, 16, 17, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 57, 58, 59, 60, 61, 62, 63, 64, 66, 69, 70, 71, 72, 73, 74, 75, 76, 77, 78, 80, 81, 82, 83, 84, 85, 86, 87, 88, 89, 90, 91, 92, 93, 94, 95, 96, 97, 99, 100, 101, 102, 103, 104, 105, 106, 107, 108, 109, 110, 111, 112, 113, 114, 115, 116, 117, 119, 120, 124, 125, 126, 127, 131, 132, 133, 134, 136, 138, 140, 141, 147, 148, 149, 151, 153, 154, 155, 156, 159, 160, 161, 162, 163, 165, 166, 167, 169, 170, 171, 177, 178, 184, 186, 188, 190, 202, 204, 206, 207, 208, 209, 211, 212, 219, 221, 222, 224, 227, 228, 229, 233, 234, 235, 238, 239, 240, 241, 242, 243, 244, 245, 246, 247, 248, 249, 251, 252, 253, 254, 255, 256, 257, 258, 260, 261, 262, 264, 266, 267, 270, 271, 273, 274, 275, 276, 278, 279, 280, 281, 284, 285, 286, 287, 288, 289, 291, 292, 293, 294, 295, 298, 299, 310, 311, 318, 319, 320, 321, 322, 324, 325, 327, 328, 331, 333, 334, 335, 337, 338, 339, 340, 341, 342, 344, 345, 346, 347, 348, 349, 350, 351, 352, 359, 360, 363, 368, 369, 372, 374, 386, 387, 391, 393, 394, 395, 397, 398, 399, 401, 402, 404, 406, 407, 408, 409, 410, 411, 412, 414, 416, 417, 418, 419, 420, 421, 422, 423, 427, 428, 429, 430, 431, 432, 433, 434, 435, 436, 439, 440, 442, 443, 444, 445, 446, 448, 449, 450, 451, 453, 454, 455, 456, 457, 458, 459, 460, 461, 462, 464, 466, 467, 470, 471, 472, 473, 474, 475, 476, 477, 478, 483, 488, 490, 491, 492, 493, 494, 495, 496, 497, 498, 499, 500, 501, 502, 503, 504, 505, 506, 508, 509, 510, 511, 512, 513, 515, 516, 517, 518, 520, 521, 522, 524, 525, 527, 528, 529, 530, 532, 533, 534, 538, 539 and 540.

INDUSTRIAL APPLICABILITY

The inventive compounds are novel compounds capable of preventing and treating plant diseases, and are therefore valuable as agricultural chemicals, for example, agricultural and horticultural pest control agents, in particular, agricultural and horticultural fungicides.

The entire contents of Japanese Patent Application No. 2017-12467 (filed: Jan. 26, 2017) are incorporated herein by reference.

All publications, patent applications and technical standards mentioned in the present specification are herein incorporated by reference to the same extent as if each individual publication, patent application or technical standard was specifically and individually indicated to be incorporated by reference.

The invention claimed is:
1. A compound represented by the formula (1), or a salt thereof:

[Chem. 132]

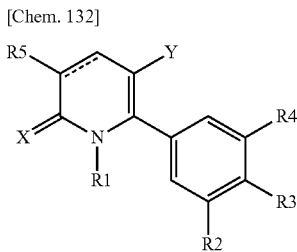

wherein R1 represents:
a hydroxy group,
a cyano group,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C3-C8 cycloalkoxy group optionally substituted with substituent(s) A,
a C2-C6 alkenyloxy group optionally substituted with substituent(s) A,
a C2-C6 haloalkenyloxy group,
a C3-C6 alkynyloxy group optionally substituted with substituent(s) A,
a C3-C6 haloalkynyloxy group, or
RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group);
R2, R3 and R4 are independent of one another and each represent:
a hydrogen atom,
a halogen atom,
a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
an aryloxy group optionally substituted with 0 to 5 substituents D,
a heteroaryloxy group optionally substituted with 0 to 2 substituents D,
an aralkyloxy group optionally substituted with 0 to 5 substituents D,
Rx1C(=O)— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)),
Rx1C(=O)O— (wherein Rx1 is the same as defined hereinabove),
a 3 to 6-membered ring group containing 1 to 2 oxygen atoms,
Rc-L- (wherein Rc represents a C1-C6 alkyl group or a C1-C6 haloalkyl group, and L represents S, SO or SO$_2$),
RaRbN— (wherein Ra and Rb are the same as defined hereinabove), or
Rx2C(=O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), and Rx3 represents a hydrogen atom, a C1-C6 alkyl group optionally substituted with substituent(s) B, a C1-C6 haloalkyl group or a C3-C8 cycloalkyl group);

R5 represents:
  a hydrogen atom,
  a halogen atom,
  a cyano group,
  a nitro group,
  a C1-C6 alkyl group optionally substituted with substituent(s) A,
  a C1-C6 haloalkyl group,
  a C3-C8 cycloalkyl group optionally substituted with substituent(s) A,
  a C2-C6 alkenyl group optionally substituted with substituent(s) A,
  a C2-C6 haloalkenyl group,
  a C2-C6 alkynyl group optionally substituted with substituent(s) A,
  a C2-C6 haloalkynyl group,
  a C1-C6 alkoxy group optionally substituted with substituent(s) A,
  a C1-C6 haloalkoxy group,
  a C3-C8 cycloalkoxy group optionally substituted with substituent(s) A,
  a C2-C6 alkenyloxy group optionally substituted with substituent(s) A,
  a C2-C6 haloalkenyloxy group,
  a C3-C6 alkynyloxy group optionally substituted with substituent(s) A,
  a C3-C6 haloalkynyloxy group,
  Rc-L- (wherein Rc and L are the same as defined hereinabove),
  RaRbN— (wherein Ra and Rb are the same as defined hereinabove), or
  R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);

X represents an oxygen atom or a sulfur atom;

Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group,
  the phenyl group is substituted with R6 at an ortho position and is further optionally substituted with 0 to 4 substituents R7 independent of one another,
  the pyridyl group, the pyrazinyl group, the pyrimidinyl group, the pyridazinyl group, the triazinyl group or the tetrazinyl group is substituted with R6 at an ortho position and is further optionally substituted with 0 to 3 substituents R7 independent of one another,
  the thienyl group, the thiazolyl group, the isothiazolyl group or the thiadiazolyl group is substituted with R6 at an ortho position and is further optionally substituted with 0 to 2 substituents R7 independent of one another;

R6 represents:
  a halogen atom,
  a hydroxy group,
  a cyano group,
  a nitro group,
  a C1-C6 alkyl group optionally substituted with substituent(s) C,
  a C1-C6 haloalkyl group,
  a C3-C8 cycloalkyl group optionally substituted with substituent(s) C,
  a C2-C6 alkenyl group optionally substituted with substituent(s) C,
  a C2-C6 haloalkenyl group,
  a C2-C6 alkynyl group optionally substituted with substituent(s) C,
  a C2-C6 haloalkynyl group,
  a C1-C6 alkoxy group optionally substituted with substituent(s) C,
  a C1-C6 haloalkoxy group,
  a C3-C8 cycloalkoxy group optionally substituted with substituent(s) C,
  a C2-C6 alkenyloxy group optionally substituted with substituent(s) C,
  a C2-C6 haloalkenyloxy group,
  a C3-C6 alkynyloxy group optionally substituted with substituent(s) C,
  a C3-C6 haloalkynyloxy group,
  an aryloxy group optionally substituted with 0 to 5 substituents D,
  a heteroaryloxy group optionally substituted with 0 to 2 substituents D,
  an aralkyloxy group optionally substituted with 0 to 5 substituents D,
  Rx1C(=O)— (wherein Rx1 is the same as defined hereinabove),
  Rx1C(=O)O— (wherein Rx1 is the same as defined hereinabove),
  a 3 to 6-membered ring group containing 1 to 2 oxygen atoms,
  Rc-L- (wherein Rc and L are the same as defined hereinabove),
  RaRbN— (wherein Ra and Rb are the same as defined hereinabove), or
  Rx2C(=O)N(Rx3)- (wherein Rx2 and Rx3 are the same as defined hereinabove);

R7 is defined the same as R6 described hereinabove;

the bond including the broken line represents a double bond or a single bond;

the substituent(s) A is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove);

the substituent(s) B is at least one selected from the group consisting of cyano group, C1-C6 alkoxy groups, C1-C6 haloalkoxy groups and C3-C8 cycloalkoxy groups;

the substituent(s) C is at least one selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— (wherein Ra and Rb are the same as defined hereinabove), Rc-L- (wherein Rc and L are the same as defined hereinabove), RdC(=O)—(wherein Rd is defined the same as Rx1 described hereinabove) and 3 to 6-membered ring groups containing 1 to 2 oxygen atoms; and the substituent(s) D is at least one selected from the group consisting of halogen atoms, hydroxy group, cyano group, nitro group, C1-C6 alkyl groups optionally substituted with substituent(s) B, C1-C6 haloalkyl groups, C3-C8 cycloalkyl groups, C1-C6 alkoxy groups, C1-C6 haloalkoxy groups and C3-C8 cycloalkoxy groups.

2. The compound according to claim 1, or a salt thereof, wherein

R1 represents:
  a C1-C6 alkyl group optionally substituted with substituent(s) A,
  a C1-C6 haloalkyl group,
  a C2-C6 alkenyl group optionally substituted with substituent(s) A, or
  a C2-C6 haloalkenyl group;

R2, R3 and R4 are independent of one another and each represent:
  a hydrogen atom,
  a halogen atom,
  a hydroxy group,
  a cyano group,
  a C1-C6 alkyl group optionally substituted with substituent(s) C,
  a C1-C6 haloalkyl group,
  a C2-C6 alkenyl group optionally substituted with substituent(s) C,
  a C2-C6 alkynyl group optionally substituted with substituent(s) C,
  a C1-C6 alkoxy group optionally substituted with substituent(s) C,
  a C1-C6 haloalkoxy group,
  a C2-C6 alkenyloxy group optionally substituted with substituent(s) C,
  a C2-C6 haloalkenyloxy group,
  a C3-C6 alkynyloxy group optionally substituted with substituent(s) C,
  a C3-C6 haloalkynyloxy group,
  an aralkyloxy group optionally substituted with 0 to 5 substituents D, or
  Rx1C(=O)O— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group));

R5 represents:
  a hydrogen atom,
  a halogen atom,
  a C1-C6 alkyl group optionally substituted with substituent(s) A,
  a C1-C6 haloalkyl group,
  a C2-C6 alkenyl group optionally substituted with substituent(s) A,
  a C2-C6 alkynyl group optionally substituted with substituent(s) A,
  a C1-C6 alkoxy group optionally substituted with substituent(s) A,
  a C2-C6 alkenyloxy group optionally substituted with substituent(s) A,
  a C3-C6 alkynyloxy group optionally substituted with substituent(s) A, or
  R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);

Y represents a phenyl group or a pyridyl group,
  the phenyl group is substituted with R6 at an ortho position and is further optionally substituted with 0 to 4 substituents R7 independent of one another,
  the pyridyl group is substituted with R6 at an ortho position and is further optionally substituted with 0 to 3 substituents R7 independent of one another;

R6 represents:
  a halogen atom,
  a hydroxy group,
  a cyano group,
  a C1-C6 alkyl group optionally substituted with substituent(s) C,
  a C1-C6 alkoxy group optionally substituted with substituent(s) C,
  a C2-C6 alkenyloxy group optionally substituted with substituent(s) C, or
  a C3-C6 alkynyloxy group optionally substituted with substituent(s) C; and R7 represents:
  a halogen atom,
  a hydroxy group,
  a cyano group,
  a C1-C6 alkyl group optionally substituted with substituent(s) C,
  a C1-C6 haloalkyl group,
  a C2-C6 alkenyl group optionally substituted with substituent(s) C,
  a C2-C6 alkynyl group optionally substituted with substituent(s) C,
  a C1-C6 alkoxy group optionally substituted with substituent(s) C,
  a C1-C6 haloalkoxy group,
  a C2-C6 alkenyloxy group optionally substituted with substituent(s) C,
  a C3-C6 alkynyloxy group optionally substituted with substituent(s) C,
  a heteroaryloxy group optionally substituted with 0 to 2 substituents D,
  an aralkyloxy group optionally substituted with 0 to 5 substituents D,
  Rx1C(=O)— (wherein Rx1 is the same as defined hereinabove), or
  Rx1C(=O)O— (wherein Rx1 is the same as defined hereinabove).

3. The compound according to claim 2, or a salt thereof, wherein

R1 represents:
  a C1-C6 alkyl group optionally substituted with substituent(s) A,
  a C1-C6 haloalkyl group, or
  a C2-C6 haloalkenyl group;

R2, R3 and R4 are independent of one another and each represent:
  a hydrogen atom,
  a halogen atom,
  a hydroxy group,
  a cyano group,
  a C1-C6 alkyl group optionally substituted with substituent(s) C,
  a C1-C6 haloalkyl group,
  a C2-C6 alkynyl group optionally substituted with substituent(s) C,
  a C1-C6 alkoxy group optionally substituted with substituent(s) C,
  a C1-C6 haloalkoxy group, a C2-C6 alkenyloxy group optionally substituted with substituent(s) C, a C3-C6 alkynyloxy group optionally substituted with substituent(s) C, an aralkyloxy group optionally substituted with 0 to 5 substituents D, or Rx1C(=O)O— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group));

R5 represents:
a hydrogen atom,
a halogen atom,
a C1-C6 alkyl group optionally substituted with substituent(s) A,
a C1-C6 haloalkyl group,
a C2-C6 alkynyl group optionally substituted with substituent(s) A,
a C1-C6 alkoxy group optionally substituted with substituent(s) A, or
R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);

R6 represents:
a halogen atom,
a cyano group,
a C1-C6 alkyl group optionally substituted with substituent(s) C, or
a C1-C6 alkoxy group optionally substituted with substituent(s) C; and R7 represents:
a halogen atom,
a hydroxy group,
a C1-C6 alkyl group optionally substituted with substituent(s) C,
a C1-C6 haloalkyl group,
a C1-C6 alkoxy group optionally substituted with substituent(s) C,
a C1-C6 haloalkoxy group,
a C3-C6 alkynyloxy group optionally substituted with substituent(s) C,
a heteroaryloxy group optionally substituted with 0 to 2 substituents D,
an aralkyloxy group optionally substituted with 0 to 5 substituents D,
Rx1C(=O)— (wherein Rx1 is the same as defined hereinabove), or
Rx1C(=O)O— (wherein Rx1 is the same as defined hereinabove).

4. A compound represented by the formula (2), or a salt thereof:

[Chem. 133]

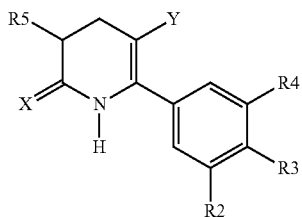

wherein R2, R3 and R4 are independent of one another and each represent:
a hydrogen atom,
a halogen atom,
a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
an aryloxy group optionally substituted with 0 to 5 substituents D,
a heteroaryloxy group optionally substituted with 0 to 2 substituents D,
an aralkyloxy group optionally substituted with 0 to 5 substituents D,
Rx1C(=O)— (wherein Rx1 represents a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a homopiperidinyl group or an azocanyl group)),
Rx1C(=O)O— (wherein Rx1 is the same as defined hereinabove),
a 3 to 6-membered ring group containing 1 to 2 oxygen atoms, Rc-L- (wherein Rc represents a C1-C6 alkyl group or a C1-C6 haloalkyl group, and L represents S, SO or SO$_2$), RaRbN— (wherein Ra and Rb are the same as defined hereinabove), or Rx2C(=O)N(Rx3)- (wherein Rx2 represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove), and Rx3 represents a hydrogen atom, a C1-C6 alkyl group optionally substituted with substituent(s) B, a C1-C6 haloalkyl group or a C3-C8 cycloalkyl group);

R5 represents:
 a hydrogen atom,
 a halogen atom,
 a cyano group,
 a nitro group,
 a C1-C6 alkyl group optionally substituted with substituent(s) A,
 a C1-C6 haloalkyl group,
 a C3-C8 cycloalkyl group optionally substituted with substituent(s) A,
 a C2-C6 alkenyl group optionally substituted with substituent(s) A,
 a C2-C6 haloalkenyl group,
 a C2-C6 alkynyl group optionally substituted with substituent(s) A,
 a C2-C6 haloalkynyl group,
 a C1-C6 alkoxy group optionally substituted with substituent(s) A,
 a C1-C6 haloalkoxy group,
 a C2-C6 alkenyloxy group optionally substituted with substituent(s) A,
 a C2-C6 haloalkenyloxy group,
 a C3-C6 alkynyloxy group optionally substituted with substituent(s) A,
 a C3-C6 haloalkynyloxy group,
 Rc-L- (wherein Rc and L are the same as defined hereinabove),
 RaRbN— (wherein Ra and Rb are the same as defined hereinabove), or
 R51C(=O)— (wherein R51 represents a hydroxy group, a C1-C6 alkyl group optionally substituted with substituent(s) B, a C1-C6 haloalkyl group, a C3-C8 cycloalkyl group or a C1-C6 alkoxy group);

X represents an oxygen atom or a sulfur atom;

Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, the phenyl group is substituted with R6 at an ortho position and is further optionally substituted with 0 to 4 substituents R7 independent of one another, the pyridyl group, the pyrazinyl group, the pyrimidinyl group, the pyridazinyl group, the triazinyl group or the tetrazinyl group is substituted with R6 at an ortho position and is further optionally substituted with 0 to 3 substituents R7 independent of one another, the thienyl group, the thiazolyl group, the isothiazolyl group or the thiadiazolyl group is substituted with R6 at an ortho position and is further optionally substituted with 0 to 2 substituents R7 independent of one another;

R6 represents:
 a halogen atom,
 a hydroxy group,
 a cyano group,
 a nitro group,
 a C1-C6 alkyl group optionally substituted with substituent(s) C,
 a C1-C6 haloalkyl group,
 a C3-C8 cycloalkyl group optionally substituted with substituent(s) C,
 a C2-C6 alkenyl group optionally substituted with substituent(s) C,
 a C2-C6 haloalkenyl group,
 a C2-C6 alkynyl group optionally substituted with substituent(s) C,
 a C2-C6 haloalkynyl group,
 a C1-C6 alkoxy group optionally substituted with substituent(s) C,
 a C1-C6 haloalkoxy group,
 a C3-C8 cycloalkoxy group optionally substituted with substituent(s) C,
 a C2-C6 alkenyloxy group optionally substituted with substituent(s) C,
 a C2-C6 haloalkenyloxy group,
 a C3-C6 alkynyloxy group optionally substituted with substituent(s) C,
 a C3-C6 haloalkynyloxy group,
 an aryloxy group optionally substituted with 0 to 5 substituents D,
 a heteroaryloxy group optionally substituted with 0 to 2 substituents D,
 an aralkyloxy group optionally substituted with 0 to 5 substituents D,
 Rx1C(=O)— (wherein Rx1 is the same as defined hereinabove),
 Rx1C(=O)O— (wherein Rx1 is the same as defined hereinabove),
 a 3 to 6-membered ring group containing 1 to 2 oxygen atoms,
 Rc-L- (wherein Rc and L are the same as defined hereinabove),
 RaRbN— (wherein Ra and Rb are the same as defined hereinabove), or
 Rx2C(=O)N(Rx3)- (wherein Rx2 and Rx3 are the same as defined hereinabove);

R7 is defined the same as R6 described hereinabove;

the substituent(s) A is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove);

the substituent(s) B is at least one selected from the group consisting of cyano group, C1-C6 alkoxy groups, C1-C6 haloalkoxy groups and C3-C8 cycloalkoxy groups;

the substituent(s) C is at least one selected from the group consisting of hydroxy group, cyano group, C3-C8 cycloalkyl groups, C1-C6 alkoxy groups, C1-C6 haloalkoxy groups, C3-C8 cycloalkoxy groups, C2-C6 alkoxyalkoxy groups, RaRbN— (wherein Ra and Rb are the same as defined hereinabove), Rc-L- (wherein Rc and L are the same as defined hereinabove), RdC(=O)— (wherein Rd is defined the same as Rx1 described hereinabove) and 3 to 6-membered ring groups containing 1 to 2 oxygen atoms; and the substituent(s) D is at least one selected from the group consisting of halogen atoms, hydroxy group, cyano group, nitro group, C1-C6 alkyl groups optionally substituted with substituent(s) B, C1-C6 haloalkyl groups, C3-C8 cycloalkyl groups, C1-C6 alkoxy groups, C1-C6 haloalkoxy groups and C3-C8 cycloalkoxy groups.

5. An agricultural and horticultural pest control agent comprising the compound described in claim 1, or a salt thereof, as an active ingredient.

6. An agricultural and horticultural fungicide comprising the compound described in claim 1, or a salt thereof, as an active ingredient.

7. A method for preventing and/or treating a plant disease, comprising applying the agricultural and horticultural pest control agent described in claim 5 to a plant, a plant seed or a soil for plant culvation.

8. A method for preventing and/or treating a plant disease, comprising applying the agricultural and horticultural fungicide described in claim 6 to a plant, a plant seed or a soil for plant culvation.

* * * * *